US007285380B2

(12) United States Patent
Noel et al.

(10) Patent No.: US 7,285,380 B2
(45) Date of Patent: Oct. 23, 2007

(54) METHODS OF PRODUCING POLYKETIDE SYNTHASE MUTANTS AND COMPOSITIONS AND USES THEREOF

(75) Inventors: Joseph P. Noel, San Diego, CA (US); Michael B. Austin, La Jolla, CA (US); Marianne E. Bowman, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 454 days.

(21) Appl. No.: 10/450,230

(22) PCT Filed: Dec. 14, 2001

(86) PCT No.: PCT/US01/48523

§ 371 (c)(1),
(2), (4) Date: Nov. 26, 2003

(87) PCT Pub. No.: WO02/057418

PCT Pub. Date: Jul. 25, 2002

(65) Prior Publication Data

US 2004/0106175 A1 Jun. 3, 2004

Related U.S. Application Data

(60) Provisional application No. 60/255,811, filed on Dec. 15, 2000.

(51) Int. Cl.
*C12Q 1/527* (2006.01)
*G01N 31/00* (2006.01)

(52) U.S. Cl. ............................................. 435/4; 702/27

(58) Field of Classification Search ..................... None
See application file for complete search history.

(56) References Cited

U.S. PATENT DOCUMENTS 6,390,821 B1 * 5/2002 Shokat ........................ 434/194

FOREIGN PATENT DOCUMENTS

WO       WO 01/07579       2/2001

OTHER PUBLICATIONS

Lukacin et al. "Transformation of acridone synthase to chalcone synthase" FEBS Lett. (2001), 413-417.*
Tropf et al. Evidence that stilbene synthase have developed from chalcone synthase several time in the cource of evolution. J. Mol. Evol. (1994) 38, 610-618.*
Cohen et al. Molecular modeling software and methods for medicinal chemistry. J. Med. Chem. 1990, 33, 883-894.*
Eckermann et al., "New pathway to polyketides in plants." *Nature* 396:387-390, (1998).
Ferrar et al., "Chalcone synnthase from alfalfa." Database for 'Online!, ID 1BI5, Jun. 22, 1999.

(Continued)

*Primary Examiner*—Nashaat T. Nashed
(74) *Attorney, Agent, or Firm*—Foley & Lardner LLP; Stephen E. Reiter

(57) ABSTRACT

The present invention comprises crystalline polyketide synthases, isolated non-native polyketide synthases having the structural coordinates of said crystalline polyketide synthases, and nucleic acids encoding such non-native polyketide synthases. Also disclosed are methods of producing mutant polyketide synthases, and methods of altering the activity and/or substrate specificity of putative polyketide synthases.

40 Claims, 24 Drawing Sheets

OTHER PUBLICATIONS

Ferrar et al., "Structure of chalcone synthase and the molecular basis of plant polyketide biosynthesis." *Nature Structural Biology*, 8: 775-784, 1999.

He et al., "Structural modeling and site-directed mutagenesis of the actinorhodin β-ketoacyl-acyl carrier protein synthase." *Journal of Bacteriology*, 182: 2619-1623, 2000.

Helariuttra et al., "Chalcone synthase-like genes active during corolla development are differently expressed and encode enzymes with different catalytic properties in *Gerbera hybrida* (Asteraceae)." *Plant Molecular Biology*, 28: 47-60, 1995.

Huang et al., "Crystal structure of β-ketoacyl-acyl carrier protein synthase II from *E.coli* reveals the molecular architecture of condensing enzymes." *The EMBO Journal*, 17: 1183-1191, 1998.

Jez et al., "Dissection of malonyl-coenzyme A decarboxylation from polyketide formation in the reaction mechanism of a plant polyketide synthase." *Biochemistry*, 39:890-902, 2000.

Jez et al., "Structure of chalcone synthase and the molacular basis of plant ppolyketide biosynthesis." Meeting information: Annual Meeting of the American Societies for Experimental Biology on Biochemistry and Molecular Biology, San Francisco, CA., May 16-20, 1999. *FASEB Journal*: vol. 13, No. 7, p. A1392, XP002158823, Abstract 355.

Junghans et al., "Stress responses in alfalfa (*Medicago sativa* L.) 15. Characterization and expression patterns of members of a subset of the chalcone synthase multigene family." *Plant Mol. Biol.*, 22:239-253, (1993).

Kreuzaler and Hahlbrock, "Enzymic synthesis of an aromatic ring from acetate units: Partial purification and some properties of flavanone synthase from cell-suspension cultures of *petroselinum hortense.*" *Eur. J. Biochem.*, 56:205-213, (1975).

Lanz et al., "The role of cysteines in polyketide synthases: Site-directed mutagenesis of resveratrol and chalcone synthases, two key enzymes in different plant-specific pathways." *J.Biol.Chem.* 266:9971-9976, (1991).

Mathieu et al., "The 2.8 Å crystal structure of peroxisomal 3-ketoacyl-CoA thiolase of *Saccharomyces cerevisiae*: a five-layered αβαβα structure constructed from two core domains of identical topology." *Structure*, 2:797-808, (1994).

Otwinowski and Minor, "Processing of X-ray diffraction data collected in oscillation mode." *Methods Enzymol.* 276:307-26, (1997).

Preisig-Mueller et al., "Plant polyketide synthases leading to stilbenoids have a domain catalyzing malonyl-CoA:$CO_2$ exchange, malonyl-CoA decarboxylation, and covalent enzyme modification and a site for chain lengthening." *Biochemistry* 36:8349-8358, (1997).

Raiber et al., "Molecular and enzymatic characterization of two stilbene synthases from eastern white pine (*Pinus strobus*): A single Arg/His difference determines the activity and the pH dependence of the enzymes." *FEBS Letters*, 361: 299-302, 1995.

Schroder, "A family of plant-specific polyketide synthases: facts and predictions." *Trends in Plant Science*, 2: 373-378, 1997.

Schroeder et al., "Plant polyketide synthases: a chalcone synthase-type enzyme which performs a condensation reaction with methylmalonyl-CoA in the biosynthesis of C-methylated chalcones." *Biochemistry*, 37:8417-8425, (1998).

Schroder and Schroder, "Stilbene and Chalcone synthases: Related enzymes with key functions in plant-specific pathways." Zeitschrift Fuer Naturforschung. Section C. *Biosciences*, 45c: 1-8, 1990.

Tropf et al., "Reaction mechanisms of homodimeric plant polyketide synthases (stilbene and chalcone synthase)." *J.Biol. Chem.*, 270:7922-7928, (1995).

Welle & Grisebach, "Isolation of a novel NADPH-dependent reductase which coacts with chalcone synthase in the biosynthesis of 6'-deoxychalcone." *FEBS Lett.* 236:222-225, (1988).

International Search Report from International Application PCT/US00/20674.

Suh et al., "Identification of amino acid residues important in the cyclization reactions of chalcone and stilbene synthases." Biochem. J., 350: 229-235, 2000.

International Search Report for PCT Application No. PCT/US01/48523.

Gilliland and Ladner, Crystallization of biological macromolecules for X-ray diffraction studies. Curr. Opin. Struct. Biol. 6:595-603, 1996.

Ke and Doudna, Crystallization of RNA and RNA-protein complexes. Methods, 34:408-414, 2004.

Wiencek, New strategies for protein crystal growth, Ann. Rev. Biomed. Eng., 1:505-534, 1999.

* cited by examiner

```
                                 250        260        270
chs2 (alfalfa)          ...SEGAIDGHLREAGLTFHLLKDVPG...
chs2 (barley)           ...SEGAIDGHLTEAGLTIHLLKDVPG...
acs (Ruta graveolens)   ...SDGAIEGHIREEGLTVHLKKDVPA...
sts1 (peanut)           ...SHGAIGGLLREVGLTFYLNKSVPD...
sts1 (pine)             ...SDGAISGKLREVGLTFQLKGAVPD...
bbs (Phalaenopsis sp)   ...SAGAIGGHVSEGGLLATLHRDVPQ...
```

FIGURE 6C

```
                      1         10        20        30        40        50
                      •         •         •         •         •         •
P.sylvestris STS   ---MGGVDFEGFRKLQRADGEASILAIGTANPPNAVDQSTYPDFYFRITGNEHNTELKDK
P.sylvestris CHS   MAAGMMKDLEAFRKAQRADGPATILAIGTATPPNAVDQSSYPDYYFKITNSEHMTELKEK
M.sativa     CHS   -----MVSVSEIRKAQRAEGPATILAIGTANPANCVEQSTYPDFYFKITNSEHKTELKEK 60        70        80        90       100       110
                      •         •         •         •         •         •
P.sylvestris STS   FKRICERSAIKQRYMYLTEEILKKNPDVCAFVEVPSLDARQAMLAMEVPRLAKEAAEKAI
P.sylvestris CHS   FRRMCDKSAIKKRYMYLTEEILKENPKVCEYMA-PSLDARQDMVVVEVPRLGKEAAAKAI
M.sativa     CHS   FQRMCDKSMIKRRYMYLTEEILKENPNVCEYMA-PSLDARQDMVVVEVPRLGKEAAVKAI A 1
                     120       130       140       150       160       170
                      •         •         •         •         •         •
P.sylvestris STS   QEWGQSKSGITHLIFCSTTTPDLPGADFEVAKLLGLHPSVKRVGVFQHGCFAGGTVLRMA
P.sylvestris CHS   KEWGQPKSKITHVIFCTTSGVDMPGADYQLTKLLGLRPSVKRVMMYQQGCFAGGTVLRVA
M.sativa     CHS   KEWGQPKSKITHLIVCTTSGVDMPGADYQLTKLLGLRPYVKRYMMYQQGCFAGGTVLRLA A 2                   A 3
                     180       190       200       210       220       230
                      •         •         •         •         •         •
P.sylvestris STS   KDLAENNRGARVLVICSETTAVTFRGPSETHLDSLVGQALFGDGASALIVGADPIPQVEK
P.sylvestris CHS   KDLAENNRGARVLVVCSEITAVTFRGPSDTHLDSMVGQALFGDGAAALIVGADPVPEVEK
M.sativa     CHS   KDLAENNKGARVLVVCSEVTAVTFRGPSDTHLDSLVGQALFGDGAAALIVGSDPVPEIEK 240       250       260       270       280       290
                      •         •         •         •         •         •
P.sylvestris STS   ACFEIVWTAQTVVPNSEGAIGGKVREVGLTFQLKGAVPDLISANIENCMVEAFSQFKISD
P.sylvestris CHS   PCFELMWTAQTILPDSDGAIDGHLREVGLTFHLLKDVPGLISKNIEKSLVEAFQQFGISD
M.sativa     CHS   PIFEMVWTAQTIAPDSEGAIDGHLREAGLTFHLLKDVPGIVSKNITKALVEAFEPLGISD B 1      A 4
                     300       310       320       330       340       350
                      •         •         •         •         •         •
P.sylvestris STS   WNKLFWVVHPGGRAILDRVEAKLNLDPTKLIPTRHVMSEYGNMSSACVHFILDQTRKASL
P.sylvestris CHS   WNQLFWIAHPGGPAILDQVEAKLNLDPKKLSATRQVLSDYGNMSSACVHFILDEMRKSSK
M.sativa     CHS   YNSIFWIAHPGGPAILDQVEQKLALKPEKMNATREVLSEYGNMSSACVLFILDEMRKKST 360       370       380       390
                      •         •         •         •
P.sylvestris STS   QNGCSTTGEGLEMGVLFGFGPGLTIETVVLKSVPIQ-
P.sylvestris CHS   EKGCSTTGEGLDVGVLFGFGPGLTVETVVLKSVPLLD
M.sativa     CHS   QNGLKTTGEGLEWGVLFGFGPGLTIETVVLRSVAI--
```

FIGURE 11

Aldol Cyclization Switch Region
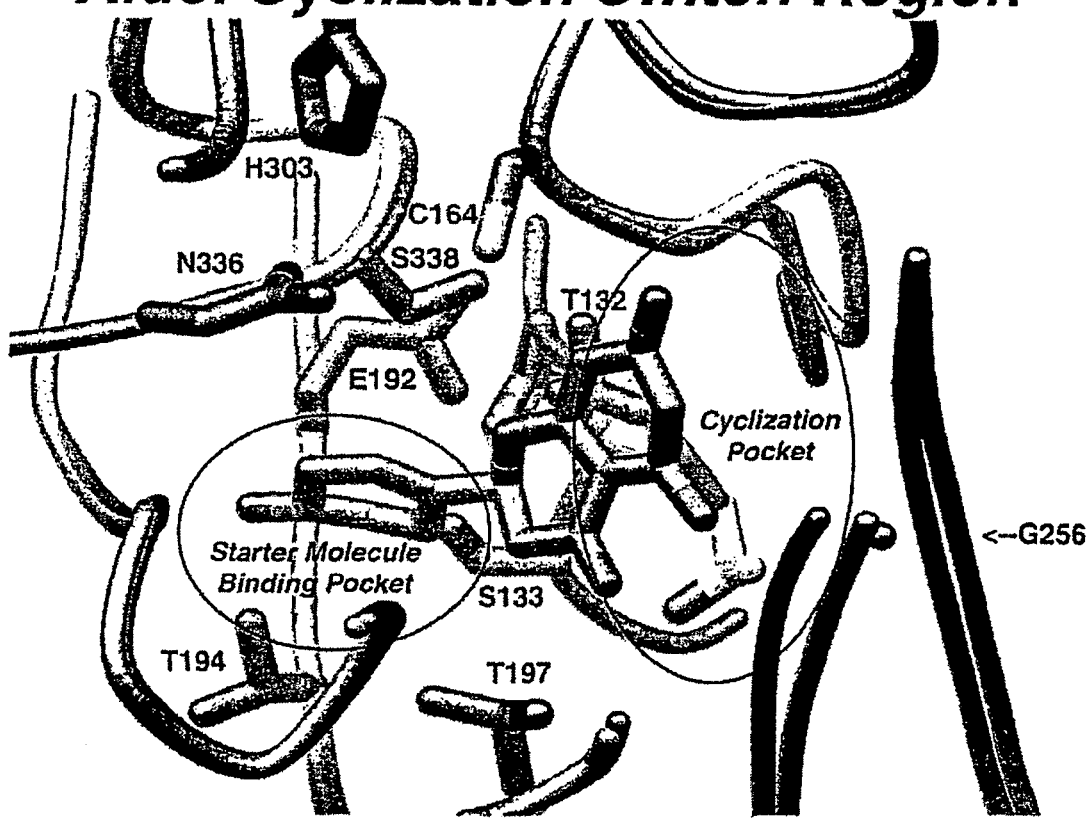
(Both views are from the CoA-Binding Tunnel)
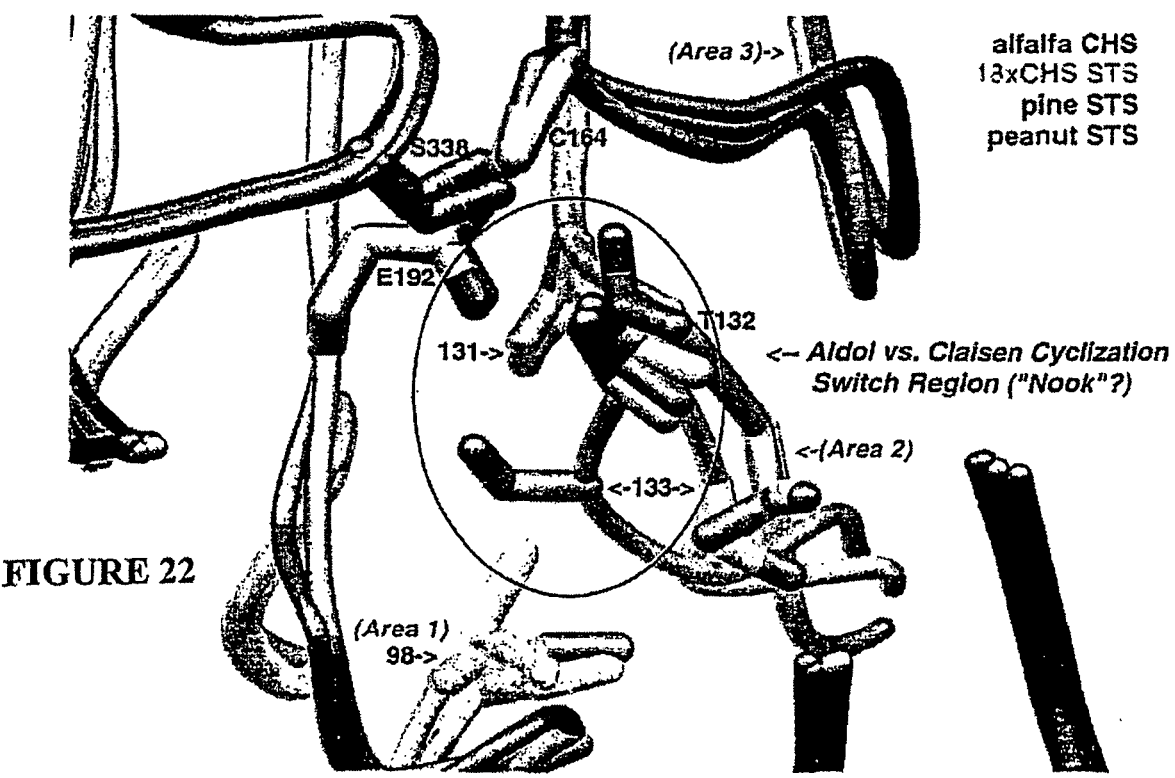
FIGURE 22

SEQUENCE LISTING

<160> NUMBER OF SEQ ID NOS: 64

<210> SEQ ID NO 1
<211> LENGTH: 389
<212> TYPE: PRT
<213> ORGANISM: Medicago sativa

<400> SEQUENCE: 1

Met Val Ser Val Ser Glu Ile Arg Lys Ala Gln Arg Ala Glu Gly Pro
 1               5                  10                  15

Ala Thr Ile Leu Ala Ile Gly Thr Ala Asn Pro Ala Asn Cys Val Glu
             20                  25                  30

Gln Ser Thr Tyr Pro Asp Phe Tyr Phe Lys Ile Thr Asn Ser Glu His
         35                  40                  45

Lys Thr Glu Leu Lys Glu Lys Phe Gln Arg Met Cys Asp Lys Ser Met
     50                  55                  60

-continued

```
Ile Lys Arg Arg Tyr Met Tyr Leu Thr Glu Glu Ile Leu Lys Glu Asn
 65                  70                  75                  80

Pro Asn Val Cys Glu Tyr Met Ala Pro Ser Leu Asp Ala Arg Gln Asp
                 85                  90                  95

Met Val Val Val Glu Val Pro Arg Leu Gly Lys Glu Ala Ala Val Lys
            100                 105                 110

Ala Ile Lys Glu Trp Gly Gln Pro Lys Ser Lys Ile Thr His Leu Ile
        115                 120                 125

Val Cys Thr Thr Ser Gly Val Asp Met Pro Gly Ala Asp Tyr Gln Leu
130                 135                 140

Thr Lys Leu Leu Gly Leu Arg Pro Tyr Val Lys Arg Tyr Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Val Thr Ala Val Thr Phe Arg Gly Pro Ser Asp Thr His Leu Asp Ser
        195                 200                 205

Leu Val Gly Gln Ala Leu Phe Gly Asp Gly Ala Ala Ala Leu Ile Val
210                 215                 220

Gly Ser Asp Pro Val Pro Glu Ile Glu Lys Pro Ile Phe Glu Met Val
225                 230                 235                 240

Trp Thr Ala Gln Thr Ile Ala Pro Asp Ser Glu Gly Ala Ile Asp Gly
                245                 250                 255

His Leu Arg Glu Ala Gly Leu Thr Phe His Leu Leu Lys Asp Val Pro
            260                 265                 270

Gly Ile Val Ser Lys Asn Ile Thr Lys Ala Leu Val Glu Ala Phe Glu
        275                 280                 285

Pro Leu Gly Ile Ser Asp Tyr Asn Ser Ile Phe Trp Ile Ala His Pro
290                 295                 300

Gly Gly Pro Ala Ile Leu Asp Gln Val Glu Gln Lys Leu Ala Leu Lys
305                 310                 315                 320

Pro Glu Lys Met Asn Ala Thr Arg Glu Val Leu Ser Glu Tyr Gly Asn
                325                 330                 335

Met Ser Ser Ala Cys Val Leu Phe Ile Leu Asp Glu Met Arg Lys Lys
            340                 345                 350

Ser Thr Gln Asn Gly Leu Lys Thr Thr Gly Glu Gly Leu Glu Trp Gly
        355                 360                 365

Val Leu Phe Gly Phe Gly Pro Gly Leu Thr Ile Glu Thr Val Val Leu
370                 375                 380

Arg Ser Val Ala Ile
385

<210> SEQ ID NO 2
<211> LENGTH: 24
<212> TYPE: PRT
<213> ORGANISM: Medicago sativa

<400> SEQUENCE: 2

Ser Glu Gly Ala Ile Asp Gly His Leu Arg Glu Ala Gly Leu Thr Phe
 1               5                  10                  15

His Leu Leu Lys Asp Val Pro Gly
                20

<210> SEQ ID NO 3
```

```
<211> LENGTH: 24
<212> TYPE: PRT
<213> ORGANISM: Hordeum vulgare

<400> SEQUENCE: 3

Ser Glu Gly Ala Ile Asp Gly His Leu Thr Glu Ala Gly Leu Thr Ile
 1               5                  10                  15

His Leu Leu Lys Asp Val Pro Gly
             20

<210> SEQ ID NO 4
<211> LENGTH: 24
<212> TYPE: PRT
<213> ORGANISM: Ruta graveolens

<400> SEQUENCE: 4

Ser Asp Gly Ala Ile Glu Gly His Ile Arg Glu Gly Leu Thr Val
 1               5                  10                  15

His Leu Lys Lys Asp Val Pro Ala
             20

<210> SEQ ID NO 5
<211> LENGTH: 24
<212> TYPE: PRT
<213> ORGANISM: Arachis hypogaea

<400> SEQUENCE: 5

Ser His Gly Ala Ile Gly Gly Leu Leu Arg Glu Val Gly Leu Thr Phe
 1               5                  10                  15

Tyr Leu Asn Lys Ser Val Pro Asp
             20

<210> SEQ ID NO 6
<211> LENGTH: 24
<212> TYPE: PRT
<213> ORGANISM: Pinus sp.

<400> SEQUENCE: 6

Ser Asp Gly Ala Ile Ser Gly Lys Leu Arg Glu Val Gly Leu Thr Phe
 1               5                  10                  15

Gln Leu Lys Gly Ala Val Pro Asp
             20

<210> SEQ ID NO 7
<211> LENGTH: 24
<212> TYPE: PRT
<213> ORGANISM: Phalaenopsis sp.

<400> SEQUENCE: 7

Ser Ala Gly Ala Ile Gly Gly His Val Ser Glu Gly Leu Leu Ala
 1               5                  10                  15

Thr Leu His Arg Asp Val Pro Gln
             20

<210> SEQ ID NO 8
<211> LENGTH: 393
<212> TYPE: PRT
<213> ORGANISM: Pinus sylvestris

<400> SEQUENCE: 8

Met Gly Gly Val Asp Phe Glu Gly Phe Arg Lys Leu Gln Arg Ala Asp
 1               5                  10                  15
```

```
Gly Phe Ala Ser Ile Leu Ala Ile Gly Thr Ala Asn Pro Pro Asn Ala
                20                  25                  30

Val Asp Gln Ser Thr Tyr Pro Asp Phe Tyr Arg Ile Thr Gly Asn
        35                  40                  45

Glu His Asn Thr Glu Leu Lys Asp Lys Phe Lys Arg Ile Cys Glu Arg
     50                  55                  60

Ser Ala Ile Lys Gln Arg Tyr Met Tyr Leu Thr Glu Ile Leu Lys
65                  70                  75                  80

Lys Asn Pro Asp Val Cys Ala Phe Val Glu Val Pro Ser Leu Asp Ala
                85                  90                  95

Arg Gln Ala Met Leu Ala Met Glu Val Pro Arg Leu Ala Lys Glu Ala
                100                 105                 110

Ala Glu Lys Ala Ile Gln Glu Trp Gly Gln Ser Lys Ser Gly Ile Thr
            115                 120                 125

His Leu Ile Phe Cys Ser Thr Thr Pro Asp Leu Pro Gly Ala Asp
    130                 135                 140

Phe Glu Val Ala Lys Leu Leu Gly Leu His Pro Ser Val Lys Arg Val
145                 150                 155                 160

Gly Val Phe Gln His Gly Cys Phe Ala Gly Thr Val Leu Arg Met
                165                 170                 175

Ala Lys Asp Leu Ala Glu Asn Asn Arg Gly Ala Arg Val Leu Val Ile
            180                 185                 190

Cys Ser Glu Thr Thr Ala Val Thr Phe Arg Gly Pro Ser Glu Thr His
        195                 200                 205

Leu Asp Ser Leu Val Gly Gln Ala Leu Phe Gly Asp Gly Ala Ser Ala
    210                 215                 220

Leu Ile Val Gly Ala Asp Pro Ile Pro Gln Val Glu Lys Ala Cys Phe
225                 230                 235                 240

Glu Ile Val Trp Thr Ala Gln Thr Val Val Pro Asn Ser Glu Gly Ala
                245                 250                 255

Ile Gly Gly Lys Val Arg Glu Val Gly Leu Thr Phe Gln Leu Lys Gly
                260                 265                 270

Ala Val Pro Asp Leu Ile Ser Ala Asn Ile Glu Asn Cys Met Val Glu
            275                 280                 285

Ala Phe Ser Gln Phe Lys Ile Ser Asp Trp Asn Lys Leu Phe Trp Val
    290                 295                 300

Val His Pro Gly Gly Arg Ala Ile Leu Asp Arg Val Glu Ala Lys Leu
305                 310                 315                 320

Asn Leu Asp Pro Thr Lys Leu Ile Pro Thr Arg His Val Met Ser Glu
                325                 330                 335

Tyr Gly Asn Met Ser Ser Ala Cys Val His Phe Ile Leu Asp Gln Thr
                340                 345                 350

Arg Lys Ala Ser Leu Gln Asn Gly Cys Ser Thr Thr Gly Glu Gly Leu
            355                 360                 365

Glu Met Gly Val Leu Phe Gly Phe Gly Pro Gly Leu Thr Ile Glu Thr
    370                 375                 380

Val Val Leu Lys Ser Val Pro Ile Gln
385                 390

<210> SEQ ID NO 9
<211> LENGTH: 396
<212> TYPE: PRT
<213> ORGANISM: Pinus sylvestris

<400> SEQUENCE: 9
```

```
Met Ala Ala Gly Met Met Lys Asp Leu Glu Ala Phe Arg Lys Ala Gln
 1               5                  10                  15

Arg Ala Asp Gly Pro Ala Thr Ile Leu Ala Ile Gly Thr Ala Thr Pro
             20                  25                  30

Pro Asn Ala Val Asp Gln Ser Ser Tyr Pro Asp Tyr Phe Lys Ile
         35                  40                  45

Thr Asn Ser Glu His Met Thr Glu Leu Lys Lys Phe Arg Arg Met
 50                  55                  60

Cys Asp Lys Ser Ala Ile Lys Lys Arg Tyr Met Tyr Leu Thr Glu Glu
 65                  70                  75                  80

Ile Leu Lys Glu Asn Pro Lys Val Cys Glu Tyr Met Ala Pro Ser Leu
                 85                  90                  95

Asp Ala Arg Gln Asp Met Val Val Glu Val Pro Arg Leu Gly Lys
             100                 105                 110

Glu Ala Ala Lys Ala Ile Lys Glu Trp Gly Gln Pro Lys Ser Lys
             115                 120                 125

Ile Thr His Val Ile Phe Cys Thr Thr Ser Gly Val Asp Met Pro Gly
 130                 135                 140

Ala Asp Tyr Gln Leu Thr Lys Leu Leu Gly Leu Arg Pro Ser Val Lys
145                 150                 155                 160

Arg Val Met Met Tyr Gln Gln Gly Cys Phe Ala Gly Gly Thr Val Leu
                 165                 170                 175

Arg Val Ala Lys Asp Leu Ala Glu Asn Asn Arg Gly Ala Arg Val Leu
             180                 185                 190

Val Val Cys Ser Glu Ile Thr Ala Val Thr Phe Arg Gly Pro Ser Asp
             195                 200                 205

Thr His Leu Asp Ser Met Val Gly Gln Ala Leu Phe Gly Asp Gly Ala
 210                 215                 220

Ala Ala Leu Ile Val Gly Ala Asp Pro Val Pro Glu Val Glu Lys Pro
225                 230                 235                 240

Cys Phe Glu Leu Met Trp Thr Ala Gln Thr Ile Leu Pro Asp Ser Asp
                 245                 250                 255

Gly Ala Ile Asp Gly His Leu Arg Glu Val Gly Leu Thr Phe His Leu
             260                 265                 270

Leu Lys Asp Val Pro Gly Leu Ile Ser Lys Asn Ile Glu Lys Ser Leu
     275                 280                 285

Val Glu Ala Phe Gln Gln Phe Gly Ile Ser Asp Trp Asn Gln Leu Phe
 290                 295                 300

Trp Ile Ala His Pro Gly Gly Pro Ala Ile Leu Asp Gln Val Glu Ala
305                 310                 315                 320

Lys Leu Asn Leu Asp Pro Lys Lys Leu Ser Ala Thr Arg Gln Val Leu
             325                 330                 335

Ser Asp Tyr Gly Asn Met Ser Ser Ala Cys Val His Phe Ile Leu Asp
             340                 345                 350

Glu Met Arg Lys Ser Ser Lys Glu Lys Gly Cys Ser Thr Thr Gly Glu
             355                 360                 365

Gly Leu Asp Val Gly Val Leu Phe Gly Phe Gly Pro Gly Leu Thr Val
     370                 375                 380

Glu Thr Val Val Leu Lys Ser Val Pro Leu Leu Asp
385                 390                 395

<210> SEQ ID NO 10
<211> LENGTH: 389
```

```
<212> TYPE: PRT
<213> ORGANISM: Medicago sativa

<400> SEQUENCE: 10

Met Val Ser Val Ser Glu Ile Arg Lys Ala Gln Arg Ala Glu Gly Pro
 1               5                  10                  15

Ala Thr Ile Leu Ala Ile Gly Thr Ala Asn Pro Ala Asn Cys Val Glu
             20                  25                  30

Gln Ser Thr Tyr Pro Asp Phe Tyr Phe Lys Ile Thr Asn Ser Glu His
         35                  40                  45

Lys Thr Glu Leu Lys Glu Lys Phe Gln Arg Met Cys Asp Lys Ser Met
 50                  55                  60

Ile Lys Arg Arg Tyr Met Tyr Leu Thr Glu Glu Ile Leu Lys Glu Asn
65                  70                  75                  80

Pro Asn Val Cys Glu Tyr Met Ala Pro Ser Leu Asp Ala Arg Gln Asp
                 85                  90                  95

Met Val Val Glu Val Pro Arg Leu Gly Lys Glu Ala Val Lys
            100                 105                 110

Ala Ile Lys Glu Trp Gly Gln Pro Lys Ser Lys Ile Thr His Leu Ile
        115                 120                 125

Val Cys Thr Thr Ser Gly Val Asp Met Pro Gly Ala Asp Tyr Gln Leu
    130                 135                 140

Thr Lys Leu Leu Gly Leu Arg Pro Tyr Val Lys Arg Tyr Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Val Thr Ala Val Thr Phe Arg Gly Pro Ser Asp Thr His Leu Asp Ser
        195                 200                 205

Leu Val Gly Gln Ala Leu Phe Gly Asp Gly Ala Ala Ala Leu Ile Val
    210                 215                 220

Gly Ser Asp Pro Val Pro Glu Ile Glu Lys Pro Ile Phe Glu Met Val
225                 230                 235                 240

Trp Thr Ala Gln Thr Ile Ala Pro Asp Ser Glu Gly Ala Ile Asp Gly
                245                 250                 255

His Leu Arg Glu Ala Gly Leu Thr Phe His Leu Leu Lys Asp Val Pro
            260                 265                 270

Gly Ile Val Ser Lys Asn Ile Thr Lys Ala Leu Val Glu Ala Phe Glu
        275                 280                 285

Pro Leu Gly Ile Ser Asp Tyr Asn Ser Ile Phe Trp Ile Ala His Pro
    290                 295                 300

Gly Gly Pro Ala Ile Leu Asp Gln Val Glu Gln Lys Leu Ala Leu Lys
305                 310                 315                 320

Pro Glu Lys Met Asn Ala Thr Arg Glu Val Leu Ser Glu Tyr Gly Asn
                325                 330                 335

Met Ser Ser Ala Cys Val Leu Phe Ile Leu Asp Glu Met Arg Lys Lys
            340                 345                 350

Ser Thr Gln Asn Gly Leu Lys Thr Thr Gly Glu Gly Leu Glu Trp Gly
        355                 360                 365

Val Leu Phe Gly Phe Gly Pro Gly Leu Thr Ile Glu Thr Val Val Leu
    370                 375                 380

Arg Ser Val Ala Ile
385
```

<210> SEQ ID NO 11
<211> LENGTH: 11
<212> TYPE: PRT
<213> ORGANISM: Pinus sylvestris

<400> SEQUENCE: 11

Arg Gln Ala Met Leu Ala Met Glu Val Pro Arg
1               5                   10

<210> SEQ ID NO 12
<211> LENGTH: 12
<212> TYPE: PRT
<213> ORGANISM: Pinus sylvestris

<400> SEQUENCE: 12

Phe Cys Ser Thr Thr Thr Pro Asp Leu Pro Gly Ala
1               5                   10

<210> SEQ ID NO 13
<211> LENGTH: 11
<212> TYPE: PRT
<213> ORGANISM: Pinus sylvestris

<400> SEQUENCE: 13

Val Lys Arg Val Gly Val Phe Gln His Gly Cys
1               5                   10

<210> SEQ ID NO 14
<211> LENGTH: 27
<212> TYPE: PRT
<213> ORGANISM: Pinus sylvestris

<400> SEQUENCE: 14

Gly Ala Ile Gly Gly Lys Val Arg Glu Val Gly Leu Thr Phe Gln Leu
1               5                   10                  15

Lys Gly Ala Val Pro Asp Leu Ile Ser Ala Asn
            20                  25

<210> SEQ ID NO 15
<211> LENGTH: 11
<212> TYPE: PRT
<213> ORGANISM: Pinus sp.

<400> SEQUENCE: 15

Arg Gln Ala Met Leu Ala Ala Glu Val Pro Arg
1               5                   10

<210> SEQ ID NO 16
<211> LENGTH: 12
<212> TYPE: PRT
<213> ORGANISM: Pinus sp.

<400> SEQUENCE: 16

Phe Cys Thr Thr Thr Thr Pro Asp Leu Pro Gly Ala
1               5                   10

<210> SEQ ID NO 17
<211> LENGTH: 11
<212> TYPE: PRT
<213> ORGANISM: Pinus sp.

<400> SEQUENCE: 17

Val Lys Arg Val Gly Val Phe Gln His Gly Cys

<210> SEQ ID NO 18
<211> LENGTH: 27
<212> TYPE: PRT
<213> ORGANISM: Pinus sp.

<400> SEQUENCE: 18

Gly Ala Ile Ser Gly Lys Leu Arg Glu Val Gly Leu Thr Phe Gln Leu
 1               5                  10                  15
Lys Gly Ala Val Pro Asp Leu Ile Ser Thr Asn
                20                  25

<210> SEQ ID NO 19
<211> LENGTH: 11
<212> TYPE: PRT
<213> ORGANISM: Pinus strobus

<400> SEQUENCE: 19

Arg Gln Ala Met Leu Ala Val Glu Val Pro Arg
 1               5                  10

<210> SEQ ID NO 20
<211> LENGTH: 12
<212> TYPE: PRT
<213> ORGANISM: Pinus strobus

<400> SEQUENCE: 20

Phe Cys Thr Thr Thr Thr Pro Asp Leu Pro Gly Ala
 1               5                  10

<210> SEQ ID NO 21
<211> LENGTH: 11
<212> TYPE: PRT
<213> ORGANISM: Pinus strobus

<400> SEQUENCE: 21

Val Lys Arg Val Gly Val Phe Gln His Gly Cys
 1               5                  10

<210> SEQ ID NO 22
<211> LENGTH: 27
<212> TYPE: PRT
<213> ORGANISM: Pinus strobus

<400> SEQUENCE: 22

Gly Ala Ile Ser Gly Lys Leu Arg Glu Val Gly Leu Thr Phe Gln Leu
 1               5                  10                  15
Lys Gly Ala Val Pro Asp Leu Ile Ser Thr Asn
                20                  25

<210> SEQ ID NO 23
<211> LENGTH: 11
<212> TYPE: PRT
<213> ORGANISM: Vitis vinifera

<400> SEQUENCE: 23

Arg Gln Glu Ile Ile Thr Ala Glu Val Pro Lys
 1               5                  10

<210> SEQ ID NO 24
<211> LENGTH: 12
<212> TYPE: PRT
<213> ORGANISM: Vitis vinifera

<400> SEQUENCE: 24

```
Phe Cys Thr Thr Ser Gly Val Glu Met Pro Gly Ala
 1               5                  10

<210> SEQ ID NO 25
<211> LENGTH: 11
<212> TYPE: PRT
<213> ORGANISM: Vitis vinifera

<400> SEQUENCE: 25

Val Arg Arg Val Met Leu Asp Gln Gln Gly Cys
 1               5                  10

<210> SEQ ID NO 26
<211> LENGTH: 27
<212> TYPE: PRT
<213> ORGANISM: Vitis vinifera

<400> SEQUENCE: 26

Gly Ala Ile Ala Gly Asn Leu Arg Glu Val Gly Leu Thr Phe His Leu
 1               5                  10                  15

Trp Pro Asn Val Pro Thr Leu Ile Ser Glu Asn
            20                  25

<210> SEQ ID NO 27
<211> LENGTH: 11
<212> TYPE: PRT
<213> ORGANISM: Arachis hypogaea

<400> SEQUENCE: 27

Arg Glu Asp Met Met Ile Arg Glu Val Pro Arg
 1               5                  10

<210> SEQ ID NO 28
<211> LENGTH: 12
<212> TYPE: PRT
<213> ORGANISM: Arachis hypogaea

<400> SEQUENCE: 28

Phe Cys Thr Thr Ser Gly Val Ala Leu Pro Gly Val
 1               5                  10

<210> SEQ ID NO 29
<211> LENGTH: 11
<212> TYPE: PRT
<213> ORGANISM: Arachis hypogaea

<400> SEQUENCE: 29

Val Lys Arg Tyr Met Met Tyr His Gln Gly Cys
 1               5                  10

<210> SEQ ID NO 30
<211> LENGTH: 27
<212> TYPE: PRT
<213> ORGANISM: Arachis hypogaea

<400> SEQUENCE: 30

Gly Ala Ile Gly Gly Leu Leu Arg Glu Val Gly Leu Thr Phe Tyr Leu
 1               5                  10                  15

Asn Lys Ser Val Pro Asp Ile Ile Ser Gln Asn
            20                  25

<210> SEQ ID NO 31
<211> LENGTH: 11
```

```
<212> TYPE: PRT
<213> ORGANISM: Pinus sylvestris

<400> SEQUENCE: 31

Arg Gln Asp Met Val Val Val Glu Val Pro Arg
  1               5                  10

<210> SEQ ID NO 32
<211> LENGTH: 12
<212> TYPE: PRT
<213> ORGANISM: Pinus sylvestris

<400> SEQUENCE: 32

Phe Cys Thr Thr Ser Gly Val Asp Met Pro Gly Ala
  1               5                  10

<210> SEQ ID NO 33
<211> LENGTH: 11
<212> TYPE: PRT
<213> ORGANISM: Pinus sylvestris

<400> SEQUENCE: 33

Val Lys Arg Val Met Met Tyr Gln Gln Gly Cys
  1               5                  10

<210> SEQ ID NO 34
<211> LENGTH: 27
<212> TYPE: PRT
<213> ORGANISM: Pinus sylvestris

<400> SEQUENCE: 34

Gly Ala Ile Asp Gly His Leu Arg Glu Val Gly Leu Thr Phe His Leu
  1               5                  10                  15

Leu Lys Asp Val Pro Gly Leu Ile Ser Lys Asn
             20                  25

<210> SEQ ID NO 35
<211> LENGTH: 11
<212> TYPE: PRT
<213> ORGANISM: Medicago sativa

<400> SEQUENCE: 35

Arg Gln Asp Met Val Val Val Glu Val Pro Arg
  1               5                  10

<210> SEQ ID NO 36
<211> LENGTH: 12
<212> TYPE: PRT
<213> ORGANISM: Medicago sativa

<400> SEQUENCE: 36

Val Cys Thr Thr Ser Gly Val Asp Met Pro Gly Ala
  1               5                  10

<210> SEQ ID NO 37
<211> LENGTH: 11
<212> TYPE: PRT
<213> ORGANISM: Medicago sativa

<400> SEQUENCE: 37

Val Lys Arg Tyr Met Met Tyr Gln Gln Gly Cys
  1               5                  10

<210> SEQ ID NO 38
```

```
<211> LENGTH: 27
<212> TYPE: PRT
<213> ORGANISM: Medicago sativa

<400> SEQUENCE: 38

Gly Ala Ile Asp Gly His Leu Arg Glu Ala Gly Leu Thr Phe His Leu
 1               5                  10                  15

Leu Lys Asp Val Pro Gly Ile Val Ser Lys Asn
            20                  25

<210> SEQ ID NO 39
<211> LENGTH: 11
<212> TYPE: PRT
<213> ORGANISM: Solanum tuberosum

<400> SEQUENCE: 39

Arg Gln Asp Ile Val Val Glu Val Pro Lys
 1               5                  10

<210> SEQ ID NO 40
<211> LENGTH: 12
<212> TYPE: PRT
<213> ORGANISM: Solanum tuberosum

<400> SEQUENCE: 40

Phe Cys Thr Thr Ser Gly Val Asp Met Pro Gly Ala
 1               5                  10

<210> SEQ ID NO 41
<211> LENGTH: 11
<212> TYPE: PRT
<213> ORGANISM: Solanum tuberosum

<400> SEQUENCE: 41

Val Lys Arg Leu Met Met Tyr Gln Gln Gly Cys
 1               5                  10

<210> SEQ ID NO 42
<211> LENGTH: 27
<212> TYPE: PRT
<213> ORGANISM: Solanum tuberosum

<400> SEQUENCE: 42

Gly Ala Ile Asp Gly His Leu Arg Glu Val Gly Leu Thr Phe His Leu
 1               5                  10                  15

Leu Lys Asp Val Pro Gly Leu Ile Ser Lys Asn
            20                  25

<210> SEQ ID NO 43
<211> LENGTH: 11
<212> TYPE: PRT
<213> ORGANISM: Ipomoea purpurea

<400> SEQUENCE: 43

Arg Gln Asp Ile Leu Val Ser Glu Val Pro Lys
 1               5                  10

<210> SEQ ID NO 44
<211> LENGTH: 12
<212> TYPE: PRT
<213> ORGANISM: Ipomoea purpurea

<400> SEQUENCE: 44

Phe Cys Thr Thr Ser Gly Val Asp Met Pro Gly Ala
```

-continued

```
1               5                   10
```

<210> SEQ ID NO 45
<211> LENGTH: 11
<212> TYPE: PRT
<213> ORGANISM: Ipomoea purpurea

<400> SEQUENCE: 45

```
Val Lys Arg Leu Met Met Tyr Gln Gln Gly Cys
1               5                   10
```

<210> SEQ ID NO 46
<211> LENGTH: 27
<212> TYPE: PRT
<213> ORGANISM: Ipomoea purpurea

<400> SEQUENCE: 46

```
Ser Tyr Leu Lys Leu Gln Leu Arg Glu Met Gly Leu Thr Phe His Cys
1               5                   10                  15

Ser Lys Ala Val Pro Ser Leu Ile Thr Gln Asn
            20                  25
```

<210> SEQ ID NO 47
<211> LENGTH: 11
<212> TYPE: PRT
<213> ORGANISM: Gerbera hybrida

<400> SEQUENCE: 47

```
Arg Gln Asp Leu Val Val Thr Gly Val Pro Met
1               5                   10
```

<210> SEQ ID NO 48
<211> LENGTH: 12
<212> TYPE: PRT
<213> ORGANISM: Gerbera hybrida

<400> SEQUENCE: 48

```
Phe Cys Thr Thr Ala Gly Val Asp Met Pro Gly Ala
1               5                   10
```

<210> SEQ ID NO 49
<211> LENGTH: 11
<212> TYPE: PRT
<213> ORGANISM: Gerbera hybrida

<400> SEQUENCE: 49

```
Val Lys Arg Tyr Met Leu Tyr Gln Gln Gly Cys
1               5                   10
```

<210> SEQ ID NO 50
<211> LENGTH: 27
<212> TYPE: PRT
<213> ORGANISM: Gerbera hybrida

<400> SEQUENCE: 50

```
Lys Ala Val Lys Leu His Leu Arg Glu Gly Gly Leu Thr Phe Gln Leu
1               5                   10                  15

His Arg Asp Val Pro Leu Met Val Ala Lys Asn
            20                  25
```

<210> SEQ ID NO 51
<211> LENGTH: 7
<212> TYPE: PRT
<213> ORGANISM: Pinus sp.

```
<400> SEQUENCE: 51

Ser Thr Thr Thr Pro Asp Leu
  1               5

<210> SEQ ID NO 52
<211> LENGTH: 7
<212> TYPE: PRT
<213> ORGANISM: Pinus sp.

<400> SEQUENCE: 52

Ser Thr Thr Thr Pro Asp Leu
  1               5

<210> SEQ ID NO 53
<211> LENGTH: 7
<212> TYPE: PRT
<213> ORGANISM: Pinus sp.

<400> SEQUENCE: 53

Thr Thr Thr Thr Pro Asp Leu
  1               5

<210> SEQ ID NO 54
<211> LENGTH: 7
<212> TYPE: PRT
<213> ORGANISM: Vitis sp.

<400> SEQUENCE: 54

Thr Thr Ser Gly Val Glu Met
  1               5

<210> SEQ ID NO 55
<211> LENGTH: 7
<212> TYPE: PRT
<213> ORGANISM: Arachis hypogaea

<400> SEQUENCE: 55

Thr Thr Ser Gly Val Ala Leu
  1               5

<210> SEQ ID NO 56
<211> LENGTH: 7
<212> TYPE: PRT
<213> ORGANISM: Pinus sp.

<400> SEQUENCE: 56

Thr Thr Ser Gly Val Asp Met
  1               5

<210> SEQ ID NO 57
<211> LENGTH: 7
<212> TYPE: PRT
<213> ORGANISM: Medicago sativa

<400> SEQUENCE: 57

Thr Thr Ser Gly Val Asp Met
  1               5

<210> SEQ ID NO 58
<211> LENGTH: 5
<212> TYPE: PRT
<213> ORGANISM: Pinus sp.

<400> SEQUENCE: 58
```

```
His Leu Leu Lys Asp
  1               5

<210> SEQ ID NO 59
<211> LENGTH: 5
<212> TYPE: PRT
<213> ORGANISM: Pinus sp.

<400> SEQUENCE: 59

Gln Leu Lys Gly Ala
  1               5

<210> SEQ ID NO 60
<211> LENGTH: 5
<212> TYPE: PRT
<213> ORGANISM: Pinus sp.

<400> SEQUENCE: 60

Gln Leu Lys Gly Ala
  1               5

<210> SEQ ID NO 61
<211> LENGTH: 5
<212> TYPE: PRT
<213> ORGANISM: Vitis sp.

<400> SEQUENCE: 61

His Leu Trp Pro Asn
  1               5

<210> SEQ ID NO 62
<211> LENGTH: 5
<212> TYPE: PRT
<213> ORGANISM: Arachis hypogaea

<400> SEQUENCE: 62

Tyr Leu Asn Lys Ser
  1               5

<210> SEQ ID NO 63
<211> LENGTH: 5
<212> TYPE: PRT
<213> ORGANISM: Pinus sp.

<400> SEQUENCE: 63

His Leu Leu Lys Asp
  1               5

<210> SEQ ID NO 64
<211> LENGTH: 5
<212> TYPE: PRT
<213> ORGANISM: Medicago sativa

<400> SEQUENCE: 64

His Leu Leu Lys Asp
  1               5
```

US 7,285,380 B2

METHODS OF PRODUCING POLYKETIDE SYNTHASE MUTANTS AND COMPOSITIONS AND USES THEREOF

STATEMENT OF GOVERNMENT SUPPORT

This work is supported in part by grant numbers MCB-9982586 from the National Science Foundation. The Government has certain rights to this invention.

FIELD OF THE INVENTION

The present invention relates to methods for producing mutant polyketide synthases, and for altering the activity and/or substrate specificity of putative native and mutant polyketide synthases. The present invention further relates to compositions and uses of mutant polyketide synthases.

BACKGROUND

Advances in molecular biology have allowed the development of biological agents useful in modulating protein or nucleic acid activity or expression, respectively. Many of these advances are based on identifying the primary sequence of the molecule to be modulated. For example, determining the nucleic acid sequence of DNA or RNA allows the development of antisense or ribozyme molecules. Similarly, identifying the primary sequence allows for the identification of sequences that may be useful in creating monoclonal antibodies. However, often the primary sequence of a protein is insufficient to develop therapeutic or diagnostic molecules due to the secondary, tertiary or quartenary structure of the protein from which the primary sequence is obtained. The process of designing potent and specific inhibitors or activators has improved with the arrival of techniques for determining the three-dimensional structure of an enzyme or polypeptide to be modulated.

The phenylpropanoid synthetic pathway in plants produces a class of compounds know as anthocyanins, which are used for a variety of applications. Anthocyanins are involved in pigmentation and protection against UV photodamage, synthesis of anti-microbial phytoalexins, and are flavonoid inducers of *Rhizobium* modulation genes 1-4. As medicinal natural products, the phenylpropanoids exhibit cancer chemopreventive activity, as well as anti-mitotic, estrogenic, anti-malarial, anti-oxidant, and antiasthmatic activities. The benefits of consuming red wine, which contains significant amounts of 3,4',5-trihydroxystilbene (resveratrol) and other phenylpropanoids, highlight the dietary importance of these compounds. Chalcone synthase (CHS), a polyketide synthase, plays an essential role in the biosynthesis of plant phenylpropanoids.

An improvement in the understanding of the structure/function of these enzymes would allow for the exploitation of the synthetic capabilities of known enzymes for production of useful new chemical compounds, or allow for the creation of novel non-native enzymes having new synthetic capabilities. A need exists, therefore, for a detailed understanding of the molecular basis of the chemical reactions involved in polyketide synthesis. The present invention addresses this and related needs.

SUMMARY OF THE INVENTION

In accordance with the present invention there are presented crystalline polyketide synthases and the three-dimensional coordinates derived therefrom. Three-dimensional coordinates have been obtained for an active form of chalcone synthase and several active and inactive mutants thereof, both with and without substrate or substrate analog. Similar results have been obtained for the polyketide synthases stilbene synthase (STS) and pyrone synthase (2-PS).

One aspect of the present invention that is made possible by results described herein is that the three-dimensional properties of polyketide synthase proteins are determined, in particular the three-dimensional properties of the active site. The invention features specific coordinates of at least fourteen α carbon atoms defined for the active site in three-dimensional space. R-groups attached to said α-carbons are defined such that mutants can be made by changing at least one R-group found in the synthase active site. Such mutants may have unique and useful properties. Thus, in another embodiment of the invention, there are provided isolated non-native (e.g., mutant) synthase(s) having at least fourteen active site α-carbons having the structural coordinates disclosed herein (see, for example Table 1) and one or more R-groups other than those found in native polyketide synthase(s).

The three-dimensional coordinates disclosed herein can be employed in a variety of methods. The polyketide synthase used in the crystallization studies disclosed herein is a chalcone synthase derived from *Medicago sataiva* (alfalfa). A large number of proteins have been isolated and sequenced which have primary amino acid sequence similar to that of chalcone synthase, but for which substrate specificity and/or product is unknown. Thus, in another embodiment of the present invention, there are provided methods for altering the activity and/or substrate specificity of a putative polyketide synthase. There are further provided methods for altering the polyketide content of a plant.

Other aspects, embodiments, advantages, and features of the present invention will become apparent from the following specification.

BRIEF DESCRIPTION OF FIGURES

FIG. 6C presents representative sequence alignment of the β1d-β2d region is given with positions 255, 266 and 268 highlighted. The first three sequences (SEQ ID NOS 2-4. respectively in order of appearance) follow a CHS-like cyclization pathway, while the last three (SEQ ID NOS 5-7, respectively in order of appearance) use the STS-cyclization pathway. FIG. prepared with MOLSCRIPT and rendered with POV-Ray.

FIG. 11 shows an amino acid sequence alignment of *P. sylvestris* STS (SEQ ID NO: 8) and *M. sativa* CHS (SEQ ID NO: 10) along with an evolutionary intermediate, *P. sylvestris* CHS (SEQ ID NO: 9).

FIG. 22 shows the aldol cyclization switch region as viewed from the CoA-ginding tunnel, involved in the mechanisms depicted in FIG. 21.

DETAILED DESCRIPTION OF THE INVENTION

Figure 1:
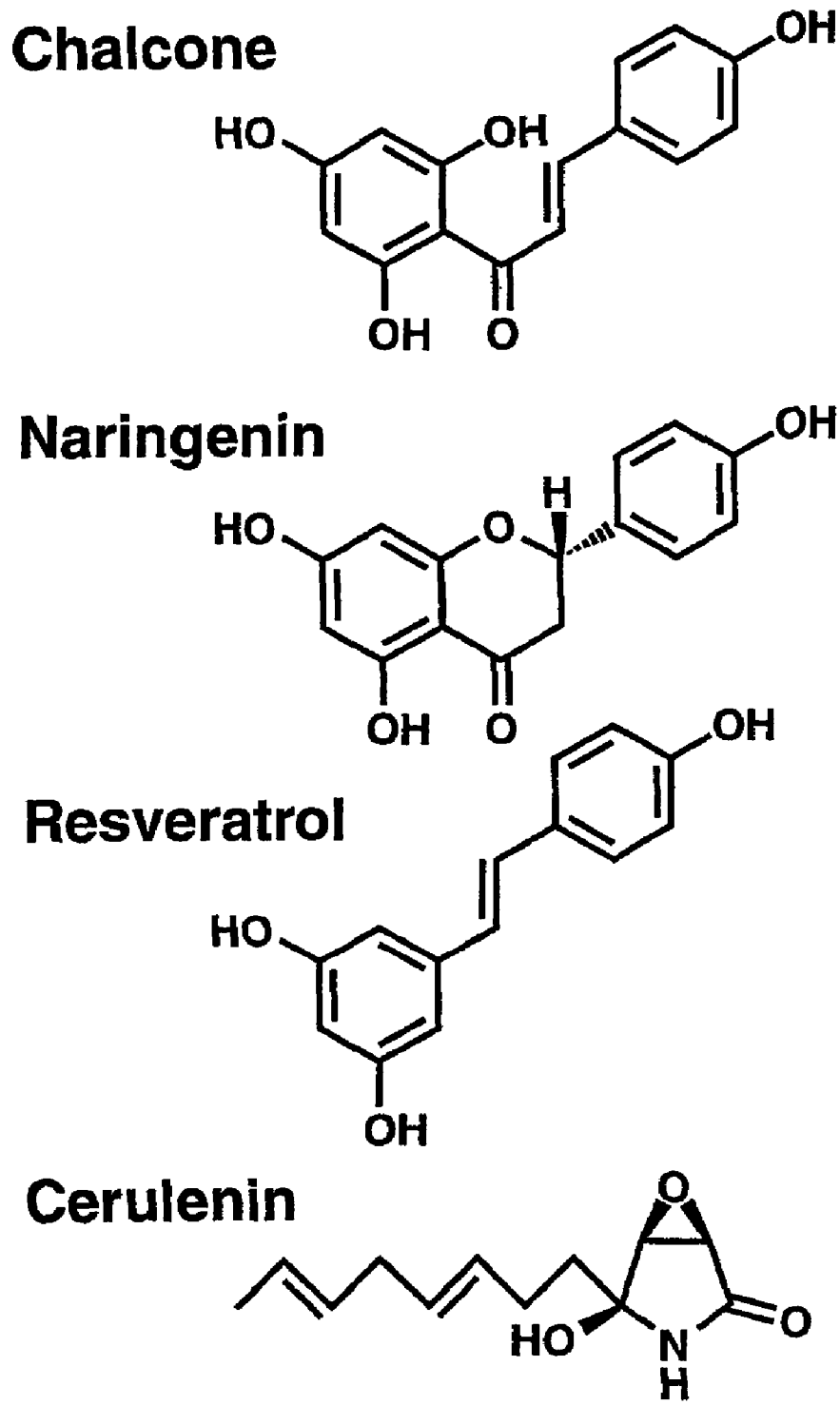
FIG. 1 presents the chemical structures of chalcone, naringenin, resveratrol, and cerulenin.

The phenylpropanoid synthetic pathway in plants produces a class of compounds know as anthocyanins, which are used for a variety of applications. Anthocyanins are involved in pigmentation and protection against UV photodamage, synthesis of anti-microbial phytoalexins, and are flavonoid inducers of *Rhizobium* modulation genes 1-4. As medicinal natural products, the phenylpropanoids exhibit cancer chemopreventive activity, as well as anti-mitotic, estrogenic, anti-malarial, anti-oxidant, and antiasthmatic activities. The benefits of consuming red wine, which contains significant amounts of 3,4',5-trihydroxystilbene (resveratrol) and other phenylpropanoids, highlight the dietary importance of these compounds.

Polyketides are a large class of compounds and include a broad range of antibiotics, immunosuppressants and anti-cancer agents which together account for sales of over $5 billion per year. Polyketides are molecules which are an extremely rich source of bioactivities, including antibiotics (e.g., tetracyclines and erythromycin), anti-cancer agents (e.g., daunomycin), immunosuppressants (e.g., FK506 and rapamycin), and veterinary products (e.g., monensin) and the like. Many polyketides (produced by polyketide synthases) are valuable as therapeutic agents. Polyketide synthases are multifunctional enzymes that catalyze the biosynthesis of a huge variety of carbon chains differing in length and patterns of functionality and cyclization.

Chalcone synthase (CHS), a polyketide synthase, plays an essential role in the biosynthesis of plant phenylpropanoids. CHS supplies 4,2',4',6'-tetrahydroxychalcone (chalcone) to downstream enzymes that synthesize a diverse set of flavonoid phytoalexins and anthocyanin pigments. Synthesis of chalcone by CHS involves the sequential condensation of one p-coumaroyl- and three malonyl-Coenzyme-A (CoA) molecules (Kreuzaler and Hahlbrock, Eur. J. Biochem. 56:205-213, 1975). After initial capture of the p-coumaroyl moiety, each subsequent condensation step begins with decarboxylation of malonyl-CoA at the CHS active site; the resulting acetyl-CoA carbanion then serves as the nucleophile for chain elongation.

Ultimately, these reactions generate a tetraketide intermediate that cyclizes by a Claisen condensation into a hydroxylated aromatic ring system. This mechanism mirrors those of the fatty acid and polyketide synthases but with significant differences. CHS uses CoA-thioesters for shuttling substrates and intermediate polyketides instead of the acyl carrier proteins used by the fatty acid synthases. Also, unlike these enzymes, which function as either multichain or multimodular enzyme complexes catalyzing distinct reactions at different active sites, CHS functions as a unimodular polyketide synthase and carries out a series of decarboxylation, condensation, cyclization, and aromatization reactions at a single active site.

A number of plant and bacterial polyketide synthases related to CHS by sequence identity, including stilbene synthase (STS), bibenzyl synthase (BBS), and acridone synthase (ACS), share a common chemical mechanism, but differ from CHS in their substrate specificity and/or in the stereochemistry of the polyketide cyclization reaction. For example, STS condenses one coumaroyl- and three malonyl-CoA molecules, like CHS, but synthesizes resveratrol through a structurally distinct cyclization intermediate.

While the cloning of over 400 CHS-related genes, and characterization of some of these proteins, provides insight into their biological function, it remains unclear how these enzymes perform multiple decarboxylation and condensation reactions and how they dictate the stereochemistry of the final polyketide cyclization reaction. Furthermore, despite significant advances in the biosynthetic manipulation of structurally complex and biologically important natural products, there remains a lack of structural information on polyketide synthases from any source.

As used herein, "naturally occurring amino acid" and "naturally occurring R-group" includes L-isomers of the twenty amino acids naturally occurring in proteins. Naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, and lysine. Unless specially indicated, all amino acids referred to in this application are in the L-form.

"Unnatural amino acid" and "unnatural R-group" includes amino acids that are not naturally found in proteins. Examples of unnatural amino acids included herein are racemic mixtures of selenocysteine and selenomethionine. In addition, unnatural amino acids include the D or L forms of, for example, nor-leucine, para-nitrophenylalanine, homophenylalanine, para-fluorophenylalanine, 3-amino-2-benzylpropionic acid, homoarginines, D-phenylalanine, and the like.

"R-group" refers to the substituent attached to the α-carbon of an amino acid residue. An R-group is an important determinant of the overall chemical character of an amino acid. There are twenty natural R-groups found in proteins, which make up the twenty naturally occurring amino acids.

"α-carbon" refers to the chiral carbon atom found in an amino acid residue. Typically, four substituents will be covalently bound to said α-carbon including an amine group, a carboxylic acid group, a hydrogen atom, and an R-group. The α-carbon atoms can also be referred to by their crystal structure coordinates as a convenient reference point. Table 1 provides the structural coordinates of α-carbons found in the active site of a polyketide of the present invention.

TABLE 1

| Active Site-Carbon Number | X Position | Y Position | Z Position | Amino Acid (SEQ ID NO: 1) |
| --- | --- | --- | --- | --- |
| 1 | 25.378 | 49.320 | 57.979 | Thr 132 |
| 2 | 26.089 | 45.704 | 56.981 | Ser 133 |
| 3 | 35.423 | 42.296 | 66.622 | Met 137* |
| 4 | 25.212 | 49.977 | 62.196 | Gln 161 |
| 5 | 22.745 | 44.120 | 51.193 | Thr 194 |
| 6 | 19.022 | 42.892 | 54.600 | Thr 197 |
| 7 | 13.850 | 48.144 | 50.791 | Gly 211 |
| 8 | 22.118 | 48.048 | 46.357 | Gly 216 |
| 9 | 13.001 | 54.666 | 59.688 | Ile 254 |
| 10 | 16.434 | 48.819 | 61.334 | Gly 256 |
| 11 | 18.715 | 43.328 | 59.526 | Leu 263 |
| 12 | 13.943 | 47.516 | 57.567 | Phe 265 |
| 13 | 9.252 | 52.715 | 57.456 | Leu 267 |
| 14 | 23.141 | 53.552 | 52.148 | Ser 338 |

*Met 137 from the second monomer

"Positively charged amino acid" and "positively charged R-group" includes any naturally occurring or unnatural amino acid having a side chain which is positively charged under normal physiological conditions. Examples of positively charged, naturally occurring amino acids include arginine, lysine, histidine, and the like.

"Negatively charged amino acid" and "negatively charged R-group" includes any naturally occurring or unnatural amino acid having a side chain which is negatively charged under normal physiological conditions. Examples of negatively charged, naturally occurring amino acids include aspartic acid, glutamic acid, and the like.

"Hydrophobic amino acid" and "hydrophobic R-group" includes any naturally occurring or unnatural amino acid that is relatively insoluble in water. Examples of naturally occurring hydrophobic amino acids are alanine, leucine, isoleucine, valine, proline, phenylalanine, tryptophan, methionine, and the like.

"Hydrophilic amino acid" and "hydrophilic R-group" includes any naturally occurring or unnatural amino acid that is relatively soluble in water. Examples of naturally occurring hydrophilic amino acids include serine, threonine, tyrosine, asparagine, glutamine, cysteine, and the like.

"Mutant" or "mutated synthase" refers to a polyketide synthase polypeptide containing amino acid residues that have been substituted or modified with respect to a wild type polyketide synthase (for example, the alfalfa CHS having the crystal structure coordinates of Protein Data Bank (PDB) Accession No. 1BI5, SEQ ID NO:69). Examples of mutant or mutated synthase polypeptides include those having PDB Accession Nos. 1D6F (SEQ ID NO:69), 1D6I (SEQ ID NO:69), and 1D6H (SEQ ID NO:69) (the content of which are incorporated by reference herein in their entirety). Further examples of mutant or mutated synthase polypeptides are set forth in a set of crystal structure coordinates in Appendix C, the 18×CHS mutant (SEQ ID NO:67). Access to the foregoing information in the Protein Data Bank can be found on the World Wide Web at rscb.org/pdb. The Protein Data Bank is operated by the Research Collaboratory for Structural Bioinformatics (RCSB).

The R-groups of known isolated polyketide synthases can be readily determined by consulting sequence databases well known in the art, such as, for example, Genbank. Additional R-groups found inside and/or outside of the active site may or may not be the same. R-groups may be a natural R-group, unnatural R-group, hydrophobic R-group, hydrophilic R-group, positively charged R-group, negatively charged R-group, and the like. The term "mutant" refers to the configuration of R-groups within the active site and/or groups involved in second-tier interactions, for example those resulting in the alteration of CHS native activity.

"Non-native" or "non-native synthase" refers to synthase proteins that are not found in nature, whether isolated or not. A non-native synthase may, for example, be a mutated synthase (see, for example, PDB Accession Nos. 1D6F, 1D6I, 1D6H and Appendix C).

"Native" or "native synthase" or "wild type synthase" refers to synthase proteins that are produced in nature, e.g., are not mutants (see, for example, PDB Accession Nos. 1BI5 (CHS), 1EE0 (2-PS)).

"Isolated" refers to a protein or nucleic acid that has been identified and separated from its natural environment. Contaminant components of its natural environment may include enzymes, hormones, and other proteinaceous or non-proteinaceous solutes. In one embodiment, the isolated molecule, in the case of a protein, will be purified to a degree sufficient to obtain at least 15 residues of N-terminal or internal amino acid sequence or to homogeneity by SDS-PAGE under reducing or non-reducing conditions using Coomassie blue or silver stain. In the case of a nucleic acid the isolated molecule will preferably be purified to a degree sufficient to obtain a nucleic acid sequence using standard sequencing methods.

"Degenerate variations thereof" refers to changing a gene sequence using the degenerate nature of the genetic code to encode proteins having the same amino acid sequence yet having a different gene sequence. For example, polyketide synthases of the present invention are based on amino acid sequences. Degenerate gene variations thereof can be made encoding the same protein due to the plasticity of the genetic code, as described herein.

"Expression" refers to transcription of a gene or nucleic acid sequence, stable accumulation of nucleic acid, and the translation of that nucleic acid to a polypeptide sequence. Expression of genes also involves transcription of the gene to make RNA, processing of RNA into mRNA in eukaryotic systems, and translation of mRNA into proteins. It is not necessary for the genes to integrate into the genome of a cell in order to achieve expression. This definition in no way limits expression to a particular system or to being confined to cells or a particular cell type and is meant to include cellular, transient, in vitro, in vivo, and viral expression systems in both prokaryotic, eukaryotic cells, and the like.

"Foreign" or "heterologous" genes refers to a gene encoding a protein whose exact amino acid sequence is not normally found in the host cell.

"Promoter" and "promoter regulatory element", and the like, refers to a nucleotide sequence element within a nucleic acid fragment or gene that controls the expression of that gene. These can also include expression control sequences. Promoter regulatory elements, and the like, from a variety of sources can be used efficiently to promote gene expression. Promoter regulatory elements are meant to include constitutive, tissue-specific, developmental-specific, inducible, subgenomic promoters, and the like. Promoter regulatory elements may also include certain enhancer elements or silencing elements that improve or regulate transcriptional efficiency. Promoter regulatory elements are recognized by RNA polymerases, promote the binding thereof, and facilitate RNA transcription.

A polypeptide is a chain of amino acids, regardless of length or post-translational modification (e.g., glycosylation or phosphorylation). A polypeptide or protein refers to a polymer in which the monomers are amino acid residues, which are joined together through amide bonds. When the amino acids are alpha-amino acids, either the L-optical isomer or the D-optical isomer can be used, the L-isomers being typical. A synthase polypeptide of the invention is intended to encompass an amino acid sequence as set forth in SEQ ID NO:1 (see Table 2), or SEQ ID NO:1 having one or more mutations. Mutations include deletions and additions of amino acid residues, and substitutions of one amino acid residue for another. For example substitutions include: D96A (where D at position 96 of a wild type CHS is changed to A), V98L, V99A, V100M, T131S, S133T, G134T, V135P, M137L, Y157V, M158G, M159V, Y160F, C164A, Q165H, D255G, H257K, L258V, H266Q, L268K, K269G, D270A, G273D, H303Q, N336A, mutants, variants and conservative substitutions thereof comprising L- or D-amino acids and include modified sequences such as glycoproteins.

TABLE 2

(SEQ ID NO:1)
MVSVSEIRKA QRAEGPATIL AIGTANPANC VEQSTYPDFY FKITNSEHKT ELKEKFQRMC

DKSMIKRRYM YLTEEILKEN PNVCEYMAPS LDARQDMVVV EVPRLGKEAA VKAIKEWGQP

TABLE 2-continued

```
KSKITHLIVC  TTSGVDMPGA  DYQLTKLLGL  RPYVKRYMMY  QQGCFAGGTV  LRLAKDLAEN

NKGARVLVVC  SEVTAVTFRG  PSDTHLDSLV  GQALFGDGAA  ALIVGSDPVP  EIEKPIFEMV

WTAQTIAPDS  EGAIDGHLRE  AGLTFHLLKD  VPGIVSKNIT  KALVEAFEPL  GISDYNSIFW

IAHPGGPAIL  DQVEQKLALK  PEKMNATREV  LSEYGNMSSA  CVLFILDEMR  KKSTQNGLKT

TGEGLEWGVL  FGFGPGLTIE  TVVLRSVAI
```

Accordingly, the polypeptides of the invention are intended to cover naturally occurring proteins, as well as those which are recombinantly or synthetically synthesized. Polypeptide or protein fragments are also encompassed by the invention. Fragments can have the same or substantially the same amino acid sequence as the naturally occurring protein. A polypeptide or peptide having substantially the same sequence means that an amino acid sequence is largely, but not entirely, the same, but retains a functional activity of the sequence to which it is related. In general polypeptides of the invention include peptides, or full-length protein, that contains substitutions, deletions, or insertions into the protein backbone, that would still have an approximately 70%-90% homology to the original protein over the corresponding portion. A yet greater degree of departure from homology is allowed if like-amino acids, i.e. conservative amino acid substitutions, do not count as a change in the sequence.

A polypeptide may be substantially related but for a conservative variation, such polypeptides being encompassed by the invention. A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine, and the like. The term "conservative variation" also includes the use of a substituted amino acid in place of an unsubstituted parent amino acid provided that antibodies raised to the substituted polypeptide also immunoreact with the unsubstituted polypeptide.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra-amino acids, glycosylation sites, cytosine for specific disulfide bridge formation. The modified peptides can be chemically synthesized, or the isolated gene can be site-directed mutagenized, or a synthetic gene can be synthesized and expressed in bacteria, yeast, baculovirus, tissue culture and so on.

Chalcone synthase polypeptides of the invention include synthase polypeptides from plants, prokaryotes, eukaryotes, including, for example, invertebrates, mammals and humans and include sequences as set forth in SEQ ID NO:1, as well as sequences that have at least 50% homology, preferably at least 60% homology, more preferably at least 70% homology to the sequence of SEQ ID NO:1, fragments, variants, or conservative substitutions of any of the foregoing sequences.

The term "variant" refers to polypeptides modified at one or more amino acid residues yet still retain the biological activity of a synthase polypeptide. Variants can be produced by any number of means known in the art, including, for example, methods such as, for example, error-prone PCR, shuffling, oligonucleotide-directed mutagenesis, assembly PCR, sexual PCR mutagenesis, and the like, as well as any combination thereof.

By "substantially identical" is meant a polypeptide or nucleic acid exhibiting at least 50%, preferably 85%, more preferably 90%, and most preferably 95% homology to a reference amino acid or nucleic acid sequence.

Sequence homology and identity are often measured using sequence analysis software (e.g., Sequence Analysis Software Package of the Genetics Computer Group, University of Wisconsin Biotechnology Center, 1710 University Avenue, Madison, Wis. 53705). The term "identity" in the context of two or more nucleic acids or polypeptide sequences, refers to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. The term "homology" in the context of two or more nucleic acids or polypeptide sequences, refers to two or more sequences or subsequences that are homologous or have a specified percentage of amino acid residues or nucleotides that are homologous when compared and aligned for maximum correspondence over a comparison window or designated region as measured using any number of sequence comparison algorithms or by manual alignment and visual inspection. Programs as mentioned above allow for amino acid substitutions with similar amino acids matches by assigning degrees of homology to determine a degree of homology between the sequences being compared.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated.

Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol 48:443, 1970, by the search for similarity method of Person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fnstensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (J. Roach, on the World Wide Web at weber.u.Washington.edu/~roach/human_genome_progress2.html) (Gibbs, 1995). At least twenty-one other genomes have already been sequenced, including, for example, *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Several databases containing genomic information annotated with some functional information are maintained by different organization, and are accessible via the internet, for example, on the World Wide Web at tigr.org/tdb, genetics.wisc.edu, genome-www.stanford.edu, hiv-web.lanl.gov, ncbi.nlm.nih.gov, cbi.ac.uk, Pasteur.fr/other/biology, and genome.wi.mlt.edu.

One example of a useful algorithm is BLAST and BLAST 2.0algorithms, which are described in Altschul et al., Nuc. Acids Res. 25:33 89-3402, 1977, and Altschul et al., J. Mol. Biol. 215:403-410, 1990, respectively. Software for performing BLAST analyses is publicly available through the National Center for Biotechnology Information available on the World Wide Web at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, $M=5$, $N=-4$ and a comparison of both strands. For amino acid sequences, the BLASTP program uses as defaults a wordlength of 3, and expectations (E) of 10, and the BLOSUM62 scoring matrix (see Henikoff& Henikoff, Proc. Natl. Acad. Sci. USA 89:10915, 1989) alignments (B) of 50, expectation (E) of 10, $M=5$, $N=-4$, and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet etal., Science 256:1443-1445, 1992; Henikoff and Henikoff, Proteins 17:49-61, 1993). Less preferably,the PAM or PAM250 matrices may also be used (see, e.g., Schwartz and Dayhoff, eds., 1978, *Matrices for Detecting Distance Relationships. Atlas of Protein Sequence and Structure*, Washington: National Biomedical Research Foundation). BLAST programs are accessible through the U.S. National Library of Medicine, e.g., on the World Wide Web at ncbi.nlm.nih.gov.

The parameters used with the above algorithms may be adapted depending on the sequence length and degree of homology studied. In some embodiments, the parameters may be the default parameters used by the algorithms in the absence of instructions from the user.

By a "substantially pure polypeptide" is meant a synthase polypeptide (e.g., a chalcone synthase) which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, synthase polypeptide. A substantially pure synthase polypeptide may be obtained, for example, by extraction from a natural source; by expression of a recombinant nucleic acid encoding an synthase polypeptide; or by chemically synthesizing the protein. Purity can be measured by any appropriate method (e.g., column chromatography, polyacrylamide gel electrophoresis, or by HPLC analysis).

One aspect of the invention resides in obtaining crystals of the synthase polypeptide, chalcone synthase, of sufficient quality to determine the three dimensional (tertiary) structure of the protein by X-ray diffraction methods. The knowledge obtained concerning the three-dimensional structure of chalcone synthase can be used in the determination of the three dimensional structure of other synthase polypeptides in the polyketide synthesis pathway. The structural coordinates of chalcone synthase can be used to develop new polyketide synthesis enzymes or synthase inhibitors using various computer models. Based on the structural coordinates of the chalcone synthase polypeptide (e.g., the three dimensional protein structure), as described herein, novel polyketide synthases can be engineered. In addition, small molecules which mimic or are capable of interacting with a functional domain of a synthase molecule, can be designed and synthesized to modulate chalcone synthase, pyrone synthase, and other polyketide synthase biological functions as well as the biological functions of other polyketide synthases. Accordingly, in one embodiment, the invention provides a method of "rational" enzyme or drug design. Another approach to "rational" enzyme or drug design is based on a lead compound that is discovered using high throughput screens; the lead compound is further modified based on a crystal structure of the binding regions of the molecule in question. Accordingly, another aspect of the invention is to provide related protein sequences or material which is a starting material in the rational design of new synthases or drugs which lead to the synthesis of new polyketides or modify the polyketide synthesis pathway.

"Active Site" refers to a site in a synthase defined by amino acid residues that interact with substrate and facilitate a biosynthetic reaction that allows one or more products to be produced. For example, an active site is comprised of α-carbon atoms that are indirectly linked via peptide bonds and have the structural coordinates disclosed in Table 1±2.3 angstroms. Other active site amino acids for chalcone synthase include C164, H303, and N336. The position in three-dimensional space of an α-carbon at the active site of a synthase and of R-groups associated therewith can be determined using techniques such as three-dimensional modeling, X-ray crystallography, and/or techniques associated therewith. Active sites can be specified by a set of amino acid residues. Other residues can play a reole in substrate specificity and enzyme activity by modulating size, shape, charge, and the like of the active site. In addition, second tier residues may also modulate the specificity and/or activity of the enzyme.

In CHS, at least five areas of primary sequence containing residues that play a role modulating enzyme specificity and/or activity are found. Each area contains a total of about four to about fifteen amino acid residues. Within each area, about three to six, and preferably four or five amino acid residues that interact with substrate are found. Residues may be directly within or lining the active site to modulate specificity and/or activity. Residues may also be involved in second tier interactions that modulate the specificity and/or activity of the active site, without being physically located within the active site. Various mutants of these residues have been prepared to evaluate the role of these residues in CHS function and activity, including substrate specificity and product formation. Table 3 presents some of the mutations of CHS that have been made to affect CHS function.

TABLE 3

Mutants of CHS

| Mutant Name | Mutant Code | Mutations relative to alfalfa CHS |
| --- | --- | --- |
| A4 | 0002 | A4 (L268K, K269G, D270A, G273D) |
| 14B (=6xCHS) | 1200 | A1 (V98L,) |
|  |  | A2 (T131S, S133T, G134T, V135P, M137L) |
| 2B | 2200 | A1 (D96A, V98L, V99A, V100M) |
|  |  | A2 (T131S, S133T, G134T, V135P, M137L) |
| 16B (=8xCHS) | 1210 | A1 (V98L,) |
|  |  | A2 (T131S, S133T, G134T, V135P, M137L) |
|  |  | A3 (M158G, Y160F) |
| 4B | 2211 | A1 (D96A, V98L, V99A, V100M) |
|  |  | A2 (T131S, S133T, G134T, V135P, M137L) |
|  |  | A3 (M158G, Y160F) |
|  |  | A4 (K269G) |
| 6B | 1220 | A1 (V98L,) |
|  |  | A2 (T131S, S133T, G134T, V135P, M137L) |
|  |  | A3 (Y157V, M158G, M159V, Y160F, Q165H); |
| 18xCHS | 2222 | A1 (D96A, V98L, V99A, V100M) |
|  |  | A2 (T131S, S133T, G134T, V135P, M137L) |
|  |  | A3 (Y157V, M158G, M159V, Y160F, Q165H) |
|  |  | A4 (L268K, K269G, D270A, G273D) |
| 22xCHS | 2222 + Area B1 | A1 (D96A, V98L, V99A, V100M) |
|  |  | A2 (T131S, S133T, G134T, V135P, M137L) |
|  |  | A3 (Y157V, M158G, M159V, Y160F, Q165H) |
|  |  | B1 (D255G, H257K, L258V, H266Q) |
|  |  | A4 (L268K, K269G, D270A, G273D) |

Figure 15:
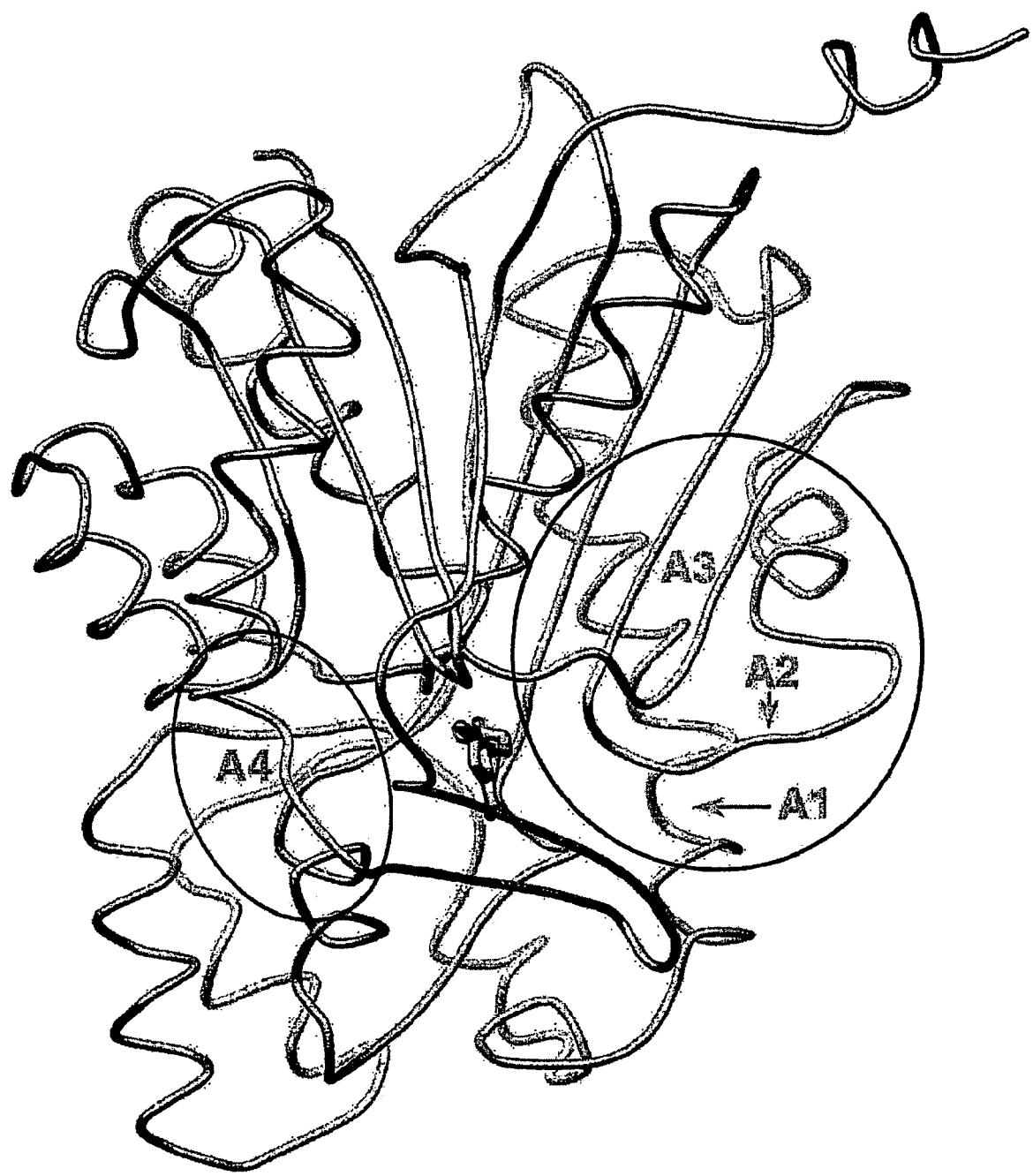
FIG. 15 shows the crystalline structure of CHS. Circled areas A1 to A4 represent regions in which mutations result in the conversion of CHS activity to STS-like activity. The 18×CHS mutant contains mutations in these regions.

A polyketide synthase can be divided into regional areas A1-A4 and B1. Areas A1 and A3 flank area A2, from below and above, respectively (see FIG. 15). Both areas seem to have importance mainly in regards to compensatory steric changes which allow a proline induced kink in area A2 relative to the CHS position. The backbone C-alpha traces of A1 and A3 do not actually vary much from CHS to STS, but length of indicated residues does. In area A1, amino acids involved in the modulation of enzyme specificity and/or activity for chalcone synthase include D96, V98, V99 and V100. In area A3, such amino acids include Y157, M158, M159, Y160 and Q165. Mutations at V98 and V99 in area A1, and at M158 and Y160 in area A3 appear especially important for modifying activity.

Area A2 appears to be the most important area, and is located at the dimer interface, directly between the active site cavities of each monomer. In area A2 amino acids involved in the modulation of enzyme specificity and/or activity include T131, S133, G134, V135 and M137. Mutations at G134 and V135 appear especially important for modifying activity.

Area A4 is located on the outside of the protein, near the active site entrance. A4 mutations made to wild type CHS seems to have no effect on cyclization specificity, indicating that this area is not important to the conversion of activity seen in the certain mutants, for example, the 18xCHS mutant. However, this area may be important in the improvements to conversion seen with the addition of four more mutants (at B1, see FIG. 16 and below) in the 22× CHS mutant. In area A4, amino acids involved in the modulation of enzyme specificity and/or activity include L268, K269, D270 and G273.

Area B1 flanks A4 and bridges the gap between A1-A3 and A4. In area B1, amino acids involved in the modulation of enzyme specificity and/or activity include D255, H257L258 and H266. These mutations are in an area predicted in by Ferrer, et al. and are important for cyclization specificity.

"Altered substrate specificity" or "altered activity" includes a change in the ability of a mutant synthase to use a particular substrate and/or produce a polyketide product as compared to a non-mutated synthase. Altered substrate specificity may include the ability of a synthase to exhibit different enzymatic parameters relative to a non-mutated synthase ($K_m$, $V_{max}$, etc), use different substrates, and/or produce products that are different from those of known synthases.

"Structure coordinates" refers to Cartesian coordinates (x, y, and z positions) derived from mathematical equations involving Fourier synthesis as determined from patterns obtained via diffraction of a monochromatic beam of X-rays by the atoms (scattering centers) of a polyketide synthase molecule in crystal form. Diffraction data are used to calculate electron density maps of repeating protein units in the crystal (unit cell). Electron density maps are used to establish the positions of individual atoms within a crystal's unit cell. The term "crystal structure coordinates" refers to mathematical coordinates derived from mathematical equations related to the patterns obtained on diffraction of a monochromatic beam of X-rays by the atoms (scattering centers) of a synthase polypeptide (e.g., a chalcone synthase protein molecule) in crystal form. The diffraction data are used to calculate an electron density map of the repeating unit of the crystal. The electron density maps are used to establish the positions of the individual atoms within the unit cell of the crystal. The crystal structure coordinates of a synthase can be obtained from crystals and can also be obtained by means of computational analysis.

The term "selenomethionine substitution" refers to the method of producing a chemically modified form of the crystal of a synthase (e.g., a chalcone synthase). The synthase protein is expressed by bacteria in media that is depleted in methionine and supplement with selenomethionine. Selenium is thereby incorporated into the crystal in place of methionine sulfurs. The location(s) of selenium are determined by X-ray diffraction analysis of the crystal. This information is used to generate the phase information used to construct a three-dimensional structure of the protein.

"Heavy atom derivatization" refers to a method of producing a chemically modified form of a synthase crystal. In practice, a crystal is soaked in a solution containing heavy atom salts or organometallic compounds, e.g., lead chloride, gold thiomalate, thirerosal, uranyl acetate, and the like, which can diffuse through the crystal and bind to the protein's surface. Locations of the bound heavy atoms can be determined by X-ray diffraction analysis of the soaked crystal. This information is then used to construct phase information which can then be used to construct three-dimensional structures of the enzyme as described in Blundel, T. L., and Johnson, N. L., Protein Crystallography, Academic Press (1976), which is incorporated by reference herein.

"Unit cell" refers to a basic parallelepiped shaped block. Regular assembly of such blocks may construct the entire volume of a crystal. Each unit cell comprises a complete representation of the unit pattern, the repetition of which builds up the crystal.

"Mutagenesis" refers to the changing of one R-group for another as defined herein. This can be most easily performed by changing the coding sequence of the nucleic acid encoding the amino acid residue. In the context of the present invention, mutagenesis does not change the carbon coordinates beyond the limits defined herein.

"Space Group" refers to the arrangement of symmetry elements within a crystal.

"Molecular replacement" refers to generating a preliminary model of a polyketide synthase whose structural coordinates are unknown, by orienting and positioning a molecule whose structural coordinates are known within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This in turn can be subject to any of the several forms of refinement to provide a final, accurate structure of the unknown crystal (Lattman, E., 1985, in Methods in Enzymology, 11 5.55-77; Rossmann, M G., ed., "The Molecular Replacement Method" 1972, Int, Sci. Rev. Ser., No. 13, Gordon & Breach, New York). Using structure coordinates of the polyketide synthase provided herein (see e.g., PDB Accession Numbers) molecular replacement may be used to determine the structural coordinates of a crystalline mutant, homologue, or a different crystal form of polyketide synthase.

A "synthase" or a "polyketide synthase" includes any one of a family of enzymes that catalyze the formation of polyketide compounds. Polyketide synthases are generally homodimers, with each monomer being enzymatically acitve.

"Substrate" refers to the Coenzyme-A (CoA) thioesters that are acted on by the polyketide synthases and mutants thereof disclosed herein, such as malonyl-CoA, coumaroyl-CoA, hexamoyl-CoA, ACP or NAC thioesters and the like.

The present invention relates to crystallized polyketide synthases and mutants thereof from which the position of specific α-carbon atoms and R-groups associated therewith comprising the active site can be determined in three-dimensional space. The invention also relates to structural coordinates of said polyketide synthases, use of said structural coordinates to develop structural information related to polyketide synthase homologues, mutants, and the like, and to crystal forms of such synthases. Furthermore, the invention, as disclosed herein, provides a method whereby said α-carbon structural coordinates specifically determined for atoms comprising the active site of said synthase, as shown in Table 1 and including C164, H303, and N336, can be used to develop synthases wherein R-groups associated with active site α-carbon atoms are different from the R-groups found in native CHS, e.g., are mutant synthases. In addition, the present invention provides for production of mutant polyketide synthases based on the structural information of synthases (and provided herein) and for use of said mutant synthases to make a variety of polyketide compounds using a variety of substrates (as described in PCT Application US00/20674, filed Jul. 27, 2000, incorporated by reference in its entirety herein). The present invention also provides methods of producing novel mutant polyketide synthases by comparing the crystal structures of two different polyketide synthases.

The present invention further provides, for the first time, crystals of several polyketide synthases, as exemplified by chalcone synthase (CHS; PDB Accession No. 1B15, SEQ ID NO:69), stilbene synthase (STS; *Pinus sylvestris*, pine—Appendix A, SEQ ID NO:65; and *Arachis hypogaea*, peanut—Appendix B, SEQ ID NO:66), and pyrone synthase (2-PS; PDB Accession No. 1EE0, SEQ ID NO:68). Also provided are coordinates for crystals which are grown in the presence and absence of substrate, substrate analogues, and products, thus allowing definition of the structural or atomic coordinates associated therewith. Said structural coordinates allow determination of the carbon atoms comprising the active site, R-groups associated therewith, and the interaction of said α-carbons and said R-groups with each other. For example, Table 4 identifies various substrates and products that were grown with chalcone synthase as well as their PDB accession numbers, all of which are incorporated by reference herein in their entirety.

TABLE 4

| Complex | PDB Accession No. | (SEQ ID NO:) |
|---|---|---|
| CHS-coA complex | 1BQ6 | (SEQ ID NO: 69) |
| CHS-malonyl-CoA complex | 1CML | (SEQ ID NO: 69) |
| CHS-hexanoyl-CoA complex | 1CHW | (SEQ ID NO: 69) |
| CHS-naringenin complex | 1CGK | (SEQ ID NO: 69) |
| CHS-resveratrol complex | 1CGZ | (SEQ ID NO: 69) |

The crystals of the present invention belong to the tetragonal space group. The unit cell dimensions vary by a few angstroms between crystals but on average belong to the space groups with unit cell dimensions as in Table 5.

TABLE 5

Crystals of Polyketide Synthases

| Crystal | Space Group | Unit Cell Dimensions | | | | | |
|---|---|---|---|---|---|---|---|
| | | a (Å) | b (Å) | c (Å) | α (°) | β (°) | γ (°) |
| CHS (alfalfa) (SEQ ID NO: 1) | P 32 2 1 | 97.54 | 97.54 | 65.52 | 90.00 | 90.00 | 120.00 |
| STS (pine) (SEQ ID NO: 65) | P2 (1) | 57.221 | 361.291 | 57.317 | 90.00 | 98.39 | 90.00 |
| STS (peanut) (SEQ ID NO: 66) | P2 (1) | 74.348 | 101.747 | 113.609 | 90.00 | 108.84 | 90.00 |
| 2-PS (SEQ ID NO: 68) | P 31 2 1 | 83.41 | 83.41 | 240.62 | 90.00 | 90.00 | 120.00 |
| 18xCHS (SEQ ID NO: 67) | P2 (1) | 71.638 | 59.753 | 82.539 | 90.00 | 108.166 | 90.00 |

Crystal structures are preferably obtained at a resolution of about 1.56 angstroms to about 3 angstroms for a polyketide synthase in the presence and in the absence of bound substrate or substrate analog. Coordinates for a polyketide synthase in the absence of a substrate bound in the active site have been deposited at the Protein Data Bank, accession number 1BI5. Those skilled in the art understand that a set of structure coordinates determined by X-ray crystallography is not without standard error. Therefore, for the purpose of this invention, any set of structure coordinates wherein the active site α-carbons of a polyketide synthase, synthase homologue, or mutants thereof, have a root mean square deviation less than ±2.3 angstroms when superimposed using the structural coordinates listed in Table 1 and PDB Accession No. 1BI5, shall be considered identical.

Figure 2:
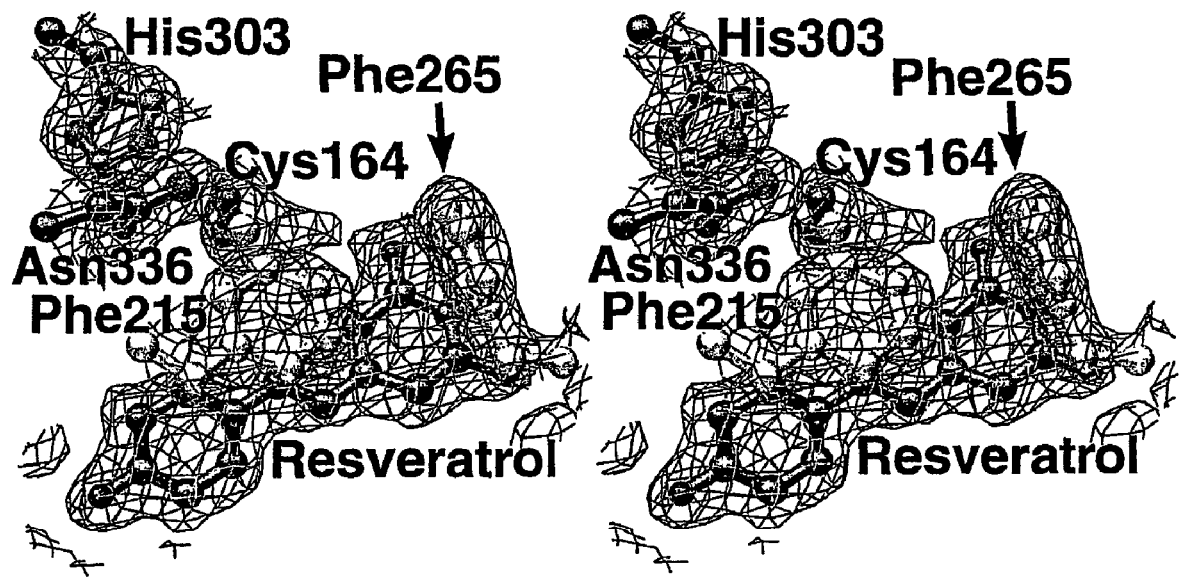
FIG. 2 presents final SIGMAA-weighted 2Fo-Fc electron density map of the CHS-resveratrol complex in the vicinity of the resveratrol binding site. The map is contoured at 1σ.
Figure 3:
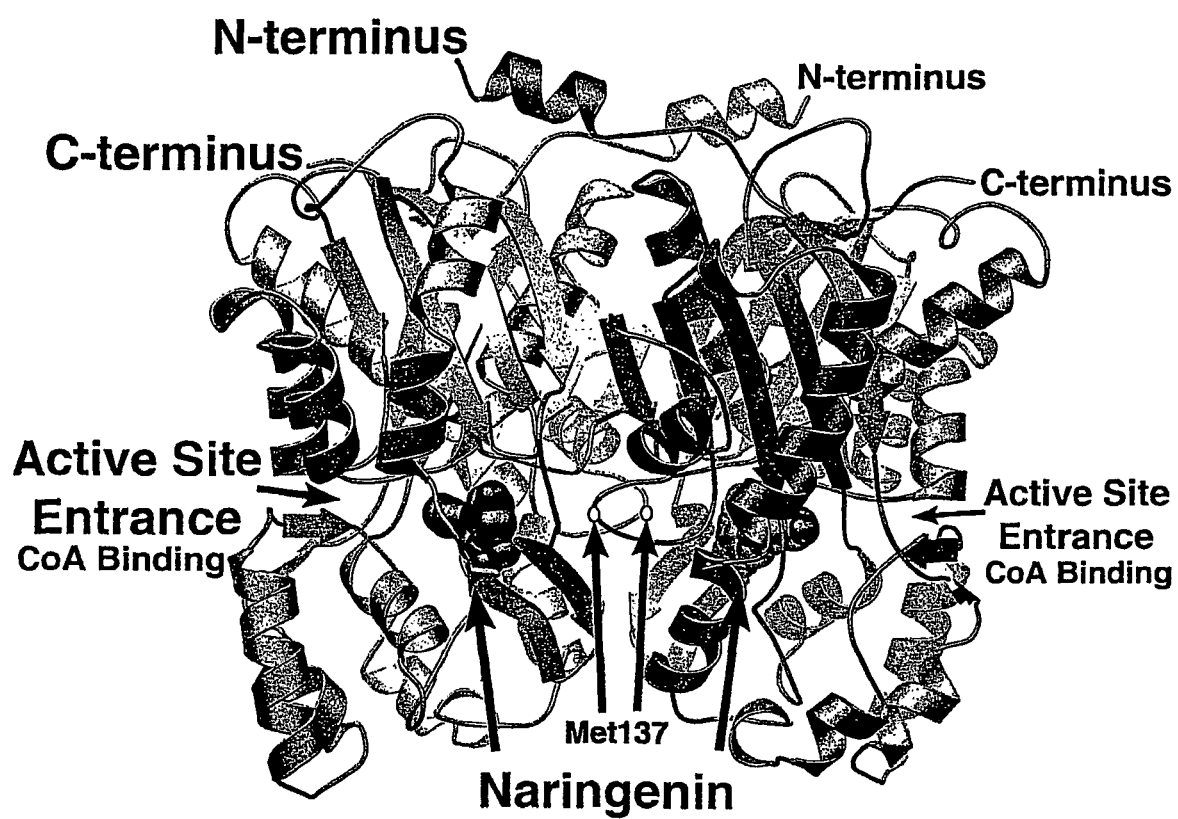
FIG. 3 shows a ribbon representation of the CHS homodimer. The approximate alpha carbon positions of Met 137 from each of the monomers are labeled accordingly. Naringenin completely fills the coumaroyl-binding and cyclization pockets while the CoA binding tunnels are highlighted by black arrows. Produced with MOLSCRIPT and rendered with POV-Ray.
Figure 4:
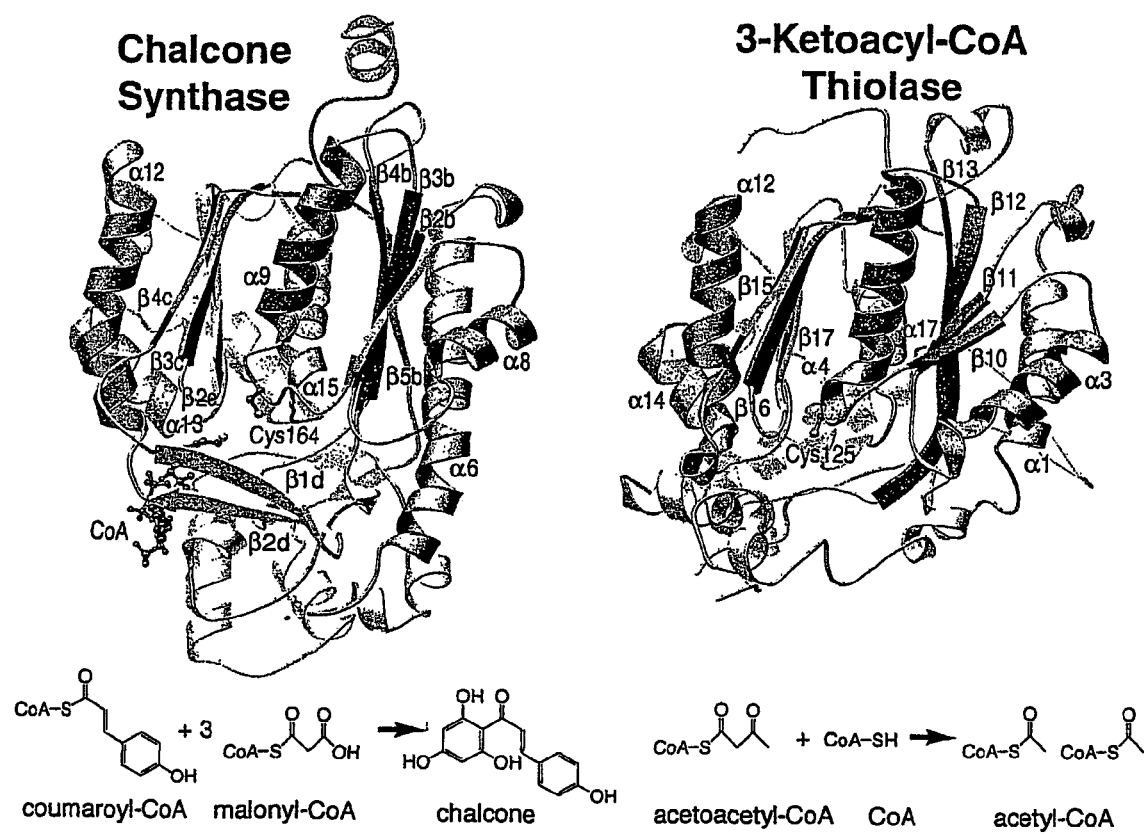
FIG. 4 shows a comparison of chalcone synthase and 3-ketoacyl-CoA thiolase. Ribbon view of the CHS monomer is oriented perpendicular to the dimer interface. The active site cysteine (Cys 164) and the location of bound CoA are rendered as ball and stick models. In addition, strands β1d and β2d of the cyclization pocket are noted. The reaction catalyzed by CHS is illustrated with the coumaroyl- and malonyl-derived portions of chalcone, respectively. The thiolase monomer is depicted in the same orientation as CHS with the Active site cysteine (Cys 125) modeled and the reaction of thiolase as indicated. Figure prepared with MOLSCRIPT and rendered with POV-Ray.
Figure 5A:
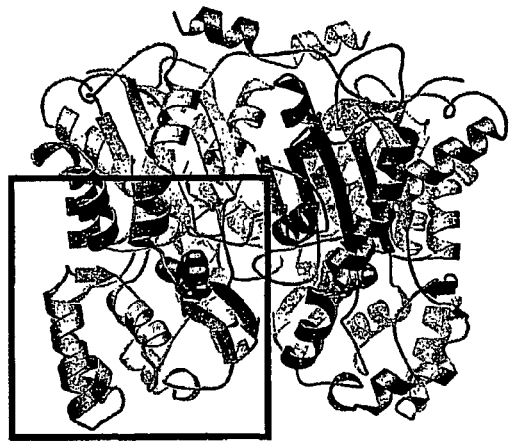
FIG. 5 collectively shows structures of CHS-Acyl-CoA complexes. The ribbon diagram in panel FIG. 5A (on the top left) is the same as FIG. 3. The CoA binding region depicted in stereo is bounded by a black box in the upper ribbon diagram. Close-up stereoviews of the $C_{164}S$ mutant CoA binding region for the malonyl- and hexanoyl-CoA complexes are depicted in FIGS. 5B and 5C, respectively. This mutant retains decarboxylation activity and an acetyl-CoA complex is observed crystallographically for the malonyl-CoA complex. In each complex, placement of the Met 137 loop originating from the dyad-related molecule spatially defines one wall of the cyclization pocket. Hydrogen bonds are depicted as spheres. Figure prepared with MOLSCRIPT and rendered with POV-Ray.
Figure 5B:
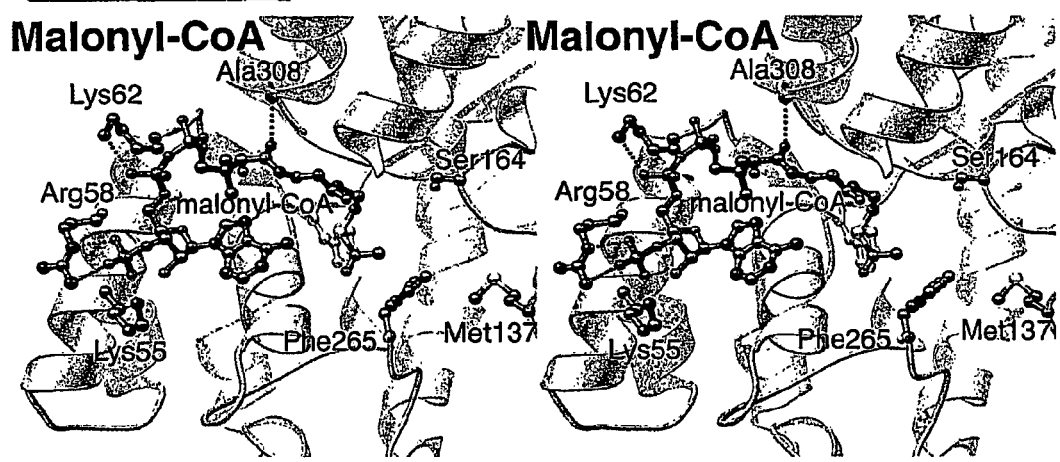
Figure 5C:
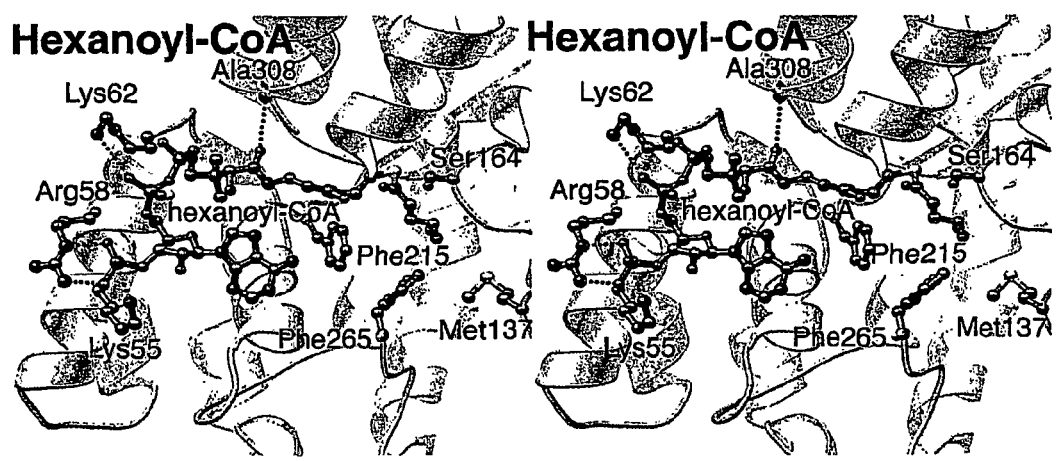

A schematic representation of the three-dimensional shape of a CHS homodimer is shown in FIG. 2a, which was prepared by MOLSCRIPT (Kraulis, J. Appl. Crystallogr. 24:946-950, 1991). CHS functions as a homodimer of two 42 kDa polypeptides. The structure of CHS reveals that the enzyme forms a symmetric dimer with each monomer related by a 2-fold crystallographic axis. The dimer interface buries approximately 1580 angstroms with interactions occurring along a fairly flat surface. Two distinct structural features delineate the ends of this interface. First, the N-terminal helix of monomer A entwines with the corresponding helix of monomer B. Second, a tight loop containing a cis-peptide bond between $Met_{137}$ and $Pro_{138}$ exposes the methionine sidechain as a knob on the monomer surface. Across the interface, $Met_{137}$ protrudes into a hole found in the surface of the adjoining monomer to form part of the cyclization pocket (discussed below).

The CHS homodimer contains two functionally independent active sites (Tropf, et al, J. Biol. Chem. 270:7922-7928, 1995). Consistent with this information, bound CoA thioesters and product analogs occupy both active sites of the homodimer in the CHS complex structures. These structures identify the location of the active site at the cleft between the upper and lower domains of each monomer. Each active site consists almost entirely of residues from a single monomer, with $Met_{137}$ from the adjoining monomer being the only exception. A detailed description of the active site structure is presented in the Examples section, below.

An isolated, polyketide synthase of the invention comprises at least fourteen active site α-carbons having the structural coordinates of Table 1±2.3 angstroms. The active site α-carbons of Table 1 generally are not all contiguous, i.e., are not adjacent to one another in the primary amino acid sequence of a polyketide synthase due to intervening amino acid residues between various active site α-carbons. Nevertheless, it should be appreciated that certain active site α-carbons can be adjacent to one another in some instances. Active site α-carbons are numbered in Table 1 for convenience only and may be situated in any suitable order in the primary amino acid sequence that achieves the structural coordinates given in Table 1.

An appropriate combination of R-groups, linked to active site α-carbons, can facilitate the formation of one or more desired reaction products. The combination of R-groups selected for use in a synthase can be any combination other than the ordered arrangements of R-groups found in known native isolated polyketide synthases. Typically, R-groups found on active site α-carbons are those found in naturally occurring amino acids. In some embodiments, however, R-groups other than those found in naturally occurring amino acids can be used.

The present invention permits the use of molecular design techniques to design, select, and synthesize mutant polyketide synthases that produce different and/or novel polyketide compounds using the same substrates. Mutant proteins of the present invention and nucleic acids encoding the same can be designed by genetic manipulation based on structural information about polyketide synthases. For example, one or more R-groups associated with the active site α-carbon atoms of CHS can be changed by altering the nucleotide sequence of the corresponding CHS gene, thus making one or more mutant polyketide synthases. Such genetic manipulations can be guided by structural information concerning the R-groups found in the active site α-carbons when substrate is bound to the protein upon crystallization. Alternatively, mutant polyketide syntases can be prepared by standard protocols for polypeptide synthesis as is well known in the art.

Mutant proteins of the present invention may be prepared in a number of ways available to the skilled artisan. For example, the gene encoding wild-type CHS may be mutated at those sites identified herein as corresponding to amino acid residues identified in the active site by means currently available to the artisan skilled in molecular biology techniques. Said techniques include oligonucleotide-directed mutagenesis, deletion, chemical mutagenesis, and the like. The protein encoded by the mutant gene is then produced by expressing the gene in, for example, a bacterial or plant expression system.

Alternatively, polyketide synthase mutants may be generated by site specific-replacement of a particular amino acid with an unnaturally occurring amino acid. As such, polyketide synthase mutants may be generated through replacement of an amino acid residue or a particular cysteine or methionine residue with selenocysteine or selenomethionine. This may be achieved by growing a host organism capable of expressing either the wild-type or mutant polypeptide on a growth medium depleted of natural cysteine or methionine or both and growing on medium enriched with either selenocysteine, selenomethionine, or both. These and similar techniques are described in Sambrook et al., (Molecular Cloning, A Laboratory Manual, $2^{nd}$ Ed. (1989) Cold Spring Harbor Laboratory Press).

Another suitable method of creating mutant synthases of the present invention is based on a procedure described in Noel and Tsal (1989) J. Cell. Biochem., 40:309-320. In so doing, the nucleic acids encoding said polyketide synthase can be synthetically produced using oligonucleotides having overlapping regions, said oligonucleotides being degenerate at specific bases so that mutations are induced. Alternatively, traditional method of protein or polypeptide synthesis may be used.

According to the present invention, nucleic acid sequences encoding a mutated polyketide synthase can be produced by the methods described herein, or any alternative methods available to the skilled artisan. In designing the nucleic acid sequence of interest, it may be desirable to reengineer said gene for improved expression in a particular expression system. For example, it has been shown that many bacterially derived genes do not express well in plant systems. In some cases, plant-derived genes do not express well in bacteria. This phenomenon may be due to the non-optimal G+C content and/or A+T content of said gene relative to the expression system being used. For example, the very low G+C content of many bacterial genes results in the generation of sequences minicking or duplicating plant gene control sequences, that are highly A+T rich. The presence of A+T rich sequences within the genes introduced into plants (e.g., TATA box regions normally found in promoters) may result in aberrant transcription of the gene(s). In addition, the presence of other regulatory sequences residing in the transcribed mRNA (e.g. polyadenylation signal sequences (AAUAAA) or sequences complementary to small nuclear RNAs involved in pre-mRNA splicing) may lead to RNA instability. Therefore, one goal in the design of genes is to generate nucleic acid sequences that have a G+C content that affords mRNA stability and translation accuracy for a particular expression system.

Due to the plasticity afforded by the redundancy of the genetic code (i.e., many amino acids are specified by more than one codon), evolution of the genomes of different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. Therefore, in reengineering genes for expression, one may wish to determine the codon bias of the organism in which the gene is to be expressed. Looking at the usage of the codons as determined for genes of a particular organism deposited in GenBank can provide this information. After determining the bias thereof, the new gene sequence can be analyzed for restriction enzyme sites as well as other sites that could affect transcription such as exon:intron junctions, polyA addition signals, or RNA polymerase termination signals.

Genes encoding polyketide synthases can be placed in an appropriate vector, depending on the artisan's interest, and can be expressed using a suitable expression system. An expression vector, as is well known in the art, typically includes elements that permit replication of said vector within the host cell and may contain one or more phenotypic markers for selection of cells containing said gene. The expression vector will typically contain sequences that control expression such as promoter sequences, ribosome binding sites, and translational initiation and termination sequences. Expression vectors may also contain elements such as subgenomic promoters, a repressor gene or various activator genes. The artisan may also choose to include nucleic acid sequences that result in secretion of the gene product, movement of said product to a particular organelle such as a plant plastid (see U.S. Pat. Nos. 4,762,785; 5,451,513 and 5,545,817, which are incorporated by reference herein) or other sequences that increase the ease of peptide purification, such as an affinity tag.

A wide variety of expression control sequences are useful in expressing the mutated polyketide synthases when operably linked thereto. Such expression control sequences include, for example, the early and late promoters of SV40 for animal cells, the lac system, the trp system, major operator and promoter systems of phage S, and the control regions of coat proteins, particularly those from RNA viruses in plants. In *E. coli*, a useful transcriptional control sequence is the T7 RNA polymerase binding promoter, which can be incorporated into a pET vector as described by Studier et al., (1990) Methods Enzymology, 185:60-89, which is incorporated by reference herein.

For expression, a desired gene should be operably linked to the expression control sequence and maintain the appropriate reading frame to permit production of the desired polyketide synthase. Any of a wide variety of well-known expression vectors are of use to the present invention. These include, for example, vectors comprising segments of chromosomal, non-chromosomal and synthetic DNA sequences such as those derived from SV40, bacterial plasmids including those from *E. coli* such as col E1, pCR1, pBR322 and derivatives thereof, pMB9), wider host range plasmids such as RP4, phage DNA such as phage S, NM989, M13, and other such systems as described by Sambrook et al., (Molecular Cloning, A Laboratory Manual, $2^{nd}$ Ed. (1989) Cold Spring Harbor Laboratory Press), which is incorporated by reference herein.

A wide variety of host cells are available for expressing synthase mutants of the present invention. Such host cells include, for example, bacteria such as *E. coli, Bacillus* and *Streptomyces*, fungi, yeast, animal cells, plant cells, insect cells, and the like. Preferred embodiments of the present invention include chalcone synthase mutants that are expressed in *E. coli* or in plant cells. Said plant cells can either be in suspension culture or a transgenic plant as further described herein.

As stated previously, genes encoding synthases of the present invention can be expressed in transgenic plant cells. In order to produce transgenic plants, vectors containing the nucleic acid construct encoding polyketide synthases and mutants thereof are inserted into the plant genome. Preferably, these recombinant vectors are capable of stable integration into the plant genome. One variable in making a transgenic plant is the choice of a selectable marker. A selectable marker is used to identify transformed cells against a high background of untransformed cells. The preference for a particular marker is at the discretion of the artisan, but any of the selectable markers may be used along with any other gene not listed herein that could function as a selectable marker. Such selectable markers include aminoglycoside phosphotransferase gene of transposon Tn5 (Aph 11) (which encodes resistance to the antibiotics kanamycin), genes encoding resistance to neomycin or G418, as well as those genes which code for resistance or tolerance to glyphosate, hygromycin, methotrexate, phosphinothricin, imidazolinones, sulfonylureas, triazolophyrimidine herbicides, such as chlorosulfuron, bromoxynil, dalapon, and the like. In addition to a selectable marker, it may be desirable to use a reporter gene. In some instances a reporter gene may be used with a selectable marker. Reporter genes allow the detection of transformed cells and may be used at the discretion of the artisan. A list of these reporter genes is provided in K. Wolsing et al., 1988, Ann. Rev. Genetics, 22:421.

Said genes are expressed either by promoters expressing in all tissues at all times (constitutive promoters), by promoters expressing in specific tissues (tissue-specific promoters), promoters expressing at specific stages of development (developmental promoters), and/or promoter expression in response to a stimulus or stimuli (inducible promoters). The choice of these is at the discretion of the artisan.

Several techniques exist for introducing foreign genes into plant cells, and for obtaining plants that stably maintain and express the introduced gene. Such techniques include acceleration of genetic material coated on a substrate directly into cells (U.S. Pat. No. 4,945,050 to Comell): Plant cells may also be transformed using *Agrobacterium* technology (see, for example, U.S. Pat. No. 5,177,010 to University of Toledo, U.S. Pat. No. 5,104,310 to Texas A&M, U.S. Pat. Nos. 5,149,645, 5,469,976, 5,464,763, 4,940,838, and 4,693,976 to Schilperoot, European Patent Applications 116718, 290799, 320500 to Max Planck, European Patent Applications 604662,627752 and U.S. Pat. No. 5,591,616 to Japan Tobacco, European Patent Applications 0267159, 0292435 and U.S. Pat. No. 5,231,019 to Ciba-Geigy, U.S. Pat. Nos. 5,463,174 and 4,762,785 to Calgene, and U.S. Pat. Nos. 5,004,863 and 5,159,135 to Agracetus). Other transformation technologies include whiskers technology (see U.S. Pat. Nos. 5,302,523 and 5,464,765 to Zeneca). Electroporation technology has also been used to transform plants (see WO 87106614 to Boyce Thompson Institute, U.S. Pat. Nos. 5,472,869 and 5,384,253 to Dakalb, and WO 92/09696 and WO 93/21335 to Plant Genetic Systems, all which are incorporated by reference). Viral vector expression systems can also be used such as those described in U.S. Pat. Nos. 5,316,931, 5,589,367, 5,811,653, and 5,866,785 to BioSource, which are incorporated by reference herein.

In addition to numerous technologies for transforming plants, the type of tissue that is contacted with the genes of interest may vary as well. Suitable tissue includes, for example, embryonic tissue, callus tissue, hypocotyl, meristem, and the like. Almost all plant tissues may be transformed during de-differentiation using the appropriate techniques described herein.

In addition, it may be desirable to change the polyketide production of a polyketide synthase within a plant. For example, it may be beneficial to increase the production of resveratrol in a plant. Resveratrol, the natural product made by the CHS-related stilbene synthase (STS) enzymes, is an antifungal compound produced in a few families of plants, including pine trees, grapevines, and peanuts. When stilbene synthase is introduced into plants like tobacco or alfalfa, which normally lack this enzyme, the transgenic plant becomes resistant to fungal infection (Mol. Plant Microbe Interact. 13(5):551-62, 2000; and Nature 361(6408):153-6, 1993). Since STS uses the exact same substrates as CHS, which is ubiquitous in higher plants, expression of the STS gene in any of these species should be sufficient to achieve the in vivo biosynthesis of resveratrol.

Furthermore, resveratrol has also been shown to have a number of beneficial medicinal activities, including copper chelation, anti-oxidant scavenging of free radicals, inhibition of both platelet aggregation and lipid peroxidation, anti-inflammation, vasodilation, anti-cancer (Life Sci. 66(8): 663-73, 2000), and the like. These effects of resveratrol contribute to the health benefits of the moderate consumption of red wine, known as "the French paradox". Red wine has a higher resveratrol content than grape juice or white wine, due to the inclusion of the resveratrol-rich grape skins during the fermentation process.

Thus, production of resveratrol in plants which lack it is biologically useful for the plant, and medicinally useful for humans who consume the plant. While transgenic introduction of the stilbene synthase gene has proven effective, enzymes are often best-adapted for expression and stability within their own species. The ability to engineer full or partial STS activity into a native CHS of a given species confers the benefits of resveratrol production to that species, while avoiding all of the negative effects of foreign transgene expression.

Figure 14:
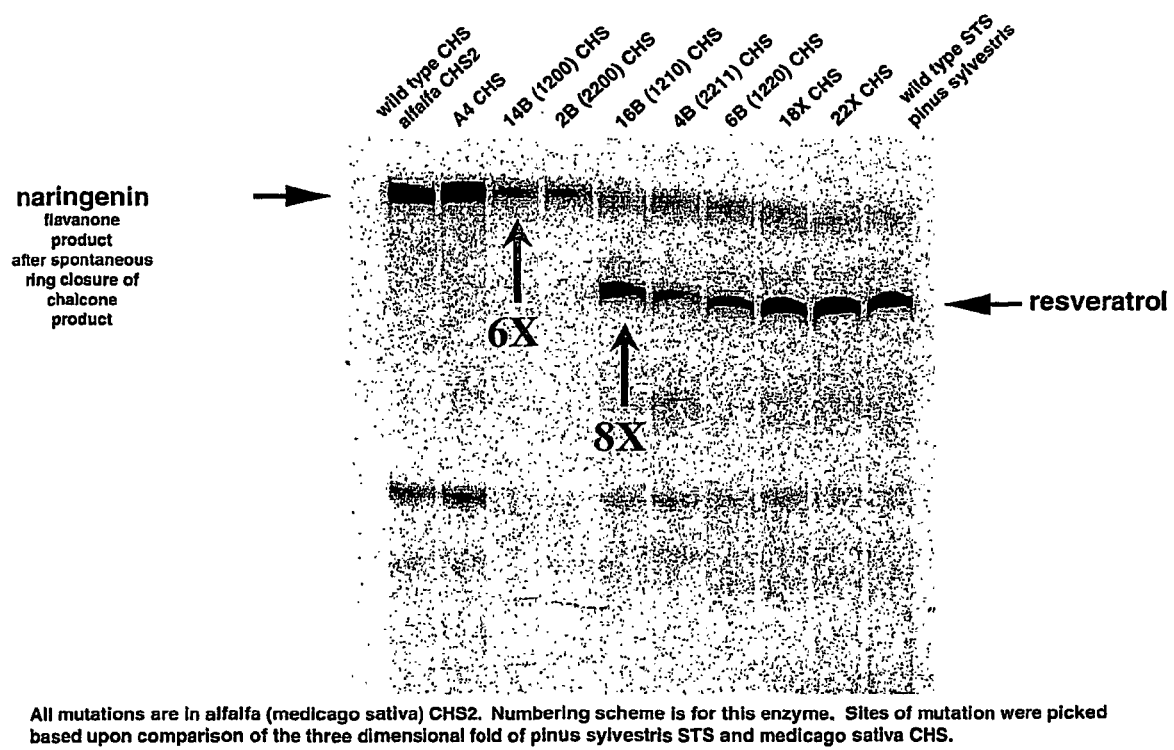
FIG. 14 shows an autoradiographic gel following thin layer chromatography. Wild type CHS produces chalcone, which spontaneously converts to naringenin, the position of which is indicated by the arrow on the left. Wild type STS produces resveratrol, the position of which is indicated by the arrow of the right. Function conversion of CHS to STS (i.e., the production of the alternate product from the same intermediate) results in diminished production of naringenin and increased production of resveratrol. Various mutants of CHS produce varying degrees of resveratrol, showing that CHS activity can be altered to STS-like activity to different extents by different mutations.

The mutants of the present invention show that it is possible to mutate a native CHS to a STS-like activity (see FIG. 14). Furthermore, it is possible to produce the STS product resveratrol to varying degrees with different mutants. Thus, a plant can be manipulated to produce varying levels of resveratrol, without eliminating the production of the chalcone product required for viability.

Regardless of the transformation system used, a gene encoding a mutant polyketide synthase is preferably incorporated into a gene transfer vector adapted to express said gene in a plant cell by including in the vector an expression control sequence (plant promoter regulatory element). In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter, and the like, may be used. Promoters of viral origin, such as the cauliflower mosaic virus (35S and 19S) are also desirable. Plant promoter regulatory elements also include ribulose-1, 6-bisphosphate carboxylase small subunit promoter, beta-conglycinin promoter, phaseolin promoter, ADH promoter, heat-shock promoters, tissue specific promoters, and the like. Numerous promoters are available to skilled artisans for use at their discretion.

It should be understood that not all expression vectors and expression systems function in the same way to express the mutated gene sequences of the present invention. Neither do all host cells function equally well with the same expression system. However, one skilled in the art may make a selection among these vectors, expression control sequences, and host without undue experimentation and without departing from the scope of this invention.

Once a synthase of the present invention is expressed, the protein obtained therefrom can be purified so that structural analysis, modeling, and/or biochemical analysis can be performed, as exemplified herein. The nature of the protein obtained can be dependent on the expression system used. For example, genes, when expressed in mammalian or other eukaryotic cells, may contain latent signal sequences that may result in glycosylation, phosphorylation, or other post-translational modifications, which may or may not alter function. Therefore, a preferred embodiment of the present invention is the expression of mutant synthase genes in *E. coli* cells. Once said proteins are expressed, they can be easily purified using techniques common to the person having ordinary skill in the art of protein biochemistry, such as, for example, techniques described in Colligan et al., (1997) Current Protocols in Protein Science, Chanda, V. B., Ed., John Wiley & Sons, Inc., which is incorporated by reference herein. Such techniques often include the use of cation-exchange or anion-exchange chromatography, gel filtration-size exclusion chromatography, and the like. Another technique that may be commonly used is affinity chromatography. Affinity chromatography can include the use of antibodies, substrate analogs, or histidine residues (His-tag technology).

Once purified, mutants of the present invention may be characterized by any of several different properties. For example, such mutants may have altered active site surface charges of one or more charge units. In addition, said mutants may have altered substrate specificity or product capability relative to a non-mutated polyketide synthase.

The present invention allows for the characterization of polyketide synthase mutants by crystallization followed by X-ray diffraction. Polypeptide crystallization occurs in solutions where the polypeptide concentration exceeds it solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Compounds known as "precipitants" are often used to decrease the solubility of the polypeptide in a concentrated solution by forming an energetically unfavorable precipitating layer around the polypeptide molecules (Weber, *Advances in Protein Chemistry*, 41:1-36, 1991). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol.

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, the vessel is sealed, and set aside until crystals appear. In the dialysis method, polypeptide is retained in a sealed dialysis membrane that is placed into a solution containing precipitant. Equilibration across the membrane increases the polypeptide and precipitant concentrations thereby causing the polypeptide to reach supersaturation levels.

In the preferred hanging drop technique (McPherson, *J. Biol Chem*, 6300-6306, 1976), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide will form.

Another method of crystallization introduces a nucleation site into a concentrated polypeptide solution. Generally, a concentrated polypeptide solution is prepared and a seed crystal of the polypeptide is introduced into this solution. If the concentration of the polypeptide and any precipitants are correct, the seed crystal will provide a nucleation site around which a larger crystal forms. In preferred embodiments, the crystals of the present invention are formed in hanging drops.

Some proteins may be recalcitrant to crystallization. However, several techniques are available to the skilled artisan. Quite often the removal of polypeptide segments at the amino or caroxy terminal end of the protein is necessary to produce crystalline protein samples. Said procedures involve either the treatment of the protein with one of several proteases including trypsin, chymotrypsin, substilisin, and the like. This treatment often results in the removal of flexible polypeptide segments that are likely to negatively affect crystallization. Alternatively, the removal of coding sequences from the protein's gene facilitates the recombinant expression of shortened proteins that can be screened for crystallization.

The crystals so produced have a wide range of uses. For example, high quality crystals are suitable for X-ray or neutron diffraction analysis to determine the three-dimensional structure of a mutant polyketide synthase and to design additional mutants thereof. In addition, crystallization can serve as a further purification method. In some instances, a polypeptide or protein will crystallize from a heterogeneous mixture into crystals. Isolation of such crystals by filtration, centrifugation, etc., followed by redissolving the polypeptide affords a purified solution suitable for use in growing the high-quality crystals needed for diffraction studies. The high-quality crystals may also be dissolved in water and then formulated to provide an aqueous solution having other uses as desired.

Because synthases may crystallize in more than one crystal form, the structural coordinates of α-carbons of an active site determined from a synthase or portions thereof, as provided by this invention, are particularly useful to solve the structure of other crystal forms of synthases. Said structural coordinates, as provided herein, may also be used to solve the structure of synthases having α-carbons positioned within the active sites in a manner similar to the wild-type, yet having R-groups that may or may not be identical.

Furthermore, the structural coordinates disclosed herein may be used to determine the structure of the crystalline form of other proteins with significant amino acid or structural homology to any functional domain of a synthase. One method that may be employed for such purpose is molecular replacement. In this method, the unknown crystal structure, whether it is another crystal form of a synthase, a synthase having a mutated active site, or the crystal of some other protein with significant sequence and/or structural homology to a polyketide synthase may be determined using the coordinates given in Table 1. This method provides sufficient structural form for the unknown crystal more efficiently than attempting to determine such information ab initio. In addition, this method can be used to determine whether or not a given polyketide synthase in question falls within the scope of this invention.

As further disclosed herein, polyketide synthases and mutants thereof may be crystallized in the presence or absence of substrates and substrate analogs. The crystal structures of a series of complexes may then be solved by molecular replacement and compared to that of the wild-type to assist in determination of suitable replacements for R-groups within the active site, thus making synthase mutants according to the present invention.

All mutants of the present inventions may be modeled using the information disclosed herein without necessarily having to crystallize and solve the structure for each and every mutant. For example, one skilled in the art may use one of several specialized computer programs to assist in the process of designing synthases having mutated active sites relative to the wild-type. Examples of such programs include: GRID (Goodford, 1985, *J. Mod. Chem.*:28:849-857), MCSS (Miranker and Karplus, 1991, Proteins: Structure, Function and Genetics, 11:29-34); AUTODOCK (Goodsell and Olsen, 1990, Proteins. Structure, Fumtion, and Genetics, 8:195-202); and DOCK (Kuntz et al., 1982, *J. Mol Biol*:161:269-288), and the like, as well as those discussed in the Examples below. In addition, specific computer programs are also available to evaluate specific substrate-active site interactions and the deformation energies and electrostatic interactions resulting therefrom. MODELLER is a computer program often used for homology or comparative modeling of the three-dimensional structure of a protein. A. Saii & T. L. Blundell. *J. Mol. Biol.* 234:779-815, 1993. A sequence to be modeled is aligned with one or more known related structures and the MODELLER program is used to calculate a full-atom model, based on optimum satisfaction of spatial restraints. Such restraints can include, inter alia, homologous structures, site-directed mutagenesis, fluorescence spectroscopy, NMR experiments, or atom-atom potentials of mean force.

The present invention enables polyketide synthase mutants to be made and the crystal structure thereof to be solved. Moreover, by virtue of the present invention, the location of the active site and the interface of substrate therewith permit the identification of desirable R-groups for mutagenesis.

The three-dimensional coordinates of the polyketide synthase provided herein may additionally be used to predict the activity and or substrate specificity of a protein whose primary amino acid sequence suggests that it may have polyketide synthase activity. The family of CHS-related enzymes is defined, in part, by the presence of four highly conserved amino acid residues, $Cys_{164}$, $Phe_{215}$, $His_{303}$, and $Asn_{336}$. More than 400 enzymes having these conserved residues have been identified to date, including several bacterial proteins. The functions, substrates, and products of many of these enzymes remains unknown. However, by employing the three-dimensional coordinates disclosed herein and computer modeling programs, structural comparisons of CHS can be made with a putative enzyme. Similarities and differences between the two would provide the skilled artisan with information regarding the activity and/or substrate specificity of the putative enzyme. This procedure is demonstrated in the Examples section below.

Thus, in another embodiment of the invention, there is provided a method of predicting the activity and/or substrate specificity of a putative polyketide synthase comprising (a) generating a three-dimentional representation of a known polyketide synthase using three-dimentional coordinate data, (b) generating a predicted three-dimentional representation of a putative polyketide synthase, and (c) comparing the representation of the known polyketide synthase with the representation of the putative polyketide synthase, wherein the similarities and/or differences between the two representations are predictive of activity and/or substrate specificity of the putative polyketide synthase.

In a further embodiment of the present invention, there is also provided a method of identifying a potential substrate of a polyketide synthase comprising (a) defining the active site of the polyketide synthase based on the atomic coordinates of said polyketide synthase, (b) identifying a potential substrate that fits the defined active site, and (c) contacting the polyketide synthase with the potential substrate of (b) and determining the activity thereon. Techniques for computer modeling and structural comparisons similar to those described herein for predicting putative polyketide synthase activity and/or substrate specificity can be used to identify novel substrates for polyketide synthases.

In addition, the structural coordinates and three-dimensional models disclosed herein can be used to design or identify polyketide synthase inhibitors. Using the modeling techniques disclosed herein, potential inhibitor structures can be modeled with the polyketide synthase active site and those that appear to interact therewith can subsequently be tested in activity assays in the presence of substrate.

Methods of using crystal structure data to design binding agents or substrates are known in the art. Thus, the crystal structure data provided herein can be used in the design of new or improved inhibitors, substrates or binding agents. For example, the synthase polypeptide coordinates can be superimposed onto other available coordinates of similar enzymes to identify modifications in the active sites of the enzymes to create novel products of enzymatic activity or to modulate polyketide synthesis. Alternatively, the synthase polypeptide coordinates can be superimposed onto other available coordinates of similar enzymes which have substrates or inhibitors bound to them to give an approximation of the way these and related substrates or inhibitors might bind to a synthase. Alternatively, computer programs employed in the practice of rational drug design can be used to identify compounds that reproduce interaction characteristics similar to those found between a synthase polypeptide and a co-crystallized substrate. Furthermore, detailed knowledge of the nature of binding site interactions allows for the modification of compounds to alter or improve solubility, pharmacokinetics, etc. without affecting binding activity.

Computer programs are widely available that are capable of carrying out the activities necessary to design agents using the crystal structure information provided herein. Examples include, but are not limited to, the computer programs listed below:

CATALYST DATABASES™—an information retrieval program accessing chemical databases such as BioByte Master File, Derwent WDI and ACD;

CATALYST/HYPO™—generates models of compounds and hypotheses to explain variations of activity with the structure of drug candidates;

LUDI™—fits molecules into the active site of a protein by identifying and matching complementary polar and hydrophobic groups;

LEAPFROG™—"grows" new ligands using a genetic algorithm with parameters under the control of the user.

In addition, various general purpose machines may be used with programs written in accordance with the teachings herein, or it may be more convenient to construct more specialized apparatus to perform the operations. However, preferably the embodiment is implemented in one or more computer programs executing on programmable systems each comprising at least one processor, at least one data storage system (including volatile and non-volatile memory and/or storage elements), at least one input device, and at least one output device. The program is executed on the processor to perform the functions described herein.

Each such program may be implemented in any desired computer language (including machine, assembly, high level procedural, object oriented programming languages, or the like) to communicate with a computer system. In any case, the language may be a compiled or interpreted language. The computer program will typically be stored on a storage media or device (e.g., ROM, CD-ROM, or magnetic or optical media) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

Figure 9:
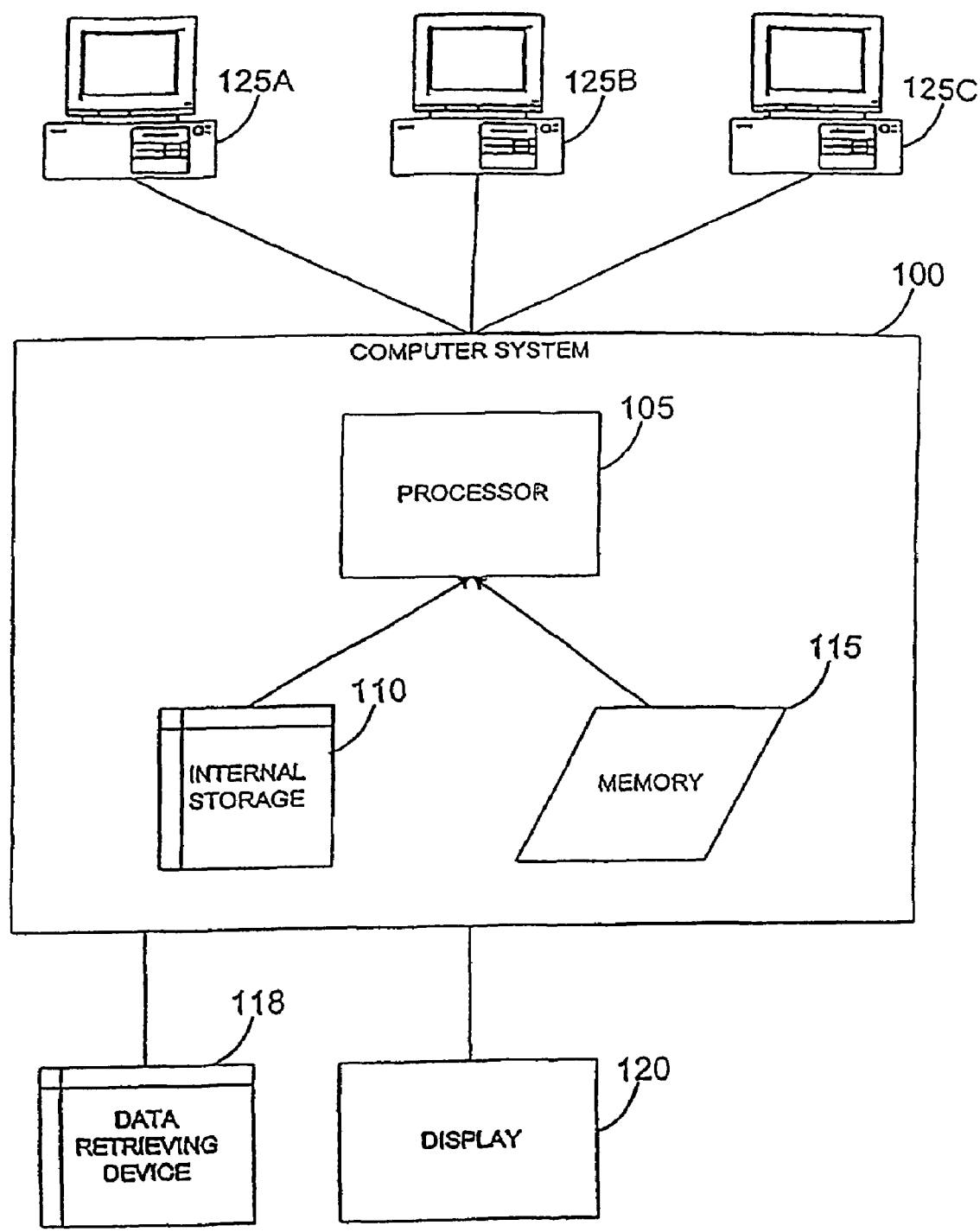
FIG. 9 shows an example of a computer system in block diagram form.

Embodiments of the invention include systems (e.g., internet based systems), particularly computer systems which store and manipulate the coordinate and sequence information described herein. One example of a computer system 100 is illustrated in block diagram form in FIG. 9. As used herein, "a computer system" refers to the hardware components, software components, and data storage components used to analyze the coordinates and sequences as set forth in one or more of Accession Nos. 1BI5, 1D6F, 1D6I, 1D6H, 1BQ6, 1CML, 1CHW, 1CGK, 1CGZ, Table 1, and Appendix A. The computer system 100 typically includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

Typically the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125*a-c* in a network or wide area network to provide centralized access to the computer system 100.

Software for accessing and processing the coordinate and sequences described herein, (such as search tools, compare tools, and modeling tools etc.) may reside in main memory 115 during execution.

For the first time, the present invention permits the use of molecular design techniques to design, select and synthesize novel enzymes, chemical entities and compounds, including inhibitory compounds, capable of binding to a polyketide synthase polypeptide (e.g., a chalcone synthase polypeptide), in whole or in part.

One approach enabled by this invention, is to use the structure coordinates as set forth in one or more of Accession Nos. 1BI5 (SEQ ID NO:69), 1D6F (SEQ ID NO:69), 1D6I (SEQ ID NO:69), 1D6H (SEQ ID NO:69), 1BQ6 (SEQ ID NO:69), 1CML (SEQ ID NO:69), 1CHW (SEQ ID NO:69), 1CGK (SEQ ID NO:69), 1CGZ (SEQ ID NO:69), 1EE0 (SEQ ID NO:68), Table 1, Appendix A (SEQ ID NO:65), Appendix B (SEQ ID NO:66) and Appendix C (SEQ ID NO:67) to design new enzymes capable of synthesizing novel and known polyketides. For example, polyketide synthases (PKSs) generate molecular diversity in their products by utilizing different starter molecules and by varying the final size of the polyketide chain. The structural coordinates disclosed herein allow the elucidation of the nature by which PKSs achieve starter molecule selectivity and control polyketide chain length. For example, by comparing the structure of chalcone synthase, which yields a tetraketide product to 2-pyrone synthases which forms a triketide product the invention demonstrated that 2-pyrone synthase maintains a smaller initiation/elongation cavity. Accordingly, generation of a chalcone synthase mutant with an active site sterically analogous to 2-pyrone synthase results in the synthesis of a polyketide product of a different size. As discussed more fully below, this invention allows for the strategic development and biosynthesis of more diverse polyketides and demonstrates a structural basis for control of polyketide chain length in other PKSs. In addition, the structural coordinates allow for the development of substrates or binding agents that bind to the polypeptide and alter the physical properties of the compounds in different ways, e.g., solubility.

In another approach a polyketide synthase polypeptide crystal is probed with molecules composed of a variety of different chemical entities to determine optimal sites for interaction between candidate binding molecules (e.g., substrates) and the polyketide synthase (e.g., chalcone synthase).

In another embodiment, an approach made possible and enabled by this invention, is to screen computationally small molecule data bases for chemical entities or compounds that can bind in whole, or in part, to a polyketide synthase polypeptide or fragment thereof. In this screening, the quality of fit of such entities or compounds to the binding site may be judged either by shape complementarity or by estimated interaction energy. Meng, E. C. et al., *J. Comp. Chem.*, 13:505-524 (1992).

Because chalcone synthase is a highly representative member of a family of polyketide synthase polypeptides, many of which have similar functional activity, the structure coordinates of chalcone synthase, or portions thereof, as provided by this invention are particularly useful to solve the structure, function or activity of other crystal forms of polyketide synthase molecules. They may also be used to solve the structure of a polyketide synthase or a chalcone synthase mutant.

One method that may be employed for this purpose is molecular replacement. In this method, the unknown crystal structure, whether it is another polyketide synthase crystal form, a polyketide synthase or chalcone synthase mutant, or a polyketide synthase complexed with a substrate or other molecule, or the crystal of some other protein with significant amino acid sequence homology to any polyketide synthase polypeptide, may be determined using the structure coordinates as provided in one or more of Accession Nos. 1BI5 (SEQ ID NO:69), 1D6F (SEQ ID NO:69), 1D6I (SEQ ID NO:69), 1D6H (SEQ ID NO:69), 1BQ6 (SEQ ID NO:69), 1CML (SEQ ID NO:69), 1CHW (SEQ ID NO:69), 1CGK (SEQ ID NO:69), 1CGZ (SEQ ID NO:69), 1EE0 (SEQ ID NO:68, Table 1, Appendix A (SEQ ID NO:65), Appendix B (SEQ ID NO:66) or Appendix C (SEQ ID NO:67). This method will provide an accurate structural form for the unknown crystal more quickly and efficiently than attempting to determine such information ab initio.

In addition, in accordance with the present invention, a polyketide synthase or chalcone synthase polypeptide mutant maybe crystallized in association or complex with known polyketide synthase binding agents, substrates, products or inhibitors. The crystal structures of a series of such complexes may then be solved by molecular replacement and compared with that of wild-type polyketide synthase molecules. Potential sites for modification within the synthase molecule may thus be identified. This information provides an additional tool for determining the most efficient binding interactions between a polyketide synthase and a chemical entity, substrate, product or compound.

All of the complexes referred to above may be studied using well-known X-ray diffraction techniques and may be refined to 2-3 Å resolution X-ray data to an R value of about 0.20 or less using computer software, such as X-PLOR (Yale University, 1992, distributed by Molecular Simulations, Inc.). See, e.g., Blundel & Johnson, supra; Methods in Enzymology, vol. 114 and 115, H. W. Wyckoff et al., eds., Academic Press (1985). This information may thus be used to optimize known classes of polyketide synthase substrates or binding agents (e.g., inhibitors), and to design and synthesize novel classes of polyketide synthases, substrates, and binding agents (e.g. inhibitors).

The design of substrates, compounds or binding agents that bind to or inhibit a polyketide synthase polypeptide according to the invention generally involves consideration of two factors. First, the substrate, compound or binding agent must be capable of physically and structurally associating with a polyketide synthase molecule. Non-covalent molecular interactions important in the association of a polyketide synthase with a substrate include hydrogen bonding, van der Waals and hydrophobic interactions, and the like.

Second, the substrate, compound or binding agent must be able to assume a conformation that allows it to associate with a polyketide synthase molecule. Although certain portions of the substrate, compound or binding agent will not directly participate in this association, those portions may still influence the overall conformation of the molecule. This, in turn, may have a significant impact on potency. Such conformational requirements include the overall three-dimensional structure and orientation of the chemical entity or compound in relation to all or a portion of the binding site, e.g., active site or accessory binding site of a polyketide synthase (e.g., a chalcone synthase polypeptide), or the spacing between functional groups of a substrate or compound comprising several chemical entities that directly interact with a polyketide synthase.

The potential binding effect of a substrate or chemical compound on a polyketide synthase or the activity a newly synthesized or mutated polyketide synthase might have on a known substrate may be analyzed prior to its actual synthesis and testing by the use of computer modeling techniques. For example, if the theoretical structure of the given substrate or compound suggests insufficient interaction and association between it and a polyketide synthase, synthesis and testing of the compound may be obviated. However, if computer modeling indicates a strong interaction, the molecule may then be tested for its ability to bind to, initiate catalysis or elongation of a polyketide by a polyketide synthase. Methods of assaying for polyketide synthase activity are known in the art (as identified and discussed herein). Methods for assaying the effect of a newly created polyketide synthase or a potential substrate or binding agent can be performed in the presence of a known binding agent or polyketide synthase. For example, the effect of the potential binding agent can be assayed by measuring the ability of the potential binding agent to compete with a known substrate.

A mutagenized synthase, novel synthase, substrate or other binding compound of an polyketide synthase may be computationally evaluated and designed by means of a series of steps in which chemical entities or fragments are screened and selected for their ability to associate with binding pockets or other areas of the polyketide synthase.

One skilled in the art may use one of several methods to screen chemical entities or fragments for their ability to associate with a polyketide synthase and more particularly with the individual binding pockets of a chalcone synthase polypeptide. This process may begin by visual inspection of, for example, the active site on the computer screen based on the coordinates in one or more of Accession Nos. 1BI5 (SEQ ID NO:69), 1D6F (SEQ ID NO:69), 1D6I (SEQ ID NO:69), 1D6H (SEQ ID NO:69), 1BQ6 (SEQ ID NO:69), 1CML (SEQ ID NO:69), 1CHW (SEQ ID NO:69), 1CGK (SEQ ID NO:69), 1CGZ (SEQ ID NO:69), 1EE0 (SEQ ID NO:68), Table 1, Appendix A (SEQ ID NO:65), Appendix B (SEQ ID NO:66) or Appendix C (SEQ ID NO:67). Selected fragments or substrates or chemical entities may then be positioned in a variety of orientations, or docked, within an individual binding pocket of a polyketide synthase. Docking may be accomplished using software such as Quanta and Sybyl, followed by energy minimization and molecular dynamics with standard molecular mechanics forcefields, such as CHARMM and AMBER.

Specialized computer programs may also assist in the process of selecting fragments or chemical entities. These include:

1. GRID (Goodford, P. J., "A Computational Procedure for Determining Energetically Favorable Binding Sites on Biologically Important Macromolecules", *J. Med. Chem.*, 28:849-857 (1985)). GRID is available from Oxford University, Oxford, UK.

2. MCSS (Miranker, A. and M. Karplus, "Functionality Maps of Binding Sites: A Multiple Copy Simultaneous Search Method." *Proteins: Structure. Function and Genetics*, 11:29-34 (1991)). MCSS is available from Molecular Simulations, Burlington, Mass.

3. AUTODOCK (Goodsell, D. S. and A. J. Olsen, "Automated Docking of Substrates to Proteins by Simulated Annealing", *Proteins: Structure. Function, and Genetics*, 8:195-202 (1990)). AUTODOCK is available from Scripps Research Institute, La Jolla, Calif.

4. DOCK (Kuntz, I. D. et al, "A Geometric Approach to Macromolecule-Ligand Interactions", *J. Mol. Biol.*, 161: 269-288 (1982)). DOCK is available from University of California, San Francisco, Calif.

Once suitable substrates, chemical entities or fragments have been selected, they can be assembled into a single polypeptide, compound or binding agent (e.g., an inhibitor). Assembly may be performed by visual inspection of the relationship of the fragments to each other on the three-dimensional image displayed on a computer screen in relation to the structure coordinates of the molecules as set forth in one or more of Accession Nos. 1BI5 (SEQ ID NO:69), 1D6F (SEQ ID NO:69), 1D6I (SEQ ID NO:69), 1D6H (SEQ ID NO:69), 1BQ6 (SEQ ID NO:69), 1CML (SEQ ID NO:69), 1CHW (SEQ ID NO:69), 1CGK (SEQ ID NO:69), 1CGZ (SEQ ID NO:69). 1EE0 (SEQ ID NO:68), Table 1, Appendix A (SEQ ID NO:65), Appendix B (SEQ ID NO:66) or Appendix C (SEQ ID NO:67). This would be followed by manual model building using software such as Quanta or Sybyl.

Useful programs to aid one of skill in the art in connecting the individual chemical entities or fragments include:

1. CAVEAT (Bartlett, P. A. et al, "CAVEAT: A Program to Facilitate the Structure-Derived Design of Biologically Active Molecules". In "Molecular Recognition in Chemical and Biological Problems", Special Pub., Royal Chem. Soc., 78, pp. 182-196 (1989)). CAVEAT is available from the University of California, Berkeley, Calif.

2. 3D Database systems such as MACCS-3D (MDL Information Systems, San Leandro, Calif.). This area is reviewed in Martin, Y. C., "3D Database Searching in Drug Design", *J. Med. Chem.*, 35:2145-2154 (1992)).

3. HOOK (available from Molecular Simulations, Burlington, Mass.).

In addition to the method of building or identifying novel enzymes or a polyketide synthase substrate or binding agent in a step-wise fashion one fragment or chemical entity at a time as described above, substrates, inhibitors or other polyketide synthase interactions may be designed as a whole or "de novo" using either an empty active site or optionally including some portion(s) of known substrates, binding agents or inhibitors. These methods include:

1. LUDI (Bohm, H.-J., "The Computer Program LUDI: A New Method for the De Novo Design of Enzyme Inhibitors", *J. Comp. Aid. Molec. Design*, 6:61-78 (1992)). LUDI is available from Biosym Technologies, San Diego, Calif.

2. LEGEND (Nishibata, Y. and A. Itai, *Tetrahedron*, 47:8985 (1991)). LEGEND is available from Molecular Simulations, Burlington, Mass.

3. LeapFrog (available from Tripos Associates, St. Louis, Mo.).

Other molecular modeling techniques may also be employed in accordance with this invention. See, e.g., Cohen, N. C. et al., "Molecular Modeling Software and Methods for Medicinal Chemistry", *J. Med. Chem.*, 33:883-894 (1990). See also, Navia, M. A. and M. A. Murcko, "The Use of Structural Information in Drug Design", *Current Opinions in Structural Biology*, 2:202-210 (1992).

Once a substrate, compound or binding agent has been designed or selected by the above methods, the efficiency with which that substrate, or binding agent may bind to a polyketide synthase may be tested and optimized by computational evaluation.

A substrate or compound designed or selected as a polyketide binding agent may be further computationally optimized so that in its bound state it would preferably lack repulsive electrostatic interaction with the target site. Such non-complementary (e.g., electrostatic) interactions include repulsive charge-charge, dipole-dipole and charge-dipole interactions. Specifically, the sum of all electrostatic interactions between the binding agent and the polyketide synthase when the binding agent is bound to the synthase, preferably make a neutral or favorable contribution to the enthalpy of binding.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa., 1992); AMBER, version 4.0 (P. A. Kollman, University of California at San Francisco, 1994); QUANTA/CHARMM (Molecular Simulations, Inc., Burlington, Mass. 1994); and Insight II/Discover (Biosysm Technologies Inc., San Diego, Calif., 1994). These programs maybe implemented, for example, using a Silicon Graphics workstation, IRIS 4D/35 or IBM RISC/6000 workstation model 550. Other hardware systems and software packages will be known to those skilled in the art of which the speed and capacity are continually modified Once a polyketide synthase, polyketide synthase substrate or polyketide synthase binding agent has been selected or designed, as described above, substitutions may then be made in some of its atoms or side groups in order to improve or modify its binding properties. Generally, initial substitutions are conservative, e.g., the replacement group will have approximately the same size, shape, hydrophobicity and charge as the original group. Such substituted chemical compounds may then be analyzed for efficiency of fit to a polyketide synthase substrate or fit of a modified substrate to a polyketide synthase having a structure defined by the coordinates in one or more of Accession Nos. 1BI5, 1D6F, 1D6I, 1D6H, 1BQ6, 1CML, 1CHW, 1CGK, 1CGZ, 1EE0, Table 1, Appendix A, Appendix B, or Appendix C, by the same computer methods described, above.

Conserved regions of the polyketide family synthases lend themselves to the methods and compositions of the invention. For example, pyrone synthase and chalcone synthase have conserved residues present within their active sites (as described more fully below). Accordingly, modification to the active site of chalcone synthase or a chalcone synthase substrate can be extrapolated to other conserved members of the polyketide family of synthases such as, for example, pyrone synthase.

Functional fragments of polyketide synthase polypeptides such as, for example, fragments of chalcone synthase can be designed based on the crystal structure and atomic coordinates described herein. Fragments of a chalcone synthase polypeptide and the fragment's corresponding atomic coordinates can be used in the modeling described herein. In addition, such fragments may be used to design novel substrates or modified active sites to create new diverse polyketides.

In one embodiment of the present invention, the crystal structure and atomic coordinates allow for the design of novel polyketide synthases and novel polyketide synthase substrates. The development of new polyketide synthases will lead to the development a biodiverse repetoir of polyketides for use as antibiotics, anti-cancer agents, antifungal agents and other therapeutic agents as described herein or known in the art. In vitro assay systems for production and determination of activity are known in the art. For example, antibiotic activities of novel polyketides can be measured by any number of anti-microbial techniques currently used in hospitals and laboratories. In addition, anticancer activity can be determined by contacting cells having a cell proliferative disorder with a newly synthesized polyketide and measuring the proliferation or apoptosis of the cells before and after contact with the polyketide. Specific examples of apoptosis assays are provided in the following references: Lymphocyte: C. J. Li et al., *Science*, 268:429-431, 1995; D. Gibellini et al., *Br. J. Haematol.* 89:24-33, 1995; S. J. Martin et al., *J. Immunol.* 152:330-42, 1994; C. Terai et al., *J. Clin Invest.* 87:1710-5, 1991; J. Dhein et al., *Nature* 373:438441, 1995; P. D. Katsikis et al., *J. Exp. Med.* 1815:2029-2036, 1995; Michael O. Westendorp et al., *Nature* 375:497, 1995; DeRossi et ad, *Virology* 198:234-44, 1994. Fibroblasts: H. Vossbeck et al., *Int. J. Cancer* 61:92-97, 1995; S. Gomppi et al., *Oncogene* 9:1537-44, 1994; A. Fernandez et al., *Oncogene* 9:2009-17, 1994; E. A. Harrington et al., *Embo J.* 13:3286-3295, 1994; N. Itoh et al., *J. Biol. Chem.* 268:10932-7, 1993. Neuronal Cells: G. Melino et al., *Mol. Cell. Biol.* 14:6584-6596, 1994; D. M. Rosenbaum et al., *Ann. Neurol.* 36:864-870, 1994; N. Sato et al., *J. Neurobiol* 25:1227-1234, 1994; G. Ferrari et al., *J. Neurosci.* 1516:2857-2866, 1995; A. K. Talley et al., *Mol. Cell Biol.* 1585:2359-2366, 1995; A. K. Talley et al., *Mol. and Cell. Biol.* 15:2359-2366, 1995; G. Walkinshaw et al., *J. Clin. Invest.* 95:2458-2464, 1995. Insect Cells: R. J. Clem et al., *Science* 254:1388-90, 1991; N. E. Crook et al., *J. Virol.* 67:2168-74, 1993; S. Rabizadeh et al., *J. Neurochem.* 61:2318-21, 1993; M. J. Birnbaum et al., *J. Virol* 68:2521-8, 1994; R. J. Clem et al., *Mol. Cell. Biol.* 14:5212-5222, (1994). Other assays are well within the ability of those of skill in the art.

Product of novel polyketides or polyketide synthases can be carried out in culture. For example, mammalian expression constructs carrying polyketide synthases can be introduced into various cell lines such as CHO, 3T3, HL60, Rat-1, or Jurkart cells, for example. In addition, SF21 insect cells may be used in which case the polyketide synthase gene is expressed using an insect heat shock promotor.

In another embodiment of the present invention, there is provided a method of designing a mutant polyketide synthese. The method include comparing a crystal structure of a wild type polyketide synthase with the crystal structure of a second polyketide synthase and substituting one or more animo acids with the amino acid residues at homologous positions in the second polyketide synthase. Invention methods can guide the required areas or active sites, and second tier interaction residues for synthase activity. Such areas can be mutated to modify one synthase to resemble another synthase, thereby allowing production of a product not typically synthesized by the wild type enzyme.

In another embodiment of the present invention, once a novel substrate or binding agent is developed by the computer methodology discussed above, the invention provides a method for determining the ability of the substrate or agent to be acted upon by a polyketide synthase. The method includes contacting components comprising the substrate or agent and a polyketide synthase polypeptide, or a recombinant cell expressing a polyketide synthase polypeptide, under conditions sufficient to allow the substrate or agent to interact and determining the affect of the agent on the activity of the polypeptide. The term "affect", as used herein, encompasses any means by which protein activity can be modulated, and includes measuring the interaction of the agent with the polyketide synthase molecule by physical means including, for example, fluorescence detection of the binding of an agent to the polypeptide. Such agents can include, for example, polypeptides, peptidomimetics, chemical compounds, small molecules, substrates and biologic agents as described herein. Examples of small molecules include but are not limited to small peptides or peptide-like molecules.

Contacting or incubating includes conditions which allow contact between the test agent or substrate and a polyketide synthase or modified polyketide synthase polypeptide or a cell expressing a polyketide synthase or modified polyketide synthase polypeptide. Contacting includes in solution and in solid phase. The substrate or test agent may optionally be a combinatorial library for screening a plurality of substrates or test agents. Agents identified in the method of the invention can be further evaluated by chromatography, cloning, sequencing, and the like.

Although methods and materials similar or equivalent to those described herein can be used to practice the invention, suitable methods and materials are described below. All publications, patent applications, patents and other references mentioned herein are incorporated by reference in their entirety. The invention is described in greater detail by reference to the following non-limiting examples.

EXAMPLES

Mutagenesis, expression, and purification. Alfalfa CHS2 (SEQ ID NO:1) cDNA (Junghans, H., et al., *Plant Mol. Biol.* 22:239-253, 1993) was subcloned into pHIS8 plasmid vector derived from pET-28a(+) (Novagen). PCR-based mutagenesis using the QuikChange system (Stratagene) generated the various mutants including $C_{164}S$, $C_{164}D$, $H_{303}A$, $H_{303}Q$, $H_{303}D$, $H_{303}T$, $N_{336}A$, $N_{336}D$, $N_{336}Q$, $N_{366}H$, $F_{215}S$, $F_{215}Y$ and F215W (see SEQ ID NO:1). N-teminal His8-tagged CHS (see SEQ ID NO:1) was expressed in BL21 (DE3) *E. coli* cells. Cells were harvested and lysed by sonication. His-tagged CHS (see SEQ ID NO:1) was purified from bacterial sonicates using a NI-NTA (Qiagen) column. Thrombin digest removed the His-tag and the protein was passed over another NI-NTA column and a benzamidine-Sepharose (Pharmacia) column. The final purification step used a Superdex 200 16/60 (Pharmacia) column.

Crystallization. CHS crystals (wild-type and $C_{164}S$ mutant; see SEQ ID NO:1) were grown by vapor diffusion at 4° C. in 2 µl drops containing a 1:1 mixture of 25 mg/ml protein and crystallization buffer (2.2-2.4 M ammoniumsulfate and 0.1 M PIPES, pH 6.5) in the presence or absence of 5 mM DIT. Prior to freezing at 105° K, crystals were stabilized in 40% (v/v) PEG400, 0.1 M PIPES (pH 6.5), and 0.050-0.075 M ammonium sulfate. This cryoprotectant was used for heavy atom soaks. Likewise, all substrate and product analog complexes were obtained by soaking crystals in cryoprotectant containing 10-20 mM of the compound.

STS from *Pinus sylvestris* (SEQ ID NO:65) was crystallized using 13-14% PEG 8000, 0.3M ammonium acetate, 0.1M HEPES buffer (pH 7.4) at 4° C. Crystals were soaked for 60 seconds in the same solution plus 10% glycerol.

STS from *Arachis hypogaea* (SEQ ID NO:66) was crystallized using 14% PEG 8000, 0.1M MOPSO buffer (pH 7.0), with 3% ethylene glycol at 4° C. Crystals were soaked for 30 seconds in the same solution plus 10% ethylene glycol. 18×CHS mutant (SEQ ID NO:67) was crystallized using 21% PEG 8000, 0.3M ammonium acetate, 0.1M HEPES buffer (pH 7.5) at 4° C. Crystals were soaked for 60 seconds in the same solution plus 10% glycerol.

Data Collection and Processing, X-ray diffraction data were collected at 105° K using a DIP2000 imaging plate system (Mac-Science Corporation, Japan) and CuK radiation produced by a rotating anode operated at 45 kV and 100 mA and equipped with double focusing Pt/Ni coated mirrors. Native CHS crystals belong to space group $P3_221$ with unit cell dimensions of a=b=97.54 Å; c=65.52 Å with a single monomer per asymmetric unit. Data were indexed and integrated using DENZO (Otwinowski & Minor, *Meth. Enzymol.* 276:307-326, 1997) and scaled with SCALEPACK (Otwinowski & Minor, *Meth. Enzymol.* 276:307-326, 1997). The heavy atom derivative datasets were scaled against the native dataset with SCALEIT (CCP4 Suite: Programs for protein crystallography, *Acta Crystallogr.* D 50:760-763, 1994).

Structure determination. MIRAS was used to solve the structure of native CHS (SEQ ID NO:1) using native data set 1 (1.8 Å). Initial phasing was performed with derivative datasets including reflections to 2.3 Å resolution. Heavy atom positions for the $Hg(OAc)_2$ derivative were estimated by inspection of difference Patterson maps using the program XTALVIEW (McRee, *J. Mci. Graph.* 10:44-46, 1992) and initially refined with MLPHARE (Otwinowski, Z. in CCP4 Proc. 80-88, Daresbury Laboratory, Warrington, UK, 1991). Heavy atom positions for the additional derivative data sets were determined by difference Fourier analysis using phases calculated from the $Hg(OAc)_2$ data set and the Hg positions. These sites were confirmed by inspection of difference Patterson maps. Final refinement of heavy atom parameters, identification of minor heavy atom binding sites, and phase-angle calculations were performed with the program SHARP (de La Fortelle, & Bricogne, Meth. Enzymol. 276:472-494, 1997). MIRAS phases were improved and extended to 1.8 Å by solvent flipping using the CCP4 program SOLOMON (Abrahams and Leslie, *Acta Crystallogr.* D 52:30-42, 1996).

Model building and refinement The program O (Jones, et al., *Acta Crystallogr.* D 49:148-157, 1993) was used for model building and graphical display of the molecules and electron-density maps. The experimental map for the native 1 dataset at 1.8 Å was of high quality and allowed unambiguous modeling of residues 3 to 389. The model was first refined with REFMAC (Murshudov, et al., *Acta Crystallogr.* D 53:240-255, 1997) and ARP (Lamzin and Wilson, *Acta Crystallogr.* D 49:129-147, 1993) against the native 1 dataset. This was followed by manual adjustments using $I2F_o-F_c1$ difference maps. Water molecules introduced by ARP were edited using the $I2F_o-F_c1$ and $IF_o-F_c1$ maps. A second refinement with SHELX-97 (Sheldrick & Schneider, Meth. Enzymol. 277:319-343, 1997) was then carried out against the native 2 data set to 1.56 Å resolution. Structures of CHS complexed with naringenin and resveratrol and the $C_{164}S$ mutant complexed with malonyl- and hexanoyl-CoA were obtained using difference Fourier methods and were refined with REFMAC and ARP. All structures were checked with PROCHECK (Laskowski, et al., *J. Appl Crystallogr.* 26:283-291, 1993). 91.3% of the residues in CHS are in the most favored regions of the Ramachandran plot, 8.4% in the additional allowed region, and 0.3% in the generously allowed region.

Three Dimensional Structure Determination and Description

Recombinant alfalfa CHS2 was expressed in *E. coli*, affinity purified using an N-terminal poly-His linker, and crystallized. The structure of wild-type CHS was determined using multiple isomorphous replacement supplemented with anomalous scattering (MIRAS). The final 1.56 Å resolution apoenzyme model of CHS included 2982 protein atoms and 355 water molecules. In addition, the structures of a series of complexes were obtained by difference Fourier analysis. First, a crystal of a mutant ($C_{164}S$) was soaked with malonyl-CoA. This mutant retains limited catalytic activity, and the resulting acetyl-CoA complex yields insight on the decarboxylation reaction. The same mutant was also complexed with hexanoyl-CoA to mimic the structure of a linear polyketide-CoA reaction intermediate. Finally, two product analogs, naringenin and resveratrol (see FIG. 1) were complexed with CHS to provide information on how the enzyme governs sequential addition of acetates to the coumaroyl moiety and how CHS controls the stereochemistry of the polyketide cyclization reaction. In plants, chalcone isomerase rapidly and stereospecifically converts chalcone to naringenin ((-)(2S)-5,7,4'-trihydroxyflavanone) through an additional ring closure. This reaction also occurs at a slower rate and non-stereospecifically in solution. As such, naringenin provides a suitable mimic of the CHS reaction product. Finally, since STS uses the same substrates as CHS but a different cyclization pathway for the biosynthesis of resveratrol, resveratrol was also soaked into CHS to investigate the structural features governing cyclization of the same substrates into two different products.

CHS functions as a homodimer of two 42 kDa polypeptides. The structure of CHS revealed that the enzyme forms a symmetric dimer with each monomer related by a 2-fold crystallographic axis (see FIG. 2). The dimer interface buries approximately 1580 Å$^2$ with interactions occurring along a fairly flat surface. Two distinct structural features delineate the ends of this interface. First, the N-terminal helix of monomer A entwines with the corresponding helix of monomer B. Second, a tight loop containing a cis-peptide bond between $Met_{137}$ and $Pro_{138}$ exposes the methionine sidechain as a knob on the monomer surface. Across the interface, $Met_{137}$ protrudes into a hole found in the surface of the adjoining monomer to form part of the cyclization pocket.

Each CHS monomer consists of two structural domains. The upper domain exhibits an xBxBx pseudo-symmetric motif originally observed in thiolase from *Saccharomyces cerevisiae* (Mathieu, et al, Structure 2:797-808, 1994). The upper domains of CHS and thiolase are superimposeable with a r.m.s. deviation of 3.3 Å for 266 equivalent C-atoms. Both enzymes use a cysteine as a nucleophile and shuttle reaction intermediates via CoA molecules. However, CHS condenses a p-coumaroyl- and three malonyl-CoA molecules through an iterative series of reactions, whereas thiolase generates two acetyl-CoA molecules from acetoacetyl-CoA and free CoA. The drastic structural differences in the lower domain of CHS create a larger active site than that of thiolase and provide space for the polyketide reaction intermediates required for chalcone formation.

The CHS homodimer contains two functionally independent active sites. Consistent with this information, bound CoA thioesters and product analogs occupy both active sites of the homodimer in the CHS complex structures. These structures identify the location of the active site at the cleft between the upper and lower domains of each monomer. Each active site consists almost entirely of residues from a single monomer with $Met_{137}$ from the adjoining monomer being the only exception. There are remarkably few chemically reactive residues in the active site. Four residues conserved in all the known CHS-related enzymes ($Cys_{164}$, $Phe_{215}$, $His_{303}$, and $Asn_{336}$) define the active site. $Cys_{164}$ apparently serves as the nucleophile and as the attachment site for polyketide intermediates as previously suggested for both CHS and STS (Lanz, et al, J. Biol. Chem. 266:9971-9976, 1991). $His_{303}$ most likely acts as a general base during the generation of a nucleophilic thiolate anion from $Cys_{164}$, since the Nγ of $His_{303}$ is within hydrogen bonding distance of the sulfur of $Cys_{164}$. $Phe_{215}$ and $Asn_{336}$ may function in the decarboxylation reaction, as discussed below. Topologically, three interconnected cavities intersect with these four residues and form the active site architecture of CHS. These cavities include a CoA-binding tunnel, a coumaroyl-binding pocket, and a cyclization pocket.

The CoA-binding tunnel is 16 angstroms long and links the surrounding solvent with the buried active site. Binding of the CoA moiety in this tunnel positions substrates at the active site, as observed in the $C_{164}S$ mutant (described in greater detail below) complexed with malonyl- or hexanoyl-CoA. The conformation of the CoA molecules bound to CHS resembles that observed in other CoA binding enzymes. The adenosine nucleoside is in the 2'-endo conformation with an anti-glycosidic bond torsion angle. At the tunnel entrance, $Lys_{55}$, $Arg_{58}$, and $Lys_{62}$ hydrogen bond with two phosphates of CoA. Apart from these interactions, and an additional hydrogen bond between the backbone amide nitrogen of $Ala_{308}$ and the first carbonyl of the pantetheine moiety, van der Waals contacts dominate the remaining interactions between CHS and CoA. The pantetheine arm of the CoA extends into the enzyme positioning the terminally bound thioester-linked substrates near $Cys_{164}$.

Both naringenin and resveratrol bind at the active site end of the CoA-binding tunnel. The interactions observed in the naringenin and resveratrol complexes define the coumaroyl-binding and cyclization: pockets. The space to the lower left of the CoA-binding tunnel's end serves as the coumaroyl-binding pocket. Residues of this pocket ($Ser_{133}$, $Glu_{192}$, $Thr_{194}$, $Thr_{197}$, and $Ser_{338}$) surround the coumaroyl-derived portion of the bound naringenin and resveratrol molecules and interact primarily through van der Waals contacts. However, the carbonyl oxygen of $Gly_{216}$ hydrogen bonds to the phenolic oxygen of both naringenin and resveratrol and the hydroxyl of $Thr_{197}$ interacts with the carbonyl of naringenin derived from coumaroyl-CoA. The identity of the residues in this pocket likely contributes to the preference for coumaroyl-CoA as a substrate for parsley CHS over other cinnamoyl-CoA starter molecules, like caffeoyl- or feruloyl-CoA.

In both the naringenin and resveratrol complexes, the malonyl-derived portion of each molecule occupies a large pocket adjacent to Cys164 suggesting this is where the polyketide reaction intermediate cyclizes into the new ring system and where aromatization of the ring occurs. The six-carbon chain of hexanoyl-CoA also binds in this pocket. Physically, the size of the pocket limits the number of acetate additions to three. $Phe_{265}$ separates the coumaroyl-binding site from the cyclization pocket and may function as a mobile steric gate during successive rounds of polyketide elongation. Although a polyketide possesses a number of hydrogen bond acceptors through which specific interactions could aid in proper folding for the cyclization reaction, the residues of the cyclization pocket, including $Thr_{132}$, $Met_{137}$, $Phe_{215}$, $Ile_{254}$, $Gly_{256}$, $Phe_{265}$, and $Pro_{375}$, provide few potential hydrogen bond donors. As in the coumaroyl-binding pocket, van der Waals contacts dominate the interaction between CHS and both naringenin and resveratrol. Thus, the surface topology of the cyclization pocket dictates how the malonyl-derived portion of the polyketide is folded and how the stereochemistry of the cyclization reaction leading to chalcone formation in CHS and resveratrol formation in STS is controlled.

Reaction Mechanism

Figure 6A:
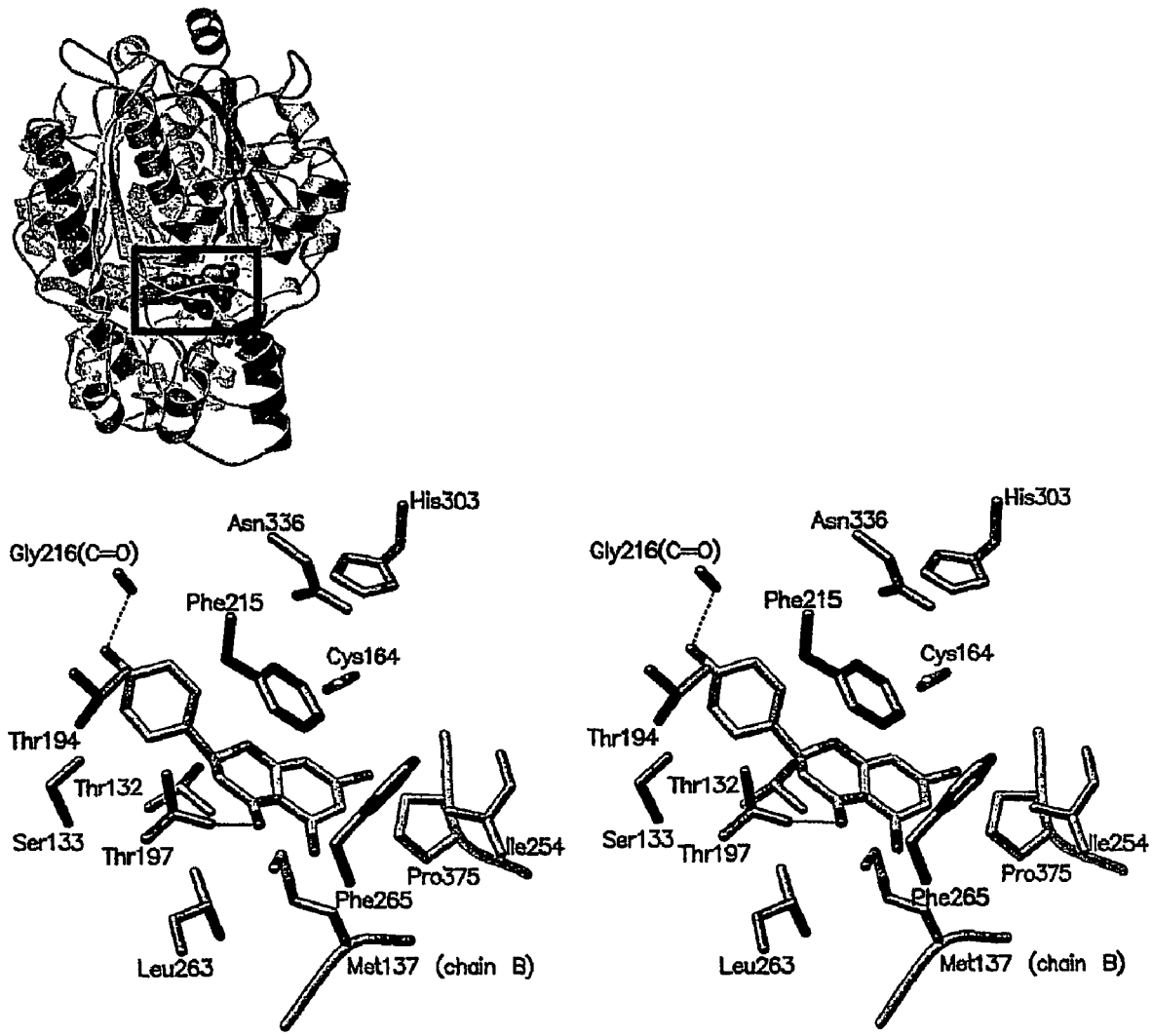
FIG. 6A shows the CHS-naringenin complex viewed down the CoA-binding tunnel. The ribbon diagram at the top left has been rotated 90 degrees around the y-axis from the orientation shown in FIG. 3. This view approximates the global orientation of the CHS dimer used for the close-up view of the naringenin binding site depicted in stereo. Again, the black box highlights the region of CHS shown in stereo close-up. Hydrogen bonds are depicted as dashed cylinders.
Figure 6B:
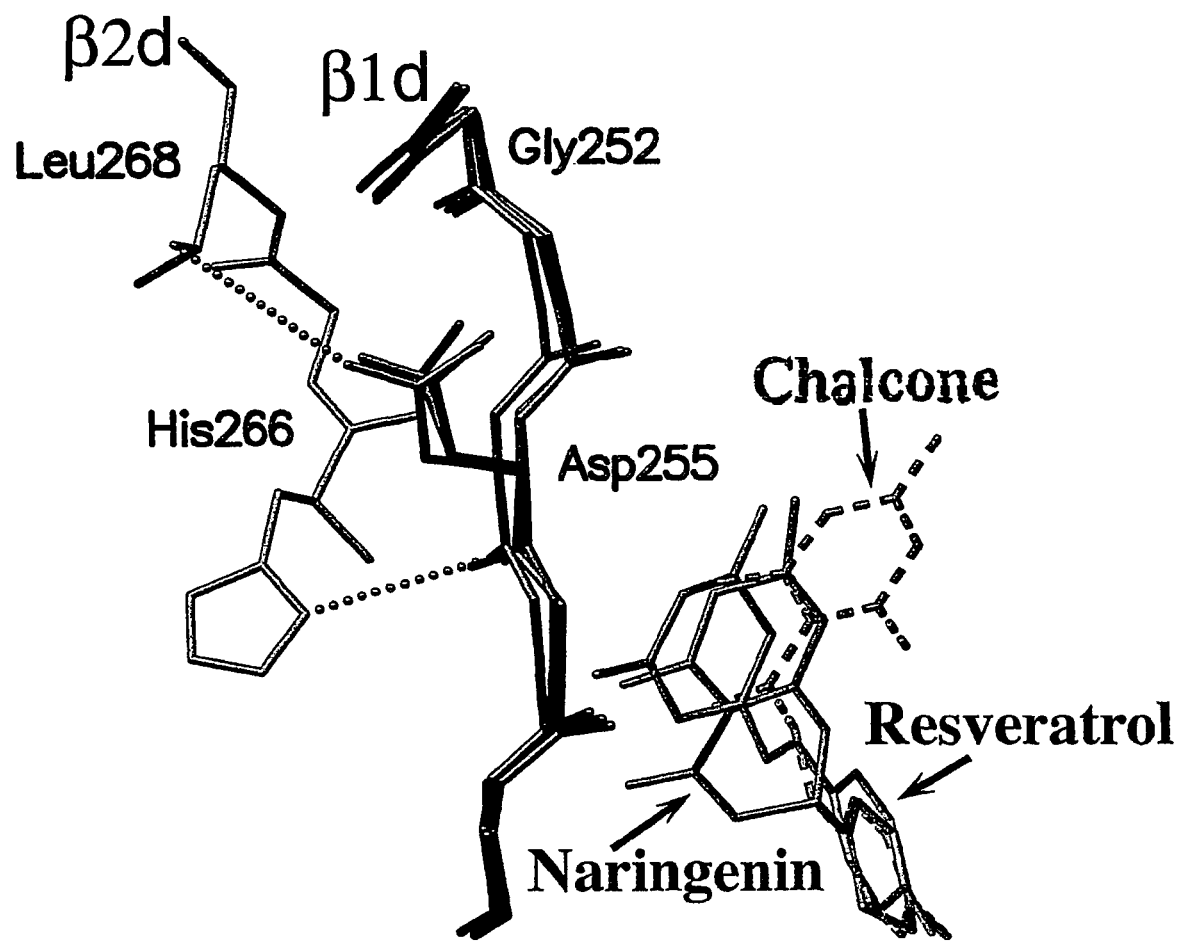
FIG. 6B illustrates a comparison of the CHS apoenzyme, CHS-naringenin, and CHS-resveratrol structures. Protein backbone atoms for the three refined structures (apoenzyme, naringenin, and resveratrol) were superimposed by least squares fit in O. The position of bound naringenin and resveratrol are shown. For reference, a modeled low energy conformation of chalcone is indicated by dashed cylinders. Strands β1d and β2d for each complex are also depicted (see FIG. 4). β2d does not change in all the complexes examined, but β1d moves in the CHS-resveratrol complex.

The position of the CoA thioesters and product analogs in the CHS active site suggest binding modes for substrates and intermediates in the polyketide elongation mechanism that are consistent with the known product specificity of CHS. In addition, the stereochemical features of the substrate and product analog complexes elucidate the roles of $Cys_{164}$, $Phe_{215}$, $His_{303}$, and $Asn_{336}$ in the reaction mechanism. Utilizing structural constraints derived from the available complexes, the following reaction sequence is proposed (see FIG. 6).

In the mechanism, binding of p-coumaroyl-CoA initiates the CHS reaction. Functional and structural evidence supports a coumaroyl-first mechanism over a malonyl-first one. Cerulenin, a potent irreversible inhibitor of CHS, covalently modifies $Cys_{164}$ in CHS (Lanz, et al., J. Biol. Chem. 266: 9971-9976, 1991). Preincubation of CHS with coumaroyl-CoA prevents inactivation by cerulenin, but pre-incubation with malonyl-CoA does not (Preisig-Mueller, et al., Biochemistry 36:8349-8358, 1997). Also, the location of the coumaroyl-derived portion of naringenin and resveratrol in the CHS complexes agrees with a coumaroyl first mechanism, since the presence of a triketide reaction intermediate attached to $Cys_{164}$ would limit access to the coumaroyl-binding pocket.

After p-coumaroyl-CoA binds to CHS, $Cys_{164}$, activated by $His_{303}$, attacks the thioester linkage, transferring the coumaroyl moiety to $Cys_{164}$ (Monoketide Intermediate). $Asn_{336}$ hydrogen bonds with the carbonyl oxygen of the thioester further stabilizing formation of the tetrahedral reaction intermediate. CoA then dissociates from the enzyme, leaving a coumaroyl-thioester at $Cys_{164}$. Binding of the first malonyl-CoA positions the bridging methylene carbon of the malonyl moiety near the carbonyl carbon of the covalently attached coumaroyl-thioester. Decarboxylation of malonyl-CoA leads to carbanion formation. Resonance between the keto and enol species stabilizes the carbanion. Attack of this carbanion on the coumaroyl-thioester releases the thiolate anion of $Cys_{164}$ and transfers the coumaroyl group to the acetyl moiety of the CoA thioester (Diketide CoA Thioester). Capture of this elongated diketide-CoA by $Cys_{164}$ and release of CoA sets the stage for two additional rounds of elongation resulting in formation of the tetraketide reaction intermediate.

$Asn_{336}$ appears to play a crucial role in the decarboxylation reaction. Structural evidence shows that the decarboxylation reaction does not require transfer of the malonyl moiety to $Cys_{164}$ as originally indicated by $CO_2$ exchange assays. Decarboxylation occurs without $Cys_{164}$, since the $C_{164}S$ mutant produces acetyl-CoA as determined crystallographically and confirmed by a functional assay. In the hexanoyl-CoA complex, the side chain amide of $Asn_{336}$ provides a hydrogen bond to the carbonyl oxygen of the thioester. This interaction would stabilize the enolate anion resulting from decarboxylation of malonyl-CoA (see FIG. 6). At the same time, the lack of formal positive charge at $Asn_{336}$ may preserve the partial carbanion character of this resonance-stabilized anion, and thus the nucleophilicity of the carbanion form.

The role of $Phe_{215}$ in the catalytic mechanism is subtler than that of $Asn_{336}$. Its position in both CoA complexes suggests that it provide van der Waals interactions for substrate binding. However, its conservation in bacterial enzymes related to CHS that do not make flavonoids or stilbenes may indicate a more general catalytic role for $Phe_{215}$. Its position near the acetyl moiety of the malonyl-CoA complex suggests that it participates in decarboxylation by favoring conversion of the negatively charged carboxyl group to a neutral carbon dioxide molecule.

Figure 7:
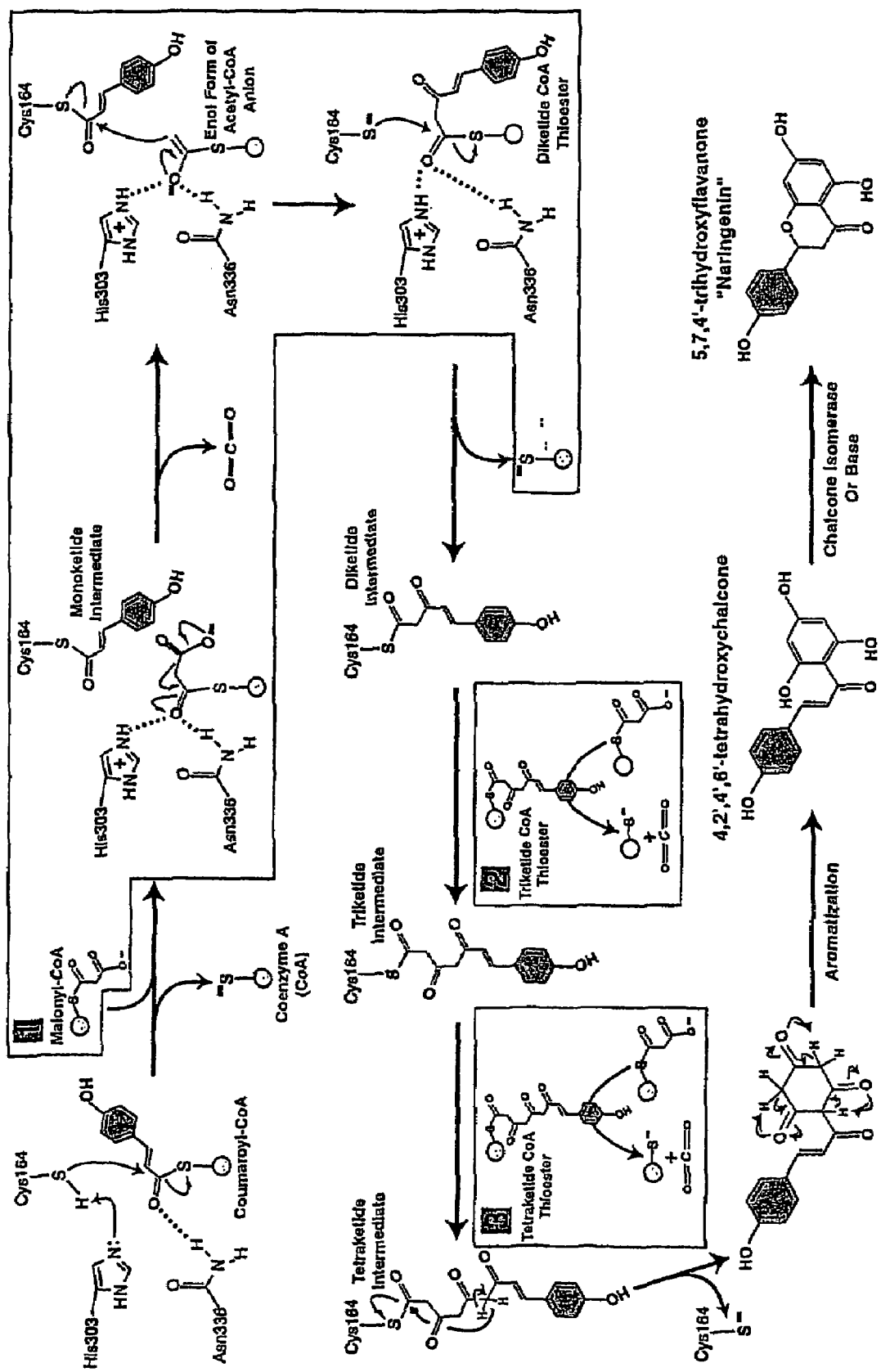
FIG. 7 presents the proposed reaction mechanism for chalcone synthesis. The three boxed regions labeled 1, 2, and 3 depict the addition of acetate units derived from malonyl-CoA during the elongation of polyketide intermediates. Box 1 is depicted in expanded fashion to illustrate the mechanistic details governing the decarboxylation, enolization, and condensation phase of ketide elongation. Smaller black arrows depict the flow of electrons. Each acetate unit of the malonyl-CoA thioesters is coded to emphasize the portions of chalcone derived from each of three elongation reactions using malonyl-CoA. Cyclization and aromatization of the enzyme bound tetraketide leads to formation of chalcone. Hydrogen bonds are shown as dashed lines. Coenzyme A is symbolized as a circle.

FIG. 7A depicts the addition of the third malonyl-CoA molecule as a three-dimensional model. The position of the coumaroyl ring in the modeled triketide intermediate is as observed in the naringenin and resveratrol complexes. The coumaroyl-binding pocket locks this moiety in position, while the acetate units added in subsequent chain extension steps bend to fill the cyclization pocket. The backbone of bound hexanoyl-CoA provides a guide for modeling the triketide reaction intermediate attached to $Cys_{164}$. Based on the observed acetyl-CoA complex, a rotation of the acetyl group would place the terminal methylene of the decarboxylated malonyl-CoA in position for nucleophilic attack on the triketide thioester linkage resulting in formation of a tetraketide CoA thioester.

The cyclization reaction catalyzed by CHS is an intramolecular Claisen condensation encompassing the three acetate units derived from three malonyl-CoAs. During cyclization, the nucleophilic methylene group nearest the coumaroyl moiety attacks the carbonyl carbon of the thioester linked to $Cys_{164}$. Ring closure proceeds through an internal proton transfer from the nucleophilic carbon to the carbonyl oxygen. Modeling of the tetraketide intermediate in a conformation leading to chalcone formation places one of the acidic protons of the nucleophilic carbon (C6) proximal to the target carbonyl (C1) (see FIG. 7B). Since there is no base capable of proton abstraction from the tetraketide, it is proposed that the intermediate itself provides the driving force for carbanion formation. Protonation of the carbonyl oxygen would also stabilize the negative charge on the tetrahedral intermediate. Breakdown of this tetrahedral intermediate expels the newly cyclized ring system from $Cys_{164}$. Subsequent aromatization of the trione ring through a second series of facile internal proton transfers yields chalcone.

Although the cyclization reaction has been modeled as occurring via a polyketide intermediate attached to $Cys_{164}$, it is possible that the reaction proceeds when the polyketide is attached to CoA. The rate of cyclization versus the rate of reattachment to $Cys_{164}$ would dictate which of the two cyclization alternatives is mechanistically preferred.

An important question in the biosynthesis of chalcones concerns the exchangeability of the polyketide reaction intermediates. In the presence of chalcone reductase (CHR), CHS produces 6-deoxychalcone (Welle & Grisebach, FEBS Lett. 236:22-225, 1988). Mechanistically, CHR must reduce a ketone on the polyketide intermediate before cyclization occurs. Based on the CHS structure, any polyketide attached to $Cys_{164}$ would be inaccessible to CHR unless a drastic structural change occurs in CHS upon interaction with CHR. While this conformational change is possible, such a change is difficult to imagine given the buried nature of the CHS active site. This would argue for the presence of moderately exchangeable polyketide-CoA reaction intermediates. Consistent with this idea, a recently identified CHS-like enzyme from *Pinus strobus* involved in the biosynthesis of C-methylated chalcones is active only with a starter molecule that is sterically analogous to the diketide-CoA intermediate postulated to be formed after the first condensation reaction in CHS30. These results suggest that the enzymes involved in the biosynthesis of plant polyketides may require specific localization in the plant cell to allow efficient channeling of intermediates from one enzyme to another during the production of particular products.

Cyclization Specificity of CHS and STS

Elucidation of the structure of CHS provided mechanistic insight and active site configuration for CHS reaction. Homology modeling and sequence alignments suggested evolutionary functional divergence of CHS superfamily (type III PKSs) occurs via the preservation of catalytic residues while using steric variation of other active site residues. Elucidation of the structure of 2-PS confirms the above 'steric modulation' model, by revealing substrate and product specificity differences achieved by only three active site mutations, as suggested by homology model of 2-PS based upon CHS 3D structure.

However, with these structures alone, the structural cause/determinants of the alternate cyclization seen in the stilbene synthase (STS) subfamily of CHS-like enzymes remained unknown. STS makes the same tetraketide intermediate as CHS, but cyclizes it differently (C2->C7 attack instead of C6->C1). STS evolved from CHS independently at least three times, with no clear STS consensus sequence.

Figure 18:
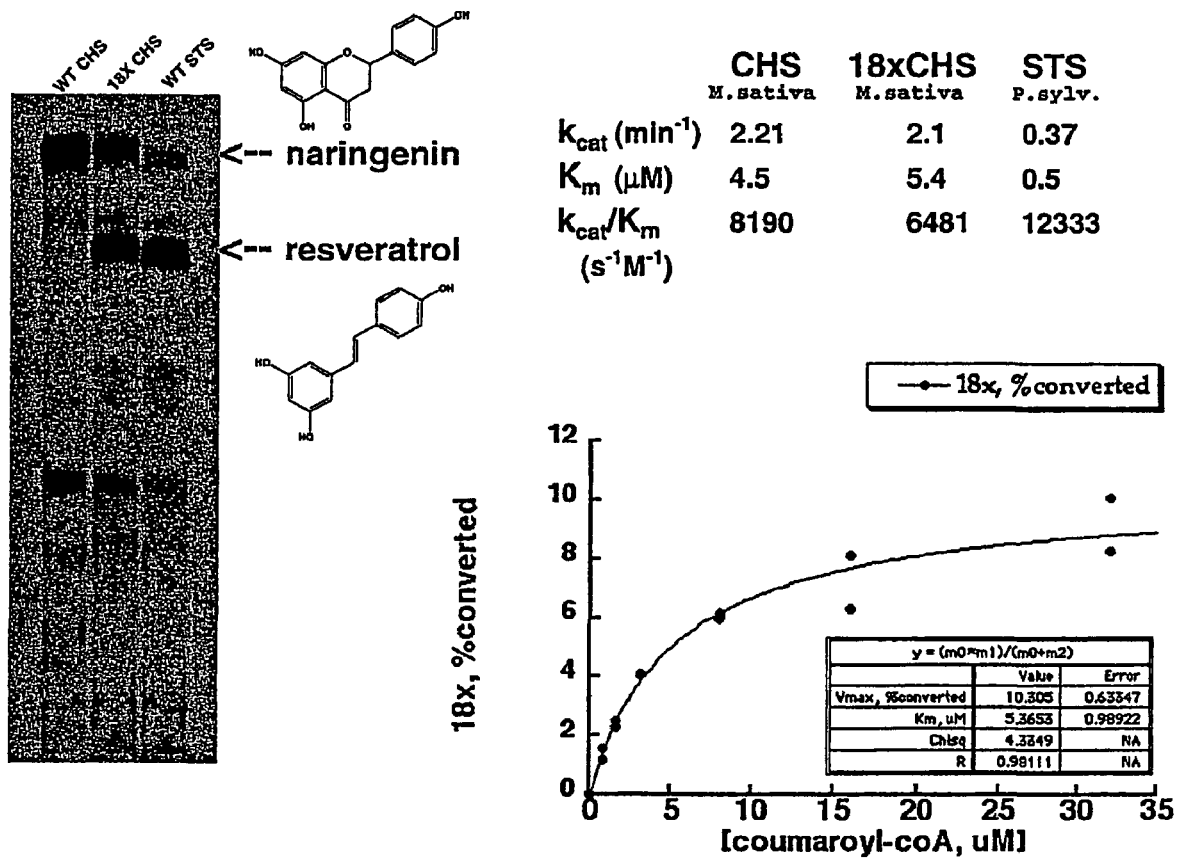
FIG. 18 shows the kinetics of the 18xCHS in comparison to the wild type CHS and STS.

Elucidation of the structure of pine (*Pinus sylvestris*) STS according to the present invention reveals a similar active site configuration, with minor differences. Furthermore, an 18×CHS mutant encompassing observed STS structural backbone differences proves to have activity and kinetics similar to STS (see FIG. 18), confirming that observed structural differences between CHS and STS are relevant to mechanistic differences.

Figure 19:
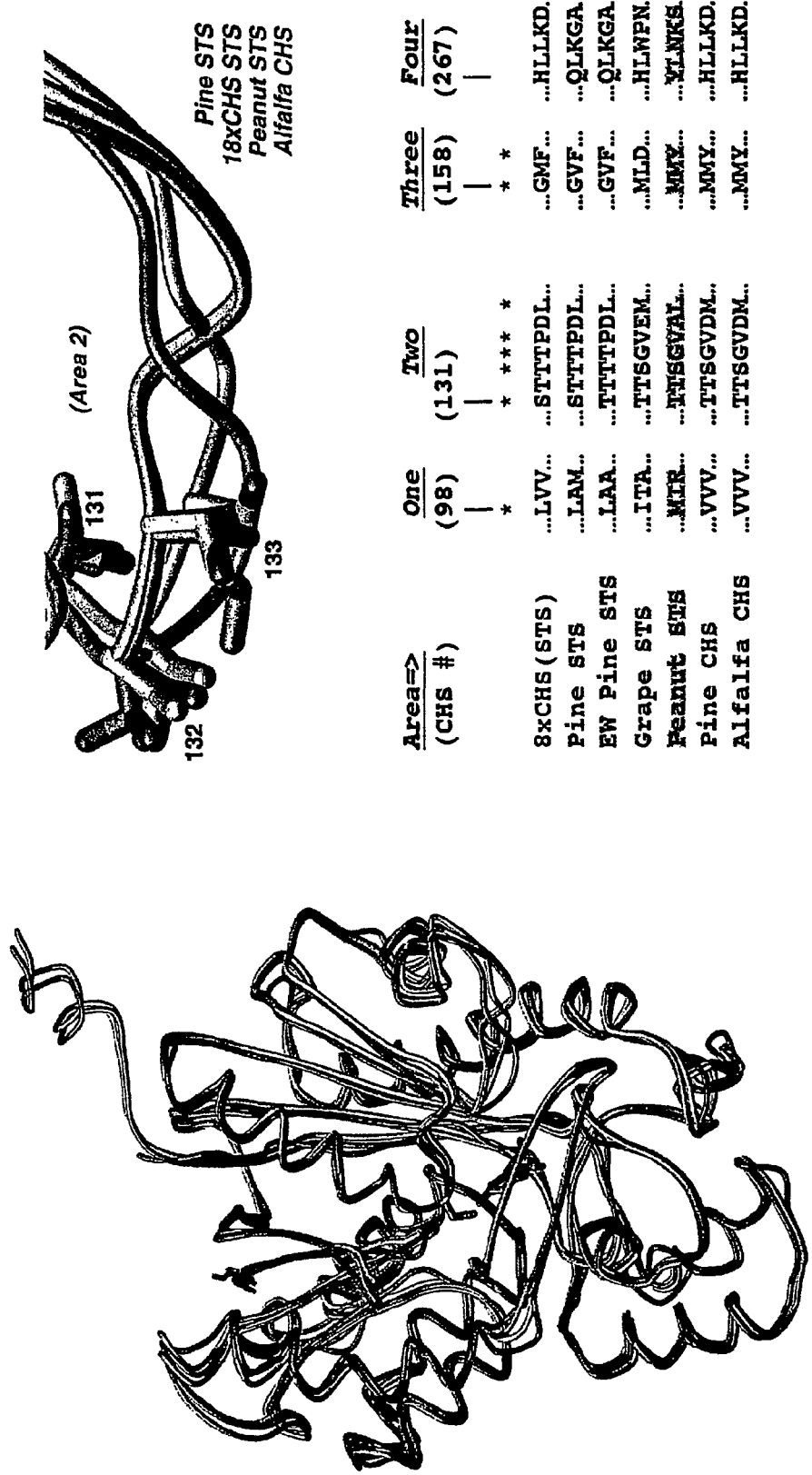
FIG. 19 (SEQ ID NOS 51-57, respectively in order of appearance on the left, and SEQ ID NOS 58-64, respectively in order of appearance on the right) shows a comparison of the crystal structures of the wild type CHS (alfalfa), two types of STS (pine and peanut) and the 18×CHS mutant. Areas A1 to A4 are as indicated in FIG. 14. A comparison of the amino acid sequence in these areas is also provided. The stars indicated the residues mutated in the 8×CHS mutant.

It was further determined that ten of the eighteen mutations in 18×CHS prove to be neutral (not related to functional conversion, i.e. an alteration in CHS activity), and an 8×CHS mutant with similar STS-like activity is made. All of the 8×CHS changes are clustered in a single area, although encoded on three different stretches of primary sequence (see FIG. 19). This area is thus implicated as important for STS-like versus CHS-like cyclization.

Figure 20:
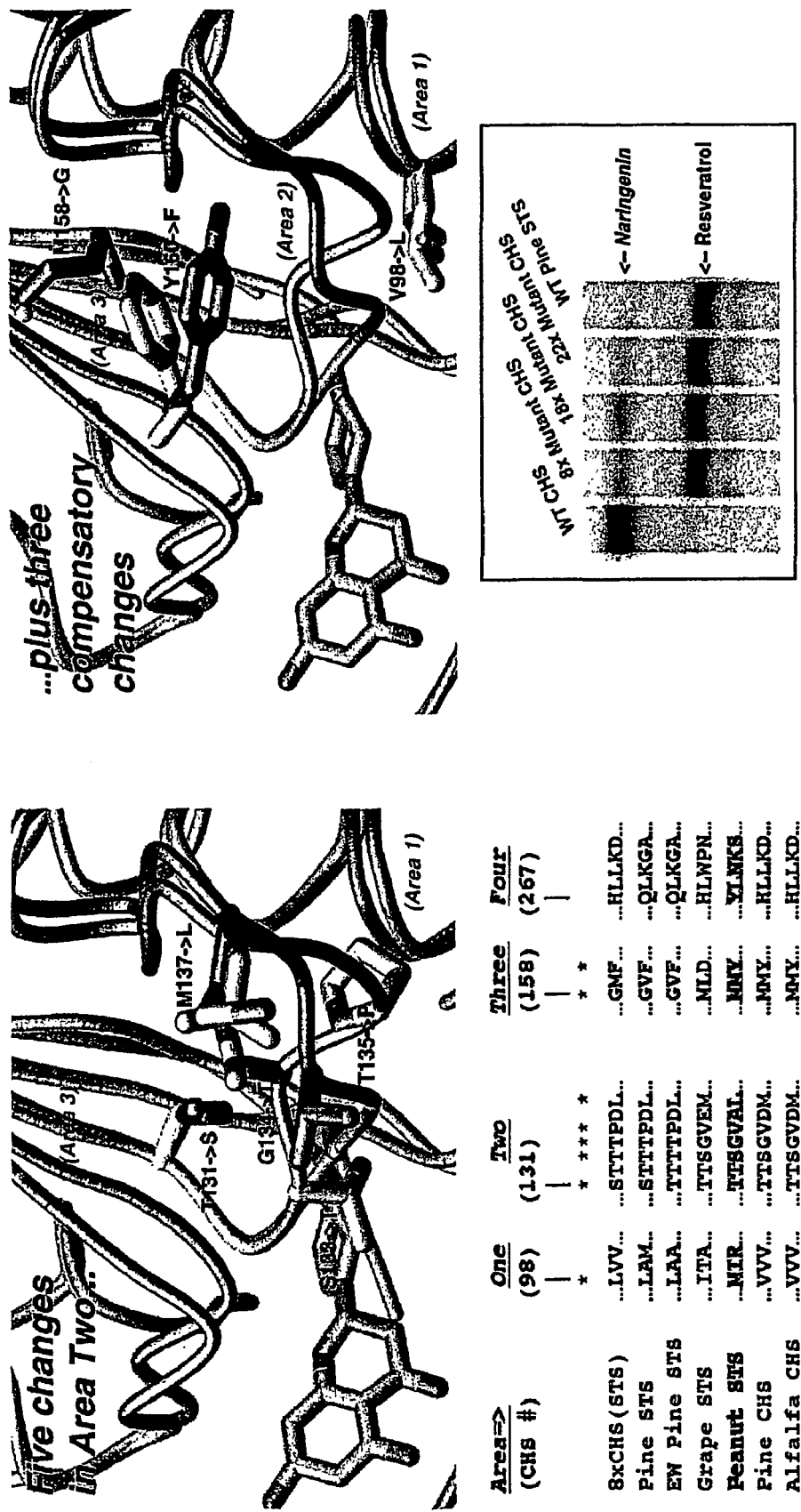
FIG. 20 (SEQ ID NOS 51-57, respectively in order of appearance on the left, and SEQ ID NOS 58-64, respectively in order of appearance on the right), shows that the 8×CHS mutant has activity that is similar to the 18×CHS mutant, i.e. an alteration of the CHS activity to an STS-like activity. The 8×CHS mutant contains five mutations in Area A2 and three additional changes in Areas A1 and A3. The mutations in the 8×CHS are a subset of the mutations in the 18×CHS mutant, eliminating 10 neutral mutations found in the 18CHS mutant.

Elucidation of the structure of peanut (*Arachis hypogaea*) STS, as well as of the 18×CHS engineered STS, show similar three-dimensional conformational changes in the area implicated by the 8×CHS mutagenic conversion of CHS to STS (see FIG. 20). This implies that a single 3D solution to the CHS to STS conversion problem has been found by all three STS subfamilies, despite variation in primary sequence. A compensatory increase in bulkiness at CHS residue 98 seems to be involved in all three families of STS.

Figure 21:
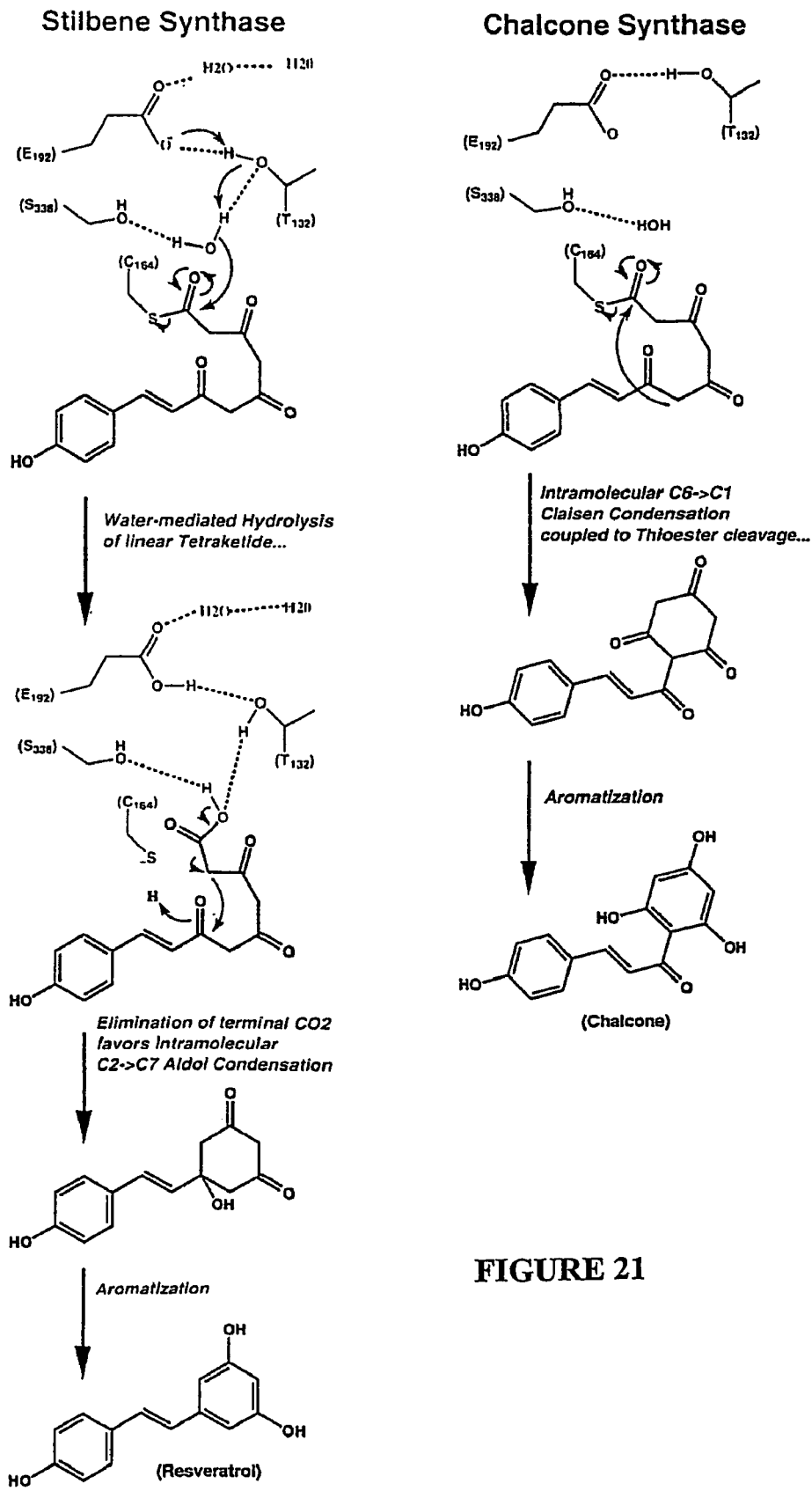
FIG. 21 shows the proposed mechanism of cyclization specificity in STS as compared to CHS, which results in the different end-products. STS elimination of terminal $CO_2$ favors intramolecular C2 to C7 Aldol Condensation, while CHS causes intramolecular C6 to C1 Claisen Condensation coupled to thioester cleavage.

A closer look at where the altered region meets the active site (see FIG. 22) reveals a consistent change in STS-like enzymes that suggests a cyclization switch mechanism (see FIG. 21), involving movement of Thr132 to allow a hydrogen-bond chain to transfer an electron from Glu192, through Thr132 and a water (bonded to Ser 338). This electron is proposed to encourage hydrolysis of the tetraketide intermediate off of the catalytic cysteine, where decarboxylation of the terminal carboxyl group drives the STS reaction toward a C2->C7 cyclization. In CHS, this hydrolysis does not occur, and so the C6->C1 cyclization is encouraged, as it serves to break the thioester bond to cysteine.

To test this proposed mechanism, various mutations were made in the 18×CHS engineered STS enzyme, in an attempt to revert the product specificity back to that of CHS, without reversing the other structural changes. Single mutations designed to disrupt only the hydrogen-bonding character in the relevant region succeeded in reverting 18CHS's activity from STS-like to CHS-like. A few of these mutants produce almost equal amounts of resveratrol and chalcone, which might be useful when engineered into a plant. This way, the beneficial resveratrol antifungal natural product could be made, without completely abrogating the vital CHS-like activity necessary in plants.

The residue implicated as the crucial base for STS-like behavior (Glu192) is not altered in STS. Instead, the adjacent Thr132 changes positions. As a further test of the proposed aldol mechanism, the residue equivalent to CHS Glu192 was mutated to Gln in both the pine and peanut STS wild type enzymes. As predicted, both of these single mutants made more chalcone and less resveratrol than the wild type STS enzymes. The ratio of products supports the proposed mechanism. The decrease in overall activity of these mutants is due to the fact that Glu192 is also important for folding and/or stability, apart from its role in cyclization specificity.

Structural Basis for Functionally Novel CHS-like Enzymes

Absolute conservation of $Cys_{164}$, $Phe_{215}$, $His_{303}$, and $Asn_{336}$ occurs in CHS-like sequences, including several bacterial proteins possessing very low (typically 20-30%) amino acid sequence identity. Moreover, all CHS-like proteins exhibit strong conservation of residues shaping the geometry of the active site. Although the functions of the bacterial CHS-like proteins remain unknown, these enzymes likely form polyketides or polyketide-CoA thioesters in a manner resembling CHS. However, steric differences resulting from sequence variation in both the coumaroyl-binding pocket and the cyclization pocket strongly suggest alternate substrate and product specificity in the bacterial enzymes.

The sequence databases include approximately 150 plant enzyme sequences classified as CHS like proteins. The substrate and product specificity of a majority of these sequences remains to be determined. In addition, the high sequence similarity of all plant sequences complicates classification of these sequences as authentic CHS, STS, ACS, or BBS enzymes. The information provided by the three-dimensional structure of CHS should make new substrate and product specificity more readily discernible from sequence information.

Figure 8:
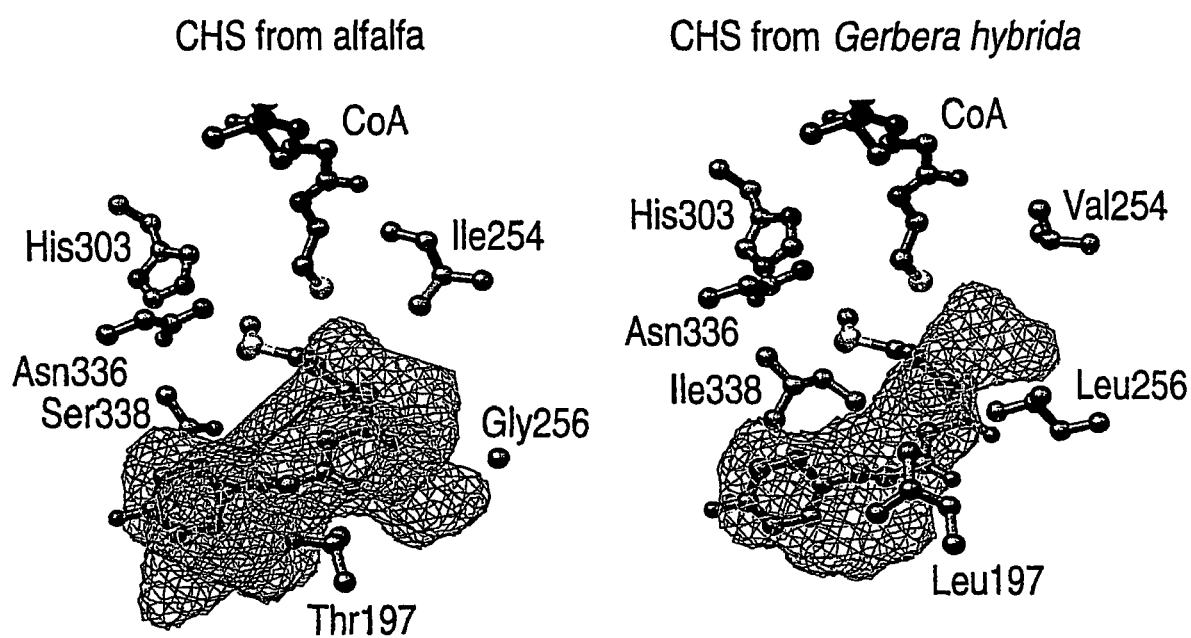
FIG. 8 presents a comparison of the active site volumes of CHS from alfalfa and CHS from *Gerbera hybrida*. The active site volumes available for binding ketide intermediates were calculated with VOID00 for the CHS-COA complex and for a homology model of GCHS2 with CoA. The cavities are shown as a wire mesh. The homology model of GCHS2 was generated using MODELER and the volume calculated and displayed as for CHS. The numbering scheme is for alfalfa CHS homodimer. Figure prepared with MOL-SCRIPT and rendered with POV-Ray.

To illustrate the usefulness of structural information in identifying potentially new activities, a CHS-related sequence from *Gerbera hybrida* (GCHS2)32 that is 74% identical with alfalfa CHS2 (SEQ ID NO:1) was examined. Modeling the active site architecture of GCHS2 using the structure of alfalfa CHS2 as a template indicates that GCHS2 will not catalyze either the CHS-like or STS-like reaction (see FIG. 8). This variation in reaction specificity results from striking steric differences in the coumaroyl binding and cyclization pockets that substantially reduce the volume of both pockets from 923 $Å^3$ in CHS to 269 $Å^3$ in GCHS2. Side chain variation at positions 197 and 338 (see SEQ ID NO:1) alter the coumaroyl binding pocket, while the identity of residue 256 (see SEQ ID NO:1) dictates major steric changes in the cyclization pocket. The reduced size of these pockets in GCHS2 suggests that fewer than three acetate additions will occur, and that a CoA thioester with an acyl moiety smaller than p-coumaroyl initiates the reaction. Recent functional characterization of GCHS2 confirms this prediction and demonstrates that this enzyme uses acetyl-CoA or benzoyl-CoA and two condensation reactions with malonyl-CoA to form pyrone products (Eckermann, et al., Nature 396:397-396, 1998).

Crystallization of Additional Polyketide Synthases

Stilbene synthase from *Pinus sylvestris* (SEQ ID NO:65) was overexpressed in *E. coli* as an octahistidyl N-terminal fusion protein, purified to >90% homogeneity by metal affinity and gel filtration chromatography, and crystallized in the preparation lacking the N-terminal polyhistidine tag (removed by thrombin cleavage) from 13% (w/v) polyethylene glycol (PEG8000), 0.05 M MOPSO, 0.3 M ammonium acetate at pH 7.0. This STS is 396 amino acids in length and, like alfalfa CHS (SEQ ID NO:1). exists as a homodimer in solution. The structural coordinates of this pine STS are presented in Appendix A. STS from *Arachis hypogaea* (SEQ ID NO:66) was similarly expressed and crystallized. The structural coordinates of this peanut STS are presented in Appendix B.

2-Pyrone synthase (2-PS) from *Gerbera hybrida* (SEQ ID NO:68) was expressed and purified from *E. coli* in a similar manner to CHS (SEQ ID NO:1) and STS (SEQ ID NO:65). Crystals were obtained from 1.5 M ammonium sulfate, 011 M Na$^+$—succinate, 0.002 MDTTatpH 5.5.

2-Pyrone synthase (2-PS) from *Gerbera hybrida* (SEQ ID NO:68 forms a triketide from an acetyl-CoA initiator and two acetyl-CoA α-carbanions derived from decarboxylation of two malonyl-CoAs that cyclizes into the 6-methyl-4-hydroxy-2-pyrone. In comparison, alfalfa chalcone synthase 2 (SEQ ID NO:1; CHS2; 74% amino acid sequence identity to 2-PS), condenses p-coumaroyl-CoA and three acetyl-CoA α-carbanions derived from decarboxylation of three malonyl-CoAs into a tetraketide that cyclizes into chalcone. A homology model of 2-PS based on the structure of CHS (SEQ ID NO:1) suggested that the 2-PS initiation/elongation cavity is smaller than that of CHS. A smaller cavity would account for the terminal formation of a triketide intermediate prior to cyclization by 2-PS.

Expression, Purification and Crystallization of 2-PS.

2-PS was expressed in *E. coli*, purified and crystallized as described above. *Gerbera hybrida* 2-PS (SEQ ID NO:68) was expressed in *E. coli* using the pHIS8 vector and was purified as described for CHS. 2-PS crystals grew at 4° C. in hanging-drops containing a 1:1 mixture of 25 mg ml$^{-1}$ protein and crystallization buffer (1.5 M ammonium sulfate, 50 mM succinic acid (pH 5.5), and 5 mM DTT). Before freezing at 105° K, crystals (P3$_1$21; unit cell dimensions a=82.15 Å, c=241.33 Å; one 2-PS dimer per asymmetric unit) were stepped through stabilizer (50 mM succinic acid (pH 5.5), 50 mM ammonium sulfate, and 5 mM DTT) containing 5 mM acetoacetyl-CoA and increasing concentrations of glycerol (30% (v/v) final). Diffraction data were collected using a DIP2030 imaging plate system and CuK radiation produced by a rotating anode (wavelength 1.54 Å). All images were processed with DENZO/SCALEPACK (Z. Otwinowski, W. Minor, *Methods Enzymol.* 276:307 (1997)). A total of 179,623 reflections were merged to give 60,824 unique reflections (98.2% complete overall to 2.05 Å and 98.1% complete in the highest resolution shell) with an R$_{sym}$=0.042 (0.206 in the highest resolution shell) and an α/_of 21.7 (4.5 in the highest resolution shell). The structure of 2-PS complexed with acetoacetyl-CoA was determined by molecular replacement using CHS (SEQ ID NO:1) as a search model and was refined to 2.05 Å resolution. The overall fold of 2-PS is the αβαβα motif found in CHS and β-ketoacyl synthase II (KAS II). In addition, the positions of the catalytic residues of 2-PS (Cys$_{169}$, His$_{308}$, and Asn$_{341}$; see SEQ ID NO:68), CHS (Cys$_{163}$, His$_{303}$, Asn$_{336}$: see SEQ ID NO:1), and KAS II (Cys$_{163}$, His$_{303}$, and His$_{340}$) are structurally analogous. As expected from sequence homology, the structures of 2-PS and CHS are nearly identical and superimpose with a r.m.s. deviation of 0.64 Å for the two proteins' α-carbon atoms. Similar to CHS, the 2-PS dimerization surface buries 1805 Å$^2$ of surface area per monomer and a loop containing a cis-peptide bond between Met$_{142}$ and Pro$_{143}$ allows the methionine of one monomer to protrude into the adjoining monomer's active site. Thus, dimerization allows formation of the complete 2-PS active site.

Acetoacetyl-CoA is a reaction intermediate of 2-PS (SEQ ID NO:68). Electron density for the ligand is well defined in the 2-PS active site and shows that the acetoacetyl moiety extends from the CoA pantetheine arm into a large internal cavity. The electron density also reveals oxidation of the catalytic cysteine's (Cys$_{169}$) sulfhydryl to sulfinic acid (—SO$_2$H) (see SEQ ID NO:1). This oxidation state prevents formation of a covalent acetoacetyl-enzyme complex but allows trapping of the bound acetoacetyl-CoA intermediate. Extensive protein-ligand contacts position CoA at the entrance to the active site and orient the acetoacetyl moiety at the end of a 15 Å long tunnel that opens into a cavity that defines the initiation and elongation steps of polyketide formation.

The 2-PS (SEQ ID NO:68) active site cavity consists of twenty-seven residues from one monomer and Met142 from the adjoining monomer. Phe$_{220}$ and Phe$_{270}$ (see SEQ ID NO:68) mark the boundary between the CoA binding site and the initiation/elongation cavity. Near the CoA thioester, Cys$_{169}$, His$_{308}$, and Asn$_{341}$ form the catalytic center of 2-PS (see SEQ ID NO:68). These residues are conserved in all homodimeric iterative PKSs. Based on this, catalytic roles were proposed for each residue that are analogous to the corresponding residues in CHS. Cys169 (see SEQ ID NO:68) acts as the nucleophile in the reaction and as the attachment site for the elongating polyketide chain. Interaction between His$_{308}$ and Cys$_{169}$ (see SEQ ID NO:68) maintains the thiolate required for condensation of the starter molecule. His$_{308}$ and Asn341 (see SEQ ID NO:68) catalyze malonyl-CoA decarboxylation and stabilize the transition states during the condensation steps by forming an oxyanion hole that accommodates the negatively charged tetravalent transition state. Following the first condensation reaction, a diketide remains attached to Cys$_{169}$ (see SEQ ID NO:68). The second malonyl-CoA then binds, undergoes decarboxylation, and the resulting nucleophilic acetyl-coA α-carbanion performs a second condensation reaction with the enzyme bound diketide, ultimately generating the triketide that cyclizes into methylpyrone.

Comparison of the initiation/elongation cavities of 2-PS (SEQ ID NO:68) and CHS (SEQ ID NO:1) reveal four amino acid differences. In 2-PS, Leu$_{202}$, Met$_{259}$, Leu$_{261}$, and Ile$_{343}$ replace Thr$_{197}$, Ile$_{254}$, Gly$_{256}$, and Ser$_{338}$, respectively, of CHS. These four substitutions reduce cavity volume from 923 Å$^3$ in CHS to 274 Å$^3$ in 2-PS. A model of methylpyrone in the 2-PS cavity, based on the position of acetoacetyl-CoA, emphasizes the volume change compared to the CHS-naringenin complex (Accession No. 1 CGK, SEQ ID NO:69). Leu$_{202}$ and Ile$_{343}$ occlude the portion of the 2-PS cavity corresponding to the coumaroyl-binding site of CHS. Replacement of Gly$_{256}$ in CHS by Leu$_{261}$ in 2-PS severely reduces the size of the active site cavity. Substitution of Met$_{259}$ in 2-PS for Ile$_{254}$ in CHS produces a modest alteration in cavity volume. To examine the functional importance of these amino acid differences, the initiation/elongation cavity of CHS was altered by mutagenesis to resemble that of 2-PS. The resulting mutant proteins were screened for activity using either p-coumaroyl-CoA or acetyl-CoA as starter molecules. Activities of 2-PS, CHS, and the CHS mutants were determined by monitoring product formation using a TLC-based radiometric assay. Assay conditions were 100 mM Hepes (pH 7.0), 30 µM starter-CoA (either p-coumaroyl-CoA or acetyl-CoA), and 60 µM [$^{14}$C]-malonyl-CoA (50,000 cpm) in 100 µl at 25° C. Reactions were quenched with 5% acetic acid, extracted with ethyl acetate, and applied to TLC plates and developed. Due to the spontaneous cyclization of chalcone into the flavanone naringenin, activities of CHS are referenced to nanngenin formation.

The x-ray crystal structures of 2-PS (SEQ ID NO:68) and CHS (SEQ ID NO:1) imply that the size of the active site cavity limits polyketide length and modulates folding of the polyketide chain. Wild-type CHS (SEQ ID NO:1) generates the tetraketide chalcone and 2-PS produces the triketide methylpyrone. Likewise, the CHS I254M mutant (see SEQ ID NO:1) also yields chalcone. Interestingly, the T197L, G256L, and S338I mutants (see SEQ ID NO:1) do not form chalcone. Crystallographic analysis of the G256L and S338I mutants (see SEQ ID NO:1) demonstrates that the substituted side-chains adopt conformations similar to the corresponding residues in 2-PS without altering the position of the protein backbone. Since the T197L, G256L, and S338Imutants (see SEQ ID NO:1) altered product formation, a CHS triple mutant was generated. Consistent with the proposal that cavity volume dictates polyketide length, the T197L/G256L/S338I mutant (see SEQ ID NO:1) produces only methylpyrone, as confirmed by liquid chromatography/mass spectroscopy (LC/MS). LC/MS/MS analysis was performed by the Mass Spectroscopy facility of the Scripps Research Institute. Scaled-up assays (2 ml reaction volume) with the CHS T197L/G256L/S338I mutant (see SEQ ID NO:1) and 2-PS (SEQ ID NO:68) were performed. Extracts were analyzed on a Hewlett-Packard HP1100 MSD single quadrupole mass spectrometer coupled to a Zorbax SB-$C_{18}$ column (5 µm, 2.1 mm×150 mm). HPLC conditions were as follows: gradient system from 0 to 100% methanol in water (each containing 0.2% acetic acid) within 10 mm; flow rate 0.25 ml min$^{-1}$. LC/MS/MS data from both reactions were identical: 6-methyl-4-hydroxy-2-pyrone, $R_f$=5.068 mm; [M-H]$^-$125; [M-H—$CO_2$]$^{-81}$. The numbers show m/z values with relative intensities in parenthesis. The observed fragmentation matches previously published data.

In addition, the size of the cavity in 2-PS (SEQ ID NO:68) and CHS (SEQ ID NO:1) confers starter molecule specificity. 2-PS accepts acetyl-CoA but does not use p-coumaroyl-CoA. Structurally, the constricted 2-PS active site excludes the bulky coumaroyl group. As such, incubation of 2-PS in the presence of coumaroyl-CoA and malonyl-CoA yields methylpyrone produced from three malonyl-CoA molecules. In comparison, the larger initiation/elongation cavity of CHS allows for different sized aliphatic and aromatic starter molecules to be used in vitro with varying efficiencies. CHS exhibits a 230-fold preference for p-coumaroyl-CoA versus acetyl-CoA. Alterations in the active site cavity of CHS, affect starter molecule preference. The CHS I254M mutant (see SEQ ID NO:1) is functionally comparable to wild-type enzyme with a modest reduction in specific activity. The T197L and S338I mutants exhibit 10-fold and 3-fold preferences, respectively, for coumaroyl-CoA. Moreover, both form a distinct product using coumaroyl-CoA as a starter molecule. In contrast, the G256L mutant favors acetyl-CoA 3-fold. Like 2-PS (SEQ ID NO:68), the CHS T197L/G256L/ S338I (3×) mutant (see SEQ ID NO:1) only accepts acetyl-CoA (or malonyl-CoA) as the starter molecule.

Functional diversity among other homodimeric iterative PKSs, like p-coumaroyltriacetic acid synthase (CTAS), acridone synthase (ACS), and the rppA protein from *Streptomyces griseus*, likely results from variations of residues lining the initiation/elongation cavity. As demonstrated, positions 197, 256, and 338 (see SEQ ID NO:1) distinguish between tetraketide products derived from a final Claisen condensation in wild-type CHS and triketide products derived from an enolate-directed condensation in the CHS triple mutant. Although CHS, CTAS, and ACS generate tetraketides, each enzyme differs in either the cyclization reaction or in the identity of the starter molecule. CTAS forms the same enzyme-bound tetraketide as CHS but does not catalyze the final cyclization reaction. Comparison of these two enzymes reveals that substitution of Thr 197 in CHS (see SEQ ID NO:1) with an asparagine in CTAS may prevent the covalently-bound tetraketide intermediate from undergoing cyclization into chalcone. ACS uses N-methylanthranoyl-CoA as a starting substrate to produce the alkaloid acridone. Three differences between CHS (Thr$_{132}$, Ser$_{133}$, and Phe$_{265}$; see SEQ ID NO:1) and ACS (Ser$_{132}$, Ala$_{133}$, and Val$_{265}$) may alter starter molecule specificity. In ACS, these changes likely widen the portion of the cavity corresponding to the p-coumaroyl-binding site in CHS to accommodate N-methylanthranoyl-CoA binding. Comparative changes in the active site cavity allow formation of longer polyketides. The rppA protein forms a pentaketide from five acetates derived from malonyl-CoA decarboxylation. Thr$_{137}$, Ala$_{138}$, Thr$_{199}$, Leu$_{202}$, Met$_{259}$, Leu$_{261}$, Leu$_{268}$, Pro$_{304}$, and Ile$_{343}$ of 2-PS are replaced by Cys$_{106}$, Thr$_{107}$, Cys$_{168}$, Cys$_{177}$, Ile$_{228}$, Tyr$_{230}$, Phe$_{237}$, Ala$_{261}$, and Ala$_{295}$, respectively, in the rppA protein. Models of the rppA protein based on the 2-PS and CHS structures show that cavity volume is 1145 Å$^3$ in the rppA protein versus 274 Å$^3$ in 2-PS (or 923 Å in CHS). Manipulation of the active site through amino acid substitutions offers a strategy for increasing the molecular diversity of polyketide formation through both the choice of starter molecule and the number of subsequent condensation steps.

The reaction mechanism for polyketide formation and the structural basis for controlling polyketide length described here may be shared with other more complex iterative (e.g., actinorhodin (act) PKS and tetracenomycin (tcm) PKS) and modular PKSs (e.g., 6-deoxyerythronolide B synthase (DEBS)). The structural similarity of the 2-PS, CHS, and KAS II active sites, the sequence homology of KAS II and the ketosynthases of act PKS, tcm PKS, and DEBS, and mutagenesis studies of CHS and act PKS demonstrating similar roles for the catalytic residues of each protein indicate that a conserved active site architecture catalyzes similar reactions in these enzymes.

As in 2-PS and CHS, the volume of the active site cavities in other PKSs likely limits the size of the final polyketide. For example, act PKS and tcm PKS generate octaketide and decaketide products, respectively, at a single active site. This suggests that the active site cavities of these PKSs differ in size, and are larger than those of 2-PS or CHS. Similarly, the ketosynthases of different DEBS modules accept polyketide intermediates ranging in length from five to twelve carbons. Modular PKSs, like DEBS, use an assembly-line system in which an individual module catalyzes one elongation reaction and passes the growing polyketide to the next module. Although the ketosynthase domains of DEBS are functionally permissive, modulation of active site volume in each module's ketosynthase would provide selectivity for the proper sized intermediate at each elongation step. Structural differences among PKSs alter the volume of the initiation/elongation cavity to allow discrimination between starter molecules and to vary the number of elongation steps to ultimately direct the nature and length of the polyketide product.

Functional Conversion of Chalcone Synthase to Stilbene Synthase

Figure 10:
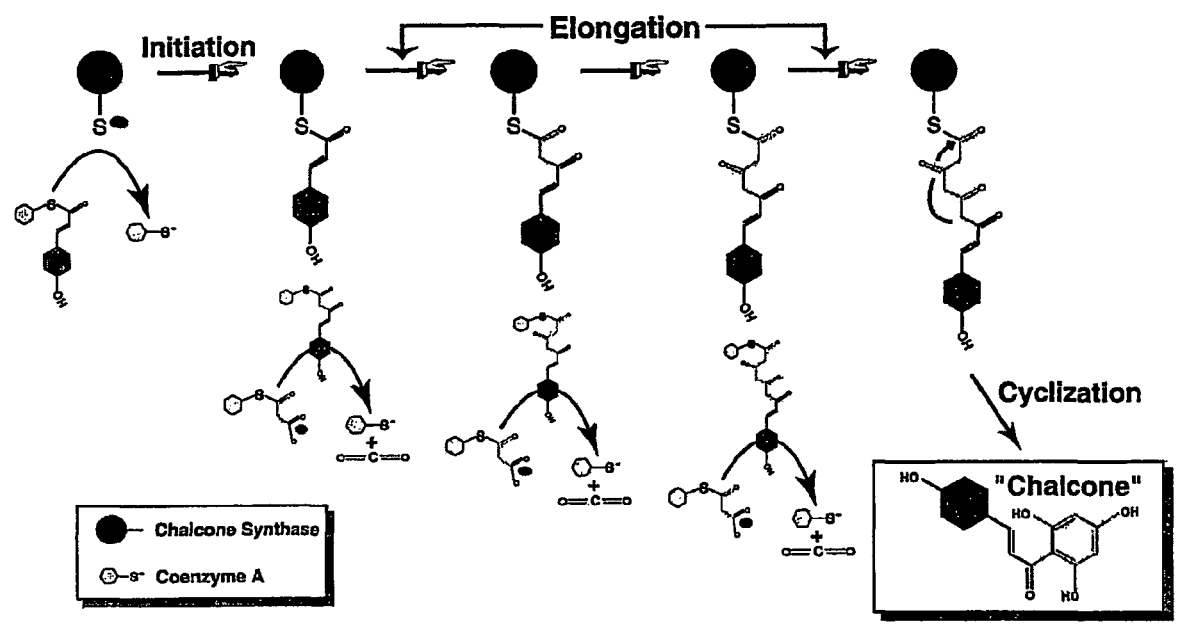
FIG. 10 shows the chalcone synthase reaction sequence including initiation, elongation and cyclization.

All CHS-like enzymes utilize a small number of absolutely conserved catalytic residues within a single active site to catalyze the iteratiVe addition of acetate units to a starter molecule. A chalcone synthase reaction sequence starts with initiation, is followed by elongation, and ends with cyclization (see FIG. 10). CHS family members differ in their choice of starter molecule, number of acetyl additions and cyclization pathway of the resulting polyketide. Structural and functional characterization of CHS from M. sativa (SEQ ID NO:1) suggested that substrate specificity is modulated in the chalcone synthase superfamily by steric constraints. Such constraints are provided by a set of variable residues lining the active site. Functional conversion through mutagenesis of alfalfa CHS to a pyrone synthase, and the structural characterization of pyrone synthase (PS) from G. hybrida (daisy) (SEQ ID NO:68) support this model. Thus, homology modeling is a valid approach to gain insight into the specificity's of chalcone synthase superfamily members, including members that are identified and/or characterized as well as those still to be identified and characterized.

Figure 12:
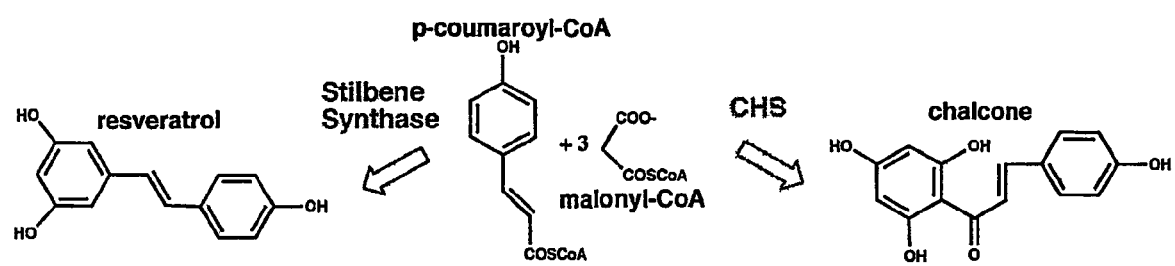
FIG. 12 shows phenylpropanoid metabolism. From a common linear phenylpropanoid tetraketide intermediate, resveratrol is formed by STS and chalcone is formed by CHS.
Figure 13:
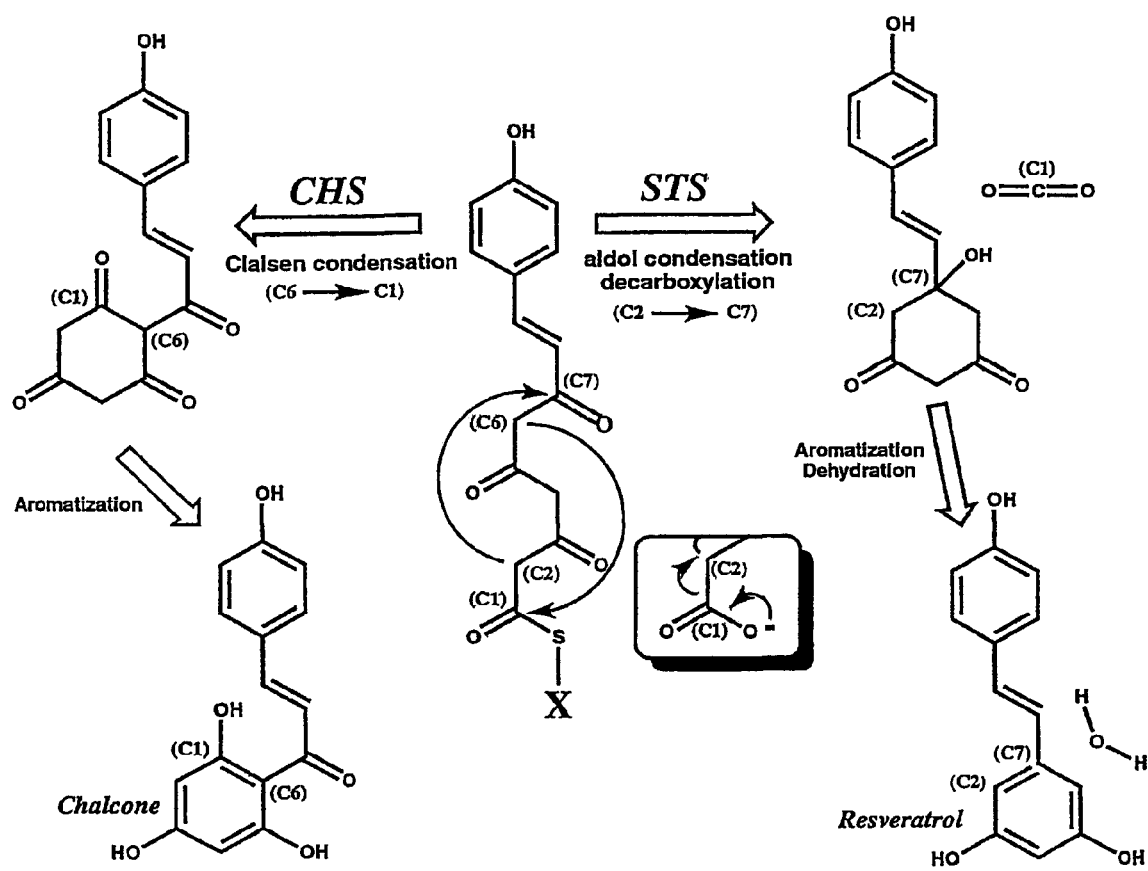
FIG. 13 shows different reaction schemes of CHS and STS. STS forms resveratrol via an intramolecular aldol condensation and CHS utilizes an intramolecular Claisen condensation to produce chalcone.

Stilbene synthase (STS) is related to CHS, and is thought to have arisen from CHS on at least three independent occasions. An amino acid sequence alignment of P. sylvesfris STS (SEQ ID NO:8) and M. sativa CHS (SEQ ID NO:10), along with an evolutionary intermediate, P. sylvestris CHS (SEQ ID NO:9) shows amino acid sequence homology (FIG. 11). Both CHS and STS form the same linear phenylpropanoid tetraketide intermediate via the sequential condensation of three acetyl units derived from decarboxylation of malonyl-CoA with one coumaroyl-CoA starter (FIG. 12). STS forms resveratrol via an intramolecular aldol condensation. In contrast, CHS utilizes an intramolecular Claisen condensation to produce chalcone (FIG. 13).

Function conversion is achieved by mutations of CHS. Mutation of M. sativa (alfalfa) CHS (SEQ ID NO:1) confers wild type STS activity resulting in an STS-like product profile from mutant CHS activity. Specifically, alfalfa wild type CHS activity results in the production of the plant polyketide synthase product, naringenin, a flavanone product resulting from spontaneous ring closure of chalcone product. Mutant CHS activity results in the production of resveratrol, an expected product of wild type STS activity, and a decrease in the production of naringenin (see FIG. 14).

Based on the structural information, a variety of mutant CHS (SEQ ID NO:1) molecules can be designed. Mutant CHS enzymes can vary with respect to starter preference, activity, product formation, and the like. Various CHS mutants as shown in Table 3 above were designed by invention methods and prepared, and were tested for activity.

Mutant CHS (SEQ ID NO: 1) has altered activity based on assays conducted with $^{14}C$ malonyl-CoA. Products were extracted with ethyl acetate and analyzed by silica gel thin layer chromatography (TLC) and visualized by autoradiography. Mutants 14B and 2B (Table 3) showed reduced amounts of naringenin compared to wild type CHS and little or no resveratrol. Mutants 16B, 4B, 6B, 18× and 22× (Table 3) showed reduced amounts of naringenin compared to wild type CHS and various amounts of resveratrol. Mutants 18×CHS (SEQ ID NO:67) and 22×CHS (Table 3) showed the lowest naringenin amounts and the highest resveratrol amounts, in fact, in 22× the naringenin:resveratrol ratio is similar to that seen with wild type STS from P. sylvestris (SEQ ID NO:65).

Specific mutations in 18×CHS (SEQ ID NO:67) by area are as follows, with areas underlined showing residue changes especially important for altering activity (Appendix C. SEQ ID NO:67): A1: D96A, V98L. V99A, V100M; A2: T131S, S133T, G134T, V135P, M137L; A3: Y157V, M159G, M159V, Y160F, Q165H; A4: L268K, K269G, D270A, G273D.

Figure 16:
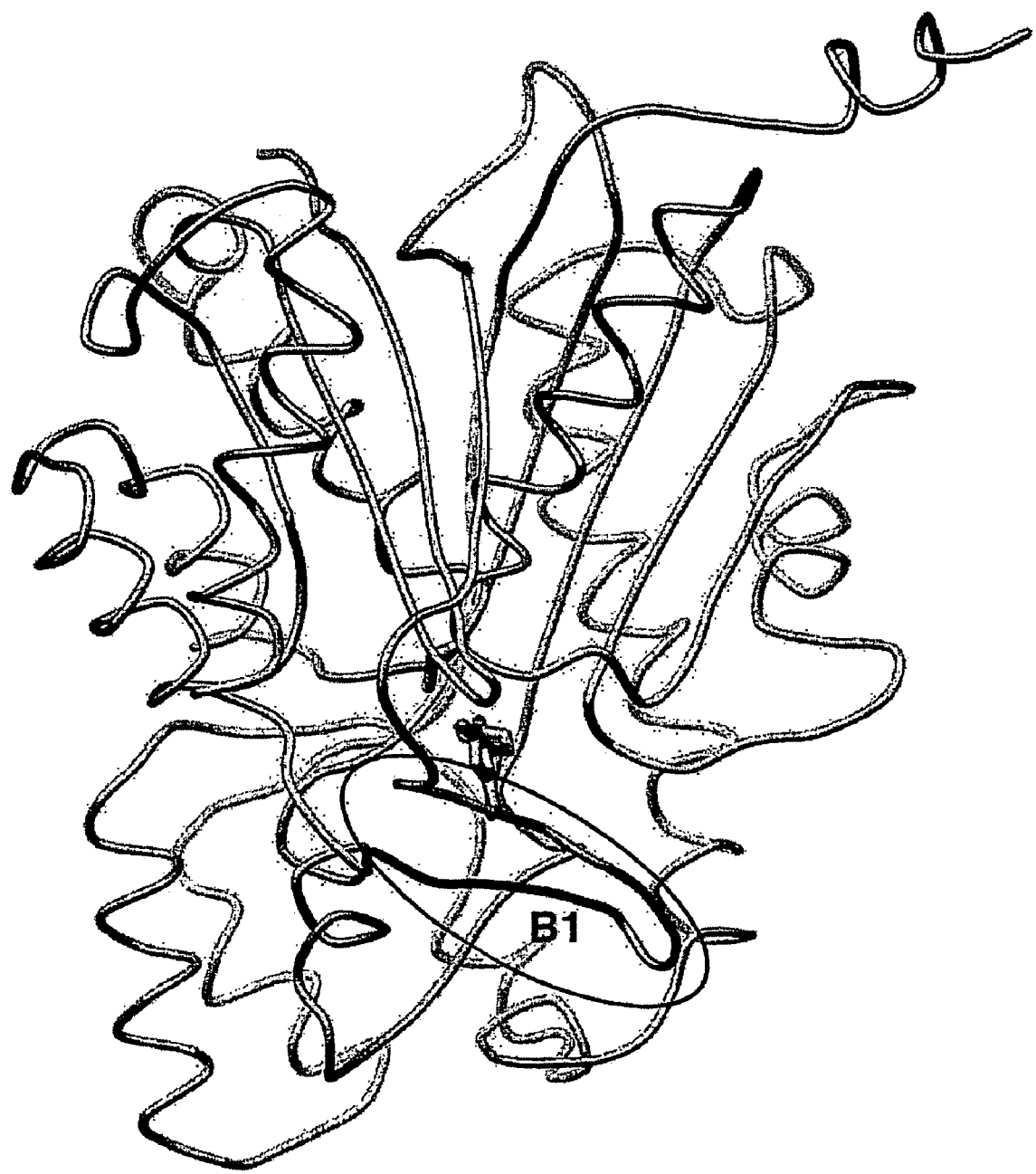
FIG. 16 shows the crystalline structure of CHS with area B1, mutated in the 22×CHS mutant circled.
Figure 17:
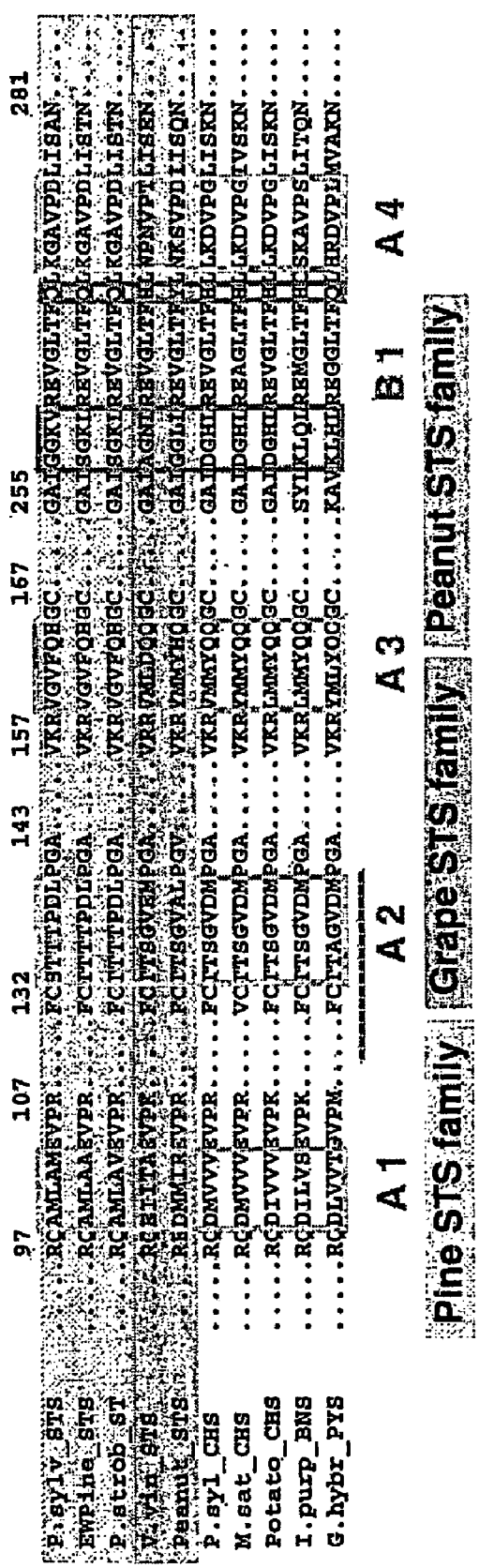
FIG. 17 shows amino acid sequences of homologous sequences from STS family members (SEQ ID NOS 11-50, respectively in order of appearance from left to right).

The 22× mutant consists of 18×CHS (SEQ ID NO:67) plus four additional mutations in area B1, which flanks A4, and bridges the gap between A1-A3 and A4 (see FIG. 16). The 22×CHS has decreased naringenin production (relative to 18×CHS), matching identically the product profile of wild type STS. These mutations are in an area predicted to be important for cyclization specificity, due to changes seen here in comparing the CHS/resveratrol complex structure to apo and other complexes of CHS. Note that final mutation is only two residues before the first change in A4 region.

Specific mutations in 22×CHS (Table 3) by area are as follows, with areas underlined showing residue changes especially important for altering activity: A1: D96A, V98L, V99A, V100M; A2: T131S, S133T, G134T, V135P, M137L; A3: Y157V, M158G, M159V, Y160F, Q165H; A4: L268K, K269G, D270A, G273D; B1: D255G, H257K, L258V, H266Q.

The crystal structural coordinates of the 18×CHS mutant (SEQ ID NO:67) are presented in Appendix C. Table 6 shows the relative active site a-carbon coordinates of the 18×CHS mutant possessing STS-like activity.

TABLE 6

| Active Site α-Carbon Number | X Position | Y Position | Z Position | Amino Acid (SEQ ID NO: 1) |
|---|---|---|---|---|
| 1 | 3.754 | −8.620 | 58.411 | Thr 132 |
| 2 | 0.541 | −10.075 | 59.960 | Thr 133 |
| 3 | 0.228 | −9.423 | 49.613 | Met 137* |
| 4 | 0.230 | −7.076 | 55.634 | Gln 161 |
| 5 | 9.260 | −15.931 | 61.148 | Thr 194 |
| 6 | 6.542 | −18.097 | 57.263 | Thr 197 |
| 7 | 13.288 | −17.295 | 51.888 | Gly 211 |
| 8 | 15.195 | −13.751 | 60.585 | Gly 216 |
| 9 | 6.827 | −10.404 | 45.169 | Ile 254 |
| 10 | 2.304 | −13.379 | 49.664 | Gly 256 |
| 11 | 1.944 | −17.210 | 54.954 | Leu 263 |
| 12 | 5.520 | −16.124 | 49.059 | Phe 265 |
| 13 | 8.197 | −14.531 | 42.889 | Leu 267 |
| 14 | 11.540 | −7.480 | 56.987 | Ser 338 |
| 15 | 8.611 | −9.306 | 62.954 | Glu 192 |

*Met 137 from the second monomer

Table 7 shows the wild type CHS (SEQ ID NO:1) active site positions that differ from the coordinates listed in Table 6. The unlisted positions are equivalent for both CHS-like Claissen and STS-like aldol cyclization specificity.

TABLE 7

| Active Site α-Carbon Number | X Position | Y Position | Z Position | Amino Acid (SEQ ID NO: 1) |
|---|---|---|---|---|
| 1 | 4.033 | −8.884 | 58.744 | Thr 132 |
| 2 | 3.656 | −11.697 | 61.297 | Ser 133 |

Table 8 shows various amino acid positions where mutations thereof can enable or enhance STS-like activity in CHS mutants. The α-carbon positions are those observed in the 18×CHS (SEQ ID NO:67) crystal structure. The comparison of crystal structure may identify further positions that produce similar results.

TABLE 8

| Enabling α-Carbon Number | X Position | Y Position | Z Position | Mutation (SEQ ID NO: 1) | Location Designation |
|---|---|---|---|---|---|
| 1 | 2.452 | −14.634 | 67.063 | V98L | A1 |
| 2 | −0.144 | −13.492 | 69.602 | V99A | A1 |
| 3 | 2.537 | −13.818 | 72.285 | V100M | A1 |
| 4 | 4.117 | −6.516 | 61.579 | S131T | A2 |
| 5 | 0.541 | −10.075 | 59.960 | T133S | A2 |
| 6 | −1.599 | −9.886 | 63.127 | G134T | A2 |
| 7 | −3.665 | −12.840 | 64.483 | V135P | A2 |
| 8 | 0.228 | −9.423 | 49.613 | M137L* | A2 |
| 9 | −1.725 | −0.801 | 63.145 | M158G | A3 |
| 10 | −0.401 | −5.049 | 58.793 | Y160F | A3 |
| 11 | 3.525 | −11.762 | 46.471 | D255G | B1 |
| 12 | −0.844 | −15.289 | 50.586 | H257K | B1 |
| 13 | −2.269 | −15.735 | 54.104 | L258V | B1 |
| 14 | 5.803 | −16.354 | 45.249 | H266Q | B1 |
| 15 | 8.069 | −13.510 | 39.218 | L268K | A4 |
| 16 | 10.985 | −12.040 | 37.288 | K269G | A4 |
| 17 | 14.223 | −10.808 | 38.865 | D270A | A4 |

These results show that a function conversion of CHS to STS can be achieved by designing mutations in the CHS sequence (SEQ ID NO:1) based on CHS structural information.

Table 9. PDB Accession No. 1EE0. The content of Table 9 is hereby incorporated by reference under 37 C.F.R. § 52(e)(1)(iii) to file "1EE0.txt" of CD-R disk "S2370-3", created Mar. 20, 2007, with size 577,940 bytes.

Table 10. PDB Accession No. 1BI5. The content of Table 10 is hereby incorporated by reference under 37 C.F.R. § 1.52(e)(1)(iii) to file "1BI5.txt" of CD-R disk "S2370-3", created Mar. 20, 2007, with size 619,924 bytes.

Table 11. PDB Accession No. 1D6F. The content of Table 11 is hereby incorporated by reference under 37 C.F.R. § 1.52(e)(1)(iii) to file "1D6F.txt" of CD-R disk "S2370-3", created Mar. 20, 2007, with size 313,654 bytes.

Table 12. PDB Accession No. 1D6I. The content of Table 12 is hereby incorporated by reference under 37 C.F.R. § 1.52(e)(1)(iii) to file "1D6I.txt" of CD-R disk "S2370-3", created Mar. 20, 2007, with size 557,686 bytes.

Table 13. PDB Accession No. 1D6H. The content of Table 13 is hereby incorporated by reference under 37 C.F.R. § 1.52(e)(1)(iii) to file "1D6H.txt" of CD-R disk "S2370-3", created Mar. 20, 2007, with size 302,256 bytes.

Table 14. PDB Accession No. 1BQ6. The content of Table 14 is hereby incorporated by reference under 37 C.F.R. Å 1.52(e)(1)(iii) to file "1BQ6.txt" of CD-R disk "S2370-3", created Mar. 20, 2007, with size 610,166 bytes.

Table 15. PDB Accession No. 1CML. The content of Table 15 is hereby incorporated by reference under 37 C.F.R. Å 1.52(e)(1)(iii) to file "1CML.txt" of CD-R disk "S2370-3", created Mar. 20, 2007, with size 334,974 bytes.

Table 16. PDB Accession No. 1CHW. The content of Table 16 is hereby incorporated by reference under 37 C.F.R. Å 1.52(e)(1)(iii) to file "1 CHW.txt" of CD-R disk "S2370-3", created Mar. 20, 2007, with size 592,700 bytes.

Table 17. PDB Accession No. 1CGK. The content of Table 17 is hereby incorporated by reference under 37 C.F.R. Å 1.52(e)(1)(iii) to file "1 CGK.txt" of CD-R disk "S2370-3", created Mar. 20, 2007, with size 319,968 bytes.

Table 18. PDB Accession No. 1CGZ. The content of Table 18 is hereby incorporated by reference under 37 C.F.R. Å 1.52(e)(1)(iii) to file "1CGZ.txt" of CD-R disk "S2370-3", created Mar. 20, 2007, with size 318,328 bytes.

Additional References Cited

Schroeder, J. (1999) The Chalcone/Stilbene Synthase-type Family of Condensing Enzymes in *Comprehensive Natural Products Chemistry* Barton, D. & Nakanishi, K. (ed.) 1 (Elsevier Science Ltd., Amsterdam 1999).

Ferrer, J.-L., Jez, J. M., Bowman, M. E., Dixon, R. A., and Noel, J. P. (1999) Structure of Chalcone Synthase and the Molecular Basis of Plant Polyketide Biosynthesis. *Nature Structural Biology*, 6: 775-783.

Jez, J. M., Ferrer, J.-L., Bowman, M. E., Dixon, R. A., and Noel, J. P. (2000) Dissection of malonyl-CoA decarboxylation from polyketide formation in the reaction mechanism of a plant polyketide synthase. *Biochemistry*, 39: 890-902.

Jez, J. M. & Noel, J. P. (2000) Mechanism of chalcone synthase: pKa of the catalytic cysteine and the role of the conserved histidine in a plant polyketide synthase. *J. Biol. Chem.* 2000 Sep 26 [epub ahead of print—in press].

Jez, J. M., Austin, M. B., Ferrer, J.-L., Bowman, M. E., Schroder, J., and Noel, J. P. (2000) Structural control of polyketide formation in plant-specific polyketide synthases. *Chemistry & Biology* 7(12):919-930.

Tropf S, Lanz T, Rensing S A, Schroder J, Schroder G Evidence that stilbene synthases have developed from chalcone synthases several times in the course of evolution J Mol Evol 1994 June;38(6):610-8.

Suh D Y, Fukuma K, Kagami J, Yamazaki Y, Shibuya M, Ebizuka Y, Sankawa U Identification of amino acid residues important in the cyclization reactions of chalcone and stilbene synthases Biochem J 2000 Aug. 15;350(Pt 1):229-235.

While the foregoing has been presented with reference to particular embodiments of the invention, it will be appreciated by those skilled in the art that changes in these embodiments may be made without departing from the principles and spirit of the invention, the scope of which is defined by the appended claims.

APPENDIX A

*Pinus sylvestris* STS

| ATOM | # | TYPE | RES | | | X | Y | Z | OCC | B | |
|---|---|---|---|---|---|---|---|---|---|---|---|
| ATOM | 1 | CB | ASP | A | 5 | 15.478 | −29.459 | 49.168 | 1.00 | 67.43 | A |
| ATOM | 2 | CG | ASP | A | 5 | 16.008 | −30.062 | 47.877 | 1.00 | 68.10 | A |
| ATOM | 3 | OD1 | ASP | A | 5 | 17.184 | −30.480 | 47.850 | 1.00 | 68.26 | A |
| ATOM | 4 | OD2 | ASP | A | 5 | 15.247 | −30.116 | 46.890 | 1.00 | 68.59 | A |
| ATOM | 5 | C | ASP | A | 5 | 16.056 | −27.113 | 48.532 | 1.00 | 65.16 | A |
| ATOM | 6 | O | ASP | A | 5 | 17.024 | −26.582 | 47.995 | 1.00 | 64.39 | A |
| ATOM | 7 | N | ASP | A | 5 | 15.729 | −27.703 | 50.902 | 1.00 | 67.43 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 8 | CA | ASP | A | 5 | 16.237 | −28.193 | 49.588 | 1.00 | 66.83 | A |
| ATOM | 9 | N | PHE | A | 6 | 14.800 | −26.782 | 48.261 | 1.00 | 64.20 | A |
| ATOM | 10 | CA | PHE | A | 6 | 14.453 | −25.779 | 47.266 | 1.00 | 63.13 | A |
| ATOM | 11 | CB | PHE | A | 6 | 12.938 | −25.783 | 47.053 | 1.00 | 63.60 | A |
| ATOM | 12 | CG | PHE | A | 6 | 12.353 | −27.157 | 46.885 | 1.00 | 64.51 | A |
| ATOM | 13 | CD1 | PHE | A | 6 | 11.522 | −27.695 | 47.866 | 1.00 | 66.17 | A |
| ATOM | 14 | CD2 | PHE | A | 6 | 12.642 | −27.923 | 45.760 | 1.00 | 63.90 | A |
| ATOM | 15 | CE1 | PHE | A | 6 | 10.987 | −28.976 | 47.729 | 1.00 | 65.63 | A |
| ATOM | 16 | CE2 | PHE | A | 6 | 12.113 | −29.206 | 45.613 | 1.00 | 63.56 | A |
| ATOM | 17 | CZ | PHE | A | 6 | 11.285 | −29.734 | 46.598 | 1.00 | 64.57 | A |
| ATOM | 18 | C | PHE | A | 6 | 14.926 | −24.360 | 47.606 | 1.00 | 62.05 | A |
| ATOM | 19 | O | PHE | A | 6 | 15.234 | −23.577 | 46.707 | 1.00 | 61.61 | A |
| ATOM | 20 | N | GLU | A | 7 | 14.982 | −24.029 | 48.895 | 1.00 | 61.34 | A |
| ATOM | 21 | CA | GLU | A | 7 | 15.416 | −22.699 | 49.317 | 1.00 | 59.88 | A |
| ATOM | 22 | CB | GLU | A | 7 | 15.345 | −22.556 | 50.845 | 1.00 | 61.69 | A |
| ATOM | 23 | CG | GLU | A | 7 | 15.802 | −21.182 | 51.365 | 1.00 | 63.25 | A |
| ATOM | 24 | CD | GLU | A | 7 | 15.466 | −20.956 | 52.840 | 1.00 | 64.35 | A |
| ATOM | 25 | OE1 | GLU | A | 7 | 14.263 | −20.904 | 53.183 | 1.00 | 64.96 | A |
| ATOM | 26 | OE2 | GLU | A | 7 | 16.401 | −20.823 | 53.661 | 1.00 | 64.20 | A |
| ATOM | 27 | C | GLU | A | 7 | 16.832 | −22.421 | 48.838 | 1.00 | 57.91 | A |
| ATOM | 28 | O | GLU | A | 7 | 17.322 | −21.298 | 48.950 | 1.00 | 58.52 | A |
| ATOM | 29 | N | GLY | A | 8 | 17.487 | −23.455 | 48.315 | 1.00 | 56.11 | A |
| ATOM | 30 | CA | GLY | A | 8 | 18.839 | −23.312 | 47.796 | 1.00 | 52.75 | A |
| ATOM | 31 | C | GLY | A | 8 | 18.787 | −23.324 | 46.277 | 1.00 | 50.24 | A |
| ATOM | 32 | O | GLY | A | 8 | 19.523 | −22.595 | 45.601 | 1.00 | 49.08 | A |
| ATOM | 33 | N | PHE | A | 9 | 17.899 | −24.163 | 45.748 | 1.00 | 47.36 | A |
| ATOM | 34 | CA | PHE | A | 9 | 17.696 | −24.287 | 44.312 | 1.00 | 45.44 | A |
| ATOM | 35 | CB | PHE | A | 9 | 16.631 | −25.347 | 44.028 | 1.00 | 46.27 | A |
| ATOM | 36 | CG | PHE | A | 9 | 16.463 | −25.670 | 42.569 | 1.00 | 46.38 | A |
| ATOM | 37 | CD1 | PHE | A | 9 | 17.453 | −26.362 | 41.878 | 1.00 | 45.31 | A |
| ATOM | 38 | CD2 | PHE | A | 9 | 15.308 | −25.296 | 41.889 | 1.00 | 46.41 | A |
| ATOM | 39 | CE1 | PHE | A | 9 | 17.294 | −26.678 | 40.532 | 1.00 | 46.87 | A |
| ATOM | 40 | CE2 | PHE | A | 9 | 15.139 | −25.608 | 40.540 | 1.00 | 46.26 | A |
| ATOM | 41 | CZ | PHE | A | 9 | 16.131 | −26.299 | 39.862 | 1.00 | 46.36 | A |
| ATOM | 42 | C | PHE | A | 9 | 17.219 | −22.938 | 43.779 | 1.00 | 43.88 | A |
| ATOM | 43 | O | PHE | A | 9 | 17.610 | −22.503 | 42.695 | 1.00 | 42.95 | A |
| ATOM | 44 | N | ARG | A | 10 | 16.369 | −22.285 | 44.559 | 1.00 | 42.46 | A |
| ATOM | 45 | CA | ARG | A | 10 | 15.820 | −20.988 | 44.199 | 1.00 | 41.78 | A |
| ATOM | 46 | CB | ARG | A | 10 | 14.759 | −20.587 | 45.227 | 1.00 | 42.76 | A |
| ATOM | 47 | CG | ARG | A | 10 | 13.336 | −20.513 | 44.699 | 1.00 | 45.24 | A |
| ATOM | 48 | CD | ARG | A | 10 | 13.108 | −19.253 | 43.870 | 1.00 | 46.91 | A |
| ATOM | 49 | NE | ARG | A | 10 | 13.803 | −19.267 | 42.582 | 1.00 | 47.12 | A |
| ATOM | 50 | CZ | ARG | A | 10 | 13.848 | −18.226 | 41.753 | 1.00 | 47.04 | A |
| ATOM | 51 | NH1 | ARG | A | 10 | 13.243 | −17.092 | 42.083 | 1.00 | 46.16 | A |
| ATOM | 52 | NH2 | ARG | A | 10 | 14.490 | −18.316 | 40.599 | 1.00 | 45.13 | A |
| ATOM | 53 | C | ARG | A | 10 | 16.912 | −19.923 | 44.145 | 1.00 | 41.81 | A |
| ATOM | 54 | O | ARG | A | 10 | 17.039 | −19.191 | 43.158 | 1.00 | 40.31 | A |
| ATOM | 55 | N | LYS | A | 11 | 17.704 | −19.848 | 45.211 | 1.00 | 41.51 | A |
| ATOM | 56 | CA | LYS | A | 11 | 18.771 | −18.859 | 45.306 | 1.00 | 42.45 | A |
| ATOM | 57 | CB | LYS | A | 11 | 19.441 | −18.946 | 46.679 | 1.00 | 44.35 | A |
| ATOM | 58 | CG | LYS | A | 11 | 18.520 | −18.561 | 47.831 | 1.00 | 47.24 | A |
| ATOM | 59 | CD | LYS | A | 11 | 19.157 | −18.828 | 49.194 | 1.00 | 47.39 | A |
| ATOM | 60 | CE | LYS | A | 11 | 18.222 | −18.392 | 50.321 | 1.00 | 48.83 | A |
| ATOM | 61 | NZ | LYS | A | 11 | 18.760 | −18.701 | 51.673 | 1.00 | 49.79 | A |
| ATOM | 62 | C | LYS | A | 11 | 19.819 | −18.981 | 44.214 | 1.00 | 41.73 | A |
| ATOM | 63 | O | LYS | A | 11 | 20.409 | −17.980 | 43.801 | 1.00 | 41.36 | A |
| ATOM | 64 | N | LEU | A | 12 | 20.048 | −20.206 | 43.749 | 1.00 | 41.94 | A |
| ATOM | 65 | CA | LEU | A | 12 | 21.042 | −20.465 | 42.705 | 1.00 | 41.33 | A |
| ATOM | 66 | CB | LEU | A | 12 | 21.631 | −21.869 | 42.864 | 1.00 | 41.99 | A |
| ATOM | 67 | CG | LEU | A | 12 | 23.057 | −21.952 | 43.411 | 1.00 | 42.59 | A |
| ATOM | 68 | CD1 | LEU | A | 12 | 23.449 | −23.403 | 43.608 | 1.00 | 44.32 | A |
| ATOM | 69 | CD2 | LEU | A | 12 | 24.010 | −21.276 | 42.445 | 1.00 | 42.25 | A |
| ATOM | 70 | C | LEU | A | 12 | 20.483 | −20.321 | 41.299 | 1.00 | 40.77 | A |
| ATOM | 71 | O | LEU | A | 12 | 21.224 | −20.037 | 40.357 | 1.00 | 41.09 | A |
| ATOM | 72 | N | GLN | A | 13 | 19.175 | −20.520 | 41.167 | 1.00 | 39.79 | A |
| ATOM | 73 | CA | GLN | A | 13 | 18.490 | −20.431 | 39.884 | 1.00 | 38.24 | A |
| ATOM | 74 | CB | GLN | A | 13 | 17.119 | −21.113 | 39.996 | 1.00 | 38.10 | A |
| ATOM | 75 | CG | GLN | A | 13 | 16.185 | −20.943 | 38.793 | 1.00 | 38.78 | A |
| ATOM | 76 | CD | GLN | A | 13 | 14.899 | −21.761 | 38.934 | 1.00 | 39.17 | A |
| ATOM | 77 | OE1 | GLN | A | 13 | 14.231 | −21.723 | 39.975 | 1.00 | 35.94 | A |
| ATOM | 78 | NE2 | GLN | A | 13 | 14.549 | −22.500 | 37.884 | 1.00 | 36.91 | A |
| ATOM | 79 | C | GLN | A | 13 | 18.329 | −18.996 | 39.395 | 1.00 | 38.22 | A |
| ATOM | 80 | O | GLN | A | 13 | 18.228 | −18.764 | 38.195 | 1.00 | 39.15 | A |
| ATOM | 81 | N | ARG | A | 14 | 18.328 | −18.040 | 40.322 | 1.00 | 37.88 | A |
| ATOM | 82 | CA | ARG | A | 14 | 18.149 | −16.628 | 39.990 | 1.00 | 37.89 | A |

APPENDIX A-continued

*Pinus sylvestris* STS

| ATOM | # | TYPE | RES | | | X | Y | Z | OCC | B | |
|------|---|------|-----|---|----|--------|---------|--------|------|-------|---|
| ATOM | 83 | CB | ARG | A | 14 | 17.136 | −16.013 | 40.950 | 1.00 | 40.76 | A |
| ATOM | 84 | CG | ARG | A | 14 | 17.583 | −16.012 | 42.406 | 1.00 | 44.03 | A |
| ATOM | 85 | CD | ARG | A | 14 | 16.477 | −15.471 | 43.280 | 1.00 | 46.98 | A |
| ATOM | 86 | NE | ARG | A | 14 | 16.898 | −15.263 | 44.661 | 1.00 | 49.61 | A |
| ATOM | 87 | CZ | ARG | A | 14 | 16.112 | −14.748 | 45.600 | 1.00 | 50.12 | A |
| ATOM | 88 | NH1 | ARG | A | 14 | 14.868 | −14.394 | 45.298 | 1.00 | 51.87 | A |
| ATOM | 89 | NH2 | ARG | A | 14 | 16.567 | −14.577 | 46.833 | 1.00 | 49.78 | A |
| ATOM | 90 | C | ARG | A | 14 | 19.431 | −15.796 | 40.010 | 1.00 | 37.27 | A |
| ATOM | 91 | O | ARG | A | 14 | 20.383 | −16.128 | 40.708 | 1.00 | 37.71 | A |
| ATOM | 92 | N | ALA | A | 15 | 19.434 | −14.702 | 39.250 | 1.00 | 36.59 | A |
| ATOM | 93 | CA | ALA | A | 15 | 20.592 | −13.811 | 39.144 | 1.00 | 36.04 | A |
| ATOM | 94 | CB | ALA | A | 15 | 20.561 | −13.083 | 37.805 | 1.00 | 35.74 | A |
| ATOM | 95 | C | ALA | A | 15 | 20.675 | −12.797 | 40.285 | 1.00 | 36.64 | A |
| ATOM | 96 | O | ALA | A | 15 | 19.668 | −12.470 | 40.906 | 1.00 | 36.28 | A |
| ATOM | 97 | N | ASP | A | 16 | 21.877 | −12.284 | 40.540 | 1.00 | 36.70 | A |
| ATOM | 98 | CA | ASP | A | 16 | 22.093 | −11.331 | 41.626 | 1.00 | 37.04 | A |
| ATOM | 99 | CB | ASP | A | 16 | 23.517 | −11.467 | 42.181 | 1.00 | 37.71 | A |
| ATOM | 100 | CG | ASP | A | 16 | 23.864 | −12.885 | 42.578 | 1.00 | 39.12 | A |
| ATOM | 101 | OD1 | ASP | A | 16 | 23.005 | −13.579 | 43.161 | 1.00 | 41.62 | A |
| ATOM | 102 | OD2 | ASP | A | 16 | 25.010 | −13.301 | 42.319 | 1.00 | 39.23 | A |
| ATOM | 103 | C | ASP | A | 16 | 21.871 | −9.857 | 41.292 | 1.00 | 37.37 | A |
| ATOM | 104 | O | ASP | A | 16 | 21.127 | −9.152 | 41.978 | 1.00 | 38.64 | A |
| ATOM | 105 | N | GLY | A | 17 | 22.523 | −9.387 | 40.240 | 1.00 | 35.60 | A |
| ATOM | 106 | CA | GLY | A | 17 | 22.422 | −7.984 | 39.903 | 1.00 | 35.63 | A |
| ATOM | 107 | C | GLY | A | 17 | 21.159 | −7.453 | 39.272 | 1.00 | 35.92 | A |
| ATOM | 108 | O | GLY | A | 17 | 20.077 | −8.023 | 39.380 | 1.00 | 35.96 | A |
| ATOM | 109 | N | PHE | A | 18 | 21.329 | −6.318 | 38.607 | 1.00 | 36.31 | A |
| ATOM | 110 | CA | PHE | A | 18 | 20.253 | −5.636 | 37.923 | 1.00 | 34.75 | A |
| ATOM | 111 | CB | PHE | A | 18 | 20.466 | −4.126 | 38.012 | 1.00 | 37.21 | A |
| ATOM | 112 | CG | PHE | A | 18 | 19.578 | −3.441 | 39.004 | 1.00 | 39.74 | A |
| ATOM | 113 | CD1 | PHE | A | 18 | 20.048 | −2.351 | 39.732 | 1.00 | 39.87 | A |
| ATOM | 114 | CD2 | PHE | A | 18 | 18.262 | −3.862 | 39.195 | 1.00 | 40.31 | A |
| ATOM | 115 | CE1 | PHE | A | 18 | 19.223 | −1.690 | 40.637 | 1.00 | 40.82 | A |
| ATOM | 116 | CE2 | PHE | A | 18 | 17.426 | −3.204 | 40.101 | 1.00 | 40.34 | A |
| ATOM | 117 | CZ | PHE | A | 18 | 17.910 | −2.119 | 40.823 | 1.00 | 41.49 | A |
| ATOM | 118 | C | PHE | A | 18 | 20.257 | −6.048 | 36.469 | 1.00 | 33.11 | A |
| ATOM | 119 | O | PHE | A | 18 | 21.321 | −6.251 | 35.886 | 1.00 | 30.89 | A |
| ATOM | 120 | N | ALA | A | 19 | 19.066 | −6.184 | 35.895 | 1.00 | 32.19 | A |
| ATOM | 121 | CA | ALA | A | 19 | 18.932 | −6.528 | 34.488 | 1.00 | 32.21 | A |
| ATOM | 122 | CB | ALA | A | 19 | 17.458 | −6.639 | 34.106 | 1.00 | 32.97 | A |
| ATOM | 123 | C | ALA | A | 19 | 19.593 | −5.362 | 33.746 | 1.00 | 32.44 | A |
| ATOM | 124 | O | ALA | A | 19 | 19.319 | −4.187 | 34.039 | 1.00 | 30.18 | A |
| ATOM | 125 | N | SER | A | 20 | 20.464 | −5.673 | 32.792 | 1.00 | 30.51 | A |
| ATOM | 126 | CA | SER | A | 20 | 21.158 | −4.611 | 32.095 | 1.00 | 29.55 | A |
| ATOM | 127 | CB | SER | A | 20 | 22.575 | −4.502 | 32.646 | 1.00 | 29.41 | A |
| ATOM | 128 | OG | SER | A | 20 | 22.544 | −4.494 | 34.062 | 1.00 | 31.94 | A |
| ATOM | 129 | C | SER | A | 20 | 21.210 | −4.779 | 30.598 | 1.00 | 29.71 | A |
| ATOM | 130 | O | SER | A | 20 | 21.222 | −5.897 | 30.083 | 1.00 | 31.07 | A |
| ATOM | 131 | N | ILE | A | 21 | 21.231 | −3.651 | 29.900 | 1.00 | 28.89 | A |
| ATOM | 132 | CA | ILE | A | 21 | 21.324 | −3.651 | 28.454 | 1.00 | 29.32 | A |
| ATOM | 133 | CB | ILE | A | 21 | 20.827 | −2.328 | 27.862 | 1.00 | 29.06 | A |
| ATOM | 134 | CG2 | ILE | A | 21 | 20.864 | −2.401 | 26.358 | 1.00 | 29.04 | A |
| ATOM | 135 | CG1 | ILE | A | 21 | 19.403 | −2.033 | 28.344 | 1.00 | 30.26 | A |
| ATOM | 136 | CD1 | ILE | A | 21 | 18.400 | −3.115 | 28.026 | 1.00 | 33.08 | A |
| ATOM | 137 | C | ILE | A | 21 | 22.817 | −3.802 | 28.185 | 1.00 | 30.88 | A |
| ATOM | 138 | O | ILE | A | 21 | 23.619 | −2.964 | 28.602 | 1.00 | 30.81 | A |
| ATOM | 139 | N | LEU | A | 22 | 23.194 | −4.872 | 27.500 | 1.00 | 30.73 | A |
| ATOM | 140 | CA | LEU | A | 22 | 24.600 | −5.121 | 27.240 | 1.00 | 29.37 | A |
| ATOM | 141 | CB | LEU | A | 22 | 24.926 | −6.563 | 27.606 | 1.00 | 27.95 | A |
| ATOM | 142 | CG | LEU | A | 22 | 24.496 | −6.947 | 29.019 | 1.00 | 26.37 | A |
| ATOM | 143 | CD1 | LEU | A | 22 | 24.854 | −8.404 | 29.301 | 1.00 | 26.97 | A |
| ATOM | 144 | CD2 | LEU | A | 22 | 25.178 | −6.019 | 30.006 | 1.00 | 27.73 | A |
| ATOM | 145 | C | LEU | A | 22 | 25.000 | −4.843 | 25.801 | 1.00 | 30.57 | A |
| ATOM | 146 | O | LEU | A | 22 | 26.190 | −4.902 | 25.457 | 1.00 | 30.82 | A |
| ATOM | 147 | N | ALA | A | 23 | 24.007 | −4.537 | 24.966 | 1.00 | 29.20 | A |
| ATOM | 148 | CA | ALA | A | 23 | 24.255 | −4.240 | 23.556 | 1.00 | 27.79 | A |
| ATOM | 149 | CB | ALA | A | 23 | 24.867 | −5.449 | 22.865 | 1.00 | 24.35 | A |
| ATOM | 150 | C | ALA | A | 23 | 22.989 | −3.804 | 22.825 | 1.00 | 27.34 | A |
| ATOM | 151 | O | ALA | A | 23 | 21.877 | −4.233 | 23.150 | 1.00 | 25.25 | A |
| ATOM | 152 | N | ILE | A | 24 | 23.169 | −2.934 | 21.837 | 1.00 | 27.98 | A |
| ATOM | 153 | CA | ILE | A | 24 | 22.048 | −2.444 | 21.054 | 1.00 | 27.20 | A |
| ATOM | 154 | CB | ILE | A | 24 | 21.643 | −1.002 | 21.444 | 1.00 | 26.17 | A |
| ATOM | 155 | CG2 | ILE | A | 24 | 20.398 | −.596 | 20.665 | 1.00 | 26.40 | A |
| ATOM | 156 | CG1 | ILE | A | 24 | 21.361 | −.895 | 22.945 | 1.00 | 26.96 | A |
| ATOM | 157 | CD1 | ILE | A | 24 | 20.943 | .540 | 23.399 | 1.00 | 22.86 | A |

APPENDIX A-continued

*Pinus sylvestris* STS

| ATOM | # | TYPE | RES | | | X | Y | Z | OCC | B | |
|------|---|------|-----|---|---|---|---|---|-----|---|---|
| ATOM | 158 | C | ILE | A | 24 | 22.409 | −2.437 | 19.572 | 1.00 | 27.82 | A |
| ATOM | 159 | O | ILE | A | 24 | 23.418 | −1.859 | 19.165 | 1.00 | 27.57 | A |
| ATOM | 160 | N | GLY | A | 25 | 21.568 | −3.098 | 18.782 | 1.00 | 28.16 | A |
| ATOM | 161 | CA | GLY | A | 25 | 21.746 | −3.166 | 17.347 | 1.00 | 26.42 | A |
| ATOM | 162 | C | GLY | A | 25 | 20.512 | −2.563 | 16.685 | 1.00 | 28.50 | A |
| ATOM | 163 | O | GLY | A | 25 | 19.409 | −2.612 | 17.241 | 1.00 | 26.10 | A |
| ATOM | 164 | N | THR | A | 26 | 20.699 | −2.012 | 15.490 | 1.00 | 28.50 | A |
| ATOM | 165 | CA | THR | A | 26 | 19.621 | −1.377 | 14.741 | 1.00 | 30.82 | A |
| ATOM | 166 | CB | THR | A | 26 | 19.708 | .168 | 14.908 | 1.00 | 32.46 | A |
| ATOM | 167 | OG1 | THR | A | 26 | 18.878 | .576 | 16.003 | 1.00 | 32.28 | A |
| ATOM | 168 | CG2 | THR | A | 26 | 19.302 | .894 | 13.629 | 1.00 | 34.07 | A |
| ATOM | 169 | C | THR | A | 26 | 19.691 | −1.746 | 13.258 | 1.00 | 30.38 | A |
| ATOM | 170 | O | THR | A | 26 | 20.776 | −1.870 | 12.694 | 1.00 | 30.95 | A |
| ATOM | 171 | N | ALA | A | 27 | 18.533 | −1.914 | 12.630 | 1.00 | 28.84 | A |
| ATOM | 172 | CA | ALA | A | 27 | 18.495 | −2.263 | 11.220 | 1.00 | 27.36 | A |
| ATOM | 173 | CB | ALA | A | 27 | 18.361 | −3.753 | 11.075 | 1.00 | 26.92 | A |
| ATOM | 174 | C | ALA | A | 27 | 17.346 | −1.564 | 10.506 | 1.00 | 26.05 | A |
| ATOM | 175 | O | ALA | A | 27 | 16.306 | −1.337 | 11.089 | 1.00 | 23.77 | A |
| ATOM | 176 | N | ASN | A | 28 | 17.536 | −1.231 | 9.235 | 1.00 | 28.03 | A |
| ATOM | 177 | CA | ASN | A | 28 | 16.490 | −.573 | 8.457 | 1.00 | 28.64 | A |
| ATOM | 178 | CB | ASN | A | 28 | 16.646 | .948 | 8.528 | 1.00 | 27.80 | A |
| ATOM | 179 | CG | ASN | A | 28 | 16.309 | 1.503 | 9.893 | 1.00 | 29.20 | A |
| ATOM | 180 | OD1 | ASN | A | 28 | 17.197 | 1.766 | 10.715 | 1.00 | 28.54 | A |
| ATOM | 181 | ND2 | ASN | A | 28 | 15.013 | 1.675 | 10.152 | 1.00 | 26.02 | A |
| ATOM | 182 | C | ASN | A | 28 | 16.481 | −1.001 | 6.989 | 1.00 | 28.59 | A |
| ATOM | 183 | O | ASN | A | 28 | 17.525 | −1.282 | 6.420 | 1.00 | 28.02 | A |
| ATOM | 184 | N | PRO | A | 29 | 15.292 | −1.034 | 6.356 | 1.00 | 29.65 | A |
| ATOM | 185 | CD | PRO | A | 29 | 13.967 | −.696 | 6.908 | 1.00 | 28.87 | A |
| ATOM | 186 | CA | PRO | A | 29 | 15.179 | −1.425 | 4.947 | 1.00 | 29.12 | A |
| ATOM | 187 | CB | PRO | A | 29 | 13.671 | −1.388 | 4.686 | 1.00 | 30.72 | A |
| ATOM | 188 | CG | PRO | A | 29 | 13.061 | −1.530 | 6.048 | 1.00 | 32.13 | A |
| ATOM | 189 | C | PRO | A | 29 | 15.932 | −.409 | 4.083 | 1.00 | 31.07 | A |
| ATOM | 190 | O | PRO | A | 29 | 16.037 | .768 | 4.444 | 1.00 | 29.67 | A |
| ATOM | 191 | N | PRO | A | 30 | 16.452 | −.853 | 2.927 | 1.00 | 32.61 | A |
| ATOM | 192 | CD | PRO | A | 30 | 16.229 | −2.205 | 2.388 | 1.00 | 33.12 | A |
| ATOM | 193 | CA | PRO | A | 30 | 17.210 | −.045 | 1.966 | 1.00 | 33.75 | A |
| ATOM | 194 | CB | PRO | A | 30 | 17.300 | −.956 | .748 | 1.00 | 33.69 | A |
| ATOM | 195 | CG | PRO | A | 30 | 17.308 | −2.305 | 1.351 | 1.00 | 34.85 | A |
| ATOM | 196 | C | PRO | A | 30 | 16.553 | 1.276 | 1.618 | 1.00 | 34.72 | A |
| ATOM | 197 | O | PRO | A | 30 | 17.123 | 2.352 | 1.826 | 1.00 | 33.78 | A |
| ATOM | 198 | N | ASN | A | 31 | 15.342 | 1.172 | 1.084 | 1.00 | 36.47 | A |
| ATOM | 199 | CA | ASN | A | 31 | 14.577 | 2.332 | .656 | 1.00 | 35.87 | A |
| ATOM | 200 | CB | ASN | A | 31 | 13.179 | 1.898 | .222 | 1.00 | 37.58 | A |
| ATOM | 201 | CG | ASN | A | 31 | 12.379 | 3.033 | −.377 | 1.00 | 38.77 | A |
| ATOM | 202 | OD1 | ASN | A | 31 | 12.852 | 3.738 | −1.267 | 1.00 | 42.91 | A |
| ATOM | 203 | ND2 | ASN | A | 31 | 11.158 | 3.208 | .097 | 1.00 | 38.97 | A |
| ATOM | 204 | C | ASN | A | 31 | 14.466 | 3.444 | 1.682 | 1.00 | 36.12 | A |
| ATOM | 205 | O | ASN | A | 31 | 13.752 | 3.330 | 2.678 | 1.00 | 35.66 | A |
| ATOM | 206 | N | ALA | A | 32 | 15.190 | 4.526 | 1.431 | 1.00 | 35.45 | A |
| ATOM | 207 | CA | ALA | A | 32 | 15.139 | 5.680 | 2.300 | 1.00 | 35.87 | A |
| ATOM | 208 | CB | ALA | A | 32 | 16.501 | 6.300 | 2.428 | 1.00 | 34.90 | A |
| ATOM | 209 | C | ALA | A | 32 | 14.186 | 6.633 | 1.603 | 1.00 | 36.32 | A |
| ATOM | 210 | O | ALA | A | 32 | 14.450 | 7.062 | .481 | 1.00 | 36.89 | A |
| ATOM | 211 | N | VAL | A | 33 | 13.066 | 6.935 | 2.254 | 1.00 | 37.11 | A |
| ATOM | 212 | CA | VAL | A | 33 | 12.072 | 7.838 | 1.687 | 1.00 | 38.65 | A |
| ATOM | 213 | CB | VAL | A | 33 | 10.628 | 7.294 | 1.858 | 1.00 | 39.24 | A |
| ATOM | 214 | CG1 | VAL | A | 33 | 10.507 | 5.921 | 1.248 | 1.00 | 38.32 | A |
| ATOM | 215 | CG2 | VAL | A | 33 | 10.255 | 7.256 | 3.337 | 1.00 | 39.28 | A |
| ATOM | 216 | C | VAL | A | 33 | 12.135 | 9.195 | 2.371 | 1.00 | 40.05 | A |
| ATOM | 217 | O | VAL | A | 33 | 12.190 | 9.281 | 3.597 | 1.00 | 40.74 | A |
| ATOM | 218 | N | ASP | A | 34 | 12.120 | 10.259 | 1.579 | 1.00 | 41.52 | A |
| ATOM | 219 | CA | ASP | A | 34 | 12.159 | 11.601 | 2.140 | 1.00 | 42.79 | A |
| ATOM | 220 | CB | ASP | A | 34 | 12.984 | 12.526 | 1.239 | 1.00 | 45.56 | A |
| ATOM | 221 | CG | ASP | A | 34 | 14.476 | 12.234 | 1.316 | 1.00 | 47.51 | A |
| ATOM | 222 | OD1 | ASP | A | 34 | 15.219 | 12.722 | .439 | 1.00 | 49.63 | A |
| ATOM | 223 | OD2 | ASP | A | 34 | 14.905 | 11.524 | 2.258 | 1.00 | 48.98 | A |
| ATOM | 224 | C | ASP | A | 34 | 10.735 | 12.120 | 2.287 | 1.00 | 42.33 | A |
| ATOM | 225 | O | ASP | A | 34 | 9.951 | 12.093 | 1.338 | 1.00 | 42.08 | A |
| ATOM | 226 | N | GLN | A | 35 | 10.407 | 12.582 | 3.490 | 1.00 | 41.73 | A |
| ATOM | 227 | CA | GLN | A | 35 | 9.076 | 13.098 | 3.787 | 1.00 | 41.81 | A |
| ATOM | 228 | CB | GLN | A | 35 | 9.020 | 13.584 | 5.243 | 1.00 | 40.69 | A |
| ATOM | 229 | CG | GLN | A | 35 | 7.627 | 13.923 | 5.764 | 1.00 | 40.17 | A |
| ATOM | 230 | CD | GLN | A | 35 | 6.798 | 12.688 | 6.067 | 1.00 | 40.34 | A |
| ATOM | 231 | OE1 | GLN | A | 35 | 6.692 | 11.785 | 5.244 | 1.00 | 39.84 | A |
| ATOM | 232 | NE2 | GLN | A | 35 | 6.200 | 12.649 | 7.252 | 1.00 | 39.72 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 233 | C | GLN | A | 35 | 8.686 | 14.241 | 2.843 | 1.00 | 42.93 | A |
| ATOM | 234 | O | GLN | A | 35 | 7.504 | 14.483 | 2.613 | 1.00 | 44.31 | A |
| ATOM | 235 | N | SER | A | 36 | 9.677 | 14.940 | 2.294 | 1.00 | 43.00 | A |
| ATOM | 236 | CA | SER | A | 36 | 9.404 | 16.056 | 1.391 | 1.00 | 42.43 | A |
| ATOM | 237 | CB | SER | A | 36 | 10.701 | 16.798 | 1.060 | 1.00 | 42.98 | A |
| ATOM | 238 | OG | SER | A | 36 | 11.126 | 17.582 | 2.162 | 1.00 | 44.09 | A |
| ATOM | 239 | C | SER | A | 36 | 8.705 | 15.666 | .092 | 1.00 | 41.13 | A |
| ATOM | 240 | O | SER | A | 36 | 7.772 | 16.339 | −.345 | 1.00 | 39.36 | A |
| ATOM | 241 | N | THR | A | 37 | 9.155 | 14.579 | −.522 | 1.00 | 39.75 | A |
| ATOM | 242 | CA | THR | A | 37 | 8.575 | 14.134 | −1.783 | 1.00 | 39.31 | A |
| ATOM | 243 | CB | THR | A | 37 | 9.686 | 13.652 | −2.762 | 1.00 | 39.54 | A |
| ATOM | 244 | OG1 | THR | A | 37 | 10.694 | 14.666 | −2.877 | 1.00 | 39.51 | A |
| ATOM | 245 | CG2 | THR | A | 37 | 9.107 | 13.383 | −4.151 | 1.00 | 40.15 | A |
| ATOM | 246 | C | THR | A | 37 | 7.557 | 13.010 | −1.590 | 1.00 | 38.36 | A |
| ATOM | 247 | O | THR | A | 37 | 7.066 | 12.434 | −2.564 | 1.00 | 38.53 | A |
| ATOM | 248 | N | TYR | A | 38 | 7.225 | 12.697 | −.342 | 1.00 | 36.06 | A |
| ATOM | 249 | CA | TYR | A | 38 | 6.274 | 11.625 | −.124 | 1.00 | 36.72 | A |
| ATOM | 250 | CB | TYR | A | 38 | 6.232 | 11.187 | 1.335 | 1.00 | 35.69 | A |
| ATOM | 251 | CG | TYR | A | 38 | 5.647 | 9.801 | 1.479 | 1.00 | 35.07 | A |
| ATOM | 252 | CD1 | TYR | A | 38 | 6.260 | 8.704 | .873 | 1.00 | 35.39 | A |
| ATOM | 253 | CE1 | TYR | A | 38 | 5.724 | 7.420 | .983 | 1.00 | 34.19 | A |
| ATOM | 254 | CD2 | TYR | A | 38 | 4.476 | 9.585 | 2.201 | 1.00 | 35.84 | A |
| ATOM | 255 | CE2 | TYR | A | 38 | 3.930 | 8.308 | 2.320 | 1.00 | 34.78 | A |
| ATOM | 256 | CZ | TYR | A | 38 | 4.561 | 7.229 | 1.710 | 1.00 | 33.22 | A |
| ATOM | 257 | OH | TYR | A | 38 | 4.037 | 5.967 | 1.840 | 1.00 | 30.24 | A |
| ATOM | 258 | C | TYR | A | 38 | 4.875 | 12.002 | −.572 | 1.00 | 37.11 | A |
| ATOM | 259 | O | TYR | A | 38 | 4.125 | 11.151 | −1.057 | 1.00 | 36.68 | A |
| ATOM | 260 | N | PRO | A | 39 | 4.495 | 13.279 | −.407 | 1.00 | 36.61 | A |
| ATOM | 261 | CD | PRO | A | 39 | 5.087 | 14.349 | .413 | 1.00 | 35.84 | A |
| ATOM | 262 | CA | PRO | A | 39 | 3.151 | 13.648 | −.841 | 1.00 | 36.96 | A |
| ATOM | 263 | CB | PRO | A | 39 | 3.068 | 15.118 | −.459 | 1.00 | 37.53 | A |
| ATOM | 264 | CG | PRO | A | 39 | 3.869 | 15.155 | .811 | 1.00 | 37.43 | A |
| ATOM | 265 | C | PRO | A | 39 | 2.917 | 13.399 | −2.330 | 1.00 | 36.68 | A |
| ATOM | 266 | O | PRO | A | 39 | 1.939 | 12.749 | −2.700 | 1.00 | 37.75 | A |
| ATOM | 267 | N | ASP | A | 40 | 3.803 | 13.901 | −3.187 | 1.00 | 35.67 | A |
| ATOM | 268 | CA | ASP | A | 40 | 3.626 | 13.681 | −4.617 | 1.00 | 37.12 | A |
| ATOM | 269 | CB | ASP | A | 40 | 4.714 | 14.387 | −5.438 | 1.00 | 38.06 | A |
| ATOM | 270 | CG | ASP | A | 40 | 4.556 | 15.905 | −5.457 | 1.00 | 41.46 | A |
| ATOM | 271 | OD1 | ASP | A | 40 | 3.426 | 16.411 | −5.246 | 1.00 | 41.34 | A |
| ATOM | 272 | OD2 | ASP | A | 40 | 5.570 | 16.595 | −5.709 | 1.00 | 43.90 | A |
| ATOM | 273 | C | ASP | A | 40 | 3.663 | 12.187 | −4.913 | 1.00 | 36.95 | A |
| ATOM | 274 | O | ASP | A | 40 | 2.752 | 11.654 | −5.547 | 1.00 | 38.21 | A |
| ATOM | 275 | N | PHE | A | 41 | 4.715 | 11.521 | −4.439 | 1.00 | 35.19 | A |
| ATOM | 276 | CA | PHE | A | 41 | 4.907 | 10.090 | −4.637 | 1.00 | 35.05 | A |
| ATOM | 277 | CB | PHE | A | 41 | 6.236 | 9.647 | −4.021 | 1.00 | 35.93 | A |
| ATOM | 278 | CG | PHE | A | 41 | 6.379 | 8.155 | −3.916 | 1.00 | 34.85 | A |
| ATOM | 279 | CD1 | PHE | A | 41 | 6.487 | 7.375 | −5.051 | 1.00 | 36.28 | A |
| ATOM | 280 | CD2 | PHE | A | 41 | 6.354 | 7.527 | −2.681 | 1.00 | 36.32 | A |
| ATOM | 281 | CE1 | PHE | A | 41 | 6.566 | 5.982 | −4.960 | 1.00 | 36.91 | A |
| ATOM | 282 | CE2 | PHE | A | 41 | 6.431 | 6.138 | −2.579 | 1.00 | 35.53 | A |
| ATOM | 283 | CZ | PHE | A | 41 | 6.536 | 5.365 | −3.724 | 1.00 | 35.23 | A |
| ATOM | 284 | C | PHE | A | 41 | 3.792 | 9.203 | −4.071 | 1.00 | 34.73 | A |
| ATOM | 285 | O | PHE | A | 41 | 3.370 | 8.253 | −4.724 | 1.00 | 32.31 | A |
| ATOM | 286 | N | TYR | A | 42 | 3.347 | 9.501 | −2.848 | 1.00 | 35.03 | A |
| ATOM | 287 | CA | TYR | A | 42 | 2.283 | 8.734 | −2.189 | 1.00 | 36.12 | A |
| ATOM | 288 | CB | TYR | A | 42 | 2.042 | 9.251 | −.761 | 1.00 | 37.39 | A |
| ATOM | 289 | CG | TYR | A | 42 | .882 | 8.580 | −.041 | 1.00 | 39.07 | A |
| ATOM | 290 | CD1 | TYR | A | 42 | .912 | 7.220 | .270 | 1.00 | 38.88 | A |
| ATOM | 291 | CE1 | TYR | A | 42 | −.164 | 6.599 | .908 | 1.00 | 40.03 | A |
| ATOM | 292 | CD2 | TYR | A | 42 | −.256 | 9.306 | .311 | 1.00 | 41.58 | A |
| ATOM | 293 | CE2 | TYR | A | 42 | −1.339 | 8.695 | .950 | 1.00 | 42.57 | A |
| ATOM | 294 | CZ | TYR | A | 42 | −1.286 | 7.340 | 1.242 | 1.00 | 42.03 | A |
| ATOM | 295 | OH | TYR | A | 42 | −2.371 | 6.730 | 1.837 | 1.00 | 42.82 | A |
| ATOM | 296 | C | TYR | A | 42 | .972 | 8.797 | −2.966 | 1.00 | 35.76 | A |
| ATOM | 297 | O | TYR | A | 42 | .263 | 7.794 | −3.067 | 1.00 | 35.92 | A |
| ATOM | 298 | N | PHE | A | 43 | .657 | 9.973 | −3.511 | 1.00 | 35.17 | A |
| ATOM | 299 | CA | PHE | A | 43 | −.570 | 10.157 | −4.275 | 1.00 | 35.00 | A |
| ATOM | 300 | CB | PHE | A | 43 | −1.008 | 11.621 | −4.227 | 1.00 | 34.32 | A |
| ATOM | 301 | CG | PHE | A | 43 | −1.821 | 11.946 | −3.019 | 1.00 | 35.42 | A |
| ATOM | 302 | CD1 | PHE | A | 43 | −1.258 | 11.874 | −1.749 | 1.00 | 36.46 | A |
| ATOM | 303 | CD2 | PHE | A | 43 | −3.182 | 12.209 | −3.131 | 1.00 | 36.17 | A |
| ATOM | 304 | CE1 | PHE | A | 43 | −2.043 | 12.050 | −.605 | 1.00 | 36.76 | A |
| ATOM | 305 | CE2 | PHE | A | 43 | −3.973 | 12.385 | −1.995 | 1.00 | 36.73 | A |
| ATOM | 306 | CZ | PHE | A | 43 | −3.402 | 12.303 | −.733 | 1.00 | 36.01 | A |
| ATOM | 307 | C | PHE | A | 43 | −.466 | 9.674 | −5.711 | 1.00 | 34.97 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 308 | O | PHE | A | 43 | −1.464 | 9.296 | −6.324 | 1.00 | 35.50 | A |
| ATOM | 309 | N | ARG | A | 44 | .749 | 9.670 | −6.238 | 1.00 | 35.11 | A |
| ATOM | 310 | CA | ARG | A | 44 | .978 | 9.213 | −7.594 | 1.00 | 36.10 | A |
| ATOM | 311 | CB | ARG | A | 44 | 2.377 | 9.628 | −8.067 | 1.00 | 35.40 | A |
| ATOM | 312 | CG | ARG | A | 44 | 2.664 | 9.344 | −9.535 | 1.00 | 35.13 | A |
| ATOM | 313 | CD | ARG | A | 44 | 4.163 | 9.339 | −9.811 | 1.00 | 35.91 | A |
| ATOM | 314 | NE | ARG | A | 44 | 4.677 | 7.973 | −9.832 | 1.00 | 37.90 | A |
| ATOM | 315 | CZ | ARG | A | 44 | 5.852 | 7.593 | −9.347 | 1.00 | 36.82 | A |
| ATOM | 316 | NH1 | ARG | A | 44 | 6.669 | 8.472 | −8.787 | 1.00 | 35.87 | A |
| ATOM | 317 | NH2 | ARG | A | 44 | 6.203 | 6.319 | −9.420 | 1.00 | 35.52 | A |
| ATOM | 318 | C | ARG | A | 44 | .875 | 7.692 | −7.596 | 1.00 | 36.32 | A |
| ATOM | 319 | O | ARG | A | 44 | .045 | 7.116 | −8.289 | 1.00 | 37.41 | A |
| ATOM | 320 | N | ILE | A | 45 | 1.724 | 7.051 | −6.801 | 1.00 | 36.73 | A |
| ATOM | 321 | CA | ILE | A | 45 | 1.761 | 5.597 | −6.709 | 1.00 | 36.73 | A |
| ATOM | 322 | CB | ILE | A | 45 | 2.832 | 5.150 | −5.657 | 1.00 | 37.01 | A |
| ATOM | 323 | CG2 | ILE | A | 45 | 2.165 | 4.717 | −4.354 | 1.00 | 36.42 | A |
| ATOM | 324 | CG1 | ILE | A | 45 | 3.705 | 4.028 | −6.238 | 1.00 | 36.57 | A |
| ATOM | 325 | CD1 | ILE | A | 45 | 2.967 | 2.746 | −6.571 | 1.00 | 38.47 | A |
| ATOM | 326 | C | ILE | A | 45 | .391 | 4.990 | −6.379 | 1.00 | 36.30 | A |
| ATOM | 327 | O | ILE | A | 45 | .153 | 3.810 | −6.621 | 1.00 | 34.20 | A |
| ATOM | 328 | N | THR | A | 46 | −.515 | 5.801 | −5.838 | 1.00 | 38.01 | A |
| ATOM | 329 | CA | THR | A | 46 | −1.850 | 5.310 | −5.493 | 1.00 | 37.39 | A |
| ATOM | 330 | CB | THR | A | 46 | −2.252 | 5.740 | −4.074 | 1.00 | 36.17 | A |
| ATOM | 331 | OG1 | THR | A | 46 | −1.982 | 7.136 | −3.893 | 1.00 | 33.06 | A |
| ATOM | 332 | CG2 | THR | A | 46 | −1.479 | 4.926 | −3.048 | 1.00 | 37.56 | A |
| ATOM | 333 | C | THR | A | 46 | −2.958 | 5.728 | −6.457 | 1.00 | 38.51 | A |
| ATOM | 334 | O | THR | A | 46 | −4.132 | 5.436 | −6.219 | 1.00 | 37.81 | A |
| ATOM | 335 | N | GLY | A | 47 | −2.584 | 6.408 | −7.540 | 1.00 | 39.96 | A |
| ATOM | 336 | CA | GLY | A | 47 | −3.565 | 6.846 | −8.521 | 1.00 | 42.56 | A |
| ATOM | 337 | C | GLY | A | 47 | −4.502 | 7.909 | −7.984 | 1.00 | 44.81 | A |
| ATOM | 338 | O | GLY | A | 47 | −5.650 | 8.022 | −8.420 | 1.00 | 43.82 | A |
| ATOM | 339 | N | ASN | A | 48 | −4.005 | 8.694 | −7.035 | 1.00 | 46.78 | A |
| ATOM | 340 | CA | ASN | A | 48 | −4.797 | 9.746 | −6.421 | 1.00 | 49.83 | A |
| ATOM | 341 | CB | ASN | A | 48 | −4.906 | 9.495 | −4.911 | 1.00 | 49.33 | A |
| ATOM | 342 | CG | ASN | A | 48 | −5.900 | 8.388 | −4.562 | 1.00 | 49.27 | A |
| ATOM | 343 | OD1 | ASN | A | 48 | −7.092 | 8.641 | −4.364 | 1.00 | 47.01 | A |
| ATOM | 344 | ND2 | ASN | A | 48 | −5.410 | 7.156 | −4.494 | 1.00 | 47.58 | A |
| ATOM | 345 | C | ASN | A | 48 | −4.222 | 11.141 | −6.674 | 1.00 | 52.04 | A |
| ATOM | 346 | O | ASN | A | 48 | −4.160 | 11.965 | −5.765 | 1.00 | 51.94 | A |
| ATOM | 347 | N | GLU | A | 49 | −3.800 | 11.407 | −7.906 | 1.00 | 54.73 | A |
| ATOM | 348 | CA | GLU | A | 49 | −3.246 | 12.720 | −8.234 | 1.00 | 57.69 | A |
| ATOM | 349 | CB | GLU | A | 49 | −2.369 | 12.637 | −9.485 | 1.00 | 59.73 | A |
| ATOM | 350 | CG | GLU | A | 49 | −.879 | 12.518 | −9.183 | 1.00 | 63.54 | A |
| ATOM | 351 | CD | GLU | A | 49 | −.007 | 12.726 | −10.417 | 1.00 | 66.25 | A |
| ATOM | 352 | OE1 | GLU | A | 49 | −.282 | 13.681 | −11.186 | 1.00 | 65.49 | A |
| ATOM | 353 | OE2 | GLU | A | 49 | .959 | 11.945 | −10.605 | 1.00 | 66.00 | A |
| ATOM | 354 | C | GLU | A | 49 | −4.329 | 13.776 | −8.446 | 1.00 | 58.31 | A |
| ATOM | 355 | O | GLU | A | 49 | −4.185 | 14.927 | −8.035 | 1.00 | 59.07 | A |
| ATOM | 356 | N | HIS | A | 50 | −5.418 | 13.371 | −9.084 | 1.00 | 58.62 | A |
| ATOM | 357 | CA | HIS | A | 50 | −6.527 | 14.268 | −9.374 | 1.00 | 59.61 | A |
| ATOM | 358 | CB | HIS | A | 50 | −7.610 | 13.497 | −10.121 | 1.00 | 60.54 | A |
| ATOM | 359 | CG | HIS | A | 50 | −8.106 | 12.301 | −9.376 | 1.00 | 61.50 | A |
| ATOM | 360 | CD2 | HIS | A | 50 | −7.982 | 10.977 | −9.629 | 1.00 | 62.11 | A |
| ATOM | 361 | ND1 | HIS | A | 50 | −8.800 | 12.402 | −8.190 | 1.00 | 62.16 | A |
| ATOM | 362 | CE1 | HIS | A | 50 | −9.084 | 11.191 | −7.744 | 1.00 | 62.79 | A |
| ATOM | 363 | NE2 | HIS | A | 50 | −8.599 | 10.309 | −8.599 | 1.00 | 62.52 | A |
| ATOM | 364 | C | HIS | A | 50 | −7.149 | 14.957 | −8.153 | 1.00 | 59.88 | A |
| ATOM | 365 | O | HIS | A | 50 | −7.651 | 16.080 | −8.270 | 1.00 | 60.59 | A |
| ATOM | 366 | N | ASN | A | 51 | −7.128 | 14.296 | −6.995 | 1.00 | 58.82 | A |
| ATOM | 367 | CA | ASN | A | 51 | −7.719 | 14.870 | −5.781 | 1.00 | 56.81 | A |
| ATOM | 368 | CB | ASN | A | 51 | −8.203 | 13.767 | −4.843 | 1.00 | 56.29 | A |
| ATOM | 369 | CG | ASN | A | 51 | −9.152 | 14.286 | −3.790 | 1.00 | 56.26 | A |
| ATOM | 370 | OD1 | ASN | A | 51 | −8.874 | 15.284 | −3.123 | 1.00 | 56.98 | A |
| ATOM | 371 | ND2 | ASN | A | 51 | −10.282 | 13.614 | −3.632 | 1.00 | 56.27 | A |
| ATOM | 372 | C | ASN | A | 51 | −6.760 | 15.785 | −5.028 | 1.00 | 56.35 | A |
| ATOM | 373 | O | ASN | A | 51 | −6.394 | 15.529 | −3.877 | 1.00 | 55.87 | A |
| ATOM | 374 | N | THR | A | 52 | −6.376 | 16.860 | −5.705 | 1.00 | 55.80 | A |
| ATOM | 375 | CA | THR | A | 52 | −5.463 | 17.865 | −5.188 | 1.00 | 54.81 | A |
| ATOM | 376 | CB | THR | A | 52 | −5.459 | 19.087 | −6.111 | 1.00 | 55.61 | A |
| ATOM | 377 | OG1 | THR | A | 52 | −6.814 | 19.464 | −6.398 | 1.00 | 54.96 | A |
| ATOM | 378 | CG2 | THR | A | 52 | −4.736 | 18.764 | −7.417 | 1.00 | 55.96 | A |
| ATOM | 379 | C | THR | A | 52 | −5.750 | 18.336 | −3.767 | 1.00 | 53.99 | A |
| ATOM | 380 | O | THR | A | 52 | −4.838 | 18.786 | −3.071 | 1.00 | 53.61 | A |
| ATOM | 381 | N | GLU | A | 53 | −7.007 | 18.241 | −3.339 | 1.00 | 53.25 | A |
| ATOM | 382 | CA | GLU | A | 53 | −7.384 | 18.670 | −1.991 | 1.00 | 52.66 | A |

APPENDIX A-continued

*Pinus sylvestris* STS

| ATOM | # | TYPE | RES | | | X | Y | Z | OCC | B | |
|------|---|------|-----|---|----|--------|--------|--------|------|-------|---|
| ATOM | 383 | CB | GLU | A | 53 | −8.908 | 18.712 | −1.848 | 1.00 | 53.87 | A |
| ATOM | 384 | CG | GLU | A | 53 | −9.545 | 19.936 | −2.469 | 1.00 | 56.65 | A |
| ATOM | 385 | CD | GLU | A | 53 | −9.077 | 21.226 | −1.809 | 1.00 | 58.56 | A |
| ATOM | 386 | OE1 | GLU | A | 53 | −9.448 | 21.471 | −.638 | 1.00 | 59.21 | A |
| ATOM | 387 | OE2 | GLU | A | 53 | −8.331 | 21.990 | −2.460 | 1.00 | 59.26 | A |
| ATOM | 388 | C | GLU | A | 53 | −6.795 | 17.774 | −.902 | 1.00 | 51.50 | A |
| ATOM | 389 | O | GLU | A | 53 | −6.097 | 18.248 | −.001 | 1.00 | 50.48 | A |
| ATOM | 390 | N | LEU | A | 54 | −7.084 | 16.479 | −.986 | 1.00 | 50.21 | A |
| ATOM | 391 | CA | LEU | A | 54 | −6.580 | 15.524 | −.006 | 1.00 | 49.09 | A |
| ATOM | 392 | CB | LEU | A | 54 | −7.098 | 14.123 | −.324 | 1.00 | 46.64 | A |
| ATOM | 393 | CG | LEU | A | 54 | −6.867 | 13.107 | .787 | 1.00 | 45.40 | A |
| ATOM | 394 | CD1 | LEU | A | 54 | −7.488 | 13.628 | 2.071 | 1.00 | 43.87 | A |
| ATOM | 395 | CD2 | LEU | A | 54 | −7.464 | 11.766 | .393 | 1.00 | 44.37 | A |
| ATOM | 396 | C | LEU | A | 54 | −5.057 | 15.524 | −.019 | 1.00 | 49.00 | A |
| ATOM | 397 | O | LEU | A | 54 | −4.411 | 15.498 | 1.033 | 1.00 | 47.49 | A |
| ATOM | 398 | N | LYS | A | 55 | −4.497 | 15.556 | −1.226 | 1.00 | 48.68 | A |
| ATOM | 399 | CA | LYS | A | 55 | −3.055 | 15.572 | −1.408 | 1.00 | 47.72 | A |
| ATOM | 400 | CB | LYS | A | 55 | −2.729 | 15.647 | −2.901 | 1.00 | 48.44 | A |
| ATOM | 401 | CG | LYS | A | 55 | −1.262 | 15.406 | −3.270 | 1.00 | 50.21 | A |
| ATOM | 402 | CD | LYS | A | 55 | −1.057 | 15.477 | −4.794 | 1.00 | 50.11 | A |
| ATOM | 403 | CE | LYS | A | 55 | .398 | 15.232 | −5.188 | 1.00 | 51.15 | A |
| ATOM | 404 | NZ | LYS | A | 55 | .637 | 15.423 | −6.646 | 1.00 | 51.72 | A |
| ATOM | 405 | C | LYS | A | 55 | −2.465 | 16.773 | −.667 | 1.00 | 46.95 | A |
| ATOM | 406 | O | LYS | A | 55 | −1.555 | 16.624 | .148 | 1.00 | 45.99 | A |
| ATOM | 407 | N | ASP | A | 56 | −2.993 | 17.962 | −.938 | 1.00 | 47.40 | A |
| ATOM | 408 | CA | ASP | A | 56 | −2.487 | 19.158 | −.277 | 1.00 | 48.44 | A |
| ATOM | 409 | CB | ASP | A | 56 | −3.171 | 20.423 | −.811 | 1.00 | 50.05 | A |
| ATOM | 410 | CG | ASP | A | 56 | −2.567 | 21.706 | −.233 | 1.00 | 52.26 | A |
| ATOM | 411 | OD1 | ASP | A | 56 | −1.327 | 21.769 | −.059 | 1.00 | 52.72 | A |
| ATOM | 412 | OD2 | ASP | A | 56 | −3.332 | 22.656 | .038 | 1.00 | 53.74 | A |
| ATOM | 413 | C | ASP | A | 56 | −2.716 | 19.027 | 1.217 | 1.00 | 47.51 | A |
| ATOM | 414 | O | ASP | A | 56 | −1.932 | 19.538 | 2.026 | 1.00 | 47.63 | A |
| ATOM | 415 | N | LYS | A | 57 | −3.793 | 18.337 | 1.582 | 1.00 | 46.00 | A |
| ATOM | 416 | CA | LYS | A | 57 | −4.098 | 18.115 | 2.988 | 1.00 | 45.09 | A |
| ATOM | 417 | CB | LYS | A | 57 | −5.500 | 17.525 | 3.150 | 1.00 | 46.26 | A |
| ATOM | 418 | CG | LYS | A | 57 | −5.753 | 16.920 | 4.524 | 1.00 | 47.34 | A |
| ATOM | 419 | CD | LYS | A | 57 | −7.006 | 17.481 | 5.180 | 1.00 | 48.29 | A |
| ATOM | 420 | CE | LYS | A | 57 | −8.282 | 17.064 | 4.462 | 1.00 | 46.87 | A |
| ATOM | 421 | NZ | LYS | A | 57 | −9.480 | 17.627 | 5.149 | 1.00 | 46.62 | A |
| ATOM | 422 | C | LYS | A | 57 | −3.068 | 17.164 | 3.593 | 1.00 | 42.98 | A |
| ATOM | 423 | O | LYS | A | 57 | −2.712 | 17.280 | 4.762 | 1.00 | 41.90 | A |
| ATOM | 424 | N | PHE | A | 58 | −2.587 | 16.229 | 2.786 | 1.00 | 41.09 | A |
| ATOM | 425 | CA | PHE | A | 58 | −1.606 | 15.270 | 3.261 | 1.00 | 40.95 | A |
| ATOM | 426 | CB | PHE | A | 58 | −1.620 | 14.033 | 2.371 | 1.00 | 40.96 | A |
| ATOM | 427 | CG | PHE | A | 58 | −.646 | 12.975 | 2.786 | 1.00 | 42.12 | A |
| ATOM | 428 | CD1 | PHE | A | 58 | .574 | 12.838 | 2.128 | 1.00 | 42.03 | A |
| ATOM | 429 | CD2 | PHE | A | 58 | −.957 | 12.093 | 3.815 | 1.00 | 41.57 | A |
| ATOM | 430 | CE1 | PHE | A | 58 | 1.470 | 11.834 | 2.484 | 1.00 | 42.26 | A |
| ATOM | 431 | CE2 | PHE | A | 58 | −.064 | 11.085 | 4.181 | 1.00 | 42.43 | A |
| ATOM | 432 | CZ | PHE | A | 58 | 1.150 | 10.955 | 3.512 | 1.00 | 40.79 | A |
| ATOM | 433 | C | PHE | A | 58 | −.219 | 15.888 | 3.300 | 1.00 | 41.74 | A |
| ATOM | 434 | O | PHE | A | 58 | .610 | 15.528 | 4.141 | 1.00 | 40.63 | A |
| ATOM | 435 | N | LYS | A | 59 | .034 | 16.823 | 2.389 | 1.00 | 42.14 | A |
| ATOM | 436 | CA | LYS | A | 59 | 1.327 | 17.496 | 2.363 | 1.00 | 42.84 | A |
| ATOM | 437 | CB | LYS | A | 59 | 1.445 | 18.441 | 1.158 | 1.00 | 44.84 | A |
| ATOM | 438 | CG | LYS | A | 59 | 1.444 | 17.756 | −.206 | 1.00 | 47.75 | A |
| ATOM | 439 | CD | LYS | A | 59 | 1.788 | 18.739 | −1.329 | 1.00 | 49.41 | A |
| ATOM | 440 | CE | LYS | A | 59 | 1.789 | 18.050 | −2.697 | 1.00 | 51.02 | A |
| ATOM | 441 | NZ | LYS | A | 59 | 2.057 | 18.999 | −3.823 | 1.00 | 51.85 | A |
| ATOM | 442 | C | LYS | A | 59 | 1.403 | 18.307 | 3.639 | 1.00 | 41.25 | A |
| ATOM | 443 | O | LYS | A | 59 | 2.446 | 18.388 | 4.278 | 1.00 | 40.75 | A |
| ATOM | 444 | N | ARG | A | 60 | .274 | 18.898 | 4.005 | 1.00 | 40.74 | A |
| ATOM | 445 | CA | ARG | A | 60 | .198 | 19.713 | 5.205 | 1.00 | 42.28 | A |
| ATOM | 446 | CB | ARG | A | 60 | −1.133 | 20.473 | 5.239 | 1.00 | 46.48 | A |
| ATOM | 447 | CG | ARG | A | 60 | −1.243 | 21.564 | 4.174 | 1.00 | 51.56 | A |
| ATOM | 448 | CD | ARG | A | 60 | −.227 | 22.673 | 4.426 | 1.00 | 56.26 | A |
| ATOM | 449 | NE | ARG | A | 60 | −.197 | 23.681 | 3.364 | 1.00 | 60.76 | A |
| ATOM | 450 | CZ | ARG | A | 60 | .504 | 24.812 | 3.426 | 1.00 | 62.22 | A |
| ATOM | 451 | NH1 | ARG | A | 60 | 1.233 | 25.084 | 4.501 | 1.00 | 62.02 | A |
| ATOM | 452 | NH2 | ARG | A | 60 | .486 | 25.670 | 2.412 | 1.00 | 62.68 | A |
| ATOM | 453 | C | ARG | A | 60 | .374 | 18.885 | 6.475 | 1.00 | 40.66 | A |
| ATOM | 454 | O | ARG | A | 60 | .823 | 19.402 | 7.496 | 1.00 | 41.04 | A |
| ATOM | 455 | N | ILE | A | 61 | .024 | 17.603 | 6.421 | 1.00 | 38.03 | A |
| ATOM | 456 | CA | ILE | A | 61 | .192 | 16.746 | 7.590 | 1.00 | 34.21 | A |
| ATOM | 457 | CB | ILE | A | 61 | −.631 | 15.456 | 7.497 | 1.00 | 32.45 | A |

APPENDIX A-continued

*Pinus sylvestris* STS

| ATOM | # | TYPE | RES | | | X | Y | Z | OCC | B | |
|------|---|------|-----|---|----|--------|--------|--------|------|-------|---|
| ATOM | 458 | CG2 | ILE | A | 61 | -.228 | 14.520 | 8.638 | 1.00 | 29.47 | A |
| ATOM | 459 | CG1 | ILE | A | 61 | -2.127 | 15.776 | 7.548 | 1.00 | 31.31 | A |
| ATOM | 460 | CD1 | ILE | A | 61 | -3.010 | 14.567 | 7.320 | 1.00 | 30.86 | A |
| ATOM | 461 | C | ILE | A | 61 | 1.654 | 16.344 | 7.689 | 1.00 | 33.40 | A |
| ATOM | 462 | O | ILE | A | 61 | 2.230 | 16.326 | 8.773 | 1.00 | 30.59 | A |
| ATOM | 463 | N | CYS | A | 62 | 2.235 | 16.012 | 6.539 | 1.00 | 34.39 | A |
| ATOM | 464 | CA | CYS | A | 62 | 3.630 | 15.605 | 6.469 | 1.00 | 36.39 | A |
| ATOM | 465 | CB | CYS | A | 62 | 4.009 | 15.211 | 5.035 | 1.00 | 35.67 | A |
| ATOM | 466 | SG | CYS | A | 62 | 3.392 | 13.621 | 4.435 | 1.00 | 36.68 | A |
| ATOM | 467 | C | CYS | A | 62 | 4.543 | 16.736 | 6.937 | 1.00 | 37.23 | A |
| ATOM | 468 | O | CYS | A | 62 | 5.539 | 16.498 | 7.615 | 1.00 | 36.14 | A |
| ATOM | 469 | N | GLU | A | 63 | 4.190 | 17.968 | 6.585 | 1.00 | 38.33 | A |
| ATOM | 470 | CA | GLU | A | 63 | 4.996 | 19.124 | 6.961 | 1.00 | 39.37 | A |
| ATOM | 471 | CB | GLU | A | 63 | 4.608 | 20.325 | 6.097 | 1.00 | 41.87 | A |
| ATOM | 472 | CG | GLU | A | 63 | 5.008 | 20.131 | 4.637 | 1.00 | 44.04 | A |
| ATOM | 473 | CD | GLU | A | 63 | 4.621 | 21.296 | 3.752 | 1.00 | 45.93 | A |
| ATOM | 474 | OE1 | GLU | A | 63 | 3.407 | 21.593 | 3.652 | 1.00 | 47.07 | A |
| ATOM | 475 | OE2 | GLU | A | 63 | 5.533 | 21.909 | 3.152 | 1.00 | 46.35 | A |
| ATOM | 476 | C | GLU | A | 63 | 4.957 | 19.483 | 8.442 | 1.00 | 37.95 | A |
| ATOM | 477 | O | GLU | A | 63 | 5.798 | 20.250 | 8.915 | 1.00 | 37.13 | A |
| ATOM | 478 | N | ARG | A | 64 | 3.986 | 18.934 | 9.166 | 1.00 | 36.39 | A |
| ATOM | 479 | CA | ARG | A | 64 | 3.886 | 19.163 | 10.608 | 1.00 | 37.43 | A |
| ATOM | 480 | CB | ARG | A | 64 | 2.428 | 19.371 | 11.037 | 1.00 | 37.43 | A |
| ATOM | 481 | CG | ARG | A | 64 | 1.829 | 20.731 | 10.710 | 1.00 | 40.40 | A |
| ATOM | 482 | CD | ARG | A | 64 | .612 | 20.995 | 11.592 | 1.00 | 42.29 | A |
| ATOM | 483 | NE | ARG | A | 64 | -.415 | 19.974 | 11.406 | 1.00 | 43.14 | A |
| ATOM | 484 | CZ | ARG | A | 64 | -1.196 | 19.897 | 10.335 | 1.00 | 44.35 | A |
| ATOM | 485 | NH1 | ARG | A | 64 | -1.065 | 20.785 | 9.360 | 1.00 | 44.07 | A |
| ATOM | 486 | NH2 | ARG | A | 64 | -2.103 | 18.933 | 10.234 | 1.00 | 44.06 | A |
| ATOM | 487 | C | ARG | A | 64 | 4.454 | 17.952 | 11.377 | 1.00 | 37.08 | A |
| ATOM | 488 | O | ARG | A | 64 | 4.840 | 18.067 | 12.539 | 1.00 | 38.38 | A |
| ATOM | 489 | N | SER | A | 65 | 4.506 | 16.801 | 10.714 | 1.00 | 36.12 | A |
| ATOM | 490 | CA | SER | A | 65 | 4.997 | 15.570 | 11.314 | 1.00 | 35.70 | A |
| ATOM | 491 | CB | SER | A | 65 | 5.048 | 14.464 | 10.265 | 1.00 | 35.60 | A |
| ATOM | 492 | OG | SER | A | 65 | 6.067 | 14.711 | 9.310 | 1.00 | 34.83 | A |
| ATOM | 493 | C | SER | A | 65 | 6.364 | 15.665 | 11.982 | 1.00 | 36.13 | A |
| ATOM | 494 | O | SER | A | 65 | 6.655 | 14.899 | 12.890 | 1.00 | 36.64 | A |
| ATOM | 495 | N | ALA | A | 66 | 7.207 | 16.593 | 11.540 | 1.00 | 36.59 | A |
| ATOM | 496 | CA | ALA | A | 66 | 8.544 | 16.736 | 12.115 | 1.00 | 34.73 | A |
| ATOM | 497 | CB | ALA | A | 66 | 8.451 | 16.912 | 13.624 | 1.00 | 34.03 | A |
| ATOM | 498 | C | ALA | A | 66 | 9.372 | 15.497 | 11.780 | 1.00 | 35.37 | A |
| ATOM | 499 | O | ALA | A | 66 | 10.364 | 15.199 | 12.444 | 1.00 | 37.03 | A |
| ATOM | 500 | N | ILE | A | 67 | 8.947 | 14.765 | 10.753 | 1.00 | 34.92 | A |
| ATOM | 501 | CA | ILE | A | 67 | 9.651 | 13.566 | 10.312 | 1.00 | 33.47 | A |
| ATOM | 502 | CB | ILE | A | 67 | 8.673 | 12.386 | 10.079 | 1.00 | 30.76 | A |
| ATOM | 503 | CG2 | ILE | A | 67 | 9.438 | 11.146 | 9.666 | 1.00 | 29.23 | A |
| ATOM | 504 | CG1 | ILE | A | 67 | 7.872 | 12.108 | 11.348 | 1.00 | 28.84 | A |
| ATOM | 505 | CD1 | ILE | A | 67 | 6.788 | 11.067 | 11.151 | 1.00 | 28.29 | A |
| ATOM | 506 | C | ILE | A | 67 | 10.312 | 13.925 | 8.989 | 1.00 | 34.28 | A |
| ATOM | 507 | O | ILE | A | 67 | 9.624 | 14.239 | 8.017 | 1.00 | 36.16 | A |
| ATOM | 508 | N | LYS | A | 68 | 11.638 | 13.873 | 8.943 | 1.00 | 34.27 | A |
| ATOM | 509 | CA | LYS | A | 68 | 12.352 | 14.235 | 7.724 | 1.00 | 34.52 | A |
| ATOM | 510 | CB | LYS | A | 68 | 13.688 | 14.891 | 8.090 | 1.00 | 35.42 | A |
| ATOM | 511 | CG | LYS | A | 68 | 13.505 | 16.015 | 9.091 | 1.00 | 41.45 | A |
| ATOM | 512 | CD | LYS | A | 68 | 14.753 | 16.865 | 9.328 | 1.00 | 44.25 | A |
| ATOM | 513 | CE | LYS | A | 68 | 14.409 | 18.006 | 10.300 | 1.00 | 45.99 | A |
| ATOM | 514 | NZ | LYS | A | 68 | 15.554 | 18.899 | 10.677 | 1.00 | 46.24 | A |
| ATOM | 515 | C | LYS | A | 68 | 12.569 | 13.077 | 6.760 | 1.00 | 33.29 | A |
| ATOM | 516 | O | LYS | A | 68 | 12.737 | 13.287 | 5.555 | 1.00 | 33.72 | A |
| ATOM | 517 | N | GLN | A | 69 | 12.560 | 11.854 | 7.283 | 1.00 | 31.93 | A |
| ATOM | 518 | CA | GLN | A | 69 | 12.756 | 10.679 | 6.441 | 1.00 | 30.12 | A |
| ATOM | 519 | CB | GLN | A | 69 | 14.211 | 10.591 | 5.963 | 1.00 | 32.01 | A |
| ATOM | 520 | CG | GLN | A | 69 | 15.208 | 10.263 | 7.060 | 1.00 | 34.66 | A |
| ATOM | 521 | CD | GLN | A | 69 | 15.994 | 8.989 | 6.779 | 1.00 | 37.65 | A |
| ATOM | 522 | OE1 | GLN | A | 69 | 15.416 | 7.908 | 6.627 | 1.00 | 42.24 | A |
| ATOM | 523 | NE2 | GLN | A | 69 | 17.317 | 9.108 | 6.717 | 1.00 | 35.40 | A |
| ATOM | 524 | C | GLN | A | 69 | 12.410 | 9.400 | 7.174 | 1.00 | 27.55 | A |
| ATOM | 525 | O | GLN | A | 69 | 12.518 | 9.318 | 8.389 | 1.00 | 26.69 | A |
| ATOM | 526 | N | ARG | A | 70 | 12.009 | 8.396 | 6.414 | 1.00 | 26.61 | A |
| ATOM | 527 | CA | ARG | A | 70 | 11.648 | 7.110 | 6.973 | 1.00 | 28.66 | A |
| ATOM | 528 | CB | ARG | A | 70 | 10.129 | 6.982 | 7.054 | 1.00 | 29.52 | A |
| ATOM | 529 | CG | ARG | A | 70 | 9.441 | 7.999 | 7.946 | 1.00 | 31.27 | A |
| ATOM | 530 | CD | ARG | A | 70 | 7.912 | 7.856 | 7.848 | 1.00 | 32.64 | A |
| ATOM | 531 | NE | ARG | A | 70 | 7.373 | 8.476 | 6.636 | 1.00 | 31.85 | A |
| ATOM | 532 | CZ | ARG | A | 70 | 6.126 | 8.330 | 6.190 | 1.00 | 33.49 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 533 | NH1 | ARG | A | 70 | 5.253 | 7.571 | 6.844 | 1.00 | 33.87 | A |
| ATOM | 534 | NH2 | ARG | A | 70 | 5.746 | 8.952 | 5.083 | 1.00 | 33.20 | A |
| ATOM | 535 | C | ARG | A | 70 | 12.202 | 6.021 | 6.065 | 1.00 | 28.42 | A |
| ATOM | 536 | O | ARG | A | 70 | 12.528 | 6.280 | 4.908 | 1.00 | 26.75 | A |
| ATOM | 537 | N | TYR | A | 71 | 12.322 | 4.809 | 6.596 | 1.00 | 28.10 | A |
| ATOM | 538 | CA | TYR | A | 71 | 12.811 | 3.683 | 5.814 | 1.00 | 28.19 | A |
| ATOM | 539 | CB | TYR | A | 71 | 13.940 | 2.958 | 6.556 | 1.00 | 28.62 | A |
| ATOM | 540 | CG | TYR | A | 71 | 15.224 | 3.761 | 6.650 | 1.00 | 29.33 | A |
| ATOM | 541 | CD1 | TYR | A | 71 | 15.475 | 4.597 | 7.735 | 1.00 | 29.31 | A |
| ATOM | 542 | CE1 | TYR | A | 71 | 16.651 | 5.341 | 7.812 | 1.00 | 31.09 | A |
| ATOM | 543 | CD2 | TYR | A | 71 | 16.180 | 3.690 | 5.643 | 1.00 | 28.03 | A |
| ATOM | 544 | CE2 | TYR | A | 71 | 17.350 | 4.426 | 5.710 | 1.00 | 30.76 | A |
| ATOM | 545 | CZ | TYR | A | 71 | 17.581 | 5.248 | 6.794 | 1.00 | 30.97 | A |
| ATOM | 546 | OH | TYR | A | 71 | 18.748 | 5.974 | 6.847 | 1.00 | 34.98 | A |
| ATOM | 547 | C | TYR | A | 71 | 11.637 | 2.740 | 5.558 | 1.00 | 29.16 | A |
| ATOM | 548 | O | TYR | A | 71 | 11.068 | 2.161 | 6.486 | 1.00 | 26.84 | A |
| ATOM | 549 | N | MET | A | 72 | 11.275 | 2.599 | 4.288 | 1.00 | 28.94 | A |
| ATOM | 550 | CA | MET | A | 72 | 10.147 | 1.773 | 3.907 | 1.00 | 27.84 | A |
| ATOM | 551 | CB | MET | A | 72 | 9.169 | 2.600 | 3.062 | 1.00 | 27.20 | A |
| ATOM | 552 | CG | MET | A | 72 | 8.753 | 3.911 | 3.706 | 1.00 | 27.56 | A |
| ATOM | 553 | SD | MET | A | 72 | 7.148 | 4.518 | 3.144 | 1.00 | 22.93 | A |
| ATOM | 554 | CE | MET | A | 72 | 6.139 | 3.616 | 4.227 | 1.00 | 26.94 | A |
| ATOM | 555 | C | MET | A | 72 | 10.528 | .516 | 3.151 | 1.00 | 26.70 | A |
| ATOM | 556 | O | MET | A | 72 | 11.360 | .551 | 2.241 | 1.00 | 25.56 | A |
| ATOM | 557 | N | TYR | A | 73 | 9.918 | −.597 | 3.549 | 1.00 | 24.06 | A |
| ATOM | 558 | CA | TYR | A | 73 | 10.147 | −1.876 | 2.895 | 1.00 | 23.85 | A |
| ATOM | 559 | CB | TYR | A | 73 | 9.463 | −3.014 | 3.658 | 1.00 | 24.18 | A |
| ATOM | 560 | CG | TYR | A | 73 | 9.171 | −4.217 | 2.779 | 1.00 | 24.55 | A |
| ATOM | 561 | CD1 | TYR | A | 73 | 10.193 | −5.055 | 2.348 | 1.00 | 21.59 | A |
| ATOM | 562 | CE1 | TYR | A | 73 | 9.928 | −6.136 | 1.525 | 1.00 | 27.28 | A |
| ATOM | 563 | CD2 | TYR | A | 73 | 7.869 | −4.495 | 2.357 | 1.00 | 26.09 | A |
| ATOM | 564 | CE2 | TYR | A | 73 | 7.594 | −5.581 | 1.531 | 1.00 | 26.05 | A |
| ATOM | 565 | CZ | TYR | A | 73 | 8.630 | −6.395 | 1.125 | 1.00 | 26.65 | A |
| ATOM | 566 | OH | TYR | A | 73 | 8.371 | −7.483 | .340 | 1.00 | 30.63 | A |
| ATOM | 567 | C | TYR | A | 73 | 9.501 | −1.756 | 1.531 | 1.00 | 24.72 | A |
| ATOM | 568 | O | TYR | A | 73 | 10.066 | −2.153 | .516 | 1.00 | 25.42 | A |
| ATOM | 569 | N | LEU | A | 74 | 8.291 | −1.220 | 1.529 | 1.00 | 24.58 | A |
| ATOM | 570 | CA | LEU | A | 74 | 7.547 | −1.023 | .297 | 1.00 | 27.00 | A |
| ATOM | 571 | CB | LEU | A | 74 | 6.134 | −.524 | .597 | 1.00 | 26.63 | A |
| ATOM | 572 | CG | LEU | A | 74 | 5.223 | −1.486 | 1.347 | 1.00 | 23.99 | A |
| ATOM | 573 | CD1 | LEU | A | 74 | 4.071 | −.711 | 1.932 | 1.00 | 24.50 | A |
| ATOM | 574 | CD2 | LEU | A | 74 | 4.749 | −2.579 | .420 | 1.00 | 23.90 | A |
| ATOM | 575 | C | LEU | A | 74 | 8.242 | .004 | −.576 | 1.00 | 27.44 | A |
| ATOM | 576 | O | LEU | A | 74 | 8.339 | 1.174 | −.211 | 1.00 | 26.38 | A |
| ATOM | 577 | N | THR | A | 75 | 8.733 | −.447 | −1.724 | 1.00 | 29.33 | A |
| ATOM | 578 | CA | THR | A | 75 | 9.385 | .427 | −2.685 | 1.00 | 28.26 | A |
| ATOM | 579 | CB | THR | A | 75 | 10.624 | −.258 | −3.316 | 1.00 | 27.99 | A |
| ATOM | 580 | OG1 | THR | A | 75 | 10.243 | −1.499 | −3.918 | 1.00 | 27.29 | A |
| ATOM | 581 | CG2 | THR | A | 75 | 11.671 | −.542 | −2.260 | 1.00 | 30.37 | A |
| ATOM | 582 | C | THR | A | 75 | 8.331 | .701 | −3.764 | 1.00 | 29.52 | A |
| ATOM | 583 | O | THR | A | 75 | 7.188 | .229 | −3.664 | 1.00 | 25.85 | A |
| ATOM | 584 | N | GLU | A | 76 | 8.699 | 1.464 | −4.788 | 1.00 | 30.38 | A |
| ATOM | 585 | CA | GLU | A | 76 | 7.758 | 1.758 | −5.853 | 1.00 | 31.86 | A |
| ATOM | 586 | CB | GLU | A | 76 | 8.277 | 2.888 | −6.730 | 1.00 | 34.29 | A |
| ATOM | 587 | CG | GLU | A | 76 | 7.227 | 3.361 | −7.709 | 1.00 | 37.84 | A |
| ATOM | 588 | CD | GLU | A | 76 | 7.774 | 4.305 | −8.738 | 1.00 | 40.62 | A |
| ATOM | 589 | OE1 | GLU | A | 76 | 8.541 | 5.215 | −8.359 | 1.00 | 41.20 | A |
| ATOM | 590 | OE2 | GLU | A | 76 | 7.422 | 4.144 | −9.926 | 1.00 | 44.13 | A |
| ATOM | 591 | C | GLU | A | 76 | 7.562 | .511 | −6.707 | 1.00 | 32.06 | A |
| ATOM | 592 | O | GLU | A | 76 | 6.453 | .199 | −7.154 | 1.00 | 31.57 | A |
| ATOM | 593 | N | GLU | A | 77 | 8.662 | −.192 | −6.936 | 1.00 | 30.45 | A |
| ATOM | 594 | CA | GLU | A | 77 | 8.656 | −1.412 | −7.720 | 1.00 | 32.97 | A |
| ATOM | 595 | CB | GLU | A | 77 | 10.080 | −1.949 | −7.790 | 1.00 | 35.54 | A |
| ATOM | 596 | CG | GLU | A | 77 | 10.284 | −3.126 | −8.705 | 1.00 | 43.11 | A |
| ATOM | 597 | CD | GLU | A | 77 | 11.767 | −3.446 | −8.885 | 1.00 | 46.08 | A |
| ATOM | 598 | OE1 | GLU | A | 77 | 12.485 | −2.654 | −9.543 | 1.00 | 47.40 | A |
| ATOM | 599 | OE2 | GLU | A | 77 | 12.218 | −4.484 | −8.358 | 1.00 | 47.34 | A |
| ATOM | 600 | C | GLU | A | 77 | 7.727 | −2.445 | −7.089 | 1.00 | 33.13 | A |
| ATOM | 601 | O | GLU | A | 77 | 7.005 | −3.150 | −7.789 | 1.00 | 33.97 | A |
| ATOM | 602 | N | ILE | A | 78 | 7.737 | −2.525 | −5.761 | 1.00 | 32.98 | A |
| ATOM | 603 | CA | ILE | A | 78 | 6.890 | −3.482 | −5.045 | 1.00 | 33.29 | A |
| ATOM | 604 | CB | ILE | A | 78 | 7.368 | −3.668 | −3.584 | 1.00 | 32.97 | A |
| ATOM | 605 | CG2 | ILE | A | 78 | 6.397 | −4.556 | −2.814 | 1.00 | 34.53 | A |
| ATOM | 606 | CG1 | ILE | A | 78 | 8.745 | −4.330 | −3.571 | 1.00 | 31.63 | A |
| ATOM | 607 | CD1 | ILE | A | 78 | 9.382 | −4.396 | −2.195 | 1.00 | 33.04 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 608 | C | ILE | A | 78 | 5.419 | −3.066 | −5.051 | 1.00 | 34.05 | A |
| ATOM | 609 | O | ILE | A | 78 | 4.544 | −3.902 | −5.262 | 1.00 | 32.38 | A |
| ATOM | 610 | N | LEU | A | 79 | 5.145 | −1.782 | −4.813 | 1.00 | 35.12 | A |
| ATOM | 611 | CA | LEU | A | 79 | 3.770 | −1.297 | −4.834 | 1.00 | 36.98 | A |
| ATOM | 612 | CB | LEU | A | 79 | 3.698 | .167 | −4.389 | 1.00 | 37.47 | A |
| ATOM | 613 | CG | LEU | A | 79 | 3.811 | .411 | −2.887 | 1.00 | 37.60 | A |
| ATOM | 614 | CD1 | LEU | A | 79 | 3.898 | 1.899 | −2.597 | 1.00 | 36.08 | A |
| ATOM | 615 | CD2 | LEU | A | 79 | 2.611 | −.216 | −2.202 | 1.00 | 35.79 | A |
| ATOM | 616 | C | LEU | A | 79 | 3.191 | −1.433 | −6.243 | 1.00 | 38.11 | A |
| ATOM | 617 | O | LEU | A | 79 | 2.002 | −1.705 | −6.405 | 1.00 | 39.23 | A |
| ATOM | 618 | N | LYS | A | 80 | 4.038 | −1.262 | −7.257 | 1.00 | 39.10 | A |
| ATOM | 619 | CA | LYS | A | 80 | 3.600 | −1.368 | −8.649 | 1.00 | 40.27 | A |
| ATOM | 620 | CB | LYS | A | 80 | 4.706 | −.885 | −9.589 | 1.00 | 42.10 | A |
| ATOM | 621 | CG | LYS | A | 80 | 4.913 | .627 | −9.598 | 1.00 | 43.49 | A |
| ATOM | 622 | CD | LYS | A | 80 | 4.325 | 1.294 | −10.844 | 1.00 | 44.07 | A |
| ATOM | 623 | CE | LYS | A | 80 | 2.802 | 1.242 | −10.867 | 1.00 | 46.55 | A |
| ATOM | 624 | NZ | LYS | A | 80 | 2.232 | 2.001 | −12.020 | 1.00 | 47.24 | A |
| ATOM | 625 | C | LYS | A | 80 | 3.171 | −2.787 | −9.043 | 1.00 | 39.71 | A |
| ATOM | 626 | O | LYS | A | 80 | 2.313 | −2.958 | −9.910 | 1.00 | 39.42 | A |
| ATOM | 627 | N | LYS | A | 81 | 3.777 | −3.799 | −8.425 | 1.00 | 39.39 | A |
| ATOM | 628 | CA | LYS | A | 81 | 3.420 | −5.188 | −8.709 | 1.00 | 39.36 | A |
| ATOM | 629 | CB | LYS | A | 81 | 4.599 | −6.129 | −8.454 | 1.00 | 40.38 | A |
| ATOM | 630 | CG | LYS | A | 81 | 5.848 | −5.880 | −9.269 | 1.00 | 42.46 | A |
| ATOM | 631 | CD | LYS | A | 81 | 6.940 | −6.882 | −8.883 | 1.00 | 44.35 | A |
| ATOM | 632 | CE | LYS | A | 81 | 6.480 | −8.334 | −9.111 | 1.00 | 45.75 | A |
| ATOM | 633 | NZ | LYS | A | 81 | 7.512 | −9.371 | −8.780 | 1.00 | 43.48 | A |
| ATOM | 634 | C | LYS | A | 81 | 2.289 | −5.598 | −7.772 | 1.00 | 38.94 | A |
| ATOM | 635 | O | LYS | A | 81 | 1.782 | −6.711 | −7.850 | 1.00 | 40.01 | A |
| ATOM | 636 | N | ASN | A | 82 | 1.897 | −4.693 | −6.884 | 1.00 | 39.20 | A |
| ATOM | 637 | CA | ASN | A | 82 | .849 | −4.992 | −5.918 | 1.00 | 38.88 | A |
| ATOM | 638 | CB | ASN | A | 82 | 1.475 | −5.246 | −4.543 | 1.00 | 38.01 | A |
| ATOM | 639 | CG | ASN | A | 82 | 2.231 | −6.562 | −4.482 | 1.00 | 36.74 | A |
| ATOM | 640 | OD1 | ASN | A | 82 | 1.639 | −7.619 | −4.291 | 1.00 | 35.51 | A |
| ATOM | 641 | ND2 | ASN | A | 82 | 3.541 | −6.500 | −4.663 | 1.00 | 34.42 | A |
| ATOM | 642 | C | ASN | A | 82 | −.193 | −3.890 | −5.807 | 1.00 | 38.13 | A |
| ATOM | 643 | O | ASN | A | 82 | −.275 | −3.195 | −4.788 | 1.00 | 39.26 | A |
| ATOM | 644 | N | PRO | A | 83 | −1.017 | −3.724 | −6.851 | 1.00 | 36.98 | A |
| ATOM | 645 | CD | PRO | A | 83 | −1.086 | −4.574 | −8.051 | 1.00 | 34.43 | A |
| ATOM | 646 | CA | PRO | A | 83 | −2.069 | −2.698 | −6.867 | 1.00 | 37.02 | A |
| ATOM | 647 | CB | PRO | A | 83 | −2.780 | −2.957 | −8.195 | 1.00 | 36.28 | A |
| ATOM | 648 | CG | PRO | A | 83 | −2.530 | −4.442 | −8.435 | 1.00 | 34.63 | A |
| ATOM | 649 | C | PRO | A | 83 | −3.042 | −2.735 | −5.673 | 1.00 | 37.05 | A |
| ATOM | 650 | O | PRO | A | 83 | −3.478 | −1.686 | −5.192 | 1.00 | 39.34 | A |
| ATOM | 651 | N | ASP | A | 84 | −3.367 | −3.930 | −5.185 | 1.00 | 35.56 | A |
| ATOM | 652 | CA | ASP | A | 84 | −4.308 | −4.062 | −4.078 | 1.00 | 33.46 | A |
| ATOM | 653 | CB | ASP | A | 84 | −4.649 | −5.530 | −3.853 | 1.00 | 34.51 | A |
| ATOM | 654 | CG | ASP | A | 84 | −5.314 | −6.158 | −5.061 | 1.00 | 35.83 | A |
| ATOM | 655 | OD1 | ASP | A | 84 | −6.199 | −5.499 | −5.646 | 1.00 | 37.72 | A |
| ATOM | 656 | OD2 | ASP | A | 84 | −4.961 | −7.308 | −5.420 | 1.00 | 37.56 | A |
| ATOM | 657 | C | ASP | A | 84 | −3.845 | −3.426 | −2.774 | 1.00 | 33.39 | A |
| ATOM | 658 | O | ASP | A | 84 | −4.665 | −2.968 | −1.982 | 1.00 | 31.87 | A |
| ATOM | 659 | N | VAL | A | 85 | −2.534 | −3.411 | −2.547 | 1.00 | 31.84 | A |
| ATOM | 660 | CA | VAL | A | 85 | −1.970 | −2.804 | −1.349 | 1.00 | 29.40 | A |
| ATOM | 661 | CB | VAL | A | 85 | −.464 | −3.168 | −1.201 | 1.00 | 31.38 | A |
| ATOM | 662 | CG1 | VAL | A | 85 | .244 | −2.216 | −.222 | 1.00 | 32.10 | A |
| ATOM | 663 | CG2 | VAL | A | 85. | −.336 | −4.600 | −.718 | 1.00 | 29.20 | A |
| ATOM | 664 | C | VAL | A | 85 | −2.134 | −1.282 | −1.449 | 1.00 | 29.43 | A |
| ATOM | 665 | O | VAL | A | 85 | −2.082 | −.574 | −.445 | 1.00 | 26.13 | A |
| ATOM | 666 | N | CYS | A | 86 | −2.344 | −.791 | −2.670 | 1.00 | 29.46 | A |
| ATOM | 667 | CA | CYS | A | 86 | −2.524 | .638 | −2.904 | 1.00 | 29.39 | A |
| ATOM | 668 | CB | CYS | A | 86 | −2.097 | 1.001 | −4.328 | 1.00 | 30.74 | A |
| ATOM | 669 | SG | CYS | A | 86 | −.317 | .843 | −4.599 | 1.00 | 36.69 | A |
| ATOM | 670 | C | CYS | A | 86 | −3.953 | 1.107 | −2.664 | 1.00 | 29.64 | A |
| ATOM | 671 | O | CYS | A | 86 | −4.179 | 2.262 | −2.306 | 1.00 | 30.15 | A |
| ATOM | 672 | N | ALA | A | 87 | −4.925 | .228 | −2.864 | 1.00 | 26.40 | A |
| ATOM | 673 | CA | ALA | A | 87 | −6.295 | .642 | −2.636 | 1.00 | 28.82 | A |
| ATOM | 674 | CB | ALA | A | 87 | −7.256 | −.483 | −2.988 | 1.00 | 25.62 | A |
| ATOM | 675 | C | ALA | A | 87 | −6.429 | 1.031 | −1.161 | 1.00 | 29.47 | A |
| ATOM | 676 | O | ALA | A | 87 | −5.489 | .881 | −.385 | 1.00 | 29.21 | A |
| ATOM | 677 | N | PHE | A | 88 | −7.591 | 1.548 | −.779 | 1.00 | 30.50 | A |
| ATOM | 678 | CA | PHE | A | 88 | −7.817 | 1.946 | .604 | 1.00 | 31.87 | A |
| ATOM | 679 | CB | PHE | A | 88 | −8.753 | 3.157 | .667 | 1.00 | 31.60 | A |
| ATOM | 680 | CG | PHE | A | 88 | −9.116 | 3.567 | 2.064 | 1.00 | 31.92 | A |
| ATOM | 681 | CD1 | PHE | A | 88 | −8.127 | 3.926 | 2.979 | 1.00 | 32.89 | A |
| ATOM | 682 | CD2 | PHE | A | 88 | −10.443 | 3.592 | 2.471 | 1.00 | 30.33 | A |

APPENDIX A-continued

*Pinus sylvestris* STS

| ATOM | # | TYPE | RES | | | X | Y | Z | OCC | B | |
|------|---|------|-----|---|---|---|---|---|-----|---|---|
| ATOM | 683 | CE1 | PHE | A | 88 | −8.463 | 4.303 | 4.271 | 1.00 | 31.78 | A |
| ATOM | 684 | CE2 | PHE | A | 88 | −10.786 | 3.967 | 3.761 | 1.00 | 30.31 | A |
| ATOM | 685 | CZ | PHE | A | 88 | −9.798 | 4.323 | 4.663 | 1.00 | 30.55 | A |
| ATOM | 686 | C | PHE | A | 88 | −8.432 | .775 | 1.352 | 1.00 | 32.46 | A |
| ATOM | 687 | O | PHE | A | 88 | −7.846 | .258 | 2.297 | 1.00 | 33.36 | A |
| ATOM | 688 | N | VAL | A | 89 | −9.614 | .358 | .907 | 1.00 | 31.48 | A |
| ATOM | 689 | CA | VAL | A | 89 | −10.315 | −.759 | 1.518 | 1.00 | 31.02 | A |
| ATOM | 690 | CB | VAL | A | 89 | −11.000 | −.330 | 2.835 | 1.00 | 32.10 | A |
| ATOM | 691 | CG1 | VAL | A | 89 | −12.350 | .336 | 2.543 | 1.00 | 30.78 | A |
| ATOM | 692 | CG2 | VAL | A | 89 | −11.183 | −1.527 | 3.737 | 1.00 | 33.25 | A |
| ATOM | 693 | C | VAL | A | 89 | −11.377 | −1.316 | .563 | 1.00 | 30.23 | A |
| ATOM | 694 | O | VAL | A | 89 | −12.263 | −2.036 | .997 | 1.00 | 26.54 | A |
| ATOM | 695 | N | GLU | A | 90 | −11.284 | −.980 | −.729 | 1.00 | 32.29 | A |
| ATOM | 696 | CA | GLU | A | 90 | −12.246 | −1.465 | −1.729 | 1.00 | 32.87 | A |
| ATOM | 697 | CB | GLU | A | 90 | −12.260 | −.598 | −2.989 | 1.00 | 35.11 | A |
| ATOM | 698 | CG | GLU | A | 90 | −12.132 | .884 | −2.780 | 1.00 | 39.52 | A |
| ATOM | 699 | CD | GLU | A | 90 | −10.703 | 1.296 | −2.502 | 1.00 | 40.81 | A |
| ATOM | 700 | OE1 | GLU | A | 90 | −10.391 | 1.564 | −1.326 | 1.00 | 44.46 | A |
| ATOM | 701 | OE2 | GLU | A | 90 | −9.893 | 1.341 | −3.457 | 1.00 | 42.34 | A |
| ATOM | 702 | C | GLU | A | 90 | −11.945 | −2.885 | −2.166 | 1.00 | 32.49 | A |
| ATOM | 703 | O | GLU | A | 90 | −12.815 | −3.577 | −2.663 | 1.00 | 32.58 | A |
| ATOM | 704 | N | VAL | A | 91 | −10.696 | −3.311 | −2.019 | 1.00 | 34.49 | A |
| ATOM | 705 | CA | VAL | A | 91 | −10.318 | −4.673 | −2.384 | 1.00 | 34.27 | A |
| ATOM | 706 | CB | VAL | A | 91 | −9.548 | −4.719 | −3.734 | 1.00 | 34.98 | A |
| ATOM | 707 | CG1 | VAL | A | 91 | −10.522 | −4.597 | −4.887 | 1.00 | 36.02 | A |
| ATOM | 708 | CG2 | VAL | A | 91 | −8.528 | −3.595 | −3.805 | 1.00 | 34.63 | A |
| ATOM | 709 | C | VAL | A | 91 | −9.450 | −5.265 | −1.282 | 1.00 | 34.25 | A |
| ATOM | 710 | O | VAL | A | 91 | −8.662 | −4.553 | −.650 | 1.00 | 36.76 | A |
| ATOM | 711 | N | PRO | A | 92 | −9.587 | −6.573 | −1.022 | 1.00 | 32.30 | A |
| ATOM | 712 | CD | PRO | A | 92 | −10.508 | −7.541 | −1.637 | 1.00 | 31.68 | A |
| ATOM | 713 | CA | PRO | A | 92 | −8.783 | −7.210 | .027 | 1.00 | 31.47 | A |
| ATOM | 714 | CB | PRO | A | 92 | −9.387 | −8.608 | .120 | 1.00 | 28.44 | A |
| ATOM | 715 | CG | PRO | A | 92 | −9.877 | −8.851 | −1.263 | 1.00 | 30.17 | A |
| ATOM | 716 | C | PRO | A | 92 | −7.282 | −7.223 | −.286 | 1.00 | 30.77 | A |
| ATOM | 717 | O | PRO | A | 92 | −6.888 | −7.231 | −1.457 | 1.00 | 31.24 | A |
| ATOM | 718 | N | SER | A | 93 | −6.450 | −7.213 | .756 | 1.00 | 29.04 | A |
| ATOM | 719 | CA | SER | A | 93 | −5.000 | −7.212 | .560 | 1.00 | 28.86 | A |
| ATOM | 720 | CB | SER | A | 93 | −4.488 | −5.774 | .406 | 1.00 | 27.99 | A |
| ATOM | 721 | OG | SER | A | 93 | −4.609 | −5.050 | 1.615 | 1.00 | 24.98 | A |
| ATOM | 722 | C | SER | A | 93 | −4.222 | −7.900 | 1.679 | 1.00 | 28.57 | A |
| ATOM | 723 | O | SER | A | 93 | −2.994 | −7.841 | 1.710 | 1.00 | 30.63 | A |
| ATOM | 724 | N | LEU | A | 94 | −4.934 | −8.567 | 2.584 | 1.00 | 27.50 | A |
| ATOM | 725 | CA | LEU | A | 94 | −4.311 | −9.263 | 3.712 | 1.00 | 24.56 | A |
| ATOM | 726 | CB | LEU | A | 94 | −5.394 | −9.949 | 4.558 | 1.00 | 22.81 | A |
| ATOM | 727 | CG | LEU | A | 94 | −5.266 | −10.012 | 6.088 | 1.00 | 24.83 | A |
| ATOM | 728 | CD1 | LEU | A | 94 | −5.765 | −11.375 | 6.568 | 1.00 | 20.33 | A |
| ATOM | 729 | CD2 | LEU | A | 94 | −3.824 | −9.778 | 6.536 | 1.00 | 21.99 | A |
| ATOM | 730 | C | LEU | A | 94 | −3.260 | −10.310 | 3.295 | 1.00 | 23.22 | A |
| ATOM | 731 | O | LEU | A | 94 | −2.144 | −10.312 | 3.799 | 1.00 | 21.73 | A |
| ATOM | 732 | N | ASP | A | 95 | −3.631 | −11.198 | 2.381 | 1.00 | 22.41 | A |
| ATOM | 733 | CA | ASP | A | 95 | −2.733 | −12.253 | 1.923 | 1.00 | 24.20 | A |
| ATOM | 734 | CB | ASP | A | 95 | −3.446 | −13.139 | .896 | 1.00 | 25.44 | A |
| ATOM | 735 | CG | ASP | A | 95 | −4.614 | −13.932 | 1.507 | 1.00 | 29.88 | A |
| ATOM | 736 | OD1 | ASP | A | 95 | −5.294 | −14.653 | .749 | 1.00 | 34.47 | A |
| ATOM | 737 | OD2 | ASP | A | 95 | −4.851 | −13.849 | 2.737 | 1.00 | 29.62 | A |
| ATOM | 738 | C | ASP | A | 95 | −1.426 | −11.727 | 1.356 | 1.00 | 24.33 | A |
| ATOM | 739 | O | ASP | A | 95 | −.349 | −12.190 | 1.731 | 1.00 | 24.02 | A |
| ATOM | 740 | N | ALA | A | 96 | −1.515 | −10.759 | .451 | 1.00 | 24.12 | A |
| ATOM | 741 | CA | ALA | A | 96 | −.318 | −10.173 | −.124 | 1.00 | 23.91 | A |
| ATOM | 742 | CB | ALA | A | 96 | −.685 | −9.090 | −1.113 | 1.00 | 24.59 | A |
| ATOM | 743 | C | ALA | A | 96 | .550 | −9.585 | .975 | 1.00 | 25.17 | A |
| ATOM | 744 | O | ALA | A | 96 | 1.776 | −9.679 | .906 | 1.00 | 28.05 | A |
| ATOM | 745 | N | ARG | A | 97 | −.076 | −8.981 | 1.987 | 1.00 | 22.01 | A |
| ATOM | 746 | CA | ARG | A | 97 | .679 | −8.381 | 3.084 | 1.00 | 21.90 | A |
| ATOM | 747 | CB | ARG | A | 97 | −.208 | −7.447 | 3.911 | 1.00 | 20.08 | A |
| ATOM | 748 | CG | ARG | A | 97 | −.695 | −6.199 | 3.155 | 1.00 | 21.02 | A |
| ATOM | 749 | CD | ARG | A | 97 | −1.827 | −5.559 | 3.909 | 1.00 | 19.89 | A |
| ATOM | 750 | NE | ARG | A | 97 | −2.538 | −4.543 | 3.141 | 1.00 | 24.71 | A |
| ATOM | 751 | CZ | ARG | A | 97 | −2.095 | −3.307 | 2.938 | 1.00 | 23.62 | A |
| ATOM | 752 | NH1 | ARG | A | 97 | −.931 | −2.931 | 3.443 | 1.00 | 23.02 | A |
| ATOM | 753 | NH2 | ARG | A | 97 | −2.832 | −2.440 | 2.254 | 1.00 | 25.63 | A |
| ATOM | 754 | C | ARG | A | 97 | 1.315 | −9.415 | 4.008 | 1.00 | 23.99 | A |
| ATOM | 755 | O | ARG | A | 97 | 2.438 | −9.221 | 4.495 | 1.00 | 25.02 | A |
| ATOM | 756 | N | GLN | A | 98 | .603 | −10.510 | 4.255 | 1.00 | 22.43 | A |
| ATOM | 757 | CA | GLN | A | 98 | 1.124 | −11.538 | 5.125 | 1.00 | 22.91 | A |

APPENDIX A-continued

*Pinus sylvestris* STS

| ATOM | # | TYPE | RES | | | X | Y | Z | OCC | B | |
|------|---|------|-----|---|----|--------|---------|--------|------|-------|---|
| ATOM | 758 | CB | GLN | A | 98 | .081 | −12.645 | 5.340 | 1.00 | 21.13 | A |
| ATOM | 759 | CG | GLN | A | 98 | −1.261 | −12.154 | 5.938 | 1.00 | 20.57 | A |
| ATOM | 760 | CD | GLN | A | 98 | −1.161 | −11.687 | 7.391 | 1.00 | 19.43 | A |
| ATOM | 761 | OE1 | GLN | A | 98 | −1.797 | −12.254 | 8.283 | 1.00 | 19.15 | A |
| ATOM | 762 | NE2 | GLN | A | 98 | −.366 | −10.654 | 7.630 | 1.00 | 15.68 | A |
| ATOM | 763 | C | GLN | A | 98 | 2.400 | −12.097 | 4.504 | 1.00 | 24.91 | A |
| ATOM | 764 | O | GLN | A | 98 | 3.366 | −12.364 | 5.218 | 1.00 | 24.11 | A |
| ATOM | 765 | N | ALA | A | 99 | 2.410 | −12.238 | 3.174 | 1.00 | 26.86 | A |
| ATOM | 766 | CA | ALA | A | 99 | 3.580 | −12.766 | 2.455 | 1.00 | 28.83 | A |
| ATOM | 767 | CB | ALA | A | 99 | 3.268 | −12.934 | .961 | 1.00 | 28.35 | A |
| ATOM | 768 | C | ALA | A | 99 | 4.764 | −11.825 | 2.640 | 1.00 | 27.98 | A |
| ATOM | 769 | O | ALA | A | 99 | 5.875 | −12.258 | 2.955 | 1.00 | 29.15 | A |
| ATOM | 770 | N | MET | A | 100 | 4.515 | −10.535 | 2.438 | 1.00 | 27.72 | A |
| ATOM | 771 | CA | MET | A | 100 | 5.537 | −9.507 | 2.599 | 1.00 | 26.42 | A |
| ATOM | 772 | CB | MET | A | 100 | 4.941 | −8.106 | 2.390 | 1.00 | 24.11 | A |
| ATOM | 773 | CG | MET | A | 100 | 4.634 | −7.739 | .940 | 1.00 | 24.57 | A |
| ATOM | 774 | SD | MET | A | 100 | 3.735 | −6.165 | .749 | 1.00 | 18.38 | A |
| ATOM | 775 | CE | MET | A | 100 | 2.752 | −6.545 | −.586 | 1.00 | 21.64 | A |
| ATOM | 776 | C | MET | A | 100 | 6.096 | −9.597 | 4.005 | 1.00 | 25.75 | A |
| ATOM | 777 | O | MET | A | 100 | 7.305 | −9.547 | 4.203 | 1.00 | 24.42 | A |
| ATOM | 778 | N | LEU | A | 101 | 5.194 | −9.742 | 4.971 | 1.00 | 26.33 | A |
| ATOM | 779 | CA | LEU | A | 101 | 5.540 | −9.819 | 6.388 | 1.00 | 27.46 | A |
| ATOM | 780 | CB | LEU | A | 101 | 4.262 | −9.777 | 7.225 | 1.00 | 26.83 | A |
| ATOM | 781 | CG | LEU | A | 101 | 4.012 | −8.510 | 8.029 | 1.00 | 29.59 | A |
| ATOM | 782 | CD1 | LEU | A | 101 | 4.229 | −7.300 | 7.144 | 1.00 | 30.34 | A |
| ATOM | 783 | CD2 | LEU | A | 101 | 2.600 | −8.536 | 8.587 | 1.00 | 28.87 | A |
| ATOM | 784 | C | LEU | A | 101 | 6.349 | −11.050 | 6.785 | 1.00 | 27.33 | A |
| ATOM | 785 | O | LEU | A | 101 | 7.377 | −10.944 | 7.457 | 1.00 | 28.56 | A |
| ATOM | 786 | N | ALA | A | 102 | 5.881 | −12.218 | 6.371 | 1.00 | 25.00 | A |
| ATOM | 787 | CA | ALA | A | 102 | 6.560 | −13.457 | 6.716 | 1.00 | 27.48 | A |
| ATOM | 788 | CB | ALA | A | 102 | 5.894 | −14.627 | 5.994 | 1.00 | 23.71 | A |
| ATOM | 789 | C | ALA | A | 102 | 8.056 | −13.395 | 6.381 | 1.00 | 28.69 | A |
| ATOM | 790 | O | ALA | A | 102 | 8.870 | −13.987 | 7.084 | 1.00 | 29.73 | A |
| ATOM | 791 | N | MET | A | 103 | 8.415 | −12.661 | 5.329 | 1.00 | 29.35 | A |
| ATOM | 792 | CA | MET | A | 103 | 9.818 | −12.560 | 4.924 | 1.00 | 32.04 | A |
| ATOM | 793 | CB | MET | A | 103 | 9.941 | −12.662 | 3.401 | 1.00 | 34.43 | A |
| ATOM | 794 | CG | MET | A | 103 | 9.850 | −14.076 | 2.841 | 1.00 | 38.55 | A |
| ATOM | 795 | SD | MET | A | 103 | 11.158 | −15.155 | 3.475 | 1.00 | 44.76 | A |
| ATOM | 796 | CE | MET | A | 103 | 10.276 | −16.041 | 4.747 | 1.00 | 39.47 | A |
| ATOM | 797 | C | MET | A | 103 | 10.568 | −11.314 | 5.387 | 1.00 | 31.24 | A |
| ATOM | 798 | O | MET | A | 103 | 11.695 | −11.402 | 5.864 | 1.00 | 31.61 | A |
| ATOM | 799 | N | GLU | A | 104 | 9.951 | −10.153 | 5.257 | 1.00 | 31.59 | A |
| ATOM | 800 | CA | GLU | A | 104 | 10.626 | −8.915 | 5.630 | 1.00 | 31.31 | A |
| ATOM | 801 | CB | GLU | A | 104 | 9.865 | −7.731 | 5.045 | 1.00 | 30.05 | A |
| ATOM | 802 | CG | GLU | A | 104 | 10.553 | −6.406 | 5.240 | 1.00 | 32.44 | A |
| ATOM | 803 | CD | GLU | A | 104 | 11.995 | −6.407 | 4.762 | 1.00 | 33.01 | A |
| ATOM | 804 | OE1 | GLU | A | 104 | 12.390 | −7.309 | 3.989 | 1.00 | 33.54 | A |
| ATOM | 805 | OE2 | GLU | A | 104 | 12.735 | −5.485 | 5.158 | 1.00 | 33.64 | A |
| ATOM | 806 | C | GLU | A | 104 | 10.900 | −8.671 | 7.118 | 1.00 | 30.88 | A |
| ATOM | 807 | O | GLU | A | 104 | 11.992 | −8.211 | 7.482 | 1.00 | 29.95 | A |
| ATOM | 808 | N | VAL | A | 105 | 9.926 | −8.974 | 7.976 | 1.00 | 30.76 | A |
| ATOM | 809 | CA | VAL | A | 105 | 10.085 | −8.749 | 9.417 | 1.00 | 29.41 | A |
| ATOM | 810 | CB | VAL | A | 105 | 8.766 | −8.996 | 10.161 | 1.00 | 28.39 | A |
| ATOM | 811 | CG1 | VAL | A | 105 | 8.985 | −8.867 | 11.646 | 1.00 | 28.65 | A |
| ATOM | 812 | CG2 | VAL | A | 105 | 7.715 | −8.003 | 9.688 | 1.00 | 27.81 | A |
| ATOM | 813 | C | VAL | A | 105 | 11.199 | −9.569 | 10.062 | 1.00 | 28.24 | A |
| ATOM | 814 | O | VAL | A | 105 | 11.977 | −9.046 | 10.858 | 1.00 | 28.68 | A |
| ATOM | 815 | N | PRO | A | 106 | 11.264 | −10.877 | 9.762 | 1.00 | 28.43 | A |
| ATOM | 816 | CD | PRO | A | 106 | 10.166 | −11.740 | 9.283 | 1.00 | 28.16 | A |
| ATOM | 817 | CA | PRO | A | 106 | 12.336 | −11.688 | 10.357 | 1.00 | 25.95 | A |
| ATOM | 818 | CB | PRO | A | 106 | 11.905 | −13.120 | 10.035 | 1.00 | 25.33 | A |
| ATOM | 819 | CG | PRO | A | 106 | 10.418 | −13.032 | 10.058 | 1.00 | 27.25 | A |
| ATOM | 820 | C | PRO | A | 106 | 13.703 | −11.332 | 9.742 | 1.00 | 24.31 | A |
| ATOM | 821 | O | PRO | A | 106 | 14.732 | −11.423 | 10.400 | 1.00 | 20.89 | A |
| ATOM | 822 | N | ARG | A | 107 | 13.695 | −10.934 | 8.473 | 1.00 | 24.37 | A |
| ATOM | 823 | CA | ARG | A | 107 | 14.920 | −10.556 | 7.785 | 1.00 | 29.22 | A |
| ATOM | 824 | CB | ARG | A | 107 | 14.641 | −10.194 | 6.330 | 1.00 | 32.72 | A |
| ATOM | 825 | CG | ARG | A | 107 | 15.902 | −9.914 | 5.510 | 1.00 | 36.87 | A |
| ATOM | 826 | CD | ARG | A | 107 | 15.684 | −8.778 | 4.525 | 1.00 | 40.02 | A |
| ATOM | 827 | NE | ARG | A | 107 | 15.873 | −7.473 | 5.164 | 1.00 | 45.13 | A |
| ATOM | 828 | CZ | ARG | A | 107 | 15.466 | −6.313 | 4.653 | 1.00 | 47.15 | A |
| ATOM | 829 | NH1 | ARG | A | 107 | 14.832 | −6.282 | 3.488 | 1.00 | 50.56 | A |
| ATOM | 830 | NH2 | ARG | A | 107 | 15.702 | −5.181 | 5.304 | 1.00 | 47.09 | A |
| ATOM | 831 | C | ARG | A | 107 | 15.504 | −9.341 | 8.485 | 1.00 | 28.90 | A |
| ATOM | 832 | O | ARG | A | 107 | 16.661 | −9.357 | 8.908 | 1.00 | 29.13 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 833 | N | LEU | A | 108 | 14.695 | −8.289 | 8.616 | 1.00 | 28.98 | A |
| ATOM | 834 | CA | LEU | A | 108 | 15.142 | −7.067 | 9.280 | 1.00 | 28.70 | A |
| ATOM | 835 | CB | LEU | A | 108 | 14.043 | −6.000 | 9.261 | 1.00 | 30.81 | A |
| ATOM | 836 | CG | LEU | A | 108 | 14.376 | −4.716 | 8.483 | 1.00 | 34.16 | A |
| ATOM | 837 | CD1 | LEU | A | 108 | 13.264 | −3.690 | 8.653 | 1.00 | 33.94 | A |
| ATOM | 838 | CD2 | LEU | A | 108 | 15.694 | −4.138 | 8.981 | 1.00 | 33.48 | A |
| ATOM | 839 | C | LEU | A | 108 | 15.558 | −7.350 | 10.716 | 1.00 | 26.96 | A |
| ATOM | 840 | O | LEU | A | 108 | 16.597 | −6.879 | 11.170 | 1.00 | 27.32 | A |
| ATOM | 841 | N | ALA | A | 109 | 14.748 | −8.124 | 11.429 | 1.00 | 25.77 | A |
| ATOM | 842 | CA | ALA | A | 109 | 15.052 | −8.471 | 12.816 | 1.00 | 24.84 | A |
| ATOM | 843 | CB | ALA | A | 109 | 13.973 | −9.388 | 13.379 | 1.00 | 26.69 | A |
| ATOM | 844 | C | ALA | A | 109 | 16.409 | −9.161 | 12.914 | 1.00 | 25.54 | A |
| ATOM | 845 | O | ALA | A | 109 | 17.164 | −8.924 | 13.855 | 1.00 | 23.26 | A |
| ATOM | 846 | N | LYS | A | 110 | 16.710 | −10.008 | 11.934 | 1.00 | 25.63 | A |
| ATOM | 847 | CA | LYS | A | 110 | 17.966 | −10.745 | 11.917 | 1.00 | 27.86 | A |
| ATOM | 848 | CB | LYS | A | 110 | 17.955 | −11.805 | 10.811 | 1.00 | 29.07 | A |
| ATOM | 849 | CG | LYS | A | 110 | 19.306 | −12.492 | 10.620 | 1.00 | 28.94 | A |
| ATOM | 850 | CD | LYS | A | 110 | 19.309 | −13.385 | 9.389 | 1.00 | 30.99 | A |
| ATOM | 851 | CE | LYS | A | 110 | 20.569 | −14.242 | 9.321 | 1.00 | 31.04 | A |
| ATOM | 852 | NZ | LYS | A | 110 | 21.804 | −13.436 | 9.126 | 1.00 | 31.14 | A |
| ATOM | 853 | C | LYS | A | 110 | 19.166 | −9.831 | 11.716 | 1.00 | 28.05 | A |
| ATOM | 854 | O | LYS | A | 110 | 20.223 | −10.049 | 12.296 | 1.00 | 28.69 | A |
| ATOM | 855 | N | GLU | A | 111 | 19.011 | −8.821 | 10.873 | 1.00 | 27.50 | A |
| ATOM | 856 | CA | GLU | A | 111 | 20.100 | −7.897 | 10.622 | 1.00 | 28.58 | A |
| ATOM | 857 | CB | GLU | A | 111 | 19.718 | −6.956 | 9.487 | 1.00 | 33.09 | A |
| ATOM | 858 | CG | GLU | A | 111 | 20.666 | −5.789 | 9.264 | 1.00 | 37.76 | A |
| ATOM | 859 | CD | GLU | A | 111 | 20.122 | −4.809 | 8.231 | 1.00 | 41.62 | A |
| ATOM | 860 | OE1 | GLU | A | 111 | 19.723 | −5.269 | 7.138 | 1.00 | 42.07 | A |
| ATOM | 861 | OE2 | GLU | A | 111 | 20.094 | −3.586 | 8.512 | 1.00 | 45.45 | A |
| ATOM | 862 | C | GLU | A | 111 | 20.407 | −7.097 | 11.886 | 1.00 | 28.49 | A |
| ATOM | 863 | O | GLU | A | 111 | 21.571 | −6.841 | 12.205 | 1.00 | 27.38 | A |
| ATOM | 864 | N | ALA | A | 112 | 19.359 | −6.720 | 12.612 | 1.00 | 26.03 | A |
| ATOM | 865 | CA | ALA | A | 112 | 19.512 | −5.944 | 13.833 | 1.00 | 26.94 | A |
| ATOM | 866 | CB | ALA | A | 112 | 18.143 | −5.504 | 14.354 | 1.00 | 28.28 | A |
| ATOM | 867 | C | ALA | A | 112 | 20.241 | −6.715 | 14.918 | 1.00 | 27.67 | A |
| ATOM | 868 | O | ALA | A | 112 | 21.086 | −6.161 | 15.616 | 1.00 | 25.90 | A |
| ATOM | 869 | N | ASP | A | 113 | 19.918 | −7.995 | 15.066 | 1.00 | 28.66 | A |
| ATOM | 870 | CA | ASP | A | 113 | 20.551 | −8.775 | 16.109 | 1.00 | 29.69 | A |
| ATOM | 871 | CB | ASP | A | 113 | 19.677 | −9.961 | 16.490 | 1.00 | 36.80 | A |
| ATOM | 872 | CG | ASP | A | 113 | 18.955 | −10.548 | 15.311 | 1.00 | 42.93 | A |
| ATOM | 873 | OD1 | ASP | A | 113 | 19.629 | −10.976 | 14.352 | 1.00 | 47.19 | A |
| ATOM | 874 | OD2 | ASP | A | 113 | 17.707 | −10.583 | 15.346 | 1.00 | 49.00 | A |
| ATOM | 875 | C | ASP | A | 113 | 21.951 | −9.231 | 15.791 | 1.00 | 27.88 | A |
| ATOM | 876 | O | ASP | A | 113 | 22.744 | −9.424 | 16.696 | 1.00 | 29.10 | A |
| ATOM | 877 | N | GLU | A | 114 | 22.270 | −9.411 | 14.520 | 1.00 | 27.42 | A |
| ATOM | 878 | CA | GLU | A | 114 | 23.629 | −9.802 | 14.181 | 1.00 | 29.07 | A |
| ATOM | 879 | CB | GLU | A | 114 | 23.759 | −10.072 | 12.679 | 1.00 | 32.21 | A |
| ATOM | 880 | CG | GLU | A | 114 | 23.033 | −11.347 | 12.216 | 1.00 | 36.51 | A |
| ATOM | 881 | CD | GLU | A | 114 | 23.752 | −12.637 | 12.619 | 1.00 | 37.69 | A |
| ATOM | 882 | OE1 | GLU | A | 114 | 24.350 | −12.673 | 13.715 | 1.00 | 38.62 | A |
| ATOM | 883 | OE2 | GLU | A | 114 | 23.710 | −13.621 | 11.842 | 1.00 | 39.78 | A |
| ATOM | 884 | C | GLU | A | 114 | 24.514 | −8.632 | 14.616 | 1.00 | 28.69 | A |
| ATOM | 885 | O | GLU | A | 114 | 25.608 | −8.834 | 15.156 | 1.00 | 26.64 | A |
| ATOM | 886 | N | LYS | A | 115 | 24.030 | −7.409 | 14.394 | 1.00 | 28.82 | A |
| ATOM | 887 | CA | LYS | A | 115 | 24.757 | −6.213 | 14.815 | 1.00 | 29.61 | A |
| ATOM | 888 | CB | LYS | A | 115 | 24.007 | −4.929 | 14.448 | 1.00 | 31.35 | A |
| ATOM | 889 | CG | LYS | A | 115 | 24.182 | −4.438 | 13.028 | 1.00 | 33.87 | A |
| ATOM | 890 | CD | LYS | A | 115 | 23.587 | −3.040 | 12.893 | 1.00 | 37.24 | A |
| ATOM | 891 | CE | LYS | A | 115 | 23.869 | −2.444 | 11.530 | 1.00 | 38.63 | A |
| ATOM | 892 | NZ | LYS | A | 115 | 23.370 | −3.328 | 10.448 | 1.00 | 40.84 | A |
| ATOM | 893 | C | LYS | A | 115 | 24.863 | −6.276 | 16.324 | 1.00 | 28.63 | A |
| ATOM | 894 | O | LYS | A | 115 | 25.950 | −6.214 | 16.888 | 1.00 | 29.75 | A |
| ATOM | 895 | N | ALA | A | 116 | 23.711 | −6.412 | 16.971 | 1.00 | 28.40 | A |
| ATOM | 896 | CA | ALA | A | 116 | 23.637 | −6.497 | 18.427 | 1.00 | 28.89 | A |
| ATOM | 897 | CB | ALA | A | 116 | 22.187 | −6.743 | 18.864 | 1.00 | 29.26 | A |
| ATOM | 898 | C | ALA | A | 116 | 24.538 | −7.605 | 18.976 | 1.00 | 28.49 | A |
| ATOM | 899 | O | ALA | A | 116 | 25.285 | −7.391 | 19.931 | 1.00 | 29.43 | A |
| ATOM | 900 | N | ILE | A | 117 | 24.462 | −8.782 | 18.374 | 1.00 | 28.53 | A |
| ATOM | 901 | CA | ILE | A | 117 | 25.265 | −9.910 | 18.829 | 1.00 | 31.21 | A |
| ATOM | 902 | CB | ILE | A | 117 | 25.027 | −11.179 | 17.971 | 1.00 | 29.88 | A |
| ATOM | 903 | CG2 | ILE | A | 117 | 25.823 | −12.339 | 18.538 | 1.00 | 28.55 | A |
| ATOM | 904 | CG1 | ILE | A | 117 | 23.549 | −11.577 | 17.997 | 1.00 | 32.55 | A |
| ATOM | 905 | CD1 | ILE | A | 117 | 23.062 | −12.008 | 19.351 | 1.00 | 33.54 | A |
| ATOM | 906 | C | ILE | A | 117 | 26.738 | −9.563 | 18.766 | 1.00 | 32.35 | A |
| ATOM | 907 | O | ILE | A | 117 | 27.474 | −9.769 | 19.732 | 1.00 | 30.97 | A |

APPENDIX A-continued

*Pinus sylvestris* STS

| ATOM | # | TYPE | RES | | | X | Y | Z | OCC | B | |
|------|---|------|-----|---|---|---|---|---|-----|---|---|
| ATOM | 908 | N | GLN | A | 118 | 27.152 | −9.024 | 17.625 | 1.00 | 34.54 | A |
| ATOM | 909 | CA | GLN | A | 118 | 28.544 | −8.646 | 17.402 | 1.00 | 37.18 | A |
| ATOM | 910 | CB | GLN | A | 118 | 28.690 | −7.981 | 16.039 | 1.00 | 40.03 | A |
| ATOM | 911 | CG | GLN | A | 118 | 30.113 | −7.648 | 15.668 | 1.00 | 44.57 | A |
| ATOM | 912 | CD | GLN | A | 118 | 30.200 | −7.018 | 14.300 | 1.00 | 47.69 | A |
| ATOM | 913 | OE1 | GLN | A | 118 | 29.776 | −7.611 | 13.302 | 1.00 | 49.39 | A |
| ATOM | 914 | NE2 | GLN | A | 118 | 30.748 | −5.807 | 14.239 | 1.00 | 49.45 | A |
| ATOM | 915 | C | GLN | A | 118 | 29.112 | −7.727 | 18.478 | 1.00 | 37.04 | A |
| ATOM | 916 | O | GLN | A | 118 | 30.203 | −7.977 | 18.988 | 1.00 | 37.17 | A |
| ATOM | 917 | N | GLU | A | 119 | 28.380 | −6.666 | 18.820 | 1.00 | 36.89 | A |
| ATOM | 918 | CA | GLU | A | 119 | 28.828 | −5.715 | 19.846 | 1.00 | 36.40 | A |
| ATOM | 919 | CB | GLU | A | 119 | 27.773 | −4.638 | 20.082 | 1.00 | 36.37 | A |
| ATOM | 920 | CG | GLU | A | 119 | 28.216 | −3.559 | 21.045 | 1.00 | 36.77 | A |
| ATOM | 921 | CD | GLU | A | 119 | 27.063 | −2.710 | 21.534 | 1.00 | 38.45 | A |
| ATOM | 922 | OE1 | GLU | A | 119 | 26.097 | −2.525 | 20.768 | 1.00 | 38.88 | A |
| ATOM | 923 | OE2 | GLU | A | 119 | 27.132 | −2.213 | 22.677 | 1.00 | 38.52 | A |
| ATOM | 924 | C | GLU | A | 119 | 29.071 | −6.444 | 21.161 | 1.00 | 35.77 | A |
| ATOM | 925 | O | GLU | A | 119 | 30.134 | −6.340 | 21.778 | 1.00 | 36.48 | A |
| ATOM | 926 | N | TRP | A | 120 | 28.054 | −7.177 | 21.580 | 1.00 | 35.05 | A |
| ATOM | 927 | CA | TRP | A | 120 | 28.097 | −7.950 | 22.805 | 1.00 | 34.32 | A |
| ATOM | 928 | CB | TRP | A | 120 | 26.802 | −8.747 | 22.903 | 1.00 | 31.27 | A |
| ATOM | 929 | CG | TRP | A | 120 | 26.695 | −9.670 | 24.050 | 1.00 | 29.64 | A |
| ATOM | 930 | CD2 | TRP | A | 120 | 26.228 | −11.019 | 24.001 | 1.00 | 28.18 | A |
| ATOM | 931 | CE2 | TRP | A | 120 | 26.168 | −11.486 | 25.328 | 1.00 | 28.95 | A |
| ATOM | 932 | CE3 | TRP | A | 120 | 25.849 | −11.879 | 22.960 | 1.00 | 28.14 | A |
| ATOM | 933 | CD1 | TRP | A | 120 | 26.903 | −9.380 | 25.365 | 1.00 | 27.98 | A |
| ATOM | 934 | NE1 | TRP | A | 120 | 26.583 | −10.464 | 26.141 | 1.00 | 28.05 | A |
| ATOM | 935 | CZ2 | TRP | A | 120 | 25.742 | −12.788 | 25.647 | 1.00 | 30.03 | A |
| ATOM | 936 | CZ3 | TRP | A | 120 | 25.425 | −13.172 | 23.278 | 1.00 | 30.61 | A |
| ATOM | 937 | CH2 | TRP | A | 120 | 25.378 | −13.612 | 24.611 | 1.00 | 27.55 | A |
| ATOM | 938 | C | TRP | A | 120 | 29.309 | −8.863 | 22.735 | 1.00 | 34.10 | A |
| ATOM | 939 | O | TRP | A | 120 | 29.861 | −9.269 | 23.757 | 1.00 | 36.05 | A |
| ATOM | 940 | N | GLY | A | 121 | 29.711 | −9.178 | 21.510 | 1.00 | 34.61 | A |
| ATOM | 941 | CA | GLY | A | 121 | 30.864 | −10.028 | 21.283 | 1.00 | 35.14 | A |
| ATOM | 942 | C | GLY | A | 121 | 30.900 | −11.386 | 21.961 | 1.00 | 35.69 | A |
| ATOM | 943 | O | GLY | A | 121 | 31.983 | −11.912 | 22.194 | 1.00 | 36.76 | A |
| ATOM | 944 | N | GLN | A | 122 | 29.743 | −11.960 | 22.273 | 1.00 | 35.13 | A |
| ATOM | 945 | CA | GLN | A | 122 | 29.683 | −13.276 | 22.910 | 1.00 | 35.20 | A |
| ATOM | 946 | CB | GLN | A | 122 | 28.897 | −13.209 | 24.224 | 1.00 | 35.80 | A |
| ATOM | 947 | CG | GLN | A | 122 | 29.639 | −12.555 | 25.362 | 1.00 | 38.25 | A |
| ATOM | 948 | CD | GLN | A | 122 | 30.903 | −13.313 | 25.745 | 1.00 | 40.71 | A |
| ATOM | 949 | OE1 | GLN | A | 122 | 30.849 | −14.458 | 26.210 | 1.00 | 41.52 | A |
| ATOM | 950 | NE2 | GLN | A | 122 | 32.050 | −12.678 | 25.549 | 1.00 | 40.42 | A |
| ATOM | 951 | C | GLN | A | 122 | 29.022 | −14.291 | 21.977 | 1.00 | 34.64 | A |
| ATOM | 952 | O | GLN | A | 122 | 28.359 | −13.922 | 21.009 | 1.00 | 34.92 | A |
| ATOM | 953 | N | SER | A | 123 | 29.205 | −15.571 | 22.268 | 1.00 | 33.07 | A |
| ATOM | 954 | CA | SER | A | 123 | 28.622 | −16.626 | 21.449 | 1.00 | 33.33 | A |
| ATOM | 955 | CB | SER | A | 123 | 28.974 | −17.989 | 22.045 | 1.00 | 31.42 | A |
| ATOM | 956 | OG | SER | A | 123 | 28.341 | −19.041 | 21.349 | 1.00 | 29.57 | A |
| ATOM | 957 | C | SER | A | 123 | 27.103 | −16.487 | 21.352 | 1.00 | 34.17 | A |
| ATOM | 958 | O | SER | A | 123 | 26.471 | −15.885 | 22.220 | 1.00 | 35.47 | A |
| ATOM | 959 | N | LYS | A | 124 | 26.529 | −17.018 | 20.276 | 1.00 | 35.18 | A |
| ATOM | 960 | CA | LYS | A | 124 | 25.083 | −16.992 | 20.093 | 1.00 | 33.65 | A |
| ATOM | 961 | CB | LYS | A | 124 | 24.689 | −17.401 | 18.674 | 1.00 | 33.98 | A |
| ATOM | 962 | CG | LYS | A | 124 | 24.815 | −16.325 | 17.623 | 1.00 | 36.96 | A |
| ATOM | 963 | CD | LYS | A | 124 | 24.322 | −16.850 | 16.280 | 1.00 | 37.21 | A |
| ATOM | 964 | CE | LYS | A | 124 | 24.557 | −15.840 | 15.171 | 1.00 | 40.53 | A |
| ATOM | 965 | NZ | LYS | A | 124 | 24.053 | −14.487 | 15.527 | 1.00 | 40.81 | A |
| ATOM | 966 | C | LYS | A | 124 | 24.527 | −18.021 | 21.060 | 1.00 | 32.99 | A |
| ATOM | 967 | O | LYS | A | 124 | 23.502 | −17.791 | 21.707 | 1.00 | 31.91 | A |
| ATOM | 968 | N | SER | A | 125 | 25.224 | −19.154 | 21.157 | 1.00 | 30.09 | A |
| ATOM | 969 | CA | SER | A | 125 | 24.813 | −20.243 | 22.037 | 1.00 | 31.14 | A |
| ATOM | 970 | CB | SER | A | 125 | 25.904 | −21.328 | 22.104 | 1.00 | 30.57 | A |
| ATOM | 971 | OG | SER | A | 125 | 27.056 | −20.885 | 22.806 | 1.00 | 29.74 | A |
| ATOM | 972 | C | SER | A | 125 | 24.503 | −19.733 | 23.438 | 1.00 | 29.64 | A |
| ATOM | 973 | O | SER | A | 125 | 23.612 | −20.245 | 24.109 | 1.00 | 30.79 | A |
| ATOM | 974 | N | GLY | A | 126 | 25.236 | −18.712 | 23.867 | 1.00 | 29.37 | A |
| ATOM | 975 | CA | GLY | A | 126 | 25.018 | −18.154 | 25.192 | 1.00 | 29.53 | A |
| ATOM | 976 | C | GLY | A | 126 | 23.653 | −17.512 | 25.375 | 1.00 | 27.71 | A |
| ATOM | 977 | O | GLY | A | 126 | 23.261 | −17.163 | 26.489 | 1.00 | 25.74 | A |
| ATOM | 978 | N | ILE | A | 127 | 22.938 | −17.344 | 24.268 | 1.00 | 26.99 | A |
| ATOM | 979 | CA | ILE | A | 127 | 21.605 | −16.751 | 24.287 | 1.00 | 25.17 | A |
| ATOM | 980 | CB | ILE | A | 127 | 21.237 | −16.221 | 22.886 | 1.00 | 22.05 | A |
| ATOM | 981 | CG2 | ILE | A | 127 | 19.752 | −15.896 | 22.811 | 1.00 | 22.05 | A |
| ATOM | 982 | CG1 | ILE | A | 127 | 22.106 | −15.001 | 22.577 | 1.00 | 18.84 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 983 | CD1 | ILE | A | 127 | 21.862 | −14.406 | 21.238 | 1.00 | 17.66 | A |
| ATOM | 984 | C | ILE | A | 127 | 20.610 | −17.810 | 24.754 | 1.00 | 24.70 | A |
| ATOM | 985 | O | ILE | A | 127 | 20.363 | −18.790 | 24.060 | 1.00 | 26.26 | A |
| ATOM | 986 | N | THR | A | 128 | 20.047 | −17.594 | 25.939 | 1.00 | 25.26 | A |
| ATOM | 987 | CA | THR | A | 128 | 19.101 | −18.526 | 26.555 | 1.00 | 25.26 | A |
| ATOM | 988 | CB | THR | A | 128 | 19.418 | −18.698 | 28.053 | 1.00 | 27.22 | A |
| ATOM | 989 | OG1 | THR | A | 128 | 19.208 | −17.446 | 28.731 | 1.00 | 27.55 | A |
| ATOM | 990 | CG2 | THR | A | 128 | 20.866 | −19.134 | 28.245 | 1.00 | 27.17 | A |
| ATOM | 991 | C | THR | A | 128 | 17.646 | −18.090 | 26.454 | 1.00 | 25.40 | A |
| ATOM | 992 | O | THR | A | 128 | 16.730 | −18.854 | 26.798 | 1.00 | 24.68 | A |
| ATOM | 993 | N | HIS | A | 129 | 17.435 | −16.857 | 26.007 | 1.00 | 22.77 | A |
| ATOM | 994 | CA | HIS | A | 129 | 16.097 | −16.303 | 25.892 | 1.00 | 20.64 | A |
| ATOM | 995 | CB | HIS | A | 129 | 15.762 | −15.456 | 27.122 | 1.00 | 18.09 | A |
| ATOM | 996 | CG | HIS | A | 129 | 15.565 | −16.245 | 28.378 | 1.00 | 21.09 | A |
| ATOM | 997 | CD2 | HIS | A | 129 | 14.433 | −16.640 | 29.013 | 1.00 | 19.20 | A |
| ATOM | 998 | ND1 | HIS | A | 129 | 16.615 | −16.724 | 29.130 | 1.00 | 18.25 | A |
| ATOM | 999 | CE1 | HIS | A | 129 | 16.137 | −17.379 | 30.175 | 1.00 | 18.16 | A |
| ATOM | 1000 | NE2 | HIS | A | 129 | 14.817 | −17.342 | 30.128 | 1.00 | 17.69 | A |
| ATOM | 1001 | C | HIS | A | 129 | 15.975 | −15.408 | 24.673 | 1.00 | 22.13 | A |
| ATOM | 1002 | O | HIS | A | 129 | 16.953 | −14.800 | 24.243 | 1.00 | 21.06 | A |
| ATOM | 1003 | N | LEU | A | 130 | 14.762 | −15.336 | 24.129 | 1.00 | 22.34 | A |
| ATOM | 1004 | CA | LEU | A | 130 | 14.463 | −14.477 | 22.993 | 1.00 | 22.64 | A |
| ATOM | 1005 | CB | LEU | A | 130 | 14.471 | −15.241 | 21.672 | 1.00 | 24.24 | A |
| ATOM | 1006 | CG | LEU | A | 130 | 13.867 | −14.417 | 20.522 | 1.00 | 22.91 | A |
| ATOM | 1007 | CD1 | LEU | A | 130 | 14.786 | −13.246 | 20.200 | 1.00 | 24.49 | A |
| ATOM | 1008 | CD2 | LEU | A | 130 | 13.647 | −15.289 | 19.303 | 1.00 | 21.22 | A |
| ATOM | 1009 | C | LEU | A | 130 | 13.071 | −13.894 | 23.199 | 1.00 | 24.28 | A |
| ATOM | 1010 | O | LEU | A | 130 | 12.117 | −14.611 | 23.505 | 1.00 | 22.97 | A |
| ATOM | 1011 | N | ILE | A | 131 | 12.978 | −12.580 | 23.051 | 1.00 | 23.85 | A |
| ATOM | 1012 | CA | ILE | A | 131 | 11.718 | −11.867 | 23.177 | 1.00 | 22.17 | A |
| ATOM | 1013 | CB | ILE | A | 131 | 11.752 | −10.834 | 24.320 | 1.00 | 19.17 | A |
| ATOM | 1014 | CG2 | ILE | A | 131 | 10.523 | −9.914 | 24.219 | 1.00 | 17.23 | A |
| ATOM | 1015 | CG1 | ILE | A | 131 | 11.822 | −11.557 | 25.666 | 1.00 | 15.59 | A |
| ATOM | 1016 | CD1 | ILE | A | 131 | 11.885 | −10.632 | 26.867 | 1.00 | 16.20 | A |
| ATOM | 1017 | C | ILE | A | 131 | 11.572 | −11.139 | 21.856 | 1.00 | 22.74 | A |
| ATOM | 1018 | O | ILE | A | 131 | 12.378 | −10.260 | 21.537 | 1.00 | 24.68 | A |
| ATOM | 1019 | N | PHE | A | 132 | 10.571 | −11.522 | 21.075 | 1.00 | 21.87 | A |
| ATOM | 1020 | CA | PHE | A | 132 | 10.364 | −10.896 | 19.788 | 1.00 | 22.84 | A |
| ATOM | 1021 | CB | PHE | A | 132 | 10.407 | −11.935 | 18.658 | 1.00 | 25.22 | A |
| ATOM | 1022 | CG | PHE | A | 132 | 10.347 | −11.327 | 17.282 | 1.00 | 26.03 | A |
| ATOM | 1023 | CD1 | PHE | A | 132 | 9.126 | −11.002 | 16.699 | 1.00 | 27.91 | A |
| ATOM | 1024 | CD2 | PHE | A | 132 | 11.516 | −11.014 | 16.596 | 1.00 | 26.87 | A |
| ATOM | 1025 | CE1 | PHE | A | 132 | 9.074 | −10.370 | 15.456 | 1.00 | 27.98 | A |
| ATOM | 1026 | CE2 | PHE | A | 132 | 11.469 | −10.383 | 15.356 | 1.00 | 26.12 | A |
| ATOM | 1027 | CZ | PHE | A | 132 | 10.249 | −10.061 | 14.787 | 1.00 | 27.33 | A |
| ATOM | 1028 | C | PHE | A | 132 | 9.054 | −10.142 | 19.757 | 1.00 | 23.78 | A |
| ATOM | 1029 | O | PHE | A | 132 | 8.020 | −10.636 | 20.235 | 1.00 | 25.01 | A |
| ATOM | 1030 | N | CYS | A | 133 | 9.108 | −8.948 | 19.176 | 1.00 | 21.79 | A |
| ATOM | 1031 | CA | CYS | A | 133 | 7.951 | −8.082 | 19.076 | 1.00 | 22.75 | A |
| ATOM | 1032 | CB | CYS | A | 133 | 8.129 | −6.891 | 20.026 | 1.00 | 25.53 | A |
| ATOM | 1033 | SG | CYS | A | 133 | 6.991 | −5.537 | 19.732 | 1.00 | 27.54 | A |
| ATOM | 1034 | C | CYS | A | 133 | 7.676 | −7.562 | 17.669 | 1.00 | 21.50 | A |
| ATOM | 1035 | O | CYS | A | 133 | 8.592 | −7.180 | 16.940 | 1.00 | 22.97 | A |
| ATOM | 1036 | N | SER | A | 134 | 6.399 | −7.533 | 17.309 | 1.00 | 21.18 | A |
| ATOM | 1037 | CA | SER | A | 134 | 5.954 | −7.031 | 16.009 | 1.00 | 22.43 | A |
| ATOM | 1038 | CB | SER | A | 134 | 6.173 | −8.095 | 14.925 | 1.00 | 22.07 | A |
| ATOM | 1039 | OG | SER | A | 134 | 6.351 | −7.508 | 13.641 | 1.00 | 21.45 | A |
| ATOM | 1040 | C | SER | A | 134 | 4.464 | −6.733 | 16.168 | 1.00 | 24.43 | A |
| ATOM | 1041 | O | SER | A | 134 | 3.756 | −7.503 | 16.838 | 1.00 | 24.55 | A |
| ATOM | 1042 | N | THR | A | 135 | 3.977 | −5.637 | 15.580 | 1.00 | 24.20 | A |
| ATOM | 1043 | CA | THR | A | 135 | 2.555 | −5.313 | 15.716 | 1.00 | 26.34 | A |
| ATOM | 1044 | CB | THR | A | 135 | 2.107 | −4.107 | 14.846 | 1.00 | 26.54 | A |
| ATOM | 1045 | OG1 | THR | A | 135 | 1.786 | −4.562 | 13.530 | 1.00 | 28.93 | A |
| ATOM | 1046 | CG2 | THR | A | 135 | 3.199 | −3.045 | 14.786 | 1.00 | 25.74 | A |
| ATOM | 1047 | C | THR | A | 135 | 1.712 | −6.537 | 15.349 | 1.00 | 25.69 | A |
| ATOM | 1048 | O | THR | A | 135 | .660 | −6.749 | 15.929 | 1.00 | 26.52 | A |
| ATOM | 1049 | N | THR | A | 136 | 2.168 | −7.329 | 14.379 | 1.00 | 25.88 | A |
| ATOM | 1050 | CA | THR | A | 136 | 1.479 | −8.567 | 14.007 | 1.00 | 25.55 | A |
| ATOM | 1051 | CB | THR | A | 136 | .460 | −8.402 | 12.834 | 1.00 | 24.45 | A |
| ATOM | 1052 | OG1 | THR | A | 136 | 1.149 | −8.006 | 11.648 | 1.00 | 22.72 | A |
| ATOM | 1053 | CG2 | THR | A | 136 | −.625 | −7.396 | 13.173 | 1.00 | 25.44 | A |
| ATOM | 1054 | C | THR | A | 136 | 2.497 | −9.623 | 13.558 | 1.00 | 25.00 | A |
| ATOM | 1055 | O | THR | A | 136 | 3.692 | −9.343 | 13.416 | 1.00 | 23.29 | A |
| ATOM | 1056 | N | THR | A | 137 | 2.004 | −10.839 | 13.360 | 1.00 | 24.15 | A |
| ATOM | 1057 | CA | THR | A | 137 | 2.808 | −11.957 | 12.875 | 1.00 | 24.60 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 1058 | CB | THR | A | 137 | 3.378 | −12.819 | 14.045 | 1.00 | 23.38 | A |
| ATOM | 1059 | OG1 | THR | A | 137 | 4.548 | −13.503 | 13.580 | 1.00 | 25.80 | A |
| ATOM | 1060 | CG2 | THR | A | 137 | 2.370 | −13.837 | 14.543 | 1.00 | 20.20 | A |
| ATOM | 1061 | C | THR | A | 137 | 1.814 | −12.724 | 11.997 | 1.00 | 23.38 | A |
| ATOM | 1062 | O | THR | A | 137 | .676 | −12.959 | 12.393 | 1.00 | 21.68 | A |
| ATOM | 1063 | N | PRO | A | 138 | 2.225 | −13.099 | 10.781 | 1.00 | 24.14 | A |
| ATOM | 1064 | CD | PRO | A | 138 | 3.545 | −12.846 | 10.175 | 1.00 | 23.44 | A |
| ATOM | 1065 | CA | PRO | A | 138 | 1.347 | −13.816 | 9.851 | 1.00 | 24.04 | A |
| ATOM | 1066 | CB | PRO | A | 138 | 2.069 | −13.657 | 8.523 | 1.00 | 24.17 | A |
| ATOM | 1067 | CG | PRO | A | 138 | 3.504 | −13.700 | 8.930 | 1.00 | 23.06 | A |
| ATOM | 1068 | C | PRO | A | 138 | .927 | −15.259 | 10.100 | 1.00 | 24.49 | A |
| ATOM | 1069 | O | PRO | A | 138 | −.168 | −15.662 | 9.699 | 1.00 | 24.01 | A |
| ATOM | 1070 | N | ASP | A | 139 | 1.765 | −16.043 | 10.757 | 1.00 | 24.32 | A |
| ATOM | 1071 | CA | ASP | A | 139 | 1.427 | −17.443 | 10.959 | 1.00 | 26.63 | A |
| ATOM | 1072 | CB | ASP | A | 139 | 2.227 | −18.311 | 9.970 | 1.00 | 30.30 | A |
| ATOM | 1073 | CG | ASP | A | 139 | 2.354 | −17.683 | 8.582 | 1.00 | 34.13 | A |
| ATOM | 1074 | OD1 | ASP | A | 139 | 3.341 | −17.999 | 7.875 | 1.00 | 38.40 | A |
| ATOM | 1075 | OD2 | ASP | A | 139 | 1.474 | −16.893 | 8.179 | 1.00 | 34.14 | A |
| ATOM | 1076 | C | ASP | A | 139 | 1.741 | −17.938 | 12.358 | 1.00 | 26.12 | A |
| ATOM | 1077 | O | ASP | A | 139 | 2.041 | −17.175 | 13.270 | 1.00 | 25.57 | A |
| ATOM | 1078 | N | LEU | A | 140 | 1.654 | −19.253 | 12.499 | 1.00 | 27.76 | A |
| ATOM | 1079 | CA | LEU | A | 140 | 2.002 | −19.949 | 13.731 | 1.00 | 26.83 | A |
| ATOM | 1080 | CB | LEU | A | 140 | .778 | −20.555 | 14.399 | 1.00 | 28.40 | A |
| ATOM | 1081 | CG | LEU | A | 140 | −.177 | −19.538 | 15.008 | 1.00 | 30.52 | A |
| ATOM | 1082 | CD1 | LEU | A | 140 | −.928 | −18.799 | 13.904 | 1.00 | 32.48 | A |
| ATOM | 1083 | CD2 | LEU | A | 140 | −1.132 | −20.254 | 15.923 | 1.00 | 30.95 | A |
| ATOM | 1084 | C | LEU | A | 140 | 2.929 | −21.052 | 13.244 | 1.00 | 27.18 | A |
| ATOM | 1085 | O | LEU | A | 140 | 2.548 | −21.853 | 12.388 | 1.00 | 28.82 | A |
| ATOM | 1086 | N | PRO | A | 141 | 4.160 | −21.104 | 13.766 | 1.00 | 25.78 | A |
| ATOM | 1087 | CD | PRO | A | 141 | 5.159 | −22.037 | 13.216 | 1.00 | 25.32 | A |
| ATOM | 1088 | CA | PRO | A | 141 | 4.766 | −20.228 | 14.775 | 1.00 | 24.99 | A |
| ATOM | 1089 | CB | PRO | A | 141 | 6.107 | −20.898 | 15.025 | 1.00 | 26.03 | A |
| ATOM | 1090 | CG | PRO | A | 141 | 6.459 | −21.422 | 13.661 | 1.00 | 26.03 | A |
| ATOM | 1091 | C | PRO | A | 141 | 4.924 | −18.763 | 14.344 | 1.00 | 24.56 | A |
| ATOM | 1092 | O | PRO | A | 141 | 4.825 | −18.427 | 13.162 | 1.00 | 23.75 | A |
| ATOM | 1093 | N | GLY | A | 142 | 5.177 | −17.894 | 15.313 | 1.00 | 24.62 | A |
| ATOM | 1094 | CA | GLY | A | 142 | 5.349 | −16.490 | 15.009 | 1.00 | 23.80 | A |
| ATOM | 1095 | C | GLY | A | 142 | 6.792 | −16.180 | 14.679 | 1.00 | 26.14 | A |
| ATOM | 1096 | O | GLY | A | 142 | 7.660 | −17.059 | 14.729 | 1.00 | 25.21 | A |
| ATOM | 1097 | N | ALA | A | 143 | 7.041 | −14.917 | 14.352 | 1.00 | 25.92 | A |
| ATOM | 1098 | CA | ALA | A | 143 | 8.363 | −14.426 | 13.999 | 1.00 | 26.94 | A |
| ATOM | 1099 | CB | ALA | A | 143 | 8.299 | −12.909 | 13.760 | 1.00 | 25.13 | A |
| ATOM | 1100 | C | ALA | A | 143 | 9.471 | −14.756 | 15.008 | 1.00 | 26.98 | A |
| ATOM | 1101 | O | ALA | A | 143 | 10.650 | −14.690 | 14.665 | 1.00 | 29.10 | A |
| ATOM | 1102 | N | ASP | A | 144 | 9.112 | −15.085 | 16.248 | 1.00 | 27.97 | A |
| ATOM | 1103 | CA | ASP | A | 144 | 10.130 | −15.435 | 17.241 | 1.00 | 28.11 | A |
| ATOM | 1104 | CB | ASP | A | 144 | 9.513 | −15.650 | 18.643 | 1.00 | 28.84 | A |
| ATOM | 1105 | CG | ASP | A | 144 | 8.364 | −16.668 | 18.662 | 1.00 | 29.51 | A |
| ATOM | 1106 | OD1 | ASP | A | 144 | 7.340 | −16.426 | 17.994 | 1.00 | 27.31 | A |
| ATOM | 1107 | OD2 | ASP | A | 144 | 8.480 | −17.703 | 19.364 | 1.00 | 30.81 | A |
| ATOM | 1108 | C | ASP | A | 144 | 10.862 | −16.697 | 16.784 | 1.00 | 27.99 | A |
| ATOM | 1109 | O | ASP | A | 144 | 12.100 | −16.747 | 16.763 | 1.00 | 26.30 | A |
| ATOM | 1110 | N | PHE | A | 145 | 10.086 | −17.711 | 16.406 | 1.00 | 26.99 | A |
| ATOM | 1111 | CA | PHE | A | 145 | 10.648 | −18.968 | 15.930 | 1.00 | 27.15 | A |
| ATOM | 1112 | CB | PHE | A | 145 | 9.536 | −19.933 | 15.544 | 1.00 | 27.87 | A |
| ATOM | 1113 | CG | PHE | A | 145 | 10.027 | −21.173 | 14.858 | 1.00 | 28.08 | A |
| ATOM | 1114 | CD1 | PHE | A | 145 | 10.427 | −22.280 | 15.594 | 1.00 | 29.08 | A |
| ATOM | 1115 | CD2 | PHE | A | 145 | 10.108 | −21.226 | 13.475 | 1.00 | 27.17 | A |
| ATOM | 1116 | CE1 | PHE | A | 145 | 10.902 | −23.430 | 14.960 | 1.00 | 28.55 | A |
| ATOM | 1117 | CE2 | PHE | A | 145 | 10.580 | −22.362 | 12.828 | 1.00 | 29.72 | A |
| ATOM | 1118 | CZ | PHE | A | 145 | 10.979 | −23.472 | 13.575 | 1.00 | 27.75 | A |
| ATOM | 1119 | C | PHE | A | 145 | 11.520 | −18.711 | 14.710 | 1.00 | 27.78 | A |
| ATOM | 1120 | O | PHE | A | 145 | 12.690 | −19.107 | 14.663 | 1.00 | 25.37 | A |
| ATOM | 1121 | N | GLU | A | 146 | 10.937 | −18.041 | 13.723 | 1.00 | 28.13 | A |
| ATOM | 1122 | CA | GLU | A | 146 | 11.652 | −17.746 | 12.504 | 1.00 | 28.43 | A |
| ATOM | 1123 | CB | GLU | A | 146 | 10.763 | −16.982 | 11.538 | 1.00 | 32.67 | A |
| ATOM | 1124 | CG | GLU | A | 146 | 10.552 | −17.733 | 10.237 | 1.00 | 39.15 | A |
| ATOM | 1125 | CD | GLU | A | 146 | 10.033 | −19.152 | 10.462 | 1.00 | 42.85 | A |
| ATOM | 1126 | OE1 | GLU | A | 146 | 8.847 | −19.299 | 10.847 | 1.00 | 43.22 | A |
| ATOM | 1127 | OE2 | GLU | A | 146 | 10.816 | −20.113 | 10.259 | 1.00 | 43.47 | A |
| ATOM | 1128 | C | GLU | A | 146 | 12.932 | −16.983 | 12.730 | 1.00 | 27.87 | A |
| ATOM | 1129 | O | GLU | A | 146 | 13.941 | −17.282 | 12.104 | 1.00 | 28.61 | A |
| ATOM | 1130 | N | VAL | A | 147 | 12.900 | −16.004 | 13.626 | 1.00 | 26.97 | A |
| ATOM | 1131 | CA | VAL | A | 147 | 14.087 | −15.210 | 13.902 | 1.00 | 27.33 | A |
| ATOM | 1132 | CB | VAL | A | 147 | 13.757 | −14.038 | 14.848 | 1.00 | 28.53 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 1133 | CG1 | VAL | A | 147 | 15.024 | −13.382 | 15.340 | 1.00 | 27.78 | A |
| ATOM | 1134 | CG2 | VAL | A | 147 | 12.912 | −13.009 | 14.102 | 1.00 | 28.86 | A |
| ATOM | 1135 | C | VAL | A | 147 | 15.154 | −16.108 | 14.509 | 1.00 | 27.76 | A |
| ATOM | 1136 | O | VAL | A | 147 | 16.338 | −15.976 | 14.199 | 1.00 | 26.81 | A |
| ATOM | 1137 | N | ALA | A | 148 | 14.721 | −17.030 | 15.365 | 1.00 | 27.35 | A |
| ATOM | 1138 | CA | ALA | A | 148 | 15.630 | −17.973 | 16.001 | 1.00 | 27.81 | A |
| ATOM | 1139 | CB | ALA | A | 148 | 14.878 | −18.841 | 17.011 | 1.00 | 26.38 | A |
| ATOM | 1140 | C | ALA | A | 148 | 16.252 | −18.849 | 14.923 | 1.00 | 28.55 | A |
| ATOM | 1141 | O | ALA | A | 148 | 17.464 | −19.061 | 14.895 | 1.00 | 27.16 | A |
| ATOM | 1142 | N | LYS | A | 149 | 15.409 | −19.344 | 14.028 | 1.00 | 28.27 | A |
| ATOM | 1143 | CA | LYS | A | 149 | 15.865 | −20.192 | 12.940 | 1.00 | 30.54 | A |
| ATOM | 1144 | CB | LYS | A | 149 | 14.655 | −20.672 | 12.125 | 1.00 | 30.34 | A |
| ATOM | 1145 | CG | LYS | A | 149 | 14.879 | −21.959 | 11.344 | 1.00 | 33.21 | A |
| ATOM | 1146 | CD | LYS | A | 149 | 15.675 | −21.726 | 10.077 | 1.00 | 35.22 | A |
| ATOM | 1147 | CE | LYS | A | 149 | 14.855 | −20.955 | 9.054 | 1.00 | 36.29 | A |
| ATOM | 1148 | NZ | LYS | A | 149 | 15.631 | −20.646 | 7.821 | 1.00 | 34.92 | A |
| ATOM | 1149 | C | LYS | A | 149 | 16.885 | −19.453 | 12.052 | 1.00 | 31.84 | A |
| ATOM | 1150 | O | LYS | A | 149 | 17.946 | −20.000 | 11.752 | 1.00 | 33.57 | A |
| ATOM | 1151 | N | LEU | A | 150 | 16.588 | −18.223 | 11.638 | 1.00 | 30.97 | A |
| ATOM | 1152 | CA | LEU | A | 150 | 17.540 | −17.480 | 10.804 | 1.00 | 31.42 | A |
| ATOM | 1153 | CB | LEU | A | 150 | 16.949 | −16.151 | 10.311 | 1.00 | 33.16 | A |
| ATOM | 1154 | CG | LEU | A | 150 | 16.023 | −16.098 | 9.091 | 1.00 | 34.92 | A |
| ATOM | 1155 | CD1 | LEU | A | 150 | 14.652 | −16.632 | 9.434 | 1.00 | 36.29 | A |
| ATOM | 1156 | CD2 | LEU | A | 150 | 15.904 | −14.657 | 8.623 | 1.00 | 36.72 | A |
| ATOM | 1157 | C | LEU | A | 150 | 18.811 | −17.166 | 11.578 | 1.00 | 30.60 | A |
| ATOM | 1158 | O | LEU | A | 150 | 19.903 | −17.155 | 11.020 | 1.00 | 31.87 | A |
| ATOM | 1159 | N | LEU | A | 151 | 18.665 | −16.893 | 12.866 | 1.00 | 29.87 | A |
| ATOM | 1160 | CA | LEU | A | 151 | 19.809 | −16.557 | 13.698 | 1.00 | 29.41 | A |
| ATOM | 1161 | CB | LEU | A | 151 | 19.340 | −15.867 | 14.980 | 1.00 | 27.66 | A |
| ATOM | 1162 | CG | LEU | A | 151 | 19.013 | −14.378 | 14.886 | 1.00 | 29.11 | A |
| ATOM | 1163 | CD1 | LEU | A | 151 | 18.489 | −13.880 | 16.225 | 1.00 | 26.30 | A |
| ATOM | 1164 | CD2 | LEU | A | 151 | 20.272 | −13.620 | 14.468 | 1.00 | 28.44 | A |
| ATOM | 1165 | C | LEU | A | 151 | 20.669 | −17.763 | 14.061 | 1.00 | 29.68 | A |
| ATOM | 1166 | O | LEU | A | 151 | 21.799 | −17.619 | 14.539 | 1.00 | 29.22 | A |
| ATOM | 1167 | N | GLY | A | 152 | 20.140 | −18.955 | 13.826 | 1.00 | 29.85 | A |
| ATOM | 1168 | CA | GLY | A | 152 | 20.886 | −20.145 | 14.176 | 1.00 | 29.71 | A |
| ATOM | 1169 | C | GLY | A | 152 | 21.021 | −20.159 | 15.687 | 1.00 | 29.47 | A |
| ATOM | 1170 | O | GLY | A | 152 | 22.076 | −20.485 | 16.231 | 1.00 | 31.09 | A |
| ATOM | 1171 | N | LEU | A | 153 | 19.950 | −19.766 | 16.367 | 1.00 | 26.59 | A |
| ATOM | 1172 | CA | LEU | A | 153 | 19.947 | −19.743 | 17.814 | 1.00 | 24.43 | A |
| ATOM | 1173 | CB | LEU | A | 153 | 18.747 | −18.947 | 18.326 | 1.00 | 25.57 | A |
| ATOM | 1174 | CG | LEU | A | 153 | 19.004 | −17.578 | 18.956 | 1.00 | 26.97 | A |
| ATOM | 1175 | CD1 | LEU | A | 153 | 19.894 | −16.771 | 18.055 | 1.00 | 26.84 | A |
| ATOM | 1176 | CD2 | LEU | A | 153 | 17.682 | −16.865 | 19.210 | 1.00 | 25.05 | A |
| ATOM | 1177 | C | LEU | A | 153 | 19.844 | −21.190 | 18.241 | 1.00 | 23.58 | A |
| ATOM | 1178 | O | LEU | A | 153 | 19.525 | −22.051 | 17.426 | 1.00 | 24.50 | A |
| ATOM | 1179 | N | HIS | A | 154 | 20.124 | −21.458 | 19.512 | 1.00 | 25.47 | A |
| ATOM | 1180 | CA | HIS | A | 154 | 20.063 | −22.818 | 20.063 | 1.00 | 23.90 | A |
| ATOM | 1181 | CB | HIS | A | 154 | 20.640 | −22.827 | 21.488 | 1.00 | 22.82 | A |
| ATOM | 1182 | CG | HIS | A | 154 | 20.888 | −24.199 | 22.031 | 1.00 | 24.68 | A |
| ATOM | 1183 | CD2 | HIS | A | 154 | 20.084 | −25.041 | 22.723 | 1.00 | 26.57 | A |
| ATOM | 1184 | ND1 | HIS | A | 154 | 22.080 | −24.869 | 21.855 | 1.00 | 25.52 | A |
| ATOM | 1185 | CE1 | HIS | A | 154 | 22.001 | −26.064 | 22.414 | 1.00 | 26.84 | A |
| ATOM | 1186 | NE2 | HIS | A | 154 | 20.800 | −26.194 | 22.949 | 1.00 | 28.28 | A |
| ATOM | 1187 | C | HIS | A | 154 | 18.612 | −23.318 | 20.081 | 1.00 | 23.62 | A |
| ATOM | 1188 | O | HIS | A | 154 | 17.693 | −22.576 | 20.407 | 1.00 | 21.68 | A |
| ATOM | 1189 | N | PRO | A | 155 | 18.391 | −24.590 | 19.740 | 1.00 | 24.80 | A |
| ATOM | 1190 | CD | PRO | A | 155 | 19.359 | −25.673 | 19.505 | 1.00 | 25.17 | A |
| ATOM | 1191 | CA | PRO | A | 155 | 17.023 | −25.109 | 19.739 | 1.00 | 25.08 | A |
| ATOM | 1192 | CB | PRO | A | 155 | 17.215 | −26.578 | 19.371 | 1.00 | 25.18 | A |
| ATOM | 1193 | CG | PRO | A | 155 | 18.576 | −26.880 | 19.928 | 1.00 | 27.56 | A |
| ATOM | 1194 | C | PRO | A | 155 | 16.277 | −24.932 | 21.058 | 1.00 | 26.29 | A |
| ATOM | 1195 | O | PRO | A | 155 | 15.053 | −24.979 | 21.088 | 1.00 | 26.00 | A |
| ATOM | 1196 | N | SER | A | 156 | 17.016 | −24.729 | 22.143 | 1.00 | 25.49 | A |
| ATOM | 1197 | CA | SER | A | 156 | 16.392 | −24.565 | 23.452 | 1.00 | 23.23 | A |
| ATOM | 1198 | CB | SER | A | 156 | 17.114 | −25.424 | 24.500 | 1.00 | 24.30 | A |
| ATOM | 1199 | OG | SER | A | 156 | 16.916 | −26.801 | 24.255 | 1.00 | 24.44 | A |
| ATOM | 1200 | C | SER | A | 156 | 16.314 | −23.133 | 23.956 | 1.00 | 21.04 | A |
| ATOM | 1201 | O | SER | A | 156 | 16.185 | −22.911 | 25.147 | 1.00 | 19.96 | A |
| ATOM | 1202 | N | VAL | A | 157 | 16.429 | −22.161 | 23.061 | 1.00 | 21.07 | A |
| ATOM | 1203 | CA | VAL | A | 157 | 16.314 | −20.779 | 23.481 | 1.00 | 20.46 | A |
| ATOM | 1204 | CB | VAL | A | 157 | 16.499 | −19.753 | 22.308 | 1.00 | 18.81 | A |
| ATOM | 1205 | CG1 | VAL | A | 157 | 16.244 | −18.331 | 22.828 | 1.00 | 19.92 | A |
| ATOM | 1206 | CG2 | VAL | A | 157 | 17.899 | −19.826 | 21.737 | 1.00 | 22.14 | A |
| ATOM | 1207 | C | VAL | A | 157 | 14.875 | −20.662 | 23.963 | 1.00 | 21.14 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 1208 | O | VAL | A | 157 | 13.962 | −21.152 | 23.312 | 1.00 | 19.78 | A |
| ATOM | 1209 | N | LYS | A | 158 | 14.673 | −20.035 | 25.110 | 1.00 | 20.85 | A |
| ATOM | 1210 | CA | LYS | A | 158 | 13.328 | −19.855 | 25.622 | 1.00 | 22.35 | A |
| ATOM | 1211 | CB | LYS | A | 158 | 13.373 | −19.711 | 27.141 | 1.00 | 23.13 | A |
| ATOM | 1212 | CG | LYS | A | 158 | 13.667 | −21.030 | 27.858 | 1.00 | 25.41 | A |
| ATOM | 1213 | CD | LYS | A | 158 | 13.697 | −20.828 | 29.357 | 1.00 | 24.19 | A |
| ATOM | 1214 | CE | LYS | A | 158 | 15.117 | −20.708 | 29.873 | 1.00 | 26.45 | A |
| ATOM | 1215 | NZ | LYS | A | 158 | 15.823 | −22.024 | 29.939 | 1.00 | 25.92 | A |
| ATOM | 1216 | C | LYS | A | 158 | 12.798 | −18.596 | 24.939 | 1.00 | 23.09 | A |
| ATOM | 1217 | O | LYS | A | 158 | 13.164 | −17.480 | 25.291 | 1.00 | 21.21 | A |
| ATOM | 1218 | N | ARG | A | 159 | 11.929 | −18.799 | 23.956 | 1.00 | 24.01 | A |
| ATOM | 1219 | CA | ARG | A | 159 | 11.380 | −17.710 | 23.155 | 1.00 | 24.63 | A |
| ATOM | 1220 | CB | ARG | A | 159 | 11.358 | −18.128 | 21.676 | 1.00 | 25.38 | A |
| ATOM | 1221 | CG | ARG | A | 159 | 12.174 | −19.388 | 21.376 | 1.00 | 27.28 | A |
| ATOM | 1222 | CD | ARG | A | 159 | 12.021 | −19.830 | 19.935 | 1.00 | 29.70 | A |
| ATOM | 1223 | NE | ARG | A | 159 | 10.669 | −20.293 | 19.622 | 1.00 | 29.95 | A |
| ATOM | 1224 | CZ | ARG | A | 159 | 10.282 | −21.565 | 19.619 | 1.00 | 29.82 | A |
| ATOM | 1225 | NH1 | ARG | A | 159 | 11.139 | −22.533 | 19.916 | 1.00 | 30.94 | A |
| ATOM | 1226 | NH2 | ARG | A | 159 | 9.028 | −21.868 | 19.313 | 1.00 | 33.57 | A |
| ATOM | 1227 | C | ARG | A | 159 | 9.982 | −17.289 | 23.561 | 1.00 | 23.52 | A |
| ATOM | 1228 | O | ARG | A | 159 | 9.217 | −18.080 | 24.097 | 1.00 | 25.02 | A |
| ATOM | 1229 | N | VAL | A | 160 | 9.665 | −16.024 | 23.311 | 1.00 | 22.32 | A |
| ATOM | 1230 | CA | VAL | A | 160 | 8.345 | −15.474 | 23.595 | 1.00 | 21.08 | A |
| ATOM | 1231 | CB | VAL | A | 160 | 8.244 | −14.796 | 24.984 | 1.00 | 22.06 | A |
| ATOM | 1232 | CG1 | VAL | A | 160 | 9.252 | −13.676 | 25.105 | 1.00 | 21.67 | A |
| ATOM | 1233 | CG2 | VAL | A | 160 | 6.838 | −14.249 | 25.175 | 1.00 | 19.10 | A |
| ATOM | 1234 | C | VAL | A | 160 | 8.035 | −14.433 | 22.540 | 1.00 | 21.72 | A |
| ATOM | 1235 | O | VAL | A | 160 | 8.852 | −13.562 | 22.231 | 1.00 | 20.95 | A |
| ATOM | 1236 | N | GLY | A | 161 | 6.847 | −14.528 | 21.976 | 1.00 | 21.41 | A |
| ATOM | 1237 | CA | GLY | A | 161 | 6.478 | −13.560 | 20.967 | 1.00 | 22.25 | A |
| ATOM | 1238 | C | GLY | A | 161 | 5.433 | −12.613 | 21.509 | 1.00 | 20.28 | A |
| ATOM | 1239 | O | GLY | A | 161 | 4.449 | −13.044 | 22.117 | 1.00 | 20.06 | A |
| ATOM | 1240 | N | VAL | A | 162 | 5.655 | −11.322 | 21.309 | 1.00 | 20.58 | A |
| ATOM | 1241 | CA | VAL | A | 162 | 4.706 | −10.314 | 21.769 | 1.00 | 22.29 | A |
| ATOM | 1242 | CB | VAL | A | 162 | 5.397 | −9.253 | 22.691 | 1.00 | 21.30 | A |
| ATOM | 1243 | CG1 | VAL | A | 162 | 6.693 | −8.821 | 22.104 | 1.00 | 24.10 | A |
| ATOM | 1244 | CG2 | VAL | A | 162 | 4.501 | −8.056 | 22.885 | 1.00 | 21.27 | A |
| ATOM | 1245 | C | VAL | A | 162 | 4.125 | −9.656 | 20.530 | 1.00 | 21.88 | A |
| ATOM | 1246 | O | VAL | A | 162 | 4.769 | −8.818 | 19.899 | 1.00 | 22.52 | A |
| ATOM | 1247 | N | PHE | A | 163 | 2.904 | −10.050 | 20.179 | 1.00 | 21.80 | A |
| ATOM | 1248 | CA | PHE | A | 163 | 2.258 | −9.516 | 18.989 | 1.00 | 20.47 | A |
| ATOM | 1249 | CB | PHE | A | 163 | 2.004 | −10.663 | 18.012 | 1.00 | 21.66 | A |
| ATOM | 1250 | CG | PHE | A | 163 | 3.212 | −11.550 | 17.792 | 1.00 | 22.63 | A |
| ATOM | 1251 | CD1 | PHE | A | 163 | 4.364 | −11.052 | 17.174 | 1.00 | 25.88 | A |
| ATOM | 1252 | CD2 | PHE | A | 163 | 3.206 | −12.875 | 18.210 | 1.00 | 22.78 | A |
| ATOM | 1253 | CE1 | PHE | A | 163 | 5.495 | −11.865 | 16.975 | 1.00 | 24.44 | A |
| ATOM | 1254 | CE2 | PHE | A | 163 | 4.329 | −13.695 | 18.017 | 1.00 | 24.67 | A |
| ATOM | 1255 | CZ | PHE | A | 163 | 5.472 | −13.187 | 17.398 | 1.00 | 21.69 | A |
| ATOM | 1256 | C | PHE | A | 163 | .960 | −8.743 | 19.261 | 1.00 | 20.46 | A |
| ATOM | 1257 | O | PHE | A | 163 | .251 | −9.001 | 20.231 | 1.00 | 20.17 | A |
| ATOM | 1258 | N | GLN | A | 164 | .662 | −7.787 | 18.390 | 1.00 | 19.59 | A |
| ATOM | 1259 | CA | GLN | A | 164 | −.538 | −6.954 | 18.500 | 1.00 | 21.23 | A |
| ATOM | 1260 | CB | GLN | A | 164 | −1.798 | −7.767 | 18.156 | 1.00 | 20.31 | A |
| ATOM | 1261 | CG | GLN | A | 164 | −1.650 | −8.597 | 16.882 | 1.00 | 21.02 | A |
| ATOM | 1262 | CD | GLN | A | 164 | −2.973 | −8.990 | 16.228 | 1.00 | 23.06 | A |
| ATOM | 1263 | OE1 | GLN | A | 164 | −2.985 | −9.831 | 15.322 | 1.00 | 21.66 | A |
| ATOM | 1264 | NE2 | GLN | A | 164 | −4.085 | −8.380 | 16.666 | 1.00 | 19.73 | A |
| ATOM | 1265 | C | GLN | A | 164 | −.699 | −6.258 | 19.858 | 1.00 | 22.09 | A |
| ATOM | 1266 | O | GLN | A | 164 | −1.791 | −6.189 | 20.425 | 1.00 | 22.31 | A |
| ATOM | 1267 | N | HIS | A | 165 | .405 | −5.748 | 20.382 | 1.00 | 22.18 | A |
| ATOM | 1268 | CA | HIS | A | 165 | .354 | −5.022 | 21.635 | 1.00 | 24.10 | A |
| ATOM | 1269 | CB | HIS | A | 165 | 1.592 | −5.307 | 22.483 | 1.00 | 21.91 | A |
| ATOM | 1270 | CG | HIS | A | 165 | 1.517 | −6.596 | 23.241 | 1.00 | 17.46 | A |
| ATOM | 1271 | CD2 | HIS | A | 165 | 1.334 | −6.842 | 24.559 | 1.00 | 15.97 | A |
| ATOM | 1272 | ND1 | HIS | A | 165 | 1.557 | −7.827 | 22.623 | 1.00 | 16.67 | A |
| ATOM | 1273 | CE1 | HIS | A | 165 | 1.395 | −8.776 | 23.527 | 1.00 | 17.09 | A |
| ATOM | 1274 | NE2 | HIS | A | 165 | 1.255 | −8.206 | 24.710 | 1.00 | 15.95 | A |
| ATOM | 1275 | C | HIS | A | 165 | .292 | −3.556 | 21.215 | 1.00 | 27.28 | A |
| ATOM | 1276 | O | HIS | A | 165 | −.587 | −2.812 | 21.642 | 1.00 | 26.92 | A |
| ATOM | 1277 | N | GLY | A | 166 | 1.211 | −3.155 | 20.348 | 1.00 | 29.59 | A |
| ATOM | 1278 | CA | GLY | A | 166 | 1.189 | −1.787 | 19.877 | 1.00 | 33.81 | A |
| ATOM | 1279 | C | GLY | A | 166 | 2.466 | −1.002 | 20.046 | 1.00 | 34.98 | A |
| ATOM | 1280 | O | GLY | A | 166 | 3.506 | −1.539 | 20.436 | 1.00 | 36.81 | A |
| ATOM | 1281 | N | CYS | A | 167 | 2.370 | .287 | 19.748 | 1.00 | 35.13 | A |
| ATOM | 1282 | CA | CYS | A | 167 | 3.490 | 1.200 | 19.847 | 1.00 | 34.95 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 1283 | CB | CYS | A | 167 | 3.049 | 2.604 | 19.435 | 1.00 | 36.37 | A |
| ATOM | 1284 | SG | CYS | A | 167 | 2.675 | 2.790 | 17.682 | 1.00 | 38.64 | A |
| ATOM | 1285 | C | CYS | A | 167 | 4.102 | 1.257 | 21.238 | 1.00 | 34.59 | A |
| ATOM | 1286 | O | CYS | A | 167 | 5.198 | 1.782 | 21.402 | 1.00 | 36.85 | A |
| ATOM | 1287 | N | PHE | A | 168 | 3.407 | .729 | 22.240 | 1.00 | 32.51 | A |
| ATOM | 1288 | CA | PHE | A | 168 | 3.936 | .761 | 23.603 | 1.00 | 31.87 | A |
| ATOM | 1289 | CB | PHE | A | 168 | 2.781 | .885 | 24.613 | 1.00 | 30.03 | A |
| ATOM | 1290 | CG | PHE | A | 168 | 1.954 | −.362 | 24.758 | 1.00 | 30.47 | A |
| ATOM | 1291 | CD1 | PHE | A | 168 | 2.428 | −1.451 | 25.477 | 1.00 | 29.65 | A |
| ATOM | 1292 | CD2 | PHE | A | 168 | .700 | −.454 | 24.165 | 1.00 | 30.86 | A |
| ATOM | 1293 | CE1 | PHE | A | 168 | 1.662 | −2.619 | 25.604 | 1.00 | 28.73 | A |
| ATOM | 1294 | CE2 | PHE | A | 168 | −.073 | −1.618 | 24.286 | 1.00 | 29.81 | A |
| ATOM | 1295 | CZ | PHE | A | 168 | .413 | −2.698 | 25.008 | 1.00 | 28.11 | A |
| ATOM | 1296 | C | PHE | A | 168 | 4.803 | −.462 | 23.932 | 1.00 | 31.42 | A |
| ATOM | 1297 | O | PHE | A | 168 | 5.464 | −.502 | 24.966 | 1.00 | 31.40 | A |
| ATOM | 1298 | N | ALA | A | 169 | 4.797 | −1.449 | 23.039 | 1.00 | 29.90 | A |
| ATOM | 1299 | CA | ALA | A | 169 | 5.554 | −2.685 | 23.227 | 1.00 | 27.01 | A |
| ATOM | 1300 | CB | ALA | A | 169 | 5.299 | −3.607 | 22.053 | 1.00 | 26.41 | A |
| ATOM | 1301 | C | ALA | A | 169 | 7.067 | −2.512 | 23.444 | 1.00 | 26.73 | A |
| ATOM | 1302 | O | ALA | A | 169 | 7.720 | −3.369 | 24.062 | 1.00 | 25.79 | A |
| ATOM | 1303 | N | GLY | A | 170 | 7.623 | −1.414 | 22.941 | 1.00 | 24.59 | A |
| ATOM | 1304 | CA | GLY | A | 170 | 9.047 | −1.176 | 23.100 | 1.00 | 24.21 | A |
| ATOM | 1305 | C | GLY | A | 170 | 9.454 | −1.313 | 24.551 | 1.00 | 25.87 | A |
| ATOM | 1306 | O | GLY | A | 170 | 10.559 | −1.776 | 24.871 | 1.00 | 25.12 | A |
| ATOM | 1307 | N | GLY | A | 171 | 8.540 | −.918 | 25.433 | 1.00 | 25.08 | A |
| ATOM | 1308 | CA | GLY | A | 171 | 8.792 | −1.002 | 26.852 | 1.00 | 25.49 | A |
| ATOM | 1309 | C | GLY | A | 171 | 8.347 | −2.307 | 27.489 | 1.00 | 25.76 | A |
| ATOM | 1310 | O | GLY | A | 171 | 9.017 | −2.805 | 28.390 | 1.00 | 24.97 | A |
| ATOM | 1311 | N | THR | A | 172 | 7.222 | −2.869 | 27.054 | 1.00 | 26.67 | A |
| ATOM | 1312 | CA | THR | A | 172 | 6.768 | −4.120 | 27.666 | 1.00 | 26.43 | A |
| ATOM | 1313 | CB | THR | A | 172 | 5.403 | −4.619 | 27.094 | 1.00 | 25.00 | A |
| ATOM | 1314 | OG1 | THR | A | 172 | 5.588 | −5.868 | 26.421 | 1.00 | 25.54 | A |
| ATOM | 1315 | CG2 | THR | A | 172 | 4.819 | −3.626 | 26.142 | 1.00 | 22.87 | A |
| ATOM | 1316 | C | THR | A | 172 | 7.841 | −5.198 | 27.459 | 1.00 | 27.23 | A |
| ATOM | 1317 | O | THR | A | 172 | 8.014 | −6.091 | 28.290 | 1.00 | 26.37 | A |
| ATOM | 1318 | N | VAL | A | 173 | 8.580 | −5.106 | 26.360 | 1.00 | 27.56 | A |
| ATOM | 1319 | CA | VAL | A | 173 | 9.623 | −6.088 | 26.122 | 1.00 | 29.17 | A |
| ATOM | 1320 | CB | VAL | A | 173 | 10.179 | −5.996 | 24.693 | 1.00 | 29.87 | A |
| ATOM | 1321 | CG1 | VAL | A | 173 | 11.413 | −6.834 | 24.591 | 1.00 | 33.23 | A |
| ATOM | 1322 | CG2 | VAL | A | 173 | 9.142 | −6.501 | 23.696 | 1.00 | 28.54 | A |
| ATOM | 1323 | C | VAL | A | 173 | 10.760 | −5.914 | 27.136 | 1.00 | 29.10 | A |
| ATOM | 1324 | O | VAL | A | 173 | 11.349 | −6.908 | 27.581 | 1.00 | 29.94 | A |
| ATOM | 1325 | N | LEU | A | 174 | 11.062 | −4.668 | 27.508 | 1.00 | 26.46 | A |
| ATOM | 1326 | CA | LEU | A | 174 | 12.107 | −4.416 | 28.504 | 1.00 | 25.15 | A |
| ATOM | 1327 | CB | LEU | A | 174 | 12.472 | −2.931 | 28.557 | 1.00 | 23.15 | A |
| ATOM | 1328 | CG | LEU | A | 174 | 13.226 | −2.342 | 27.361 | 1.00 | 22.33 | A |
| ATOM | 1329 | CD1 | LEU | A | 174 | 13.316 | −.839 | 27.523 | 1.00 | 22.43 | A |
| ATOM | 1330 | CD2 | LEU | A | 174 | 14.612 | −2.955 | 27.254 | 1.00 | 23.94 | A |
| ATOM | 1331 | C | LEU | A | 174 | 11.594 | −4.874 | 29.872 | 1.00 | 25.36 | A |
| ATOM | 1332 | O | LEU | A | 174 | 12.360 | −5.370 | 30.716 | 1.00 | 23.86 | A |
| ATOM | 1333 | N | ARG | A | 175 | 10.288 | −4.713 | 30.071 | 1.00 | 23.61 | A |
| ATOM | 1334 | CA | ARG | A | 175 | 9.635 | −5.115 | 31.304 | 1.00 | 26.33 | A |
| ATOM | 1335 | CB | ARG | A | 175 | 8.184 | −4.608 | 31.310 | 1.00 | 26.51 | A |
| ATOM | 1336 | CG | ARG | A | 175 | 7.329 | −5.182 | 32.409 | 1.00 | 29.10 | A |
| ATOM | 1337 | CD | ARG | A | 175 | 6.139 | −4.287 | 32.726 | 1.00 | 31.57 | A |
| ATOM | 1338 | NE | ARG | A | 175 | 5.198 | −4.159 | 31.620 | 1.00 | 34.18 | A |
| ATOM | 1339 | CZ | ARG | A | 175 | 4.398 | −5.132 | 31.196 | 1.00 | 35.28 | A |
| ATOM | 1340 | NH1 | ARG | A | 175 | 4.422 | −6.323 | 31.783 | 1.00 | 37.05 | A |
| ATOM | 1341 | NH2 | ARG | A | 175 | 3.554 | −4.907 | 30.198 | 1.00 | 35.45 | A |
| ATOM | 1342 | C | ARG | A | 175 | 9.690 | −6.646 | 31.394 | 1.00 | 26.56 | A |
| ATOM | 1343 | O | ARG | A | 175 | 9.846 | −7.222 | 32.481 | 1.00 | 27.45 | A |
| ATOM | 1344 | N | MET | A | 176 | 9.584 | −7.303 | 30.242 | 1.00 | 27.50 | A |
| ATOM | 1345 | CA | MET | A | 176 | 9.644 | −8.764 | 30.193 | 1.00 | 27.64 | A |
| ATOM | 1346 | CB | MET | A | 176 | 9.029 | −9.278 | 28.879 | 1.00 | 26.71 | A |
| ATOM | 1347 | CG | MET | A | 176 | 7.521 | −9.034 | 28.775 | 1.00 | 28.23 | A |
| ATOM | 1348 | SD | MET | A | 176 | 6.800 | −9.487 | 27.195 | 1.00 | 23.55 | A |
| ATOM | 1349 | CE | MET | A | 176 | 7.101 | −8.102 | 26.259 | 1.00 | 28.45 | A |
| ATOM | 1350 | C | MET | A | 176 | 11.096 | −9.221 | 30.323 | 1.00 | 27.94 | A |
| ATOM | 1351 | O | MET | A | 176 | 11.403 | −10.166 | 31.052 | 1.00 | 30.27 | A |
| ATOM | 1352 | N | ALA | A | 177 | 11.987 | −8.532 | 29.628 | 1.00 | 28.25 | A |
| ATOM | 1353 | CA | ALA | A | 177 | 13.403 | −8.868 | 29.672 | 1.00 | 29.84 | A |
| ATOM | 1354 | CB | ALA | A | 177 | 14.200 | −7.954 | 28.738 | 1.00 | 29.86 | A |
| ATOM | 1355 | C | ALA | A | 177 | 13.961 | −8.767 | 31.075 | 1.00 | 30.68 | A |
| ATOM | 1356 | O | ALA | A | 177 | 14.790 | −9.592 | 31.469 | 1.00 | 32.02 | A |
| ATOM | 1357 | N | LYS | A | 178 | 13.528 | −7.759 | 31.830 | 1.00 | 30.79 | A |

APPENDIX A-continued

*Pinus sylvestris* STS

| ATOM | # | TYPE | RES | | | X | Y | Z | OCC | B | |
|------|---|------|-----|---|---|---|---|---|-----|---|---|
| ATOM | 1358 | CA | LYS | A | 178 | 14.038 | −7.588 | 33.188 | 1.00 | 31.72 | A |
| ATOM | 1359 | CB | LYS | A | 178 | 13.477 | −6.310 | 33.830 | 1.00 | 31.12 | A |
| ATOM | 1360 | CG | LYS | A | 178 | 13.749 | −6.197 | 35.345 | 1.00 | 29.02 | A |
| ATOM | 1361 | CD | LYS | A | 178 | 13.189 | −4.903 | 35.918 | 1.00 | 29.04 | A |
| ATOM | 1362 | CE | LYS | A | 178 | 13.136 | −4.914 | 37.449 | 1.00 | 27.26 | A |
| ATOM | 1363 | NZ | LYS | A | 178 | 14.480 | −4.807 | 38.065 | 1.00 | 28.61 | A |
| ATOM | 1364 | C | LYS | A | 178 | 13.706 | −8.795 | 34.067 | 1.00 | 31.60 | A |
| ATOM | 1365 | O | LYS | A | 178 | 14.581 | −9.355 | 34.733 | 1.00 | 31.68 | A |
| ATOM | 1366 | N | ASP | A | 179 | 12.441 | −9.200 | 34.062 | 1.00 | 31.22 | A |
| ATOM | 1367 | CA | ASP | A | 179 | 12.033 | −10.329 | 34.880 | 1.00 | 30.84 | A |
| ATOM | 1368 | CB | ASP | A | 179 | 10.517 | −10.497 | 34.829 | 1.00 | 31.04 | A |
| ATOM | 1369 | CG | ASP | A | 179 | 9.797 | −9.640 | 35.859 | 1.00 | 35.44 | A |
| ATOM | 1370 | OD1 | ASP | A | 179 | 10.435 | −8.734 | 36.452 | 1.00 | 30.14 | A |
| ATOM | 1371 | OD2 | ASP | A | 179 | 8.581 | −9.875 | 36.070 | 1.00 | 37.43 | A |
| ATOM | 1372 | C | ASP | A | 179 | 12.733 | −11.607 | 34.446 | 1.00 | 29.75 | A |
| ATOM | 1373 | O | ASP | A | 179 | 13.051 | −12.450 | 35.273 | 1.00 | 28.93 | A |
| ATOM | 1374 | N | LEU | A | 180 | 12.986 | −11.744 | 33.151 | 1.00 | 28.74 | A |
| ATOM | 1375 | CA | LEU | A | 180 | 13.661 | −12.936 | 32.651 | 1.00 | 28.44 | A |
| ATOM | 1376 | CB | LEU | A | 180 | 13.561 | −13.009 | 31.132 | 1.00 | 25.80 | A |
| ATOM | 1377 | CG | LEU | A | 180 | 12.197 | −13.379 | 30.563 | 1.00 | 25.86 | A |
| ATOM | 1378 | CD1 | LEU | A | 180 | 12.387 | −13.863 | 29.142 | 1.00 | 26.09 | A |
| ATOM | 1379 | CD2 | LEU | A | 180 | 11.575 | −14.493 | 31.379 | 1.00 | 26.77 | A |
| ATOM | 1380 | C | LEU | A | 180 | 15.126 | −12.981 | 33.060 | 1.00 | 29.17 | A |
| ATOM | 1381 | O | LEU | A | 180 | 15.590 | −13.971 | 33.624 | 1.00 | 29.96 | A |
| ATOM | 1382 | N | ALA | A | 181 | 15.852 | −11.901 | 32.787 | 1.00 | 29.52 | A |
| ATOM | 1383 | CA | ALA | A | 181 | 17.273 | −11.843 | 33.116 | 1.00 | 28.81 | A |
| ATOM | 1384 | CB | ALA | A | 181 | 17.909 | −10.617 | 32.473 | 1.00 | 27.02 | A |
| ATOM | 1385 | C | ALA | A | 181 | 17.571 | −11.850 | 34.614 | 1.00 | 29.43 | A |
| ATOM | 1386 | O | ALA | A | 181 | 18.621 | −12.323 | 35.037 | 1.00 | 29.28 | A |
| ATOM | 1387 | N | GLU | A | 182 | 16.654 | −11.334 | 35.418 | 1.00 | 28.32 | A |
| ATOM | 1388 | CA | GLU | A | 182 | 16.903 | −11.283 | 36.845 | 1.00 | 28.42 | A |
| ATOM | 1389 | CB | GLU | A | 182 | 16.206 | −10.057 | 37.446 | 1.00 | 28.31 | A |
| ATOM | 1390 | CG | GLU | A | 182 | 17.074 | −8.799 | 37.425 | 1.00 | 28.39 | A |
| ATOM | 1391 | CD | GLU | A | 182 | 16.286 | −7.505 | 37.641 | 1.00 | 30.17 | A |
| ATOM | 1392 | OE1 | GLU | A | 182 | 15.276 | −7.535 | 38.378 | 1.00 | 31.81 | A |
| ATOM | 1393 | OE2 | GLU | A | 182 | 16.683 | −6.455 | 37.079 | 1.00 | 26.98 | A |
| ATOM | 1394 | C | GLU | A | 182 | 16.533 | −12.545 | 37.612 | 1.00 | 29.49 | A |
| ATOM | 1395 | O | GLU | A | 182 | 17.124 | −12.827 | 38.657 | 1.00 | 29.42 | A |
| ATOM | 1396 | N | ASN | A | 183 | 15.587 | −13.318 | 37.085 | 1.00 | 27.48 | A |
| ATOM | 1397 | CA | ASN | A | 183 | 15.139 | −14.531 | 37.747 | 1.00 | 26.14 | A |
| ATOM | 1398 | CB | ASN | A | 183 | 13.626 | −14.682 | 37.571 | 1.00 | 28.22 | A |
| ATOM | 1399 | CG | ASN | A | 183 | 13.022 | −15.678 | 38.538 | 1.00 | 27.66 | A |
| ATOM | 1400 | OD1 | ASN | A | 183 | 13.287 | −15.633 | 39.740 | 1.00 | 26.28 | A |
| ATOM | 1401 | ND2 | ASN | A | 183 | 12.190 | −16.571 | 38.023 | 1.00 | 29.55 | A |
| ATOM | 1402 | C | ASN | A | 183 | 15.844 | −15.781 | 37.236 | 1.00 | 26.45 | A |
| ATOM | 1403 | O | ASN | A | 183 | 15.562 | −16.896 | 37.690 | 1.00 | 25.91 | A |
| ATOM | 1404 | N | ASN | A | 184 | 16.755 | −15.595 | 36.288 | 1.00 | 26.39 | A |
| ATOM | 1405 | CA | ASN | A | 184 | 17.507 | −16.710 | 35.715 | 1.00 | 25.21 | A |
| ATOM | 1406 | CB | ASN | A | 184 | 17.006 | −17.015 | 34.305 | 1.00 | 23.95 | A |
| ATOM | 1407 | CG | ASN | A | 184 | 15.540 | −17.407 | 34.285 | 1.00 | 26.13 | A |
| ATOM | 1408 | OD1 | ASN | A | 184 | 15.150 | −18.407 | 34.888 | 1.00 | 27.10 | A |
| ATOM | 1409 | ND2 | ASN | A | 184 | 14.719 | −16.618 | 33.595 | 1.00 | 24.91 | A |
| ATOM | 1410 | C | ASN | A | 184 | 18.979 | −16.346 | 35.685 | 1.00 | 24.51 | A |
| ATOM | 1411 | O | ASN | A | 184 | 19.439 | −15.657 | 34.774 | 1.00 | 22.61 | A |
| ATOM | 1412 | N | ARG | A | 185 | 19.713 | −16.793 | 36.701 | 1.00 | 25.18 | A |
| ATOM | 1413 | CA | ARG | A | 185 | 21.135 | −16.489 | 36.792 | 1.00 | 26.91 | A |
| ATOM | 1414 | CB | ARG | A | 185 | 21.757 | −17.152 | 38.027 | 1.00 | 27.36 | A |
| ATOM | 1415 | CG | ARG | A | 185 | 23.194 | −16.712 | 38.326 | 1.00 | 27.62 | A |
| ATOM | 1416 | CD | ARG | A | 185 | 23.915 | −17.698 | 39.265 | 1.00 | 29.15 | A |
| ATOM | 1417 | NE | ARG | A | 185 | 23.236 | −17.834 | 40.554 | 1.00 | 32.65 | A |
| ATOM | 1418 | CZ | ARG | A | 185 | 23.199 | −16.886 | 41.491 | 1.00 | 32.73 | A |
| ATOM | 1419 | NH1 | ARG | A | 185 | 23.808 | −15.718 | 41.298 | 1.00 | 34.52 | A |
| ATOM | 1420 | NH2 | ARG | A | 185 | 22.543 | −17.102 | 42.623 | 1.00 | 32.17 | A |
| ATOM | 1421 | C | ARG | A | 185 | 21.805 | −17.000 | 35.534 | 1.00 | 27.64 | A |
| ATOM | 1422 | O | ARG | A | 185 | 21.583 | −18.142 | 35.124 | 1.00 | 26.90 | A |
| ATOM | 1423 | N | GLY | A | 186 | 22.593 | −16.131 | 34.907 | 1.00 | 29.73 | A |
| ATOM | 1424 | CA | GLY | A | 186 | 23.301 | −16.500 | 33.694 | 1.00 | 29.72 | A |
| ATOM | 1425 | C | GLY | A | 186 | 22.517 | −16.302 | 32.408 | 1.00 | 28.96 | A |
| ATOM | 1426 | O | GLY | A | 186 | 23.035 | −16.517 | 31.314 | 1.00 | 28.86 | A |
| ATOM | 1427 | N | ALA | A | 187 | 21.267 | −15.884 | 32.533 | 1.00 | 27.00 | A |
| ATOM | 1428 | CA | ALA | A | 187 | 20.423 | −15.676 | 31.369 | 1.00 | 27.51 | A |
| ATOM | 1429 | CB | ALA | A | 187 | 18.968 | −15.538 | 31.800 | 1.00 | 27.04 | A |
| ATOM | 1430 | C | ALA | A | 187 | 20.817 | −14.463 | 30.547 | 1.00 | 28.01 | A |
| ATOM | 1431 | O | ALA | A | 187 | 21.187 | −13.416 | 31.082 | 1.00 | 28.40 | A |
| ATOM | 1432 | N | ARG | A | 188 | 20.724 | −14.624 | 29.236 | 1.00 | 27.77 | A |

APPENDIX A-continued

*Pinus sylvestris* STS

| ATOM | # | TYPE | RES | | | X | Y | Z | OCC | B | |
|------|---|------|-----|---|-----|--------|---------|--------|------|-------|---|
| ATOM | 1433 | CA | ARG | A | 188 | 21.006 | −13.551 | 28.300 | 1.00 | 27.68 | A |
| ATOM | 1434 | CB | ARG | A | 188 | 22.331 | −13.810 | 27.581 | 1.00 | 26.99 | A |
| ATOM | 1435 | CG | ARG | A | 188 | 23.572 | −13.728 | 28.492 | 1.00 | 27.67 | A |
| ATOM | 1436 | CD | ARG | A | 188 | 23.868 | −12.276 | 28.890 | 1.00 | 31.52 | A |
| ATOM | 1437 | NE | ARG | A | 188 | 24.994 | −12.151 | 29.820 | 1.00 | 30.38 | A |
| ATOM | 1438 | CZ | ARG | A | 188 | 24.909 | −12.292 | 31.143 | 1.00 | 31.58 | A |
| ATOM | 1439 | NH1 | ARG | A | 188 | 23.741 | −12.562 | 31.722 | 1.00 | 24.80 | A |
| ATOM | 1440 | NH2 | ARG | A | 188 | 26.002 | −12.165 | 31.891 | 1.00 | 31.53 | A |
| ATOM | 1441 | C | ARG | A | 188 | 19.809 | −13.538 | 27.321 | 1.00 | 28.85 | A |
| ATOM | 1442 | O | ARG | A | 188 | 19.605 | −14.459 | 26.515 | 1.00 | 27.23 | A |
| ATOM | 1443 | N | VAL | A | 189 | 18.993 | −12.499 | 27.436 | 1.00 | 27.60 | A |
| ATOM | 1444 | CA | VAL | A | 189 | 17.819 | −12.367 | 26.597 | 1.00 | 26.30 | A |
| ATOM | 1445 | CB | VAL | A | 189 | 16.676 | −11.696 | 27.375 | 1.00 | 25.85 | A |
| ATOM | 1446 | CG1 | VAL | A | 189 | 15.384 | −11.786 | 26.597 | 1.00 | 24.31 | A |
| ATOM | 1447 | CG2 | VAL | A | 189 | 16.519 | −12.363 | 28.719 | 1.00 | 28.18 | A |
| ATOM | 1448 | C | VAL | A | 189 | 18.122 | −11.539 | 25.360 | 1.00 | 25.71 | A |
| ATOM | 1449 | O | VAL | A | 189 | 18.738 | −10.485 | 25.438 | 1.00 | 25.75 | A |
| ATOM | 1450 | N | LEU | A | 190 | 17.723 | −12.052 | 24.206 | 1.00 | 27.67 | A |
| ATOM | 1451 | CA | LEU | A | 190 | 17.889 | −11.319 | 22.961 | 1.00 | 27.51 | A |
| ATOM | 1452 | CB | LEU | A | 190 | 18.196 | −12.259 | 21.793 | 1.00 | 26.13 | A |
| ATOM | 1453 | CG | LEU | A | 190 | 18.194 | −11.660 | 20.379 | 1.00 | 24.00 | A |
| ATOM | 1454 | CD1 | LEU | A | 190 | 19.134 | −10.440 | 20.284 | 1.00 | 16.10 | A |
| ATOM | 1455 | CD2 | LEU | A | 190 | 18.579 | −12.758 | 19.394 | 1.00 | 20.62 | A |
| ATOM | 1456 | C | LEU | A | 190 | 16.519 | −10.687 | 22.781 | 1.00 | 27.57 | A |
| ATOM | 1457 | O | LEU | A | 190 | 15.505 | −11.383 | 22.709 | 1.00 | 29.76 | A |
| ATOM | 1458 | N | VAL | A | 191 | 16.491 | −9.365 | 22.758 | 1.00 | 27.48 | A |
| ATOM | 1459 | CA | VAL | A | 191 | 15.252 | −8.632 | 22.614 | 1.00 | 25.21 | A |
| ATOM | 1460 | CB | VAL | A | 191 | 15.171 | −7.544 | 23.696 | 1.00 | 26.45 | A |
| ATOM | 1461 | CG1 | VAL | A | 191 | 14.054 | −6.574 | 23.376 | 1.00 | 26.55 | A |
| ATOM | 1462 | CG2 | VAL | A | 191 | 14.953 | −8.198 | 25.072 | 1.00 | 23.22 | A |
| ATOM | 1463 | C | VAL | A | 191 | 15.188 | −8.022 | 21.218 | 1.00 | 25.89 | A |
| ATOM | 1464 | O | VAL | A | 191 | 16.056 | −7.243 | 20.829 | 1.00 | 25.61 | A |
| ATOM | 1465 | N | ILE | A | 192 | 14.162 | −8.390 | 20.460 | 1.00 | 25.32 | A |
| ATOM | 1466 | CA | ILE | A | 192 | 14.026 | −7.891 | 19.102 | 1.00 | 25.33 | A |
| ATOM | 1467 | CB | ILE | A | 192 | 14.340 | −9.019 | 18.074 | 1.00 | 23.22 | A |
| ATOM | 1468 | CG2 | ILE | A | 192 | 14.375 | −8.447 | 16.664 | 1.00 | 24.09 | A |
| ATOM | 1469 | CG1 | ILE | A | 192 | 15.700 | −9.648 | 18.399 | 1.00 | 23.39 | A |
| ATOM | 1470 | CD1 | ILE | A | 192 | 16.041 | −10.889 | 17.601 | 1.00 | 21.13 | A |
| ATOM | 1471 | C | ILE | A | 192 | 12.654 | −7.286 | 18.792 | 1.00 | 27.03 | A |
| ATOM | 1472 | O | ILE | A | 192 | 11.616 | −7.857 | 19.117 | 1.00 | 28.27 | A |
| ATOM | 1473 | N | CYS | A | 193 | 12.676 | −6.110 | 18.176 | 1.00 | 27.44 | A |
| ATOM | 1474 | CA | CYS | A | 193 | 11.459 | −5.410 | 17.777 | 1.00 | 29.84 | A |
| ATOM | 1475 | CB | CYS | A | 193 | 11.286 | −4.079 | 18.524 | 1.00 | 29.24 | A |
| ATOM | 1476 | SG | CYS | A | 193 | 10.748 | −4.211 | 20.241 | 1.00 | 33.41 | A |
| ATOM | 1477 | C | CYS | A | 193 | 11.616 | −5.107 | 16.307 | 1.00 | 28.84 | A |
| ATOM | 1478 | O | CYS | A | 193 | 12.470 | −4.301 | 15.939 | 1.00 | 27.97 | A |
| ATOM | 1479 | N | SER | A | 194 | 10.803 | −5.761 | 15.476 | 1.00 | 28.80 | A |
| ATOM | 1480 | CA | SER | A | 194 | 10.844 | −5.541 | 14.036 | 1.00 | 28.93 | A |
| ATOM | 1481 | CB | SER | A | 194 | 11.290 | −6.816 | 13.304 | 1.00 | 28.77 | A |
| ATOM | 1482 | OG | SER | A | 194 | 11.556 | −6.556 | 11.932 | 1.00 | 27.02 | A |
| ATOM | 1483 | C | SER | A | 194 | 9.462 | −5.111 | 13.552 | 1.00 | 28.93 | A |
| ATOM | 1484 | O | SER | A | 194 | 8.457 | −5.766 | 13.833 | 1.00 | 26.74 | A |
| ATOM | 1485 | N | GLU | A | 195 | 9.425 | −4.005 | 12.816 | 1.00 | 29.64 | A |
| ATOM | 1486 | CA | GLU | A | 195 | 8.172 | −3.468 | 12.311 | 1.00 | 30.24 | A |
| ATOM | 1487 | CB | GLU | A | 195 | 7.737 | −2.305 | 13.200 | 1.00 | 31.77 | A |
| ATOM | 1488 | CG | GLU | A | 195 | 7.727 | −2.645 | 14.686 | 1.00 | 36.82 | A |
| ATOM | 1489 | CD | GLU | A | 195 | 6.410 | −3.250 | 15.148 | 1.00 | 39.92 | A |
| ATOM | 1490 | OE1 | GLU | A | 195 | 5.813 | −4.031 | 14.374 | 1.00 | 39.88 | A |
| ATOM | 1491 | OE2 | GLU | A | 195 | 5.981 | −2.948 | 16.290 | 1.00 | 40.67 | A |
| ATOM | 1492 | C | GLU | A | 195 | 8.278 | −2.994 | 10.864 | 1.00 | 29.61 | A |
| ATOM | 1493 | O | GLU | A | 195 | 9.326 | −2.519 | 10.426 | 1.00 | 28.59 | A |
| ATOM | 1494 | N | THR | A | 196 | 7.188 | −3.141 | 10.118 | 1.00 | 28.84 | A |
| ATOM | 1495 | CA | THR | A | 196 | 7.151 | −2.688 | 8.733 | 1.00 | 28.59 | A |
| ATOM | 1496 | CB | THR | A | 196 | 7.561 | −3.802 | 7.732 | 1.00 | 29.67 | A |
| ATOM | 1497 | OG1 | THR | A | 196 | 7.608 | −3.250 | 6.412 | 1.00 | 27.60 | A |
| ATOM | 1498 | CG2 | THR | A | 196 | 6.558 | −4.942 | 7.749 | 1.00 | 27.62 | A |
| ATOM | 1499 | C | THR | A | 196 | 5.741 | −2.204 | 8.394 | 1.00 | 28.47 | A |
| ATOM | 1500 | O | THR | A | 196 | 4.750 | −2.732 | 8.902 | 1.00 | 29.71 | A |
| ATOM | 1501 | N | THR | A | 197 | 5.661 | −1.194 | 7.536 | 1.00 | 26.20 | A |
| ATOM | 1502 | CA | THR | A | 197 | 4.390 | −.632 | 7.139 | 1.00 | 23.42 | A |
| ATOM | 1503 | CB | THR | A | 197 | 4.580 | .788 | 6.587 | 1.00 | 24.48 | A |
| ATOM | 1504 | OG1 | THR | A | 197 | 5.705 | .797 | 5.713 | 1.00 | 24.80 | A |
| ATOM | 1505 | CG2 | THR | A | 197 | 4.824 | 1.780 | 7.713 | 1.00 | 22.95 | A |
| ATOM | 1506 | C | THR | A | 197 | 3.666 | −1.475 | 6.099 | 1.00 | 24.32 | A |
| ATOM | 1507 | O | THR | A | 197 | 2.504 | −1.209 | 5.791 | 1.00 | 21.28 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 1508 | N | ALA | A | 198 | 4.341 | −2.490 | 5.561 | 1.00 | 23.32 | A |
| ATOM | 1509 | CA | ALA | A | 198 | 3.731 | −3.347 | 4.546 | 1.00 | 24.83 | A |
| ATOM | 1510 | CB | ALA | A | 198 | 4.631 | −4.554 | 4.259 | 1.00 | 22.22 | A |
| ATOM | 1511 | C | ALA | A | 198 | 2.327 | −3.827 | 4.944 | 1.00 | 27.02 | A |
| ATOM | 1512 | O | ALA | A | 198 | 1.436 | −3.939 | 4.099 | 1.00 | 29.39 | A |
| ATOM | 1513 | N | VAL | A | 199 | 2.129 | −4.110 | 6.225 | 1.00 | 25.63 | A |
| ATOM | 1514 | CA | VAL | A | 199 | .834 | −4.581 | 6.697 | 1.00 | 25.98 | A |
| ATOM | 1515 | CB | VAL | A | 199 | 1.001 | −5.406 | 7.999 | 1.00 | 27.15 | A |
| ATOM | 1516 | CG1 | VAL | A | 199 | 1.506 | −4.512 | 9.124 | 1.00 | 26.01 | A |
| ATOM | 1517 | CG2 | VAL | A | 199 | −.319 | −6.058 | 8.381 | 1.00 | 25.90 | A |
| ATOM | 1518 | C | VAL | A | 199 | −.198 | −3.459 | 6.943 | 1.00 | 27.11 | A |
| ATOM | 1519 | O | VAL | A | 199 | −1.385 | −3.736 | 7.171 | 1.00 | 24.23 | A |
| ATOM | 1520 | N | THR | A | 200 | .243 | −2.203 | 6.872 | 1.00 | 26.28 | A |
| ATOM | 1521 | CA | THR | A | 200 | −.649 | −1.072 | 7.127 | 1.00 | 28.77 | A |
| ATOM | 1522 | CB | THR | A | 200 | −.207 | −.306 | 8.375 | 1.00 | 28.69 | A |
| ATOM | 1523 | OG1 | THR | A | 200 | −1.236 | .617 | 8.745 | 1.00 | 34.92 | A |
| ATOM | 1524 | CG2 | THR | A | 200 | 1.082 | .468 | 8.100 | 1.00 | 29.34 | A |
| ATOM | 1525 | C | THR | A | 200 | −.812 | −.046 | 6.003 | 1.00 | 29.04 | A |
| ATOM | 1526 | O | THR | A | 200 | −1.803 | .686 | 5.966 | 1.00 | 29.83 | A |
| ATOM | 1527 | N | PHE | A | 201 | .154 | .013 | 5.093 | 1.00 | 29.37 | A |
| ATOM | 1528 | CA | PHE | A | 201 | .099 | .967 | 3.993 | 1.00 | 27.14 | A |
| ATOM | 1529 | CB | PHE | A | 201 | 1.390 | .900 | 3.164 | 1.00 | 26.36 | A |
| ATOM | 1530 | CG | PHE | A | 201 | 1.328 | 1.654 | 1.853 | 1.00 | 23.85 | A |
| ATOM | 1531 | CD1 | PHE | A | 201 | .634 | 1.131 | .762 | 1.00 | 24.10 | A |
| ATOM | 1532 | CD2 | PHE | A | 201 | 1.959 | 2.889 | 1.713 | 1.00 | 24.80 | A |
| ATOM | 1533 | CE1 | PHE | A | 201 | .567 | 1.831 | −.447 | 1.00 | 24.95 | A |
| ATOM | 1534 | CE2 | PHE | A | 201 | 1.901 | 3.597 | .513 | 1.00 | 21.90 | A |
| ATOM | 1535 | CZ | PHE | A | 201 | 1.205 | 3.072 | −.569 | 1.00 | 24.52 | A |
| ATOM | 1536 | C | PHE | A | 201 | −1.095 | .748 | 3.089 | 1.00 | 26.41 | A |
| ATOM | 1537 | O | PHE | A | 201 | −1.278 | −.325 | 2.531 | 1.00 | 24.36 | A |
| ATOM | 1538 | N | ARG | A | 202 | −1.900 | 1.789 | 2.941 | 1.00 | 24.97 | A |
| ATOM | 1539 | CA | ARG | A | 202 | −3.063 | 1.730 | 2.075 | 1.00 | 24.55 | A |
| ATOM | 1540 | CB | ARG | A | 202 | −4.299 | 1.327 | 2.883 | 1.00 | 20.28 | A |
| ATOM | 1541 | CG | ARG | A | 202 | −4.532 | 2.183 | 4.108 | 1.00 | 20.71 | A |
| ATOM | 1542 | CD | ARG | A | 202 | −5.718 | 1.693 | 4.931 | 1.00 | 23.12 | A |
| ATOM | 1543 | NE | ARG | A | 202 | −5.454 | .417 | 5.588 | 1.00 | 24.02 | A |
| ATOM | 1544 | CZ | ARG | A | 202 | −5.566 | −.771 | 4.999 | 1.00 | 23.58 | A |
| ATOM | 1545 | NH1 | ARG | A | 202 | −5.942 | −.855 | 3.736 | 1.00 | 23.59 | A |
| ATOM | 1546 | NH2 | ARG | A | 202 | −5.305 | −1.883 | 5.680 | 1.00 | 24.60 | A |
| ATOM | 1547 | C | ARG | A | 202 | −3.251 | 3.116 | 1.448 | 1.00 | 24.73 | A |
| ATOM | 1548 | O | ARG | A | 202 | −2.648 | 4.091 | 1.895 | 1.00 | 23.81 | A |
| ATOM | 1549 | N | GLY | A | 203 | −4.079 | 3.192 | .411 | 1.00 | 26.77 | A |
| ATOM | 1550 | CA | GLY | A | 203 | −4.339 | 4.458 | −.251 | 1.00 | 27.86 | A |
| ATOM | 1551 | C | GLY | A | 203 | −5.000 | 5.470 | .666 | 1.00 | 29.95 | A |
| ATOM | 1552 | O | GLY | A | 203 | −5.455 | 5.128 | 1.757 | 1.00 | 30.65 | A |
| ATOM | 1553 | N | PRO | A | 204 | −5.086 | 6.730 | .238 | 1.00 | 31.00 | A |
| ATOM | 1554 | CD | PRO | A | 204 | −4.681 | 7.238 | −1.085 | 1.00 | 31.27 | A |
| ATOM | 1555 | CA | PRO | A | 204 | −5.693 | 7.799 | 1.034 | 1.00 | 33.93 | A |
| ATOM | 1556 | CB | PRO | A | 204 | −5.127 | 9.047 | .388 | 1.00 | 33.92 | A |
| ATOM | 1557 | CG | PRO | A | 204 | −5.221 | 8.670 | −1.069 | 1.00 | 33.17 | A |
| ATOM | 1558 | C | PRO | A | 204 | −7.207 | 7.780 | .961 | 1.00 | 35.37 | A |
| ATOM | 1559 | O | PRO | A | 204 | −7.784 | 7.238 | .028 | 1.00 | 38.01 | A |
| ATOM | 1560 | N | SER | A | 205 | −7.846 | 8.387 | 1.945 | 1.00 | 37.66 | A |
| ATOM | 1561 | CA | SER | A | 205 | −9.295 | 8.452 | 1.975 | 1.00 | 39.54 | A |
| ATOM | 1562 | CB | SER | A | 205 | −9.858 | 7.242 | 2.722 | 1.00 | 40.11 | A |
| ATOM | 1563 | OG | SER | A | 205 | −11.271 | 7.211 | 2.638 | 1.00 | 45.37 | A |
| ATOM | 1564 | C | SER | A | 205 | −9.694 | 9.746 | 2.675 | 1.00 | 39.76 | A |
| ATOM | 1565 | O | SER | A | 205 | −9.102 | 10.119 | 3.687 | 1.00 | 40.03 | A |
| ATOM | 1566 | N | GLU | A | 206 | −10.685 | 10.438 | 2.129 | 1.00 | 41.11 | A |
| ATOM | 1567 | CA | GLU | A | 206 | −11.138 | 11.690 | 2.723 | 1.00 | 43.15 | A |
| ATOM | 1568 | CB | GLU | A | 206 | −11.788 | 12.585 | 1.660 | 1.00 | 44.15 | A |
| ATOM | 1569 | CG | GLU | A | 206 | −12.678 | 11.861 | .666 | 1.00 | 47.17 | A |
| ATOM | 1570 | CD | GLU | A | 206 | −11.906 | 11.275 | −.512 | 1.00 | 50.55 | A |
| ATOM | 1571 | OE1 | GLU | A | 206 | −11.174 | 10.273 | −.332 | 1.00 | 50.11 | A |
| ATOM | 1572 | OE2 | GLU | A | 206 | −12.031 | 11.830 | −1.628 | 1.00 | 51.91 | A |
| ATOM | 1573 | C | GLU | A | 206 | −12.100 | 11.481 | 3.895 | 1.00 | 43.15 | A |
| ATOM | 1574 | O | GLU | A | 206 | −12.333 | 12.392 | 4.690 | 1.00 | 44.07 | A |
| ATOM | 1575 | N | THR | A | 207 | −12.651 | 10.281 | 4.012 | 1.00 | 43.47 | A |
| ATOM | 1576 | CA | THR | A | 207 | −13.559 | 9.998 | 5.109 | 1.00 | 43.94 | A |
| ATOM | 1577 | CB | THR | A | 207 | −14.742 | 9.123 | 4.639 | 1.00 | 46.32 | A |
| ATOM | 1578 | OG1 | THR | A | 207 | −14.258 | 7.858 | 4.172 | 1.00 | 50.01 | A |
| ATOM | 1579 | CG2 | THR | A | 207 | −15.494 | 9.814 | 3.511 | 1.00 | 47.66 | A |
| ATOM | 1580 | C | THR | A | 207 | −12.831 | 9.297 | 6.260 | 1.00 | 42.70 | A |
| ATOM | 1581 | O | THR | A | 207 | −13.456 | 8.884 | 7.232 | 1.00 | 42.48 | A |
| ATOM | 1582 | N | HIS | A | 208 | −11.509 | 9.183 | 6.155 | 1.00 | 41.66 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 1583 | CA | HIS | A | 208 | −10.709 | 8.520 | 7.185 | 1.00 | 40.56 | A |
| ATOM | 1584 | CB | HIS | A | 208 | −10.471 | 7.071 | 6.761 | 1.00 | 40.63 | A |
| ATOM | 1585 | CG | HIS | A | 208 | −11.728 | 6.272 | 6.641 | 1.00 | 41.45 | A |
| ATOM | 1586 | CD2 | HIS | A | 208 | −12.552 | 6.060 | 5.588 | 1.00 | 41.71 | A |
| ATOM | 1587 | ND1 | HIS | A | 208 | −12.306 | 5.629 | 7.714 | 1.00 | 43.34 | A |
| ATOM | 1588 | CE1 | HIS | A | 208 | −13.432 | 5.056 | 7.327 | 1.00 | 42.20 | A |
| ATOM | 1589 | NE2 | HIS | A | 208 | −13.605 | 5.303 | 6.041 | 1.00 | 40.79 | A |
| ATOM | 1590 | C | HIS | A | 208 | −9.366 | 9.216 | 7.468 | 1.00 | 40.72 | A |
| ATOM | 1591 | O | HIS | A | 208 | −8.305 | 8.578 | 7.455 | 1.00 | 36.97 | A |
| ATOM | 1592 | N | LEU | A | 209 | −9.428 | 10.519 | 7.744 | 1.00 | 41.16 | A |
| ATOM | 1593 | CA | LEU | A | 209 | −8.240 | 11.328 | 8.013 | 1.00 | 42.25 | A |
| ATOM | 1594 | CB | LEU | A | 209 | −8.648 | 12.766 | 8.322 | 1.00 | 44.19 | A |
| ATOM | 1595 | CG | LEU | A | 209 | −9.250 | 13.521 | 7.130 | 1.00 | 45.60 | A |
| ATOM | 1596 | CD1 | LEU | A | 209 | −9.688 | 14.911 | 7.553 | 1.00 | 45.32 | A |
| ATOM | 1597 | CD2 | LEU | A | 209 | −8.214 | 13.608 | 6.016 | 1.00 | 45.26 | A |
| ATOM | 1598 | C | LEU | A | 209 | −7.326 | 10.806 | 9.117 | 1.00 | 43.63 | A |
| ATOM | 1599 | O | LEU | A | 209 | −6.117 | 11.059 | 9.100 | 1.00 | 43.18 | A |
| ATOM | 1600 | N | ASP | A | 210 | −7.885 | 10.077 | 10.077 | 1.00 | 44.10 | A |
| ATOM | 1601 | CA | ASP | A | 210 | −7.054 | 9.538 | 11.144 | 1.00 | 43.86 | A |
| ATOM | 1602 | CB | ASP | A | 210 | −7.921 | 8.879 | 12.224 | 1.00 | 44.72 | A |
| ATOM | 1603 | CG | ASP | A | 210 | −8.520 | 7.567 | 11.781 | 1.00 | 46.10 | A |
| ATOM | 1604 | OD1 | ASP | A | 210 | −8.932 | 7.454 | 10.606 | 1.00 | 45.79 | A |
| ATOM | 1605 | OD2 | ASP | A | 210 | −8.595 | 6.649 | 12.626 | 1.00 | 48.31 | A |
| ATOM | 1606 | C | ASP | A | 210 | −6.087 | 8.539 | 10.506 | 1.00 | 44.25 | A |
| ATOM | 1607 | O | ASP | A | 210 | −4.962 | 8.352 | 10.985 | 1.00 | 44.96 | A |
| ATOM | 1608 | N | SER | A | 211 | −6.521 | 7.928 | 9.402 | 1.00 | 42.15 | A |
| ATOM | 1609 | CA | SER | A | 211 | −5.700 | 6.970 | 8.671 | 1.00 | 40.33 | A |
| ATOM | 1610 | CB | SER | A | 211 | −6.570 | 6.078 | 7.776 | 1.00 | 41.73 | A |
| ATOM | 1611 | OG | SER | A | 211 | −5.763 | 5.245 | 6.948 | 1.00 | 40.95 | A |
| ATOM | 1612 | C | SER | A | 211 | −4.659 | 7.679 | 7.808 | 1.00 | 39.17 | A |
| ATOM | 1613 | O | SER | A | 211 | −3.592 | 7.128 | 7.550 | 1.00 | 37.98 | A |
| ATOM | 1614 | N | LEU | A | 212 | −4.979 | 8.892 | 7.355 | 1.00 | 38.41 | A |
| ATOM | 1615 | CA | LEU | A | 212 | −4.049 | 9.668 | 6.533 | 1.00 | 35.56 | A |
| ATOM | 1616 | CB | LEU | A | 212 | −4.622 | 11.048 | 6.201 | 1.00 | 34.77 | A |
| ATOM | 1617 | CG | LEU | A | 212 | −5.091 | 11.392 | 4.787 | 1.00 | 33.15 | A |
| ATOM | 1618 | CD1 | LEU | A | 212 | −5.182 | 12.915 | 4.668 | 1.00 | 32.90 | A |
| ATOM | 1619 | CD2 | LEU | A | 212 | −4.125 | 10.855 | 3.754 | 1.00 | 31.17 | A |
| ATOM | 1620 | C | LEU | A | 212 | −2.792 | 9.857 | 7.358 | 1.00 | 35.22 | A |
| ATOM | 1621 | O | LEU | A | 212 | −1.701 | 9.450 | 6.961 | 1.00 | 36.22 | A |
| ATOM | 1622 | N | VAL | A | 213 | −2.962 | 10.499 | 8.510 | 1.00 | 33.04 | A |
| ATOM | 1623 | CA | VAL | A | 213 | −1.864 | 10.745 | 9.430 | 1.00 | 32.51 | A |
| ATOM | 1624 | CB | VAL | A | 213 | −2.414 | 10.985 | 10.857 | 1.00 | 31.66 | A |
| ATOM | 1625 | CG1 | VAL | A | 213 | −1.275 | 11.153 | 11.843 | 1.00 | 31.63 | A |
| ATOM | 1626 | CG2 | VAL | A | 213 | −3.307 | 12.211 | 10.860 | 1.00 | 29.64 | A |
| ATOM | 1627 | C | VAL | A | 213 | −.911 | 9.559 | 9.439 | 1.00 | 32.48 | A |
| ATOM | 1628 | O | VAL | A | 213 | .271 | 9.660 | 9.104 | 1.00 | 32.59 | A |
| ATOM | 1629 | N | GLY | A | 214 | −1.449 | 8.378 | 9.809 | 1.00 | 31.64 | A |
| ATOM | 1630 | CA | GLY | A | 214 | −.666 | 7.158 | 9.864 | 1.00 | 31.10 | A |
| ATOM | 1631 | C | GLY | A | 214 | .185 | 6.885 | 8.638 | 1.00 | 31.81 | A |
| ATOM | 1632 | O | GLY | A | 214 | 1.283 | 6.339 | 8.760 | 1.00 | 31.87 | A |
| ATOM | 1633 | N | GLN | A | 215 | −.303 | 7.249 | 7.454 | 1.00 | 30.01 | A |
| ATOM | 1634 | CA | GLN | A | 215 | .470 | 7.016 | 6.239 | 1.00 | 29.39 | A |
| ATOM | 1635 | CB | GLN | A | 215 | −.383 | 7.249 | 4.990 | 1.00 | 29.12 | A |
| ATOM | 1636 | CG | GLN | A | 215 | −1.456 | 6.213 | 4.805 | 1.00 | 28.36 | A |
| ATOM | 1637 | CD | GLN | A | 215 | −.938 | 4.825 | 5.120 | 1.00 | 29.65 | A |
| ATOM | 1638 | OE1 | GLN | A | 215 | −1.545 | 4.095 | 5.899 | 1.00 | 27.40 | A |
| ATOM | 1639 | NE2 | GLN | A | 215 | .195 | 4.458 | 4.523 | 1.00 | 29.22 | A |
| ATOM | 1640 | C | GLN | A | 215 | 1.697 | 7.908 | 6.181 | 1.00 | 29.72 | A |
| ATOM | 1641 | O | GLN | A | 215 | 2.644 | 7.619 | 5.452 | 1.00 | 29.34 | A |
| ATOM | 1642 | N | ALA | A | 216 | 1.673 | 8.988 | 6.957 | 1.00 | 29.06 | A |
| ATOM | 1643 | CA | ALA | A | 216 | 2.781 | 9.928 | 6.977 | 1.00 | 29.34 | A |
| ATOM | 1644 | CB | ALA | A | 216 | 2.250 | 11.358 | 6.959 | 1.00 | 28.98 | A |
| ATOM | 1645 | C | ALA | A | 216 | 3.711 | 9.744 | 8.167 | 1.00 | 28.44 | A |
| ATOM | 1646 | O | ALA | A | 216 | 4.859 | 10.171 | 8.119 | 1.00 | 28.77 | A |
| ATOM | 1647 | N | LEU | A | 217 | 3.226 | 9.105 | 9.225 | 1.00 | 26.41 | A |
| ATOM | 1648 | CA | LEU | A | 217 | 4.037 | 8.934 | 10.417 | 1.00 | 26.85 | A |
| ATOM | 1649 | CB | LEU | A | 217 | 3.159 | 9.022 | 11.660 | 1.00 | 27.43 | A |
| ATOM | 1650 | CG | LEU | A | 217 | 2.419 | 10.340 | 11.889 | 1.00 | 27.77 | A |
| ATOM | 1651 | CD1 | LEU | A | 217 | 1.602 | 10.236 | 13.167 | 1.00 | 27.93 | A |
| ATOM | 1652 | CD2 | LEU | A | 217 | 3.411 | 11.495 | 11.970 | 1.00 | 28.42 | A |
| ATOM | 1653 | C | LEU | A | 217 | 4.860 | 7.660 | 10.489 | 1.00 | 28.52 | A |
| ATOM | 1654 | O | LEU | A | 217 | 6.070 | 7.707 | 10.703 | 1.00 | 29.49 | A |
| ATOM | 1655 | N | PHE | A | 218 | 4.196 | 6.524 | 10.324 | 1.00 | 28.61 | A |
| ATOM | 1656 | CA | PHE | A | 218 | 4.853 | 5.229 | 10.409 | 1.00 | 28.75 | A |
| ATOM | 1657 | CB | PHE | A | 218 | 3.794 | 4.127 | 10.391 | 1.00 | 31.22 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 1658 | CG | PHE | A | 218 | 2.703 | 4.324 | 11.403 | 1.00 | 34.00 | A |
| ATOM | 1659 | CD1 | PHE | A | 218 | 3.008 | 4.645 | 12.719 | 1.00 | 36.79 | A |
| ATOM | 1660 | CD2 | PHE | A | 218 | 1.370 | 4.170 | 11.046 | 1.00 | 36.49 | A |
| ATOM | 1661 | CE1 | PHE | A | 218 | 2.002 | 4.811 | 13.674 | 1.00 | 36.73 | A |
| ATOM | 1662 | CE2 | PHE | A | 218 | .347 | 4.333 | 11.993 | 1.00 | 38.04 | A |
| ATOM | 1663 | CZ | PHE | A | 218 | .667 | 4.654 | 13.310 | 1.00 | 37.72 | A |
| ATOM | 1664 | C | PHE | A | 218 | 5.933 | 4.916 | 9.368 | 1.00 | 27.22 | A |
| ATOM | 1665 | O | PHE | A | 218 | 5.798 | 5.219 | 8.181 | 1.00 | 25.21 | A |
| ATOM | 1666 | N | GLY | A | 219 | 7.011 | 4.300 | 9.851 | 1.00 | 28.13 | A |
| ATOM | 1667 | CA | GLY | A | 219 | 8.125 | 3.894 | 9.007 | 1.00 | 27.30 | A |
| ATOM | 1668 | C | GLY | A | 219 | 8.561 | 2.497 | 9.424 | 1.00 | 27.92 | A |
| ATOM | 1669 | O | GLY | A | 219 | 7.950 | 1.909 | 10.311 | 1.00 | 27.50 | A |
| ATOM | 1670 | N | ASP | A | 220 | 9.615 | 1.968 | 8.805 | 1.00 | 28.69 | A |
| ATOM | 1671 | CA | ASP | A | 220 | 10.100 | .626 | 9.123 | 1.00 | 27.97 | A |
| ATOM | 1672 | CB | ASP | A | 220 | 10.161 | −.243 | 7.860 | 1.00 | 27.48 | A |
| ATOM | 1673 | CG | ASP | A | 220 | 8.833 | −.326 | 7.138 | 1.00 | 28.81 | A |
| ATOM | 1674 | OD1 | ASP | A | 220 | 7.811 | .115 | 7.706 | 1.00 | 28.94 | A |
| ATOM | 1675 | OD2 | ASP | A | 220 | 8.810 | −.848 | 6.003 | 1.00 | 30.23 | A |
| ATOM | 1676 | C | ASP | A | 220 | 11.470 | .591 | 9.792 | 1.00 | 29.31 | A |
| ATOM | 1677 | O | ASP | A | 220 | 12.346 | 1.412 | 9.503 | 1.00 | 28.92 | A |
| ATOM | 1678 | N | GLY | A | 221 | 11.648 | −.388 | 10.678 | 1.00 | 29.62 | A |
| ATOM | 1679 | CA | GLY | A | 221 | 12.911 | −.556 | 11.378 | 1.00 | 27.70 | A |
| ATOM | 1680 | C | GLY | A | 221 | 12.920 | −1.746 | 12.328 | 1.00 | 26.08 | A |
| ATOM | 1681 | O | GLY | A | 221 | 11.876 | −2.273 | 12.703 | 1.00 | 24.58 | A |
| ATOM | 1682 | N | ALA | A | 222 | 14.114 | −2.173 | 12.711 | 1.00 | 26.01 | A |
| ATOM | 1683 | CA | ALA | A | 222 | 14.270 | −3.283 | 13.634 | 1.00 | 25.76 | A |
| ATOM | 1684 | CB | ALA | A | 222 | 14.657 | −4.564 | 12.885 | 1.00 | 23.29 | A |
| ATOM | 1685 | C | ALA | A | 222 | 15.343 | −2.915 | 14.644 | 1.00 | 27.10 | A |
| ATOM | 1686 | O | ALA | A | 222 | 16.394 | −2.365 | 14.292 | 1.00 | 25.67 | A |
| ATOM | 1687 | N | CYS | A | 223 | 15.071 | −3.214 | 15.906 | 1.00 | 27.08 | A |
| ATOM | 1688 | CA | CYS | A | 223 | 16.016 | −2.917 | 16.960 | 1.00 | 28.62 | A |
| ATOM | 1689 | CB | CYS | A | 223 | 15.413 | −1.939 | 17.942 | 1.00 | 33.80 | A |
| ATOM | 1690 | SG | CYS | A | 223 | 14.226 | −2.768 | 18.964 | 1.00 | 42.48 | A |
| ATOM | 1691 | C | CYS | A | 223 | 16.282 | −4.210 | 17.684 | 1.00 | 26.75 | A |
| ATOM | 1692 | O | CYS | A | 223 | 15.392 | −5.058 | 17.783 | 1.00 | 25.04 | A |
| ATOM | 1693 | N | ALA | A | 224 | 17.494 | −4.347 | 18.212 | 1.00 | 24.80 | A |
| ATOM | 1694 | CA | ALA | A | 224 | 17.872 | −5.560 | 18.923 | 1.00 | 26.10 | A |
| ATOM | 1695 | CB | ALA | A | 224 | 18.578 | −6.529 | 17.975 | 1.00 | 21.48 | A |
| ATOM | 1696 | C | ALA | A | 224 | 18.752 | −5.261 | 20.129 | 1.00 | 26.20 | A |
| ATOM | 1697 | O | ALA | A | 224 | 19.707 | −4.487 | 20.057 | 1.00 | 23.62 | A |
| ATOM | 1698 | N | LEU | A | 225 | 18.408 | −5.901 | 21.240 | 1.00 | 28.73 | A |
| ATOM | 1699 | CA | LEU | A | 225 | 19.117 | −5.738 | 22.499 | 1.00 | 29.59 | A |
| ATOM | 1700 | CB | LEU | A | 225 | 18.213 | −5.087 | 23.547 | 1.00 | 28.37 | A |
| ATOM | 1701 | CG | LEU | A | 225 | 17.447 | −3.834 | 23.171 | 1.00 | 30.11 | A |
| ATOM | 1702 | CD1 | LEU | A | 225 | 16.636 | −3.373 | 24.360 | 1.00 | 33.00 | A |
| ATOM | 1703 | CD2 | LEU | A | 225 | 18.417 | −2.757 | 22.733 | 1.00 | 30.82 | A |
| ATOM | 1704 | C | LEU | A | 225 | 19.541 | −7.077 | 23.070 | 1.00 | 28.64 | A |
| ATOM | 1705 | O | LEU | A | 225 | 18.892 | −8.099 | 22.837 | 1.00 | 26.77 | A |
| ATOM | 1706 | N | ILE | A | 226 | 20.629 | −7.036 | 23.834 | 1.00 | 27.61 | A |
| ATOM | 1707 | CA | ILE | A | 226 | 21.143 | −8.187 | 24.552 | 1.00 | 27.04 | A |
| ATOM | 1708 | CB | ILE | A | 226 | 22.659 | −8.443 | 24.267 | 1.00 | 25.88 | A |
| ATOM | 1709 | CG2 | ILE | A | 226 | 23.243 | −9.389 | 25.305 | 1.00 | 27.04 | A |
| ATOM | 1710 | CG1 | ILE | A | 226 | 22.836 | −9.095 | 22.899 | 1.00 | 25.32 | A |
| ATOM | 1711 | CD1 | ILE | A | 226 | 22.257 | −10.490 | 22.817 | 1.00 | 24.29 | A |
| ATOM | 1712 | C | ILE | A | 226 | 20.932 | −7.744 | 26.008 | 1.00 | 27.60 | A |
| ATOM | 1713 | O | ILE | A | 226 | 21.506 | −6.746 | 26.463 | 1.00 | 26.23 | A |
| ATOM | 1714 | N | VAL | A | 227 | 20.064 | −8.455 | 26.718 | 1.00 | 27.92 | A |
| ATOM | 1715 | CA | VAL | A | 227 | 19.790 | −8.127 | 28.109 | 1.00 | 29.45 | A |
| ATOM | 1716 | CB | VAL | A | 227 | 18.280 | −7.875 | 28.355 | 1.00 | 29.44 | A |
| ATOM | 1717 | CG1 | VAL | A | 227 | 17.995 | −7.745 | 29.851 | 1.00 | 27.14 | A |
| ATOM | 1718 | CG2 | VAL | A | 227 | 17.856 | −6.602 | 27.647 | 1.00 | 27.64 | A |
| ATOM | 1719 | C | VAL | A | 227 | 20.274 | −9.260 | 29.004 | 1.00 | 30.44 | A |
| ATOM | 1720 | O | VAL | A | 227 | 20.119 | −10.441 | 28.677 | 1.00 | 30.38 | A |
| ATOM | 1721 | N | GLY | A | 228 | 20.878 | −8.891 | 30.129 | 1.00 | 30.00 | A |
| ATOM | 1722 | CA | GLY | A | 228 | 21.381 | −9.893 | 31.039 | 1.00 | 30.18 | A |
| ATOM | 1723 | C | GLY | A | 228 | 21.795 | −9.294 | 32.354 | 1.00 | 31.31 | A |
| ATOM | 1724 | O | GLY | A | 228 | 22.112 | −8.109 | 32.433 | 1.00 | 31.60 | A |
| ATOM | 1725 | N | ALA | A | 229 | 21.774 | −10.126 | 33.390 | 1.00 | 32.55 | A |
| ATOM | 1726 | CA | ALA | A | 229 | 22.160 | −9.710 | 34.724 | 1.00 | 33.95 | A |
| ATOM | 1727 | CB | ALA | A | 229 | 21.252 | −10.367 | 35.764 | 1.00 | 34.17 | A |
| ATOM | 1728 | C | ALA | A | 229 | 23.619 | −10.111 | 34.961 | 1.00 | 35.33 | A |
| ATOM | 1729 | O | ALA | A | 229 | 24.164 | −10.972 | 34.256 | 1.00 | 33.08 | A |
| ATOM | 1730 | N | ASP | A | 230 | 24.248 | −9.465 | 35.942 | 1.00 | 36.86 | A |
| ATOM | 1731 | CA | ASP | A | 230 | 25.640 | −9.740 | 36.300 | 1.00 | 39.56 | A |
| ATOM | 1732 | CB | ASP | A | 230 | 25.757 | −11.083 | 37.044 | 1.00 | 41.40 | A |

APPENDIX A-continued

*Pinus sylvestris* STS

| ATOM | # | TYPE | RES | | | X | Y | Z | OCC | B | |
|------|---|------|-----|---|---|---|---|---|-----|---|---|
| ATOM | 1733 | CG | ASP | A | 230 | 24.520 | −11.413 | 37.868 | 1.00 | 43.35 | A |
| ATOM | 1734 | OD1 | ASP | A | 230 | 24.054 | −10.532 | 38.623 | 1.00 | 44.48 | A |
| ATOM | 1735 | OD2 | ASP | A | 230 | 24.022 | −12.560 | 37.767 | 1.00 | 44.89 | A |
| ATOM | 1736 | C | ASP | A | 230 | 26.532 | −9.793 | 35.066 | 1.00 | 39.71 | A |
| ATOM | 1737 | O | ASP | A | 230 | 26.951 | −10.873 | 34.651 | 1.00 | 39.33 | A |
| ATOM | 1738 | N | PRO | A | 231 | 26.831 | −8.633 | 34.456 | 1.00 | 39.86 | A |
| ATOM | 1739 | CD | PRO | A | 231 | 26.381 | −7.252 | 34.717 | 1.00 | 40.12 | A |
| ATOM | 1740 | CA | PRO | A | 231 | 27.692 | −8.692 | 33.271 | 1.00 | 40.52 | A |
| ATOM | 1741 | CB | PRO | A | 231 | 27.573 | −7.280 | 32.687 | 1.00 | 39.25 | A |
| ATOM | 1742 | CG | PRO | A | 231 | 27.353 | −6.433 | 33.884 | 1.00 | 38.53 | A |
| ATOM | 1743 | C | PRO | A | 231 | 29.136 | −9.073 | 33.629 | 1.00 | 41.54 | A |
| ATOM | 1744 | O | PRO | A | 231 | 29.692 | −8.570 | 34.605 | 1.00 | 43.36 | A |
| ATOM | 1745 | N | ILE | A | 232 | 29.723 | −9.977 | 32.850 | 1.00 | 41.13 | A |
| ATOM | 1746 | CA | ILE | A | 232 | 31.099 | −10.420 | 33.062 | 1.00 | 40.68 | A |
| ATOM | 1747 | CB | ILE | A | 232 | 31.474 | −11.530 | 32.070 | 1.00 | 40.34 | A |
| ATOM | 1748 | CG2 | ILE | A | 232 | 32.886 | −11.998 | 32.333 | 1.00 | 38.27 | A |
| ATOM | 1749 | CG1 | ILE | A | 232 | 30.465 | −12.675 | 32.178 | 1.00 | 39.77 | A |
| ATOM | 1750 | CD1 | ILE | A | 232 | 30.197 | −13.355 | 30.861 | 1.00 | 41.07 | A |
| ATOM | 1751 | C | ILE | A | 232 | 32.046 | −9.236 | 32.843 | 1.00 | 40.67 | A |
| ATOM | 1752 | O | ILE | A | 232 | 32.089 | −8.660 | 31.751 | 1.00 | 39.36 | A |
| ATOM | 1753 | N | PRO | A | 233 | 32.836 | −8.882 | 33.872 | 1.00 | 41.83 | A |
| ATOM | 1754 | CD | PRO | A | 233 | 33.100 | −9.709 | 35.064 | 1.00 | 41.56 | A |
| ATOM | 1755 | CA | PRO | A | 233 | 33.782 | −7.762 | 33.803 | 1.00 | 42.38 | A |
| ATOM | 1756 | CB | PRO | A | 233 | 34.560 | −7.888 | 35.108 | 1.00 | 42.80 | A |
| ATOM | 1757 | CG | PRO | A | 233 | 34.539 | −9.368 | 35.365 | 1.00 | 42.88 | A |
| ATOM | 1758 | C | PRO | A | 233 | 34.681 | −7.788 | 32.589 | 1.00 | 42.20 | A |
| ATOM | 1759 | O | PRO | A | 233 | 35.137 | −8.844 | 32.172 | 1.00 | 42.50 | A |
| ATOM | 1760 | N | GLN | A | 234 | 34.914 | −6.606 | 32.032 | 1.00 | 43.76 | A |
| ATOM | 1761 | CA | GLN | A | 234 | 35.764 | −6.406 | 30.860 | 1.00 | 45.45 | A |
| ATOM | 1762 | CB | GLN | A | 234 | 37.245 | −6.416 | 31.262 | 1.00 | 46.00 | A |
| ATOM | 1763 | CG | GLN | A | 234 | 37.726 | −7.729 | 31.838 | 1.00 | 48.56 | A |
| ATOM | 1764 | CD | GLN | A | 234 | 39.175 | −7.678 | 32.263 | 1.00 | 49.12 | A |
| ATOM | 1765 | OE1 | GLN | A | 234 | 39.553 | −6.892 | 33.128 | 1.00 | 50.98 | A |
| ATOM | 1766 | NE2 | GLN | A | 234 | 39.997 | −8.520 | 31.656 | 1.00 | 49.92 | A |
| ATOM | 1767 | C | GLN | A | 234 | 35.544 | −7.394 | 29.726 | 1.00 | 44.87 | A |
| ATOM | 1768 | O | GLN | A | 234 | 36.397 | −7.549 | 28.849 | 1.00 | 45.60 | A |
| ATOM | 1769 | N | VAL | A | 235 | 34.404 | −8.071 | 29.756 | 1.00 | 44.58 | A |
| ATOM | 1770 | CA | VAL | A | 235 | 34.039 | −9.028 | 28.720 | 1.00 | 43.67 | A |
| ATOM | 1771 | CB | VAL | A | 235 | 33.805 | −10.440 | 29.299 | 1.00 | 44.91 | A |
| ATOM | 1772 | CG1 | VAL | A | 235 | 33.227 | −11.353 | 28.218 | 1.00 | 45.45 | A |
| ATOM | 1773 | CG2 | VAL | A | 235 | 35.115 | −11.010 | 29.822 | 1.00 | 45.12 | A |
| ATOM | 1774 | C | VAL | A | 235 | 32.743 | −8.524 | 28.108 | 1.00 | 42.68 | A |
| ATOM | 1775 | O | VAL | A | 235 | 32.571 | −8.547 | 26.889 | 1.00 | 42.55 | A |
| ATOM | 1776 | N | GLU | A | 236 | 31.835 | −8.076 | 28.975 | 1.00 | 40.47 | A |
| ATOM | 1777 | CA | GLU | A | 236 | 30.547 | −7.527 | 28.551 | 1.00 | 39.21 | A |
| ATOM | 1778 | CB | GLU | A | 236 | 29.380 | −8.321 | 29.133 | 1.00 | 35.88 | A |
| ATOM | 1779 | CG | GLU | A | 236 | 29.437 | −9.787 | 28.844 | 1.00 | 34.44 | A |
| ATOM | 1780 | CD | GLU | A | 236 | 28.341 | −10.545 | 29.544 | 1.00 | 29.35 | A |
| ATOM | 1781 | OE1 | GLU | A | 236 | 28.117 | −10.279 | 30.740 | 1.00 | 28.34 | A |
| ATOM | 1782 | OE2 | GLU | A | 236 | 27.718 | −11.406 | 28.900 | 1.00 | 29.13 | A |
| ATOM | 1783 | C | GLU | A | 236 | 30.475 | −6.112 | 29.082 | 1.00 | 39.21 | A |
| ATOM | 1784 | O | GLU | A | 236 | 30.804 | −5.863 | 30.240 | 1.00 | 39.77 | A |
| ATOM | 1785 | N | LYS | A | 237 | 30.041 | −5.188 | 28.236 | 1.00 | 40.00 | A |
| ATOM | 1786 | CA | LYS | A | 237 | 29.946 | −3.792 | 28.630 | 1.00 | 38.96 | A |
| ATOM | 1787 | CB | LYS | A | 237 | 30.721 | −2.934 | 27.631 | 1.00 | 38.86 | A |
| ATOM | 1788 | CG | LYS | A | 237 | 30.876 | −1.475 | 28.023 | 1.00 | 41.75 | A |
| ATOM | 1789 | CD | LYS | A | 237 | 31.777 | −.743 | 27.024 | 1.00 | 44.57 | A |
| ATOM | 1790 | CE | LYS | A | 237 | 31.936 | .730 | 27.385 | 1.00 | 45.75 | A |
| ATOM | 1791 | NZ | LYS | A | 237 | 32.833 | 1.455 | 26.432 | 1.00 | 46.22 | A |
| ATOM | 1792 | C | LYS | A | 237 | 28.480 | −3.377 | 28.676 | 1.00 | 38.35 | A |
| ATOM | 1793 | O | LYS | A | 237 | 27.786 | −3.403 | 27.659 | 1.00 | 36.98 | A |
| ATOM | 1794 | N | ALA | A | 238 | 28.006 | −3.019 | 29.865 | 1.00 | 37.12 | A |
| ATOM | 1795 | CA | ALA | A | 238 | 26.625 | −2.598 | 30.031 | 1.00 | 35.90 | A |
| ATOM | 1796 | CB | ALA | A | 238 | 26.131 | −2.956 | 31.421 | 1.00 | 34.13 | A |
| ATOM | 1797 | C | ALA | A | 238 | 26.549 | −1.094 | 29.811 | 1.00 | 36.34 | A |
| ATOM | 1798 | O | ALA | A | 238 | 27.546 | −.386 | 29.977 | 1.00 | 37.36 | A |
| ATOM | 1799 | N | CYS | A | 239 | 25.375 | −.608 | 29.415 | 1.00 | 35.65 | A |
| ATOM | 1800 | CA | CYS | A | 239 | 25.179 | .824 | 29.179 | 1.00 | 34.67 | A |
| ATOM | 1801 | CB | CYS | A | 239 | 25.042 | 1.096 | 27.682 | 1.00 | 34.03 | A |
| ATOM | 1802 | SG | CYS | A | 239 | 23.884 | .011 | 26.852 | 1.00 | 39.50 | A |
| ATOM | 1803 | C | CYS | A | 239 | 23.952 | 1.345 | 29.928 | 1.00 | 32.01 | A |
| ATOM | 1804 | O | CYS | A | 239 | 23.922 | 2.488 | 30.384 | 1.00 | 29.97 | A |
| ATOM | 1805 | N | PHE | A | 240 | 22.952 | .489 | 30.073 | 1.00 | 30.69 | A |
| ATOM | 1806 | CA | PHE | A | 240 | 21.731 | .864 | 30.772 | 1.00 | 29.43 | A |
| ATOM | 1807 | CB | PHE | A | 240 | 20.651 | 1.222 | 29.753 | 1.00 | 27.09 | A |

APPENDIX A-continued

*Pinus sylvestris* STS

| ATOM | # | TYPE | RES | | | X | Y | Z | OCC | B | |
|------|---|------|-----|---|---|---|---|---|-----|---|---|
| ATOM | 1808 | CG | PHE | A | 240 | 21.002 | 2.399 | 28.886 | 1.00 | 26.17 | A |
| ATOM | 1809 | CD1 | PHE | A | 240 | 21.036 | 3.686 | 29.415 | 1.00 | 25.93 | A |
| ATOM | 1810 | CD2 | PHE | A | 240 | 21.323 | 2.223 | 27.544 | 1.00 | 28.55 | A |
| ATOM | 1811 | CE1 | PHE | A | 240 | 21.384 | 4.772 | 28.623 | 1.00 | 25.72 | A |
| ATOM | 1812 | CE2 | PHE | A | 240 | 21.673 | 3.314 | 26.743 | 1.00 | 23.97 | A |
| ATOM | 1813 | CZ | PHE | A | 240 | 21.703 | 4.583 | 27.285 | 1.00 | 23.90 | A |
| ATOM | 1814 | C | PHE | A | 240 | 21.251 | −.288 | 31.643 | 1.00 | 30.74 | A |
| ATOM | 1815 | O | PHE | A | 240 | 21.413 | −1.447 | 31.277 | 1.00 | 32.77 | A |
| ATOM | 1816 | N | GLU | A | 241 | 20.677 | .021 | 32.802 | 1.00 | 31.99 | A |
| ATOM | 1817 | CA | GLU | A | 241 | 20.147 | −1.025 | 33.678 | 1.00 | 34.57 | A |
| ATOM | 1818 | CB | GLU | A | 241 | 20.852 | −1.023 | 35.046 | 1.00 | 35.81 | A |
| ATOM | 1819 | CG | GLU | A | 241 | 22.360 | −1.271 | 34.997 | 1.00 | 37.93 | A |
| ATOM | 1820 | CD | GLU | A | 241 | 23.006 | −1.280 | 36.381 | 1.00 | 40.79 | A |
| ATOM | 1821 | OE1 | GLU | A | 241 | 22.690 | −.392 | 37.211 | 1.00 | 42.12 | A |
| ATOM | 1822 | OE2 | GLU | A | 241 | 23.845 | −2.170 | 36.638 | 1.00 | 42.83 | A |
| ATOM | 1823 | C | GLU | A | 241 | 18.648 | −.771 | 33.867 | 1.00 | 34.22 | A |
| ATOM | 1824 | O | GLU | A | 241 | 18.200 | .382 | 33.877 | 1.00 | 34.52 | A |
| ATOM | 1825 | N | ILE | A | 242 | 17.877 | −1.846 | 34.004 | 1.00 | 34.06 | A |
| ATOM | 1826 | CA | ILE | A | 242 | 16.434 | −1.733 | 34.196 | 1.00 | 32.84 | A |
| ATOM | 1827 | CB | ILE | A | 242 | 15.670 | −2.830 | 33.421 | 1.00 | 32.65 | A |
| ATOM | 1828 | CG2 | ILE | A | 242 | 14.229 | −2.383 | 33.165 | 1.00 | 31.59 | A |
| ATOM | 1829 | CG1 | ILE | A | 242 | 16.359 | −3.113 | 32.089 | 1.00 | 32.73 | A |
| ATOM | 1830 | CD1 | ILE | A | 242 | 16.466 | −1.903 | 31.191 | 1.00 | 33.02 | A |
| ATOM | 1831 | C | ILE | A | 242 | 16.124 | −1.891 | 35.683 | 1.00 | 32.33 | A |
| ATOM | 1832 | O | ILE | A | 242 | 16.073 | −3.009 | 36.199 | 1.00 | 34.81 | A |
| ATOM | 1833 | N | VAL | A | 243 | 15.903 | −.770 | 36.362 | 1.00 | 30.43 | A |
| ATOM | 1834 | CA | VAL | A | 243 | 15.624 | −.761 | 37.795 | 1.00 | 27.37 | A |
| ATOM | 1835 | CB | VAL | A | 243 | 16.016 | .621 | 38.394 | 1.00 | 28.23 | A |
| ATOM | 1836 | CG1 | VAL | A | 243 | 15.188 | .923 | 39.626 | 1.00 | 22.92 | A |
| ATOM | 1837 | CG2 | VAL | A | 243 | 17.499 | .632 | 38.740 | 1.00 | 29.02 | A |
| ATOM | 1838 | C | VAL | A | 243 | 14.196 | −1.094 | 38.247 | 1.00 | 26.31 | A |
| ATOM | 1839 | O | VAL | A | 243 | 14.000 | −1.938 | 39.119 | 1.00 | 25.11 | A |
| ATOM | 1840 | N | TRP | A | 244 | 13.213 | −.416 | 37.659 | 1.00 | 26.80 | A |
| ATOM | 1841 | CA | TRP | A | 244 | 11.806 | −.578 | 38.033 | 1.00 | 25.99 | A |
| ATOM | 1842 | CB | TRP | A | 244 | 11.459 | .445 | 39.123 | 1.00 | 24.69 | A |
| ATOM | 1843 | CG | TRP | A | 244 | 10.085 | .344 | 39.686 | 1.00 | 26.65 | A |
| ATOM | 1844 | CD2 | TRP | A | 244 | 8.923 | 1.064 | 39.252 | 1.00 | 26.94 | A |
| ATOM | 1845 | CE2 | TRP | A | 244 | 7.851 | .655 | 40.071 | 1.00 | 28.19 | A |
| ATOM | 1846 | CE3 | TRP | A | 244 | 8.684 | 2.012 | 38.249 | 1.00 | 30.14 | A |
| ATOM | 1847 | CD1 | TRP | A | 244 | 9.681 | −.448 | 40.715 | 1.00 | 27.61 | A |
| ATOM | 1848 | NE1 | TRP | A | 244 | 8.342 | −.269 | 40.956 | 1.00 | 27.74 | A |
| ATOM | 1849 | CZ2 | TRP | A | 244 | 6.554 | 1.163 | 39.923 | 1.00 | 29.62 | A |
| ATOM | 1850 | CZ3 | TRP | A | 244 | 7.387 | 2.517 | 38.100 | 1.00 | 31.77 | A |
| ATOM | 1851 | CH2 | TRP | A | 244 | 6.344 | 2.089 | 38.935 | 1.00 | 30.68 | A |
| ATOM | 1852 | C | TRP | A | 244 | 10.930 | −.360 | 36.803 | 1.00 | 25.64 | A |
| ATOM | 1853 | O | TRP | A | 244 | 11.230 | .499 | 35.968 | 1.00 | 24.94 | A |
| ATOM | 1854 | N | THR | A | 245 | 9.837 | −1.117 | 36.712 | 1.00 | 25.35 | A |
| ATOM | 1855 | CA | THR | A | 245 | 8.946 | −1.064 | 35.554 | 1.00 | 25.32 | A |
| ATOM | 1856 | CB | THR | A | 245 | 9.110 | −2.349 | 34.743 | 1.00 | 26.48 | A |
| ATOM | 1857 | OG1 | THR | A | 245 | 8.406 | −2.238 | 33.509 | 1.00 | 28.56 | A |
| ATOM | 1858 | CG2 | THR | A | 245 | 8.551 | −3.538 | 35.532 | 1.00 | 25.04 | A |
| ATOM | 1859 | C | THR | A | 245 | 7.455 | −.904 | 35.888 | 1.00 | 25.82 | A |
| ATOM | 1860 | O | THR | A | 245 | 7.029 | −1.132 | 37.024 | 1.00 | 24.99 | A |
| ATOM | 1861 | N | ALA | A | 246 | 6.665 | −.524 | 34.885 | 1.00 | 24.85 | A |
| ATOM | 1862 | CA | ALA | A | 246 | 5.228 | −.346 | 35.067 | 1.00 | 23.46 | A |
| ATOM | 1863 | CB | ALA | A | 246 | 4.957 | .788 | 36.061 | 1.00 | 26.77 | A |
| ATOM | 1864 | C | ALA | A | 246 | 4.493 | −.073 | 33.757 | 1.00 | 23.79 | A |
| ATOM | 1865 | O | ALA | A | 246 | 5.073 | .412 | 32.783 | 1.00 | 22.48 | A |
| ATOM | 1866 | N | GLN | A | 247 | 3.205 | −.394 | 33.754 | 1.00 | 23.39 | A |
| ATOM | 1867 | CA | GLN | A | 247 | 2.326 | −.210 | 32.601 | 1.00 | 25.65 | A |
| ATOM | 1868 | CB | GLN | A | 247 | 2.155 | −1.531 | 31.835 | 1.00 | 24.53 | A |
| ATOM | 1869 | CG | GLN | A | 247 | 1.151 | −1.473 | 30.682 | 1.00 | 24.31 | A |
| ATOM | 1870 | CD | GLN | A | 247 | .838 | −2.843 | 30.074 | 1.00 | 22.11 | A |
| ATOM | 1871 | OE1 | GLN | A | 247 | .257 | −3.709 | 30.726 | 1.00 | 23.16 | A |
| ATOM | 1872 | NE2 | GLN | A | 247 | 1.224 | −3.036 | 28.825 | 1.00 | 20.77 | A |
| ATOM | 1873 | C | GLN | A | 247 | .984 | .220 | 33.170 | 1.00 | 27.26 | A |
| ATOM | 1874 | O | GLN | A | 247 | .569 | −.263 | 34.222 | 1.00 | 28.63 | A |
| ATOM | 1875 | N | THR | A | 248 | .295 | 1.125 | 32.494 | 1.00 | 28.56 | A |
| ATOM | 1876 | CA | THR | A | 248 | −.988 | 1.567 | 33.017 | 1.00 | 28.92 | A |
| ATOM | 1877 | CB | THR | A | 248 | −.797 | 2.755 | 33.987 | 1.00 | 30.79 | A |
| ATOM | 1878 | OG1 | THR | A | 248 | −1.944 | 2.862 | 34.842 | 1.00 | 35.24 | A |
| ATOM | 1879 | CG2 | THR | A | 248 | −.615 | 4.060 | 33.211 | 1.00 | 31.01 | A |
| ATOM | 1880 | C | THR | A | 248 | −1.953 | 1.977 | 31.916 | 1.00 | 27.53 | A |
| ATOM | 1881 | O | THR | A | 248 | −1.539 | 2.318 | 30.812 | 1.00 | 25.84 | A |
| ATOM | 1882 | N | VAL | A | 249 | −3.241 | 1.925 | 32.226 | 1.00 | 25.93 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 1883 | CA | VAL | A | 249 | −4.272 | 2.318 | 31.279 | 1.00 | 27.96 | A |
| ATOM | 1884 | CB | VAL | A | 249 | −5.407 | 1.288 | 31.251 | 1.00 | 28.05 | A |
| ATOM | 1885 | CG1 | VAL | A | 249 | −6.550 | 1.797 | 30.397 | 1.00 | 27.80 | A |
| ATOM | 1886 | CG2 | VAL | A | 249 | −4.884 | −.038 | 30.713 | 1.00 | 28.94 | A |
| ATOM | 1887 | C | VAL | A | 249 | −4.825 | 3.679 | 31.713 | 1.00 | 27.45 | A |
| ATOM | 1888 | O | VAL | A | 249 | −5.378 | 3.810 | 32.805 | 1.00 | 26.81 | A |
| ATOM | 1889 | N | VAL | A | 250 | −4.652 | 4.700 | 30.880 | 1.00 | 27.86 | A |
| ATOM | 1890 | CA | VAL | A | 250 | −5.153 | 6.018 | 31.254 | 1.00 | 28.83 | A |
| ATOM | 1891 | CB | VAL | A | 250 | −4.656 | 7.129 | 30.318 | 1.00 | 28.90 | A |
| ATOM | 1892 | CG1 | VAL | A | 250 | −3.192 | 7.416 | 30.593 | 1.00 | 29.74 | A |
| ATOM | 1893 | CG2 | VAL | A | 250 | −4.834 | 6.717 | 28.889 | 1.00 | 30.61 | A |
| ATOM | 1894 | C | VAL | A | 250 | −6.670 | 5.968 | 31.235 | 1.00 | 28.87 | A |
| ATOM | 1895 | O | VAL | A | 250 | −7.274 | 5.444 | 30.301 | 1.00 | 27.18 | A |
| ATOM | 1896 | N | PRO | A | 251 | −7.302 | 6.513 | 32.283 | 1.00 | 28.95 | A |
| ATOM | 1897 | CD | PRO | A | 251 | −6.680 | 7.371 | 33.302 | 1.00 | 27.77 | A |
| ATOM | 1898 | CA | PRO | A | 251 | −8.760 | 6.530 | 32.405 | 1.00 | 30.93 | A |
| ATOM | 1899 | CB | PRO | A | 251 | −8.991 | 7.390 | 33.643 | 1.00 | 28.74 | A |
| ATOM | 1900 | CG | PRO | A | 251 | −7.799 | 8.286 | 33.662 | 1.00 | 30.42 | A |
| ATOM | 1901 | C | PRO | A | 251 | −9.479 | 7.053 | 31.168 | 1.00 | 33.62 | A |
| ATOM | 1902 | O | PRO | A | 251 | −8.942 | 7.863 | 30.409 | 1.00 | 34.58 | A |
| ATOM | 1903 | N | ASN | A | 252 | −10.692 | 6.550 | 30.970 | 1.00 | 36.56 | A |
| ATOM | 1904 | CA | ASN | A | 252 | −11.546 | 6.917 | 29.851 | 1.00 | 38.78 | A |
| ATOM | 1905 | CB | ASN | A | 252 | −12.471 | 8.052 | 30.291 | 1.00 | 40.73 | A |
| ATOM | 1906 | CG | ASN | A | 252 | −13.412 | 8.486 | 29.198 | 1.00 | 44.33 | A |
| ATOM | 1907 | OD1 | ASN | A | 252 | −13.037 | 9.262 | 28.321 | 1.00 | 46.53 | A |
| ATOM | 1908 | ND2 | ASN | A | 252 | −14.642 | 7.978 | 29.232 | 1.00 | 45.05 | A |
| ATOM | 1909 | C | ASN | A | 252 | −10.776 | 7.295 | 28.579 | 1.00 | 38.09 | A |
| ATOM | 1910 | O | ASN | A | 252 | −10.867 | 8.427 | 28.106 | 1.00 | 38.27 | A |
| ATOM | 1911 | N | SER | A | 253 | −10.044 | 6.331 | 28.016 | 1.00 | 36.57 | A |
| ATOM | 1912 | CA | SER | A | 253 | −9.236 | 6.568 | 26.816 | 1.00 | 36.26 | A |
| ATOM | 1913 | CB | SER | A | 253 | −7.775 | 6.719 | 27.216 | 1.00 | 34.68 | A |
| ATOM | 1914 | OG | SER | A | 253 | −7.312 | 5.503 | 27.778 | 1.00 | 32.19 | A |
| ATOM | 1915 | C | SER | A | 253 | −9.329 | 5.455 | 25.761 | 1.00 | 36.96 | A |
| ATOM | 1916 | O | SER | A | 253 | −8.391 | 5.232 | 24.998 | 1.00 | 36.84 | A |
| ATOM | 1917 | N | GLU | A | 254 | −10.455 | 4.762 | 25.719 | 1.00 | 37.92 | A |
| ATOM | 1918 | CA | GLU | A | 254 | −10.658 | 3.678 | 24.766 | 1.00 | 38.18 | A |
| ATOM | 1919 | CB | GLU | A | 254 | −11.874 | 2.865 | 25.196 | 1.00 | 40.81 | A |
| ATOM | 1920 | CG | GLU | A | 254 | −11.709 | 1.362 | 25.110 | 1.00 | 44.37 | A |
| ATOM | 1921 | CD | GLU | A | 254 | −12.993 | .637 | 25.461 | 1.00 | 44.94 | A |
| ATOM | 1922 | OE1 | GLU | A | 254 | −13.494 | .833 | 26.591 | 1.00 | 46.54 | A |
| ATOM | 1923 | OE2 | GLU | A | 254 | −13.507 | −.118 | 24.607 | 1.00 | 45.46 | A |
| ATOM | 1924 | C | GLU | A | 254 | −10.872 | 4.196 | 23.342 | 1.00 | 37.96 | A |
| ATOM | 1925 | O | GLU | A | 254 | −11.532 | 5.217 | 23.127 | 1.00 | 34.76 | A |
| ATOM | 1926 | N | GLY | A | 255 | −10.319 | 3.479 | 22.368 | 1.00 | 35.90 | A |
| ATOM | 1927 | CA | GLY | A | 255 | −10.487 | 3.881 | 20.985 | 1.00 | 34.05 | A |
| ATOM | 1928 | C | GLY | A | 255 | −9.532 | 4.966 | 20.536 | 1.00 | 33.62 | A |
| ATOM | 1929 | O | GLY | A | 255 | −9.456 | 5.283 | 19.348 | 1.00 | 34.14 | A |
| ATOM | 1930 | N | ALA | A | 256 | −8.806 | 5.549 | 21.482 | 1.00 | 32.67 | A |
| ATOM | 1931 | CA | ALA | A | 256 | −7.844 | 6.588 | 21.145 | 1.00 | 31.58 | A |
| ATOM | 1932 | CB | ALA | A | 256 | −7.138 | 7.081 | 22.399 | 1.00 | 30.56 | A |
| ATOM | 1933 | C | ALA | A | 256 | −6.840 | 6.001 | 20.169 | 1.00 | 30.51 | A |
| ATOM | 1934 | O | ALA | A | 256 | −6.523 | 6.610 | 19.155 | 1.00 | 32.75 | A |
| ATOM | 1935 | N | ILE | A | 257 | −6.348 | 4.808 | 20.482 | 1.00 | 29.54 | A |
| ATOM | 1936 | CA | ILE | A | 257 | −5.383 | 4.115 | 19.635 | 1.00 | 28.79 | A |
| ATOM | 1937 | CB | ILE | A | 257 | −3.971 | 4.131 | 20.255 | 1.00 | 28.12 | A |
| ATOM | 1938 | CG2 | ILE | A | 257 | −2.973 | 3.501 | 19.300 | 1.00 | 28.32 | A |
| ATOM | 1939 | CG1 | ILE | A | 257 | −3.553 | 5.567 | 20.566 | 1.00 | 26.99 | A |
| ATOM | 1940 | CD1 | ILE | A | 257 | −2.172 | 5.686 | 21.172 | 1.00 | 22.94 | A |
| ATOM | 1941 | C | ILE | A | 257 | −5.829 | 2.662 | 19.477 | 1.00 | 29.98 | A |
| ATOM | 1942 | O | ILE | A | 257 | −6.128 | 1.976 | 20.457 | 1.00 | 31.42 | A |
| ATOM | 1943 | N | GLY | A | 258 | −5.882 | 2.193 | 18.239 | 1.00 | 31.11 | A |
| ATOM | 1944 | CA | GLY | A | 258 | −6.300 | .826 | 18.003 | 1.00 | 27.25 | A |
| ATOM | 1945 | C | GLY | A | 258 | −6.105 | .422 | 16.561 | 1.00 | 27.85 | A |
| ATOM | 1946 | O | GLY | A | 258 | −5.851 | 1.259 | 15.682 | 1.00 | 24.88 | A |
| ATOM | 1947 | N | GLY | A | 259 | −6.223 | −.879 | 16.324 | 1.00 | 26.06 | A |
| ATOM | 1948 | CA | GLY | A | 259 | −6.054 | −1.401 | 14.987 | 1.00 | 24.94 | A |
| ATOM | 1949 | C | GLY | A | 259 | −6.788 | −2.709 | 14.848 | 1.00 | 25.74 | A |
| ATOM | 1950 | O | GLY | A | 259 | −6.904 | −3.474 | 15.804 | 1.00 | 27.81 | A |
| ATOM | 1951 | N | LYS | A | 260 | −7.280 | −2.972 | 13.648 | 1.00 | 24.91 | A |
| ATOM | 1952 | CA | LYS | A | 260 | −8.022 | −4.191 | 13.392 | 1.00 | 24.18 | A |
| ATOM | 1953 | CB | LYS | A | 260 | −9.468 | −3.834 | 13.058 | 1.00 | 23.37 | A |
| ATOM | 1954 | CG | LYS | A | 260 | −10.120 | −2.976 | 14.105 | 1.00 | 21.02 | A |
| ATOM | 1955 | CD | LYS | A | 260 | −11.477 | −2.506 | 13.624 | 1.00 | 27.51 | A |
| ATOM | 1956 | CE | LYS | A | 260 | −12.267 | −1.873 | 14.757 | 1.00 | 27.39 | A |
| ATOM | 1957 | NZ | LYS | A | 260 | −12.506 | −2.874 | 15.835 | 1.00 | 30.72 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 1958 | C | LYS | A | 260 | −7.402 | −4.988 | 12.256 | 1.00 | 23.16 | A |
| ATOM | 1959 | O | LYS | A | 260 | −7.139 | −4.452 | 11.185 | 1.00 | 26.09 | A |
| ATOM | 1960 | N | VAL | A | 261 | −7.152 | −6.265 | 12.496 | 1.00 | 22.53 | A |
| ATOM | 1961 | CA | VAL | A | 261 | −6.581 | −7.112 | 11.458 | 1.00 | 22.47 | A |
| ATOM | 1962 | CB | VAL | A | 261 | −5.764 | −8.275 | 12.056 | 1.00 | 22.44 | A |
| ATOM | 1963 | CG1 | VAL | A | 261 | −5.339 | −9.236 | 10.954 | 1.00 | 24.43 | A |
| ATOM | 1964 | CG2 | VAL | A | 261 | −4.526 | −7.728 | 12.759 | 1.00 | 23.17 | A |
| ATOM | 1965 | C | VAL | A | 261 | −7.748 | −7.640 | 10.645 | 1.00 | 21.55 | A |
| ATOM | 1966 | O | VAL | A | 261 | −8.525 | −8.473 | 11.109 | 1.00 | 20.82 | A |
| ATOM | 1967 | N | ARG | A | 262 | −7.880 | −7.126 | 9.428 | 1.00 | 21.55 | A |
| ATOM | 1968 | CA | ARG | A | 262 | −8.982 | −7.514 | 8.564 | 1.00 | 22.38 | A |
| ATOM | 1969 | CB | ARG | A | 262 | −9.961 | −6.344 | 8.452 | 1.00 | 21.69 | A |
| ATOM | 1970 | CG | ARG | A | 262 | −10.631 | −5.983 | 9.766 | 1.00 | 21.51 | A |
| ATOM | 1971 | CD | ARG | A | 262 | −11.517 | −7.128 | 10.288 | 1.00 | 22.91 | A |
| ATOM | 1972 | NE | ARG | A | 262 | −12.241 | −6.748 | 11.501 | 1.00 | 23.25 | A |
| ATOM | 1973 | CZ | ARG | A | 262 | −11.766 | −6.836 | 12.740 | 1.00 | 24.30 | A |
| ATOM | 1974 | NH1 | ARG | A | 262 | −10.547 | −7.315 | 12.972 | 1.00 | 21.08 | A |
| ATOM | 1975 | NH2 | ARG | A | 262 | −12.502 | −6.398 | 13.753 | 1.00 | 24.59 | A |
| ATOM | 1976 | C | ARG | A | 262 | −8.555 | −7.997 | 7.178 | 1.00 | 22.47 | A |
| ATOM | 1977 | O | ARG | A | 262 | −7.366 | −8.019 | 6.852 | 1.00 | 22.56 | A |
| ATOM | 1978 | N | GLU | A | 263 | −9.525 | −8.392 | 6.364 | 1.00 | 21.88 | A |
| ATOM | 1979 | CA | GLU | A | 263 | −9.207 | −8.888 | 5.035 | 1.00 | 22.36 | A |
| ATOM | 1980 | CB | GLU | A | 263 | −10.481 | −9.388 | 4.355 | 1.00 | 22.82 | A |
| ATOM | 1981 | CG | GLU | A | 263 | −11.010 | −10.653 | 5.037 | 1.00 | 28.67 | A |
| ATOM | 1982 | CD | GLU | A | 263 | −12.505 | −10.893 | 4.844 | 1.00 | 33.40 | A |
| ATOM | 1983 | OE1 | GLU | A | 263 | −13.067 | −11.739 | 5.577 | 1.00 | 32.78 | A |
| ATOM | 1984 | OE2 | GLU | A | 263 | −13.120 | −10.249 | 3.961 | 1.00 | 37.42 | A |
| ATOM | 1985 | C | GLU | A | 263 | −8.486 | −7.831 | 4.203 | 1.00 | 22.25 | A |
| ATOM | 1986 | O | GLU | A | 263 | −7.881 | −8.145 | 3.173 | 1.00 | 18.80 | A |
| ATOM | 1987 | N | VAL | A | 264 | −8.530 | −6.579 | 4.661 | 1.00 | 21.62 | A |
| ATOM | 1988 | CA | VAL | A | 264 | −7.835 | −5.508 | 3.955 | 1.00 | 21.09 | A |
| ATOM | 1989 | CB | VAL | A | 264 | −8.650 | −4.211 | 3.935 | 1.00 | 22.68 | A |
| ATOM | 1990 | CG1 | VAL | A | 264 | −9.941 | −4.419 | 3.158 | 1.00 | 23.99 | A |
| ATOM | 1991 | CG2 | VAL | A | 264 | −8.929 | −3.758 | 5.355 | 1.00 | 21.59 | A |
| ATOM | 1992 | C | VAL | A | 264 | −6.500 | −5.222 | 4.630 | 1.00 | 20.86 | A |
| ATOM | 1993 | O | VAL | A | 264 | −5.816 | −4.249 | 4.292 | 1.00 | 19.04 | A |
| ATOM | 1994 | N | GLY | A | 265 | −6.135 | −6.077 | 5.583 | 1.00 | 20.38 | A |
| ATOM | 1995 | CA | GLY | A | 265 | −4.896 | −5.897 | 6.314 | 1.00 | 22.57 | A |
| ATOM | 1996 | C | GLY | A | 265 | −5.141 | −5.198 | 7.641 | 1.00 | 24.13 | A |
| ATOM | 1997 | O | GLY | A | 265 | −6.258 | −5.210 | 8.154 | 1.00 | 24.25 | A |
| ATOM | 1998 | N | LEU | A | 266 | −4.109 | −4.575 | 8.195 | 1.00 | 24.55 | A |
| ATOM | 1999 | CA | LEU | A | 266 | −4.257 | −3.900 | 9.476 | 1.00 | 27.01 | A |
| ATOM | 2000 | CB | LEU | A | 266 | −2.935 | −3.923 | 10.259 | 1.00 | 26.32 | A |
| ATOM | 2001 | CG | LEU | A | 266 | −2.987 | −4.172 | 11.779 | 1.00 | 28.57 | A |
| ATOM | 2002 | CD1 | LEU | A | 266 | −1.872 | −3.374 | 12.425 | 1.00 | 25.69 | A |
| ATOM | 2003 | CD2 | LEU | A | 266 | −4.335 | −3.764 | 12.389 | 1.00 | 25.63 | A |
| ATOM | 2004 | C | LEU | A | 266 | −4.712 | −2.457 | 9.301 | 1.00 | 28.29 | A |
| ATOM | 2005 | O | LEU | A | 266 | −3.964 | −1.618 | 8.809 | 1.00 | 27.00 | A |
| ATOM | 2006 | N | THR | A | 267 | −5.951 | −2.182 | 9.689 | 1.00 | 29.50 | A |
| ATOM | 2007 | CA | THR | A | 267 | −6.485 | −.836 | 9.608 | 1.00 | 30.44 | A |
| ATOM | 2008 | CB | THR | A | 267 | −8.022 | −.825 | 9.574 | 1.00 | 29.41 | A |
| ATOM | 2009 | OG1 | THR | A | 267 | −8.541 | −1.701 | 10.579 | 1.00 | 28.88 | A |
| ATOM | 2010 | CG2 | THR | A | 267 | −8.512 | −1.271 | 8.220 | 1.00 | 31.59 | A |
| ATOM | 2011 | C | THR | A | 267 | −5.990 | −.143 | 10.861 | 1.00 | 32.37 | A |
| ATOM | 2012 | O | THR | A | 267 | −5.475 | −.790 | 11.762 | 1.00 | 32.42 | A |
| ATOM | 2013 | N | PHE | A | 268 | −6.153 | 1.168 | 10.931 | 1.00 | 34.52 | A |
| ATOM | 2014 | CA | PHE | A | 268 | −5.646 | 1.909 | 12.076 | 1.00 | 37.28 | A |
| ATOM | 2015 | CB | PHE | A | 268 | −4.208 | 2.318 | 11.770 | 1.00 | 35.84 | A |
| ATOM | 2016 | CG | PHE | A | 268 | −3.713 | 3.443 | 12.595 | 1.00 | 36.17 | A |
| ATOM | 2017 | CD1 | PHE | A | 268 | −3.373 | 3.249 | 13.927 | 1.00 | 38.58 | A |
| ATOM | 2018 | CD2 | PHE | A | 268 | −3.576 | 4.709 | 12.039 | 1.00 | 36.83 | A |
| ATOM | 2019 | CE1 | PHE | A | 268 | −2.895 | 4.309 | 14.700 | 1.00 | 39.39 | A |
| ATOM | 2020 | CE2 | PHE | A | 268 | −3.104 | 5.771 | 12.798 | 1.00 | 37.60 | A |
| ATOM | 2021 | CZ | PHE | A | 268 | −2.762 | 5.573 | 14.129 | 1.00 | 38.49 | A |
| ATOM | 2022 | C | PHE | A | 268 | −6.479 | 3.137 | 12.430 | 1.00 | 38.24 | A |
| ATOM | 2023 | O | PHE | A | 268 | −6.645 | 4.041 | 11.613 | 1.00 | 38.90 | A |
| ATOM | 2024 | N | GLN | A | 269 | −7.000 | 3.157 | 13.655 | 1.00 | 39.85 | A |
| ATOM | 2025 | CA | GLN | A | 269 | −7.805 | 4.274 | 14.138 | 1.00 | 40.66 | A |
| ATOM | 2026 | CB | GLN | A | 269 | −9.084 | 3.760 | 14.815 | 1.00 | 40.42 | A |
| ATOM | 2027 | CG | GLN | A | 269 | −8.836 | 2.678 | 15.859 | 1.00 | 43.55 | A |
| ATOM | 2028 | CD | GLN | A | 269 | −8.868 | 1.271 | 15.277 | 1.00 | 45.56 | A |
| ATOM | 2029 | OE1 | GLN | A | 269 | −8.456 | 1.043 | 14.135 | 1.00 | 43.46 | A |
| ATOM | 2030 | NE2 | GLN | A | 269 | −9.349 | .316 | 16.069 | 1.00 | 44.36 | A |
| ATOM | 2031 | C | GLN | A | 269 | −6.957 | 5.068 | 15.130 | 1.00 | 41.21 | A |
| ATOM | 2032 | O | GLN | A | 269 | −6.235 | 4.482 | 15.938 | 1.00 | 41.66 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 2033 | N | LEU | A | 270 | −7.041 | 6.396 | 15.061 | 1.00 | 41.43 | A |
| ATOM | 2034 | CA | LEU | A | 270 | −6.263 | 7.264 | 15.944 | 1.00 | 41.35 | A |
| ATOM | 2035 | CB | LEU | A | 270 | −4.927 | 7.598 | 15.273 | 1.00 | 40.81 | A |
| ATOM | 2036 | CG | LEU | A | 270 | −3.927 | 8.500 | 15.991 | 1.00 | 42.32 | A |
| ATOM | 2037 | CD1 | LEU | A | 270 | −3.581 | 7.908 | 17.338 | 1.00 | 43.04 | A |
| ATOM | 2038 | CD2 | LEU | A | 270 | −2.675 | 8.642 | 15.142 | 1.00 | 41.53 | A |
| ATOM | 2039 | C | LEU | A | 270 | −7.007 | 8.555 | 16.283 | 1.00 | 41.06 | A |
| ATOM | 2040 | O | LEU | A | 270 | −6.881 | 9.554 | 15.575 | 1.00 | 44.11 | A |
| ATOM | 2041 | N | LYS | A | 271 | −7.786 | 8.540 | 17.358 | 1.00 | 38.77 | A |
| ATOM | 2042 | CA | LYS | A | 271 | −8.537 | 9.730 | 17.762 | 1.00 | 37.60 | A |
| ATOM | 2043 | CB | LYS | A | 271 | −9.392 | 9.420 | 18.999 | 1.00 | 36.95 | A |
| ATOM | 2044 | CG | LYS | A | 271 | −10.504 | 8.407 | 18.714 | 1.00 | 38.43 | A |
| ATOM | 2045 | CD | LYS | A | 271 | −11.337 | 8.048 | 19.940 | 1.00 | 37.75 | A |
| ATOM | 2046 | CE | LYS | A | 271 | −12.440 | 7.055 | 19.555 | 1.00 | 40.27 | A |
| ATOM | 2047 | NZ | LYS | A | 271 | −13.165 | 6.457 | 20.723 | 1.00 | 42.36 | A |
| ATOM | 2048 | C | LYS | A | 271 | −7.577 | 10.888 | 18.053 | 1.00 | 35.81 | A |
| ATOM | 2049 | O | LYS | A | 271 | −6.477 | 10.682 | 18.557 | 1.00 | 34.82 | A |
| ATOM | 2050 | N | GLY | A | 272 | −7.998 | 12.105 | 17.724 | 1.00 | 34.36 | A |
| ATOM | 2051 | CA | GLY | A | 272 | −7.159 | 13.269 | 17.955 | 1.00 | 32.41 | A |
| ATOM | 2052 | C | GLY | A | 272 | −6.859 | 13.596 | 19.412 | 1.00 | 31.39 | A |
| ATOM | 2053 | O | GLY | A | 272 | −5.909 | 14.324 | 19.701 | 1.00 | 30.50 | A |
| ATOM | 2054 | N | ALA | A | 273 | −7.646 | 13.053 | 20.335 | 1.00 | 30.16 | A |
| ATOM | 2055 | CA | ALA | A | 273 | −7.442 | 13.316 | 21.758 | 1.00 | 30.25 | A |
| ATOM | 2056 | CB | ALA | A | 273 | −8.680 | 12.896 | 22.527 | 1.00 | 28.04 | A |
| ATOM | 2057 | C | ALA | A | 273 | −6.193 | 12.667 | 22.391 | 1.00 | 30.52 | A |
| ATOM | 2058 | O | ALA | A | 273 | −5.906 | 12.886 | 23.572 | 1.00 | 31.69 | A |
| ATOM | 2059 | N | VAL | A | 274 | −5.449 | 11.888 | 21.613 | 1.00 | 29.09 | A |
| ATOM | 2060 | CA | VAL | A | 274 | −4.255 | 11.197 | 22.124 | 1.00 | 30.02 | A |
| ATOM | 2061 | CB | VAL | A | 274 | −3.574 | 10.349 | 20.994 | 1.00 | 29.02 | A |
| ATOM | 2062 | CG1 | VAL | A | 274 | −2.120 | 10.066 | 21.328 | 1.00 | 26.26 | A |
| ATOM | 2063 | CG2 | VAL | A | 274 | −4.324 | 9.029 | 20.829 | 1.00 | 28.14 | A |
| ATOM | 2064 | C | VAL | A | 274 | −3.185 | 12.040 | 22.832 | 1.00 | 29.91 | A |
| ATOM | 2065 | O | VAL | A | 274 | −2.706 | 11.667 | 23.908 | 1.00 | 31.11 | A |
| ATOM | 2066 | N | PRO | A | 275 | −2.785 | 13.174 | 22.246 | 1.00 | 29.31 | A |
| ATOM | 2067 | CD | PRO | A | 275 | −3.039 | 13.717 | 20.903 | 1.00 | 28.93 | A |
| ATOM | 2068 | CA | PRO | A | 275 | −1.759 | 13.959 | 22.943 | 1.00 | 29.97 | A |
| ATOM | 2069 | CB | PRO | A | 275 | −1.536 | 15.141 | 22.009 | 1.00 | 29.08 | A |
| ATOM | 2070 | CG | PRO | A | 275 | −1.794 | 14.543 | 20.662 | 1.00 | 30.30 | A |
| ATOM | 2071 | C | PRO | A | 275 | −2.170 | 14.391 | 24.348 | 1.00 | 30.48 | A |
| ATOM | 2072 | O | PRO | A | 275 | −1.355 | 14.376 | 25.271 | 1.00 | 31.35 | A |
| ATOM | 2073 | N | ASP | A | 276 | −3.439 | 14.752 | 24.514 | 1.00 | 31.00 | A |
| ATOM | 2074 | CA | ASP | A | 276 | −3.931 | 15.197 | 25.810 | 1.00 | 31.59 | A |
| ATOM | 2075 | CB | ASP | A | 276 | −5.286 | 15.885 | 25.661 | 1.00 | 34.05 | A |
| ATOM | 2076 | CG | ASP | A | 276 | −5.849 | 16.327 | 26.993 | 1.00 | 35.35 | A |
| ATOM | 2077 | OD1 | ASP | A | 276 | −5.196 | 17.162 | 27.658 | 1.00 | 36.13 | A |
| ATOM | 2078 | OD2 | ASP | A | 276 | −6.927 | 15.829 | 27.384 | 1.00 | 36.47 | A |
| ATOM | 2079 | C | ASP | A | 276 | −4.060 | 14.089 | 26.838 | 1.00 | 31.20 | A |
| ATOM | 2080 | O | ASP | A | 276 | −3.790 | 14.299 | 28.016 | 1.00 | 31.91 | A |
| ATOM | 2081 | N | LEU | A | 277 | −4.492 | 12.913 | 26.400 | 1.00 | 32.16 | A |
| ATOM | 2082 | CA | LEU | A | 277 | −4.646 | 11.777 | 27.303 | 1.00 | 31.43 | A |
| ATOM | 2083 | CB | LEU | A | 277 | −5.261 | 10.598 | 26.547 | 1.00 | 30.50 | A |
| ATOM | 2084 | CG | LEU | A | 277 | −6.689 | 10.892 | 26.089 | 1.00 | 30.10 | A |
| ATOM | 2085 | CD1 | LEU | A | 277 | −7.184 | 9.828 | 25.132 | 1.00 | 30.66 | A |
| ATOM | 2086 | CD2 | LEU | A | 277 | −7.582 | 10.971 | 27.310 | 1.00 | 30.85 | A |
| ATOM | 2087 | C | LEU | A | 277 | −3.298 | 11.381 | 27.903 | 1.00 | 31.68 | A |
| ATOM | 2088 | O | LEU | A | 277 | −3.166 | 11.214 | 29.114 | 1.00 | 31.00 | A |
| ATOM | 2089 | N | ILE | A | 278 | −2.294 | 11.243 | 27.048 | 1.00 | 32.33 | A |
| ATOM | 2090 | CA | ILE | A | 278 | −.962 | 10.887 | 27.502 | 1.00 | 32.96 | A |
| ATOM | 2091 | CB | ILE | A | 278 | −.013 | 10.649 | 26.300 | 1.00 | 30.68 | A |
| ATOM | 2092 | CG2 | ILE | A | 278 | 1.422 | 10.523 | 26.777 | 1.00 | 28.01 | A |
| ATOM | 2093 | CG1 | ILE | A | 278 | −.456 | 9.391 | 25.547 | 1.00 | 29.23 | A |
| ATOM | 2094 | CD1 | ILE | A | 278 | .283 | 9.139 | 24.250 | 1.00 | 29.89 | A |
| ATOM | 2095 | C | ILE | A | 278 | −.378 | 11.966 | 28.406 | 1.00 | 34.32 | A |
| ATOM | 2096 | O | ILE | A | 278 | .168 | 11.657 | 29.455 | 1.00 | 34.80 | A |
| ATOM | 2097 | N | SER | A | 279 | −.517 | 13.229 | 28.011 | 1.00 | 36.66 | A |
| ATOM | 2098 | CA | SER | A | 279 | .025 | 14.351 | 28.790 | 1.00 | 37.98 | A |
| ATOM | 2099 | CB | SER | A | 279 | −.114 | 15.663 | 28.002 | 1.00 | 40.15 | A |
| ATOM | 2100 | OG | SER | A | 279 | .917 | 15.792 | 27.031 | 1.00 | 41.42 | A |
| ATOM | 2101 | C | SER | A | 279 | −.550 | 14.562 | 30.186 | 1.00 | 37.84 | A |
| ATOM | 2102 | O | SER | A | 279 | .193 | 14.762 | 31.151 | 1.00 | 38.76 | A |
| ATOM | 2103 | N | ALA | A | 280 | −1.870 | 14.527 | 30.294 | 1.00 | 36.55 | A |
| ATOM | 2104 | CA | ALA | A | 280 | −2.530 | 14.749 | 31.572 | 1.00 | 34.53 | A |
| ATOM | 2105 | CB | ALA | A | 280 | −3.977 | 15.142 | 31.335 | 1.00 | 34.08 | A |
| ATOM | 2106 | C | ALA | A | 280 | −2.471 | 13.547 | 32.490 | 1.00 | 35.22 | A |
| ATOM | 2107 | O | ALA | A | 280 | −3.258 | 13.450 | 33.432 | 1.00 | 35.65 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 2108 | N | ASN | A | 281 | −1.551 | 12.626 | 32.220 | 1.00 | 34.56 | A |
| ATOM | 2109 | CA | ASN | A | 281 | −1.418 | 11.437 | 33.045 | 1.00 | 33.77 | A |
| ATOM | 2110 | CB | ASN | A | 281 | −2.257 | 10.309 | 32.459 | 1.00 | 35.68 | A |
| ATOM | 2111 | CG | ASN | A | 281 | −3.730 | 10.602 | 32.520 | 1.00 | 36.67 | A |
| ATOM | 2112 | OD1 | ASN | A | 281 | −4.386 | 10.347 | 33.529 | 1.00 | 37.02 | A |
| ATOM | 2113 | ND2 | ASN | A | 281 | −4.258 | 11.169 | 31.447 | 1.00 | 37.77 | A |
| ATOM | 2114 | C | ASN | A | 281 | .017 | 10.963 | 33.187 | 1.00 | 34.57 | A |
| ATOM | 2115 | O | ASN | A | 281 | .323 | 10.141 | 34.057 | 1.00 | 33.59 | A |
| ATOM | 2116 | N | ILE | A | 282 | .900 | 11.476 | 32.339 | 1.00 | 34.05 | A |
| ATOM | 2117 | CA | ILE | A | 282 | 2.291 | 11.057 | 32.383 | 1.00 | 36.36 | A |
| ATOM | 2118 | CB | ILE | A | 282 | 3.060 | 11.550 | 31.128 | 1.00 | 36.30 | A |
| ATOM | 2119 | CG2 | ILE | A | 282 | 3.278 | 13.054 | 31.197 | 1.00 | 35.15 | A |
| ATOM | 2120 | CG1 | ILE | A | 282 | 4.388 | 10.803 | 31.010 | 1.00 | 36.39 | A |
| ATOM | 2121 | CD1 | ILE | A | 282 | 5.063 | 10.962 | 29.679 | 1.00 | 35.07 | A |
| ATOM | 2122 | C | ILE | A | 282 | 2.976 | 11.540 | 33.661 | 1.00 | 39.22 | A |
| ATOM | 2123 | O | ILE | A | 282 | 3.876 | 10.874 | 34.183 | 1.00 | 40.83 | A |
| ATOM | 2124 | N | GLU | A | 283 | 2.534 | 12.687 | 34.172 | 1.00 | 38.71 | A |
| ATOM | 2125 | CA | GLU | A | 283 | 3.095 | 13.251 | 35.395 | 1.00 | 38.20 | A |
| ATOM | 2126 | CB | GLU | A | 283 | 2.403 | 14.586 | 35.710 | 1.00 | 39.81 | A |
| ATOM | 2127 | CG | GLU | A | 283 | 2.918 | 15.313 | 36.936 | 1.00 | 41.71 | A |
| ATOM | 2128 | CD | GLU | A | 283 | 4.340 | 15.821 | 36.761 | 1.00 | 46.24 | A |
| ATOM | 2129 | OE1 | GLU | A | 283 | 4.717 | 16.782 | 37.472 | 1.00 | 45.68 | A |
| ATOM | 2130 | OE2 | GLU | A | 283 | 5.079 | 15.260 | 35.915 | 1.00 | 46.93 | A |
| ATOM | 2131 | C | GLU | A | 283 | 2.868 | 12.260 | 36.535 | 1.00 | 37.62 | A |
| ATOM | 2132 | O | GLU | A | 283 | 3.760 | 11.988 | 37.340 | 1.00 | 37.84 | A |
| ATOM | 2133 | N | ASN | A | 284 | 1.654 | 11.726 | 36.579 | 1.00 | 37.45 | A |
| ATOM | 2134 | CA | ASN | A | 284 | 1.237 | 10.757 | 37.584 | 1.00 | 36.64 | A |
| ATOM | 2135 | CB | ASN | A | 284 | −.211 | 10.353 | 37.300 | 1.00 | 38.10 | A |
| ATOM | 2136 | CG | ASN | A | 284 | −.766 | 9.388 | 38.322 | 1.00 | 40.96 | A |
| ATOM | 2137 | OD1 | ASN | A | 284 | −1.919 | 8.971 | 38.219 | 1.00 | 43.35 | A |
| ATOM | 2138 | ND2 | ASN | A | 284 | .042 | 9.028 | 39.316 | 1.00 | 41.64 | A |
| ATOM | 2139 | C | ASN | A | 284 | 2.138 | 9.522 | 37.567 | 1.00 | 36.15 | A |
| ATOM | 2140 | O | ASN | A | 284 | 2.421 | 8.932 | 38.606 | 1.00 | 34.35 | A |
| ATOM | 2141 | N | CYS | A | 285 | 2.582 | 9.136 | 36.377 | 1.00 | 35.52 | A |
| ATOM | 2142 | CA | CYS | A | 285 | 3.449 | 7.977 | 36.232 | 1.00 | 37.87 | A |
| ATOM | 2143 | CB | CYS | A | 285 | 3.511 | 7.556 | 34.764 | 1.00 | 39.05 | A |
| ATOM | 2144 | SG | CYS | A | 285 | 1.908 | 7.052 | 34.114 | 1.00 | 43.04 | A |
| ATOM | 2145 | C | CYS | A | 285 | 4.858 | 8.242 | 36.761 | 1.00 | 36.43 | A |
| ATOM | 2146 | O | CYS | A | 285 | 5.515 | 7.339 | 37.268 | 1.00 | 36.47 | A |
| ATOM | 2147 | N | MET | A | 286 | 5.309 | 9.486 | 36.649 | 1.00 | 35.56 | A |
| ATOM | 2148 | CA | MET | A | 286 | 6.639 | 9.860 | 37.118 | 1.00 | 34.53 | A |
| ATOM | 2149 | CB | MET | A | 286 | 7.033 | 11.227 | 36.566 | 1.00 | 29.51 | A |
| ATOM | 2150 | CG | MET | A | 286 | 7.148 | 11.285 | 35.060 | 1.00 | 27.11 | A |
| ATOM | 2151 | SD | MET | A | 286 | 8.518 | 10.331 | 34.419 | 1.00 | 17.52 | A |
| ATOM | 2152 | CE | MET | A | 286 | 9.910 | 11.357 | 34.834 | 1.00 | 24.72 | A |
| ATOM | 2153 | C | MET | A | 286 | 6.725 | 9.892 | 38.641 | 1.00 | 34.62 | A |
| ATOM | 2154 | O | MET | A | 286 | 7.770 | 9.561 | 39.206 | 1.00 | 34.71 | A |
| ATOM | 2155 | N | VAL | A | 287 | 5.639 | 10.292 | 39.305 | 1.00 | 34.59 | A |
| ATOM | 2156 | CA | VAL | A | 287 | 5.648 | 10.352 | 40.764 | 1.00 | 34.53 | A |
| ATOM | 2157 | CB | VAL | A | 287 | 4.551 | 11.294 | 41.337 | 1.00 | 33.53 | A |
| ATOM | 2158 | CG1 | VAL | A | 287 | 4.518 | 12.594 | 40.551 | 1.00 | 32.05 | A |
| ATOM | 2159 | CG2 | VAL | A | 287 | 3.198 | 10.602 | 41.339 | 1.00 | 33.56 | A |
| ATOM | 2160 | C | VAL | A | 287 | 5.448 | 8.964 | 41.348 | 1.00 | 36.11 | A |
| ATOM | 2161 | O | VAL | A | 287 | 5.612 | 8.764 | 42.551 | 1.00 | 38.82 | A |
| ATOM | 2162 | N | GLU | A | 288 | 5.087 | 8.011 | 40.490 | 1.00 | 37.10 | A |
| ATOM | 2163 | CA | GLU | A | 288 | 4.879 | 6.630 | 40.912 | 1.00 | 36.49 | A |
| ATOM | 2164 | CB | GLU | A | 288 | 3.735 | 5.994 | 40.121 | 1.00 | 37.81 | A |
| ATOM | 2165 | CG | GLU | A | 288 | 2.351 | 6.394 | 40.608 | 1.00 | 41.70 | A |
| ATOM | 2166 | CD | GLU | A | 288 | 1.246 | 5.589 | 39.945 | 1.00 | 43.46 | A |
| ATOM | 2167 | OE1 | GLU | A | 288 | .071 | 5.752 | 40.335 | 1.00 | 42.08 | A |
| ATOM | 2168 | OE2 | GLU | A | 288 | 1.555 | 4.791 | 39.032 | 1.00 | 45.61 | A |
| ATOM | 2169 | C | GLU | A | 288 | 6.154 | 5.812 | 40.724 | 1.00 | 34.02 | A |
| ATOM | 2170 | O | GLU | A | 288 | 6.383 | 4.826 | 41.417 | 1.00 | 35.06 | A |
| ATOM | 2171 | N | ALA | A | 289 | 6.988 | 6.243 | 39.792 | 1.00 | 32.31 | A |
| ATOM | 2172 | CA | ALA | A | 289 | 8.229 | 5.553 | 39.504 | 1.00 | 34.35 | A |
| ATOM | 2173 | CB | ALA | A | 289 | 8.374 | 5.370 | 38.005 | 1.00 | 32.96 | A |
| ATOM | 2174 | C | ALA | A | 289 | 9.464 | 6.259 | 40.043 | 1.00 | 35.81 | A |
| ATOM | 2175 | O | ALA | A | 289 | 10.570 | 5.746 | 39.895 | 1.00 | 36.21 | A |
| ATOM | 2176 | N | PHE | A | 290 | 9.303 | 7.422 | 40.672 | 1.00 | 37.04 | A |
| ATOM | 2177 | CA | PHE | A | 290 | 10.480 | 8.126 | 41.163 | 1.00 | 38.53 | A |
| ATOM | 2178 | CB | PHE | A | 290 | 10.824 | 9.258 | 40.196 | 1.00 | 37.84 | A |
| ATOM | 2179 | CG | PHE | A | 290 | 11.510 | 8.785 | 38.945 | 1.00 | 37.15 | A |
| ATOM | 2180 | CD1 | PHE | A | 290 | 12.854 | 8.420 | 38.971 | 1.00 | 35.74 | A |
| ATOM | 2181 | CD2 | PHE | A | 290 | 10.808 | 8.675 | 37.746 | 1.00 | 36.63 | A |
| ATOM | 2182 | CE1 | PHE | A | 290 | 13.488 | 7.950 | 37.822 | 1.00 | 35.20 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 2183 | CE2 | PHE | A | 290 | 11.431 | 8.207 | 36.592 | 1.00 | 34.21 | A |
| ATOM | 2184 | CZ | PHE | A | 290 | 12.772 | 7.843 | 36.631 | 1.00 | 35.84 | A |
| ATOM | 2185 | C | PHE | A | 290 | 10.510 | 8.643 | 42.600 | 1.00 | 39.68 | A |
| ATOM | 2186 | O | PHE | A | 290 | 11.593 | 8.932 | 43.129 | 1.00 | 38.64 | A |
| ATOM | 2187 | N | SER | A | 291 | 9.352 | 8.768 | 43.238 | 1.00 | 40.39 | A |
| ATOM | 2188 | CA | SER | A | 291 | 9.340 | 9.240 | 44.615 | 1.00 | 41.28 | A |
| ATOM | 2189 | CB | SER | A | 291 | 7.902 | 9.336 | 45.138 | 1.00 | 41.61 | A |
| ATOM | 2190 | OG | SER | A | 291 | 7.321 | 8.052 | 45.305 | 1.00 | 42.21 | A |
| ATOM | 2191 | C | SER | A | 291 | 10.153 | 8.248 | 45.461 | 1.00 | 41.72 | A |
| ATOM | 2192 | O | SER | A | 291 | 10.838 | 8.634 | 46.411 | 1.00 | 41.43 | A |
| ATOM | 2193 | N | GLN | A | 292 | 10.078 | 6.970 | 45.088 | 1.00 | 41.71 | A |
| ATOM | 2194 | CA | GLN | A | 292 | 10.798 | 5.899 | 45.776 | 1.00 | 41.58 | A |
| ATOM | 2195 | CB | GLN | A | 292 | 10.393 | 4.537 | 45.198 | 1.00 | 41.30 | A |
| ATOM | 2196 | CG | GLN | A | 292 | 10.805 | 4.334 | 43.744 | 1.00 | 43.26 | A |
| ATOM | 2197 | CD | GLN | A | 292 | 10.166 | 3.102 | 43.106 | 1.00 | 43.82 | A |
| ATOM | 2198 | OE1 | GLN | A | 292 | 10.242 | 1.992 | 43.644 | 1.00 | 44.70 | A |
| ATOM | 2199 | NE2 | GLN | A | 292 | 9.538 | 3.295 | 41.943 | 1.00 | 43.31 | A |
| ATOM | 2200 | C | GLN | A | 292 | 12.312 | 6.090 | 45.642 | 1.00 | 41.07 | A |
| ATOM | 2201 | O | GLN | A | 292 | 13.095 | 5.469 | 46.365 | 1.00 | 40.68 | A |
| ATOM | 2202 | N | PHE | A | 293 | 12.717 | 6.944 | 44.708 | 1.00 | 40.42 | A |
| ATOM | 2203 | CA | PHE | A | 293 | 14.129 | 7.232 | 44.498 | 1.00 | 40.51 | A |
| ATOM | 2204 | CB | PHE | A | 293 | 14.511 | 7.016 | 43.033 | 1.00 | 39.74 | A |
| ATOM | 2205 | CG | PHE | A | 293 | 14.218 | 5.639 | 42.543 | 1.00 | 39.95 | A |
| ATOM | 2206 | CD1 | PHE | A | 293 | 14.845 | 4.543 | 43.113 | 1.00 | 38.79 | A |
| ATOM | 2207 | CD2 | PHE | A | 293 | 13.273 | 5.429 | 41.548 | 1.00 | 40.76 | A |
| ATOM | 2208 | CE1 | PHE | A | 293 | 14.533 | 3.258 | 42.702 | 1.00 | 40.38 | A |
| ATOM | 2209 | CE2 | PHE | A | 293 | 12.955 | 4.146 | 41.131 | 1.00 | 38.84 | A |
| ATOM | 2210 | CZ | PHE | A | 293 | 13.584 | 3.061 | 41.710 | 1.00 | 39.21 | A |
| ATOM | 2211 | C | PHE | A | 293 | 14.369 | 8.676 | 44.900 | 1.00 | 40.43 | A |
| ATOM | 2212 | O | PHE | A | 293 | 15.233 | 9.353 | 44.351 | 1.00 | 41.10 | A |
| ATOM | 2213 | N | LYS | A | 294 | 13.589 | 9.126 | 45.876 | 1.00 | 41.39 | A |
| ATOM | 2214 | CA | LYS | A | 294 | 13.673 | 10.482 | 46.396 | 1.00 | 42.03 | A |
| ATOM | 2215 | CB | LYS | A | 294 | 14.806 | 10.593 | 47.425 | 1.00 | 42.52 | A |
| ATOM | 2216 | CG | LYS | A | 294 | 16.217 | 10.478 | 46.856 | 1.00 | 44.37 | A |
| ATOM | 2217 | CD | LYS | A | 294 | 17.124 | 11.572 | 47.438 | 1.00 | 46.80 | A |
| ATOM | 2218 | CE | LYS | A | 294 | 18.469 | 11.658 | 46.725 | 1.00 | 46.23 | A |
| ATOM | 2219 | NZ | LYS | A | 294 | 19.268 | 12.839 | 47.195 | 1.00 | 46.98 | A |
| ATOM | 2220 | C | LYS | A | 294 | 13.893 | 11.502 | 45.285 | 1.00 | 42.25 | A |
| ATOM | 2221 | O | LYS | A | 294 | 14.693 | 12.423 | 45.435 | 1.00 | 42.94 | A |
| ATOM | 2222 | N | ILE | A | 295 | 13.182 | 11.345 | 44.171 | 1.00 | 42.75 | A |
| ATOM | 2223 | CA | ILE | A | 295 | 13.318 | 12.281 | 43.058 | 1.00 | 43.31 | A |
| ATOM | 2224 | CB | ILE | A | 295 | 13.915 | 11.616 | 41.814 | 1.00 | 42.40 | A |
| ATOM | 2225 | CG2 | ILE | A | 295 | 13.899 | 12.598 | 40.657 | 1.00 | 42.02 | A |
| ATOM | 2226 | CG1 | ILE | A | 295 | 15.351 | 11.165 | 42.092 | 1.00 | 42.85 | A |
| ATOM | 2227 | CD1 | ILE | A | 295 | 16.017 | 10.483 | 40.918 | 1.00 | 42.43 | A |
| ATOM | 2228 | C | ILE | A | 295 | 11.995 | 12.902 | 42.660 | 1.00 | 44.46 | A |
| ATOM | 2229 | O | ILE | A | 295 | 11.004 | 12.201 | 42.444 | 1.00 | 44.51 | A |
| ATOM | 2230 | N | SER | A | 296 | 11.995 | 14.228 | 42.564 | 1.00 | 46.30 | A |
| ATOM | 2231 | CA | SER | A | 296 | 10.801 | 14.978 | 42.192 | 1.00 | 47.21 | A |
| ATOM | 2232 | CB | SER | A | 296 | 10.308 | 15.827 | 43.369 | 1.00 | 48.70 | A |
| ATOM | 2233 | OG | SER | A | 296 | 9.921 | 15.012 | 44.463 | 1.00 | 52.02 | A |
| ATOM | 2234 | C | SER | A | 296 | 11.048 | 15.877 | 40.989 | 1.00 | 46.34 | A |
| ATOM | 2235 | O | SER | A | 296 | 10.104 | 16.280 | 40.314 | 1.00 | 47.29 | A |
| ATOM | 2236 | N | ASP | A | 297 | 12.309 | 16.203 | 40.720 | 1.00 | 45.60 | A |
| ATOM | 2237 | CA | ASP | A | 297 | 12.613 | 17.048 | 39.574 | 1.00 | 44.42 | A |
| ATOM | 2238 | CB | ASP | A | 297 | 13.785 | 17.981 | 39.878 | 1.00 | 46.17 | A |
| ATOM | 2239 | CG | ASP | A | 297 | 14.192 | 18.825 | 38.666 | 1.00 | 47.06 | A |
| ATOM | 2240 | OD1 | ASP | A | 297 | 13.296 | 19.317 | 37.948 | 1.00 | 47.00 | A |
| ATOM | 2241 | OD2 | ASP | A | 297 | 15.407 | 19.000 | 38.436 | 1.00 | 47.36 | A |
| ATOM | 2242 | C | ASP | A | 297 | 12.920 | 16.219 | 38.329 | 1.00 | 44.32 | A |
| ATOM | 2243 | O | ASP | A | 297 | 14.036 | 15.727 | 38.135 | 1.00 | 44.05 | A |
| ATOM | 2244 | N | TRP | A | 298 | 11.905 | 16.079 | 37.488 | 1.00 | 42.80 | A |
| ATOM | 2245 | CA | TRP | A | 298 | 12.001 | 15.327 | 36.253 | 1.00 | 40.26 | A |
| ATOM | 2246 | CB | TRP | A | 298 | 10.742 | 15.587 | 35.438 | 1.00 | 38.68 | A |
| ATOM | 2247 | CG | TRP | A | 298 | 9.506 | 15.431 | 36.245 | 1.00 | 35.51 | A |
| ATOM | 2248 | CD2 | TRP | A | 298 | 9.313 | 14.553 | 37.363 | 1.00 | 35.36 | A |
| ATOM | 2249 | CE2 | TRP | A | 298 | 7.985 | 14.735 | 37.812 | 1.00 | 33.05 | A |
| ATOM | 2250 | CE3 | TRP | A | 298 | 10.133 | 13.631 | 38.028 | 1.00 | 32.97 | A |
| ATOM | 2251 | CD1 | TRP | A | 298 | 8.326 | 16.087 | 36.065 | 1.00 | 36.11 | A |
| ATOM | 2252 | NE1 | TRP | A | 298 | 7.408 | 15.675 | 37.003 | 1.00 | 34.29 | A |
| ATOM | 2253 | CZ2 | TRP | A | 298 | 7.456 | 14.029 | 38.896 | 1.00 | 32.55 | A |
| ATOM | 2254 | CZ3 | TRP | A | 298 | 9.607 | 12.929 | 39.105 | 1.00 | 33.62 | A |
| ATOM | 2255 | CH2 | TRP | A | 298 | 8.278 | 13.133 | 39.529 | 1.00 | 33.12 | A |
| ATOM | 2256 | C | TRP | A | 298 | 13.239 | 15.674 | 35.438 | 1.00 | 39.63 | A |
| ATOM | 2257 | O | TRP | A | 298 | 13.873 | 14.797 | 34.862 | 1.00 | 36.85 | A |

APPENDIX A-continued

*Pinus sylvestris* STS

| ATOM | # | TYPE | RES | | | X | Y | Z | OCC | B | |
|------|---|------|-----|---|---|---|---|---|-----|---|---|
| ATOM | 2258 | N | ASN | A | 299 | 13.584 | 16.956 | 35.399 | 1.00 | 40.40 | A |
| ATOM | 2259 | CA | ASN | A | 299 | 14.744 | 17.401 | 34.633 | 1.00 | 41.92 | A |
| ATOM | 2260 | CB | ASN | A | 299 | 14.784 | 18.925 | 34.561 | 1.00 | 43.62 | A |
| ATOM | 2261 | CG | ASN | A | 299 | 13.930 | 19.460 | 33.447 | 1.00 | 46.32 | A |
| ATOM | 2262 | OD1 | ASN | A | 299 | 14.021 | 18.982 | 32.312 | 1.00 | 46.16 | A |
| ATOM | 2263 | ND2 | ASN | A | 299 | 13.094 | 20.456 | 33.752 | 1.00 | 45.79 | A |
| ATOM | 2264 | C | ASN | A | 299 | 16.093 | 16.889 | 35.119 | 1.00 | 41.44 | A |
| ATOM | 2265 | O | ASN | A | 299 | 17.114 | 17.152 | 34.487 | 1.00 | 41.03 | A |
| ATOM | 2266 | N | LYS | A | 300 | 16.105 | 16.162 | 36.233 | 1.00 | 41.82 | A |
| ATOM | 2267 | CA | LYS | A | 300 | 17.355 | 15.615 | 36.753 | 1.00 | 40.46 | A |
| ATOM | 2268 | CB | LYS | A | 300 | 17.286 | 15.495 | 38.279 | 1.00 | 42.21 | A |
| ATOM | 2269 | CG | LYS | A | 300 | 16.950 | 16.803 | 38.973 | 1.00 | 42.69 | A |
| ATOM | 2270 | CD | LYS | A | 300 | 17.123 | 16.740 | 40.487 | 1.00 | 44.99 | A |
| ATOM | 2271 | CE | LYS | A | 300 | 16.055 | 15.890 | 41.162 | 1.00 | 47.76 | A |
| ATOM | 2272 | NZ | LYS | A | 300 | 16.154 | 15.946 | 42.660 | 1.00 | 49.25 | A |
| ATOM | 2273 | C | LYS | A | 300 | 17.583 | 14.237 | 36.121 | 1.00 | 38.83 | A |
| ATOM | 2274 | O | LYS | A | 300 | 18.601 | 13.581 | 36.370 | 1.00 | 38.08 | A |
| ATOM | 2275 | N | LEU | A | 301 | 16.628 | 13.827 | 35.285 | 1.00 | 36.04 | A |
| ATOM | 2276 | CA | LEU | A | 301 | 16.647 | 12.531 | 34.601 | 1.00 | 34.97 | A |
| ATOM | 2277 | CB | LEU | A | 301 | 15.353 | 11.768 | 34.924 | 1.00 | 32.81 | A |
| ATOM | 2278 | CG | LEU | A | 301 | 15.066 | 11.287 | 36.350 | 1.00 | 32.28 | A |
| ATOM | 2279 | CD1 | LEU | A | 301 | 15.321 | 12.393 | 37.346 | 1.00 | 34.57 | A |
| ATOM | 2280 | CD2 | LEU | A | 301 | 13.619 | 10.856 | 36.448 | 1.00 | 30.89 | A |
| ATOM | 2281 | C | LEU | A | 301 | 16.766 | 12.645 | 33.078 | 1.00 | 35.04 | A |
| ATOM | 2282 | O | LEU | A | 301 | 16.238 | 13.590 | 32.484 | 1.00 | 36.33 | A |
| ATOM | 2283 | N | PHE | A | 302 | 17.460 | 11.697 | 32.439 | 1.00 | 34.85 | A |
| ATOM | 2284 | CA | PHE | A | 302 | 17.538 | 11.719 | 30.973 | 1.00 | 33.91 | A |
| ATOM | 2285 | CB | PHE | A | 302 | 18.796 | 11.008 | 30.441 | 1.00 | 33.60 | A |
| ATOM | 2286 | CG | PHE | A | 302 | 18.885 | 9.555 | 30.790 | 1.00 | 32.97 | A |
| ATOM | 2287 | CD1 | PHE | A | 302 | 19.357 | 9.150 | 32.030 | 1.00 | 33.68 | A |
| ATOM | 2288 | CD2 | PHE | A | 302 | 18.534 | 8.585 | 29.855 | 1.00 | 34.78 | A |
| ATOM | 2289 | CE1 | PHE | A | 302 | 19.488 | 7.788 | 32.342 | 1.00 | 36.33 | A |
| ATOM | 2290 | CE2 | PHE | A | 302 | 18.657 | 7.221 | 30.151 | 1.00 | 36.72 | A |
| ATOM | 2291 | CZ | PHE | A | 302 | 19.139 | 6.822 | 31.402 | 1.00 | 36.20 | A |
| ATOM | 2292 | C | PHE | A | 302 | 16.256 | 11.056 | 30.439 | 1.00 | 32.30 | A |
| ATOM | 2293 | O | PHE | A | 302 | 15.631 | 10.246 | 31.137 | 1.00 | 29.60 | A |
| ATOM | 2294 | N | TRP | A | 303 | 15.857 | 11.402 | 29.216 | 1.00 | 32.29 | A |
| ATOM | 2295 | CA | TRP | A | 303 | 14.607 | 10.881 | 28.660 | 1.00 | 31.71 | A |
| ATOM | 2296 | CB | TRP | A | 303 | 13.634 | 12.035 | 28.421 | 1.00 | 30.02 | A |
| ATOM | 2297 | CG | TRP | A | 303 | 13.095 | 12.620 | 29.662 | 1.00 | 31.30 | A |
| ATOM | 2298 | CD2 | TRP | A | 303 | 11.745 | 12.559 | 30.113 | 1.00 | 31.48 | A |
| ATOM | 2299 | CE2 | TRP | A | 303 | 11.682 | 13.259 | 31.340 | 1.00 | 31.80 | A |
| ATOM | 2300 | CE3 | TRP | A | 303 | 10.579 | 11.981 | 29.602 | 1.00 | 32.51 | A |
| ATOM | 2301 | CD1 | TRP | A | 303 | 13.783 | 13.325 | 30.603 | 1.00 | 31.26 | A |
| ATOM | 2302 | NE1 | TRP | A | 303 | 12.941 | 13.714 | 31.617 | 1.00 | 31.13 | A |
| ATOM | 2303 | CZ2 | TRP | A | 303 | 10.496 | 13.398 | 32.062 | 1.00 | 31.38 | A |
| ATOM | 2304 | CZ3 | TRP | A | 303 | 9.399 | 12.118 | 30.321 | 1.00 | 32.50 | A |
| ATOM | 2305 | CH2 | TRP | A | 303 | 9.368 | 12.823 | 31.538 | 1.00 | 32.74 | A |
| ATOM | 2306 | C | TRP | A | 303 | 14.581 | 10.016 | 27.413 | 1.00 | 30.99 | A |
| ATOM | 2307 | O | TRP | A | 303 | 15.311 | 10.233 | 26.460 | 1.00 | 30.40 | A |
| ATOM | 2308 | N | VAL | A | 304 | 13.688 | 9.036 | 27.443 | 1.00 | 31.60 | A |
| ATOM | 2309 | CA | VAL | A | 304 | 13.469 | 8.151 | 26.313 | 1.00 | 31.46 | A |
| ATOM | 2310 | CB | VAL | A | 304 | 14.114 | 6.774 | 26.487 | 1.00 | 30.67 | A |
| ATOM | 2311 | CG1 | VAL | A | 304 | 13.707 | 5.886 | 25.324 | 1.00 | 28.82 | A |
| ATOM | 2312 | CG2 | VAL | A | 304 | 15.631 | 6.909 | 26.533 | 1.00 | 30.09 | A |
| ATOM | 2313 | C | VAL | A | 304 | 11.970 | 7.961 | 26.256 | 1.00 | 31.13 | A |
| ATOM | 2314 | O | VAL | A | 304 | 11.416 | 7.160 | 27.002 | 1.00 | 32.32 | A |
| ATOM | 2315 | N | VAL | A | 305 | 11.318 | 8.713 | 25.377 | 1.00 | 30.86 | A |
| ATOM | 2316 | CA | VAL | A | 305 | 9.869 | 8.656 | 25.224 | 1.00 | 30.15 | A |
| ATOM | 2317 | CB | VAL | A | 305 | 9.240 | 10.050 | 25.528 | 1.00 | 31.70 | A |
| ATOM | 2318 | CG1 | VAL | A | 305 | 7.786 | 10.106 | 25.043 | 1.00 | 30.98 | A |
| ATOM | 2319 | CG2 | VAL | A | 305 | 9.308 | 10.322 | 27.028 | 1.00 | 30.26 | A |
| ATOM | 2320 | C | VAL | A | 305 | 9.516 | 8.220 | 23.805 | 1.00 | 29.92 | A |
| ATOM | 2321 | O | VAL | A | 305 | 10.157 | 8.637 | 22.840 | 1.00 | 29.78 | A |
| ATOM | 2322 | N | HIS | A | 306 | 8.510 | 7.363 | 23.679 | 1.00 | 29.35 | A |
| ATOM | 2323 | CA | HIS | A | 306 | 8.105 | 6.899 | 22.360 | 1.00 | 30.96 | A |
| ATOM | 2324 | CB | HIS | A | 306 | 6.968 | 5.877 | 22.474 | 1.00 | 31.60 | A |
| ATOM | 2325 | CG | HIS | A | 306 | 6.353 | 5.517 | 21.160 | 1.00 | 32.17 | A |
| ATOM | 2326 | CD2 | HIS | A | 306 | 5.099 | 5.701 | 20.683 | 1.00 | 31.92 | A |
| ATOM | 2327 | ND1 | HIS | A | 306 | 7.063 | 4.907 | 20.149 | 1.00 | 33.80 | A |
| ATOM | 2328 | CE1 | HIS | A | 306 | 6.271 | 4.727 | 19.105 | 1.00 | 34.13 | A |
| ATOM | 2329 | NE2 | HIS | A | 306 | 5.074 | 5.201 | 19.404 | 1.00 | 32.34 | A |
| ATOM | 2330 | C | HIS | A | 306 | 7.672 | 8.087 | 21.487 | 1.00 | 30.79 | A |
| ATOM | 2331 | O | HIS | A | 306 | 6.827 | 8.909 | 21.881 | 1.00 | 30.02 | A |
| ATOM | 2332 | N | PRO | A | 307 | 8.253 | 8.192 | 20.285 | 1.00 | 30.01 | A |

APPENDIX A-continued

*Pinus sylvestris* STS

| ATOM | # | TYPE | RES | | | X | Y | Z | OCC | B | |
|------|---|------|-----|---|---|---|---|---|-----|---|---|
| ATOM | 2333 | CD | PRO | A | 307 | 9.351 | 7.348 | 19.777 | 1.00 | 29.05 | A |
| ATOM | 2334 | CA | PRO | A | 307 | 7.946 | 9.272 | 19.346 | 1.00 | 29.75 | A |
| ATOM | 2335 | CB | PRO | A | 307 | 9.168 | 9.273 | 18.441 | 1.00 | 29.53 | A |
| ATOM | 2336 | CG | PRO | A | 307 | 9.482 | 7.804 | 18.352 | 1.00 | 28.95 | A |
| ATOM | 2337 | C | PRO | A | 307 | 6.642 | 9.052 | 18.578 | 1.00 | 30.91 | A |
| ATOM | 2338 | O | PRO | A | 307 | 6.641 | 8.956 | 17.347 | 1.00 | 30.21 | A |
| ATOM | 2339 | N | GLY | A | 308 | 5.532 | 8.984 | 19.308 | 1.00 | 32.39 | A |
| ATOM | 2340 | CA | GLY | A | 308 | 4.243 | 8.767 | 18.671 | 1.00 | 34.41 | A |
| ATOM | 2341 | C | GLY | A | 308 | 3.936 | 9.818 | 17.622 | 1.00 | 35.01 | A |
| ATOM | 2342 | O | GLY | A | 308 | 3.438 | 9.505 | 16.538 | 1.00 | 35.38 | A |
| ATOM | 2343 | N | GLY | A | 309 | 4.246 | 11.068 | 17.952 | 1.00 | 34.47 | A |
| ATOM | 2344 | CA | GLY | A | 309 | 4.010 | 12.181 | 17.046 | 1.00 | 32.80 | A |
| ATOM | 2345 | C | GLY | A | 309 | 4.426 | 13.490 | 17.695 | 1.00 | 32.13 | A |
| ATOM | 2346 | O | GLY | A | 309 | 4.268 | 13.647 | 18.901 | 1.00 | 31.23 | A |
| ATOM | 2347 | N | ARG | A | 310 | 4.954 | 14.426 | 16.904 | 1.00 | 32.09 | A |
| ATOM | 2348 | CA | ARG | A | 310 | 5.399 | 15.717 | 17.424 | 1.00 | 33.38 | A |
| ATOM | 2349 | CB | ARG | A | 310 | 5.408 | 16.791 | 16.323 | 1.00 | 35.32 | A |
| ATOM | 2350 | CG | ARG | A | 310 | 5.632 | 18.197 | 16.902 | 1.00 | 36.45 | A |
| ATOM | 2351 | CD | ARG | A | 310 | 5.225 | 19.329 | 15.976 | 1.00 | 38.46 | A |
| ATOM | 2352 | NE | ARG | A | 310 | 6.254 | 19.662 | 14.998 | 1.00 | 40.77 | A |
| ATOM | 2353 | CZ | ARG | A | 310 | 6.164 | 20.681 | 14.147 | 1.00 | 42.99 | A |
| ATOM | 2354 | NH1 | ARG | A | 310 | 5.094 | 21.467 | 14.156 | 1.00 | 44.81 | A |
| ATOM | 2355 | NH2 | ARG | A | 310 | 7.138 | 20.918 | 13.280 | 1.00 | 44.76 | A |
| ATOM | 2356 | C | ARG | A | 310 | 4.536 | 16.227 | 18.576 | 1.00 | 33.42 | A |
| ATOM | 2357 | O | ARG | A | 310 | 5.048 | 16.539 | 19.653 | 1.00 | 32.55 | A |
| ATOM | 2358 | N | ALA | A | 311 | 3.228 | 16.301 | 18.330 | 1.00 | 34.76 | A |
| ATOM | 2359 | CA | ALA | A | 311 | 2.251 | 16.787 | 19.304 | 1.00 | 34.37 | A |
| ATOM | 2360 | CB | ALA | A | 311 | .842 | 16.595 | 18.766 | 1.00 | 34.77 | A |
| ATOM | 2361 | C | ALA | A | 311 | 2.383 | 16.133 | 20.666 | 1.00 | 35.11 | A |
| ATOM | 2362 | O | ALA | A | 311 | 2.488 | 16.832 | 21.673 | 1.00 | 36.46 | A |
| ATOM | 2363 | N | ILE | A | 312 | 2.367 | 14.800 | 20.705 | 1.00 | 34.41 | A |
| ATOM | 2364 | CA | ILE | A | 312 | 2.514 | 14.079 | 21.971 | 1.00 | 33.63 | A |
| ATOM | 2365 | CB | ILE | A | 312 | 2.652 | 12.553 | 21.751 | 1.00 | 34.10 | A |
| ATOM | 2366 | CG2 | ILE | A | 312 | 3.117 | 11.869 | 23.044 | 1.00 | 31.59 | A |
| ATOM | 2367 | CG1 | ILE | A | 312 | 1.312 | 11.965 | 21.296 | 1.00 | 34.90 | A |
| ATOM | 2368 | CD1 | ILE | A | 312 | 1.319 | 10.436 | 21.175 | 1.00 | 32.76 | A |
| ATOM | 2369 | C | ILE | A | 312 | 3.760 | 14.564 | 22.717 | 1.00 | 32.93 | A |
| ATOM | 2370 | O | ILE | A | 312 | 3.725 | 14.810 | 23.924 | 1.00 | 33.02 | A |
| ATOM | 2371 | N | LEU | A | 313 | 4.865 | 14.693 | 21.995 | 1.00 | 32.22 | A |
| ATOM | 2372 | CA | LEU | A | 313 | 6.109 | 15.152 | 22.602 | 1.00 | 32.28 | A |
| ATOM | 2373 | CB | LEU | A | 313 | 7.268 | 14.982 | 21.615 | 1.00 | 30.74 | A |
| ATOM | 2374 | CG | LEU | A | 313 | 7.430 | 13.580 | 21.009 | 1.00 | 29.06 | A |
| ATOM | 2375 | CD1 | LEU | A | 313 | 8.656 | 13.542 | 20.117 | 1.00 | 27.85 | A |
| ATOM | 2376 | CD2 | LEU | A | 313 | 7.551 | 12.544 | 22.128 | 1.00 | 29.06 | A |
| ATOM | 2377 | C | LEU | A | 313 | 5.988 | 16.615 | 23.022 | 1.00 | 33.58 | A |
| ATOM | 2378 | O | LEU | A | 313 | 6.449 | 17.002 | 24.095 | 1.00 | 31.21 | A |
| ATOM | 2379 | N | ASP | A | 314 | 5.352 | 17.428 | 22.185 | 1.00 | 34.88 | A |
| ATOM | 2380 | CA | ASP | A | 314 | 5.203 | 18.836 | 22.512 | 1.00 | 37.14 | A |
| ATOM | 2381 | CB | ASP | A | 314 | 4.623 | 19.620 | 21.335 | 1.00 | 36.64 | A |
| ATOM | 2382 | CG | ASP | A | 314 | 5.573 | 19.681 | 20.156 | 1.00 | 37.32 | A |
| ATOM | 2383 | OD1 | ASP | A | 314 | 6.778 | 19.406 | 20.343 | 1.00 | 39.89 | A |
| ATOM | 2384 | OD2 | ASP | A | 314 | 5.123 | 20.013 | 19.039 | 1.00 | 38.32 | A |
| ATOM | 2385 | C | ASP | A | 314 | 4.337 | 19.038 | 23.740 | 1.00 | 38.58 | A |
| ATOM | 2386 | O | ASP | A | 314 | 4.613 | 19.921 | 24.554 | 1.00 | 41.29 | A |
| ATOM | 2387 | N | ARG | A | 315 | 3.298 | 18.226 | 23.891 | 1.00 | 38.56 | A |
| ATOM | 2388 | CA | ARG | A | 315 | 2.420 | 18.367 | 25.051 | 1.00 | 39.30 | A |
| ATOM | 2389 | CB | ARG | A | 315 | 1.076 | 17.661 | 24.801 | 1.00 | 39.89 | A |
| ATOM | 2390 | CG | ARG | A | 315 | −.038 | 18.094 | 25.756 | 1.00 | 41.38 | A |
| ATOM | 2391 | CD | ARG | A | 315 | −.534 | 19.514 | 25.461 | 1.00 | 39.72 | A |
| ATOM | 2392 | NE | ARG | A | 315 | −1.525 | 19.517 | 24.391 | 1.00 | 39.62 | A |
| ATOM | 2393 | CZ | ARG | A | 315 | −2.757 | 19.034 | 24.517 | 1.00 | 38.98 | A |
| ATOM | 2394 | NH1 | ARG | A | 315 | −3.151 | 18.512 | 25.670 | 1.00 | 41.14 | A |
| ATOM | 2395 | NH2 | ARG | A | 315 | −3.594 | 19.063 | 23.491 | 1.00 | 40.18 | A |
| ATOM | 2396 | C | ARG | A | 315 | 3.095 | 17.816 | 26.311 | 1.00 | 37.88 | A |
| ATOM | 2397 | O | ARG | A | 315 | 3.120 | 18.474 | 27.345 | 1.00 | 38.21 | A |
| ATOM | 2398 | N | VAL | A | 316 | 3.650 | 16.614 | 26.220 | 1.00 | 38.10 | A |
| ATOM | 2399 | CA | VAL | A | 316 | 4.341 | 16.005 | 27.353 | 1.00 | 37.54 | A |
| ATOM | 2400 | CB | VAL | A | 316 | 5.071 | 14.695 | 26.932 | 1.00 | 38.03 | A |
| ATOM | 2401 | CG1 | VAL | A | 316 | 6.071 | 14.282 | 28.005 | 1.00 | 35.70 | A |
| ATOM | 2402 | CG2 | VAL | A | 316 | 4.061 | 13.579 | 26.713 | 1.00 | 36.09 | A |
| ATOM | 2403 | C | VAL | A | 316 | 5.379 | 16.965 | 27.941 | 1.00 | 38.14 | A |
| ATOM | 2404 | O | VAL | A | 316 | 5.415 | 17.191 | 29.145 | 1.00 | 37.74 | A |
| ATOM | 2405 | N | GLU | A | 317 | 6.217 | 17.520 | 27.071 | 1.00 | 39.36 | A |
| ATOM | 2406 | CA | GLU | A | 317 | 7.275 | 18.444 | 27.462 | 1.00 | 40.74 | A |
| ATOM | 2407 | CB | GLU | A | 317 | 8.078 | 18.846 | 26.227 | 1.00 | 42.43 | A |

APPENDIX A-continued

*Pinus sylvestris* STS

| ATOM | # | TYPE | RES | | | X | Y | Z | OCC | B | |
|------|---|------|-----|---|---|---|---|---|-----|---|---|
| ATOM | 2408 | CG | GLU | A | 317 | 9.155 | 19.873 | 26.491 | 1.00 | 46.61 | A |
| ATOM | 2409 | CD | GLU | A | 317 | 10.033 | 20.092 | 25.280 | 1.00 | 49.20 | A |
| ATOM | 2410 | OE1 | GLU | A | 317 | 9.485 | 20.393 | 24.197 | 1.00 | 50.31 | A |
| ATOM | 2411 | OE2 | GLU | A | 317 | 11.269 | 19.959 | 25.409 | 1.00 | 51.28 | A |
| ATOM | 2412 | C | GLU | A | 317 | 6.748 | 19.691 | 28.161 | 1.00 | 40.41 | A |
| ATOM | 2413 | O | GLU | A | 317 | 7.250 | 20.092 | 29.215 | 1.00 | 40.12 | A |
| ATOM | 2414 | N | ALA | A | 318 | 5.736 | 20.305 | 27.568 | 1.00 | 40.32 | A |
| ATOM | 2415 | CA | ALA | A | 318 | 5.148 | 21.502 | 28.140 | 1.00 | 40.04 | A |
| ATOM | 2416 | CB | ALA | A | 318 | 4.103 | 22.067 | 27.197 | 1.00 | 39.47 | A |
| ATOM | 2417 | C | ALA | A | 318 | 4.517 | 21.164 | 29.482 | 1.00 | 40.63 | A |
| ATOM | 2418 | O | ALA | A | 318 | 4.609 | 21.938 | 30.436 | 1.00 | 40.11 | A |
| ATOM | 2419 | N | LYS | A | 319 | 3.890 | 19.996 | 29.561 | 1.00 | 40.54 | A |
| ATOM | 2420 | CA | LYS | A | 319 | 3.236 | 19.585 | 30.793 | 1.00 | 43.33 | A |
| ATOM | 2421 | CB | LYS | A | 319 | 2.442 | 18.294 | 30.568 | 1.00 | 43.96 | A |
| ATOM | 2422 | CG | LYS | A | 319 | 1.144 | 18.225 | 31.361 | 1.00 | 44.46 | A |
| ATOM | 2423 | CD | LYS | A | 319 | 1.434 | 18.187 | 32.849 | 1.00 | 45.75 | A |
| ATOM | 2424 | CE | LYS | A | 319 | .164 | 18.197 | 33.671 | 1.00 | 46.68 | A |
| ATOM | 2425 | NZ | LYS | A | 319 | .483 | 18.182 | 35.128 | 1.00 | 48.59 | A |
| ATOM | 2426 | C | LYS | A | 319 | 4.237 | 19.405 | 31.930 | 1.00 | 44.12 | A |
| ATOM | 2427 | O | LYS | A | 319 | 4.156 | 20.091 | 32.949 | 1.00 | 45.62 | A |
| ATOM | 2428 | N | LEU | A | 320 | 5.186 | 18.493 | 31.757 | 1.00 | 44.99 | A |
| ATOM | 2429 | CA | LEU | A | 320 | 6.200 | 18.242 | 32.781 | 1.00 | 45.19 | A |
| ATOM | 2430 | CB | LEU | A | 320 | 6.893 | 16.903 | 32.521 | 1.00 | 43.92 | A |
| ATOM | 2431 | CG | LEU | A | 320 | 6.180 | 15.639 | 33.016 | 1.00 | 43.85 | A |
| ATOM | 2432 | CD1 | LEU | A | 320 | 4.669 | 15.835 | 33.062 | 1.00 | 43.96 | A |
| ATOM | 2433 | CD2 | LEU | A | 320 | 6.550 | 14.490 | 32.106 | 1.00 | 41.61 | A |
| ATOM | 2434 | C | LEU | A | 320 | 7.243 | 19.346 | 32.848 | 1.00 | 45.43 | A |
| ATOM | 2435 | O | LEU | A | 320 | 8.073 | 19.363 | 33.752 | 1.00 | 47.16 | A |
| ATOM | 2436 | N | ASN | A | 321 | 7.200 | 20.268 | 31.892 | 1.00 | 45.91 | A |
| ATOM | 2437 | CA | ASN | A | 321 | 8.156 | 21.371 | 31.857 | 1.00 | 46.17 | A |
| ATOM | 2438 | CB | ASN | A | 321 | 7.984 | 22.276 | 33.089 | 1.00 | 48.27 | A |
| ATOM | 2439 | CG | ASN | A | 321 | 7.324 | 23.613 | 32.757 | 1.00 | 50.11 | A |
| ATOM | 2440 | OD1 | ASN | A | 321 | 7.887 | 24.431 | 32.016 | 1.00 | 51.37 | A |
| ATOM | 2441 | ND2 | ASN | A | 321 | 6.128 | 23.842 | 33.306 | 1.00 | 47.30 | A |
| ATOM | 2442 | C | ASN | A | 321 | 9.577 | 20.826 | 31.812 | 1.00 | 45.21 | A |
| ATOM | 2443 | O | ASN | A | 321 | 10.381 | 21.081 | 32.705 | 1.00 | 45.20 | A |
| ATOM | 2444 | N | LEU | A | 322 | 9.875 | 20.066 | 30.766 | 1.00 | 43.89 | A |
| ATOM | 2445 | CA | LEU | A | 322 | 11.195 | 19.487 | 30.592 | 1.00 | 43.18 | A |
| ATOM | 2446 | CB | LEU | A | 322 | 11.094 | 18.173 | 29.817 | 1.00 | 42.20 | A |
| ATOM | 2447 | CG | LEU | A | 322 | 10.099 | 17.116 | 30.300 | 1.00 | 41.74 | A |
| ATOM | 2448 | CD1 | LEU | A | 322 | 10.180 | 15.896 | 29.386 | 1.00 | 40.69 | A |
| ATOM | 2449 | CD2 | LEU | A | 322 | 10.398 | 16.736 | 31.741 | 1.00 | 39.97 | A |
| ATOM | 2450 | C | LEU | A | 322 | 12.082 | 20.455 | 29.818 | 1.00 | 44.00 | A |
| ATOM | 2451 | O | LEU | A | 322 | 11.597 | 21.240 | 29.002 | 1.00 | 45.63 | A |
| ATOM | 2452 | N | ASP | A | 323 | 13.381 | 20.405 | 30.077 | 1.00 | 44.78 | A |
| ATOM | 2453 | CA | ASP | A | 323 | 14.317 | 21.265 | 29.369 | 1.00 | 47.10 | A |
| ATOM | 2454 | CB | ASP | A | 323 | 15.717 | 21.187 | 29.992 | 1.00 | 49.02 | A |
| ATOM | 2455 | CG | ASP | A | 323 | 15.898 | 22.151 | 31.147 | 1.00 | 51.43 | A |
| ATOM | 2456 | OD1 | ASP | A | 323 | 15.816 | 23.377 | 30.911 | 1.00 | 52.39 | A |
| ATOM | 2457 | OD2 | ASP | A | 323 | 16.122 | 21.687 | 32.287 | 1.00 | 52.60 | A |
| ATOM | 2458 | C | ASP | A | 323 | 14.390 | 20.801 | 27.926 | 1.00 | 46.91 | A |
| ATOM | 2459 | O | ASP | A | 323 | 14.444 | 19.605 | 27.655 | 1.00 | 48.47 | A |
| ATOM | 2460 | N | PRO | A | 324 | 14.396 | 21.743 | 26.978 | 1.00 | 46.22 | A |
| ATOM | 2461 | CD | PRO | A | 324 | 14.387 | 23.200 | 27.195 | 1.00 | 46.91 | A |
| ATOM | 2462 | CA | PRO | A | 324 | 14.465 | 21.436 | 25.550 | 1.00 | 46.06 | A |
| ATOM | 2463 | CB | PRO | A | 324 | 14.791 | 22.787 | 24.930 | 1.00 | 45.50 | A |
| ATOM | 2464 | CG | PRO | A | 324 | 14.066 | 23.731 | 25.817 | 1.00 | 46.39 | A |
| ATOM | 2465 | C | PRO | A | 324 | 15.525 | 20.393 | 25.216 | 1.00 | 45.77 | A |
| ATOM | 2466 | O | PRO | A | 324 | 15.591 | 19.916 | 24.086 | 1.00 | 47.09 | A |
| ATOM | 2467 | N | THR | A | 325 | 16.359 | 20.049 | 26.193 | 1.00 | 44.47 | A |
| ATOM | 2468 | CA | THR | A | 325 | 17.424 | 19.071 | 25.974 | 1.00 | 43.36 | A |
| ATOM | 2469 | CB | THR | A | 325 | 18.654 | 19.335 | 26.885 | 1.00 | 42.49 | A |
| ATOM | 2470 | OG1 | THR | A | 325 | 18.310 | 19.086 | 28.259 | 1.00 | 40.55 | A |
| ATOM | 2471 | CG2 | THR | A | 325 | 19.144 | 20.768 | 26.715 | 1.00 | 39.78 | A |
| ATOM | 2472 | C | THR | A | 325 | 16.977 | 17.635 | 26.206 | 1.00 | 42.40 | A |
| ATOM | 2473 | O | THR | A | 325 | 17.518 | 16.716 | 25.607 | 1.00 | 43.43 | A |
| ATOM | 2474 | N | LYS | A | 326 | 15.994 | 17.442 | 27.075 | 1.00 | 41.96 | A |
| ATOM | 2475 | CA | LYS | A | 326 | 15.510 | 16.104 | 27.369 | 1.00 | 41.14 | A |
| ATOM | 2476 | CB | LYS | A | 326 | 14.252 | 16.172 | 28.233 | 1.00 | 40.16 | A |
| ATOM | 2477 | CG | LYS | A | 326 | 14.337 | 17.055 | 29.466 | 1.00 | 40.21 | A |
| ATOM | 2478 | CD | LYS | A | 326 | 15.143 | 16.444 | 30.595 | 1.00 | 42.29 | A |
| ATOM | 2479 | CE | LYS | A | 326 | 16.623 | 16.764 | 30.488 | 1.00 | 42.30 | A |
| ATOM | 2480 | NZ | LYS | A | 326 | 17.346 | 16.315 | 31.715 | 1.00 | 42.85 | A |
| ATOM | 2481 | C | LYS | A | 326 | 15.197 | 15.314 | 26.093 | 1.00 | 41.72 | A |
| ATOM | 2482 | O | LYS | A | 326 | 15.702 | 14.205 | 25.902 | 1.00 | 42.51 | A |

APPENDIX A-continued

*Pinus sylvestris* STS

| ATOM | # | TYPE | RES | | | X | Y | Z | OCC | B | |
|------|---|------|-----|---|-----|--------|--------|--------|------|-------|---|
| ATOM | 2483 | N | LEU | A | 327 | 14.381 | 15.893 | 25.214 | 1.00 | 42.21 | A |
| ATOM | 2484 | CA | LEU | A | 327 | 13.976 | 15.212 | 23.977 | 1.00 | 41.89 | A |
| ATOM | 2485 | CB | LEU | A | 327 | 12.533 | 15.590 | 23.617 | 1.00 | 40.14 | A |
| ATOM | 2486 | CG | LEU | A | 327 | 11.472 | 15.344 | 24.689 | 1.00 | 40.48 | A |
| ATOM | 2487 | CD1 | LEU | A | 327 | 10.115 | 15.709 | 24.124 | 1.00 | 40.17 | A |
| ATOM | 2488 | CD2 | LEU | A | 327 | 11.491 | 13.888 | 25.138 | 1.00 | 40.61 | A |
| ATOM | 2489 | C | LEU | A | 327 | 14.854 | 15.410 | 22.740 | 1.00 | 41.12 | A |
| ATOM | 2490 | O | LEU | A | 327 | 14.371 | 15.279 | 21.612 | 1.00 | 40.40 | A |
| ATOM | 2491 | N | ILE | A | 328 | 16.129 | 15.728 | 22.930 | 1.00 | 38.12 | A |
| ATOM | 2492 | CA | ILE | A | 328 | 17.003 | 15.895 | 21.780 | 1.00 | 36.92 | A |
| ATOM | 2493 | CB | ILE | A | 328 | 18.380 | 16.460 | 22.183 | 1.00 | 36.66 | A |
| ATOM | 2494 | CG2 | ILE | A | 328 | 19.230 | 16.700 | 20.942 | 1.00 | 36.52 | A |
| ATOM | 2495 | CG1 | ILE | A | 328 | 18.199 | 17.772 | 22.945 | 1.00 | 36.61 | A |
| ATOM | 2496 | CD1 | ILE | A | 328 | 17.422 | 18.817 | 22.186 | 1.00 | 35.30 | A |
| ATOM | 2497 | C | ILE | A | 328 | 17.174 | 14.509 | 21.162 | 1.00 | 36.34 | A |
| ATOM | 2498 | O | ILE | A | 328 | 17.106 | 14.343 | 19.939 | 1.00 | 37.30 | A |
| ATOM | 2499 | N | PRO | A | 329 | 17.396 | 13.488 | 22.003 | 1.00 | 34.69 | A |
| ATOM | 2500 | CD | PRO | A | 329 | 17.854 | 13.543 | 23.400 | 1.00 | 32.67 | A |
| ATOM | 2501 | CA | PRO | A | 329 | 17.559 | 12.135 | 21.462 | 1.00 | 35.34 | A |
| ATOM | 2502 | CB | PRO | A | 329 | 17.974 | 11.329 | 22.687 | 1.00 | 33.96 | A |
| ATOM | 2503 | CG | PRO | A | 329 | 18.737 | 12.337 | 23.491 | 1.00 | 33.23 | A |
| ATOM | 2504 | C | PRO | A | 329 | 16.273 | 11.610 | 20.819 | 1.00 | 33.93 | A |
| ATOM | 2505 | O | PRO | A | 329 | 16.307 | 11.036 | 19.739 | 1.00 | 34.28 | A |
| ATOM | 2506 | N | THR | A | 330 | 15.142 | 11.826 | 21.482 | 1.00 | 34.73 | A |
| ATOM | 2507 | CA | THR | A | 330 | 13.848 | 11.363 | 20.978 | 1.00 | 34.57 | A |
| ATOM | 2508 | CB | THR | A | 330 | 12.718 | 11.627 | 22.004 | 1.00 | 35.22 | A |
| ATOM | 2509 | OG1 | THR | A | 330 | 12.959 | 10.873 | 23.200 | 1.00 | 36.60 | A |
| ATOM | 2510 | CG2 | THR | A | 330 | 11.376 | 11.209 | 21.430 | 1.00 | 36.40 | A |
| ATOM | 2511 | C | THR | A | 330 | 13.448 | 12.006 | 19.651 | 1.00 | 32.86 | A |
| ATOM | 2512 | O | THR | A | 330 | 13.133 | 11.309 | 18.685 | 1.00 | 32.91 | A |
| ATOM | 2513 | N | ARG | A | 331 | 13.459 | 13.334 | 19.614 | 1.00 | 32.31 | A |
| ATOM | 2514 | CA | ARG | A | 331 | 13.088 | 14.081 | 18.418 | 1.00 | 31.64 | A |
| ATOM | 2515 | CB | ARG | A | 331 | 13.008 | 15.586 | 18.712 | 1.00 | 32.71 | A |
| ATOM | 2516 | CG | ARG | A | 331 | 11.900 | 16.012 | 19.676 | 1.00 | 31.50 | A |
| ATOM | 2517 | CD | ARG | A | 331 | 11.844 | 17.535 | 19.818 | 1.00 | 33.90 | A |
| ATOM | 2518 | NE | ARG | A | 331 | 10.822 | 17.981 | 20.761 | 1.00 | 33.69 | A |
| ATOM | 2519 | CZ | ARG | A | 331 | 9.509 | 17.953 | 20.528 | 1.00 | 37.09 | A |
| ATOM | 2520 | NH1 | ARG | A | 331 | 9.031 | 17.506 | 19.373 | 1.00 | 36.82 | A |
| ATOM | 2521 | NH2 | ARG | A | 331 | 8.663 | 18.357 | 21.466 | 1.00 | 36.77 | A |
| ATOM | 2522 | C | ARG | A | 331 | 14.065 | 13.855 | 17.282 | 1.00 | 33.23 | A |
| ATOM | 2523 | O | ARG | A | 331 | 13.693 | 13.967 | 16.116 | 1.00 | 36.66 | A |
| ATOM | 2524 | N | HIS | A | 332 | 15.314 | 13.540 | 17.614 | 1.00 | 32.09 | A |
| ATOM | 2525 | CA | HIS | A | 332 | 16.322 | 13.308 | 16.588 | 1.00 | 32.07 | A |
| ATOM | 2526 | CB | HIS | A | 332 | 17.720 | 13.310 | 17.210 | 1.00 | 35.42 | A |
| ATOM | 2527 | CG | HIS | A | 332 | 18.796 | 12.893 | 16.258 | 1.00 | 38.11 | A |
| ATOM | 2528 | CD2 | HIS | A | 332 | 19.765 | 13.608 | 15.637 | 1.00 | 38.88 | A |
| ATOM | 2529 | ND1 | HIS | A | 332 | 18.922 | 11.597 | 15.800 | 1.00 | 38.66 | A |
| ATOM | 2530 | CE1 | HIS | A | 332 | 19.921 | 11.534 | 14.938 | 1.00 | 39.10 | A |
| ATOM | 2531 | NE2 | HIS | A | 332 | 20.448 | 12.740 | 14.821 | 1.00 | 39.79 | A |
| ATOM | 2532 | C | HIS | A | 332 | 16.093 | 12.000 | 15.821 | 1.00 | 31.77 | A |
| ATOM | 2533 | O | HIS | A | 332 | 16.307 | 11.935 | 14.605 | 1.00 | 32.24 | A |
| ATOM | 2534 | N | VAL | A | 333 | 15.677 | 10.959 | 16.536 | 1.00 | 29.94 | A |
| ATOM | 2535 | CA | VAL | A | 333 | 15.398 | 9.673 | 15.912 | 1.00 | 28.63 | A |
| ATOM | 2536 | CB | VAL | A | 333 | 15.344 | 8.544 | 16.975 | 1.00 | 29.30 | A |
| ATOM | 2537 | CG1 | VAL | A | 333 | 14.872 | 7.221 | 16.336 | 1.00 | 29.02 | A |
| ATOM | 2538 | CG2 | VAL | A | 333 | 16.731 | 8.371 | 17.602 | 1.00 | 24.24 | A |
| ATOM | 2539 | C | VAL | A | 333 | 14.060 | 9.747 | 15.156 | 1.00 | 28.45 | A |
| ATOM | 2540 | O | VAL | A | 333 | 13.942 | 9.263 | 14.022 | 1.00 | 28.50 | A |
| ATOM | 2541 | N | MET | A | 334 | 13.055 | 10.363 | 15.768 | 1.00 | 26.42 | A |
| ATOM | 2542 | CA | MET | A | 334 | 11.771 | 10.472 | 15.098 | 1.00 | 26.67 | A |
| ATOM | 2543 | CB | MET | A | 334 | 10.756 | 11.270 | 15.937 | 1.00 | 23.62 | A |
| ATOM | 2544 | CG | MET | A | 334 | 9.286 | 11.001 | 15.511 | 1.00 | 24.33 | A |
| ATOM | 2545 | SD | MET | A | 334 | 8.068 | 12.270 | 15.942 | 1.00 | 20.82 | A |
| ATOM | 2546 | CE | MET | A | 334 | 7.430 | 11.702 | 17.373 | 1.00 | 19.41 | A |
| ATOM | 2547 | C | MET | A | 334 | 12.010 | 11.178 | 13.774 | 1.00 | 27.99 | A |
| ATOM | 2548 | O | MET | A | 334 | 11.385 | 10.851 | 12.767 | 1.00 | 29.09 | A |
| ATOM | 2549 | N | SER | A | 335 | 12.937 | 12.133 | 13.776 | 1.00 | 29.25 | A |
| ATOM | 2550 | CA | SER | A | 335 | 13.241 | 12.888 | 12.568 | 1.00 | 32.40 | A |
| ATOM | 2551 | CB | SER | A | 335 | 14.107 | 14.104 | 12.888 | 1.00 | 31.79 | A |
| ATOM | 2552 | OG | SER | A | 335 | 14.464 | 14.759 | 11.683 | 1.00 | 32.15 | A |
| ATOM | 2553 | C | SER | A | 335 | 13.932 | 12.086 | 11.475 | 1.00 | 32.33 | A |
| ATOM | 2554 | O | SER | A | 335 | 13.676 | 12.296 | 10.288 | 1.00 | 34.30 | A |
| ATOM | 2555 | N | GLU | A | 336 | 14.815 | 11.181 | 11.871 | 1.00 | 32.37 | A |
| ATOM | 2556 | CA | GLU | A | 336 | 15.535 | 10.372 | 10.901 | 1.00 | 31.39 | A |
| ATOM | 2557 | CB | GLU | A | 336 | 16.951 | 10.077 | 11.415 | 1.00 | 32.84 | A |

APPENDIX A-continued

*Pinus sylvestris* STS

| ATOM | # | TYPE | RES | | | X | Y | Z | OCC | B | |
|------|---|------|-----|---|---|---|---|---|-----|---|---|
| ATOM | 2558 | CG | GLU | A | 336 | 17.593 | 8.849 | 10.775 | 1.00 | 39.41 | A |
| ATOM | 2559 | CD | GLU | A | 336 | 19.103 | 8.788 | 10.950 | 1.00 | 42.04 | A |
| ATOM | 2560 | OE1 | GLU | A | 336 | 19.606 | 9.199 | 12.022 | 1.00 | 44.89 | A |
| ATOM | 2561 | OE2 | GLU | A | 336 | 19.785 | 8.312 | 10.013 | 1.00 | 42.62 | A |
| ATOM | 2562 | C | GLU | A | 336 | 14.844 | 9.061 | 10.514 | 1.00 | 29.79 | A |
| ATOM | 2563 | O | GLU | A | 336 | 15.141 | 8.502 | 9.456 | 1.00 | 28.00 | A |
| ATOM | 2564 | N | TYR | A | 337 | 13.914 | 8.585 | 11.345 | 1.00 | 28.26 | A |
| ATOM | 2565 | CA | TYR | A | 337 | 13.235 | 7.313 | 11.076 | 1.00 | 27.55 | A |
| ATOM | 2566 | CB | TYR | A | 337 | 13.656 | 6.273 | 12.118 | 1.00 | 25.68 | A |
| ATOM | 2567 | CG | TYR | A | 337 | 15.134 | 6.010 | 12.148 | 1.00 | 22.44 | A |
| ATOM | 2568 | CD1 | TYR | A | 337 | 15.719 | 5.099 | 11.272 | 1.00 | 21.51 | A |
| ATOM | 2569 | CE1 | TYR | A | 337 | 17.100 | 4.881 | 11.279 | 1.00 | 22.79 | A |
| ATOM | 2570 | CD2 | TYR | A | 337 | 15.959 | 6.698 | 13.031 | 1.00 | 21.39 | A |
| ATOM | 2571 | CE2 | TYR | A | 337 | 17.336 | 6.489 | 13.046 | 1.00 | 23.04 | A |
| ATOM | 2572 | CZ | TYR | A | 337 | 17.896 | 5.579 | 12.170 | 1.00 | 22.73 | A |
| ATOM | 2573 | OH | TYR | A | 337 | 19.244 | 5.356 | 12.205 | 1.00 | 25.92 | A |
| ATOM | 2574 | C | TYR | A | 337 | 11.714 | 7.351 | 11.047 | 1.00 | 28.12 | A |
| ATOM | 2575 | O | TYR | A | 337 | 11.091 | 6.623 | 10.269 | 1.00 | 29.61 | A |
| ATOM | 2576 | N | GLY | A | 338 | 11.122 | 8.172 | 11.910 | 1.00 | 27.01 | A |
| ATOM | 2577 | CA | GLY | A | 338 | 9.674 | 8.261 | 11.985 | 1.00 | 28.08 | A |
| ATOM | 2578 | C | GLY | A | 338 | 9.171 | 7.349 | 13.095 | 1.00 | 29.03 | A |
| ATOM | 2579 | O | GLY | A | 338 | 9.949 | 6.964 | 13.973 | 1.00 | 30.16 | A |
| ATOM | 2580 | N | ASN | A | 339 | 7.884 | 7.003 | 13.083 | 1.00 | 29.06 | A |
| ATOM | 2581 | CA | ASN | A | 339 | 7.364 | 6.111 | 14.112 | 1.00 | 28.44 | A |
| ATOM | 2582 | CB | ASN | A | 339 | 5.871 | 6.359 | 14.353 | 1.00 | 29.87 | A |
| ATOM | 2583 | CG | ASN | A | 339 | 5.361 | 5.702 | 15.643 | 1.00 | 32.77 | A |
| ATOM | 2584 | OD1 | ASN | A | 339 | 5.898 | 4.682 | 16.094 | 1.00 | 32.86 | A |
| ATOM | 2585 | ND2 | ASN | A | 339 | 4.311 | 6.280 | 16.233 | 1.00 | 31.79 | A |
| ATOM | 2586 | C | ASN | A | 339 | 7.577 | 4.662 | 13.664 | 1.00 | 27.69 | A |
| ATOM | 2587 | O | ASN | A | 339 | 6.814 | 4.135 | 12.864 | 1.00 | 26.14 | A |
| ATOM | 2588 | N | MET | A | 340 | 8.643 | 4.038 | 14.156 | 1.00 | 28.00 | A |
| ATOM | 2589 | CA | MET | A | 340 | 8.939 | 2.646 | 13.834 | 1.00 | 26.29 | A |
| ATOM | 2590 | CB | MET | A | 340 | 10.443 | 2.411 | 13.799 | 1.00 | 24.42 | A |
| ATOM | 2591 | CG | MET | A | 340 | 11.178 | 3.042 | 12.626 | 1.00 | 21.65 | A |
| ATOM | 2592 | SD | MET | A | 340 | 12.917 | 2.677 | 12.788 | 1.00 | 11.19 | A |
| ATOM | 2593 | CE | MET | A | 340 | 13.287 | 3.727 | 14.106 | 1.00 | 12.59 | A |
| ATOM | 2594 | C | MET | A | 340 | 8.311 | 1.787 | 14.932 | 1.00 | 27.65 | A |
| ATOM | 2595 | O | MET | A | 340 | 8.795 | .706 | 15.263 | 1.00 | 29.01 | A |
| ATOM | 2596 | N | SER | A | 341 | 7.219 | 2.300 | 15.487 | 1.00 | 28.65 | A |
| ATOM | 2597 | CA | SER | A | 341 | 6.481 | 1.638 | 16.553 | 1.00 | 28.94 | A |
| ATOM | 2598 | CB | SER | A | 341 | 5.703 | .440 | 16.001 | 1.00 | 30.35 | A |
| ATOM | 2599 | OG | SER | A | 341 | 4.905 | −.161 | 17.013 | 1.00 | 33.28 | A |
| ATOM | 2600 | C | SER | A | 341 | 7.368 | 1.204 | 17.716 | 1.00 | 28.35 | A |
| ATOM | 2601 | O | SER | A | 341 | 8.144 | 2.004 | 18.247 | 1.00 | 27.65 | A |
| ATOM | 2602 | N | SER | A | 342 | 7.253 | −.067 | 18.097 | 1.00 | 28.96 | A |
| ATOM | 2603 | CA | SER | A | 342 | 7.997 | −.622 | 19.222 | 1.00 | 29.52 | A |
| ATOM | 2604 | CB | SER | A | 342 | 7.624 | −2.101 | 19.419 | 1.00 | 29.14 | A |
| ATOM | 2605 | OG | SER | A | 342 | 7.844 | −2.873 | 18.249 | 1.00 | 28.82 | A |
| ATOM | 2606 | C | SER | A | 342 | 9.516 | −.474 | 19.197 | 1.00 | 30.70 | A |
| ATOM | 2607 | O | SER | A | 342 | 10.142 | −.355 | 20.249 | 1.00 | 30.85 | A |
| ATOM | 2608 | N | ALA | A | 343 | 10.118 | −.464 | 18.016 | 1.00 | 31.45 | A |
| ATOM | 2609 | CA | ALA | A | 343 | 11.570 | −.344 | 17.952 | 1.00 | 33.64 | A |
| ATOM | 2610 | CB | ALA | A | 343 | 12.083 | −.983 | 16.662 | 1.00 | 35.55 | A |
| ATOM | 2611 | C | ALA | A | 343 | 12.136 | 1.080 | 18.105 | 1.00 | 33.98 | A |
| ATOM | 2612 | O | ALA | A | 343 | 13.344 | 1.246 | 18.233 | 1.00 | 34.35 | A |
| ATOM | 2613 | N | CYS | A | 344 | 11.279 | 2.098 | 18.108 | 1.00 | 33.68 | A |
| ATOM | 2614 | CA | CYS | A | 344 | 11.746 | 3.484 | 18.244 | 1.00 | 33.68 | A |
| ATOM | 2615 | CB | CYS | A | 344 | 10.566 | 4.455 | 18.206 | 1.00 | 34.53 | A |
| ATOM | 2616 | SG | CYS | A | 344 | 9.710 | 4.519 | 16.638 | 1.00 | 37.50 | A |
| ATOM | 2617 | C | CYS | A | 344 | 12.547 | 3.761 | 19.515 | 1.00 | 32.20 | A |
| ATOM | 2618 | O | CYS | A | 344 | 13.679 | 4.257 | 19.455 | 1.00 | 30.61 | A |
| ATOM | 2619 | N | VAL | A | 345 | 11.953 | 3.438 | 20.661 | 1.00 | 30.76 | A |
| ATOM | 2620 | CA | VAL | A | 345 | 12.594 | 3.672 | 21.950 | 1.00 | 30.62 | A |
| ATOM | 2621 | CB | VAL | A | 345 | 11.700 | 3.227 | 23.104 | 1.00 | 30.70 | A |
| ATOM | 2622 | CG1 | VAL | A | 345 | 10.457 | 4.082 | 23.138 | 1.00 | 29.52 | A |
| ATOM | 2623 | CG2 | VAL | A | 345 | 11.339 | 1.764 | 22.939 | 1.00 | 29.04 | A |
| ATOM | 2624 | C | VAL | A | 345 | 13.942 | 2.984 | 22.091 | 1.00 | 30.41 | A |
| ATOM | 2625 | O | VAL | A | 345 | 14.762 | 3.389 | 22.914 | 1.00 | 31.73 | A |
| ATOM | 2626 | N | HIS | A | 346 | 14.177 | 1.941 | 21.306 | 1.00 | 29.02 | A |
| ATOM | 2627 | CA | HIS | A | 346 | 15.456 | 1.254 | 21.377 | 1.00 | 28.83 | A |
| ATOM | 2628 | CB | HIS | A | 346 | 15.314 | −.201 | 20.924 | 1.00 | 29.96 | A |
| ATOM | 2629 | CG | HIS | A | 346 | 14.336 | −.983 | 21.747 | 1.00 | 32.17 | A |
| ATOM | 2630 | CD2 | HIS | A | 346 | 13.228 | −1.681 | 21.400 | 1.00 | 32.87 | A |
| ATOM | 2631 | ND1 | HIS | A | 346 | 14.434 | −1.083 | 23.118 | 1.00 | 33.79 | A |
| ATOM | 2632 | CE1 | HIS | A | 346 | 13.430 | −1.809 | 23.580 | 1.00 | 34.75 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 2633 | NE2 | HIS | A | 346 | 12.684 | −2.186 | 22.557 | 1.00 | 34.86 | A |
| ATOM | 2634 | C | HIS | A | 346 | 16.397 | 2.045 | 20.486 | 1.00 | 28.71 | A |
| ATOM | 2635 | O | HIS | A | 346 | 17.579 | 2.204 | 20.805 | 1.00 | 27.87 | A |
| ATOM | 2636 | N | PHE | A | 347 | 15.864 | 2.564 | 19.381 | 1.00 | 27.48 | A |
| ATOM | 2637 | CA | PHE | A | 347 | 16.660 | 3.398 | 18.488 | 1.00 | 28.08 | A |
| ATOM | 2638 | CB | PHE | A | 347 | 15.820 | 3.906 | 17.314 | 1.00 | 25.80 | A |
| ATOM | 2639 | CG | PHE | A | 347 | 15.953 | 3.083 | 16.070 | 1.00 | 26.73 | A |
| ATOM | 2640 | CD1 | PHE | A | 347 | 15.493 | 1.768 | 16.031 | 1.00 | 24.87 | A |
| ATOM | 2641 | CD2 | PHE | A | 347 | 16.539 | 3.621 | 14.927 | 1.00 | 24.25 | A |
| ATOM | 2642 | CE1 | PHE | A | 347 | 15.613 | 1.007 | 14.862 | 1.00 | 25.10 | A |
| ATOM | 2643 | CE2 | PHE | A | 347 | 16.666 | 2.863 | 13.758 | 1.00 | 23.84 | A |
| ATOM | 2644 | CZ | PHE | A | 347 | 16.201 | 1.558 | 13.727 | 1.00 | 25.46 | A |
| ATOM | 2645 | C | PHE | A | 347 | 17.123 | 4.595 | 19.311 | 1.00 | 29.17 | A |
| ATOM | 2646 | O | PHE | A | 347 | 18.265 | 5.032 | 19.198 | 1.00 | 30.41 | A |
| ATOM | 2647 | N | ILE | A | 348 | 16.220 | 5.115 | 20.144 | 1.00 | 29.54 | A |
| ATOM | 2648 | CA | ILE | A | 348 | 16.519 | 6.269 | 20.992 | 1.00 | 31.74 | A |
| ATOM | 2649 | CB | ILE | A | 348 | 15.237 | 6.805 | 21.670 | 1.00 | 30.12 | A |
| ATOM | 2650 | CG2 | ILE | A | 348 | 15.585 | 7.905 | 22.673 | 1.00 | 29.86 | A |
| ATOM | 2651 | CG1 | ILE | A | 348 | 14.285 | 7.351 | 20.600 | 1.00 | 30.80 | A |
| ATOM | 2652 | CD1 | ILE | A | 348 | 12.905 | 7.697 | 21.121 | 1.00 | 29.48 | A |
| ATOM | 2653 | C | ILE | A | 348 | 17.564 | 5.941 | 22.057 | 1.00 | 33.22 | A |
| ATOM | 2654 | O | ILE | A | 348 | 18.451 | 6.753 | 22.331 | 1.00 | 32.42 | A |
| ATOM | 2655 | N | LEU | A | 349 | 17.447 | 4.756 | 22.659 | 1.00 | 34.52 | A |
| ATOM | 2656 | CA | LEU | A | 349 | 18.402 | 4.312 | 23.673 | 1.00 | 33.45 | A |
| ATOM | 2657 | CB | LEU | A | 349 | 18.131 | 2.862 | 24.075 | 1.00 | 32.73 | A |
| ATOM | 2658 | CG | LEU | A | 349 | 17.008 | 2.663 | 25.082 | 1.00 | 31.86 | A |
| ATOM | 2659 | CD1 | LEU | A | 349 | 16.621 | 1.218 | 25.144 | 1.00 | 32.57 | A |
| ATOM | 2660 | CD2 | LEU | A | 349 | 17.469 | 3.159 | 26.437 | 1.00 | 35.89 | A |
| ATOM | 2661 | C | LEU | A | 349 | 19.783 | 4.393 | 23.072 | 1.00 | 32.83 | A |
| ATOM | 2662 | O | LEU | A | 349 | 20.693 | 4.986 | 23.642 | 1.00 | 33.55 | A |
| ATOM | 2663 | N | ASP | A | 350 | 19.912 | 3.791 | 21.898 | 1.00 | 32.31 | A |
| ATOM | 2664 | CA | ASP | A | 350 | 21.160 | 3.751 | 21.163 | 1.00 | 32.68 | A |
| ATOM | 2665 | CB | ASP | A | 350 | 20.953 | 2.948 | 19.883 | 1.00 | 31.76 | A |
| ATOM | 2666 | CG | ASP | A | 350 | 22.252 | 2.579 | 19.211 | 1.00 | 33.89 | A |
| ATOM | 2667 | OD1 | ASP | A | 350 | 23.090 | 1.926 | 19.866 | 1.00 | 34.37 | A |
| ATOM | 2668 | OD2 | ASP | A | 350 | 22.431 | 2.936 | 18.028 | 1.00 | 34.98 | A |
| ATOM | 2669 | C | ASP | A | 350 | 21.662 | 5.162 | 20.836 | 1.00 | 34.32 | A |
| ATOM | 2670 | O | ASP | A | 350 | 22.793 | 5.513 | 21.161 | 1.00 | 33.23 | A |
| ATOM | 2671 | N | GLN | A | 351 | 20.820 | 5.971 | 20.202 | 1.00 | 35.14 | A |
| ATOM | 2672 | CA | GLN | A | 351 | 21.214 | 7.332 | 19.853 | 1.00 | 36.60 | A |
| ATOM | 2673 | CB | GLN | A | 351 | 20.072 | 8.052 | 19.134 | 1.00 | 37.06 | A |
| ATOM | 2674 | CG | GLN | A | 351 | 20.442 | 9.464 | 18.680 | 1.00 | 39.34 | A |
| ATOM | 2675 | CD | GLN | A | 351 | 21.369 | 9.479 | 17.472 | 1.00 | 40.13 | A |
| ATOM | 2676 | OE1 | GLN | A | 351 | 22.018 | 10.480 | 17.198 | 1.00 | 40.84 | A |
| ATOM | 2677 | NE2 | GLN | A | 351 | 21.419 | 8.370 | 16.736 | 1.00 | 41.79 | A |
| ATOM | 2678 | C | GLN | A | 351 | 21.617 | 8.128 | 21.097 | 1.00 | 36.53 | A |
| ATOM | 2679 | O | GLN | A | 351 | 22.511 | 8.977 | 21.039 | 1.00 | 34.64 | A |
| ATOM | 2680 | N | THR | A | 352 | 20.945 | 7.844 | 22.213 | 1.00 | 36.55 | A |
| ATOM | 2681 | CA | THR | A | 352 | 21.219 | 8.507 | 23.481 | 1.00 | 37.35 | A |
| ATOM | 2682 | CB | THR | A | 352 | 20.143 | 8.164 | 24.523 | 1.00 | 36.83 | A |
| ATOM | 2683 | OG1 | THR | A | 352 | 18.919 | 8.808 | 24.159 | 1.00 | 36.13 | A |
| ATOM | 2684 | CG2 | THR | A | 352 | 20.559 | 8.628 | 25.914 | 1.00 | 36.00 | A |
| ATOM | 2685 | C | THR | A | 352 | 22.600 | 8.137 | 24.032 | 1.00 | 39.55 | A |
| ATOM | 2686 | O | THR | A | 352 | 23.302 | 8.996 | 24.571 | 1.00 | 39.76 | A |
| ATOM | 2687 | N | ARG | A | 353 | 22.995 | 6.872 | 23.902 | 1.00 | 38.72 | A |
| ATOM | 2688 | CA | ARG | A | 353 | 24.308 | 6.468 | 24.387 | 1.00 | 39.16 | A |
| ATOM | 2689 | CB | ARG | A | 353 | 24.395 | 4.949 | 24.547 | 1.00 | 38.70 | A |
| ATOM | 2690 | CG | ARG | A | 353 | 24.307 | 4.168 | 23.270 | 1.00 | 38.81 | A |
| ATOM | 2691 | CD | ARG | A | 353 | 24.503 | 2.685 | 23.524 | 1.00 | 38.69 | A |
| ATOM | 2692 | NE | ARG | A | 353 | 24.489 | 1.938 | 22.272 | 1.00 | 37.26 | A |
| ATOM | 2693 | CZ | ARG | A | 353 | 24.949 | .702 | 22.131 | 1.00 | 36.50 | A |
| ATOM | 2694 | NH1 | ARG | A | 353 | 25.463 | .060 | 23.175 | 1.00 | 36.43 | A |
| ATOM | 2695 | NH2 | ARG | A | 353 | 24.910 | .114 | 20.940 | 1.00 | 33.66 | A |
| ATOM | 2696 | C | ARG | A | 353 | 25.402 | 6.966 | 23.441 | 1.00 | 38.75 | A |
| ATOM | 2697 | O | ARG | A | 353 | 26.491 | 7.322 | 23.889 | 1.00 | 38.89 | A |
| ATOM | 2698 | N | LYS | A | 354 | 25.110 | 6.999 | 22.140 | 1.00 | 38.70 | A |
| ATOM | 2699 | CA | LYS | A | 354 | 26.072 | 7.483 | 21.141 | 1.00 | 38.91 | A |
| ATOM | 2700 | CB | LYS | A | 354 | 25.530 | 7.291 | 19.716 | 1.00 | 39.12 | A |
| ATOM | 2701 | CG | LYS | A | 354 | 25.177 | 5.870 | 19.341 | 1.00 | 41.11 | A |
| ATOM | 2702 | CD | LYS | A | 354 | 26.367 | 4.939 | 19.472 | 1.00 | 41.53 | A |
| ATOM | 2703 | CE | LYS | A | 354 | 25.948 | 3.481 | 19.275 | 1.00 | 43.16 | A |
| ATOM | 2704 | NZ | LYS | A | 354 | 25.334 | 3.220 | 17.934 | 1.00 | 42.80 | A |
| ATOM | 2705 | C | LYS | A | 354 | 26.345 | 8.981 | 21.355 | 1.00 | 39.02 | A |
| ATOM | 2706 | O | LYS | A | 354 | 27.486 | 9.438 | 21.281 | 1.00 | 39.72 | A |
| ATOM | 2707 | N | ALA | A | 355 | 25.284 | 9.740 | 21.610 | 1.00 | 37.76 | A |

APPENDIX A-continued

*Pinus sylvestris* STS

| ATOM | # | TYPE | RES | | | X | Y | Z | OCC | B | |
|------|---|------|-----|---|-----|--------|--------|--------|------|-------|---|
| ATOM | 2708 | CA | ALA | A | 355 | 25.403 | 11.168 | 21.827 | 1.00 | 37.38 | A |
| ATOM | 2709 | CB | ALA | A | 355 | 24.016 | 11.788 | 21.926 | 1.00 | 35.63 | A |
| ATOM | 2710 | C | ALA | A | 355 | 26.214 | 11.460 | 23.093 | 1.00 | 38.06 | A |
| ATOM | 2711 | O | ALA | A | 355 | 27.016 | 12.392 | 23.124 | 1.00 | 39.13 | A |
| ATOM | 2712 | N | SER | A | 356 | 26.003 | 10.660 | 24.134 | 1.00 | 38.24 | A |
| ATOM | 2713 | CA | SER | A | 356 | 26.717 | 10.834 | 25.396 | 1.00 | 38.77 | A |
| ATOM | 2714 | CB | SER | A | 356 | 26.194 | 9.849 | 26.448 | 1.00 | 39.74 | A |
| ATOM | 2715 | OG | SER | A | 356 | 24.828 | 10.086 | 26.754 | 1.00 | 40.96 | A |
| ATOM | 2716 | C | SER | A | 356 | 28.200 | 10.579 | 25.167 | 1.00 | 39.15 | A |
| ATOM | 2717 | O | SER | A | 356 | 29.061 | 11.172 | 25.811 | 1.00 | 40.88 | A |
| ATOM | 2718 | N | LEU | A | 357 | 28.486 | 9.700 | 24.224 | 1.00 | 37.61 | A |
| ATOM | 2719 | CA | LEU | A | 357 | 29.847 | 9.341 | 23.900 | 1.00 | 37.06 | A |
| ATOM | 2720 | CB | LEU | A | 357 | 29.813 | 8.048 | 23.096 | 1.00 | 34.46 | A |
| ATOM | 2721 | CG | LEU | A | 357 | 31.079 | 7.221 | 22.966 | 1.00 | 35.15 | A |
| ATOM | 2722 | CD1 | LEU | A | 357 | 31.762 | 7.084 | 24.316 | 1.00 | 33.86 | A |
| ATOM | 2723 | CD2 | LEU | A | 357 | 30.701 | 5.861 | 22.387 | 1.00 | 35.10 | A |
| ATOM | 2724 | C | LEU | A | 357 | 30.569 | 10.455 | 23.130 | 1.00 | 38.07 | A |
| ATOM | 2725 | O | LEU | A | 357 | 31.624 | 10.935 | 23.554 | 1.00 | 37.75 | A |
| ATOM | 2726 | N | GLN | A | 358 | 29.992 | 10.860 | 22.003 | 1.00 | 39.64 | A |
| ATOM | 2727 | CA | GLN | A | 358 | 30.555 | 11.912 | 21.150 | 1.00 | 41.15 | A |
| ATOM | 2728 | CB | GLN | A | 358 | 29.603 | 12.218 | 19.987 | 1.00 | 43.94 | A |
| ATOM | 2729 | CG | GLN | A | 358 | 29.325 | 11.065 | 19.026 | 1.00 | 46.51 | A |
| ATOM | 2730 | CD | GLN | A | 358 | 30.239 | 11.076 | 17.807 | 1.00 | 49.21 | A |
| ATOM | 2731 | OE1 | GLN | A | 358 | 30.413 | 12.109 | 17.150 | 1.00 | 50.20 | A |
| ATOM | 2732 | NE2 | GLN | A | 358 | 30.817 | 9.923 | 17.491 | 1.00 | 50.25 | A |
| ATOM | 2733 | C | GLN | A | 358 | 30.807 | 13.213 | 21.901 | 1.00 | 41.73 | A |
| ATOM | 2734 | O | GLN | A | 358 | 31.811 | 13.894 | 21.676 | 1.00 | 41.83 | A |
| ATOM | 2735 | N | ASN | A | 359 | 29.885 | 13.557 | 22.792 | 1.00 | 41.97 | A |
| ATOM | 2736 | CA | ASN | A | 359 | 29.978 | 14.795 | 23.549 | 1.00 | 42.02 | A |
| ATOM | 2737 | CB | ASN | A | 359 | 28.585 | 15.207 | 24.022 | 1.00 | 42.01 | A |
| ATOM | 2738 | CG | ASN | A | 359 | 27.546 | 15.082 | 22.924 | 1.00 | 42.17 | A |
| ATOM | 2739 | OD1 | ASN | A | 359 | 27.892 | 14.891 | 21.761 | 1.00 | 44.07 | A |
| ATOM | 2740 | ND2 | ASN | A | 359 | 26.269 | 15.186 | 23.285 | 1.00 | 42.37 | A |
| ATOM | 2741 | C | ASN | A | 359 | 30.930 | 14.721 | 24.728 | 1.00 | 43.88 | A |
| ATOM | 2742 | O | ASN | A | 359 | 31.404 | 15.755 | 25.208 | 1.00 | 45.52 | A |
| ATOM | 2743 | N | GLY | A | 360 | 31.207 | 13.506 | 25.197 | 1.00 | 43.60 | A |
| ATOM | 2744 | CA | GLY | A | 360 | 32.118 | 13.332 | 26.320 | 1.00 | 41.65 | A |
| ATOM | 2745 | C | GLY | A | 360 | 31.478 | 13.426 | 27.695 | 1.00 | 40.93 | A |
| ATOM | 2746 | O | GLY | A | 360 | 32.099 | 13.920 | 28.641 | 1.00 | 39.86 | A |
| ATOM | 2747 | N | CYS | A | 361 | 30.244 | 12.938 | 27.813 | 1.00 | 40.23 | A |
| ATOM | 2748 | CA | CYS | A | 361 | 29.508 | 12.974 | 29.071 | 1.00 | 39.86 | A |
| ATOM | 2749 | CB | CYS | A | 361 | 28.021 | 12.710 | 28.816 | 1.00 | 41.39 | A |
| ATOM | 2750 | SG | CYS | A | 361 | 27.254 | 13.841 | 27.604 | 1.00 | 46.32 | A |
| ATOM | 2751 | C | CYS | A | 361 | 30.043 | 11.968 | 30.083 | 1.00 | 39.25 | A |
| ATOM | 2752 | O | CYS | A | 361 | 30.757 | 11.038 | 29.730 | 1.00 | 39.13 | A |
| ATOM | 2753 | N | SER | A | 362 | 29.680 | 12.163 | 31.344 | 1.00 | 39.05 | A |
| ATOM | 2754 | CA | SER | A | 362 | 30.128 | 11.303 | 32.428 | 1.00 | 38.13 | A |
| ATOM | 2755 | CB | SER | A | 362 | 29.856 | 11.983 | 33.765 | 1.00 | 37.35 | A |
| ATOM | 2756 | OG | SER | A | 362 | 28.480 | 12.268 | 33.906 | 1.00 | 37.41 | A |
| ATOM | 2757 | C | SER | A | 362 | 29.487 | 9.920 | 32.432 | 1.00 | 39.61 | A |
| ATOM | 2758 | O | SER | A | 362 | 30.080 | 8.962 | 32.926 | 1.00 | 39.97 | A |
| ATOM | 2759 | N | THR | A | 363 | 28.273 | 9.814 | 31.902 | 1.00 | 39.04 | A |
| ATOM | 2760 | CA | THR | A | 363 | 27.582 | 8.527 | 31.864 | 1.00 | 38.14 | A |
| ATOM | 2761 | CB | THR | A | 363 | 26.482 | 8.449 | 32.943 | 1.00 | 38.58 | A |
| ATOM | 2762 | OG1 | THR | A | 363 | 25.378 | 9.284 | 32.569 | 1.00 | 34.35 | A |
| ATOM | 2763 | CG2 | THR | A | 363 | 27.028 | 8.903 | 34.289 | 1.00 | 38.03 | A |
| ATOM | 2764 | C | THR | A | 363 | 26.928 | 8.299 | 30.507 | 1.00 | 37.71 | A |
| ATOM | 2765 | O | THR | A | 363 | 26.925 | 9.185 | 29.652 | 1.00 | 38.00 | A |
| ATOM | 2766 | N | THR | A | 364 | 26.373 | 7.107 | 30.312 | 1.00 | 36.07 | A |
| ATOM | 2767 | CA | THR | A | 364 | 25.710 | 6.779 | 29.055 | 1.00 | 34.36 | A |
| ATOM | 2768 | CB | THR | A | 364 | 25.442 | 5.262 | 28.944 | 1.00 | 32.76 | A |
| ATOM | 2769 | OG1 | THR | A | 364 | 25.132 | 4.734 | 30.238 | 1.00 | 31.72 | A |
| ATOM | 2770 | CG2 | THR | A | 364 | 26.657 | 4.547 | 28.389 | 1.00 | 33.27 | A |
| ATOM | 2771 | C | THR | A | 364 | 24.397 | 7.539 | 28.917 | 1.00 | 34.89 | A |
| ATOM | 2772 | O | THR | A | 364 | 23.788 | 7.552 | 27.855 | 1.00 | 33.55 | A |
| ATOM | 2773 | N | GLY | A | 365 | 23.971 | 8.174 | 30.001 | 1.00 | 37.02 | A |
| ATOM | 2774 | CA | GLY | A | 365 | 22.738 | 8.939 | 29.985 | 1.00 | 39.62 | A |
| ATOM | 2775 | C | GLY | A | 365 | 23.031 | 10.424 | 29.873 | 1.00 | 41.66 | A |
| ATOM | 2776 | O | GLY | A | 365 | 22.526 | 11.231 | 30.655 | 1.00 | 41.20 | A |
| ATOM | 2777 | N | GLU | A | 366 | 23.864 | 10.776 | 28.899 | 1.00 | 42.25 | A |
| ATOM | 2778 | CA | GLU | A | 366 | 24.248 | 12.161 | 28.660 | 1.00 | 44.72 | A |
| ATOM | 2779 | CB | GLU | A | 366 | 23.085 | 12.903 | 27.996 | 1.00 | 47.19 | A |
| ATOM | 2780 | CG | GLU | A | 366 | 22.598 | 12.219 | 26.721 | 1.00 | 52.43 | A |
| ATOM | 2781 | CD | GLU | A | 366 | 21.451 | 12.950 | 26.035 | 1.00 | 56.02 | A |
| ATOM | 2782 | OE1 | GLU | A | 366 | 20.404 | 13.181 | 26.686 | 1.00 | 56.50 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 2783 | OE2 | GLU | A | 366 | 21.600 | 13.285 | 24.837 | 1.00 | 57.47 | A |
| ATOM | 2784 | C | GLU | A | 366 | 24.700 | 12.887 | 29.933 | 1.00 | 44.50 | A |
| ATOM | 2785 | O | GLU | A | 366 | 24.523 | 14.100 | 30.064 | 1.00 | 42.81 | A |
| ATOM | 2786 | N | GLY | A | 367 | 25.279 | 12.134 | 30.869 | 1.00 | 43.97 | A |
| ATOM | 2787 | CA | GLY | A | 367 | 25.770 | 12.721 | 32.106 | 1.00 | 42.81 | A |
| ATOM | 2788 | C | GLY | A | 367 | 24.962 | 12.462 | 33.368 | 1.00 | 40.85 | A |
| ATOM | 2789 | O | GLY | A | 367 | 25.489 | 12.538 | 34.478 | 1.00 | 40.69 | A |
| ATOM | 2790 | N | LEU | A | 368 | 23.683 | 12.158 | 33.204 | 1.00 | 39.07 | A |
| ATOM | 2791 | CA | LEU | A | 368 | 22.815 | 11.904 | 34.340 | 1.00 | 37.27 | A |
| ATOM | 2792 | CB | LEU | A | 368 | 21.374 | 12.223 | 33.947 | 1.00 | 37.69 | A |
| ATOM | 2793 | CG | LEU | A | 368 | 21.029 | 13.698 | 33.694 | 1.00 | 38.92 | A |
| ATOM | 2794 | CD1 | LEU | A | 368 | 22.240 | 14.489 | 33.220 | 1.00 | 38.52 | A |
| ATOM | 2795 | CD2 | LEU | A | 368 | 19.906 | 13.766 | 32.678 | 1.00 | 37.84 | A |
| ATOM | 2796 | C | LEU | A | 368 | 22.942 | 10.458 | 34.831 | 1.00 | 37.05 | A |
| ATOM | 2797 | O | LEU | A | 368 | 23.465 | 9.590 | 34.127 | 1.00 | 36.30 | A |
| ATOM | 2798 | N | GLU | A | 369 | 22.458 | 10.206 | 36.041 | 1.00 | 36.23 | A |
| ATOM | 2799 | CA | GLU | A | 369 | 22.539 | 8.883 | 36.641 | 1.00 | 37.09 | A |
| ATOM | 2800 | CB | GLU | A | 369 | 22.701 | 9.009 | 38.157 | 1.00 | 41.29 | A |
| ATOM | 2801 | CG | GLU | A | 369 | 23.398 | 10.294 | 38.642 | 1.00 | 46.01 | A |
| ATOM | 2802 | CD | GLU | A | 369 | 22.517 | 11.551 | 38.547 | 1.00 | 47.44 | A |
| ATOM | 2803 | OE1 | GLU | A | 369 | 22.444 | 12.167 | 37.454 | 1.00 | 44.74 | A |
| ATOM | 2804 | OE2 | GLU | A | 369 | 21.894 | 11.914 | 39.578 | 1.00 | 49.56 | A |
| ATOM | 2805 | C | GLU | A | 369 | 21.327 | 7.999 | 36.340 | 1.00 | 35.30 | A |
| ATOM | 2806 | O | GLU | A | 369 | 21.481 | 6.847 | 35.939 | 1.00 | 35.73 | A |
| ATOM | 2807 | N | MET | A | 370 | 20.130 | 8.540 | 36.549 | 1.00 | 32.75 | A |
| ATOM | 2808 | CA | MET | A | 370 | 18.886 | 7.808 | 36.308 | 1.00 | 31.28 | A |
| ATOM | 2809 | CB | MET | A | 370 | 18.032 | 7.785 | 37.584 | 1.00 | 31.18 | A |
| ATOM | 2810 | CG | MET | A | 370 | 18.348 | 6.665 | 38.567 | 1.00 | 29.86 | A |
| ATOM | 2811 | SD | MET | A | 370 | 17.143 | 6.652 | 39.910 | 1.00 | 28.54 | A |
| ATOM | 2812 | CE | MET | A | 370 | 17.895 | 7.805 | 40.972 | 1.00 | 31.46 | A |
| ATOM | 2813 | C | MET | A | 370 | 18.056 | 8.413 | 35.159 | 1.00 | 31.15 | A |
| ATOM | 2814 | O | MET | A | 370 | 18.125 | 9.615 | 34.893 | 1.00 | 29.39 | A |
| ATOM | 2815 | N | GLY | A | 371 | 17.268 | 7.574 | 34.491 | 1.00 | 28.64 | A |
| ATOM | 2816 | CA | GLY | A | 371 | 16.449 | 8.051 | 33.388 | 1.00 | 28.20 | A |
| ATOM | 2817 | C | GLY | A | 371 | 15.117 | 7.328 | 33.246 | 1.00 | 26.64 | A |
| ATOM | 2818 | O | GLY | A | 371 | 14.882 | 6.297 | 33.879 | 1.00 | 24.42 | A |
| ATOM | 2819 | N | VAL | A | 372 | 14.236 | 7.861 | 32.408 | 1.00 | 25.98 | A |
| ATOM | 2820 | CA | VAL | A | 372 | 12.929 | 7.253 | 32.223 | 1.00 | 25.78 | A |
| ATOM | 2821 | CB | VAL | A | 372 | 11.784 | 8.175 | 32.695 | 1.00 | 25.32 | A |
| ATOM | 2822 | CG1 | VAL | A | 372 | 11.584 | 9.324 | 31.708 | 1.00 | 24.95 | A |
| ATOM | 2823 | CG2 | VAL | A | 372 | 10.496 | 7.371 | 32.830 | 1.00 | 25.78 | A |
| ATOM | 2824 | C | VAL | A | 372 | 12.670 | 6.920 | 30.776 | 1.00 | 26.21 | A |
| ATOM | 2825 | O | VAL | A | 372 | 13.163 | 7.587 | 29.869 | 1.00 | 27.38 | A |
| ATOM | 2826 | N | LEU | A | 373 | 11.892 | 5.873 | 30.566 | 1.00 | 27.08 | A |
| ATOM | 2827 | CA | LEU | A | 373 | 11.536 | 5.466 | 29.223 | 1.00 | 27.81 | A |
| ATOM | 2828 | CB | LEU | A | 373 | 12.218 | 4.149 | 28.866 | 1.00 | 29.56 | A |
| ATOM | 2829 | CG | LEU | A | 373 | 11.907 | 3.634 | 27.459 | 1.00 | 31.75 | A |
| ATOM | 2830 | CD1 | LEU | A | 373 | 13.171 | 3.065 | 26.836 | 1.00 | 29.26 | A |
| ATOM | 2831 | CD2 | LEU | A | 373 | 10.791 | 2.591 | 27.531 | 1.00 | 31.43 | A |
| ATOM | 2832 | C | LEU | A | 373 | 10.026 | 5.317 | 29.194 | 1.00 | 27.20 | A |
| ATOM | 2833 | O | LEU | A | 373 | 9.427 | 4.811 | 30.148 | 1.00 | 26.34 | A |
| ATOM | 2834 | N | PHE | A | 374 | 9.418 | 5.779 | 28.106 | 1.00 | 26.82 | A |
| ATOM | 2835 | CA | PHE | A | 374 | 7.972 | 5.712 | 27.942 | 1.00 | 27.12 | A |
| ATOM | 2836 | CB | PHE | A | 374 | 7.369 | 7.108 | 28.029 | 1.00 | 28.61 | A |
| ATOM | 2837 | CG | PHE | A | 374 | 7.242 | 7.630 | 29.421 | 1.00 | 31.11 | A |
| ATOM | 2838 | CD1 | PHE | A | 374 | 6.239 | 7.159 | 30.263 | 1.00 | 32.22 | A |
| ATOM | 2839 | CD2 | PHE | A | 374 | 8.110 | 8.609 | 29.891 | 1.00 | 31.24 | A |
| ATOM | 2840 | CE1 | PHE | A | 374 | 6.093 | 7.655 | 31.558 | 1.00 | 32.81 | A |
| ATOM | 2841 | CE2 | PHE | A | 374 | 7.977 | 9.118 | 31.187 | 1.00 | 33.42 | A |
| ATOM | 2842 | CZ | PHE | A | 374 | 6.960 | 8.637 | 32.024 | 1.00 | 33.49 | A |
| ATOM | 2843 | C | PHE | A | 374 | 7.537 | 5.087 | 26.622 | 1.00 | 28.09 | A |
| ATOM | 2844 | O | PHE | A | 374 | 8.186 | 5.247 | 25.592 | 1.00 | 28.61 | A |
| ATOM | 2845 | N | GLY | A | 375 | 6.423 | 4.370 | 26.671 | 1.00 | 27.67 | A |
| ATOM | 2846 | CA | GLY | A | 375 | 5.870 | 3.765 | 25.480 | 1.00 | 25.79 | A |
| ATOM | 2847 | C | GLY | A | 375 | 4.377 | 4.025 | 25.530 | 1.00 | 25.72 | A |
| ATOM | 2848 | O | GLY | A | 375 | 3.764 | 3.878 | 26.583 | 1.00 | 26.86 | A |
| ATOM | 2849 | N | PHE | A | 376 | 3.789 | 4.430 | 24.410 | 1.00 | 27.30 | A |
| ATOM | 2850 | CA | PHE | A | 376 | 2.349 | 4.694 | 24.363 | 1.00 | 26.31 | A |
| ATOM | 2851 | CB | PHE | A | 376 | 2.061 | 6.168 | 24.072 | 1.00 | 27.66 | A |
| ATOM | 2852 | CG | PHE | A | 376 | 2.995 | 7.120 | 24.748 | 1.00 | 28.81 | A |
| ATOM | 2853 | CD1 | PHE | A | 376 | 3.222 | 7.044 | 26.115 | 1.00 | 30.56 | A |
| ATOM | 2854 | CD2 | PHE | A | 376 | 3.628 | 8.117 | 24.019 | 1.00 | 28.26 | A |
| ATOM | 2855 | CE1 | PHE | A | 376 | 4.069 | 7.949 | 26.751 | 1.00 | 30.43 | A |
| ATOM | 2856 | CE2 | PHE | A | 376 | 4.475 | 9.026 | 24.643 | 1.00 | 29.11 | A |
| ATOM | 2857 | CZ | PHE | A | 376 | 4.698 | 8.943 | 26.011 | 1.00 | 29.04 | A |

APPENDIX A-continued

*Pinus sylvestris* STS

| ATOM | # | TYPE | RES | | | X | Y | Z | OCC | B | |
|---|---|---|---|---|---|---|---|---|---|---|---|
| ATOM | 2858 | C | PHE | A | 376 | 1.708 | 3.870 | 23.259 | 1.00 | 25.27 | A |
| ATOM | 2859 | O | PHE | A | 376 | 2.239 | 3.781 | 22.156 | 1.00 | 25.32 | A |
| ATOM | 2860 | N | GLY | A | 377 | .555 | 3.284 | 23.552 | 1.00 | 25.39 | A |
| ATOM | 2861 | CA | GLY | A | 377 | −.127 | 2.502 | 22.545 | 1.00 | 24.04 | A |
| ATOM | 2862 | C | GLY | A | 377 | −1.590 | 2.234 | 22.854 | 1.00 | 23.88 | A |
| ATOM | 2863 | O | GLY | A | 377 | −2.155 | 2.812 | 23.785 | 1.00 | 20.92 | A |
| ATOM | 2864 | N | PRO | A | 378 | −2.225 | 1.347 | 22.068 | 1.00 | 24.59 | A |
| ATOM | 2865 | CD | PRO | A | 378 | −1.538 | .702 | 20.934 | 1.00 | 22.15 | A |
| ATOM | 2866 | CA | PRO | A | 378 | −3.617 | .900 | 22.134 | 1.00 | 26.44 | A |
| ATOM | 2867 | CB | PRO | A | 378 | −3.608 | −.340 | 21.259 | 1.00 | 23.96 | A |
| ATOM | 2868 | CG | PRO | A | 378 | −2.682 | .086 | 20.164 | 1.00 | 23.62 | A |
| ATOM | 2869 | C | PRO | A | 378 | −4.134 | .609 | 23.529 | 1.00 | 28.16 | A |
| ATOM | 2870 | O | PRO | A | 378 | −3.376 | .220 | 24.411 | 1.00 | 27.70 | A |
| ATOM | 2871 | N | GLY | A | 379 | −5.446 | .775 | 23.690 | 1.00 | 31.23 | A |
| ATOM | 2872 | CA | GLY | A | 379 | −6.111 | .572 | 24.963 | 1.00 | 33.70 | A |
| ATOM | 2873 | C | GLY | A | 379 | −5.864 | 1.875 | 25.669 | 1.00 | 36.78 | A |
| ATOM | 2874 | O | GLY | A | 379 | −6.661 | 2.378 | 26.468 | 1.00 | 35.21 | A |
| ATOM | 2875 | N | LEU | A | 380 | −4.724 | 2.421 | 25.259 | 1.00 | 38.76 | A |
| ATOM | 2876 | CA | LEU | A | 380 | −4.119 | 3.652 | 25.716 | 1.00 | 37.20 | A |
| ATOM | 2877 | CB | LEU | A | 380 | −5.125 | 4.780 | 25.869 | 1.00 | 38.70 | A |
| ATOM | 2878 | CG | LEU | A | 380 | −4.492 | 6.083 | 25.356 | 1.00 | 41.13 | A |
| ATOM | 2879 | CD1 | LEU | A | 380 | −3.071 | 6.240 | 25.923 | 1.00 | 42.02 | A |
| ATOM | 2880 | CD2 | LEU | A | 380 | −4.421 | 6.061 | 23.837 | 1.00 | 40.14 | A |
| ATOM | 2881 | C | LEU | A | 380 | −3.443 | 3.328 | 27.021 | 1.00 | 34.99 | A |
| ATOM | 2882 | O | LEU | A | 380 | −3.848 | 3.763 | 28.098 | 1.00 | 34.48 | A |
| ATOM | 2883 | N | THR | A | 381 | −2.406 | 2.514 | 26.893 | 1.00 | 31.04 | A |
| ATOM | 2884 | CA | THR | A | 381 | −1.639 | 2.088 | 28.034 | 1.00 | 30.02 | A |
| ATOM | 2885 | CB | THR | A | 381 | −1.361 | .549 | 28.000 | 1.00 | 29.09 | A |
| ATOM | 2886 | OG1 | THR | A | 381 | −.002 | .288 | 27.613 | 1.00 | 28.59 | A |
| ATOM | 2887 | CG2 | THR | A | 381 | −2.282 | −.117 | 27.011 | 1.00 | 26.08 | A |
| ATOM | 2888 | C | THR | A | 381 | −.355 | 2.860 | 27.933 | 1.00 | 29.20 | A |
| ATOM | 2889 | O | THR | A | 381 | −.025 | 3.380 | 26.874 | 1.00 | 29.92 | A |
| ATOM | 2890 | N | ILE | A | 382 | .358 | 2.951 | 29.042 | 1.00 | 29.88 | A |
| ATOM | 2891 | CA | ILE | A | 382 | 1.622 | 3.663 | 29.073 | 1.00 | 28.14 | A |
| ATOM | 2892 | CB | ILE | A | 382 | 1.520 | 4.957 | 29.914 | 1.00 | 26.61 | A |
| ATOM | 2893 | CG2 | ILE | A | 382 | 2.809 | 5.750 | 29.803 | 1.00 | 28.80 | A |
| ATOM | 2894 | CG1 | ILE | A | 382 | .324 | 5.800 | 29.461 | 1.00 | 29.96 | A |
| ATOM | 2895 | CD1 | ILE | A | 382 | .455 | 6.415 | 28.079 | 1.00 | 29.52 | A |
| ATOM | 2896 | C | ILE | A | 382 | 2.607 | 2.729 | 29.759 | 1.00 | 27.30 | A |
| ATOM | 2897 | O | ILE | A | 382 | 2.322 | 2.189 | 30.829 | 1.00 | 26.16 | A |
| ATOM | 2898 | N | GLU | A | 383 | 3.747 | 2.502 | 29.130 | 1.00 | 27.01 | A |
| ATOM | 2899 | CA | GLU | A | 383 | 4.758 | 1.667 | 29.753 | 1.00 | 28.35 | A |
| ATOM | 2900 | CB | GLU | A | 383 | 5.385 | .701 | 28.751 | 1.00 | 28.01 | A |
| ATOM | 2901 | CG | GLU | A | 383 | 4.434 | −.408 | 28.312 | 1.00 | 29.73 | A |
| ATOM | 2902 | CD | GLU | A | 383 | 4.552 | −1.679 | 29.141 | 1.00 | 29.55 | A |
| ATOM | 2903 | OE1 | GLU | A | 383 | 5.000 | −1.623 | 30.304 | 1.00 | 30.70 | A |
| ATOM | 2904 | OE2 | GLU | A | 383 | 4.179 | −2.748 | 28.626 | 1.00 | 31.96 | A |
| ATOM | 2905 | C | GLU | A | 383 | 5.792 | 2.644 | 30.261 | 1.00 | 28.17 | A |
| ATOM | 2906 | O | GLU | A | 383 | 6.263 | 3.496 | 29.523 | 1.00 | 28.48 | A |
| ATOM | 2907 | N | THR | A | 384 | 6.098 | 2.535 | 31.545 | 1.00 | 29.87 | A |
| ATOM | 2908 | CA | THR | A | 384 | 7.083 | 3.379 | 32.192 | 1.00 | 29.87 | A |
| ATOM | 2909 | CB | THR | A | 384 | 6.516 | 4.060 | 33.458 | 1.00 | 31.48 | A |
| ATOM | 2910 | OG1 | THR | A | 384 | 5.424 | 4.922 | 33.099 | 1.00 | 35.27 | A |
| ATOM | 2911 | CG2 | THR | A | 384 | 7.617 | 4.869 | 34.160 | 1.00 | 29.36 | A |
| ATOM | 2912 | C | THR | A | 384 | 8.240 | 2.496 | 32.620 | 1.00 | 29.37 | A |
| ATOM | 2913 | O | THR | A | 384 | 8.040 | 1.476 | 33.286 | 1.00 | 27.65 | A |
| ATOM | 2914 | N | VAL | A | 385 | 9.447 | 2.888 | 32.230 | 1.00 | 28.94 | A |
| ATOM | 2915 | CA | VAL | A | 385 | 10.632 | 2.137 | 32.603 | 1.00 | 28.87 | A |
| ATOM | 2916 | CB | VAL | A | 385 | 11.220 | 1.386 | 31.392 | 1.00 | 26.12 | A |
| ATOM | 2917 | CG1 | VAL | A | 385 | 12.213 | .339 | 31.862 | 1.00 | 28.78 | A |
| ATOM | 2918 | CG2 | VAL | A | 385 | 10.125 | .744 | 30.601 | 1.00 | 25.84 | A |
| ATOM | 2919 | C | VAL | A | 385 | 11.702 | 3.074 | 33.177 | 1.00 | 30.37 | A |
| ATOM | 2920 | O | VAL | A | 385 | 12.218 | 3.957 | 32.475 | 1.00 | 31.40 | A |
| ATOM | 2921 | N | VAL | A | 386 | 12.014 | 2.900 | 34.461 | 1.00 | 31.00 | A |
| ATOM | 2922 | CA | VAL | A | 386 | 13.044 | 3.709 | 35.104 | 1.00 | 30.62 | A |
| ATOM | 2923 | CB | VAL | A | 386 | 12.781 | 3.842 | 36.636 | 1.00 | 30.34 | A |
| ATOM | 2924 | CG1 | VAL | A | 386 | 12.562 | 2.499 | 37.232 | 1.00 | 31.84 | A |
| ATOM | 2925 | CG2 | VAL | A | 386 | 13.953 | 4.525 | 37.332 | 1.00 | 31.28 | A |
| ATOM | 2926 | C | VAL | A | 386 | 14.377 | 3.012 | 34.818 | 1.00 | 30.23 | A |
| ATOM | 2927 | O | VAL | A | 386 | 14.593 | 1.855 | 35.190 | 1.00 | 30.15 | A |
| ATOM | 2928 | N | LEU | A | 387 | 15.254 | 3.725 | 34.120 | 1.00 | 30.35 | A |
| ATOM | 2929 | CA | LEU | A | 387 | 16.556 | 3.213 | 33.724 | 1.00 | 29.55 | A |
| ATOM | 2930 | CB | LEU | A | 387 | 16.787 | 3.490 | 32.244 | 1.00 | 27.05 | A |
| ATOM | 2931 | CG | LEU | A | 387 | 15.906 | 2.768 | 31.236 | 1.00 | 24.51 | A |
| ATOM | 2932 | CD1 | LEU | A | 387 | 16.047 | 3.379 | 29.854 | 1.00 | 23.58 | A |

APPENDIX A-continued

*Pinus sylvestris* STS

| ATOM | # | TYPE | RES | | | X | Y | Z | OCC | B | |
|------|---|------|-----|---|---|---|---|---|-----|---|---|
| ATOM | 2933 | CD2 | LEU | A | 387 | 16.310 | 1.333 | 31.215 | 1.00 | 23.31 | A |
| ATOM | 2934 | C | LEU | A | 387 | 17.722 | 3.801 | 34.498 | 1.00 | 32.46 | A |
| ATOM | 2935 | O | LEU | A | 387 | 17.719 | 4.977 | 34.866 | 1.00 | 33.52 | A |
| ATOM | 2936 | N | LYS | A | 388 | 18.726 | 2.965 | 34.724 | 1.00 | 34.19 | A |
| ATOM | 2937 | CA | LYS | A | 388 | 19.938 | 3.373 | 35.414 | 1.00 | 35.44 | A |
| ATOM | 2938 | CB | LYS | A | 388 | 20.313 | 2.348 | 36.483 | 1.00 | 37.24 | A |
| ATOM | 2939 | CG | LYS | A | 388 | 20.113 | 2.838 | 37.904 | 1.00 | 37.74 | A |
| ATOM | 2940 | CD | LYS | A | 388 | 21.123 | 3.910 | 38.251 | 1.00 | 37.39 | A |
| ATOM | 2941 | CE | LYS | A | 388 | 22.518 | 3.331 | 38.292 | 1.00 | 36.28 | A |
| ATOM | 2942 | NZ | LYS | A | 388 | 22.602 | 2.295 | 39.339 | 1.00 | 37.97 | A |
| ATOM | 2943 | C | LYS | A | 388 | 21.056 | 3.445 | 34.379 | 1.00 | 37.08 | A |
| ATOM | 2944 | O | LYS | A | 388 | 21.298 | 2.484 | 33.633 | 1.00 | 36.42 | A |
| ATOM | 2945 | N | SER | A | 389 | 21.726 | 4.590 | 34.320 | 1.00 | 36.60 | A |
| ATOM | 2946 | CA | SER | A | 389 | 22.825 | 4.769 | 33.387 | 1.00 | 36.00 | A |
| ATOM | 2947 | CB | SER | A | 389 | 23.022 | 6.259 | 33.114 | 1.00 | 37.01 | A |
| ATOM | 2948 | OG | SER | A | 389 | 24.013 | 6.455 | 32.130 | 1.00 | 38.47 | A |
| ATOM | 2949 | C | SER | A | 389 | 24.100 | 4.173 | 33.995 | 1.00 | 35.19 | A |
| ATOM | 2950 | O | SER | A | 389 | 24.103 | 3.753 | 35.152 | 1.00 | 32.14 | A |
| ATOM | 2951 | N | VAL | A | 390 | 25.171 | 4.125 | 33.208 | 1.00 | 36.45 | A |
| ATOM | 2952 | CA | VAL | A | 390 | 26.465 | 3.617 | 33.677 | 1.00 | 38.33 | A |
| ATOM | 2953 | CB | VAL | A | 390 | 26.885 | 2.274 | 32.987 | 1.00 | 39.52 | A |
| ATOM | 2954 | CG1 | VAL | A | 390 | 25.856 | 1.194 | 33.265 | 1.00 | 38.28 | A |
| ATOM | 2955 | CG2 | VAL | A | 390 | 27.069 | 2.473 | 31.481 | 1.00 | 38.97 | A |
| ATOM | 2956 | C | VAL | A | 390 | 27.521 | 4.669 | 33.355 | 1.00 | 39.34 | A |
| ATOM | 2957 | O | VAL | A | 390 | 27.405 | 5.399 | 32.367 | 1.00 | 39.68 | A |
| ATOM | 2958 | N | PRO | A | 391 | 28.567 | 4.767 | 34.189 | 1.00 | 40.39 | A |
| ATOM | 2959 | CD | PRO | A | 391 | 28.836 | 4.016 | 35.428 | 1.00 | 39.55 | A |
| ATOM | 2960 | CA | PRO | A | 391 | 29.614 | 5.759 | 33.937 | 1.00 | 40.79 | A |
| ATOM | 2961 | CB | PRO | A | 391 | 30.398 | 5.773 | 35.248 | 1.00 | 39.73 | A |
| ATOM | 2962 | CG | PRO | A | 391 | 30.282 | 4.369 | 35.712 | 1.00 | 39.36 | A |
| ATOM | 2963 | C | PRO | A | 391 | 30.473 | 5.395 | 32.736 | 1.00 | 42.01 | A |
| ATOM | 2964 | O | PRO | A | 391 | 30.563 | 4.223 | 32.354 | 1.00 | 42.53 | A |
| ATOM | 2965 | N | ILE | A | 392 | 31.084 | 6.414 | 32.135 | 1.00 | 43.00 | A |
| ATOM | 2966 | CA | ILE | A | 392 | 31.949 | 6.240 | 30.978 | 1.00 | 43.81 | A |
| ATOM | 2967 | CB | ILE | A | 392 | 31.547 | 7.201 | 29.836 | 1.00 | 43.31 | A |
| ATOM | 2968 | CG2 | ILE | A | 392 | 32.465 | 7.006 | 28.631 | 1.00 | 43.26 | A |
| ATOM | 2969 | CG1 | ILE | A | 392 | 30.100 | 6.932 | 29.424 | 1.00 | 43.24 | A |
| ATOM | 2970 | CD1 | ILE | A | 392 | 29.649 | 7.728 | 28.224 | 1.00 | 43.15 | A |
| ATOM | 2971 | C | ILE | A | 392 | 33.389 | 6.526 | 31.391 | 1.00 | 46.16 | A |
| ATOM | 2972 | O | ILE | A | 392 | 33.938 | 7.571 | 31.052 | 1.00 | 46.65 | A |
| ATOM | 2973 | N | GLN | A | 393 | 33.978 | 5.586 | 32.130 | 1.00 | 48.86 | A |
| ATOM | 2974 | CA | GLN | A | 393 | 35.349 | 5.683 | 32.631 | 1.00 | 52.16 | A |
| ATOM | 2975 | CB | GLN | A | 393 | 35.644 | 7.096 | 33.149 | 1.00 | 54.15 | A |
| ATOM | 2976 | CG | GLN | A | 393 | 36.288 | 8.014 | 32.121 | 1.00 | 56.36 | A |
| ATOM | 2977 | CD | GLN | A | 393 | 37.683 | 7.566 | 31.722 | 1.00 | 57.85 | A |
| ATOM | 2978 | OE1 | GLN | A | 393 | 37.946 | 6.370 | 31.554 | 1.00 | 57.70 | A |
| ATOM | 2979 | NE2 | GLN | A | 393 | 38.585 | 8.529 | 31.553 | 1.00 | 58.57 | A |
| ATOM | 2980 | C | GLN | A | 393 | 35.601 | 4.682 | 33.756 | 1.00 | 53.17 | A |
| ATOM | 2981 | O | GLN | A | 393 | 34.634 | 4.021 | 34.186 | 1.00 | 54.06 | A |
| ATOM | 2982 | OXT | GLN | A | 393 | 36.764 | 4.579 | 34.205 | 1.00 | 54.19 | A |

APPENDIX B

*Arachis hypogaea* STS

| ATOM | # | TYPE | RES | | | X | Y | Z | OCC | B | |
|------|---|------|-----|---|---|---|---|---|-----|---|---|
| ATOM | 1 | CB | VAL | A | 8 | 6.075 | 38.920 | 83.477 | 1.00 | 46.46 | A |
| ATOM | 2 | CG1 | VAL | A | 8 | 5.638 | 40.112 | 82.631 | 1.00 | 47.07 | A |
| ATOM | 3 | CG2 | VAL | A | 8 | 6.142 | 37.664 | 82.618 | 1.00 | 46.26 | A |
| ATOM | 4 | C | VAL | A | 8 | 7.420 | 40.545 | 84.830 | 1.00 | 43.72 | A |
| ATOM | 5 | O | VAL | A | 8 | 7.656 | 41.588 | 84.215 | 1.00 | 43.86 | A |
| ATOM | 6 | N | VAL | A | 8 | 7.847 | 38.099 | 85.052 | 1.00 | 45.93 | A |
| ATOM | 7 | CA | VAL | A | 8 | 7.460 | 39.195 | 84.117 | 1.00 | 45.01 | A |
| ATOM | 8 | N | GLN | A | 9 | 7.122 | 40.527 | 86.125 | 1.00 | 40.46 | A |
| ATOM | 9 | CA | GLN | A | 9 | 7.067 | 41.763 | 86.892 | 1.00 | 36.43 | A |
| ATOM | 10 | CB | GLN | A | 9 | 5.854 | 41.761 | 87.831 | 1.00 | 38.00 | A |
| ATOM | 11 | CG | GLN | A | 9 | 5.885 | 40.706 | 88.921 | 1.00 | 41.02 | A |
| ATOM | 12 | CD | GLN | A | 9 | 4.619 | 40.706 | 89.764 | 1.00 | 43.48 | A |
| ATOM | 13 | OE1 | GLN | A | 9 | 3.533 | 40.370 | 89.283 | 1.00 | 43.47 | A |
| ATOM | 14 | NE2 | GLN | A | 9 | 4.752 | 41.091 | 91.029 | 1.00 | 46.37 | A |
| ATOM | 15 | C | GLN | A | 9 | 8.354 | 41.972 | 87.688 | 1.00 | 32.96 | A |

APPENDIX B-continued

*Arachis hypogaea* STS

| ATOM | # | TYPE | RES | | | X | Y | Z | OCC | B | |
|------|---|------|-----|---|---|---|---|---|-----|---|---|
| ATOM | 16 | O | GLN | A | 9 | 8.509 | 42.974 | 88.380 | 1.00 | 30.32 | A |
| ATOM | 17 | N | ARG | A | 10 | 9.278 | 41.024 | 87.575 | 1.00 | 29.75 | A |
| ATOM | 18 | CA | ARG | A | 10 | 10.556 | 41.114 | 88.277 | 1.00 | 28.77 | A |
| ATOM | 19 | CB | ARG | A | 10 | 10.931 | 39.750 | 88.860 | 1.00 | 30.32 | A |
| ATOM | 20 | CG | ARG | A | 10 | 11.250 | 38.689 | 87.819 | 1.00 | 31.19 | A |
| ATOM | 21 | CD | ARG | A | 10 | 11.006 | 37.297 | 88.382 | 1.00 | 33.88 | A |
| ATOM | 22 | NE | ARG | A | 10 | 11.685 | 37.098 | 89.662 | 1.00 | 34.38 | A |
| ATOM | 23 | CZ | ARG | A | 10 | 11.524 | 36.031 | 90.441 | 1.00 | 35.70 | A |
| ATOM | 24 | NH1 | ARG | A | 10 | 10.700 | 35.053 | 90.078 | 1.00 | 34.56 | A |
| ATOM | 25 | NH2 | ARG | A | 10 | 12.189 | 35.942 | 91.587 | 1.00 | 30.48 | A |
| ATOM | 26 | C | ARG | A | 10 | 11.643 | 41.582 | 87.314 | 1.00 | 27.02 | A |
| ATOM | 27 | O | ARG | A | 10 | 11.532 | 41.382 | 86.107 | 1.00 | 24.60 | A |
| ATOM | 28 | N | ALA | A | 11 | 12.686 | 42.215 | 87.848 | 1.00 | 24.89 | A |
| ATOM | 29 | CA | ALA | A | 11 | 13.791 | 42.692 | 87.023 | 1.00 | 23.28 | A |
| ATOM | 30 | CB | ALA | A | 11 | 14.584 | 43.761 | 87.765 | 1.00 | 23.85 | A |
| ATOM | 31 | C | ALA | A | 11 | 14.689 | 41.510 | 86.674 | 1.00 | 24.68 | A |
| ATOM | 32 | O | ALA | A | 11 | 14.634 | 40.467 | 87.332 | 1.00 | 23.55 | A |
| ATOM | 33 | N | GLU | A | 12 | 15.521 | 41.674 | 85.649 | 1.00 | 24.82 | A |
| ATOM | 34 | CA | GLU | A | 12 | 16.402 | 40.597 | 85.208 | 1.00 | 27.69 | A |
| ATOM | 35 | CB | GLU | A | 12 | 16.503 | 40.599 | 83.682 | 1.00 | 29.83 | A |
| ATOM | 36 | CG | GLU | A | 12 | 15.246 | 40.125 | 82.979 | 1.00 | 36.49 | A |
| ATOM | 37 | CD | GLU | A | 12 | 14.809 | 38.741 | 83.440 | 1.00 | 39.68 | A |
| ATOM | 38 | OE1 | GLU | A | 12 | 14.131 | 38.637 | 84.489 | 1.00 | 42.41 | A |
| ATOM | 39 | OE2 | GLU | A | 12 | 15.155 | 37.754 | 82.756 | 1.00 | 42.52 | A |
| ATOM | 40 | C | GLU | A | 12 | 17.813 | 40.577 | 85.783 | 1.00 | 27.17 | A |
| ATOM | 41 | O | GLU | A | 12 | 18.260 | 39.553 | 86.306 | 1.00 | 28.17 | A |
| ATOM | 42 | N | GLY | A | 13 | 18.515 | 41.699 | 85.673 | 1.00 | 23.56 | A |
| ATOM | 43 | CA | GLY | A | 13 | 19.887 | 41.758 | 86.147 | 1.00 | 22.50 | A |
| ATOM | 44 | C | GLY | A | 13 | 20.132 | 42.174 | 87.584 | 1.00 | 19.30 | A |
| ATOM | 45 | O | GLY | A | 13 | 19.203 | 42.469 | 88.335 | 1.00 | 18.70 | A |
| ATOM | 46 | N | PRO | A | 14 | 21.402 | 42.203 | 87.997 | 1.00 | 17.89 | A |
| ATOM | 47 | CD | PRO | A | 14 | 22.595 | 41.786 | 87.239 | 1.00 | 19.36 | A |
| ATOM | 48 | CA | PRO | A | 14 | 21.751 | 42.591 | 89.366 | 1.00 | 17.15 | A |
| ATOM | 49 | CB | PRO | A | 14 | 23.218 | 42.177 | 89.475 | 1.00 | 18.61 | A |
| ATOM | 50 | CG | PRO | A | 14 | 23.721 | 42.365 | 88.068 | 1.00 | 19.45 | A |
| ATOM | 51 | C | PRO | A | 14 | 21.546 | 44.085 | 89.615 | 1.00 | 15.71 | A |
| ATOM | 52 | O | PRO | A | 14 | 21.722 | 44.896 | 88.710 | 1.00 | 16.79 | A |
| ATOM | 53 | N | ALA | A | 15 | 21.153 | 44.433 | 90.837 | 1.00 | 13.60 | A |
| ATOM | 54 | CA | ALA | A | 15 | 20.950 | 45.831 | 91.205 | 1.00 | 13.69 | A |
| ATOM | 55 | CB | ALA | A | 15 | 20.537 | 45.933 | 92.662 | 1.00 | 16.43 | A |
| ATOM | 56 | C | ALA | A | 15 | 22.270 | 46.562 | 90.973 | 1.00 | 14.74 | A |
| ATOM | 57 | O | ALA | A | 15 | 23.349 | 46.064 | 91.325 | 1.00 | 15.66 | A |
| ATOM | 58 | N | THR | A | 16 | 22.181 | 47.748 | 90.391 | 1.00 | 14.49 | A |
| ATOM | 59 | CA | THR | A | 16 | 23.369 | 48.520 | 90.063 | 1.00 | 14.54 | A |
| ATOM | 60 | CB | THR | A | 16 | 23.540 | 48.550 | 88.540 | 1.00 | 16.93 | A |
| ATOM | 61 | OG1 | THR | A | 16 | 23.544 | 47.204 | 88.044 | 1.00 | 18.63 | A |
| ATOM | 62 | CG2 | THR | A | 16 | 24.837 | 49.247 | 88.151 | 1.00 | 19.92 | A |
| ATOM | 63 | C | THR | A | 16 | 23.309 | 49.957 | 90.578 | 1.00 | 15.11 | A |
| ATOM | 64 | O | THR | A | 16 | 22.254 | 50.580 | 90.570 | 1.00 | 13.61 | A |
| ATOM | 65 | N | VAL | A | 17 | 24.446 | 50.468 | 91.039 | 1.00 | 14.91 | A |
| ATOM | 66 | CA | VAL | A | 17 | 24.522 | 51.846 | 91.520 | 1.00 | 15.45 | A |
| ATOM | 67 | CB | VAL | A | 17 | 25.762 | 52.059 | 92.407 | 1.00 | 16.50 | A |
| ATOM | 68 | CG1 | VAL | A | 17 | 25.853 | 53.524 | 92.836 | 1.00 | 16.06 | A |
| ATOM | 69 | CG2 | VAL | A | 17 | 25.683 | 51.144 | 93.628 | 1.00 | 16.07 | A |
| ATOM | 70 | C | VAL | A | 17 | 24.644 | 52.691 | 90.249 | 1.00 | 14.23 | A |
| ATOM | 71 | O | VAL | A | 17 | 25.572 | 52.499 | 89.462 | 1.00 | 14.44 | A |
| ATOM | 72 | N | LEU | A | 18 | 23.701 | 53.606 | 90.052 | 1.00 | 13.45 | A |
| ATOM | 73 | CA | LEU | A | 18 | 23.665 | 54.443 | 88.857 | 1.00 | 14.26 | A |
| ATOM | 74 | CB | LEU | A | 18 | 22.253 | 54.403 | 88.255 | 1.00 | 15.14 | A |
| ATOM | 75 | CG | LEU | A | 18 | 21.680 | 52.998 | 88.049 | 1.00 | 16.97 | A |
| ATOM | 76 | CD1 | LEU | A | 18 | 20.242 | 53.088 | 87.568 | 1.00 | 18.78 | A |
| ATOM | 77 | CD2 | LEU | A | 18 | 22.549 | 52.235 | 87.047 | 1.00 | 17.90 | A |
| ATOM | 78 | C | LEU | A | 18 | 24.073 | 55.898 | 89.076 | 1.00 | 14.73 | A |
| ATOM | 79 | O | LEU | A | 18 | 24.351 | 56.613 | 88.120 | 1.00 | 14.38 | A |
| ATOM | 80 | N | ALA | A | 19 | 24.098 | 56.340 | 90.329 | 1.00 | 15.35 | A |
| ATOM | 81 | CA | ALA | A | 19 | 24.475 | 57.717 | 90.636 | 1.00 | 15.25 | A |
| ATOM | 82 | CB | ALA | A | 19 | 23.388 | 58.680 | 90.168 | 1.00 | 14.75 | A |
| ATOM | 83 | C | ALA | A | 19 | 24.694 | 57.874 | 92.133 | 1.00 | 14.72 | A |
| ATOM | 84 | O | ALA | A | 19 | 24.086 | 57.166 | 92.942 | 1.00 | 14.23 | A |
| ATOM | 85 | N | ILE | A | 20 | 25.572 | 58.804 | 92.484 | 1.00 | 12.39 | A |
| ATOM | 86 | CA | ILE | A | 20 | 25.891 | 59.091 | 93.877 | 1.00 | 13.68 | A |
| ATOM | 87 | CB | ILE | A | 20 | 27.221 | 58.442 | 94.304 | 1.00 | 14.33 | A |
| ATOM | 88 | CG2 | ILE | A | 20 | 27.465 | 58.691 | 95.795 | 1.00 | 14.65 | A |
| ATOM | 89 | CG1 | ILE | A | 20 | 27.188 | 56.939 | 94.044 | 1.00 | 13.59 | A |
| ATOM | 90 | CD1 | ILE | A | 20 | 28.534 | 56.272 | 94.254 | 1.00 | 14.71 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 91 | C | ILE | A | 20 | 26.066 | 60.598 | 94.048 | 1.00 | 13.50 | A |
| ATOM | 92 | O | ILE | A | 20 | 26.766 | 61.231 | 93.260 | 1.00 | 15.34 | A |
| ATOM | 93 | N | GLY | A | 21 | 25.433 | 61.152 | 95.075 | 1.00 | 14.62 | A |
| ATOM | 94 | CA | GLY | A | 21 | 25.554 | 62.571 | 95.373 | 1.00 | 14.32 | A |
| ATOM | 95 | C | GLY | A | 21 | 25.774 | 62.738 | 96.872 | 1.00 | 15.92 | A |
| ATOM | 96 | O | GLY | A | 21 | 25.226 | 61.975 | 97.667 | 1.00 | 15.96 | A |
| ATOM | 97 | N | THR | A | 22 | 26.573 | 63.718 | 97.279 | 1.00 | 14.15 | A |
| ATOM | 98 | CA | THR | A | 22 | 26.816 | 63.918 | 98.703 | 1.00 | 13.46 | A |
| ATOM | 99 | CB | THR | A | 22 | 28.236 | 63.435 | 99.115 | 1.00 | 16.43 | A |
| ATOM | 100 | OG1 | THR | A | 22 | 29.230 | 64.250 | 98.474 | 1.00 | 14.65 | A |
| ATOM | 101 | CG2 | THR | A | 22 | 28.450 | 61.966 | 98.705 | 1.00 | 14.38 | A |
| ATOM | 102 | C | THR | A | 22 | 26.677 | 65.382 | 99.094 | 1.00 | 13.65 | A |
| ATOM | 103 | O | THR | A | 22 | 26.700 | 66.267 | 98.239 | 1.00 | 13.92 | A |
| ATOM | 104 | N | ALA | A | 23 | 26.555 | 65.625 | 100.394 | 1.00 | 12.89 | A |
| ATOM | 105 | CA | ALA | A | 23 | 26.417 | 66.981 | 100.911 | 1.00 | 13.53 | A |
| ATOM | 106 | CB | ALA | A | 23 | 24.999 | 67.467 | 100.696 | 1.00 | 13.62 | A |
| ATOM | 107 | C | ALA | A | 23 | 26.759 | 67.018 | 102.394 | 1.00 | 13.65 | A |
| ATOM | 108 | O | ALA | A | 23 | 26.660 | 66.007 | 103.090 | 1.00 | 12.16 | A |
| ATOM | 109 | N | ASN | A | 24 | 27.171 | 68.186 | 102.879 | 1.00 | 13.77 | A |
| ATOM | 110 | CA | ASN | A | 24 | 27.510 | 68.348 | 104.291 | 1.00 | 12.71 | A |
| ATOM | 111 | CB | ASN | A | 24 | 29.010 | 68.177 | 104.559 | 1.00 | 15.73 | A |
| ATOM | 112 | CG | ASN | A | 24 | 29.599 | 66.941 | 103.929 | 1.00 | 16.23 | A |
| ATOM | 113 | OD1 | ASN | A | 24 | 29.953 | 66.940 | 102.747 | 1.00 | 16.19 | A |
| ATOM | 114 | ND2 | ASN | A | 24 | 29.726 | 65.881 | 104.719 | 1.00 | 13.70 | A |
| ATOM | 115 | C | ASN | A | 24 | 27.199 | 69.776 | 104.702 | 1.00 | 15.49 | A |
| ATOM | 116 | O | ASN | A | 24 | 27.161 | 70.675 | 103.865 | 1.00 | 14.90 | A |
| ATOM | 117 | N | PRO | A | 25 | 26.965 | 70.001 | 105.998 | 1.00 | 17.07 | A |
| ATOM | 118 | CD | PRO | A | 25 | 26.692 | 69.058 | 107.094 | 1.00 | 16.81 | A |
| ATOM | 119 | CA | PRO | A | 25 | 26.694 | 71.381 | 106.403 | 1.00 | 17.11 | A |
| ATOM | 120 | CB | PRO | A | 25 | 26.360 | 71.250 | 107.892 | 1.00 | 17.63 | A |
| ATOM | 121 | CG | PRO | A | 25 | 26.961 | 69.912 | 108.300 | 1.00 | 19.53 | A |
| ATOM | 122 | C | PRO | A | 25 | 27.996 | 72.152 | 106.118 | 1.00 | 20.50 | A |
| ATOM | 123 | O | PRO | A | 25 | 29.087 | 71.580 | 106.161 | 1.00 | 18.51 | A |
| ATOM | 124 | N | PRO | A | 26 | 27.897 | 73.451 | 105.805 | 1.00 | 20.76 | A |
| ATOM | 125 | CD | PRO | A | 26 | 26.654 | 74.240 | 105.817 | 1.00 | 22.95 | A |
| ATOM | 126 | CA | PRO | A | 26 | 29.053 | 74.305 | 105.499 | 1.00 | 21.72 | A |
| ATOM | 127 | CB | PRO | A | 26 | 28.399 | 75.619 | 105.080 | 1.00 | 24.14 | A |
| ATOM | 128 | CG | PRO | A | 26 | 27.176 | 75.660 | 105.947 | 1.00 | 25.19 | A |
| ATOM | 129 | C | PRO | A | 26 | 30.106 | 74.512 | 106.590 | 1.00 | 21.55 | A |
| ATOM | 130 | O | PRO | A | 26 | 31.299 | 74.601 | 106.296 | 1.00 | 23.48 | A |
| ATOM | 131 | N | ASN | A | 27 | 29.671 | 74.598 | 107.839 | 1.00 | 20.95 | A |
| ATOM | 132 | CA | ASN | A | 27 | 30.589 | 74.813 | 108.954 | 1.00 | 21.75 | A |
| ATOM | 133 | CB | ASN | A | 27 | 29.788 | 74.956 | 110.245 | 1.00 | 20.97 | A |
| ATOM | 134 | CG | ASN | A | 27 | 30.650 | 75.307 | 111.433 | 1.00 | 22.82 | A |
| ATOM | 135 | OD1 | ASN | A | 27 | 31.412 | 76.273 | 111.396 | 1.00 | 21.91 | A |
| ATOM | 136 | ND2 | ASN | A | 27 | 30.524 | 74.530 | 112.507 | 1.00 | 21.17 | A |
| ATOM | 137 | C | ASN | A | 27 | 31.620 | 73.695 | 109.108 | 1.00 | 21.96 | A |
| ATOM | 138 | O | ASN | A | 27 | 31.258 | 72.544 | 109.367 | 1.00 | 21.55 | A |
| ATOM | 139 | N | CYS | A | 28 | 32.898 | 74.042 | 108.957 | 1.00 | 21.41 | A |
| ATOM | 140 | CA | CYS | A | 28 | 33.993 | 73.077 | 109.082 | 1.00 | 24.36 | A |
| ATOM | 141 | CB | CYS | A | 28 | 34.957 | 73.194 | 107.905 | 1.00 | 26.72 | A |
| ATOM | 142 | SG | CYS | A | 28 | 34.296 | 72.622 | 106.349 | 1.00 | 32.06 | A |
| ATOM | 143 | C | CYS | A | 28 | 34.793 | 73.287 | 110.351 | 1.00 | 25.08 | A |
| ATOM | 144 | O | CYS | A | 28 | 35.100 | 74.422 | 110.713 | 1.00 | 26.06 | A |
| ATOM | 145 | N | ILE | A | 29 | 35.143 | 72.197 | 111.024 | 1.00 | 23.86 | A |
| ATOM | 146 | CA | ILE | A | 29 | 35.940 | 72.317 | 112.233 | 1.00 | 23.59 | A |
| ATOM | 147 | CB | ILE | A | 29 | 35.266 | 71.650 | 113.451 | 1.00 | 26.59 | A |
| ATOM | 148 | CG2 | ILE | A | 29 | 33.906 | 72.300 | 113.715 | 1.00 | 26.52 | A |
| ATOM | 149 | CG1 | ILE | A | 29 | 35.128 | 70.148 | 113.215 | 1.00 | 27.45 | A |
| ATOM | 150 | CD1 | ILE | A | 29 | 34.664 | 69.387 | 114.434 | 1.00 | 32.28 | A |
| ATOM | 151 | C | ILE | A | 29 | 37.322 | 71.711 | 112.042 | 1.00 | 22.44 | A |
| ATOM | 152 | O | ILE | A | 29 | 37.474 | 70.597 | 111.536 | 1.00 | 19.22 | A |
| ATOM | 153 | N | ASP | A | 30 | 38.334 | 72.476 | 112.435 | 1.00 | 21.63 | A |
| ATOM | 154 | CA | ASP | A | 30 | 39.718 | 72.044 | 112.340 | 1.00 | 21.62 | A |
| ATOM | 155 | CB | ASP | A | 30 | 40.640 | 73.254 | 112.432 | 1.00 | 25.37 | A |
| ATOM | 156 | CG | ASP | A | 30 | 42.069 | 72.915 | 112.107 | 1.00 | 26.61 | A |
| ATOM | 157 | OD1 | ASP | A | 30 | 42.551 | 71.875 | 112.595 | 1.00 | 29.92 | A |
| ATOM | 158 | OD2 | ASP | A | 30 | 42.713 | 73.691 | 111.369 | 1.00 | 31.88 | A |
| ATOM | 159 | C | ASP | A | 30 | 39.978 | 71.105 | 113.517 | 1.00 | 20.05 | A |
| ATOM | 160 | O | ASP | A | 30 | 39.899 | 71.513 | 114.671 | 1.00 | 19.05 | A |
| ATOM | 161 | N | GLN | A | 31 | 40.292 | 69.849 | 113.221 | 1.00 | 20.36 | A |
| ATOM | 162 | CA | GLN | A | 31 | 40.529 | 68.856 | 114.265 | 1.00 | 19.11 | A |
| ATOM | 163 | CB | GLN | A | 31 | 40.742 | 67.480 | 113.625 | 1.00 | 17.44 | A |
| ATOM | 164 | CG | GLN | A | 31 | 40.787 | 66.306 | 114.596 | 1.00 | 21.06 | A |
| ATOM | 165 | CD | GLN | A | 31 | 39.430 | 65.957 | 115.189 | 1.00 | 21.80 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 166 | OE1 | GLN | A | 31 | 39.207 | 64.826 | 115.619 | 1.00 | 25.66 | A |
| ATOM | 167 | NE2 | GLN | A | 31 | 38.525 | 66.926 | 115.230 | 1.00 | 18.69 | A |
| ATOM | 168 | C | GLN | A | 31 | 41.722 | 69.200 | 115.151 | 1.00 | 19.87 | A |
| ATOM | 169 | O | GLN | A | 31 | 41.703 | 68.931 | 116.348 | 1.00 | 18.46 | A |
| ATOM | 170 | N | SER | A | 32 | 42.752 | 69.803 | 114.564 | 1.00 | 20.70 | A |
| ATOM | 171 | CA | SER | A | 32 | 43.956 | 70.157 | 115.311 | 1.00 | 22.04 | A |
| ATOM | 172 | CB | SER | A | 32 | 45.019 | 70.734 | 114.363 | 1.00 | 22.43 | A |
| ATOM | 173 | OG | SER | A | 32 | 44.665 | 72.032 | 113.906 | 1.00 | 24.69 | A |
| ATOM | 174 | C | SER | A | 32 | 43.694 | 71.143 | 116.453 | 1.00 | 22.19 | A |
| ATOM | 175 | O | SER | A | 32 | 44.441 | 71.178 | 117.429 | 1.00 | 22.11 | A |
| ATOM | 176 | N | THR | A | 33 | 42.631 | 71.933 | 116.342 | 1.00 | 21.38 | A |
| ATOM | 177 | CA | THR | A | 33 | 42.308 | 72.911 | 117.379 | 1.00 | 20.69 | A |
| ATOM | 178 | CB | THR | A | 33 | 42.300 | 74.343 | 116.801 | 1.00 | 22.44 | A |
| ATOM | 179 | OG1 | THR | A | 33 | 41.251 | 74.459 | 115.834 | 1.00 | 22.63 | A |
| ATOM | 180 | CG2 | THR | A | 33 | 43.635 | 74.664 | 116.132 | 1.00 | 24.73 | A |
| ATOM | 181 | C | THR | A | 33 | 40.943 | 72.663 | 118.028 | 1.00 | 18.62 | A |
| ATOM | 182 | O | THR | A | 33 | 40.438 | 73.515 | 118.754 | 1.00 | 18.50 | A |
| ATOM | 183 | N | TYR | A | 34 | 40.346 | 71.499 | 117.787 | 1.00 | 16.74 | A |
| ATOM | 184 | CA | TYR | A | 34 | 39.029 | 71.226 | 118.355 | 1.00 | 16.94 | A |
| ATOM | 185 | CB | TYR | A | 34 | 38.451 | 69.928 | 117.801 | 1.00 | 17.19 | A |
| ATOM | 186 | CG | TYR | A | 34 | 36.975 | 69.790 | 118.083 | 1.00 | 17.35 | A |
| ATOM | 187 | CD1 | TYR | A | 34 | 36.058 | 70.685 | 117.526 | 1.00 | 17.15 | A |
| ATOM | 188 | CE1 | TYR | A | 34 | 34.693 | 70.575 | 117.788 | 1.00 | 19.47 | A |
| ATOM | 189 | CD2 | TYR | A | 34 | 36.491 | 68.780 | 118.911 | 1.00 | 16.08 | A |
| ATOM | 190 | CE2 | TYR | A | 34 | 35.133 | 68.661 | 119.183 | 1.00 | 17.26 | A |
| ATOM | 191 | CZ | TYR | A | 34 | 34.237 | 69.562 | 118.617 | 1.00 | 17.18 | A |
| ATOM | 192 | OH | TYR | A | 34 | 32.891 | 69.457 | 118.893 | 1.00 | 16.72 | A |
| ATOM | 193 | C | TYR | A | 34 | 38.992 | 71.157 | 119.874 | 1.00 | 17.22 | A |
| ATOM | 194 | O | TYR | A | 34 | 38.015 | 71.583 | 120.490 | 1.00 | 18.03 | A |
| ATOM | 195 | N | ALA | A | 35 | 40.043 | 70.604 | 120.474 | 1.00 | 17.84 | A |
| ATOM | 196 | CA | ALA | A | 35 | 40.107 | 70.489 | 121.926 | 1.00 | 18.20 | A |
| ATOM | 197 | CB | ALA | A | 35 | 41.448 | 69.913 | 122.355 | 1.00 | 18.99 | A |
| ATOM | 198 | C | ALA | A | 35 | 39.904 | 71.867 | 122.550 | 1.00 | 18.82 | A |
| ATOM | 199 | O | ALA | A | 35 | 39.091 | 72.028 | 123.448 | 1.00 | 17.85 | A |
| ATOM | 200 | N | ASP | A | 36 | 40.653 | 72.858 | 122.073 | 1.00 | 18.76 | A |
| ATOM | 201 | CA | ASP | A | 36 | 40.516 | 74.213 | 122.604 | 1.00 | 19.92 | A |
| ATOM | 202 | CB | ASP | A | 36 | 41.438 | 75.190 | 121.864 | 1.00 | 22.24 | A |
| ATOM | 203 | CG | ASP | A | 36 | 42.903 | 74.972 | 122.181 | 1.00 | 25.34 | A |
| ATOM | 204 | OD1 | ASP | A | 36 | 43.217 | 74.578 | 123.324 | 1.00 | 25.77 | A |
| ATOM | 205 | OD2 | ASP | A | 36 | 43.745 | 75.213 | 121.287 | 1.00 | 29.04 | A |
| ATOM | 206 | C | ASP | A | 36 | 39.078 | 74.709 | 122.478 | 1.00 | 20.11 | A |
| ATOM | 207 | O | ASP | A | 36 | 38.477 | 75.179 | 123.452 | 1.00 | 19.46 | A |
| ATOM | 208 | N | TYR | A | 37 | 38.538 | 74.611 | 121.266 | 1.00 | 18.02 | A |
| ATOM | 209 | CA | TYR | A | 37 | 37.180 | 75.057 | 120.991 | 1.00 | 17.23 | A |
| ATOM | 210 | CB | TYR | A | 37 | 36.846 | 74.817 | 119.514 | 1.00 | 16.64 | A |
| ATOM | 211 | CG | TYR | A | 37 | 35.399 | 75.092 | 119.152 | 1.00 | 19.58 | A |
| ATOM | 212 | CD1 | TYR | A | 37 | 34.945 | 76.396 | 118.946 | 1.00 | 19.88 | A |
| ATOM | 213 | CE1 | TYR | A | 37 | 33.615 | 76.654 | 118.611 | 1.00 | 21.95 | A |
| ATOM | 214 | CD2 | TYR | A | 37 | 34.482 | 74.046 | 119.020 | 1.00 | 18.32 | A |
| ATOM | 215 | CE2 | TYR | A | 37 | 33.153 | 74.290 | 118.690 | 1.00 | 21.26 | A |
| ATOM | 216 | CZ | TYR | A | 37 | 32.725 | 75.598 | 118.483 | 1.00 | 22.45 | A |
| ATOM | 217 | OH | TYR | A | 37 | 31.417 | 75.846 | 118.136 | 1.00 | 22.04 | A |
| ATOM | 218 | C | TYR | A | 37 | 36.158 | 74.342 | 121.865 | 1.00 | 17.32 | A |
| ATOM | 219 | O | TYR | A | 37 | 35.352 | 74.977 | 122.553 | 1.00 | 17.84 | A |
| ATOM | 220 | N | TYR | A | 38 | 36.198 | 73.013 | 121.829 | 1.00 | 17.92 | A |
| ATOM | 221 | CA | TYR | A | 38 | 35.270 | 72.178 | 122.585 | 1.00 | 17.56 | A |
| ATOM | 222 | CB | TYR | A | 38 | 35.626 | 70.702 | 122.369 | 1.00 | 16.77 | A |
| ATOM | 223 | CG | TYR | A | 38 | 34.755 | 69.726 | 123.116 | 1.00 | 16.04 | A |
| ATOM | 224 | CD1 | TYR | A | 38 | 33.436 | 69.484 | 122.724 | 1.00 | 17.14 | A |
| ATOM | 225 | CE1 | TYR | A | 38 | 32.635 | 68.580 | 123.420 | 1.00 | 17.33 | A |
| ATOM | 226 | CD2 | TYR | A | 38 | 35.251 | 69.039 | 124.224 | 1.00 | 16.93 | A |
| ATOM | 227 | CE2 | TYR | A | 38 | 34.466 | 68.140 | 124.923 | 1.00 | 17.51 | A |
| ATOM | 228 | CZ | TYR | A | 38 | 33.161 | 67.913 | 124.519 | 1.00 | 16.76 | A |
| ATOM | 229 | OH | TYR | A | 38 | 32.398 | 67.030 | 125.234 | 1.00 | 17.13 | A |
| ATOM | 230 | C | TYR | A | 38 | 35.248 | 72.506 | 124.076 | 1.00 | 18.55 | A |
| ATOM | 231 | O | TYR | A | 38 | 34.185 | 72.752 | 124.646 | 1.00 | 18.23 | A |
| ATOM | 232 | N | PHE | A | 39 | 36.412 | 72.517 | 124.714 | 1.00 | 19.37 | A |
| ATOM | 233 | CA | PHE | A | 39 | 36.453 | 72.813 | 126.143 | 1.00 | 19.56 | A |
| ATOM | 234 | CB | PHE | A | 39 | 37.816 | 72.429 | 126.722 | 1.00 | 19.04 | A |
| ATOM | 235 | CG | PHE | A | 39 | 37.907 | 70.975 | 127.108 | 1.00 | 20.13 | A |
| ATOM | 236 | CD1 | PHE | A | 39 | 37.759 | 70.583 | 128.434 | 1.00 | 21.28 | A |
| ATOM | 237 | CD2 | PHE | A | 39 | 38.075 | 69.993 | 126.135 | 1.00 | 19.97 | A |
| ATOM | 238 | CE1 | PHE | A | 39 | 37.774 | 69.230 | 128.788 | 1.00 | 21.03 | A |
| ATOM | 239 | CE2 | PHE | A | 39 | 38.091 | 68.645 | 126.476 | 1.00 | 19.95 | A |
| ATOM | 240 | CZ | PHE | A | 39 | 37.939 | 68.262 | 127.806 | 1.00 | 21.19 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 241 | C | PHE | A | 39 | 36.086 | 74.255 | 126.485 | 1.00 | 20.19 | A |
| ATOM | 242 | O | PHE | A | 39 | 35.732 | 74.553 | 127.622 | 1.00 | 22.34 | A |
| ATOM | 243 | N | ARG | A | 40 | 36.144 | 75.143 | 125.499 | 1.00 | 20.54 | A |
| ATOM | 244 | CA | ARG | A | 40 | 35.773 | 76.534 | 125.734 | 1.00 | 20.65 | A |
| ATOM | 245 | CB | ARG | A | 40 | 36.470 | 77.456 | 124.726 | 1.00 | 19.69 | A |
| ATOM | 246 | CG | ARG | A | 40 | 36.044 | 78.918 | 124.836 | 1.00 | 22.28 | A |
| ATOM | 247 | CD | ARG | A | 40 | 36.875 | 79.813 | 123.925 | 1.00 | 23.38 | A |
| ATOM | 248 | NE | ARG | A | 40 | 36.646 | 79.562 | 122.503 | 1.00 | 23.95 | A |
| ATOM | 249 | CZ | ARG | A | 40 | 35.519 | 79.851 | 121.861 | 1.00 | 24.46 | A |
| ATOM | 250 | NH1 | ARG | A | 40 | 34.507 | 80.404 | 122.510 | 1.00 | 25.71 | A |
| ATOM | 251 | NH2 | ARG | A | 40 | 35.403 | 79.585 | 120.567 | 1.00 | 26.85 | A |
| ATOM | 252 | C | ARG | A | 40 | 34.257 | 76.707 | 125.627 | 1.00 | 20.55 | A |
| ATOM | 253 | O | ARG | A | 40 | 33.620 | 77.242 | 126.540 | 1.00 | 18.76 | A |
| ATOM | 254 | N | VAL | A | 41 | 33.674 | 76.245 | 124.522 | 1.00 | 20.21 | A |
| ATOM | 255 | CA | VAL | A | 41 | 32.236 | 76.385 | 124.338 | 1.00 | 21.46 | A |
| ATOM | 256 | CB | VAL | A | 41 | 31.790 | 76.005 | 122.892 | 1.00 | 22.92 | A |
| ATOM | 257 | CG1 | VAL | A | 41 | 32.537 | 76.875 | 121.879 | 1.00 | 23.74 | A |
| ATOM | 258 | CG2 | VAL | A | 41 | 32.037 | 74.524 | 122.619 | 1.00 | 21.78 | A |
| ATOM | 259 | C | VAL | A | 41 | 31.417 | 75.599 | 125.350 | 1.00 | 21.29 | A |
| ATOM | 260 | O | VAL | A | 41 | 30.261 | 75.928 | 125.588 | 1.00 | 20.77 | A |
| ATOM | 261 | N | THR | A | 42 | 32.001 | 74.562 | 125.949 | 1.00 | 21.64 | A |
| ATOM | 262 | CA | THR | A | 42 | 31.274 | 73.785 | 126.951 | 1.00 | 22.13 | A |
| ATOM | 263 | CB | THR | A | 42 | 31.532 | 72.254 | 126.828 | 1.00 | 21.03 | A |
| ATOM | 264 | OG1 | THR | A | 42 | 32.914 | 71.968 | 127.082 | 1.00 | 19.85 | A |
| ATOM | 265 | CG2 | THR | A | 42 | 31.155 | 71.758 | 125.440 | 1.00 | 18.84 | A |
| ATOM | 266 | C | THR | A | 42 | 31.670 | 74.237 | 128.360 | 1.00 | 24.77 | A |
| ATOM | 267 | O | THR | A | 42 | 31.365 | 73.564 | 129.344 | 1.00 | 24.42 | A |
| ATOM | 268 | N | ASN | A | 43 | 32.357 | 75.375 | 128.442 | 1.00 | 25.63 | A |
| ATOM | 269 | CA | ASN | A | 43 | 32.781 | 75.945 | 129.722 | 1.00 | 27.73 | A |
| ATOM | 270 | CB | ASN | A | 43 | 31.560 | 76.502 | 130.452 | 1.00 | 32.42 | A |
| ATOM | 271 | CG | ASN | A | 43 | 30.721 | 77.407 | 129.570 | 1.00 | 36.22 | A |
| ATOM | 272 | OD1 | ASN | A | 43 | 31.175 | 78.472 | 129.145 | 1.00 | 39.75 | A |
| ATOM | 273 | ND2 | ASN | A | 43 | 29.492 | 76.985 | 129.285 | 1.00 | 38.09 | A |
| ATOM | 274 | C | ASN | A | 43 | 33.494 | 74.939 | 130.624 | 1.00 | 27.61 | A |
| ATOM | 275 | O | ASN | A | 43 | 33.232 | 74.876 | 131.829 | 1.00 | 26.66 | A |
| ATOM | 276 | N | SER | A | 44 | 34.405 | 74.168 | 130.046 | 1.00 | 26.69 | A |
| ATOM | 277 | CA | SER | A | 44 | 35.125 | 73.152 | 130.799 | 1.00 | 27.90 | A |
| ATOM | 278 | CB | SER | A | 44 | 34.892 | 71.781 | 130.161 | 1.00 | 26.68 | A |
| ATOM | 279 | OG | SER | A | 44 | 33.509 | 71.489 | 130.100 | 1.00 | 28.08 | A |
| ATOM | 280 | C | SER | A | 44 | 36.616 | 73.438 | 130.870 | 1.00 | 28.33 | A |
| ATOM | 281 | O | SER | A | 44 | 37.422 | 72.520 | 130.989 | 1.00 | 28.25 | A |
| ATOM | 282 | N | GLU | A | 45 | 36.973 | 74.717 | 130.803 | 1.00 | 30.31 | A |
| ATOM | 283 | CA | GLU | A | 45 | 38.372 | 75.137 | 130.855 | 1.00 | 32.52 | A |
| ATOM | 284 | CB | GLU | A | 45 | 38.460 | 76.666 | 130.804 | 1.00 | 36.20 | A |
| ATOM | 285 | CG | GLU | A | 45 | 37.862 | 77.296 | 129.556 | 1.00 | 40.59 | A |
| ATOM | 286 | CD | GLU | A | 45 | 38.635 | 76.954 | 128.297 | 1.00 | 43.46 | A |
| ATOM | 287 | OE1 | GLU | A | 45 | 38.290 | 77.492 | 127.224 | 1.00 | 44.77 | A |
| ATOM | 288 | OE2 | GLU | A | 45 | 39.589 | 76.148 | 128.378 | 1.00 | 46.65 | A |
| ATOM | 289 | C | GLU | A | 45 | 39.082 | 74.635 | 132.109 | 1.00 | 31.09 | A |
| ATOM | 290 | O | GLU | A | 45 | 40.261 | 74.288 | 132.069 | 1.00 | 32.23 | A |
| ATOM | 291 | N | HIS | A | 46 | 38.356 | 74.590 | 133.220 | 1.00 | 30.26 | A |
| ATOM | 292 | CA | HIS | A | 46 | 38.921 | 74.148 | 134.489 | 1.00 | 30.21 | A |
| ATOM | 293 | CB | HIS | A | 46 | 37.915 | 74.373 | 135.624 | 1.00 | 30.18 | A |
| ATOM | 294 | CG | HIS | A | 46 | 36.608 | 73.672 | 135.423 | 1.00 | 31.08 | A |
| ATOM | 295 | CD2 | HIS | A | 46 | 36.080 | 72.580 | 136.025 | 1.00 | 31.68 | A |
| ATOM | 296 | ND1 | HIS | A | 46 | 35.678 | 74.082 | 134.491 | 1.00 | 31.46 | A |
| ATOM | 297 | CE1 | HIS | A | 46 | 34.635 | 73.272 | 134.527 | 1.00 | 31.49 | A |
| ATOM | 298 | NE2 | HIS | A | 46 | 34.854 | 72.352 | 135.450 | 1.00 | 31.69 | A |
| ATOM | 299 | C | HIS | A | 46 | 39.384 | 72.691 | 134.505 | 1.00 | 29.90 | A |
| ATOM | 300 | O | HIS | A | 46 | 40.153 | 72.301 | 135.383 | 1.00 | 28.22 | A |
| ATOM | 301 | N | MET | A | 47 | 38.920 | 71.891 | 133.544 | 1.00 | 29.28 | A |
| ATOM | 302 | CA | MET | A | 47 | 39.307 | 70.477 | 133.471 | 1.00 | 28.84 | A |
| ATOM | 303 | CB | MET | A | 47 | 38.214 | 69.664 | 132.771 | 1.00 | 28.86 | A |
| ATOM | 304 | CG | MET | A | 47 | 36.808 | 69.935 | 133.286 | 1.00 | 30.82 | A |
| ATOM | 305 | SD | MET | A | 47 | 35.578 | 68.879 | 132.493 | 1.00 | 31.81 | A |
| ATOM | 306 | CE | MET | A | 47 | 35.684 | 67.427 | 133.551 | 1.00 | 33.73 | A |
| ATOM | 307 | C | MET | A | 47 | 40.621 | 70.327 | 132.705 | 1.00 | 28.88 | A |
| ATOM | 308 | O | MET | A | 47 | 40.689 | 69.627 | 131.693 | 1.00 | 27.03 | A |
| ATOM | 309 | N | THR | A | 48 | 41.665 | 70.983 | 133.199 | 1.00 | 29.25 | A |
| ATOM | 310 | CA | THR | A | 48 | 42.974 | 70.955 | 132.554 | 1.00 | 29.28 | A |
| ATOM | 311 | CB | THR | A | 48 | 44.045 | 71.626 | 133.450 | 1.00 | 30.40 | A |
| ATOM | 312 | OG1 | THR | A | 48 | 44.133 | 70.932 | 134.699 | 1.00 | 31.38 | A |
| ATOM | 313 | CG2 | THR | A | 48 | 43.681 | 73.081 | 133.710 | 1.00 | 31.23 | A |
| ATOM | 314 | C | THR | A | 48 | 43.485 | 69.575 | 132.128 | 1.00 | 29.36 | A |
| ATOM | 315 | O | THR | A | 48 | 43.883 | 69.394 | 130.977 | 1.00 | 30.13 | A |

APPENDIX B-continued

*Arachis hypogaea* STS

| ATOM | # | TYPE | RES | | | X | Y | Z | OCC | B | |
|------|---|------|-----|---|----|--------|--------|---------|------|-------|---|
| ATOM | 316 | N | ASP | A | 49 | 43.475 | 68.603 | 133.036 | 1.00 | 28.72 | A |
| ATOM | 317 | CA | ASP | A | 49 | 43.974 | 67.271 | 132.697 | 1.00 | 29.59 | A |
| ATOM | 318 | CB | ASP | A | 49 | 43.992 | 66.367 | 133.928 | 1.00 | 33.21 | A |
| ATOM | 319 | CG | ASP | A | 49 | 44.545 | 64.985 | 133.621 | 1.00 | 36.83 | A |
| ATOM | 320 | OD1 | ASP | A | 49 | 45.679 | 64.903 | 133.102 | 1.00 | 39.96 | A |
| ATOM | 321 | OD2 | ASP | A | 49 | 43.850 | 63.981 | 133.893 | 1.00 | 38.97 | A |
| ATOM | 322 | C | ASP | A | 49 | 43.172 | 66.588 | 131.592 | 1.00 | 28.05 | A |
| ATOM | 323 | O | ASP | A | 49 | 43.744 | 66.023 | 130.660 | 1.00 | 28.22 | A |
| ATOM | 324 | N | LEU | A | 50 | 41.851 | 66.637 | 131.701 | 1.00 | 25.60 | A |
| ATOM | 325 | CA | LEU | A | 50 | 40.991 | 66.011 | 130.704 | 1.00 | 23.87 | A |
| ATOM | 326 | CB | LEU | A | 50 | 39.527 | 66.120 | 131.131 | 1.00 | 21.93 | A |
| ATOM | 327 | CG | LEU | A | 50 | 38.534 | 65.261 | 130.350 | 1.00 | 19.98 | A |
| ATOM | 328 | CD1 | LEU | A | 50 | 38.945 | 63.789 | 130.429 | 1.00 | 19.09 | A |
| ATOM | 329 | CD2 | LEU | A | 50 | 37.146 | 65.460 | 130.927 | 1.00 | 20.31 | A |
| ATOM | 330 | C | LEU | A | 50 | 41.189 | 66.662 | 129.336 | 1.00 | 23.68 | A |
| ATOM | 331 | O | LEU | A | 50 | 41.215 | 65.976 | 128.313 | 1.00 | 22.19 | A |
| ATOM | 332 | N | LYS | A | 51 | 41.332 | 67.985 | 129.316 | 1.00 | 23.84 | A |
| ATOM | 333 | CA | LYS | A | 51 | 41.532 | 68.686 | 128.052 | 1.00 | 25.09 | A |
| ATOM | 334 | CB | LYS | A | 51 | 41.650 | 70.199 | 128.283 | 1.00 | 25.49 | A |
| ATOM | 335 | CG | LYS | A | 51 | 41.828 | 71.005 | 126.999 | 1.00 | 26.33 | A |
| ATOM | 336 | CD | LYS | A | 51 | 41.886 | 72.504 | 127.280 | 1.00 | 28.75 | A |
| ATOM | 337 | CE | LYS | A | 51 | 42.142 | 73.288 | 126.007 | 1.00 | 29.76 | A |
| ATOM | 338 | NZ | LYS | A | 51 | 42.144 | 74.756 | 126.260 | 1.00 | 30.99 | A |
| ATOM | 339 | C | LYS | A | 51 | 42.785 | 68.170 | 127.344 | 1.00 | 26.21 | A |
| ATOM | 340 | O | LYS | A | 51 | 42.782 | 67.971 | 126.130 | 1.00 | 24.74 | A |
| ATOM | 341 | N | LYS | A | 52 | 43.856 | 67.949 | 128.103 | 1.00 | 27.17 | A |
| ATOM | 342 | CA | LYS | A | 52 | 45.098 | 67.449 | 127.516 | 1.00 | 28.10 | A |
| ATOM | 343 | CB | LYS | A | 52 | 46.194 | 67.352 | 128.582 | 1.00 | 30.83 | A |
| ATOM | 344 | CG | LYS | A | 52 | 46.591 | 68.687 | 129.190 | 1.00 | 34.28 | A |
| ATOM | 345 | CD | LYS | A | 52 | 47.635 | 68.497 | 130.279 | 1.00 | 37.20 | A |
| ATOM | 346 | CE | LYS | A | 52 | 47.985 | 69.816 | 130.945 | 1.00 | 38.95 | A |
| ATOM | 347 | NZ | LYS | A | 52 | 48.982 | 69.624 | 132.030 | 1.00 | 41.28 | A |
| ATOM | 348 | C | LYS | A | 52 | 44.873 | 66.076 | 126.888 | 1.00 | 26.97 | A |
| ATOM | 349 | O | LYS | A | 52 | 45.366 | 65.792 | 125.797 | 1.00 | 26.02 | A |
| ATOM | 350 | N | LYS | A | 53 | 44.122 | 65.228 | 127.583 | 1.00 | 26.21 | A |
| ATOM | 351 | CA | LYS | A | 53 | 43.831 | 63.892 | 127.086 | 1.00 | 25.04 | A |
| ATOM | 352 | CB | LYS | A | 53 | 43.067 | 63.086 | 128.140 | 1.00 | 24.64 | A |
| ATOM | 353 | CG | LYS | A | 53 | 43.877 | 62.781 | 129.392 | 1.00 | 28.22 | A |
| ATOM | 354 | CD | LYS | A | 53 | 43.065 | 61.990 | 130.408 | 1.00 | 30.66 | A |
| ATOM | 355 | CE | LYS | A | 53 | 43.880 | 61.718 | 131.666 | 1.00 | 33.54 | A |
| ATOM | 356 | NZ | LYS | A | 53 | 43.126 | 60.909 | 132.667 | 1.00 | 36.02 | A |
| ATOM | 357 | C | LYS | A | 53 | 43.012 | 63.962 | 125.798 | 1.00 | 23.42 | A |
| ATOM | 358 | O | LYS | A | 53 | 43.226 | 63.173 | 124.879 | 1.00 | 22.62 | A |
| ATOM | 359 | N | PHE | A | 54 | 42.086 | 64.915 | 125.732 | 1.00 | 23.36 | A |
| ATOM | 360 | CA | PHE | A | 54 | 41.237 | 65.066 | 124.550 | 1.00 | 22.90 | A |
| ATOM | 361 | CB | PHE | A | 54 | 40.098 | 66.055 | 124.820 | 1.00 | 22.20 | A |
| ATOM | 362 | CG | PHE | A | 54 | 39.044 | 66.072 | 123.740 | 1.00 | 20.84 | A |
| ATOM | 363 | CD1 | PHE | A | 54 | 38.409 | 64.897 | 123.352 | 1.00 | 19.63 | A |
| ATOM | 364 | CD2 | PHE | A | 54 | 38.682 | 67.260 | 123.115 | 1.00 | 20.10 | A |
| ATOM | 365 | CE1 | PHE | A | 54 | 37.432 | 64.905 | 122.357 | 1.00 | 18.43 | A |
| ATOM | 366 | CE2 | PHE | A | 54 | 37.706 | 67.276 | 122.122 | 1.00 | 19.37 | A |
| ATOM | 367 | CZ | PHE | A | 54 | 37.081 | 66.097 | 121.742 | 1.00 | 18.82 | A |
| ATOM | 368 | C | PHE | A | 54 | 42.048 | 65.539 | 123.354 | 1.00 | 23.85 | A |
| ATOM | 369 | O | PHE | A | 54 | 41.812 | 65.112 | 122.219 | 1.00 | 23.78 | A |
| ATOM | 370 | N | GLN | A | 55 | 43.000 | 66.432 | 123.603 | 1.00 | 24.10 | A |
| ATOM | 371 | CA | GLN | A | 55 | 43.842 | 66.930 | 122.528 | 1.00 | 24.91 | A |
| ATOM | 372 | CB | GLN | A | 55 | 44.832 | 67.974 | 123.062 | 1.00 | 26.37 | A |
| ATOM | 373 | CG | GLN | A | 55 | 45.921 | 68.373 | 122.072 | 1.00 | 28.68 | A |
| ATOM | 374 | CD | GLN | A | 55 | 45.411 | 69.175 | 120.884 | 1.00 | 30.30 | A |
| ATOM | 375 | OE1 | GLN | A | 55 | 46.060 | 69.228 | 119.839 | 1.00 | 31.71 | A |
| ATOM | 376 | NE2 | GLN | A | 55 | 44.259 | 69.820 | 121.044 | 1.00 | 30.29 | A |
| ATOM | 377 | C | GLN | A | 55 | 44.586 | 65.725 | 121.967 | 1.00 | 24.46 | A |
| ATOM | 378 | O | GLN | A | 55 | 44.767 | 65.601 | 120.761 | 1.00 | 22.48 | A |
| ATOM | 379 | N | ARG | A | 56 | 44.997 | 64.828 | 122.858 | 1.00 | 24.95 | A |
| ATOM | 380 | CA | ARG | A | 56 | 45.719 | 63.625 | 122.468 | 1.00 | 25.91 | A |
| ATOM | 381 | CB | ARG | A | 56 | 46.171 | 62.866 | 123.720 | 1.00 | 29.99 | A |
| ATOM | 382 | CG | ARG | A | 56 | 47.559 | 62.249 | 123.624 | 1.00 | 36.86 | A |
| ATOM | 383 | CD | ARG | A | 56 | 48.647 | 63.324 | 123.571 | 1.00 | 40.43 | A |
| ATOM | 384 | NE | ARG | A | 56 | 48.699 | 64.137 | 124.787 | 1.00 | 44.69 | A |
| ATOM | 385 | CZ | ARG | A | 56 | 48.992 | 63.667 | 125.998 | 1.00 | 46.01 | A |
| ATOM | 386 | NH1 | ARG | A | 56 | 49.263 | 62.379 | 126.168 | 1.00 | 47.48 | A |
| ATOM | 387 | NH2 | ARG | A | 56 | 49.015 | 64.485 | 127.044 | 1.00 | 46.66 | A |
| ATOM | 388 | C | ARG | A | 56 | 44.804 | 62.739 | 121.618 | 1.00 | 24.27 | A |
| ATOM | 389 | O | ARG | A | 56 | 45.215 | 62.221 | 120.574 | 1.00 | 24.04 | A |
| ATOM | 390 | N | ILE | A | 57 | 43.565 | 62.572 | 122.075 | 1.00 | 21.82 | A |

APPENDIX B-continued

_Arachis hypogaea STS_

| ATOM | # | TYPE | RES | | | X | Y | Z | OCC | B | |
|------|---|------|-----|---|---|---|---|---|-----|---|---|
| ATOM | 391 | CA | ILE | A | 57 | 42.579 | 61.765 | 121.367 | 1.00 | 20.34 | A |
| ATOM | 392 | CB | ILE | A | 57 | 41.237 | 61.729 | 122.129 | 1.00 | 20.57 | A |
| ATOM | 393 | CG2 | ILE | A | 57 | 40.154 | 61.093 | 121.261 | 1.00 | 21.54 | A |
| ATOM | 394 | CG1 | ILE | A | 57 | 41.399 | 60.948 | 123.438 | 1.00 | 20.21 | A |
| ATOM | 395 | CD1 | ILE | A | 57 | 40.171 | 60.973 | 124.315 | 1.00 | 19.50 | A |
| ATOM | 396 | C | ILE | A | 57 | 42.337 | 62.329 | 119.968 | 1.00 | 20.51 | A |
| ATOM | 397 | O | ILE | A | 57 | 42.396 | 61.599 | 118.986 | 1.00 | 20.89 | A |
| ATOM | 398 | N | CYS | A | 58 | 42.076 | 63.630 | 119.879 | 1.00 | 19.30 | A |
| ATOM | 399 | CA | CYS | A | 58 | 41.823 | 64.251 | 118.587 | 1.00 | 20.99 | A |
| ATOM | 400 | CB | CYS | A | 58 | 41.533 | 65.745 | 118.759 | 1.00 | 19.32 | A |
| ATOM | 401 | SG | CYS | A | 58 | 39.917 | 66.082 | 119.509 | 1.00 | 18.88 | A |
| ATOM | 402 | C | CYS | A | 58 | 42.966 | 64.047 | 117.601 | 1.00 | 22.44 | A |
| ATOM | 403 | O | CYS | A | 58 | 42.732 | 63.850 | 116.412 | 1.00 | 23.07 | A |
| ATOM | 404 | N | GLU | A | 59 | 44.200 | 64.077 | 118.092 | 1.00 | 24.02 | A |
| ATOM | 405 | CA | GLU | A | 59 | 45.363 | 63.892 | 117.225 | 1.00 | 26.24 | A |
| ATOM | 406 | CB | GLU | A | 59 | 46.644 | 64.284 | 117.972 | 1.00 | 28.50 | A |
| ATOM | 407 | CG | GLU | A | 59 | 46.606 | 65.706 | 118.527 | 1.00 | 33.23 | A |
| ATOM | 408 | CD | GLU | A | 59 | 47.855 | 66.085 | 119.315 | 1.00 | 35.09 | A |
| ATOM | 409 | OE1 | GLU | A | 59 | 48.343 | 65.248 | 120.109 | 1.00 | 36.66 | A |
| ATOM | 410 | OE2 | GLU | A | 59 | 48.338 | 67.227 | 119.149 | 1.00 | 34.23 | A |
| ATOM | 411 | C | GLU | A | 59 | 45.455 | 62.445 | 116.741 | 1.00 | 26.77 | A |
| ATOM | 412 | O | GLU | A | 59 | 45.872 | 62.177 | 115.614 | 1.00 | 26.70 | A |
| ATOM | 413 | N | ARG | A | 60 | 45.046 | 61.518 | 117.596 | 1.00 | 26.73 | A |
| ATOM | 414 | CA | ARG | A | 60 | 45.079 | 60.100 | 117.264 | 1.00 | 28.79 | A |
| ATOM | 415 | CB | ARG | A | 60 | 44.919 | 59.274 | 118.544 | 1.00 | 33.01 | A |
| ATOM | 416 | CG | ARG | A | 60 | 46.132 | 59.301 | 119.456 | 1.00 | 39.19 | A |
| ATOM | 417 | CD | ARG | A | 60 | 47.211 | 58.346 | 118.956 | 1.00 | 45.62 | A |
| ATOM | 418 | NE | ARG | A | 60 | 47.412 | 57.224 | 119.875 | 1.00 | 49.49 | A |
| ATOM | 419 | CZ | ARG | A | 60 | 46.455 | 56.383 | 120.261 | 1.00 | 51.76 | A |
| ATOM | 420 | NH1 | ARG | A | 60 | 45.215 | 56.526 | 119.809 | 1.00 | 52.07 | A |
| ATOM | 421 | NH2 | ARG | A | 60 | 46.735 | 55.399 | 121.109 | 1.00 | 53.18 | A |
| ATOM | 422 | C | ARG | A | 60 | 44.024 | 59.664 | 116.240 | 1.00 | 25.81 | A |
| ATOM | 423 | O | ARG | A | 60 | 44.225 | 58.686 | 115.524 | 1.00 | 23.81 | A |
| ATOM | 424 | N | THR | A | 61 | 42.911 | 60.388 | 116.160 | 1.00 | 23.41 | A |
| ATOM | 425 | CA | THR | A | 61 | 41.834 | 60.023 | 115.235 | 1.00 | 22.16 | A |
| ATOM | 426 | CB | THR | A | 61 | 40.629 | 60.966 | 115.359 | 1.00 | 19.80 | A |
| ATOM | 427 | OG1 | THR | A | 61 | 41.003 | 62.269 | 114.896 | 1.00 | 17.03 | A |
| ATOM | 428 | CG2 | THR | A | 61 | 40.150 | 61.047 | 116.802 | 1.00 | 20.05 | A |
| ATOM | 429 | C | THR | A | 61 | 42.237 | 60.045 | 113.768 | 1.00 | 22.06 | A |
| ATOM | 430 | O | THR | A | 61 | 41.616 | 59.382 | 112.942 | 1.00 | 20.90 | A |
| ATOM | 431 | N | GLN | A | 62 | 43.275 | 60.814 | 113.457 | 1.00 | 21.51 | A |
| ATOM | 432 | CA | GLN | A | 62 | 43.749 | 60.979 | 112.089 | 1.00 | 21.94 | A |
| ATOM | 433 | CB | GLN | A | 62 | 44.232 | 59.649 | 111.503 | 1.00 | 24.19 | A |
| ATOM | 434 | CG | GLN | A | 62 | 45.428 | 59.093 | 112.270 | 1.00 | 25.12 | A |
| ATOM | 435 | CD | GLN | A | 62 | 46.325 | 58.218 | 111.429 | 1.00 | 28.57 | A |
| ATOM | 436 | OE1 | GLN | A | 62 | 45.857 | 57.352 | 110.687 | 1.00 | 28.23 | A |
| ATOM | 437 | NE2 | GLN | A | 62 | 47.633 | 58.430 | 111.550 | 1.00 | 29.81 | A |
| ATOM | 438 | C | GLN | A | 62 | 42.654 | 61.602 | 111.227 | 1.00 | 21.62 | A |
| ATOM | 439 | O | GLN | A | 62 | 42.545 | 61.345 | 110.021 | 1.00 | 21.13 | A |
| ATOM | 440 | N | ILE | A | 63 | 41.829 | 62.413 | 111.881 | 1.00 | 18.54 | A |
| ATOM | 441 | CA | ILE | A | 63 | 40.763 | 63.155 | 111.220 | 1.00 | 16.85 | A |
| ATOM | 442 | CB | ILE | A | 63 | 39.475 | 63.188 | 112.062 | 1.00 | 15.18 | A |
| ATOM | 443 | CG2 | ILE | A | 63 | 38.482 | 64.153 | 111.446 | 1.00 | 17.26 | A |
| ATOM | 444 | CG1 | ILE | A | 63 | 38.854 | 61.793 | 112.138 | 1.00 | 13.24 | A |
| ATOM | 445 | CD1 | ILE | A | 63 | 37.704 | 61.705 | 113.129 | 1.00 | 12.22 | A |
| ATOM | 446 | C | ILE | A | 63 | 41.334 | 64.572 | 111.167 | 1.00 | 18.36 | A |
| ATOM | 447 | O | ILE | A | 63 | 41.882 | 65.053 | 112.160 | 1.00 | 17.80 | A |
| ATOM | 448 | N | LYS | A | 64 | 41.227 | 65.231 | 110.022 | 1.00 | 18.39 | A |
| ATOM | 449 | CA | LYS | A | 64 | 41.757 | 66.587 | 109.884 | 1.00 | 20.17 | A |
| ATOM | 450 | CB | LYS | A | 64 | 42.534 | 66.715 | 108.568 | 1.00 | 21.80 | A |
| ATOM | 451 | CG | LYS | A | 64 | 43.868 | 65.976 | 108.573 | 1.00 | 27.09 | A |
| ATOM | 452 | CD | LYS | A | 64 | 44.813 | 66.599 | 109.588 | 1.00 | 31.09 | A |
| ATOM | 453 | CE | LYS | A | 64 | 46.056 | 65.749 | 109.806 | 1.00 | 33.75 | A |
| ATOM | 454 | NZ | LYS | A | 64 | 45.731 | 64.450 | 110.462 | 1.00 | 36.45 | A |
| ATOM | 455 | C | LYS | A | 64 | 40.661 | 67.637 | 109.930 | 1.00 | 20.31 | A |
| ATOM | 456 | O | LYS | A | 64 | 40.845 | 68.725 | 110.491 | 1.00 | 17.10 | A |
| ATOM | 457 | N | ASN | A | 65 | 39.520 | 67.301 | 109.335 | 1.00 | 19.52 | A |
| ATOM | 458 | CA | ASN | A | 65 | 38.376 | 68.206 | 109.273 | 1.00 | 19.30 | A |
| ATOM | 459 | CB | ASN | A | 65 | 38.409 | 68.985 | 107.950 | 1.00 | 21.83 | A |
| ATOM | 460 | CG | ASN | A | 65 | 37.084 | 69.676 | 107.634 | 1.00 | 25.41 | A |
| ATOM | 461 | OD1 | ASN | A | 65 | 36.120 | 69.041 | 107.184 | 1.00 | 26.40 | A |
| ATOM | 462 | ND2 | ASN | A | 65 | 37.031 | 70.978 | 107.871 | 1.00 | 24.80 | A |
| ATOM | 463 | C | ASN | A | 65 | 37.056 | 67.454 | 109.391 | 1.00 | 18.97 | A |
| ATOM | 464 | O | ASN | A | 65 | 36.943 | 66.299 | 108.969 | 1.00 | 17.44 | A |
| ATOM | 465 | N | ARG | A | 66 | 36.069 | 68.117 | 109.986 | 1.00 | 18.13 | A |

APPENDIX B-continued

*Arachis hypogaea* STS

| ATOM | # | TYPE | RES | | | X | Y | Z | OCC | B | |
|------|---|------|-----|---|---|---|---|---|-----|---|---|
| ATOM | 466 | CA | ARG | A | 66 | 34.733 | 67.553 | 110.146 | 1.00 | 16.96 | A |
| ATOM | 467 | CB | ARG | A | 66 | 34.529 | 67.023 | 111.566 | 1.00 | 16.26 | A |
| ATOM | 468 | CG | ARG | A | 66 | 35.173 | 65.679 | 111.852 | 1.00 | 16.61 | A |
| ATOM | 469 | CD | ARG | A | 66 | 34.738 | 65.183 | 113.224 | 1.00 | 16.24 | A |
| ATOM | 470 | NE | ARG | A | 66 | 35.405 | 65.920 | 114.289 | 1.00 | 15.56 | A |
| ATOM | 471 | CZ | ARG | A | 66 | 34.992 | 65.947 | 115.550 | 1.00 | 17.32 | A |
| ATOM | 472 | NH1 | ARG | A | 66 | 33.901 | 65.287 | 115.908 | 1.00 | 17.58 | A |
| ATOM | 473 | NH2 | ARG | A | 66 | 35.685 | 66.616 | 116.465 | 1.00 | 17.79 | A |
| ATOM | 474 | C | ARG | A | 66 | 33.701 | 68.637 | 109.880 | 1.00 | 17.04 | A |
| ATOM | 475 | O | ARG | A | 66 | 33.912 | 69.796 | 110.237 | 1.00 | 17.53 | A |
| ATOM | 476 | N | HIS | A | 67 | 32.602 | 68.277 | 109.228 | 1.00 | 15.73 | A |
| ATOM | 477 | CA | HIS | A | 67 | 31.546 | 69.245 | 108.984 | 1.00 | 17.68 | A |
| ATOM | 478 | CB | HIS | A | 67 | 30.864 | 68.997 | 107.635 | 1.00 | 18.72 | A |
| ATOM | 479 | CG | HIS | A | 67 | 31.713 | 69.348 | 106.454 | 1.00 | 21.98 | A |
| ATOM | 480 | CD2 | HIS | A | 67 | 31.716 | 70.441 | 105.653 | 1.00 | 20.76 | A |
| ATOM | 481 | ND1 | HIS | A | 67 | 32.714 | 68.527 | 105.982 | 1.00 | 21.72 | A |
| ATOM | 482 | CE1 | HIS | A | 67 | 33.295 | 69.097 | 104.941 | 1.00 | 21.39 | A |
| ATOM | 483 | NE2 | HIS | A | 67 | 32.707 | 70.259 | 104.721 | 1.00 | 23.60 | A |
| ATOM | 484 | C | HIS | A | 67 | 30.540 | 69.069 | 110.118 | 1.00 | 18.33 | A |
| ATOM | 485 | O | HIS | A | 67 | 30.176 | 67.941 | 110.464 | 1.00 | 17.18 | A |
| ATOM | 486 | N | MET | A | 68 | 30.117 | 70.178 | 110.713 | 1.00 | 16.86 | A |
| ATOM | 487 | CA | MET | A | 68 | 29.163 | 70.124 | 111.807 | 1.00 | 20.49 | A |
| ATOM | 488 | CB | MET | A | 68 | 29.893 | 70.228 | 113.155 | 1.00 | 23.32 | A |
| ATOM | 489 | CG | MET | A | 68 | 30.914 | 69.116 | 113.386 | 1.00 | 28.72 | A |
| ATOM | 490 | SD | MET | A | 68 | 31.545 | 69.023 | 115.086 | 1.00 | 37.96 | A |
| ATOM | 491 | CE | MET | A | 68 | 31.064 | 67.331 | 115.520 | 1.00 | 34.14 | A |
| ATOM | 492 | C | MET | A | 68 | 28.106 | 71.213 | 111.710 | 1.00 | 19.55 | A |
| ATOM | 493 | O | MET | A | 68 | 28.424 | 72.397 | 111.603 | 1.00 | 19.23 | A |
| ATOM | 494 | N | TYR | A | 69 | 26.844 | 70.800 | 111.736 | 1.00 | 19.71 | A |
| ATOM | 495 | CA | TYR | A | 69 | 25.733 | 71.738 | 111.685 | 1.00 | 20.15 | A |
| ATOM | 496 | CB | TYR | A | 69 | 24.401 | 70.981 | 111.659 | 1.00 | 20.47 | A |
| ATOM | 497 | CG | TYR | A | 69 | 23.253 | 71.748 | 112.277 | 1.00 | 20.28 | A |
| ATOM | 498 | CD1 | TYR | A | 69 | 22.713 | 72.874 | 111.650 | 1.00 | 22.00 | A |
| ATOM | 499 | CE1 | TYR | A | 69 | 21.668 | 73.595 | 112.239 | 1.00 | 22.79 | A |
| ATOM | 500 | CD2 | TYR | A | 69 | 22.723 | 71.363 | 113.502 | 1.00 | 20.81 | A |
| ATOM | 501 | CE2 | TYR | A | 69 | 21.688 | 72.069 | 114.094 | 1.00 | 21.13 | A |
| ATOM | 502 | CZ | TYR | A | 69 | 21.163 | 73.184 | 113.461 | 1.00 | 22.53 | A |
| ATOM | 503 | OH | TYR | A | 69 | 20.136 | 73.877 | 114.063 | 1.00 | 22.91 | A |
| ATOM | 504 | C | TYR | A | 69 | 25.789 | 72.632 | 112.918 | 1.00 | 19.58 | A |
| ATOM | 505 | O | TYR | A | 69 | 25.474 | 73.820 | 112.853 | 1.00 | 18.63 | A |
| ATOM | 506 | N | LEU | A | 70 | 26.195 | 72.052 | 114.044 | 1.00 | 17.07 | A |
| ATOM | 507 | CA | LEU | A | 70 | 26.286 | 72.799 | 115.290 | 1.00 | 18.70 | A |
| ATOM | 508 | CB | LEU | A | 70 | 26.548 | 71.846 | 116.466 | 1.00 | 16.86 | A |
| ATOM | 509 | CG | LEU | A | 70 | 25.399 | 70.921 | 116.867 | 1.00 | 17.66 | A |
| ATOM | 510 | CD1 | LEU | A | 70 | 25.866 | 69.928 | 117.930 | 1.00 | 17.33 | A |
| ATOM | 511 | CD2 | LEU | A | 70 | 24.229 | 71.755 | 117.384 | 1.00 | 16.30 | A |
| ATOM | 512 | C | LEU | A | 70 | 27.387 | 73.842 | 115.230 | 1.00 | 19.34 | A |
| ATOM | 513 | O | LEU | A | 70 | 28.546 | 73.515 | 114.963 | 1.00 | 19.14 | A |
| ATOM | 514 | N | THR | A | 71 | 27.017 | 75.094 | 115.483 | 1.00 | 19.06 | A |
| ATOM | 515 | CA | THR | A | 71 | 27.965 | 76.198 | 115.478 | 1.00 | 19.11 | A |
| ATOM | 516 | CB | THR | A | 71 | 27.529 | 77.305 | 114.514 | 1.00 | 20.64 | A |
| ATOM | 517 | OG1 | THR | A | 71 | 26.319 | 77.892 | 114.997 | 1.00 | 18.72 | A |
| ATOM | 518 | CG2 | THR | A | 71 | 27.288 | 76.737 | 113.123 | 1.00 | 21.99 | A |
| ATOM | 519 | C | THR | A | 71 | 28.023 | 76.794 | 116.878 | 1.00 | 19.23 | A |
| ATOM | 520 | O | THR | A | 71 | 27.180 | 76.500 | 117.727 | 1.00 | 17.80 | A |
| ATOM | 521 | N | GLU | A | 72 | 29.015 | 77.644 | 117.118 | 1.00 | 19.93 | A |
| ATOM | 522 | CA | GLU | A | 72 | 29.164 | 78.269 | 118.425 | 1.00 | 21.10 | A |
| ATOM | 523 | CB | GLU | A | 72 | 30.386 | 79.196 | 118.431 | 1.00 | 22.65 | A |
| ATOM | 524 | CG | GLU | A | 72 | 30.715 | 79.745 | 119.814 | 1.00 | 25.51 | A |
| ATOM | 525 | CD | GLU | A | 72 | 32.066 | 80.436 | 119.887 | 1.00 | 26.76 | A |
| ATOM | 526 | OE1 | GLU | A | 72 | 32.356 | 81.053 | 120.939 | 1.00 | 29.43 | A |
| ATOM | 527 | OE2 | GLU | A | 72 | 32.835 | 80.361 | 118.908 | 1.00 | 25.78 | A |
| ATOM | 528 | C | GLU | A | 72 | 27.908 | 79.049 | 118.806 | 1.00 | 21.16 | A |
| ATOM | 529 | O | GLU | A | 72 | 27.479 | 79.035 | 119.965 | 1.00 | 19.47 | A |
| ATOM | 530 | N | GLU | A | 73 | 27.315 | 79.727 | 117.830 | 1.00 | 22.57 | A |
| ATOM | 531 | CA | GLU | A | 73 | 26.108 | 80.506 | 118.082 | 1.00 | 23.75 | A |
| ATOM | 532 | CB | GLU | A | 73 | 25.756 | 81.340 | 116.849 | 1.00 | 28.49 | A |
| ATOM | 533 | CG | GLU | A | 73 | 26.548 | 82.651 | 116.717 | 1.00 | 35.51 | A |
| ATOM | 534 | CD | GLU | A | 73 | 27.929 | 82.617 | 117.382 | 1.00 | 41.12 | A |
| ATOM | 535 | OE1 | GLU | A | 73 | 27.995 | 82.619 | 118.635 | 1.00 | 43.42 | A |
| ATOM | 536 | OE2 | GLU | A | 73 | 28.950 | 82.594 | 116.656 | 1.00 | 44.19 | A |
| ATOM | 537 | C | GLU | A | 73 | 24.947 | 79.594 | 118.466 | 1.00 | 21.96 | A |
| ATOM | 538 | O | GLU | A | 73 | 24.190 | 79.895 | 119.390 | 1.00 | 20.37 | A |
| ATOM | 539 | N | ILE | A | 74 | 24.810 | 78.470 | 117.770 | 1.00 | 19.89 | A |
| ATOM | 540 | CA | ILE | A | 74 | 23.738 | 77.535 | 118.089 | 1.00 | 18.76 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 541 | CB | ILE | A | 74 | 23.659 | 76.390 | 117.043 | 1.00 | 18.90 | A |
| ATOM | 542 | CG2 | ILE | A | 74 | 22.714 | 75.295 | 117.521 | 1.00 | 16.71 | A |
| ATOM | 543 | CG1 | ILE | A | 74 | 23.170 | 76.954 | 115.705 | 1.00 | 20.30 | A |
| ATOM | 544 | CD1 | ILE | A | 74 | 23.046 | 75.924 | 114.596 | 1.00 | 18.88 | A |
| ATOM | 545 | C | ILE | A | 74 | 23.964 | 76.960 | 119.493 | 1.00 | 18.52 | A |
| ATOM | 546 | O | ILE | A | 74 | 23.041 | 76.895 | 120.306 | 1.00 | 20.62 | A |
| ATOM | 547 | N | LEU | A | 75 | 25.193 | 76.561 | 119.788 | 1.00 | 18.16 | A |
| ATOM | 548 | CA | LEU | A | 75 | 25.498 | 76.010 | 121.104 | 1.00 | 17.27 | A |
| ATOM | 549 | CB | LEU | A | 75 | 26.954 | 75.553 | 121.153 | 1.00 | 17.79 | A |
| ATOM | 550 | CG | LEU | A | 75 | 27.280 | 74.382 | 120.222 | 1.00 | 14.50 | A |
| ATOM | 551 | CD1 | LEU | A | 75 | 28.761 | 74.033 | 120.299 | 1.00 | 15.68 | A |
| ATOM | 552 | CD2 | LEU | A | 75 | 26.416 | 73.189 | 120.613 | 1.00 | 18.83 | A |
| ATOM | 553 | C | LEU | A | 75 | 25.225 | 77.028 | 122.212 | 1.00 | 19.75 | A |
| ATOM | 554 | O | LEU | A | 75 | 24.815 | 76.666 | 123.318 | 1.00 | 18.99 | A |
| ATOM | 555 | N | LYS | A | 76 | 25.441 | 78.303 | 121.906 | 1.00 | 20.65 | A |
| ATOM | 556 | CA | LYS | A | 76 | 25.212 | 79.369 | 122.874 | 1.00 | 23.67 | A |
| ATOM | 557 | CB | LYS | A | 76 | 25.660 | 80.713 | 122.294 | 1.00 | 25.80 | A |
| ATOM | 558 | CG | LYS | A | 76 | 25.558 | 81.874 | 123.277 | 1.00 | 31.54 | A |
| ATOM | 559 | CD | LYS | A | 76 | 25.830 | 83.205 | 122.590 | 1.00 | 34.91 | A |
| ATOM | 560 | CE | LYS | A | 76 | 25.581 | 84.377 | 123.528 | 1.00 | 36.18 | A |
| ATOM | 561 | NZ | LYS | A | 76 | 25.622 | 85.681 | 122.801 | 1.00 | 39.35 | A |
| ATOM | 562 | C | LYS | A | 76 | 23.734 | 79.434 | 123.251 | 1.00 | 23.97 | A |
| ATOM | 563 | O | LYS | A | 76 | 23.389 | 79.720 | 124.395 | 1.00 | 23.57 | A |
| ATOM | 564 | N | GLU | A | 77 | 22.865 | 79.152 | 122.283 | 1.00 | 23.60 | A |
| ATOM | 565 | CA | GLU | A | 77 | 21.424 | 79.182 | 122.516 | 1.00 | 25.27 | A |
| ATOM | 566 | CB | GLU | A | 77 | 20.668 | 79.378 | 121.197 | 1.00 | 27.47 | A |
| ATOM | 567 | CG | GLU | A | 77 | 21.266 | 80.405 | 120.247 | 1.00 | 34.00 | A |
| ATOM | 568 | CD | GLU | A | 77 | 21.546 | 81.740 | 120.909 | 1.00 | 36.99 | A |
| ATOM | 569 | OE1 | GLU | A | 77 | 20.633 | 82.284 | 121.566 | 1.00 | 40.32 | A |
| ATOM | 570 | OE2 | GLU | A | 77 | 22.679 | 82.250 | 120.764 | 1.00 | 40.16 | A |
| ATOM | 571 | C | GLU | A | 77 | 20.941 | 77.886 | 123.161 | 1.00 | 24.62 | A |
| ATOM | 572 | O | GLU | A | 77 | 19.773 | 77.770 | 123.521 | 1.00 | 24.54 | A |
| ATOM | 573 | N | ASN | A | 78 | 21.838 | 76.913 | 123.307 | 1.00 | 22.72 | A |
| ATOM | 574 | CA | ASN | A | 78 | 21.468 | 75.627 | 123.884 | 1.00 | 22.16 | A |
| ATOM | 575 | CB | ASN | A | 78 | 21.406 | 74.571 | 122.782 | 1.00 | 20.72 | A |
| ATOM | 576 | CG | ASN | A | 78 | 20.246 | 74.789 | 121.843 | 1.00 | 21.61 | A |
| ATOM | 577 | OD1 | ASN | A | 78 | 19.115 | 74.375 | 122.123 | 1.00 | 19.12 | A |
| ATOM | 578 | ND2 | ASN | A | 78 | 20.512 | 75.457 | 120.724 | 1.00 | 18.54 | A |
| ATOM | 579 | C | ASN | A | 78 | 22.402 | 75.146 | 124.984 | 1.00 | 22.23 | A |
| ATOM | 580 | O | ASN | A | 78 | 23.104 | 74.149 | 124.820 | 1.00 | 22.58 | A |
| ATOM | 581 | N | PRO | A | 79 | 22.412 | 75.844 | 126.130 | 1.00 | 21.67 | A |
| ATOM | 582 | CD | PRO | A | 79 | 21.562 | 76.985 | 126.514 | 1.00 | 21.10 | A |
| ATOM | 583 | CA | PRO | A | 79 | 23.283 | 75.441 | 127.237 | 1.00 | 21.96 | A |
| ATOM | 584 | CB | PRO | A | 79 | 22.958 | 76.465 | 128.327 | 1.00 | 22.78 | A |
| ATOM | 585 | CG | PRO | A | 79 | 21.530 | 76.853 | 128.023 | 1.00 | 23.42 | A |
| ATOM | 586 | C | PRO | A | 79 | 23.036 | 74.000 | 127.689 | 1.00 | 22.12 | A |
| ATOM | 587 | O | PRO | A | 79 | 23.959 | 73.316 | 128.119 | 1.00 | 20.55 | A |
| ATOM | 588 | N | ASN | A | 80 | 21.793 | 73.537 | 127.594 | 1.00 | 21.11 | A |
| ATOM | 589 | CA | ASN | A | 80 | 21.489 | 72.173 | 128.006 | 1.00 | 22.35 | A |
| ATOM | 590 | CB | ASN | A | 80 | 19.982 | 71.931 | 128.012 | 1.00 | 24.80 | A |
| ATOM | 591 | CG | ASN | A | 80 | 19.266 | 72.794 | 129.026 | 1.00 | 27.03 | A |
| ATOM | 592 | OD1 | ASN | A | 80 | 19.790 | 73.058 | 130.109 | 1.00 | 27.86 | A |
| ATOM | 593 | ND2 | ASN | A | 80 | 18.060 | 73.233 | 128.687 | 1.00 | 30.50 | A |
| ATOM | 594 | C | ASN | A | 80 | 22.184 | 71.144 | 127.118 | 1.00 | 22.01 | A |
| ATOM | 595 | O | ASN | A | 80 | 22.410 | 70.009 | 127.536 | 1.00 | 21.27 | A |
| ATOM | 596 | N | MET | A | 81 | 22.530 | 71.541 | 125.898 | 1.00 | 20.53 | A |
| ATOM | 597 | CA | MET | A | 81 | 23.221 | 70.635 | 124.986 | 1.00 | 21.23 | A |
| ATOM | 598 | CB | MET | A | 81 | 22.919 | 70.996 | 123.523 | 1.00 | 20.11 | A |
| ATOM | 599 | CG | MET | A | 81 | 21.541 | 70.549 | 123.044 | 1.00 | 17.66 | A |
| ATOM | 600 | SD | MET | A | 81 | 21.145 | 71.070 | 121.348 | 1.00 | 20.66 | A |
| ATOM | 601 | CE | MET | A | 81 | 22.478 | 70.287 | 120.420 | 1.00 | 19.72 | A |
| ATOM | 602 | C | MET | A | 81 | 24.728 | 70.677 | 125.235 | 1.00 | 20.83 | A |
| ATOM | 603 | O | MET | A | 81 | 25.447 | 69.745 | 124.884 | 1.00 | 19.87 | A |
| ATOM | 604 | N | CYS | A | 82 | 25.203 | 71.758 | 125.850 | 1.00 | 20.43 | A |
| ATOM | 605 | CA | CYS | A | 82 | 26.625 | 71.890 | 126.140 | 1.00 | 20.36 | A |
| ATOM | 606 | CB | CYS | A | 82 | 27.016 | 73.365 | 126.252 | 1.00 | 19.40 | A |
| ATOM | 607 | SG | CYS | A | 82 | 26.921 | 74.261 | 124.692 | 1.00 | 22.96 | A |
| ATOM | 608 | C | CYS | A | 82 | 26.971 | 71.159 | 127.428 | 1.00 | 19.46 | A |
| ATOM | 609 | O | CYS | A | 82 | 28.126 | 70.807 | 127.664 | 1.00 | 21.85 | A |
| ATOM | 610 | N | ALA | A | 83 | 25.963 | 70.932 | 128.261 | 1.00 | 19.79 | A |
| ATOM | 611 | CA | ALA | A | 83 | 26.167 | 70.232 | 129.518 | 1.00 | 19.82 | A |
| ATOM | 612 | CB | ALA | A | 83 | 24.960 | 70.417 | 130.414 | 1.00 | 20.37 | A |
| ATOM | 613 | C | ALA | A | 83 | 26.361 | 68.756 | 129.207 | 1.00 | 21.03 | A |
| ATOM | 614 | O | ALA | A | 83 | 25.891 | 68.272 | 128.175 | 1.00 | 18.48 | A |
| ATOM | 615 | N | TYR | A | 84 | 27.053 | 68.043 | 130.091 | 1.00 | 20.86 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 616 | CA | TYR | A | 84 | 27.269 | 66.615 | 129.883 | 1.00 | 21.75 | A |
| ATOM | 617 | CB | TYR | A | 84 | 28.207 | 66.045 | 130.946 | 1.00 | 20.13 | A |
| ATOM | 618 | CG | TYR | A | 84 | 28.198 | 64.531 | 130.988 | 1.00 | 20.20 | A |
| ATOM | 619 | CD1 | TYR | A | 84 | 28.805 | 63.782 | 129.986 | 1.00 | 19.11 | A |
| ATOM | 620 | CE1 | TYR | A | 84 | 28.762 | 62.387 | 130.008 | 1.00 | 21.15 | A |
| ATOM | 621 | CD2 | TYR | A | 84 | 27.547 | 63.850 | 132.017 | 1.00 | 19.79 | A |
| ATOM | 622 | CE2 | TYR | A | 84 | 27.495 | 62.468 | 132.047 | 1.00 | 23.38 | A |
| ATOM | 623 | CZ | TYR | A | 84 | 28.101 | 61.740 | 131.044 | 1.00 | 21.82 | A |
| ATOM | 624 | OH | TYR | A | 84 | 28.027 | 60.369 | 131.072 | 1.00 | 22.42 | A |
| ATOM | 625 | C | TYR | A | 84 | 25.936 | 65.885 | 129.969 | 1.00 | 22.94 | A |
| ATOM | 626 | O | TYR | A | 84 | 25.678 | 64.949 | 129.212 | 1.00 | 24.58 | A |
| ATOM | 627 | N | LYS | A | 85 | 25.091 | 66.329 | 130.895 | 1.00 | 24.59 | A |
| ATOM | 628 | CA | LYS | A | 85 | 23.786 | 65.715 | 131.116 | 1.00 | 27.30 | A |
| ATOM | 629 | CB | LYS | A | 85 | 23.937 | 64.572 | 132.128 | 1.00 | 28.97 | A |
| ATOM | 630 | CG | LYS | A | 85 | 22.680 | 64.203 | 132.905 | 1.00 | 33.37 | A |
| ATOM | 631 | CD | LYS | A | 85 | 23.016 | 63.202 | 134.011 | 1.00 | 35.36 | A |
| ATOM | 632 | CE | LYS | A | 85 | 21.856 | 63.001 | 134.975 | 1.00 | 36.29 | A |
| ATOM | 633 | NZ | LYS | A | 85 | 20.630 | 62.504 | 134.289 | 1.00 | 37.50 | A |
| ATOM | 634 | C | LYS | A | 85 | 22.743 | 66.717 | 131.613 | 1.00 | 26.53 | A |
| ATOM | 635 | O | LYS | A | 85 | 22.744 | 67.089 | 132.786 | 1.00 | 28.76 | A |
| ATOM | 636 | N | ALA | A | 86 | 21.862 | 67.150 | 130.713 | 1.00 | 23.82 | A |
| ATOM | 637 | CA | ALA | A | 86 | 20.789 | 68.089 | 131.040 | 1.00 | 21.57 | A |
| ATOM | 638 | CB | ALA | A | 86 | 21.283 | 69.519 | 130.892 | 1.00 | 20.90 | A |
| ATOM | 639 | C | ALA | A | 86 | 19.638 | 67.823 | 130.065 | 1.00 | 21.98 | A |
| ATOM | 640 | O | ALA | A | 86 | 19.885 | 67.469 | 128.913 | 1.00 | 20.68 | A |
| ATOM | 641 | N | PRO | A | 87 | 18.374 | 67.982 | 130.513 | 1.00 | 23.00 | A |
| ATOM | 642 | CD | PRO | A | 87 | 17.985 | 68.429 | 131.864 | 1.00 | 25.15 | A |
| ATOM | 643 | CA | PRO | A | 87 | 17.179 | 67.756 | 129.682 | 1.00 | 23.11 | A |
| ATOM | 644 | CB | PRO | A | 87 | 16.046 | 68.277 | 130.561 | 1.00 | 25.66 | A |
| ATOM | 645 | CG | PRO | A | 87 | 16.553 | 67.972 | 131.951 | 1.00 | 26.07 | A |
| ATOM | 646 | C | PRO | A | 87 | 17.290 | 68.510 | 128.368 | 1.00 | 23.09 | A |
| ATOM | 647 | O | PRO | A | 87 | 17.312 | 69.741 | 128.363 | 1.00 | 20.97 | A |
| ATOM | 648 | N | SER | A | 88 | 17.342 | 67.780 | 127.253 | 1.00 | 19.74 | A |
| ATOM | 649 | CA | SER | A | 88 | 17.517 | 68.434 | 125.962 | 1.00 | 16.92 | A |
| ATOM | 650 | CB | SER | A | 88 | 18.992 | 68.805 | 125.804 | 1.00 | 16.86 | A |
| ATOM | 651 | OG | SER | A | 88 | 19.797 | 67.642 | 125.909 | 1.00 | 14.70 | A |
| ATOM | 652 | C | SER | A | 88 | 17.095 | 67.626 | 124.737 | 1.00 | 17.40 | A |
| ATOM | 653 | O | SER | A | 88 | 17.387 | 68.027 | 123.613 | 1.00 | 17.18 | A |
| ATOM | 654 | N | LEU | A | 89 | 16.419 | 66.499 | 124.931 | 1.00 | 16.77 | A |
| ATOM | 655 | CA | LEU | A | 89 | 16.011 | 65.691 | 123.786 | 1.00 | 18.16 | A |
| ATOM | 656 | CB | LEU | A | 89 | 15.315 | 64.408 | 124.245 | 1.00 | 19.74 | A |
| ATOM | 657 | CG | LEU | A | 89 | 14.896 | 63.525 | 123.066 | 1.00 | 20.68 | A |
| ATOM | 658 | CD1 | LEU | A | 89 | 16.117 | 62.910 | 122.420 | 1.00 | 20.92 | A |
| ATOM | 659 | CD2 | LEU | A | 89 | 13.971 | 62.457 | 123.551 | 1.00 | 22.54 | A |
| ATOM | 660 | C | LEU | A | 89 | 15.107 | 66.441 | 122.808 | 1.00 | 17.08 | A |
| ATOM | 661 | O | LEU | A | 89 | 15.295 | 66.344 | 121.598 | 1.00 | 18.35 | A |
| ATOM | 662 | N | ASP | A | 90 | 14.135 | 67.191 | 123.320 | 1.00 | 17.39 | A |
| ATOM | 663 | CA | ASP | A | 90 | 13.222 | 67.943 | 122.453 | 1.00 | 16.14 | A |
| ATOM | 664 | CB | ASP | A | 90 | 12.218 | 68.737 | 123.294 | 1.00 | 19.36 | A |
| ATOM | 665 | CG | ASP | A | 90 | 11.162 | 67.858 | 123.942 | 1.00 | 20.42 | A |
| ATOM | 666 | OD1 | ASP | A | 90 | 10.253 | 68.421 | 124.581 | 1.00 | 22.07 | A |
| ATOM | 667 | OD2 | ASP | A | 90 | 11.234 | 66.612 | 123.821 | 1.00 | 21.79 | A |
| ATOM | 668 | C | ASP | A | 90 | 13.959 | 68.906 | 121.511 | 1.00 | 17.32 | A |
| ATOM | 669 | O | ASP | A | 90 | 13.725 | 68.920 | 120.291 | 1.00 | 14.74 | A |
| ATOM | 670 | N | ALA | A | 91 | 14.833 | 69.729 | 122.078 | 1.00 | 15.85 | A |
| ATOM | 671 | CA | ALA | A | 91 | 15.593 | 70.679 | 121.273 | 1.00 | 16.35 | A |
| ATOM | 672 | CB | ALA | A | 91 | 16.476 | 71.533 | 122.175 | 1.00 | 16.94 | A |
| ATOM | 673 | C | ALA | A | 91 | 16.449 | 69.951 | 120.235 | 1.00 | 16.25 | A |
| ATOM | 674 | O | ALA | A | 91 | 16.524 | 70.369 | 119.076 | 1.00 | 13.95 | A |
| ATOM | 675 | N | ARG | A | 92 | 17.085 | 68.855 | 120.647 | 1.00 | 14.79 | A |
| ATOM | 676 | CA | ARG | A | 92 | 17.937 | 68.091 | 119.739 | 1.00 | 14.64 | A |
| ATOM | 677 | CB | ARG | A | 92 | 18.672 | 66.981 | 120.499 | 1.00 | 14.18 | A |
| ATOM | 678 | CG | ARG | A | 92 | 19.654 | 67.461 | 121.572 | 1.00 | 13.74 | A |
| ATOM | 679 | CD | ARG | A | 92. | 20.045 | 66.282 | 122.463 | 1.00 | 13.80 | A |
| ATOM | 680 | NE | ARG | A | 92 | 20.992 | 66.630 | 123.523 | 1.00 | 13.20 | A |
| ATOM | 681 | CZ | ARG | A | 92 | 22.310 | 66.719 | 123.359 | 1.00 | 13.36 | A |
| ATOM | 682 | NH1 | ARG | A | 92 | 22.858 | 66.491 | 122.171 | 1.00 | 12.28 | A |
| ATOM | 683 | NH2 | ARG | A | 92 | 23.087 | 67.010 | 124.398 | 1.00 | 15.07 | A |
| ATOM | 684 | C | ARG | A | 92 | 17.130 | 67.475 | 118.598 | 1.00 | 14.35 | A |
| ATOM | 685 | O | ARG | A | 92 | 17.492 | 67.605 | 117.432 | 1.00 | 13.62 | A |
| ATOM | 686 | N | GLU | A | 93 | 16.037 | 66.803 | 118.939 | 1.00 | 14.60 | A |
| ATOM | 687 | CA | GLU | A | 93 | 15.192 | 66.178 | 117.925 | 1.00 | 15.88 | A |
| ATOM | 688 | CB | GLU | A | 93 | 14.073 | 65.379 | 118.597 | 1.00 | 16.99 | A |
| ATOM | 689 | CG | GLU | A | 93 | 14.580 | 64.128 | 119.313 | 1.00 | 20.99 | A |
| ATOM | 690 | CD | GLU | A | 93 | 15.046 | 63.032 | 118.348 | 1.00 | 23.76 | A |

APPENDIX B-continued

*Arachis hypogaea* STS

| ATOM | # | TYPE | RES | | | X | Y | Z | OCC | B | |
|------|---|------|-----|---|---|---|---|---|-----|---|---|
| ATOM | 691 | OE1 | GLU | A | 93 | 16.010 | 62.305 | 118.675 | 1.00 | 23.78 | A |
| ATOM | 692 | OE2 | GLU | A | 93 | 14.442 | 62.889 | 117.267 | 1.00 | 26.26 | A |
| ATOM | 693 | C | GLU | A | 93 | 14.614 | 67.214 | 116.966 | 1.00 | 15.22 | A |
| ATOM | 694 | O | GLU | A | 93 | 14.458 | 66.947 | 115.776 | 1.00 | 15.96 | A |
| ATOM | 695 | N | ASP | A | 94 | 14.309 | 68.406 | 117.465 | 1.00 | 15.22 | A |
| ATOM | 696 | CA | ASP | A | 94 | 13.777 | 69.430 | 116.576 | 1.00 | 14.70 | A |
| ATOM | 697 | CB | ASP | A | 94 | 13.340 | 70.673 | 117.360 | 1.00 | 17.50 | A |
| ATOM | 698 | CG | ASP | A | 94 | 12.052 | 70.448 | 118.151 | 1.00 | 21.10 | A |
| ATOM | 699 | OD1 | ASP | A | 94 | 11.253 | 69.564 | 117.768 | 1.00 | 23.41 | A |
| ATOM | 700 | OD2 | ASP | A | 94 | 11.826 | 71.167 | 119.150 | 1.00 | 23.08 | A |
| ATOM | 701 | C | ASP | A | 94 | 14.829 | 69.801 | 115.530 | 1.00 | 15.14 | A |
| ATOM | 702 | O | ASP | A | 94 | 14.501 | 70.018 | 114.364 | 1.00 | 14.99 | A |
| ATOM | 703 | N | MET | A | 95 | 16.094 | 69.860 | 115.944 | 1.00 | 16.52 | A |
| ATOM | 704 | CA | MET | A | 95 | 17.183 | 70.187 | 115.031 | 1.00 | 13.82 | A |
| ATOM | 705 | CB | MET | A | 95 | 18.507 | 70.321 | 115.789 | 1.00 | 14.37 | A |
| ATOM | 706 | CG | MET | A | 95 | 18.598 | 71.520 | 116.725 | 1.00 | 15.94 | A |
| ATOM | 707 | SD | MET | A | 95 | 20.178 | 71.517 | 117.624 | 1.00 | 19.13 | A |
| ATOM | 708 | CE | MET | A | 95 | 20.074 | 73.098 | 118.500 | 1.00 | 19.01 | A |
| ATOM | 709 | C | MET | A | 95 | 17.316 | 69.071 | 114.003 | 1.00 | 15.95 | A |
| ATOM | 710 | O | MET | A | 95 | 17.440 | 69.324 | 112.806 | 1.00 | 15.19 | A |
| ATOM | 711 | N | MET | A | 96 | 17.313 | 67.833 | 114.490 | 1.00 | 14.58 | A |
| ATOM | 712 | CA | MET | A | 96 | 17.428 | 66.670 | 113.618 | 1.00 | 14.52 | A |
| ATOM | 713 | CB | MET | A | 96 | 17.341 | 65.376 | 114.447 | 1.00 | 13.66 | A |
| ATOM | 714 | CG | MET | A | 96 | 18.498 | 65.155 | 115.417 | 1.00 | 15.74 | A |
| ATOM | 715 | SD | MET | A | 96 | 20.095 | 64.978 | 114.615 | 1.00 | 18.80 | A |
| ATOM | 716 | CE | MET | A | 96 | 20.010 | 63.239 | 114.121 | 1.00 | 15.04 | A |
| ATOM | 717 | C | MET | A | 96 | 16.328 | 66.673 | 112.554 | 1.00 | 14.12 | A |
| ATOM | 718 | O | MET | A | 96 | 16.609 | 66.556 | 111.366 | 1.00 | 17.99 | A |
| ATOM | 719 | N | ILE | A | 97 | 15.079 | 66.806 | 112.983 | 1.00 | 14.93 | A |
| ATOM | 720 | CA | ILE | A | 97 | 13.944 | 66.804 | 112.058 | 1.00 | 15.15 | A |
| ATOM | 721 | CB | ILE | A | 97 | 12.615 | 66.959 | 112.835 | 1.00 | 15.85 | A |
| ATOM | 722 | CG2 | ILE | A | 97 | 11.431 | 67.096 | 111.861 | 1.00 | 17.38 | A |
| ATOM | 723 | CG1 | ILE | A | 97 | 12.405 | 65.737 | 113.735 | 1.00 | 13.08 | A |
| ATOM | 724 | CD1 | ILE | A | 97 | 11.277 | 65.901 | 114.736 | 1.00 | 14.10 | A |
| ATOM | 725 | C | ILE | A | 97 | 14.062 | 67.891 | 110.984 | 1.00 | 16.23 | A |
| ATOM | 726 | O | ILE | A | 97 | 13.664 | 67.694 | 109.829 | 1.00 | 15.33 | A |
| ATOM | 727 | N | ARG | A | 98 | 14.624 | 69.033 | 111.356 | 1.00 | 15.97 | A |
| ATOM | 728 | CA | ARG | A | 98 | 14.796 | 70.123 | 110.400 | 1.00 | 18.43 | A |
| ATOM | 729 | CB | ARG | A | 98 | 15.015 | 71.435 | 111.150 | 1.00 | 19.15 | A |
| ATOM | 730 | CG | ARG | A | 98 | 15.092 | 72.667 | 110.267 | 1.00 | 24.01 | A |
| ATOM | 731 | CD | ARG | A | 98 | 15.425 | 73.900 | 111.093 | 1.00 | 25.52 | A |
| ATOM | 732 | NE | ARG | A | 98 | 14.794 | 73.866 | 112.412 | 1.00 | 27.90 | A |
| ATOM | 733 | CZ | ARG | A | 98 | 15.447 | 73.645 | 113.548 | 1.00 | 27.71 | A |
| ATOM | 734 | NH1 | ARG | A | 98 | 16.758 | 73.437 | 113.529 | 1.00 | 33.63 | A |
| ATOM | 735 | NH2 | ARG | A | 98 | 14.793 | 73.635 | 114.704 | 1.00 | 31.02 | A |
| ATOM | 736 | C | ARG | A | 98 | 15.979 | 69.889 | 109.456 | 1.00 | 17.85 | A |
| ATOM | 737 | O | ARG | A | 98 | 15.850 | 69.980 | 108.230 | 1.00 | 16.62 | A |
| ATOM | 738 | N | GLU | A | 99 | 17.127 | 69.561 | 110.034 | 1.00 | 16.61 | A |
| ATOM | 739 | CA | GLU | A | 99 | 18.352 | 69.379 | 109.267 | 1.00 | 16.47 | A |
| ATOM | 740 | CB | GLU | A | 99 | 19.543 | 69.659 | 110.181 | 1.00 | 17.68 | A |
| ATOM | 741 | CG | GLU | A | 99 | 19.471 | 71.041 | 110.816 | 1.00 | 19.11 | A |
| ATOM | 742 | CD | GLU | A | 99 | 19.564 | 72.152 | 109.786 | 1.00 | 21.20 | A |
| ATOM | 743 | OE1 | GLU | A | 99 | 19.074 | 73.271 | 110.061 | 1.00 | 23.07 | A |
| ATOM | 744 | OE2 | GLU | A | 99 | 20.139 | 71.904 | 108.705 | 1.00 | 21.85 | A |
| ATOM | 745 | C | GLU | A | 99 | 18.598 | 68.083 | 108.514 | 1.00 | 16.27 | A |
| ATOM | 746 | O | GLU | A | 99 | 19.213 | 68.098 | 107.449 | 1.00 | 16.09 | A |
| ATOM | 747 | N | VAL | A | 100 | 18.141 | 66.962 | 109.053 | 1.00 | 15.95 | A |
| ATOM | 748 | CA | VAL | A | 100 | 18.379 | 65.681 | 108.402 | 1.00 | 16.57 | A |
| ATOM | 749 | CB | VAL | A | 100 | 17.809 | 64.528 | 109.258 | 1.00 | 18.24 | A |
| ATOM | 750 | CG1 | VAL | A | 100 | 17.921 | 63.197 | 108.521 | 1.00 | 20.43 | A |
| ATOM | 751 | CG2 | VAL | A | 100 | 18.591 | 64.453 | 110.562 | 1.00 | 19.88 | A |
| ATOM | 752 | C | VAL | A | 100 | 17.827 | 65.644 | 106.980 | 1.00 | 16.27 | A |
| ATOM | 753 | O | VAL | A | 100 | 18.548 | 65.308 | 106.041 | 1.00 | 14.58 | A |
| ATOM | 754 | N | PRO | A | 101 | 16.549 | 66.013 | 106.792 | 1.00 | 18.57 | A |
| ATOM | 755 | CD | PRO | A | 101 | 15.480 | 66.240 | 107.782 | 1.00 | 20.19 | A |
| ATOM | 756 | CA | PRO | A | 101 | 16.013 | 65.983 | 105.425 | 1.00 | 18.96 | A |
| ATOM | 757 | CB | PRO | A | 101 | 14.503 | 66.063 | 105.646 | 1.00 | 20.79 | A |
| ATOM | 758 | CG | PRO | A | 101 | 14.379 | 66.821 | 106.941 | 1.00 | 21.86 | A |
| ATOM | 759 | C | PRO | A | 101 | 16.540 | 67.100 | 104.522 | 1.00 | 17.94 | A |
| ATOM | 760 | O | PRO | A | 101 | 16.618 | 66.945 | 103.308 | 1.00 | 18.12 | A |
| ATOM | 761 | N | ARG | A | 102 | 16.910 | 68.222 | 105.122 | 1.00 | 18.08 | A |
| ATOM | 762 | CA | ARG | A | 102 | 17.411 | 69.361 | 104.365 | 1.00 | 19.16 | A |
| ATOM | 763 | CB | ARG | A | 102 | 17.530 | 70.555 | 105.314 | 1.00 | 22.01 | A |
| ATOM | 764 | CG | ARG | A | 102 | 18.080 | 71.815 | 104.712 | 1.00 | 26.94 | A |
| ATOM | 765 | CD | ARG | A | 102 | 17.796 | 72.989 | 105.634 | 1.00 | 28.29 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 766 | NE | ARG | A | 102 | 18.545 | 74.166 | 105.225 | 1.00 | 30.92 | A |
| ATOM | 767 | CZ | ARG | A | 102 | 19.826 | 74.361 | 105.506 | 1.00 | 32.08 | A |
| ATOM | 768 | NH1 | ARG | A | 102 | 20.496 | 73.459 | 106.210 | 1.00 | 31.02 | A |
| ATOM | 769 | NH2 | ARG | A | 102 | 20.441 | 75.449 | 105.059 | 1.00 | 33.44 | A |
| ATOM | 770 | C | ARG | A | 102 | 18.741 | 69.055 | 103.664 | 1.00 | 18.26 | A |
| ATOM | 771 | O | ARG | A | 102 | 18.887 | 69.286 | 102.464 | 1.00 | 18.02 | A |
| ATOM | 772 | N | VAL | A | 103 | 19.705 | 68.517 | 104.402 | 1.00 | 15.63 | A |
| ATOM | 773 | CA | VAL | A | 103 | 20.999 | 68.175 | 103.817 | 1.00 | 16.43 | A |
| ATOM | 774 | CB | VAL | A | 103 | 22.037 | 67.828 | 104.907 | 1.00 | 16.44 | A |
| ATOM | 775 | CG1 | VAL | A | 103 | 23.378 | 67.471 | 104.263 | 1.00 | 17.24 | A |
| ATOM | 776 | CG2 | VAL | A | 103 | 22.194 | 69.011 | 105.856 | 1.00 | 19.29 | A |
| ATOM | 777 | C | VAL | A | 103 | 20.795 | 66.967 | 102.911 | 1.00 | 15.93 | A |
| ATOM | 778 | O | VAL | A | 103 | 21.452 | 66.834 | 101.881 | 1.00 | 14.17 | A |
| ATOM | 779 | N | GLY | A | 104 | 19.871 | 66.094 | 103.302 | 1.00 | 16.69 | A |
| ATOM | 780 | CA | GLY | A | 104 | 19.580 | 64.918 | 102.499 | 1.00 | 14.99 | A |
| ATOM | 781 | C | GLY | A | 104 | 19.068 | 65.333 | 101.126 | 1.00 | 16.35 | A |
| ATOM | 782 | O | GLY | A | 104 | 19.437 | 64.745 | 100.112 | 1.00 | 17.10 | A |
| ATOM | 783 | N | LYS | A | 105 | 18.221 | 66.356 | 101.084 | 1.00 | 16.15 | A |
| ATOM | 784 | CA | LYS | A | 105 | 17.702 | 66.820 | 99.803 | 1.00 | 17.34 | A |
| ATOM | 785 | CB | LYS | A | 105 | 16.675 | 67.936 | 99.990 | 1.00 | 17.80 | A |
| ATOM | 786 | CG | LYS | A | 105 | 16.189 | 68.486 | 98.653 | 1.00 | 21.22 | A |
| ATOM | 787 | CD | LYS | A | 105 | 15.789 | 69.941 | 98.756 | 1.00 | 25.56 | A |
| ATOM | 788 | CE | LYS | A | 105 | 15.600 | 70.553 | 97.374 | 1.00 | 28.16 | A |
| ATOM | 789 | NZ | LYS | A | 105 | 16.888 | 70.618 | 96.620 | 1.00 | 29.98 | A |
| ATOM | 790 | C | LYS | A | 105 | 18.818 | 67.336 | 98.902 | 1.00 | 16.20 | A |
| ATOM | 791 | O | LYS | A | 105 | 18.807 | 67.091 | 97.700 | 1.00 | 17.34 | A |
| ATOM | 792 | N | GLU | A | 106 | 19.773 | 68.062 | 99.477 | 1.00 | 16.91 | A |
| ATOM | 793 | CA | GLU | A | 106 | 20.881 | 68.598 | 98.696 | 1.00 | 19.15 | A |
| ATOM | 794 | CB | GLU | A | 106 | 21.835 | 69.387 | 99.600 | 1.00 | 20.83 | A |
| ATOM | 795 | CG | GLU | A | 106 | 23.047 | 69.922 | 98.862 | 1.00 | 25.52 | A |
| ATOM | 796 | CD | GLU | A | 106 | 23.920 | 70.828 | 99.716 | 1.00 | 26.98 | A |
| ATOM | 797 | OE1 | GLU | A | 106 | 25.035 | 71.164 | 99.260 | 1.00 | 27.30 | A |
| ATOM | 798 | OE2 | GLU | A | 106 | 23.495 | 71.204 | 100.832 | 1.00 | 27.96 | A |
| ATOM | 799 | C | GLU | A | 106 | 21.629 | 67.450 | 98.016 | 1.00 | 18.67 | A |
| ATOM | 800 | O | GLU | A | 106 | 21.938 | 67.504 | 96.817 | 1.00 | 16.99 | A |
| ATOM | 801 | N | ALA | A | 107 | 21.907 | 66.401 | 98.783 | 1.00 | 15.83 | A |
| ATOM | 802 | CA | ALA | A | 107 | 22.610 | 65.244 | 98.243 | 1.00 | 15.27 | A |
| ATOM | 803 | CB | ALA | A | 107 | 22.928 | 64.251 | 99.359 | 1.00 | 14.32 | A |
| ATOM | 804 | C | ALA | A | 107 | 21.778 | 64.556 | 97.162 | 1.00 | 13.90 | A |
| ATOM | 805 | O | ALA | A | 107 | 22.299 | 64.189 | 96.105 | 1.00 | 13.71 | A |
| ATOM | 806 | N | ALA | A | 108 | 20.488 | 64.380 | 97.431 | 1.00 | 14.03 | A |
| ATOM | 807 | CA | ALA | A | 108 | 19.599 | 63.720 | 96.477 | 1.00 | 15.72 | A |
| ATOM | 808 | CB | ALA | A | 108 | 18.219 | 63.519 | 97.091 | 1.00 | 15.61 | A |
| ATOM | 809 | C | ALA | A | 108 | 19.480 | 64.494 | 95.175 | 1.00 | 16.95 | A |
| ATOM | 810 | O | ALA | A | 108 | 19.442 | 63.899 | 94.098 | 1.00 | 16.28 | A |
| ATOM | 811 | N | THR | A | 109 | 19.412 | 65.820 | 95.269 | 1.00 | 15.93 | A |
| ATOM | 812 | CA | THR | A | 109 | 19.309 | 66.642 | 94.071 | 1.00 | 17.23 | A |
| ATOM | 813 | CB | THR | A | 109 | 19.206 | 68.148 | 94.432 | 1.00 | 17.73 | A |
| ATOM | 814 | OG1 | THR | A | 109 | 17.994 | 68.381 | 95.160 | 1.00 | 16.64 | A |
| ATOM | 815 | CG2 | THR | A | 109 | 19.207 | 69.004 | 93.176 | 1.00 | 21.91 | A |
| ATOM | 816 | C | THR | A | 109 | 20.538 | 66.396 | 93.192 | 1.00 | 16.50 | A |
| ATOM | 817 | O | THR | A | 109 | 20.430 | 66.291 | 91.969 | 1.00 | 15.20 | A |
| ATOM | 818 | N | LYS | A | 110 | 21.707 | 66.286 | 93.817 | 1.00 | 15.38 | A |
| ATOM | 819 | CA | LYS | A | 110 | 22.940 | 66.048 | 93.074 | 1.00 | 15.76 | A |
| ATOM | 820 | CB | LYS | A | 110 | 24.149 | 66.168 | 94.002 | 1.00 | 16.69 | A |
| ATOM | 821 | CG | LYS | A | 110 | 24.428 | 67.571 | 94.486 | 1.00 | 19.70 | A |
| ATOM | 822 | CD | LYS | A | 110 | 25.648 | 67.563 | 95.384 | 1.00 | 20.65 | A |
| ATOM | 823 | CE | LYS | A | 110 | 25.940 | 68.937 | 95.931 | 1.00 | 22.93 | A |
| ATOM | 824 | NZ | LYS | A | 110 | 27.124 | 68.891 | 96.839 | 1.00 | 21.69 | A |
| ATOM | 825 | C | LYS | A | 110 | 22.957 | 64.672 | 92.401 | 1.00 | 13.93 | A |
| ATOM | 826 | O | LYS | A | 110 | 23.397 | 64.530 | 91.257 | 1.00 | 13.99 | A |
| ATOM | 827 | N | ALA | A | 111 | 22.482 | 63.659 | 93.115 | 1.00 | 15.58 | A |
| ATOM | 828 | CA | ALA | A | 111 | 22.449 | 62.306 | 92.561 | 1.00 | 14.44 | A |
| ATOM | 829 | CB | ALA | A | 111 | 22.046 | 61.318 | 93.640 | 1.00 | 14.66 | A |
| ATOM | 830 | C | ALA | A | 111 | 21.466 | 62.245 | 91.387 | 1.00 | 15.71 | A |
| ATOM | 831 | O | ALA | A | 111 | 21.762 | 61.673 | 90.338 | 1.00 | 14.80 | A |
| ATOM | 832 | N | ILE | A | 112 | 20.297 | 62.851 | 91.560 | 1.00 | 16.78 | A |
| ATOM | 833 | CA | ILE | A | 112 | 19.298 | 62.851 | 90.499 | 1.00 | 17.55 | A |
| ATOM | 834 | CB | ILE | A | 112 | 17.973 | 63.474 | 90.993 | 1.00 | 17.59 | A |
| ATOM | 835 | CG2 | ILE | A | 112 | 16.986 | 63.620 | 89.837 | 1.00 | 17.13 | A |
| ATOM | 836 | CG1 | ILE | A | 112 | 17.386 | 62.580 | 92.092 | 1.00 | 20.85 | A |
| ATOM | 837 | CD1 | ILE | A | 112 | 16.066 | 63.064 | 92.660 | 1.00 | 22.77 | A |
| ATOM | 838 | C | ILE | A | 112 | 19.828 | 63.586 | 89.268 | 1.00 | 18.57 | A |
| ATOM | 839 | O | ILE | A | 112 | 19.568 | 63.179 | 88.139 | 1.00 | 16.83 | A |
| ATOM | 840 | N | LYS | A | 113 | 20.594 | 64.651 | 89.484 | 1.00 | 19.85 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 841 | CA | LYS | A | 113 | 21.177 | 65.401 | 88.375 | 1.00 | 21.93 | A |
| ATOM | 842 | CB | LYS | A | 113 | 21.924 | 66.633 | 88.894 | 1.00 | 24.29 | A |
| ATOM | 843 | CG | LYS | A | 113 | 22.557 | 67.478 | 87.785 | 1.00 | 26.16 | A |
| ATOM | 844 | CD | LYS | A | 113 | 23.249 | 68.717 | 88.343 | 1.00 | 30.15 | A |
| ATOM | 845 | CE | LYS | A | 113 | 23.865 | 69.549 | 87.227 | 1.00 | 32.17 | A |
| ATOM | 846 | NZ | LYS | A | 113 | 22.832 | 69.994 | 86.246 | 1.00 | 33.78 | A |
| ATOM | 847 | C | LYS | A | 113 | 22.141 | 64.515 | 87.576 | 1.00 | 22.24 | A |
| ATOM | 848 | O | LYS | A | 113 | 22.113 | 64.514 | 86.346 | 1.00 | 20.23 | A |
| ATOM | 849 | N | GLU | A | 114 | 22.994 | 63.763 | 88.274 | 1.00 | 20.31 | A |
| ATOM | 850 | CA | GLU | A | 114 | 23.941 | 62.872 | 87.603 | 1.00 | 20.76 | A |
| ATOM | 851 | CB | GLU | A | 114 | 24.858 | 62.174 | 88.615 | 1.00 | 20.34 | A |
| ATOM | 852 | CG | GLU | A | 114 | 25.945 | 61.318 | 87.961 | 1.00 | 22.36 | A |
| ATOM | 853 | CD | GLU | A | 114 | 26.594 | 60.333 | 88.922 | 1.00 | 25.31 | A |
| ATOM | 854 | OE1 | GLU | A | 114 | 26.524 | 60.562 | 90.148 | 1.00 | 23.40 | A |
| ATOM | 855 | OE2 | GLU | A | 114 | 27.188 | 59.335 | 88.449 | 1.00 | 27.34 | A |
| ATOM | 856 | C | GLU | A | 114 | 23.192 | 61.797 | 86.825 | 1.00 | 20.63 | A |
| ATOM | 857 | O | GLU | A | 114 | 23.520 | 61.506 | 85.677 | 1.00 | 20.09 | A |
| ATOM | 858 | N | TRP | A | 115 | 22.197 | 61.206 | 87.483 | 1.00 | 19.11 | A |
| ATOM | 859 | CA | TRP | A | 115 | 21.373 | 60.148 | 86.912 | 1.00 | 19.80 | A |
| ATOM | 860 | CB | TRP | A | 115 | 20.271 | 59.788 | 87.909 | 1.00 | 16.70 | A |
| ATOM | 861 | CG | TRP | A | 115 | 19.386 | 58.655 | 87.513 | 1.00 | 17.51 | A |
| ATOM | 862 | CD2 | TRP | A | 115 | 18.002 | 58.504 | 87.841 | 1.00 | 18.01 | A |
| ATOM | 863 | CE2 | TRP | A | 115 | 17.583 | 57.255 | 87.325 | 1.00 | 19.36 | A |
| ATOM | 864 | CE3 | TRP | A | 115 | 17.073 | 59.302 | 88.520 | 1.00 | 18.64 | A |
| ATOM | 865 | CD1 | TRP | A | 115 | 19.744 | 57.524 | 86.829 | 1.00 | 17.50 | A |
| ATOM | 866 | NE1 | TRP | A | 115 | 18.666 | 56.679 | 86.714 | 1.00 | 16.73 | A |
| ATOM | 867 | CZ2 | TRP | A | 115 | 16.274 | 56.788 | 87.470 | 1.00 | 20.10 | A |
| ATOM | 868 | CZ3 | TRP | A | 115 | 15.769 | 58.837 | 88.663 | 1.00 | 18.36 | A |
| ATOM | 869 | CH2 | TRP | A | 115 | 15.384 | 57.589 | 88.139 | 1.00 | 19.75 | A |
| ATOM | 870 | C | TRP | A | 115 | 20.786 | 60.613 | 85.581 | 1.00 | 20.41 | A |
| ATOM | 871 | O | TRP | A | 115 | 20.804 | 59.873 | 84.598 | 1.00 | 20.70 | A |
| ATOM | 872 | N | GLY | A | 116 | 20.278 | 61.844 | 85.560 | 1.00 | 20.64 | A |
| ATOM | 873 | CA | GLY | A | 116 | 19.727 | 62.414 | 84.341 | 1.00 | 22.03 | A |
| ATOM | 874 | C | GLY | A | 116 | 18.297 | 62.044 | 83.998 | 1.00 | 22.10 | A |
| ATOM | 875 | O | GLY | A | 116 | 17.767 | 62.487 | 82.976 | 1.00 | 21.00 | A |
| ATOM | 876 | N | GLN | A | 117 | 17.667 | 61.237 | 84.844 | 1.00 | 22.18 | A |
| ATOM | 877 | CA | GLN | A | 117 | 16.295 | 60.812 | 84.611 | 1.00 | 21.98 | A |
| ATOM | 878 | CB | GLN | A | 117 | 16.146 | 59.319 | 84.916 | 1.00 | 22.79 | A |
| ATOM | 879 | CG | GLN | A | 117 | 16.986 | 58.429 | 84.031 | 1.00 | 26.38 | A |
| ATOM | 880 | CD | GLN | A | 117 | 16.533 | 58.474 | 82.589 | 1.00 | 30.18 | A |
| ATOM | 881 | OE1 | GLN | A | 117 | 15.401 | 58.104 | 82.273 | 1.00 | 34.37 | A |
| ATOM | 882 | NE2 | GLN | A | 117 | 17.409 | 58.933 | 81.708 | 1.00 | 31.61 | A |
| ATOM | 883 | C | GLN | A | 117 | 15.330 | 61.597 | 85.482 | 1.00 | 22.74 | A |
| ATOM | 884 | O | GLN | A | 117 | 15.709 | 62.116 | 86.538 | 1.00 | 20.98 | A |
| ATOM | 885 | N | PRO | A | 118 | 14.063 | 61.698 | 85.049 | 1.00 | 22.98 | A |
| ATOM | 886 | CD | PRO | A | 118 | 13.555 | 61.274 | 83.735 | 1.00 | 24.02 | A |
| ATOM | 887 | CA | PRO | A | 118 | 13.028 | 62.418 | 85.790 | 1.00 | 23.87 | A |
| ATOM | 888 | CB | PRO | A | 118 | 11.800 | 62.261 | 84.903 | 1.00 | 24.03 | A |
| ATOM | 889 | CG | PRO | A | 118 | 12.382 | 62.200 | 83.541 | 1.00 | 25.61 | A |
| ATOM | 890 | C | PRO | A | 118 | 12.805 | 61.816 | 87.176 | 1.00 | 25.25 | A |
| ATOM | 891 | O | PRO | A | 118 | 12.820 | 60.595 | 87.351 | 1.00 | 23.22 | A |
| ATOM | 892 | N | MET | A | 119 | 12.596 | 62.694 | 88.145 | 1.00 | 24.78 | A |
| ATOM | 893 | CA | MET | A | 119 | 12.354 | 62.320 | 89.530 | 1.00 | 26.74 | A |
| ATOM | 894 | CB | MET | A | 119 | 12.156 | 63.606 | 90.334 | 1.00 | 29.70 | A |
| ATOM | 895 | CG | MET | A | 119 | 11.815 | 63.454 | 91.789 | 1.00 | 32.65 | A |
| ATOM | 896 | SD | MET | A | 119 | 11.655 | 65.110 | 92.524 | 1.00 | 35.58 | A |
| ATOM | 897 | CE | MET | A | 119 | 10.351 | 65.815 | 91.532 | 1.00 | 38.18 | A |
| ATOM | 898 | C | MET | A | 119 | 11.131 | 61.400 | 89.638 | 1.00 | 25.23 | A |
| ATOM | 899 | O | MET | A | 119 | 11.059 | 60.538 | 90.517 | 1.00 | 23.60 | A |
| ATOM | 900 | N | SER | A | 120 | 10.178 | 61.578 | 88.727 | 1.00 | 24.22 | A |
| ATOM | 901 | CA | SER | A | 120 | 8.964 | 60.768 | 88.712 | 1.00 | 23.87 | A |
| ATOM | 902 | CB | SER | A | 120 | 8.015 | 61.275 | 87.618 | 1.00 | 25.63 | A |
| ATOM | 903 | OG | SER | A | 120 | 8.630 | 61.217 | 86.343 | 1.00 | 26.27 | A |
| ATOM | 904 | C | SER | A | 120 | 9.247 | 59.277 | 88.492 | 1.00 | 22.48 | A |
| ATOM | 905 | O | SER | A | 120 | 8.394 | 58.432 | 88.762 | 1.00 | 21.93 | A |
| ATOM | 906 | N | LYS | A | 121 | 10.441 | 58.946 | 88.006 | 1.00 | 21.07 | A |
| ATOM | 907 | CA | LYS | A | 121 | 10.770 | 57.538 | 87.759 | 1.00 | 19.67 | A |
| ATOM | 908 | CB | LYS | A | 121 | 11.766 | 57.421 | 86.606 | 1.00 | 20.18 | A |
| ATOM | 909 | CG | LYS | A | 121 | 11.291 | 58.113 | 85.333 | 1.00 | 22.53 | A |
| ATOM | 910 | CD | LYS | A | 121 | 12.096 | 57.675 | 84.121 | 1.00 | 26.21 | A |
| ATOM | 911 | CE | LYS | A | 121 | 11.351 | 56.608 | 83.328 | 1.00 | 29.93 | A |
| ATOM | 912 | NZ | LYS | A | 121 | 10.074 | 57.129 | 82.751 | 1.00 | 28.97 | A |
| ATOM | 913 | C | LYS | A | 121 | 11.307 | 56.806 | 88.993 | 1.00 | 18.98 | A |
| ATOM | 914 | O | LYS | A | 121 | 11.593 | 55.604 | 88.935 | 1.00 | 18.06 | A |
| ATOM | 915 | N | ILE | A | 122 | 11.451 | 57.532 | 90.099 | 1.00 | 17.26 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 916 | CA | ILE | A | 122 | 11.909 | 56.936 | 91.352 | 1.00 | 15.68 | A |
| ATOM | 917 | CB | ILE | A | 122 | 12.485 | 58.015 | 92.321 | 1.00 | 16.42 | A |
| ATOM | 918 | CG2 | ILE | A | 122 | 12.747 | 57.406 | 93.690 | 1.00 | 16.72 | A |
| ATOM | 919 | CG1 | ILE | A | 122 | 13.789 | 58.579 | 91.748 | 1.00 | 16.79 | A |
| ATOM | 920 | CD1 | ILE | A | 122 | 14.329 | 59.777 | 92.500 | 1.00 | 16.88 | A |
| ATOM | 921 | C | ILE | A | 122 | 10.679 | 56.263 | 91.962 | 1.00 | 15.84 | A |
| ATOM | 922 | O | ILE | A | 122 | 9.640 | 56.900 | 92.173 | 1.00 | 15.43 | A |
| ATOM | 923 | N | THR | A | 123 | 10.796 | 54.966 | 92.226 | 1.00 | 14.18 | A |
| ATOM | 924 | CA | THR | A | 123 | 9.689 | 54.175 | 92.752 | 1.00 | 14.74 | A |
| ATOM | 925 | CB | THR | A | 123 | 9.549 | 52.891 | 91.934 | 1.00 | 16.36 | A |
| ATOM | 926 | OG1 | THR | A | 123 | 10.802 | 52.199 | 91.937 | 1.00 | 15.10 | A |
| ATOM | 927 | CG2 | THR | A | 123 | 9.198 | 53.221 | 90.493 | 1.00 | 17.32 | A |
| ATOM | 928 | C | THR | A | 123 | 9.810 | 53.785 | 94.221 | 1.00 | 13.87 | A |
| ATOM | 929 | O | THR | A | 123 | 8.812 | 53.493 | 94.884 | 1.00 | 12.09 | A |
| ATOM | 930 | N | HIS | A | 124 | 11.032 | 53.769 | 94.725 | 1.00 | 12.46 | A |
| ATOM | 931 | CA | HIS | A | 124 | 11.255 | 53.404 | 96.114 | 1.00 | 13.52 | A |
| ATOM | 932 | CB | HIS | A | 124 | 11.896 | 52.015 | 96.200 | 1.00 | 14.17 | A |
| ATOM | 933 | CG | HIS | A | 124 | 11.078 | 50.931 | 95.567 | 1.00 | 14.73 | A |
| ATOM | 934 | CD2 | HIS | A | 124 | 10.806 | 50.666 | 94.270 | 1.00 | 14.15 | A |
| ATOM | 935 | ND1 | HIS | A | 124 | 10.440 | 49.951 | 96.300 | 1.00 | 17.98 | A |
| ATOM | 936 | CE1 | HIS | A | 124 | 9.812 | 49.128 | 95.479 | 1.00 | 13.68 | A |
| ATOM | 937 | NE2 | HIS | A | 124 | 10.019 | 49.539 | 94.241 | 1.00 | 18.64 | A |
| ATOM | 938 | C | HIS | A | 124 | 12.168 | 54.415 | 96.778 | 1.00 | 13.52 | A |
| ATOM | 939 | O | HIS | A | 124 | 13.081 | 54.952 | 96.147 | 1.00 | 15.74 | A |
| ATOM | 940 | N | LEU | A | 125 | 11.921 | 54.660 | 98.057 | 1.00 | 15.22 | A |
| ATOM | 941 | CA | LEU | A | 125 | 12.737 | 55.586 | 98.826 | 1.00 | 13.70 | A |
| ATOM | 942 | CB | LEU | A | 125 | 11.969 | 56.874 | 99.138 | 1.00 | 12.90 | A |
| ATOM | 943 | CG | LEU | A | 125 | 12.658 | 57.787 | 100.168 | 1.00 | 14.85 | A |
| ATOM | 944 | CD1 | LEU | A | 125 | 13.951 | 58.355 | 99.576 | 1.00 | 13.04 | A |
| ATOM | 945 | CD2 | LEU | A | 125 | 11.717 | 58.916 | 100.575 | 1.00 | 13.73 | A |
| ATOM | 946 | C | LEU | A | 125 | 13.159 | 54.966 | 100.143 | 1.00 | 11.88 | A |
| ATOM | 947 | O | LEU | A | 125 | 12.311 | 54.615 | 100.960 | 1.00 | 12.37 | A |
| ATOM | 948 | N | ILE | A | 126 | 14.466 | 54.837 | 100.340 | 1.00 | 11.11 | A |
| ATOM | 949 | CA | ILE | A | 126 | 15.008 | 54.328 | 101.598 | 1.00 | 11.89 | A |
| ATOM | 950 | CB | ILE | A | 126 | 16.074 | 53.234 | 101.380 | 1.00 | 11.91 | A |
| ATOM | 951 | CG2 | ILE | A | 126 | 16.614 | 52.751 | 102.736 | 1.00 | 14.16 | A |
| ATOM | 952 | CG1 | ILE | A | 126 | 15.468 | 52.057 | 100.615 | 1.00 | 11.59 | A |
| ATOM | 953 | CD1 | ILE | A | 126 | 16.504 | 51.045 | 100.138 | 1.00 | 11.98 | A |
| ATOM | 954 | C | ILE | A | 126 | 15.691 | 55.518 | 102.274 | 1.00 | 12.26 | A |
| ATOM | 955 | O | ILE | A | 126 | 16.632 | 56.084 | 101.726 | 1.00 | 12.65 | A |
| ATOM | 956 | N | PHE | A | 127 | 15.211 | 55.895 | 103.453 | 1.00 | 10.80 | A |
| ATOM | 957 | CA | PHE | A | 127 | 15.795 | 57.007 | 104.188 | 1.00 | 12.32 | A |
| ATOM | 958 | CB | PHE | A | 127 | 14.752 | 58.082 | 104.485 | 1.00 | 13.70 | A |
| ATOM | 959 | CG | PHE | A | 127 | 15.353 | 59.410 | 104.858 | 1.00 | 16.44 | A |
| ATOM | 960 | CD1 | PHE | A | 127 | 16.100 | 59.550 | 106.025 | 1.00 | 19.42 | A |
| ATOM | 961 | CD2 | PHE | A | 127 | 15.197 | 60.515 | 104.025 | 1.00 | 18.87 | A |
| ATOM | 962 | CE1 | PHE | A | 127 | 16.689 | 60.778 | 106.358 | 1.00 | 20.68 | A |
| ATOM | 963 | CE2 | PHE | A | 127 | 15.780 | 61.744 | 104.348 | 1.00 | 19.48 | A |
| ATOM | 964 | CZ | PHE | A | 127 | 16.525 | 61.875 | 105.514 | 1.00 | 19.21 | A |
| ATOM | 965 | C | PHE | A | 127 | 16.353 | 56.469 | 105.497 | 1.00 | 12.78 | A |
| ATOM | 966 | O | PHE | A | 127 | 15.640 | 55.831 | 106.278 | 1.00 | 14.15 | A |
| ATOM | 967 | N | CYS | A | 128 | 17.626 | 56.748 | 105.737 | 1.00 | 13.01 | A |
| ATOM | 968 | CA | CYS | A | 128 | 18.301 | 56.259 | 106.930 | 1.00 | 13.64 | A |
| ATOM | 969 | CB | CYS | A | 128 | 19.359 | 55.233 | 106.513 | 1.00 | 15.39 | A |
| ATOM | 970 | SG | CYS | A | 128 | 20.377 | 54.571 | 107.831 | 1.00 | 20.31 | A |
| ATOM | 971 | C | CYS | A | 128 | 18.952 | 57.380 | 107.714 | 1.00 | 15.17 | A |
| ATOM | 972 | O | CYS | A | 128 | 19.726 | 58.159 | 107.161 | 1.00 | 14.59 | A |
| ATOM | 973 | N | THR | A | 129 | 18.622 | 57.466 | 108.999 | 1.00 | 14.32 | A |
| ATOM | 974 | CA | THR | A | 129 | 19.205 | 58.482 | 109.868 | 1.00 | 16.20 | A |
| ATOM | 975 | CB | THR | A | 129 | 18.473 | 59.832 | 109.740 | 1.00 | 18.34 | A |
| ATOM | 976 | OG1 | THR | A | 129 | 19.107 | 60.794 | 110.596 | 1.00 | 18.62 | A |
| ATOM | 977 | CG2 | THR | A | 129 | 17.006 | 59.692 | 110.122 | 1.00 | 14.76 | A |
| ATOM | 978 | C | THR | A | 129 | 19.174 | 58.022 | 111.324 | 1.00 | 16.46 | A |
| ATOM | 979 | O | THR | A | 129 | 18.273 | 57.287 | 111.731 | 1.00 | 17.28 | A |
| ATOM | 980 | N | THR | A | 130 | 20.158 | 58.463 | 112.102 | 1.00 | 18.56 | A |
| ATOM | 981 | CA | THR | A | 130 | 20.263 | 58.082 | 113.506 | 1.00 | 20.61 | A |
| ATOM | 982 | CB | THR | A | 130 | 21.558 | 58.633 | 114.131 | 1.00 | 22.58 | A |
| ATOM | 983 | OG1 | THR | A | 130 | 22.683 | 57.978 | 113.531 | 1.00 | 24.26 | A |
| ATOM | 984 | CG2 | THR | A | 130 | 21.579 | 58.379 | 115.635 | 1.00 | 24.22 | A |
| ATOM | 985 | C | THR | A | 130 | 19.074 | 58.501 | 114.359 | 1.00 | 20.30 | A |
| ATOM | 986 | O | THR | A | 130 | 18.636 | 57.741 | 115.220 | 1.00 | 21.48 | A |
| ATOM | 987 | N | SER | A | 131 | 18.552 | 59.703 | 114.140 | 1.00 | 20.01 | A |
| ATOM | 988 | CA | SER | A | 131 | 17.398 | 60.141 | 114.911 | 1.00 | 22.06 | A |
| ATOM | 989 | CB | SER | A | 131 | 17.836 | 60.640 | 116.290 | 1.00 | 23.91 | A |
| ATOM | 990 | OG | SER | A | 131 | 16.787 | 60.471 | 117.229 | 1.00 | 24.77 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 991 | C | SER | A | 131 | 16.578 | 61.211 | 114.189 | 1.00 | 22.16 | A |
| ATOM | 992 | O | SER | A | 131 | 16.799 | 61.476 | 113.008 | 1.00 | 22.30 | A |
| ATOM | 993 | N | GLY | A | 132 | 15.633 | 61.817 | 114.906 | 1.00 | 22.15 | A |
| ATOM | 994 | CA | GLY | A | 132 | 14.761 | 62.829 | 114.322 | 1.00 | 20.74 | A |
| ATOM | 995 | C | GLY | A | 132 | 13.403 | 62.167 | 114.193 | 1.00 | 19.96 | A |
| ATOM | 996 | O | GLY | A | 132 | 12.845 | 62.049 | 113.101 | 1.00 | 18.89 | A |
| ATOM | 997 | N | VAL | A | 133 | 12.868 | 61.750 | 115.335 | 1.00 | 19.25 | A |
| ATOM | 998 | CA | VAL | A | 133 | 11.606 | 61.020 | 115.401 | 1.00 | 18.86 | A |
| ATOM | 999 | CB | VAL | A | 133 | 11.562 | 60.138 | 116.673 | 1.00 | 19.36 | A |
| ATOM | 1000 | CG1 | VAL | A | 133 | 10.316 | 59.272 | 116.662 | 1.00 | 20.48 | A |
| ATOM | 1001 | CG2 | VAL | A | 133 | 12.815 | 59.288 | 116.764 | 1.00 | 21.42 | A |
| ATOM | 1002 | C | VAL | A | 133 | 10.307 | 61.810 | 115.343 | 1.00 | 18.12 | A |
| ATOM | 1003 | O | VAL | A | 133 | 9.972 | 62.554 | 116.257 | 1.00 | 15.85 | A |
| ATOM | 1004 | N | ALA | A | 134 | 9.566 | 61.603 | 114.260 | 1.00 | 17.33 | A |
| ATOM | 1005 | CA | ALA | A | 134 | 8.281 | 62.253 | 114.054 | 1.00 | 18.39 | A |
| ATOM | 1006 | CB | ALA | A | 134 | 8.480 | 63.600 | 113.376 | 1.00 | 18.75 | A |
| ATOM | 1007 | C | ALA | A | 134 | 7.428 | 61.353 | 113.170 | 1.00 | 20.02 | A |
| ATOM | 1008 | O | ALA | A | 134 | 7.955 | 60.526 | 112.426 | 1.00 | 20.00 | A |
| ATOM | 1009 | N | LEU | A | 135 | 6.112 | 61.500 | 113.275 | 1.00 | 20.90 | A |
| ATOM | 1010 | CA | LEU | A | 135 | 5.181 | 60.740 | 112.454 | 1.00 | 22.04 | A |
| ATOM | 1011 | CB | LEU | A | 135 | 4.401 | 59.715 | 113.284 | 1.00 | 22.48 | A |
| ATOM | 1012 | CG | LEU | A | 135 | 5.190 | 58.568 | 113.918 | 1.00 | 24.17 | A |
| ATOM | 1013 | CD1 | LEU | A | 135 | 5.842 | 59.046 | 115.204 | 1.00 | 24.79 | A |
| ATOM | 1014 | CD2 | LEU | A | 135 | 4.254 | 57.399 | 114.203 | 1.00 | 25.37 | A |
| ATOM | 1015 | C | LEU | A | 135 | 4.213 | 61.753 | 111.849 | 1.00 | 21.49 | A |
| ATOM | 1016 | O | LEU | A | 135 | 3.499 | 62.446 | 112.579 | 1.00 | 20.88 | A |
| ATOM | 1017 | N | PRO | A | 136 | 4.212 | 61.887 | 110.511 | 1.00 | 21.73 | A |
| ATOM | 1018 | CD | PRO | A | 136 | 3.328 | 62.816 | 109.783 | 1.00 | 22.31 | A |
| ATOM | 1019 | CA | PRO | A | 136 | 5.063 | 61.143 | 109.576 | 1.00 | 22.02 | A |
| ATOM | 1020 | CB | PRO | A | 136 | 4.528 | 61.570 | 108.209 | 1.00 | 21.01 | A |
| ATOM | 1021 | CG | PRO | A | 136 | 4.042 | 62.958 | 108.460 | 1.00 | 21.68 | A |
| ATOM | 1022 | C | PRO | A | 136 | 6.541 | 61.479 | 109.775 | 1.00 | 21.66 | A |
| ATOM | 1023 | O | PRO | A | 136 | 6.877 | 62.527 | 110.326 | 1.00 | 20.41 | A |
| ATOM | 1024 | N | GLY | A | 137 | 7.412 | 60.582 | 109.326 | 1.00 | 21.85 | A |
| ATOM | 1025 | CA | GLY | A | 137 | 8.843 | 60.771 | 109.499 | 1.00 | 22.07 | A |
| ATOM | 1026 | C | GLY | A | 137 | 9.555 | 61.689 | 108.528 | 1.00 | 21.47 | A |
| ATOM | 1027 | O | GLY | A | 137 | 8.929 | 62.373 | 107.711 | 1.00 | 20.25 | A |
| ATOM | 1028 | N | VAL | A | 138 | 10.881 | 61.705 | 108.627 | 1.00 | 21.01 | A |
| ATOM | 1029 | CA | VAL | A | 138 | 11.693 | 62.538 | 107.758 | 1.00 | 21.43 | A |
| ATOM | 1030 | CB | VAL | A | 138 | 13.150 | 62.616 | 108.258 | 1.00 | 21.99 | A |
| ATOM | 1031 | CG1 | VAL | A | 138 | 13.198 | 63.423 | 109.546 | 1.00 | 22.78 | A |
| ATOM | 1032 | CG2 | VAL | A | 138 | 13.712 | 61.223 | 108.483 | 1.00 | 20.43 | A |
| ATOM | 1033 | C | VAL | A | 138 | 11.655 | 62.064 | 106.308 | 1.00 | 20.81 | A |
| ATOM | 1034 | O | VAL | A | 138 | 12.009 | 62.815 | 105.396 | 1.00 | 20.37 | A |
| ATOM | 1035 | N | ASP | A | 139 | 11.223 | 60.824 | 106.086 | 1.00 | 20.30 | A |
| ATOM | 1036 | CA | ASP | A | 139 | 11.116 | 60.324 | 104.719 | 1.00 | 20.26 | A |
| ATOM | 1037 | CB | ASP | A | 139 | 10.771 | 58.822 | 104.710 | 1.00 | 20.86 | A |
| ATOM | 1038 | CG | ASP | A | 139 | 9.488 | 58.497 | 105.465 | 1.00 | 21.95 | A |
| ATOM | 1039 | OD1 | ASP | A | 139 | 9.282 | 59.048 | 106.568 | 1.00 | 21.43 | A |
| ATOM | 1040 | OD2 | ASP | A | 139 | 8.689 | 57.673 | 104.959 | 1.00 | 19.82 | A |
| ATOM | 1041 | C | ASP | A | 139 | 10.019 | 61.153 | 104.045 | 1.00 | 20.31 | A |
| ATOM | 1042 | O | ASP | A | 139 | 10.116 | 61.516 | 102.870 | 1.00 | 19.88 | A |
| ATOM | 1043 | N | TYR | A | 140 | 8.981 | 61.465 | 104.811 | 1.00 | 19.31 | A |
| ATOM | 1044 | CA | TYR | A | 140 | 7.875 | 62.273 | 104.311 | 1.00 | 20.68 | A |
| ATOM | 1045 | CB | TYR | A | 140 | 6.746 | 62.317 | 105.346 | 1.00 | 22.10 | A |
| ATOM | 1046 | CG | TYR | A | 140 | 5.689 | 63.360 | 105.062 | 1.00 | 25.72 | A |
| ATOM | 1047 | CD1 | TYR | A | 140 | 4.629 | 63.093 | 104.196 | 1.00 | 24.85 | A |
| ATOM | 1048 | CE1 | TYR | A | 140 | 3.664 | 64.058 | 103.921 | 1.00 | 27.16 | A |
| ATOM | 1049 | CD2 | TYR | A | 140 | 5.760 | 64.624 | 105.646 | 1.00 | 26.43 | A |
| ATOM | 1050 | CE2 | TYR | A | 140 | 4.804 | 65.596 | 105.374 | 1.00 | 28.31 | A |
| ATOM | 1051 | CZ | TYR | A | 140 | 3.758 | 65.306 | 104.512 | 1.00 | 27.72 | A |
| ATOM | 1052 | OH | TYR | A | 140 | 2.812 | 66.265 | 104.241 | 1.00 | 30.75 | A |
| ATOM | 1053 | C | TYR | A | 140 | 8.378 | 63.692 | 104.034 | 1.00 | 21.06 | A |
| ATOM | 1054 | O | TYR | A | 140 | 8.059 | 64.284 | 103.007 | 1.00 | 21.05 | A |
| ATOM | 1055 | N | GLU | A | 141 | 9.172 | 64.238 | 104.950 | 1.00 | 22.40 | A |
| ATOM | 1056 | CA | GLU | A | 141 | 9.697 | 65.587 | 104.766 | 1.00 | 23.04 | A |
| ATOM | 1057 | CB | GLU | A | 141 | 10.550 | 65.990 | 105.973 | 1.00 | 25.22 | A |
| ATOM | 1058 | CG | GLU | A | 141 | 9.806 | 65.891 | 107.310 | 1.00 | 29.34 | A |
| ATOM | 1059 | CD | GLU | A | 141 | 8.717 | 66.944 | 107.473 | 1.00 | 32.95 | A |
| ATOM | 1060 | OE1 | GLU | A | 141 | 7.895 | 66.815 | 108.407 | 1.00 | 31.49 | A |
| ATOM | 1061 | OE2 | GLU | A | 141 | 8.687 | 67.906 | 106.673 | 1.00 | 35.80 | A |
| ATOM | 1062 | C | GLU | A | 141 | 10.522 | 65.675 | 103.480 | 1.00 | 22.86 | A |
| ATOM | 1063 | O | GLU | A | 141 | 10.411 | 66.643 | 102.725 | 1.00 | 23.57 | A |
| ATOM | 1064 | N | LEU | A | 142 | 11.344 | 64.659 | 103.232 | 1.00 | 20.18 | A |
| ATOM | 1065 | CA | LEU | A | 142 | 12.178 | 64.628 | 102.033 | 1.00 | 19.91 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 1066 | CB | LEU | A | 142 | 13.115 | 63.412 | 102.057 | 1.00 | 18.95 | A |
| ATOM | 1067 | CG | LEU | A | 142 | 14.028 | 63.267 | 100.831 | 1.00 | 18.48 | A |
| ATOM | 1068 | CD1 | LEU | A | 142 | 15.022 | 64.433 | 100.771 | 1.00 | 16.40 | A |
| ATOM | 1069 | CD2 | LEU | A | 142 | 14.770 | 61.950 | 100.906 | 1.00 | 20.85 | A |
| ATOM | 1070 | C | LEU | A | 142 | 11.305 | 64.579 | 100.779 | 1.00 | 19.21 | A |
| ATOM | 1071 | O | LEU | A | 142 | 11.585 | 65.260 | 99.796 | 1.00 | 17.35 | A |
| ATOM | 1072 | N | ILE | A | 143 | 10.246 | 63.773 | 100.821 | 1.00 | 17.49 | A |
| ATOM | 1073 | CA | ILE | A | 143 | 9.331 | 63.648 | 99.683 | 1.00 | 19.30 | A |
| ATOM | 1074 | CB | ILE | A | 143 | 8.175 | 62.680 | 100.010 | 1.00 | 19.22 | A |
| ATOM | 1075 | CG2 | ILE | A | 143 | 7.062 | 62.809 | 98.972 | 1.00 | 18.33 | A |
| ATOM | 1076 | CG1 | ILE | A | 143 | 8.717 | 61.250 | 100.077 | 1.00 | 19.66 | A |
| ATOM | 1077 | CD1 | ILE | A | 143 | 7.730 | 60.236 | 100.615 | 1.00 | 22.67 | A |
| ATOM | 1078 | C | ILE | A | 143 | 8.755 | 65.019 | 99.327 | 1.00 | 20.59 | A |
| ATOM | 1079 | O | ILE | A | 143 | 8.663 | 65.382 | 98.152 | 1.00 | 20.63 | A |
| ATOM | 1080 | N | VAL | A | 144 | 8.373 | 65.770 | 100.353 | 1.00 | 21.01 | A |
| ATOM | 1081 | CA | VAL | A | 144 | 7.818 | 67.102 | 100.165 | 1.00 | 23.53 | A |
| ATOM | 1082 | CB | VAL | A | 144 | 7.307 | 67.679 | 101.501 | 1.00 | 24.60 | A |
| ATOM | 1083 | CG1 | VAL | A | 144 | 6.932 | 69.145 | 101.329 | 1.00 | 27.88 | A |
| ATOM | 1084 | CG2 | VAL | A | 144 | 6.111 | 66.883 | 101.979 | 1.00 | 26.36 | A |
| ATOM | 1085 | C | VAL | A | 144 | 8.860 | 68.055 | 99.590 | 1.00 | 22.64 | A |
| ATOM | 1086 | O | VAL | A | 144 | 8.578 | 68.805 | 98.660 | 1.00 | 21.65 | A |
| ATOM | 1087 | N | LEU | A | 145 | 10.069 | 68.015 | 100.141 | 1.00 | 23.18 | A |
| ATOM | 1088 | CA | LEU | A | 145 | 11.142 | 68.894 | 99.685 | 1.00 | 24.35 | A |
| ATOM | 1089 | CB | LEU | A | 145 | 12.331 | 68.823 | 100.644 | 1.00 | 25.00 | A |
| ATOM | 1090 | CG | LEU | A | 145 | 12.167 | 69.569 | 101.968 | 1.00 | 25.62 | A |
| ATOM | 1091 | CD1 | LEU | A | 145 | 13.325 | 69.229 | 102.901 | 1.00 | 25.97 | A |
| ATOM | 1092 | CD2 | LEU | A | 145 | 12.109 | 71.071 | 101.703 | 1.00 | 27.80 | A |
| ATOM | 1093 | C | LEU | A | 145 | 11.624 | 68.627 | 98.270 | 1.00 | 25.21 | A |
| ATOM | 1094 | O | LEU | A | 145 | 11.994 | 69.563 | 97.562 | 1.00 | 25.41 | A |
| ATOM | 1095 | N | LEU | A | 146 | 11.628 | 67.360 | 97.860 | 1.00 | 24.69 | A |
| ATOM | 1096 | CA | LEU | A | 146 | 12.074 | 66.988 | 96.519 | 1.00 | 23.80 | A |
| ATOM | 1097 | CB | LEU | A | 146 | 12.652 | 65.571 | 96.506 | 1.00 | 24.17 | A |
| ATOM | 1098 | CG | LEU | A | 146 | 14.086 | 65.321 | 96.952 | 1.00 | 22.03 | A |
| ATOM | 1099 | CD1 | LEU | A | 146 | 14.373 | 63.824 | 96.883 | 1.00 | 20.90 | A |
| ATOM | 1100 | CD2 | LEU | A | 146 | 15.048 | 66.100 | 96.055 | 1.00 | 24.88 | A |
| ATOM | 1101 | C | LEU | A | 146 | 10.958 | 67.037 | 95.495 | 1.00 | 24.42 | A |
| ATOM | 1102 | O | LEU | A | 146 | 11.162 | 67.482 | 94.366 | 1.00 | 26.11 | A |
| ATOM | 1103 | N | GLY | A | 147 | 9.787 | 66.550 | 95.890 | 1.00 | 23.14 | A |
| ATOM | 1104 | CA | GLY | A | 147 | 8.655 | 66.515 | 94.985 | 1.00 | 22.12 | A |
| ATOM | 1105 | C | GLY | A | 147 | 8.494 | 65.121 | 94.405 | 1.00 | 21.57 | A |
| ATOM | 1106 | O | GLY | A | 147 | 8.049 | 64.965 | 93.268 | 1.00 | 21.52 | A |
| ATOM | 1107 | N | LEU | A | 148 | 8.874 | 64.107 | 95.183 | 1.00 | 20.27 | A |
| ATOM | 1108 | CA | LEU | A | 148 | 8.757 | 62.711 | 94.759 | 1.00 | 21.34 | A |
| ATOM | 1109 | CB | LEU | A | 148 | 9.387 | 61.777 | 95.802 | 1.00 | 20.35 | A |
| ATOM | 1110 | CG | LEU | A | 148 | 10.909 | 61.838 | 95.961 | 1.00 | 22.06 | A |
| ATOM | 1111 | CD1 | LEU | A | 148 | 11.357 | 60.867 | 97.037 | 1.00 | 21.03 | A |
| ATOM | 1112 | CD2 | LEU | A | 148 | 11.571 | 61.512 | 94.625 | 1.00 | 21.84 | A |
| ATOM | 1113 | C | LEU | A | 148 | 7.291 | 62.336 | 94.577 | 1.00 | 20.24 | A |
| ATOM | 1114 | O | LEU | A | 148 | 6.408 | 62.970 | 95.150 | 1.00 | 19.49 | A |
| ATOM | 1115 | N | ASP | A | 149 | 7.035 | 61.303 | 93.779 | 1.00 | 21.19 | A |
| ATOM | 1116 | CA | ASP | A | 149 | 5.669 | 60.854 | 93.526 | 1.00 | 20.81 | A |
| ATOM | 1117 | CB | ASP | A | 149 | 5.678 | 59.672 | 92.550 | 1.00 | 23.34 | A |
| ATOM | 1118 | CG | ASP | A | 149 | 4.286 | 59.342 | 92.019 | 1.00 | 25.67 | A |
| ATOM | 1119 | OD1 | ASP | A | 149 | 3.482 | 58.732 | 92.757 | 1.00 | 23.21 | A |
| ATOM | 1120 | OD2 | ASP | A | 149 | 3.991 | 59.715 | 90.863 | 1.00 | 28.37 | A |
| ATOM | 1121 | C | ASP | A | 149 | 5.007 | 60.436 | 94.837 | 1.00 | 21.87 | A |
| ATOM | 1122 | O | ASP | A | 149 | 5.628 | 59.759 | 95.672 | 1.00 | 22.11 | A |
| ATOM | 1123 | N | PRO | A | 150 | 3.741 | 60.834 | 95.044 | 1.00 | 19.56 | A |
| ATOM | 1124 | CD | PRO | A | 150 | 2.883 | 61.659 | 94.177 | 1.00 | 21.27 | A |
| ATOM | 1125 | CA | PRO | A | 150 | 3.037 | 60.472 | 96.278 | 1.00 | 19.66 | A |
| ATOM | 1126 | CB | PRO | A | 150 | 1.696 | 61.199 | 96.141 | 1.00 | 20.41 | A |
| ATOM | 1127 | CG | PRO | A | 150 | 1.498 | 61.272 | 94.651 | 1.00 | 22.21 | A |
| ATOM | 1128 | C | PRO | A | 150 | 2.880 | 58.961 | 96.448 | 1.00 | 18.44 | A |
| ATOM | 1129 | O | PRO | A | 150 | 2.565 | 58.480 | 97.539 | 1.00 | 18.21 | A |
| ATOM | 1130 | N | CYS | A | 151 | 3.110 | 58.217 | 95.371 | 1.00 | 17.66 | A |
| ATOM | 1131 | CA | CYS | A | 151 | 3.000 | 56.762 | 95.425 | 1.00 | 18.31 | A |
| ATOM | 1132 | CB | CYS | A | 151 | 2.269 | 56.241 | 94.190 | 1.00 | 19.55 | A |
| ATOM | 1133 | SG | CYS | A | 151 | .546 | 56.775 | 94.144 | 1.00 | 24.40 | A |
| ATOM | 1134 | C | CYS | A | 151 | 4.349 | 56.073 | 95.561 | 1.00 | 17.28 | A |
| ATOM | 1135 | O | CYS | A | 151 | 4.465 | 54.862 | 95.353 | 1.00 | 16.35 | A |
| ATOM | 1136 | N | VAL | A | 152 | 5.377 | 56.837 | 95.913 | 1.00 | 16.24 | A |
| ATOM | 1137 | CA | VAL | A | 152 | 6.700 | 56.247 | 96.086 | 1.00 | 15.84 | A |
| ATOM | 1138 | CB | VAL | A | 152 | 7.764 | 57.336 | 96.339 | 1.00 | 15.86 | A |
| ATOM | 1139 | CG1 | VAL | A | 152 | 7.489 | 58.033 | 97.667 | 1.00 | 18.85 | A |
| ATOM | 1140 | CG2 | VAL | A | 152 | 9.159 | 56.726 | 96.323 | 1.00 | 16.14 | A |

APPENDIX B-continued

*Arachis hypogaea* STS

| ATOM | # | TYPE | RES | | | X | Y | Z | OCC | B | |
|------|---|------|-----|---|---|---|---|---|-----|---|---|
| ATOM | 1141 | C | VAL | A | 152 | 6.632 | 55.308 | 97.302 | 1.00 | 16.12 | A |
| ATOM | 1142 | O | VAL | A | 152 | 5.989 | 55.630 | 98.302 | 1.00 | 16.07 | A |
| ATOM | 1143 | N | LYS | A | 153 | 7.264 | 54.140 | 97.208 | 1.00 | 15.09 | A |
| ATOM | 1144 | CA | LYS | A | 153 | 7.268 | 53.196 | 98.325 | 1.00 | 15.78 | A |
| ATOM | 1145 | CB | LYS | A | 153 | 7.422 | 51.764 | 97.810 | 1.00 | 15.41 | A |
| ATOM | 1146 | CG | LYS | A | 153 | 6.190 | 51.244 | 97.072 | 1.00 | 18.15 | A |
| ATOM | 1147 | CD | LYS | A | 153 | 6.434 | 49.827 | 96.560 | 1.00 | 21.61 | A |
| ATOM | 1148 | CE | LYS | A | 153 | 5.205 | 49.245 | 95.886 | 1.00 | 24.97 | A |
| ATOM | 1149 | NZ | LYS | A | 153 | 4.778 | 50.049 | 94.708 | 1.00 | 28.12 | A |
| ATOM | 1150 | C | LYS | A | 153 | 8.405 | 53.551 | 99.291 | 1.00 | 14.03 | A |
| ATOM | 1151 | O | LYS | A | 153 | 9.573 | 53.586 | 98.909 | 1.00 | 14.56 | A |
| ATOM | 1152 | N | ARG | A | 154 | 8.047 | 53.803 | 100.546 | 1.00 | 14.71 | A |
| ATOM | 1153 | CA | ARG | A | 154 | 9.014 | 54.215 | 101.559 | 1.00 | 14.98 | A |
| ATOM | 1154 | CB | ARG | A | 154 | 8.448 | 55.402 | 102.346 | 1.00 | 15.82 | A |
| ATOM | 1155 | CG | ARG | A | 154 | 8.113 | 56.614 | 101.492 | 1.00 | 16.52 | A |
| ATOM | 1156 | CD | ARG | A | 154 | 6.666 | 57.044 | 101.681 | 1.00 | 19.72 | A |
| ATOM | 1157 | NE | ARG | A | 154 | 6.382 | 57.386 | 103.070 | 1.00 | 19.17 | A |
| ATOM | 1158 | CZ | ARG | A | 154 | 5.158 | 57.536 | 103.566 | 1.00 | 22.61 | A |
| ATOM | 1159 | NH1 | ARG | A | 154 | 4.097 | 57.379 | 102.786 | 1.00 | 22.37 | A |
| ATOM | 1160 | NH2 | ARG | A | 154 | 4.992 | 57.826 | 104.848 | 1.00 | 24.78 | A |
| ATOM | 1161 | C | ARG | A | 154 | 9.493 | 53.170 | 102.565 | 1.00 | 14.29 | A |
| ATOM | 1162 | O | ARG | A | 154 | 8.757 | 52.274 | 102.961 | 1.00 | 12.71 | A |
| ATOM | 1163 | N | TYR | A | 155 | 10.746 | 53.329 | 102.983 | 1.00 | 14.99 | A |
| ATOM | 1164 | CA | TYR | A | 155 | 11.375 | 52.466 | 103.972 | 1.00 | 15.35 | A |
| ATOM | 1165 | CB | TYR | A | 155 | 12.312 | 51.462 | 103.283 | 1.00 | 15.70 | A |
| ATOM | 1166 | CG | TYR | A | 155 | 11.596 | 50.631 | 102.228 | 1.00 | 15.84 | A |
| ATOM | 1167 | CD1 | TYR | A | 155 | 11.282 | 51.176 | 100.985 | 1.00 | 16.66 | A |
| ATOM | 1168 | CE1 | TYR | A | 155 | 10.528 | 50.467 | 100.051 | 1.00 | 16.19 | A |
| ATOM | 1169 | CD2 | TYR | A | 155 | 11.144 | 49.338 | 102.511 | 1.00 | 16.71 | A |
| ATOM | 1170 | CE2 | TYR | A | 155 | 10.388 | 48.613 | 101.581 | 1.00 | 17.09 | A |
| ATOM | 1171 | CZ | TYR | A | 155 | 10.078 | 49.189 | 100.355 | 1.00 | 17.25 | A |
| ATOM | 1172 | OH | TYR | A | 155 | 9.283 | 48.526 | 99.447 | 1.00 | 15.92 | A |
| ATOM | 1173 | C | TYR | A | 155 | 12.148 | 53.425 | 104.882 | 1.00 | 14.71 | A |
| ATOM | 1174 | O | TYR | A | 155 | 13.241 | 53.869 | 104.546 | 1.00 | 14.74 | A |
| ATOM | 1175 | N | MET | A | 156 | 11.550 | 53.752 | 106.022 | 1.00 | 14.82 | A |
| ATOM | 1176 | CA | MET | A | 156 | 12.134 | 54.679 | 106.992 | 1.00 | 17.67 | A |
| ATOM | 1177 | CB | MET | A | 156 | 10.997 | 55.466 | 107.663 | 1.00 | 19.67 | A |
| ATOM | 1178 | CG | MET | A | 156 | 11.412 | 56.537 | 108.663 | 1.00 | 20.86 | A |
| ATOM | 1179 | SD | MET | A | 156 | 12.370 | 57.875 | 107.942 | 1.00 | 19.21 | A |
| ATOM | 1180 | CE | MET | A | 156 | 13.973 | 57.560 | 108.704 | 1.00 | 20.63 | A |
| ATOM | 1181 | C | MET | A | 156 | 12.963 | 53.915 | 108.027 | 1.00 | 17.40 | A |
| ATOM | 1182 | O | MET | A | 156 | 12.421 | 53.225 | 108.896 | 1.00 | 16.91 | A |
| ATOM | 1183 | N | MET | A | 157 | 14.279 | 54.050 | 107.927 | 1.00 | 17.80 | A |
| ATOM | 1184 | CA | MET | A | 157 | 15.199 | 53.363 | 108.828 | 1.00 | 18.64 | A |
| ATOM | 1185 | CB | MET | A | 157 | 16.338 | 52.745 | 108.008 | 1.00 | 18.72 | A |
| ATOM | 1186 | CG | MET | A | 157 | 15.867 | 52.052 | 106.719 | 1.00 | 20.59 | A |
| ATOM | 1187 | SD | MET | A | 157 | 14.560 | 50.808 | 106.973 | 1.00 | 23.41 | A |
| ATOM | 1188 | CE | MET | A | 157 | 15.566 | 49.431 | 107.583 | 1.00 | 23.66 | A |
| ATOM | 1189 | C | MET | A | 157 | 15.769 | 54.291 | 109.911 | 1.00 | 20.02 | A |
| ATOM | 1190 | O | MET | A | 157 | 16.658 | 55.108 | 109.647 | 1.00 | 17.80 | A |
| ATOM | 1191 | N | TYR | A | 158 | 15.253 | 54.156 | 111.131 | 1.00 | 19.95 | A |
| ATOM | 1192 | CA | TYR | A | 158 | 15.695 | 54.972 | 112.256 | 1.00 | 19.35 | A |
| ATOM | 1193 | CB | TYR | A | 158 | 14.483 | 55.463 | 113.064 | 1.00 | 19.50 | A |
| ATOM | 1194 | CG | TYR | A | 158 | 13.763 | 56.698 | 112.550 | 1.00 | 20.57 | A |
| ATOM | 1195 | CD1 | TYR | A | 158 | 14.397 | 57.942 | 112.528 | 1.00 | 18.96 | A |
| ATOM | 1196 | CE1 | TYR | A | 158 | 13.713 | 59.097 | 112.154 | 1.00 | 19.96 | A |
| ATOM | 1197 | CD2 | TYR | A | 158 | 12.418 | 56.641 | 112.173 | 1.00 | 19.97 | A |
| ATOM | 1198 | CE2 | TYR | A | 158 | 11.723 | 57.801 | 111.797 | 1.00 | 21.41 | A |
| ATOM | 1199 | CZ | TYR | A | 158 | 12.379 | 59.024 | 111.794 | 1.00 | 21.79 | A |
| ATOM | 1200 | OH | TYR | A | 158 | 11.703 | 60.185 | 111.455 | 1.00 | 21.85 | A |
| ATOM | 1201 | C | TYR | A | 158 | 16.622 | 54.198 | 113.210 | 1.00 | 20.02 | A |
| ATOM | 1202 | O | TYR | A | 158 | 16.527 | 52.974 | 113.340 | 1.00 | 19.80 | A |
| ATOM | 1203 | N | HIS | A | 159 | 17.518 | 54.925 | 113.872 | 1.00 | 19.60 | A |
| ATOM | 1204 | CA | HIS | A | 159 | 18.422 | 54.340 | 114.863 | 1.00 | 20.67 | A |
| ATOM | 1205 | CB | HIS | A | 159 | 17.648 | 54.094 | 116.157 | 1.00 | 21.27 | A |
| ATOM | 1206 | CG | HIS | A | 159 | 16.600 | 55.123 | 116.445 | 1.00 | 22.15 | A |
| ATOM | 1207 | CD2 | HIS | A | 159 | 15.253 | 55.021 | 116.534 | 1.00 | 21.57 | A |
| ATOM | 1208 | ND1 | HIS | A | 159 | 16.902 | 56.444 | 116.699 | 1.00 | 22.61 | A |
| ATOM | 1209 | CE1 | HIS | A | 159 | 15.785 | 57.110 | 116.934 | 1.00 | 22.64 | A |
| ATOM | 1210 | NE2 | HIS | A | 159 | 14.771 | 56.270 | 116.841 | 1.00 | 24.23 | A |
| ATOM | 1211 | C | HIS | A | 159 | 19.062 | 53.023 | 114.436 | 1.00 | 23.07 | A |
| ATOM | 1212 | O | HIS | A | 159 | 19.092 | 52.069 | 115.218 | 1.00 | 23.59 | A |
| ATOM | 1213 | N | GLN | A | 160 | 19.584 | 52.970 | 113.218 | 1.00 | 22.10 | A |
| ATOM | 1214 | CA | GLN | A | 160 | 20.190 | 51.746 | 112.703 | 1.00 | 25.43 | A |
| ATOM | 1215 | CB | GLN | A | 160 | 20.173 | 51.759 | 111.175 | 1.00 | 24.14 | A |

APPENDIX B-continued

*Arachis hypogaea* STS

| ATOM | # | TYPE | RES | | | X | Y | Z | OCC | B | |
|------|---|------|-----|---|---|---|---|---|-----|---|---|
| ATOM | 1216 | CG | GLN | A | 160 | 18.831 | 52.116 | 110.568 | 1.00 | 26.85 | A |
| ATOM | 1217 | CD | GLN | A | 160 | 17.869 | 50.948 | 110.516 | 1.00 | 28.45 | A |
| ATOM | 1218 | OE1 | GLN | A | 160 | 18.111 | 49.964 | 109.811 | 1.00 | 28.85 | A |
| ATOM | 1219 | NE2 | GLN | A | 160 | 16.767 | 51.049 | 111.256 | 1.00 | 25.36 | A |
| ATOM | 1220 | C | GLN | A | 160 | 21.620 | 51.550 | 113.181 | 1.00 | 26.36 | A |
| ATOM | 1221 | O | GLN | A | 160 | 22.037 | 50.431 | 113.465 | 1.00 | 30.01 | A |
| ATOM | 1222 | N | GLY | A | 161 | 22.377 | 52.637 | 113.257 | 1.00 | 26.59 | A |
| ATOM | 1223 | CA | GLY | A | 161 | 23.754 | 52.524 | 113.691 | 1.00 | 26.91 | A |
| ATOM | 1224 | C | GLY | A | 161 | 24.746 | 52.665 | 112.549 | 1.00 | 26.02 | A |
| ATOM | 1225 | O | GLY | A | 161 | 24.369 | 52.731 | 111.374 | 1.00 | 25.41 | A |
| ATOM | 1226 | N | CYS | A | 162 | 26.026 | 52.682 | 112.904 | 1.00 | 22.86 | A |
| ATOM | 1227 | CA | CYS | A | 162 | 27.108 | 52.848 | 111.942 | 1.00 | 21.74 | A |
| ATOM | 1228 | CB | CYS | A | 162 | 28.428 | 53.028 | 112.698 | 1.00 | 24.49 | A |
| ATOM | 1229 | SG | CYS | A | 162 | 28.529 | 54.618 | 113.582 | 1.00 | 31.19 | A |
| ATOM | 1230 | C | CYS | A | 162 | 27.282 | 51.787 | 110.855 | 1.00 | 19.91 | A |
| ATOM | 1231 | O | CYS | A | 162 | 28.078 | 51.979 | 109.941 | 1.00 | 19.35 | A |
| ATOM | 1232 | N | PHE | A | 163 | 26.561 | 50.673 | 110.940 | 1.00 | 17.83 | A |
| ATOM | 1233 | CA | PHE | A | 163 | 26.692 | 49.640 | 109.914 | 1.00 | 19.23 | A |
| ATOM | 1234 | CB | PHE | A | 163 | 26.621 | 48.239 | 110.544 | 1.00 | 19.59 | A |
| ATOM | 1235 | CG | PHE | A | 163 | 25.314 | 47.939 | 111.239 | 1.00 | 19.53 | A |
| ATOM | 1236 | CD1 | PHE | A | 163 | 24.135 | 47.796 | 110.513 | 1.00 | 19.57 | A |
| ATOM | 1237 | CD2 | PHE | A | 163 | 25.264 | 47.817 | 112.626 | 1.00 | 21.14 | A |
| ATOM | 1238 | CE1 | PHE | A | 163 | 22.924 | 47.539 | 111.156 | 1.00 | 19.62 | A |
| ATOM | 1239 | CE2 | PHE | A | 163 | 24.061 | 47.559 | 113.279 | 1.00 | 20.54 | A |
| ATOM | 1240 | CZ | PHE | A | 163 | 22.889 | 47.421 | 112.542 | 1.00 | 24.00 | A |
| ATOM | 1241 | C | PHE | A | 163 | 25.606 | 49.775 | 108.846 | 1.00 | 18.82 | A |
| ATOM | 1242 | O | PHE | A | 163 | 25.630 | 49.077 | 107.829 | 1.00 | 19.22 | A |
| ATOM | 1243 | N | ALA | A | 164 | 24.663 | 50.679 | 109.088 | 1.00 | 16.89 | A |
| ATOM | 1244 | CA | ALA | A | 164 | 23.534 | 50.900 | 108.186 | 1.00 | 17.06 | A |
| ATOM | 1245 | CB | ALA | A | 164 | 22.663 | 52.040 | 108.710 | 1.00 | 18.50 | A |
| ATOM | 1246 | C | ALA | A | 164 | 23.877 | 51.142 | 106.724 | 1.00 | 16.53 | A |
| ATOM | 1247 | O | ALA | A | 164 | 23.015 | 50.985 | 105.859 | 1.00 | 18.01 | A |
| ATOM | 1248 | N | GLY | A | 165 | 25.115 | 51.543 | 106.443 | 1.00 | 15.99 | A |
| ATOM | 1249 | CA | GLY | A | 165 | 25.521 | 51.758 | 105.064 | 1.00 | 16.79 | A |
| ATOM | 1250 | C | GLY | A | 165 | 25.337 | 50.452 | 104.309 | 1.00 | 18.19 | A |
| ATOM | 1251 | O | GLY | A | 165 | 24.874 | 50.420 | 103.160 | 1.00 | 19.45 | A |
| ATOM | 1252 | N | GLY | A | 166 | 25.700 | 49.358 | 104.965 | 1.00 | 18.25 | A |
| ATOM | 1253 | CA | GLY | A | 166 | 25.531 | 48.056 | 104.352 | 1.00 | 17.94 | A |
| ATOM | 1254 | C | GLY | A | 166 | 24.063 | 47.644 | 104.344 | 1.00 | 17.15 | A |
| ATOM | 1255 | O | GLY | A | 166 | 23.597 | 47.031 | 103.384 | 1.00 | 18.05 | A |
| ATOM | 1256 | N | THR | A | 167 | 23.339 | 47.988 | 105.408 | 1.00 | 17.80 | A |
| ATOM | 1257 | CA | THR | A | 167 | 21.921 | 47.647 | 105.545 | 1.00 | 17.61 | A |
| ATOM | 1258 | CB | THR | A | 167 | 21.331 | 48.188 | 106.866 | 1.00 | 20.13 | A |
| ATOM | 1259 | OG1 | THR | A | 167 | 22.114 | 47.730 | 107.978 | 1.00 | 22.66 | A |
| ATOM | 1260 | CG2 | THR | A | 167 | 19.896 | 47.709 | 107.040 | 1.00 | 20.30 | A |
| ATOM | 1261 | C | THR | A | 167 | 21.076 | 48.208 | 104.400 | 1.00 | 16.77 | A |
| ATOM | 1262 | O | THR | A | 167 | 20.233 | 47.504 | 103.837 | 1.00 | 14.42 | A |
| ATOM | 1263 | N | VAL | A | 168 | 21.295 | 49.473 | 104.050 | 1.00 | 14.03 | A |
| ATOM | 1264 | CA | VAL | A | 168 | 20.512 | 50.071 | 102.974 | 1.00 | 13.42 | A |
| ATOM | 1265 | CB | VAL | A | 168 | 20.710 | 51.608 | 102.899 | 1.00 | 13.78 | A |
| ATOM | 1266 | CG1 | VAL | A | 168 | 20.145 | 52.250 | 104.155 | 1.00 | 13.71 | A |
| ATOM | 1267 | CG2 | VAL | A | 168 | 22.183 | 51.955 | 102.740 | 1.00 | 15.67 | A |
| ATOM | 1268 | C | VAL | A | 168 | 20.804 | 49.438 | 101.620 | 1.00 | 13.51 | A |
| ATOM | 1269 | O | VAL | A | 168 | 19.898 | 49.307 | 100.800 | 1.00 | 15.08 | A |
| ATOM | 1270 | N | LEU | A | 169 | 22.054 | 49.037 | 101.379 | 1.00 | 13.10 | A |
| ATOM | 1271 | CA | LEU | A | 169 | 22.397 | 48.397 | 100.107 | 1.00 | 14.82 | A |
| ATOM | 1272 | CB | LEU | A | 169 | 23.920 | 48.257 | 99.954 | 1.00 | 15.02 | A |
| ATOM | 1273 | CG | LEU | A | 169 | 24.672 | 49.559 | 99.643 | 1.00 | 15.90 | A |
| ATOM | 1274 | CD1 | LEU | A | 169 | 26.175 | 49.323 | 99.692 | 1.00 | 18.49 | A |
| ATOM | 1275 | CD2 | LEU | A | 169 | 24.259 | 50.063 | 98.272 | 1.00 | 16.52 | A |
| ATOM | 1276 | C | LEU | A | 169 | 21.731 | 47.021 | 100.059 | 1.00 | 14.69 | A |
| ATOM | 1277 | O | LEU | A | 169 | 21.208 | 46.609 | 99.019 | 1.00 | 14.57 | A |
| ATOM | 1278 | N | ARG | A | 170 | 21.743 | 46.323 | 101.194 | 1.00 | 14.14 | A |
| ATOM | 1279 | CA | ARG | A | 170 | 21.123 | 45.003 | 101.309 | 1.00 | 13.98 | A |
| ATOM | 1280 | CB | ARG | A | 170 | 21.363 | 44.457 | 102.727 | 1.00 | 18.76 | A |
| ATOM | 1281 | CG | ARG | A | 170 | 20.615 | 43.185 | 103.107 | 1.00 | 18.37 | A |
| ATOM | 1282 | CD | ARG | A | 170 | 21.288 | 42.496 | 104.306 | 1.00 | 18.20 | A |
| ATOM | 1283 | NE | ARG | A | 170 | 21.420 | 43.343 | 105.500 | 1.00 | 18.43 | A |
| ATOM | 1284 | CZ | ARG | A | 170 | 20.434 | 43.602 | 106.355 | 1.00 | 18.99 | A |
| ATOM | 1285 | NH1 | ARG | A | 170 | 19.231 | 43.082 | 106.159 | 1.00 | 15.93 | A |
| ATOM | 1286 | NH2 | ARG | A | 170 | 20.650 | 44.378 | 107.415 | 1.00 | 18.98 | A |
| ATOM | 1287 | C | ARG | A | 170 | 19.626 | 45.116 | 101.006 | 1.00 | 15.04 | A |
| ATOM | 1288 | O | ARG | A | 170 | 19.045 | 44.266 | 100.325 | 1.00 | 13.87 | A |
| ATOM | 1289 | N | LEU | A | 171 | 19.010 | 46.185 | 101.496 | 1.00 | 14.48 | A |
| ATOM | 1290 | CA | LEU | A | 171 | 17.588 | 46.412 | 101.269 | 1.00 | 16.01 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 1291 | CB | LEU | A | 171 | 17.066 | 47.488 | 102.229 | 1.00 | 16.51 | A |
| ATOM | 1292 | CG | LEU | A | 171 | 15.657 | 48.037 | 101.983 | 1.00 | 18.42 | A |
| ATOM | 1293 | CD1 | LEU | A | 171 | 14.644 | 46.910 | 101.951 | 1.00 | 19.05 | A |
| ATOM | 1294 | CD2 | LEU | A | 171 | 15.305 | 49.032 | 103.076 | 1.00 | 17.79 | A |
| ATOM | 1295 | C | LEU | A | 171 | 17.323 | 46.834 | 99.823 | 1.00 | 15.61 | A |
| ATOM | 1296 | O | LEU | A | 171 | 16.413 | 46.313 | 99.174 | 1.00 | 16.14 | A |
| ATOM | 1297 | N | ALA | A | 172 | 18.116 | 47.775 | 99.314 | 1.00 | 15.72 | A |
| ATOM | 1298 | CA | ALA | A | 172 | 17.934 | 48.241 | 97.942 | 1.00 | 15.52 | A |
| ATOM | 1299 | CB | ALA | A | 172 | 18.911 | 49.378 | 97.636 | 1.00 | 17.06 | A |
| ATOM | 1300 | C | ALA | A | 172 | 18.109 | 47.115 | 96.923 | 1.00 | 15.78 | A |
| ATOM | 1301 | O | ALA | A | 172 | 17.430 | 47.083 | 95.896 | 1.00 | 14.10 | A |
| ATOM | 1302 | N | LYS | A | 173 | 19.008 | 46.184 | 97.211 | 1.00 | 15.48 | A |
| ATOM | 1303 | CA | LYS | A | 173 | 19.251 | 45.083 | 96.288 | 1.00 | 15.99 | A |
| ATOM | 1304 | CB | LYS | A | 173 | 20.325 | 44.148 | 96.851 | 1.00 | 15.75 | A |
| ATOM | 1305 | CG | LYS | A | 173 | 20.576 | 42.910 | 96.001 | 1.00 | 16.03 | A |
| ATOM | 1306 | CD | LYS | A | 173 | 21.788 | 42.147 | 96.512 | 1.00 | 19.74 | A |
| ATOM | 1307 | CE | LYS | A | 173 | 21.600 | 40.640 | 96.392 | 1.00 | 22.75 | A |
| ATOM | 1308 | NZ | LYS | A | 173 | 21.274 | 40.183 | 95.023 | 1.00 | 21.00 | A |
| ATOM | 1309 | C | LYS | A | 173 | 17.985 | 44.289 | 95.972 | 1.00 | 16.47 | A |
| ATOM | 1310 | O | LYS | A | 173 | 17.703 | 44.008 | 94.804 | 1.00 | 16.32 | A |
| ATOM | 1311 | N | ASP | A | 174 | 17.230 | 43.924 | 97.005 | 1.00 | 15.20 | A |
| ATOM | 1312 | CA | ASP | A | 174 | 16.006 | 43.158 | 96.804 | 1.00 | 17.12 | A |
| ATOM | 1313 | CB | ASP | A | 174 | 15.496 | 42.574 | 98.126 | 1.00 | 18.01 | A |
| ATOM | 1314 | CG | ASP | A | 174 | 16.319 | 41.378 | 98.597 | 1.00 | 21.22 | A |
| ATOM | 1315 | OD1 | ASP | A | 174 | 16.943 | 40.698 | 97.752 | 1.00 | 23.11 | A |
| ATOM | 1316 | OD2 | ASP | A | 174 | 16.323 | 41.103 | 99.814 | 1.00 | 19.95 | A |
| ATOM | 1317 | C | ASP | A | 174 | 14.909 | 43.988 | 96.149 | 1.00 | 15.70 | A |
| ATOM | 1318 | O | ASP | A | 174 | 14.155 | 43.479 | 95.318 | 1.00 | 14.62 | A |
| ATOM | 1319 | N | LEU | A | 175 | 14.814 | 45.263 | 96.522 | 1.00 | 14.64 | A |
| ATOM | 1320 | CA | LEU | A | 175 | 13.804 | 46.138 | 95.936 | 1.00 | 16.58 | A |
| ATOM | 1321 | CB | LEU | A | 175 | 13.841 | 47.529 | 96.592 | 1.00 | 16.05 | A |
| ATOM | 1322 | CG | LEU | A | 175 | 13.445 | 47.613 | 98.070 | 1.00 | 16.89 | A |
| ATOM | 1323 | CD1 | LEU | A | 175 | 13.483 | 49.061 | 98.527 | 1.00 | 16.97 | A |
| ATOM | 1324 | CD2 | LEU | A | 175 | 12.060 | 47.041 | 98.269 | 1.00 | 17.52 | A |
| ATOM | 1325 | C | LEU | A | 175 | 14.015 | 46.298 | 94.430 | 1.00 | 15.43 | A |
| ATOM | 1326 | O | LEU | A | 175 | 13.073 | 46.163 | 93.642 | 1.00 | 17.97 | A |
| ATOM | 1327 | N | ALA | A | 176 | 15.246 | 46.589 | 94.021 | 1.00 | 14.64 | A |
| ATOM | 1328 | CA | ALA | A | 176 | 15.529 | 46.777 | 92.601 | 1.00 | 14.54 | A |
| ATOM | 1329 | CB | ALA | A | 176 | 16.918 | 47.382 | 92.412 | 1.00 | 16.05 | A |
| ATOM | 1330 | C | ALA | A | 176 | 15.421 | 45.508 | 91.764 | 1.00 | 15.09 | A |
| ATOM | 1331 | O | ALA | A | 176 | 14.923 | 45.536 | 90.637 | 1.00 | 13.49 | A |
| ATOM | 1332 | N | GLU | A | 177 | 15.899 | 44.398 | 92.309 | 1.00 | 14.74 | A |
| ATOM | 1333 | CA | GLU | A | 177 | 15.898 | 43.143 | 91.571 | 1.00 | 16.33 | A |
| ATOM | 1334 | CB | GLU | A | 177 | 16.949 | 42.196 | 92.170 | 1.00 | 16.12 | A |
| ATOM | 1335 | CG | GLU | A | 177 | 18.370 | 42.756 | 92.074 | 1.00 | 17.28 | A |
| ATOM | 1336 | CD | GLU | A | 177 | 19.425 | 41.845 | 92.680 | 1.00 | 18.83 | A |
| ATOM | 1337 | OE1 | GLU | A | 177 | 19.056 | 40.938 | 93.457 | 1.00 | 16.57 | A |
| ATOM | 1338 | OE2 | GLU | A | 177 | 20.624 | 42.051 | 92.388 | 1.00 | 16.51 | A |
| ATOM | 1339 | C | GLU | A | 177 | 14.568 | 42.422 | 91.445 | 1.00 | 15.11 | A |
| ATOM | 1340 | O | GLU | A | 177 | 14.355 | 41.688 | 90.479 | 1.00 | 16.69 | A |
| ATOM | 1341 | N | ASN | A | 178 | 13.667 | 42.633 | 92.398 | 1.00 | 15.01 | A |
| ATOM | 1342 | CA | ASN | A | 178 | 12.387 | 41.945 | 92.370 | 1.00 | 16.15 | A |
| ATOM | 1343 | CB | ASN | A | 178 | 11.944 | 41.597 | 93.793 | 1.00 | 14.81 | A |
| ATOM | 1344 | CG | ASN | A | 178 | 10.875 | 40.519 | 93.815 | 1.00 | 18.14 | A |
| ATOM | 1345 | OD1 | ASN | A | 178 | 11.012 | 39.493 | 93.148 | 1.00 | 14.61 | A |
| ATOM | 1346 | ND2 | ASN | A | 178 | 9.813 | 40.743 | 94.578 | 1.00 | 16.87 | A |
| ATOM | 1347 | C | ASN | A | 178 | 11.279 | 42.726 | 91.677 | 1.00 | 17.15 | A |
| ATOM | 1348 | O | ASN | A | 178 | 10.161 | 42.233 | 91.550 | 1.00 | 15.08 | A |
| ATOM | 1349 | N | ASN | A | 179 | 11.594 | 43.932 | 91.215 | 1.00 | 17.66 | A |
| ATOM | 1350 | CA | ASN | A | 179 | 10.595 | 44.773 | 90.568 | 1.00 | 18.39 | A |
| ATOM | 1351 | CB | ASN | A | 179 | 10.162 | 45.870 | 91.545 | 1.00 | 19.49 | A |
| ATOM | 1352 | CG | ASN | A | 179 | 9.505 | 45.303 | 92.787 | 1.00 | 18.74 | A |
| ATOM | 1353 | OD1 | ASN | A | 179 | 8.377 | 44.818 | 92.734 | 1.00 | 19.10 | A |
| ATOM | 1354 | ND2 | ASN | A | 179 | 10.216 | 45.341 | 93.909 | 1.00 | 19.12 | A |
| ATOM | 1355 | C | ASN | A | 179 | 11.069 | 45.393 | 89.262 | 1.00 | 18.82 | A |
| ATOM | 1356 | O | ASN | A | 179 | 11.957 | 46.248 | 89.251 | 1.00 | 18.76 | A |
| ATOM | 1357 | N | LYS | A | 180 | 10.469 | 44.960 | 88.157 | 1.00 | 18.18 | A |
| ATOM | 1358 | CA | LYS | A | 180 | 10.841 | 45.484 | 86.856 | 1.00 | 17.68 | A |
| ATOM | 1359 | CB | LYS | A | 180 | 9.980 | 44.851 | 85.759 | 1.00 | 19.83 | A |
| ATOM | 1360 | CG | LYS | A | 180 | 10.364 | 45.309 | 84.357 | 1.00 | 22.78 | A |
| ATOM | 1361 | CD | LYS | A | 180 | 9.565 | 44.576 | 83.284 | 1.00 | 28.75 | A |
| ATOM | 1362 | CE | LYS | A | 180 | 9.922 | 45.066 | 81.883 | 1.00 | 29.71 | A |
| ATOM | 1363 | NZ | LYS | A | 180 | 11.333 | 44.765 | 81.500 | 1.00 | 32.99 | A |
| ATOM | 1364 | C | LYS | A | 180 | 10.686 | 47.005 | 86.833 | 1.00 | 16.88 | A |
| ATOM | 1365 | O | LYS | A | 180 | 9.668 | 47.541 | 87.268 | 1.00 | 15.93 | A |

APPENDIX B-continued

*Arachis hypogaea* STS

| ATOM | # | TYPE | RES | | | X | Y | Z | OCC | B | |
|------|---|------|-----|---|-----|--------|--------|---------|------|-------|---|
| ATOM | 1366 | N | ASP | A | 181 | 11.725 | 47.684 | 86.355 | 1.00 | 18.30 | A |
| ATOM | 1367 | CA | ASP | A | 181 | 11.755 | 49.144 | 86.243 | 1.00 | 20.40 | A |
| ATOM | 1368 | CB | ASP | A | 181 | 10.514 | 49.645 | 85.496 | 1.00 | 22.88 | A |
| ATOM | 1369 | CG | ASP | A | 181 | 10.441 | 49.128 | 84.070 | 1.00 | 25.36 | A |
| ATOM | 1370 | OD1 | ASP | A | 181 | 11.469 | 49.186 | 83.369 | 1.00 | 27.75 | A |
| ATOM | 1371 | OD2 | ASP | A | 181 | 9.354 | 48.677 | 83.647 | 1.00 | 28.77 | A |
| ATOM | 1372 | C | ASP | A | 181 | 11.886 | 49.907 | 87.561 | 1.00 | 19.53 | A |
| ATOM | 1373 | O | ASP | A | 181 | 11.843 | 51.140 | 87.572 | 1.00 | 20.09 | A |
| ATOM | 1374 | N | ALA | A | 182 | 12.055 | 49.195 | 88.668 | 1.00 | 17.14 | A |
| ATOM | 1375 | CA | ALA | A | 182 | 12.181 | 49.873 | 89.950 | 1.00 | 16.34 | A |
| ATOM | 1376 | CB | ALA | A | 182 | 12.174 | 48.858 | 91.094 | 1.00 | 16.60 | A |
| ATOM | 1377 | C | ALA | A | 182 | 13.463 | 50.694 | 90.000 | 1.00 | 14.49 | A |
| ATOM | 1378 | O | ALA | A | 182 | 14.517 | 50.241 | 89.567 | 1.00 | 13.96 | A |
| ATOM | 1379 | N | ARG | A | 183 | 13.357 | 51.916 | 90.510 | 1.00 | 14.46 | A |
| ATOM | 1380 | CA | ARG | A | 183 | 14.516 | 52.788 | 90.668 | 1.00 | 15.12 | A |
| ATOM | 1381 | CB | ARG | A | 183 | 14.474 | 53.953 | 89.679 | 1.00 | 14.27 | A |
| ATOM | 1382 | CG | ARG | A | 183 | 14.834 | 53.538 | 88.266 | 1.00 | 14.93 | A |
| ATOM | 1383 | CD | ARG | A | 183 | 16.287 | 53.084 | 88.169 | 1.00 | 13.32 | A |
| ATOM | 1384 | NE | ARG | A | 183 | 16.653 | 52.650 | 86.819 | 1.00 | 16.28 | A |
| ATOM | 1385 | CZ | ARG | A | 183 | 16.497 | 51.413 | 86.349 | 1.00 | 17.08 | A |
| ATOM | 1386 | NH1 | ARG | A | 183 | 15.975 | 50.459 | 87.112 | 1.00 | 15.62 | A |
| ATOM | 1387 | NH2 | ARG | A | 183 | 16.892 | 51.118 | 85.119 | 1.00 | 19.64 | A |
| ATOM | 1388 | C | ARG | A | 183 | 14.446 | 53.273 | 92.104 | 1.00 | 14.84 | A |
| ATOM | 1389 | O | ARG | A | 183 | 13.512 | 53.989 | 92.495 | 1.00 | 13.87 | A |
| ATOM | 1390 | N | VAL | A | 184 | 15.435 | 52.851 | 92.886 | 1.00 | 13.98 | A |
| ATOM | 1391 | CA | VAL | A | 184 | 15.500 | 53.157 | 94.313 | 1.00 | 13.66 | A |
| ATOM | 1392 | CB | VAL | A | 184 | 15.984 | 51.919 | 95.105 | 1.00 | 12.76 | A |
| ATOM | 1393 | CG1 | VAL | A | 184 | 15.823 | 52.141 | 96.617 | 1.00 | 13.61 | A |
| ATOM | 1394 | CG2 | VAL | A | 184 | 15.224 | 50.693 | 94.651 | 1.00 | 14.50 | A |
| ATOM | 1395 | C | VAL | A | 184 | 16.413 | 54.322 | 94.663 | 1.00 | 13.84 | A |
| ATOM | 1396 | O | VAL | A | 184 | 17.550 | 54.395 | 94.202 | 1.00 | 15.51 | A |
| ATOM | 1397 | N | LEU | A | 185 | 15.894 | 55.236 | 95.475 | 1.00 | 12.87 | A |
| ATOM | 1398 | CA | LEU | A | 185 | 16.672 | 56.375 | 95.931 | 1.00 | 12.68 | A |
| ATOM | 1399 | CB | LEU | A | 185 | 15.861 | 57.679 | 95.834 | 1.00 | 11.22 | A |
| ATOM | 1400 | CG | LEU | A | 185 | 16.532 | 58.905 | 96.466 | 1.00 | 11.54 | A |
| ATOM | 1401 | CD1 | LEU | A | 185 | 17.866 | 59.176 | 95.778 | 1.00 | 13.85 | A |
| ATOM | 1402 | CD2 | LEU | A | 185 | 15.612 | 60.122 | 96.370 | 1.00 | 11.09 | A |
| ATOM | 1403 | C | LEU | A | 185 | 17.017 | 56.106 | 97.394 | 1.00 | 11.63 | A |
| ATOM | 1404 | O | LEU | A | 185 | 16.127 | 55.958 | 98.230 | 1.00 | 13.09 | A |
| ATOM | 1405 | N | ILE | A | 186 | 18.305 | 56.010 | 97.695 | 1.00 | 12.57 | A |
| ATOM | 1406 | CA | ILE | A | 186 | 18.721 | 55.803 | 99.072 | 1.00 | 12.90 | A |
| ATOM | 1407 | CB | ILE | A | 186 | 19.867 | 54.790 | 99.209 | 1.00 | 12.53 | A |
| ATOM | 1408 | CG2 | ILE | A | 186 | 20.293 | 54.706 | 100.672 | 1.00 | 15.79 | A |
| ATOM | 1409 | CG1 | ILE | A | 186 | 19.441 | 53.411 | 98.703 | 1.00 | 17.58 | A |
| ATOM | 1410 | CD1 | ILE | A | 186 | 20.562 | 52.372 | 98.791 | 1.00 | 15.67 | A |
| ATOM | 1411 | C | ILE | A | 186 | 19.265 | 57.126 | 99.580 | 1.00 | 12.87 | A |
| ATOM | 1412 | O | ILE | A | 186 | 20.041 | 57.782 | 98.899 | 1.00 | 12.60 | A |
| ATOM | 1413 | N | VAL | A | 187 | 18.851 | 57.515 | 100.776 | 1.00 | 13.22 | A |
| ATOM | 1414 | CA | VAL | A | 187 | 19.359 | 58.741 | 101.361 | 1.00 | 13.67 | A |
| ATOM | 1415 | CB | VAL | A | 187 | 18.316 | 59.866 | 101.349 | 1.00 | 14.26 | A |
| ATOM | 1416 | CG1 | VAL | A | 187 | 18.866 | 61.083 | 102.088 | 1.00 | 15.07 | A |
| ATOM | 1417 | CG2 | VAL | A | 187 | 17.967 | 60.228 | 99.917 | 1.00 | 17.12 | A |
| ATOM | 1418 | C | VAL | A | 187 | 19.763 | 58.463 | 102.795 | 1.00 | 11.28 | A |
| ATOM | 1419 | O | VAL | A | 187 | 18.930 | 58.089 | 103.618 | 1.00 | 12.82 | A |
| ATOM | 1420 | N | CYS | A | 188 | 21.051 | 58.621 | 103.071 | 1.00 | 13.30 | A |
| ATOM | 1421 | CA | CYS | A | 188 | 21.609 | 58.430 | 104.410 | 1.00 | 13.30 | A |
| ATOM | 1422 | CB | CYS | A | 188 | 22.816 | 57.490 | 104.382 | 1.00 | 14.21 | A |
| ATOM | 1423 | SG | CYS | A | 188 | 22.413 | 55.739 | 104.060 | 1.00 | 17.94 | A |
| ATOM | 1424 | C | CYS | A | 188 | 22.058 | 59.817 | 104.839 | 1.00 | 11.22 | A |
| ATOM | 1425 | O | CYS | A | 188 | 22.938 | 60.401 | 104.220 | 1.00 | 13.60 | A |
| ATOM | 1426 | N | SER | A | 189 | 21.452 | 60.332 | 105.899 | 1.00 | 12.04 | A |
| ATOM | 1427 | CA | SER | A | 189 | 21.765 | 61.675 | 106.377 | 1.00 | 12.31 | A |
| ATOM | 1428 | CB | SER | A | 189 | 20.612 | 62.615 | 106.024 | 1.00 | 14.07 | A |
| ATOM | 1429 | OG | SER | A | 189 | 20.919 | 63.953 | 106.369 | 1.00 | 13.79 | A |
| ATOM | 1430 | C | SER | A | 189 | 21.976 | 61.646 | 107.882 | 1.00 | 11.93 | A |
| ATOM | 1431 | O | SER | A | 189 | 21.054 | 61.336 | 108.638 | 1.00 | 13.29 | A |
| ATOM | 1432 | N | GLU | A | 190 | 23.185 | 61.993 | 108.314 | 1.00 | 14.10 | A |
| ATOM | 1433 | CA | GLU | A | 190 | 23.530 | 61.959 | 109.734 | 1.00 | 13.97 | A |
| ATOM | 1434 | CB | GLU | A | 190 | 24.692 | 60.989 | 109.951 | 1.00 | 16.13 | A |
| ATOM | 1435 | CG | GLU | A | 190 | 24.461 | 59.577 | 109.378 | 1.00 | 17.69 | A |
| ATOM | 1436 | CD | GLU | A | 190 | 23.440 | 58.747 | 110.160 | 1.00 | 20.46 | A |
| ATOM | 1437 | OE1 | GLU | A | 190 | 22.984 | 59.185 | 111.237 | 1.00 | 17.84 | A |
| ATOM | 1438 | OE2 | GLU | A | 190 | 23.096 | 57.638 | 109.692 | 1.00 | 22.18 | A |
| ATOM | 1439 | C | GLU | A | 190 | 23.890 | 63.345 | 110.270 | 1.00 | 14.72 | A |
| ATOM | 1440 | O | GLU | A | 190 | 24.438 | 64.184 | 109.551 | 1.00 | 13.22 | A |

APPENDIX B-continued

*Arachis hypogaea* STS

| ATOM | # | TYPE | RES | | | X | Y | Z | OCC | B | |
|------|---|------|-----|---|-----|--------|--------|---------|------|-------|---|
| ATOM | 1441 | N | ASN | A | 191 | 23.584 | 63.569 | 111.542 | 1.00 | 14.47 | A |
| ATOM | 1442 | CA | ASN | A | 191 | 23.826 | 64.860 | 112.174 | 1.00 | 16.59 | A |
| ATOM | 1443 | CB | ASN | A | 191 | 22.577 | 65.726 | 111.979 | 1.00 | 15.33 | A |
| ATOM | 1444 | CG | ASN | A | 191 | 22.778 | 67.164 | 112.405 | 1.00 | 16.18 | A |
| ATOM | 1445 | OD1 | ASN | A | 191 | 23.151 | 67.441 | 113.540 | 1.00 | 16.84 | A |
| ATOM | 1446 | ND2 | ASN | A | 191 | 22.505 | 68.094 | 111.492 | 1.00 | 16.25 | A |
| ATOM | 1447 | C | ASN | A | 191 | 24.113 | 64.643 | 113.665 | 1.00 | 17.21 | A |
| ATOM | 1448 | O | ASN | A | 191 | 23.396 | 63.894 | 114.334 | 1.00 | 16.87 | A |
| ATOM | 1449 | N | THR | A | 192 | 25.141 | 65.310 | 114.187 | 1.00 | 17.46 | A |
| ATOM | 1450 | CA | THR | A | 192 | 25.527 | 65.144 | 115.594 | 1.00 | 17.77 | A |
| ATOM | 1451 | CB | THR | A | 192 | 27.025 | 65.466 | 115.792 | 1.00 | 19.46 | A |
| ATOM | 1452 | OG1 | THR | A | 192 | 27.302 | 66.792 | 115.326 | 1.00 | 21.72 | A |
| ATOM | 1453 | CG2 | THR | A | 192 | 27.885 | 64.475 | 115.021 | 1.00 | 24.93 | A |
| ATOM | 1454 | C | THR | A | 192 | 24.719 | 65.923 | 116.637 | 1.00 | 17.73 | A |
| ATOM | 1455 | O | THR | A | 192 | 25.014 | 65.861 | 117.835 | 1.00 | 17.54 | A |
| ATOM | 1456 | N | ALA | A | 193 | 23.693 | 66.643 | 116.199 | 1.00 | 16.98 | A |
| ATOM | 1457 | CA | ALA | A | 193 | 22.872 | 67.407 | 117.131 | 1.00 | 17.82 | A |
| ATOM | 1458 | CB | ALA | A | 193 | 21.695 | 68.043 | 116.395 | 1.00 | 17.73 | A |
| ATOM | 1459 | C | ALA | A | 193 | 22.357 | 66.533 | 118.276 | 1.00 | 19.11 | A |
| ATOM | 1460 | O | ALA | A | 193 | 22.269 | 66.978 | 119.420 | 1.00 | 17.05 | A |
| ATOM | 1461 | N | VAL | A | 194 | 22.033 | 65.279 | 117.973 | 1.00 | 18.73 | A |
| ATOM | 1462 | CA | VAL | A | 194 | 21.505 | 64.391 | 119.000 | 1.00 | 18.68 | A |
| ATOM | 1463 | CB | VAL | A | 194 | 20.586 | 63.299 | 118.366 | 1.00 | 20.01 | A |
| ATOM | 1464 | CG1 | VAL | A | 194 | 21.429 | 62.229 | 117.676 | 1.00 | 21.94 | A |
| ATOM | 1465 | CG2 | VAL | A | 194 | 19.681 | 62.688 | 119.427 | 1.00 | 20.08 | A |
| ATOM | 1466 | C | VAL | A | 194 | 22.556 | 63.715 | 119.894 | 1.00 | 18.19 | A |
| ATOM | 1467 | O | VAL | A | 194 | 22.203 | 63.188 | 120.947 | 1.00 | 18.53 | A |
| ATOM | 1468 | N | THR | A | 195 | 23.830 | 63.737 | 119.497 | 1.00 | 18.59 | A |
| ATOM | 1469 | CA | THR | A | 195 | 24.892 | 63.100 | 120.293 | 1.00 | 19.00 | A |
| ATOM | 1470 | CB | THR | A | 195 | 25.701 | 62.079 | 119.456 | 1.00 | 19.71 | A |
| ATOM | 1471 | OG1 | THR | A | 195 | 26.401 | 62.754 | 118.405 | 1.00 | 19.52 | A |
| ATOM | 1472 | CG2 | THR | A | 195 | 24.785 | 61.028 | 118.860 | 1.00 | 22.73 | A |
| ATOM | 1473 | C | THR | A | 195 | 25.902 | 64.061 | 120.940 | 1.00 | 18.87 | A |
| ATOM | 1474 | O | THR | A | 195 | 26.621 | 63.692 | 121.870 | 1.00 | 18.50 | A |
| ATOM | 1475 | N | PHE | A | 196 | 25.971 | 65.290 | 120.454 | 1.00 | 19.16 | A |
| ATOM | 1476 | CA | PHE | A | 196 | 26.917 | 66.244 | 121.024 | 1.00 | 16.16 | A |
| ATOM | 1477 | CB | PHE | A | 196 | 26.878 | 67.552 | 120.230 | 1.00 | 17.37 | A |
| ATOM | 1478 | CG | PHE | A | 196 | 27.756 | 68.625 | 120.797 | 1.00 | 18.14 | A |
| ATOM | 1479 | CD1 | PHE | A | 196 | 27.339 | 69.384 | 121.885 | 1.00 | 19.21 | A |
| ATOM | 1480 | CD2 | PHE | A | 196 | 29.030 | 68.834 | 120.285 | 1.00 | 17.83 | A |
| ATOM | 1481 | CE1 | PHE | A | 196 | 28.185 | 70.333 | 122.459 | 1.00 | 19.80 | A |
| ATOM | 1482 | CE2 | PHE | A | 196 | 29.878 | 69.779 | 120.854 | 1.00 | 18.39 | A |
| ATOM | 1483 | CZ | PHE | A | 196 | 29.455 | 70.525 | 121.940 | 1.00 | 16.80 | A |
| ATOM | 1484 | C | PHE | A | 196 | 26.614 | 66.533 | 122.497 | 1.00 | 15.24 | A |
| ATOM | 1485 | O | PHE | A | 196 | 25.466 | 66.703 | 122.874 | 1.00 | 15.60 | A |
| ATOM | 1486 | N | ARG | A | 197 | 27.645 | 66.567 | 123.334 | 1.00 | 15.68 | A |
| ATOM | 1487 | CA | ARG | A | 197 | 27.447 | 66.885 | 124.745 | 1.00 | 17.09 | A |
| ATOM | 1488 | CB | ARG | A | 197 | 26.765 | 65.729 | 125.500 | 1.00 | 16.77 | A |
| ATOM | 1489 | CG | ARG | A | 197 | 27.647 | 64.546 | 125.839 | 1.00 | 18.42 | A |
| ATOM | 1490 | CD | ARG | A | 197 | 26.830 | 63.452 | 126.527 | 1.00 | 17.90 | A |
| ATOM | 1491 | NE | ARG | A | 197 | 25.711 | 63.026 | 125.689 | 1.00 | 18.84 | A |
| ATOM | 1492 | CZ | ARG | A | 197 | 24.453 | 63.420 | 125.855 | 1.00 | 17.63 | A |
| ATOM | 1493 | NH1 | ARG | A | 197 | 24.133 | 64.249 | 126.843 | 1.00 | 16.56 | A |
| ATOM | 1494 | NH2 | ARG | A | 197 | 23.517 | 63.008 | 125.012 | 1.00 | 16.66 | A |
| ATOM | 1495 | C | ARG | A | 197 | 28.758 | 67.250 | 125.421 | 1.00 | 17.09 | A |
| ATOM | 1496 | O | ARG | A | 197 | 29.842 | 66.951 | 124.904 | 1.00 | 16.37 | A |
| ATOM | 1497 | N | GLY | A | 198 | 28.642 | 67.909 | 126.572 | 1.00 | 16.23 | A |
| ATOM | 1498 | CA | GLY | A | 198 | 29.806 | 68.325 | 127.330 | 1.00 | 16.62 | A |
| ATOM | 1499 | C | GLY | A | 198 | 30.669 | 67.174 | 127.809 | 1.00 | 16.44 | A |
| ATOM | 1500 | O | GLY | A | 198 | 30.266 | 66.010 | 127.727 | 1.00 | 17.18 | A |
| ATOM | 1501 | N | PRO | A | 199 | 31.866 | 67.470 | 128.330 | 1.00 | 16.69 | A |
| ATOM | 1502 | CD | PRO | A | 199 | 32.552 | 68.775 | 128.239 | 1.00 | 16.86 | A |
| ATOM | 1503 | CA | PRO | A | 199 | 32.781 | 66.435 | 128.814 | 1.00 | 16.94 | A |
| ATOM | 1504 | CB | PRO | A | 199 | 34.146 | 67.038 | 128.518 | 1.00 | 17.97 | A |
| ATOM | 1505 | CG | PRO | A | 199 | 33.912 | 68.487 | 128.865 | 1.00 | 16.67 | A |
| ATOM | 1506 | C | PRO | A | 199 | 32.643 | 66.060 | 130.280 | 1.00 | 18.52 | A |
| ATOM | 1507 | O | PRO | A | 199 | 32.167 | 66.841 | 131.097 | 1.00 | 17.68 | A |
| ATOM | 1508 | N | SER | A | 200 | 33.073 | 64.847 | 130.598 | 1.00 | 19.80 | A |
| ATOM | 1509 | CA | SER | A | 200 | 33.057 | 64.349 | 131.964 | 1.00 | 20.75 | A |
| ATOM | 1510 | CB | SER | A | 200 | 31.718 | 63.701 | 132.311 | 1.00 | 22.74 | A |
| ATOM | 1511 | OG | SER | A | 200 | 31.780 | 63.121 | 133.608 | 1.00 | 23.95 | A |
| ATOM | 1512 | C | SER | A | 200 | 34.162 | 63.317 | 132.105 | 1.00 | 21.76 | A |
| ATOM | 1513 | O | SER | A | 200 | 34.274 | 62.396 | 131.287 | 1.00 | 18.77 | A |
| ATOM | 1514 | N | GLU | A | 201 | 34.974 | 63.480 | 133.146 | 1.00 | 19.44 | A |
| ATOM | 1515 | CA | GLU | A | 201 | 36.076 | 62.568 | 133.425 | 1.00 | 22.42 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 1516 | CB | GLU | A | 201 | 36.836 | 63.045 | 134.670 | 1.00 | 23.51 | A |
| ATOM | 1517 | CG | GLU | A | 201 | 37.728 | 64.257 | 134.419 | 1.00 | 28.88 | A |
| ATOM | 1518 | CD | GLU | A | 201 | 38.211 | 64.911 | 135.704 | 1.00 | 32.82 | A |
| ATOM | 1519 | OE1 | GLU | A | 201 | 38.427 | 64.177 | 136.694 | 1.00 | 32.22 | A |
| ATOM | 1520 | OE2 | GLU | A | 201 | 38.381 | 66.156 | 135.717 | 1.00 | 32.99 | A |
| ATOM | 1521 | C | GLU | A | 201 | 35.554 | 61.152 | 133.646 | 1.00 | 21.15 | A |
| ATOM | 1522 | O | GLU | A | 201 | 36.291 | 60.176 | 133.492 | 1.00 | 21.69 | A |
| ATOM | 1523 | N | THR | A | 202 | 34.276 | 61.053 | 133.990 | 1.00 | 21.62 | A |
| ATOM | 1524 | CA | THR | A | 202 | 33.631 | 59.766 | 134.249 | 1.00 | 23.21 | A |
| ATOM | 1525 | CB | THR | A | 202 | 32.438 | 59.943 | 135.214 | 1.00 | 24.29 | A |
| ATOM | 1526 | OG1 | THR | A | 202 | 31.389 | 60.665 | 134.550 | 1.00 | 25.61 | A |
| ATOM | 1527 | CG2 | THR | A | 202 | 32.870 | 60.724 | 136.454 | 1.00 | 23.67 | A |
| ATOM | 1528 | C | THR | A | 202 | 33.111 | 59.048 | 132.996 | 1.00 | 24.32 | A |
| ATOM | 1529 | O | THR | A | 202 | 32.641 | 57.909 | 133.087 | 1.00 | 23.55 | A |
| ATOM | 1530 | N | ASP | A | 203 | 33.206 | 59.699 | 131.837 | 1.00 | 24.26 | A |
| ATOM | 1531 | CA | ASP | A | 203 | 32.706 | 59.123 | 130.586 | 1.00 | 23.45 | A |
| ATOM | 1532 | CB | ASP | A | 203 | 31.356 | 59.772 | 130.253 | 1.00 | 23.20 | A |
| ATOM | 1533 | CG | ASP | A | 203 | 30.514 | 58.945 | 129.295 | 1.00 | 24.79 | A |
| ATOM | 1534 | OD1 | ASP | A | 203 | 29.302 | 59.243 | 129.174 | 1.00 | 25.03 | A |
| ATOM | 1535 | OD2 | ASP | A | 203 | 31.045 | 58.010 | 128.664 | 1.00 | 23.91 | A |
| ATOM | 1536 | C | ASP | A | 203 | 33.691 | 59.328 | 129.430 | 1.00 | 23.07 | A |
| ATOM | 1537 | O | ASP | A | 203 | 33.483 | 60.191 | 128.572 | 1.00 | 20.44 | A |
| ATOM | 1538 | N | MET | A | 204 | 34.761 | 58.535 | 129.410 | 1.00 | 21.83 | A |
| ATOM | 1539 | CA | MET | A | 204 | 35.771 | 58.643 | 128.362 | 1.00 | 21.76 | A |
| ATOM | 1540 | CB | MET | A | 204 | 37.010 | 57.808 | 128.720 | 1.00 | 24.97 | A |
| ATOM | 1541 | CG | MET | A | 204 | 37.825 | 58.362 | 129.886 | 1.00 | 27.70 | A |
| ATOM | 1542 | SD | MET | A | 204 | 38.360 | 60.089 | 129.663 | 1.00 | 29.97 | A |
| ATOM | 1543 | CE | MET | A | 204 | 37.140 | 60.917 | 130.571 | 1.00 | 29.70 | A |
| ATOM | 1544 | C | MET | A | 204 | 35.225 | 58.200 | 127.010 | 1.00 | 22.24 | A |
| ATOM | 1545 | O | MET | A | 204 | 35.629 | 58.722 | 125.967 | 1.00 | 20.89 | A |
| ATOM | 1546 | N | ASP | A | 205 | 34.309 | 57.232 | 127.032 | 1.00 | 21.97 | A |
| ATOM | 1547 | CA | ASP | A | 205 | 33.690 | 56.736 | 125.805 | 1.00 | 22.89 | A |
| ATOM | 1548 | CB | ASP | A | 205 | 32.629 | 55.690 | 126.133 | 1.00 | 25.54 | A |
| ATOM | 1549 | CG | ASP | A | 205 | 33.214 | 54.327 | 126.373 | 1.00 | 29.64 | A |
| ATOM | 1550 | OD1 | ASP | A | 205 | 34.441 | 54.243 | 126.610 | 1.00 | 29.17 | A |
| ATOM | 1551 | OD2 | ASP | A | 205 | 32.441 | 53.343 | 126.332 | 1.00 | 27.49 | A |
| ATOM | 1552 | C | ASP | A | 205 | 33.023 | 57.883 | 125.071 | 1.00 | 21.88 | A |
| ATOM | 1553 | O | ASP | A | 205 | 33.260 | 58.105 | 123.884 | 1.00 | 19.23 | A |
| ATOM | 1554 | N | SER | A | 206 | 32.172 | 58.606 | 125.793 | 1.00 | 21.39 | A |
| ATOM | 1555 | CA | SER | A | 206 | 31.452 | 59.726 | 125.210 | 1.00 | 22.34 | A |
| ATOM | 1556 | CB | SER | A | 206 | 30.534 | 60.361 | 126.260 | 1.00 | 24.35 | A |
| ATOM | 1557 | OG | SER | A | 206 | 29.801 | 61.441 | 125.711 | 1.00 | 28.36 | A |
| ATOM | 1558 | C | SER | A | 206 | 32.419 | 60.765 | 124.651 | 1.00 | 22.11 | A |
| ATOM | 1559 | O | SER | A | 206 | 32.205 | 61.294 | 123.560 | 1.00 | 22.41 | A |
| ATOM | 1560 | N | LEU | A | 207 | 33.489 | 61.042 | 125.395 | 1.00 | 20.55 | A |
| ATOM | 1561 | CA | LEU | A | 207 | 34.487 | 62.018 | 124.972 | 1.00 | 19.96 | A |
| ATOM | 1562 | CB | LEU | A | 207 | 35.563 | 62.184 | 126.055 | 1.00 | 19.69 | A |
| ATOM | 1563 | CG | LEU | A | 207 | 36.586 | 63.301 | 125.825 | 1.00 | 21.16 | A |
| ATOM | 1564 | CD1 | LEU | A | 207 | 35.909 | 64.664 | 125.936 | 1.00 | 20.91 | A |
| ATOM | 1565 | CD2 | LEU | A | 207 | 37.712 | 63.182 | 126.845 | 1.00 | 22.85 | A |
| ATOM | 1566 | C | LEU | A | 207 | 35.129 | 61.598 | 123.648 | 1.00 | 18.93 | A |
| ATOM | 1567 | O | LEU | A | 207 | 35.369 | 62.430 | 122.778 | 1.00 | 19.49 | A |
| ATOM | 1568 | N | VAL | A | 208 | 35.402 | 60.304 | 123.491 | 1.00 | 19.50 | A |
| ATOM | 1569 | CA | VAL | A | 208 | 35.993 | 59.811 | 122.252 | 1.00 | 18.09 | A |
| ATOM | 1570 | CB | VAL | A | 208 | 36.308 | 58.299 | 122.351 | 1.00 | 19.75 | A |
| ATOM | 1571 | CG1 | VAL | A | 208 | 36.723 | 57.760 | 120.995 | 1.00 | 22.42 | A |
| ATOM | 1572 | CG2 | VAL | A | 208 | 37.408 | 58.068 | 123.378 | 1.00 | 22.62 | A |
| ATOM | 1573 | C | VAL | A | 208 | 35.020 | 60.059 | 121.090 | 1.00 | 18.11 | A |
| ATOM | 1574 | O | VAL | A | 208 | 35.428 | 60.418 | 119.982 | 1.00 | 17.15 | A |
| ATOM | 1575 | N | GLY | A | 209 | 33.730 | 59.875 | 121.349 | 1.00 | 17.76 | A |
| ATOM | 1576 | CA | GLY | A | 209 | 32.744 | 60.102 | 120.308 | 1.00 | 18.19 | A |
| ATOM | 1577 | C | GLY | A | 209 | 32.715 | 61.554 | 119.858 | 1.00 | 19.02 | A |
| ATOM | 1578 | O | GLY | A | 209 | 32.445 | 61.843 | 118.689 | 1.00 | 20.34 | A |
| ATOM | 1579 | N | GLN | A | 210 | 32.993 | 62.472 | 120.780 | 1.00 | 17.40 | A |
| ATOM | 1580 | CA | GLN | A | 210 | 32.987 | 63.901 | 120.465 | 1.00 | 17.84 | A |
| ATOM | 1581 | CB | GLN | A | 210 | 33.053 | 64.729 | 121.754 | 1.00 | 16.99 | A |
| ATOM | 1582 | CG | GLN | A | 210 | 31.942 | 64.396 | 122.742 | 1.00 | 19.21 | A |
| ATOM | 1583 | CD | GLN | A | 210 | 30.542 | 64.568 | 122.154 | 1.00 | 20.53 | A |
| ATOM | 1584 | OE1 | GLN | A | 210 | 29.627 | 63.805 | 122.470 | 1.00 | 20.22 | A |
| ATOM | 1585 | NE2 | GLN | A | 210 | 30.369 | 65.578 | 121.314 | 1.00 | 12.91 | A |
| ATOM | 1586 | C | GLN | A | 210 | 34.133 | 64.284 | 119.534 | 1.00 | 16.80 | A |
| ATOM | 1587 | O | GLN | A | 210 | 34.113 | 65.350 | 118.921 | 1.00 | 18.59 | A |
| ATOM | 1588 | N | ALA | A | 211 | 35.123 | 63.405 | 119.415 | 1.00 | 16.27 | A |
| ATOM | 1589 | CA | ALA | A | 211 | 36.268 | 63.654 | 118.546 | 1.00 | 16.35 | A |
| ATOM | 1590 | CB | ALA | A | 211 | 37.552 | 63.197 | 119.239 | 1.00 | 18.22 | A |

APPENDIX B-continued

_Arachis hypogaea STS_

| ATOM | # | TYPE | RES | | | X | Y | Z | OCC | B | |
|---|---|---|---|---|---|---|---|---|---|---|---|
| ATOM | 1591 | C | ALA | A | 211 | 36.115 | 62.931 | 117.207 | 1.00 | 15.81 | A |
| ATOM | 1592 | O | ALA | A | 211 | 36.803 | 63.251 | 116.227 | 1.00 | 16.08 | A |
| ATOM | 1593 | N | LEU | A | 212 | 35.192 | 61.976 | 117.166 | 1.00 | 14.42 | A |
| ATOM | 1594 | CA | LEU | A | 212 | 34.961 | 61.172 | 115.968 | 1.00 | 15.87 | A |
| ATOM | 1595 | CB | LEU | A | 212 | 34.778 | 59.703 | 116.370 | 1.00 | 15.09 | A |
| ATOM | 1596 | CG | LEU | A | 212 | 35.978 | 58.937 | 116.915 | 1.00 | 20.51 | A |
| ATOM | 1597 | CD1 | LEU | A | 212 | 35.522 | 57.536 | 117.328 | 1.00 | 20.17 | A |
| ATOM | 1598 | CD2 | LEU | A | 212 | 37.067 | 58.856 | 115.853 | 1.00 | 20.66 | A |
| ATOM | 1599 | C | LEU | A | 212 | 33.805 | 61.529 | 115.040 | 1.00 | 15.76 | A |
| ATOM | 1600 | O | LEU | A | 212 | 33.991 | 61.646 | 113.830 | 1.00 | 17.03 | A |
| ATOM | 1601 | N | PHE | A | 213 | 32.609 | 61.675 | 115.605 | 1.00 | 16.08 | A |
| ATOM | 1602 | CA | PHE | A | 213 | 31.408 | 61.918 | 114.806 | 1.00 | 16.97 | A |
| ATOM | 1603 | CB | PHE | A | 213 | 30.164 | 61.636 | 115.651 | 1.00 | 17.71 | A |
| ATOM | 1604 | CG | PHE | A | 213 | 30.186 | 60.292 | 116.314 | 1.00 | 20.56 | A |
| ATOM | 1605 | CD1 | PHE | A | 213 | 30.512 | 59.152 | 115.587 | 1.00 | 22.69 | A |
| ATOM | 1606 | CD2 | PHE | A | 213 | 29.923 | 60.168 | 117.671 | 1.00 | 21.84 | A |
| ATOM | 1607 | CE1 | PHE | A | 213 | 30.583 | 57.913 | 116.206 | 1.00 | 24.50 | A |
| ATOM | 1608 | CE2 | PHE | A | 213 | 29.992 | 58.928 | 118.297 | 1.00 | 22.58 | A |
| ATOM | 1609 | CZ | PHE | A | 213 | 30.323 | 57.805 | 117.566 | 1.00 | 20.73 | A |
| ATOM | 1610 | C | PHE | A | 213 | 31.260 | 63.254 | 114.101 | 1.00 | 15.36 | A |
| ATOM | 1611 | O | PHE | A | 213 | 31.551 | 64.304 | 114.659 | 1.00 | 12.76 | A |
| ATOM | 1612 | N | ALA | A | 214 | 30.771 | 63.184 | 112.863 | 1.00 | 16.63 | A |
| ATOM | 1613 | CA | ALA | A | 214 | 30.586 | 64.363 | 112.018 | 1.00 | 15.40 | A |
| ATOM | 1614 | CB | ALA | A | 214 | 31.759 | 64.497 | 111.050 | 1.00 | 16.43 | A |
| ATOM | 1615 | C | ALA | A | 214 | 29.276 | 64.260 | 111.243 | 1.00 | 15.29 | A |
| ATOM | 1616 | O | ALA | A | 214 | 28.595 | 63.232 | 111.301 | 1.00 | 16.79 | A |
| ATOM | 1617 | N | ASP | A | 215 | 28.946 | 65.316 | 110.502 | 1.00 | 16.01 | A |
| ATOM | 1618 | CA | ASP | A | 215 | 27.700 | 65.379 | 109.735 | 1.00 | 15.93 | A |
| ATOM | 1619 | CB | ASP | A | 215 | 26.972 | 66.703 | 109.998 | 1.00 | 17.66 | A |
| ATOM | 1620 | CG | ASP | A | 215 | 26.788 | 66.996 | 111.474 | 1.00 | 22.88 | A |
| ATOM | 1621 | OD1 | ASP | A | 215 | 26.964 | 66.080 | 112.302 | 1.00 | 22.93 | A |
| ATOM | 1622 | OD2 | ASP | A | 215 | 26.452 | 68.151 | 111.805 | 1.00 | 21.11 | A |
| ATOM | 1623 | C | ASP | A | 215 | 27.896 | 65.251 | 108.231 | 1.00 | 13.47 | A |
| ATOM | 1624 | O | ASP | A | 215 | 28.892 | 65.710 | 107.682 | 1.00 | 12.91 | A |
| ATOM | 1625 | N | GLY | A | 216 | 26.914 | 64.642 | 107.571 | 1.00 | 14.99 | A |
| ATOM | 1626 | CA | GLY | A | 216 | 26.969 | 64.472 | 106.135 | 1.00 | 14.98 | A |
| ATOM | 1627 | C | GLY | A | 216 | 25.807 | 63.636 | 105.626 | 1.00 | 15.88 | A |
| ATOM | 1628 | O | GLY | A | 216 | 25.154 | 62.929 | 106.398 | 1.00 | 14.93 | A |
| ATOM | 1629 | N | ALA | A | 217 | 25.537 | 63.731 | 104.329 | 1.00 | 16.39 | A |
| ATOM | 1630 | CA | ALA | A | 217 | 24.461 | 62.961 | 103.719 | 1.00 | 15.08 | A |
| ATOM | 1631 | CB | ALA | A | 217 | 23.207 | 63.820 | 103.543 | 1.00 | 14.14 | A |
| ATOM | 1632 | C | ALA | A | 217 | 24.925 | 62.454 | 102.373 | 1.00 | 14.86 | A |
| ATOM | 1633 | O | ALA | A | 217 | 25.679 | 63.121 | 101.666 | 1.00 | 15.64 | A |
| ATOM | 1634 | N | ALA | A | 218 | 24.478 | 61.256 | 102.027 | 1.00 | 13.54 | A |
| ATOM | 1635 | CA | ALA | A | 218 | 24.828 | 60.671 | 100.750 | 1.00 | 14.40 | A |
| ATOM | 1636 | CB | ALA | A | 218 | 25.784 | 59.499 | 100.950 | 1.00 | 13.37 | A |
| ATOM | 1637 | C | ALA | A | 218 | 23.521 | 60.202 | 100.131 | 1.00 | 14.12 | A |
| ATOM | 1638 | O | ALA | A | 218 | 22.622 | 59.752 | 100.845 | 1.00 | 15.69 | A |
| ATOM | 1639 | N | ALA | A | 219 | 23.408 | 60.336 | 98.815 | 1.00 | 14.03 | A |
| ATOM | 1640 | CA | ALA | A | 219 | 22.212 | 59.908 | 98.103 | 1.00 | 15.39 | A |
| ATOM | 1641 | CB | ALA | A | 219 | 21.447 | 61.112 | 97.556 | 1.00 | 15.27 | A |
| ATOM | 1642 | C | ALA | A | 219 | 22.667 | 59.003 | 96.971 | 1.00 | 14.28 | A |
| ATOM | 1643 | O | ALA | A | 219 | 23.623 | 59.315 | 96.251 | 1.00 | 14.99 | A |
| ATOM | 1644 | N | ILE | A | 220 | 21.974 | 57.882 | 96.823 | 1.00 | 13.67 | A |
| ATOM | 1645 | CA | ILE | A | 220 | 22.325 | 56.893 | 95.819 | 1.00 | 13.44 | A |
| ATOM | 1646 | CB | ILE | A | 220 | 22.991 | 55.672 | 96.495 | 1.00 | 14.33 | A |
| ATOM | 1647 | CG2 | ILE | A | 220 | 23.609 | 54.782 | 95.461 | 1.00 | 14.98 | A |
| ATOM | 1648 | CG1 | ILE | A | 220 | 24.037 | 56.134 | 97.515 | 1.00 | 14.70 | A |
| ATOM | 1649 | CD1 | ILE | A | 220 | 23.478 | 56.354 | 98.914 | 1.00 | 16.90 | A |
| ATOM | 1650 | C | ILE | A | 220 | 21.114 | 56.389 | 95.029 | 1.00 | 13.38 | A |
| ATOM | 1651 | O | ILE | A | 220 | 20.061 | 56.123 | 95.598 | 1.00 | 14.24 | A |
| ATOM | 1652 | N | ILE | A | 221 | 21.273 | 56.264 | 93.717 | 1.00 | 13.12 | A |
| ATOM | 1653 | CA | ILE | A | 221 | 20.207 | 55.747 | 92.867 | 1.00 | 14.15 | A |
| ATOM | 1654 | CB | ILE | A | 221 | 20.057 | 56.561 | 91.562 | 1.00 | 15.24 | A |
| ATOM | 1655 | CG2 | ILE | A | 221 | 18.984 | 55.924 | 90.679 | 1.00 | 14.91 | A |
| ATOM | 1656 | CG1 | ILE | A | 221 | 19.692 | 58.013 | 91.886 | 1.00 | 16.31 | A |
| ATOM | 1657 | CD1 | ILE | A | 221 | 18.300 | 58.187 | 92.471 | 1.00 | 17.99 | A |
| ATOM | 1658 | C | ILE | A | 221 | 20.623 | 54.331 | 92.496 | 1.00 | 15.28 | A |
| ATOM | 1659 | O | ILE | A | 221 | 21.730 | 54.121 | 91.989 | 1.00 | 14.96 | A |
| ATOM | 1660 | N | ILE | A | 222 | 19.735 | 53.372 | 92.749 | 1.00 | 15.38 | A |
| ATOM | 1661 | CA | ILE | A | 222 | 19.995 | 51.971 | 92.443 | 1.00 | 15.44 | A |
| ATOM | 1662 | CB | ILE | A | 222 | 20.102 | 51.136 | 93.720 | 1.00 | 16.28 | A |
| ATOM | 1663 | CG2 | ILE | A | 222 | 20.159 | 49.646 | 93.368 | 1.00 | 15.57 | A |
| ATOM | 1664 | CG1 | ILE | A | 222 | 21.346 | 51.553 | 94.510 | 1.00 | 21.06 | A |
| ATOM | 1665 | CD1 | ILE | A | 222 | 21.400 | 50.945 | 95.884 | 1.00 | 23.56 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 1666 | C | ILE | A | 222 | 18.881 | 51.365 | 91.595 | 1.00 | 15.66 | A |
| ATOM | 1667 | O | ILE | A | 222 | 17.703 | 51.641 | 91.818 | 1.00 | 12.27 | A |
| ATOM | 1668 | N | GLY | A | 223 | 19.263 | 50.531 | 90.634 | 1.00 | 13.58 | A |
| ATOM | 1669 | CA | GLY | A | 223 | 18.270 | 49.885 | 89.792 | 1.00 | 15.55 | A |
| ATOM | 1670 | C | GLY | A | 223 | 18.839 | 48.726 | 88.998 | 1.00 | 15.80 | A |
| ATOM | 1671 | O | GLY | A | 223 | 20.040 | 48.677 | 88.737 | 1.00 | 15.51 | A |
| ATOM | 1672 | N | SER | A | 224 | 17.985 | 47.777 | 88.630 | 1.00 | 15.62 | A |
| ATOM | 1673 | CA | SER | A | 224 | 18.426 | 46.645 | 87.819 | 1.00 | 17.60 | A |
| ATOM | 1674 | CB | SER | A | 224 | 17.697 | 45.357 | 88.235 | 1.00 | 17.65 | A |
| ATOM | 1675 | CG | SER | A | 224 | 18.151 | 44.877 | 89.495 | 1.00 | 15.67 | A |
| ATOM | 1676 | C | SER | A | 224 | 18.106 | 46.970 | 86.352 | 1.00 | 18.97 | A |
| ATOM | 1677 | O | SER | A | 224 | 17.281 | 47.835 | 86.074 | 1.00 | 16.29 | A |
| ATOM | 1678 | N | ASP | A | 225 | 18.772 | 46.288 | 85.427 | 1.00 | 19.29 | A |
| ATOM | 1679 | CA | ASP | A | 225 | 18.550 | 46.486 | 83.996 | 1.00 | 20.50 | A |
| ATOM | 1680 | CB | ASP | A | 225 | 17.159 | 45.973 | 83.610 | 1.00 | 22.70 | A |
| ATOM | 1681 | CG | ASP | A | 225 | 16.916 | 44.546 | 84.075 | 1.00 | 24.43 | A |
| ATOM | 1682 | OD1 | ASP | A | 225 | 17.893 | 43.773 | 84.138 | 1.00 | 25.70 | A |
| ATOM | 1683 | OD2 | ASP | A | 225 | 15.752 | 44.198 | 84.366 | 1.00 | 25.65 | A |
| ATOM | 1684 | C | ASP | A | 225 | 18.695 | 47.941 | 83.559 | 1.00 | 21.75 | A |
| ATOM | 1685 | O | ASP | A | 225 | 17.724 | 48.571 | 83.124 | 1.00 | 19.34 | A |
| ATOM | 1686 | N | PRO | A | 226 | 19.910 | 48.499 | 83.675 | 1.00 | 22.11 | A |
| ATOM | 1687 | CD | PRO | A | 226 | 21.149 | 47.915 | 84.216 | 1.00 | 22.58 | A |
| ATOM | 1688 | CA | PRO | A | 226 | 20.113 | 49.893 | 83.272 | 1.00 | 22.76 | A |
| ATOM | 1689 | CB | PRO | A | 226 | 21.543 | 50.183 | 83.726 | 1.00 | 23.77 | A |
| ATOM | 1690 | CG | PRO | A | 226 | 22.201 | 48.835 | 83.655 | 1.00 | 24.27 | A |
| ATOM | 1691 | C | PRO | A | 226 | 19.917 | 50.108 | 81.776 | 1.00 | 24.18 | A |
| ATOM | 1692 | O | PRO | A | 226 | 20.359 | 49.300 | 80.959 | 1.00 | 23.57 | A |
| ATOM | 1693 | N | VAL | A | 227 | 19.241 | 51.200 | 81.433 | 1.00 | 25.11 | A |
| ATOM | 1694 | CA | VAL | A | 227 | 18.983 | 51.552 | 80.041 | 1.00 | 27.09 | A |
| ATOM | 1695 | CB | VAL | A | 227 | 18.034 | 52.766 | 79.941 | 1.00 | 27.14 | A |
| ATOM | 1696 | CG1 | VAL | A | 227 | 17.822 | 53.145 | 78.475 | 1.00 | 28.54 | A |
| ATOM | 1697 | CG2 | VAL | A | 227 | 16.704 | 52.444 | 80.614 | 1.00 | 26.13 | A |
| ATOM | 1698 | C | VAL | A | 227 | 20.309 | 51.909 | 79.385 | 1.00 | 29.32 | A |
| ATOM | 1699 | O | VAL | A | 227 | 20.960 | 52.883 | 79.762 | 1.00 | 30.05 | A |
| ATOM | 1700 | N | PRO | A | 228 | 20.726 | 51.127 | 78.382 | 1.00 | 31.26 | A |
| ATOM | 1701 | CD | PRO | A | 228 | 19.997 | 50.035 | 77.714 | 1.00 | 31.51 | A |
| ATOM | 1702 | CA | PRO | A | 228 | 21.994 | 51.402 | 77.707 | 1.00 | 32.21 | A |
| ATOM | 1703 | CB | PRO | A | 228 | 22.097 | 50.258 | 76.698 | 1.00 | 33.57 | A |
| ATOM | 1704 | CG | PRO | A | 228 | 20.662 | 49.991 | 76.358 | 1.00 | 33.69 | A |
| ATOM | 1705 | C | PRO | A | 228 | 22.077 | 52.779 | 77.053 | 1.00 | 33.32 | A |
| ATOM | 1706 | O | PRO | A | 228 | 21.109 | 53.270 | 76.468 | 1.00 | 33.41 | A |
| ATOM | 1707 | N | GLU | A | 229 | 23.245 | 53.398 | 77.180 | 1.00 | 35.15 | A |
| ATOM | 1708 | CA | GLU | A | 229 | 23.510 | 54.708 | 76.600 | 1.00 | 35.98 | A |
| ATOM | 1709 | CB | GLU | A | 229 | 23.274 | 54.662 | 75.086 | 1.00 | 39.82 | A |
| ATOM | 1710 | CG | GLU | A | 229 | 24.112 | 55.656 | 74.289 | 1.00 | 44.78 | A |
| ATOM | 1711 | CD | GLU | A | 229 | 25.586 | 55.274 | 74.233 | 1.00 | 48.37 | A |
| ATOM | 1712 | OE1 | GLU | A | 229 | 26.221 | 55.162 | 75.307 | 1.00 | 50.63 | A |
| ATOM | 1713 | OE2 | GLU | A | 229 | 26.111 | 55.087 | 73.113 | 1.00 | 49.28 | A |
| ATOM | 1714 | C | GLU | A | 229 | 22.677 | 55.830 | 77.221 | 1.00 | 34.20 | A |
| ATOM | 1715 | O | GLU | A | 229 | 22.714 | 56.969 | 76.751 | 1.00 | 34.48 | A |
| ATOM | 1716 | N | VAL | A | 230 | 21.926 | 55.509 | 78.270 | 1.00 | 30.04 | A |
| ATOM | 1717 | CA | VAL | A | 230 | 21.109 | 56.508 | 78.956 | 1.00 | 27.19 | A |
| ATOM | 1718 | CB | VAL | A | 230 | 19.614 | 56.160 | 78.878 | 1.00 | 28.09 | A |
| ATOM | 1719 | CG1 | VAL | A | 230 | 18.810 | 57.139 | 79.712 | 1.00 | 26.44 | A |
| ATOM | 1720 | CG2 | VAL | A | 230 | 19.153 | 56.198 | 77.428 | 1.00 | 29.81 | A |
| ATOM | 1721 | C | VAL | A | 230 | 21.543 | 56.580 | 80.418 | 1.00 | 25.17 | A |
| ATOM | 1722 | O | VAL | A | 230 | 21.904 | 57.643 | 80.919 | 1.00 | 24.16 | A |
| ATOM | 1723 | N | GLU | A | 231 | 21.498 | 55.442 | 81.099 | 1.00 | 20.97 | A |
| ATOM | 1724 | CA | GLU | A | 231 | 21.929 | 55.371 | 82.491 | 1.00 | 22.09 | A |
| ATOM | 1725 | CB | GLU | A | 231 | 21.017 | 54.425 | 83.285 | 1.00 | 19.51 | A |
| ATOM | 1726 | CG | GLU | A | 231 | 19.598 | 54.962 | 83.442 | 1.00 | 20.55 | A |
| ATOM | 1727 | CD | GLU | A | 231 | 18.638 | 53.974 | 84.084 | 1.00 | 18.71 | A |
| ATOM | 1728 | OE1 | GLU | A | 231 | 18.623 | 52.804 | 83.655 | 1.00 | 19.07 | A |
| ATOM | 1729 | OE2 | GLU | A | 231 | 17.890 | 54.370 | 85.004 | 1.00 | 17.90 | A |
| ATOM | 1730 | C | GLU | A | 231 | 23.367 | 54.855 | 82.460 | 1.00 | 22.54 | A |
| ATOM | 1731 | O | GLU | A | 231 | 23.778 | 54.217 | 81.487 | 1.00 | 23.20 | A |
| ATOM | 1732 | N | LYS | A | 232 | 24.136 | 55.120 | 83.511 | 1.00 | 22.05 | A |
| ATOM | 1733 | CA | LYS | A | 232 | 25.525 | 54.684 | 83.522 | 1.00 | 22.17 | A |
| ATOM | 1734 | CB | LYS | A | 232 | 26.435 | 55.886 | 83.249 | 1.00 | 25.60 | A |
| ATOM | 1735 | CG | LYS | A | 232 | 26.106 | 56.608 | 81.942 | 1.00 | 30.76 | A |
| ATOM | 1736 | CD | LYS | A | 232 | 26.256 | 55.672 | 80.745 | 1.00 | 36.23 | A |
| ATOM | 1737 | CE | LYS | A | 232 | 25.664 | 56.271 | 79.471 | 1.00 | 38.29 | A |
| ATOM | 1738 | NZ | LYS | A | 232 | 26.334 | 57.539 | 79.069 | 1.00 | 37.95 | A |
| ATOM | 1739 | C | LYS | A | 232 | 25.956 | 53.989 | 84.807 | 1.00 | 21.43 | A |
| ATOM | 1740 | O | LYS | A | 232 | 26.191 | 54.635 | 85.831 | 1.00 | 18.89 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 1741 | N   | PRO | A | 233 | 26.076 | 52.653 | 84.762 | 1.00 | 20.17 | A |
| ATOM | 1742 | CD  | PRO | A | 233 | 25.704 | 51.783 | 83.629 | 1.00 | 19.69 | A |
| ATOM | 1743 | CA  | PRO | A | 233 | 26.485 | 51.853 | 85.920 | 1.00 | 18.06 | A |
| ATOM | 1744 | CB  | PRO | A | 233 | 26.556 | 50.441 | 85.348 | 1.00 | 17.95 | A |
| ATOM | 1745 | CG  | PRO | A | 233 | 25.475 | 50.451 | 84.307 | 1.00 | 19.68 | A |
| ATOM | 1746 | C   | PRO | A | 233 | 27.820 | 52.297 | 86.523 | 1.00 | 17.74 | A |
| ATOM | 1747 | O   | PRO | A | 233 | 28.701 | 52.797 | 85.814 | 1.00 | 17.95 | A |
| ATOM | 1748 | N   | ILE | A | 234 | 27.955 | 52.107 | 87.833 | 1.00 | 16.92 | A |
| ATOM | 1749 | CA  | ILE | A | 234 | 29.174 | 52.449 | 88.566 | 1.00 | 16.46 | A |
| ATOM | 1750 | CB  | ILE | A | 234 | 28.901 | 53.555 | 89.610 | 1.00 | 17.04 | A |
| ATOM | 1751 | CG2 | ILE | A | 234 | 30.204 | 53.975 | 90.274 | 1.00 | 17.44 | A |
| ATOM | 1752 | CG1 | ILE | A | 234 | 28.248 | 54.759 | 88.926 | 1.00 | 16.08 | A |
| ATOM | 1753 | CD1 | ILE | A | 234 | 27.885 | 55.908 | 89.868 | 1.00 | 15.92 | A |
| ATOM | 1754 | C   | ILE | A | 234 | 29.695 | 51.194 | 89.282 | 1.00 | 16.04 | A |
| ATOM | 1755 | O   | ILE | A | 234 | 30.876 | 50.859 | 89.191 | 1.00 | 15.88 | A |
| ATOM | 1756 | N   | PHE | A | 235 | 28.799 | 50.509 | 89.987 | 1.00 | 14.55 | A |
| ATOM | 1757 | CA  | PHE | A | 235 | 29.125 | 49.275 | 90.703 | 1.00 | 15.26 | A |
| ATOM | 1758 | CB  | PHE | A | 235 | 29.483 | 49.545 | 92.174 | 1.00 | 15.43 | A |
| ATOM | 1759 | CG  | PHE | A | 235 | 30.769 | 50.301 | 92.372 | 1.00 | 16.25 | A |
| ATOM | 1760 | CD1 | PHE | A | 235 | 31.996 | 49.687 | 92.154 | 1.00 | 15.90 | A |
| ATOM | 1761 | CD2 | PHE | A | 235 | 30.745 | 51.633 | 92.788 | 1.00 | 17.19 | A |
| ATOM | 1762 | CE1 | PHE | A | 235 | 33.194 | 50.386 | 92.346 | 1.00 | 17.25 | A |
| ATOM | 1763 | CE2 | PHE | A | 235 | 31.927 | 52.344 | 92.983 | 1.00 | 14.62 | A |
| ATOM | 1764 | CZ  | PHE | A | 235 | 33.157 | 51.723 | 92.762 | 1.00 | 15.37 | A |
| ATOM | 1765 | C   | PHE | A | 235 | 27.870 | 48.414 | 90.681 | 1.00 | 16.08 | A |
| ATOM | 1766 | O   | PHE | A | 235 | 26.763 | 48.938 | 90.602 | 1.00 | 15.87 | A |
| ATOM | 1767 | N   | GLU | A | 236 | 28.043 | 47.099 | 90.739 | 1.00 | 15.93 | A |
| ATOM | 1768 | CA  | GLU | A | 236 | 26.907 | 46.180 | 90.781 | 1.00 | 16.34 | A |
| ATOM | 1769 | CB  | GLU | A | 236 | 27.027 | 45.090 | 89.715 | 1.00 | 17.35 | A |
| ATOM | 1770 | CG  | GLU | A | 236 | 27.058 | 45.559 | 88.281 | 1.00 | 20.47 | A |
| ATOM | 1771 | CD  | GLU | A | 236 | 26.908 | 44.398 | 87.313 | 1.00 | 25.69 | A |
| ATOM | 1772 | OE1 | GLU | A | 236 | 27.460 | 43.312 | 87.600 | 1.00 | 24.01 | A |
| ATOM | 1773 | OE2 | GLU | A | 236 | 26.248 | 44.571 | 86.267 | 1.00 | 28.51 | A |
| ATOM | 1774 | C   | GLU | A | 236 | 26.949 | 45.504 | 92.149 | 1.00 | 16.24 | A |
| ATOM | 1775 | O   | GLU | A | 236 | 28.034 | 45.240 | 92.673 | 1.00 | 17.59 | A |
| ATOM | 1776 | N   | LEU | A | 237 | 25.781 | 45.226 | 92.721 | 1.00 | 16.37 | A |
| ATOM | 1777 | CA  | LEU | A | 237 | 25.695 | 44.558 | 94.013 | 1.00 | 17.59 | A |
| ATOM | 1778 | CB  | LEU | A | 237 | 24.447 | 45.034 | 94.764 | 1.00 | 18.64 | A |
| ATOM | 1779 | CG  | LEU | A | 237 | 24.363 | 46.549 | 95.008 | 1.00 | 18.69 | A |
| ATOM | 1780 | CD1 | LEU | A | 237 | 23.085 | 46.887 | 95.785 | 1.00 | 18.52 | A |
| ATOM | 1781 | CD2 | LEU | A | 237 | 25.589 | 47.006 | 95.779 | 1.00 | 19.96 | A |
| ATOM | 1782 | C   | LEU | A | 237 | 25.629 | 43.050 | 93.746 | 1.00 | 18.31 | A |
| ATOM | 1783 | O   | LEU | A | 237 | 24.752 | 42.586 | 93.025 | 1.00 | 18.78 | A |
| ATOM | 1784 | N   | VAL | A | 238 | 26.557 | 42.297 | 94.329 | 1.00 | 19.02 | A |
| ATOM | 1785 | CA  | VAL | A | 238 | 26.637 | 40.849 | 94.127 | 1.00 | 18.34 | A |
| ATOM | 1786 | CB  | VAL | A | 238 | 28.117 | 40.419 | 93.976 | 1.00 | 19.89 | A |
| ATOM | 1787 | CG1 | VAL | A | 238 | 28.216 | 38.929 | 93.689 | 1.00 | 20.10 | A |
| ATOM | 1788 | CG2 | VAL | A | 238 | 28.765 | 41.213 | 92.855 | 1.00 | 19.49 | A |
| ATOM | 1789 | C   | VAL | A | 238 | 25.982 | 40.027 | 95.243 | 1.00 | 18.89 | A |
| ATOM | 1790 | O   | VAL | A | 238 | 25.114 | 39.187 | 94.989 | 1.00 | 18.23 | A |
| ATOM | 1791 | N   | SER | A | 239 | 26.410 | 40.259 | 96.479 | 1.00 | 17.69 | A |
| ATOM | 1792 | CA  | SER | A | 239 | 25.853 | 39.544 | 97.621 | 1.00 | 18.25 | A |
| ATOM | 1793 | CB  | SER | A | 239 | 26.626 | 38.252 | 97.890 | 1.00 | 18.69 | A |
| ATOM | 1794 | OG  | SER | A | 239 | 27.964 | 38.546 | 98.228 | 1.00 | 19.05 | A |
| ATOM | 1795 | C   | SER | A | 239 | 25.935 | 40.437 | 98.844 | 1.00 | 18.67 | A |
| ATOM | 1796 | O   | SER | A | 239 | 26.749 | 41.352 | 98.892 | 1.00 | 18.20 | A |
| ATOM | 1797 | N   | THR | A | 240 | 25.079 | 40.167 | 99.823 | 1.00 | 20.47 | A |
| ATOM | 1798 | CA  | THR | A | 240 | 25.040 | 40.933 | 101.061 | 1.00 | 21.73 | A |
| ATOM | 1799 | CB  | THR | A | 240 | 23.894 | 41.977 | 101.038 | 1.00 | 22.77 | A |
| ATOM | 1800 | OG1 | THR | A | 240 | 22.642 | 41.316 | 100.814 | 1.00 | 23.88 | A |
| ATOM | 1801 | CG2 | THR | A | 240 | 24.115 | 42.997 | 99.928 | 1.00 | 23.12 | A |
| ATOM | 1802 | C   | THR | A | 240 | 24.819 | 39.988 | 102.241 | 1.00 | 22.20 | A |
| ATOM | 1803 | O   | THR | A | 240 | 23.843 | 39.236 | 102.264 | 1.00 | 23.37 | A |
| ATOM | 1804 | N   | ASP | A | 241 | 25.738 | 40.011 | 103.203 | 1.00 | 19.70 | A |
| ATOM | 1805 | CA  | ASP | A | 241 | 25.636 | 39.175 | 104.397 | 1.00 | 18.27 | A |
| ATOM | 1806 | CB  | ASP | A | 241 | 26.845 | 38.232 | 104.520 | 1.00 | 20.13 | A |
| ATOM | 1807 | CG  | ASP | A | 241 | 26.980 | 37.278 | 103.344 | 1.00 | 21.50 | A |
| ATOM | 1808 | OD1 | ASP | A | 241 | 25.994 | 36.577 | 103.024 | 1.00 | 21.04 | A |
| ATOM | 1809 | OD2 | ASP | A | 241 | 28.082 | 37.220 | 102.746 | 1.00 | 20.42 | A |
| ATOM | 1810 | C   | ASP | A | 241 | 25.622 | 40.096 | 105.616 | 1.00 | 18.38 | A |
| ATOM | 1811 | O   | ASP | A | 241 | 26.094 | 41.234 | 105.545 | 1.00 | 17.12 | A |
| ATOM | 1812 | N   | GLN | A | 242 | 25.063 | 39.613 | 106.722 | 1.00 | 14.47 | A |
| ATOM | 1813 | CA  | GLN | A | 242 | 25.039 | 40.379 | 107.961 | 1.00 | 17.92 | A |
| ATOM | 1814 | CB  | GLN | A | 242 | 23.684 | 41.068 | 108.189 | 1.00 | 16.66 | A |
| ATOM | 1815 | CG  | GLN | A | 242 | 23.701 | 42.010 | 109.410 | 1.00 | 18.83 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 1816 | CD | GLN | A | 242 | 22.334 | 42.557 | 109.787 | 1.00 | 17.48 | A |
| ATOM | 1817 | OE1 | GLN | A | 242 | 21.344 | 41.834 | 109.772 | 1.00 | 21.26 | A |
| ATOM | 1818 | NE2 | GLN | A | 242 | 22.281 | 43.837 | 110.162 | 1.00 | 17.14 | A |
| ATOM | 1819 | C | GLN | A | 242 | 25.309 | 39.389 | 109.083 | 1.00 | 17.83 | A |
| ATOM | 1820 | O | GLN | A | 242 | 24.858 | 38.244 | 109.023 | 1.00 | 19.34 | A |
| ATOM | 1821 | N | LYS | A | 243 | 26.047 | 39.817 | 110.099 | 1.00 | 18.25 | A |
| ATOM | 1822 | CA | LYS | A | 243 | 26.354 | 38.927 | 111.209 | 1.00 | 17.86 | A |
| ATOM | 1823 | CB | LYS | A | 243 | 27.610 | 38.114 | 110.910 | 1.00 | 18.91 | A |
| ATOM | 1824 | CG | LYS | A | 243 | 27.935 | 37.098 | 112.007 | 1.00 | 20.00 | A |
| ATOM | 1825 | CD | LYS | A | 243 | 29.136 | 36.244 | 111.667 | 1.00 | 22.37 | A |
| ATOM | 1826 | CE | LYS | A | 243 | 29.250 | 35.069 | 112.631 | 1.00 | 26.37 | A |
| ATOM | 1827 | NZ | LYS | A | 243 | 29.364 | 35.524 | 114.037 | 1.00 | 25.10 | A |
| ATOM | 1828 | C | LYS | A | 243 | 26.552 | 39.623 | 112.548 | 1.00 | 19.29 | A |
| ATOM | 1829 | O | LYS | A | 243 | 27.176 | 40.687 | 112.633 | 1.00 | 16.88 | A |
| ATOM | 1830 | N | LEU | A | 244 | 26.019 | 38.993 | 113.589 | 1.00 | 18.07 | A |
| ATOM | 1831 | CA | LEU | A | 244 | 26.151 | 39.481 | 114.950 | 1.00 | 18.71 | A |
| ATOM | 1832 | CB | LEU | A | 244 | 24.867 | 39.232 | 115.746 | 1.00 | 19.92 | A |
| ATOM | 1833 | CG | LEU | A | 244 | 23.763 | 40.289 | 115.745 | 1.00 | 21.98 | A |
| ATOM | 1834 | CD1 | LEU | A | 244 | 22.516 | 39.719 | 116.407 | 1.00 | 21.24 | A |
| ATOM | 1835 | CD2 | LEU | A | 244 | 24.248 | 41.533 | 116.491 | 1.00 | 22.15 | A |
| ATOM | 1836 | C | LEU | A | 244 | 27.272 | 38.675 | 115.582 | 1.00 | 18.89 | A |
| ATOM | 1837 | O | LEU | A | 244 | 27.307 | 37.453 | 115.456 | 1.00 | 18.50 | A |
| ATOM | 1838 | N | VAL | A | 245 | 28.200 | 39.354 | 116.241 | 1.00 | 19.19 | A |
| ATOM | 1839 | CA | VAL | A | 245 | 29.286 | 38.656 | 116.919 | 1.00 | 20.00 | A |
| ATOM | 1840 | CB | VAL | A | 245 | 30.556 | 39.522 | 116.976 | 1.00 | 21.57 | A |
| ATOM | 1841 | CG1 | VAL | A | 245 | 31.655 | 38.800 | 117.743 | 1.00 | 19.12 | A |
| ATOM | 1842 | CG2 | VAL | A | 245 | 31.017 | 39.838 | 115.553 | 1.00 | 22.63 | A |
| ATOM | 1843 | C | VAL | A | 245 | 28.783 | 38.368 | 118.332 | 1.00 | 19.85 | A |
| ATOM | 1844 | O | VAL | A | 245 | 28.518 | 39.288 | 119.114 | 1.00 | 17.71 | A |
| ATOM | 1845 | N | PRO | A | 246 | 28.623 | 37.081 | 118.672 | 1.00 | 19.89 | A |
| ATOM | 1846 | CD | PRO | A | 246 | 28.880 | 35.885 | 117.856 | 1.00 | 21.03 | A |
| ATOM | 1847 | CA | PRO | A | 246 | 28.142 | 36.706 | 120.006 | 1.00 | 21.13 | A |
| ATOM | 1848 | CB | PRO | A | 246 | 28.244 | 35.182 | 119.996 | 1.00 | 21.02 | A |
| ATOM | 1849 | CG | PRO | A | 246 | 28.038 | 34.840 | 118.561 | 1.00 | 21.01 | A |
| ATOM | 1850 | C | PRO | A | 246 | 28.978 | 37.320 | 121.117 | 1.00 | 19.52 | A |
| ATOM | 1851 | O | PRO | A | 246 | 30.173 | 37.545 | 120.950 | 1.00 | 20.14 | A |
| ATOM | 1852 | N | GLY | A | 247 | 28.329 | 37.593 | 122.243 | 1.00 | 21.22 | A |
| ATOM | 1853 | CA | GLY | A | 247 | 29.006 | 38.152 | 123.399 | 1.00 | 21.01 | A |
| ATOM | 1854 | C | GLY | A | 247 | 29.635 | 39.525 | 123.242 | 1.00 | 22.29 | A |
| ATOM | 1855 | O | GLY | A | 247 | 30.659 | 39.802 | 123.863 | 1.00 | 23.76 | A |
| ATOM | 1856 | N | SER | A | 248 | 29.034 | 40.396 | 122.439 | 1.00 | 20.11 | A |
| ATOM | 1857 | CA | SER | A | 248 | 29.607 | 41.724 | 122.257 | 1.00 | 19.92 | A |
| ATOM | 1858 | CB | SER | A | 248 | 30.412 | 41.774 | 120.952 | 1.00 | 19.95 | A |
| ATOM | 1859 | OG | SER | A | 248 | 29.602 | 41.489 | 119.822 | 1.00 | 20.22 | A |
| ATOM | 1860 | C | SER | A | 248 | 28.584 | 42.854 | 122.282 | 1.00 | 19.40 | A |
| ATOM | 1861 | O | SER | A | 248 | 28.761 | 43.870 | 121.613 | 1.00 | 18.71 | A |
| ATOM | 1862 | N | HIS | A | 249 | 27.524 | 42.692 | 123.068 | 1.00 | 19.08 | A |
| ATOM | 1863 | CA | HIS | A | 249 | 26.494 | 43.729 | 123.156 | 1.00 | 20.12 | A |
| ATOM | 1864 | CB | HIS | A | 249 | 25.364 | 43.277 | 124.088 | 1.00 | 21.72 | A |
| ATOM | 1865 | CG | HIS | A | 249 | 24.341 | 44.339 | 124.359 | 1.00 | 21.96 | A |
| ATOM | 1866 | CD2 | HIS | A | 249 | 24.221 | 45.219 | 125.382 | 1.00 | 23.31 | A |
| ATOM | 1867 | ND1 | HIS | A | 249 | 23.290 | 44.600 | 123.505 | 1.00 | 24.75 | A |
| ATOM | 1868 | CE1 | HIS | A | 249 | 22.566 | 45.593 | 123.991 | 1.00 | 20.55 | A |
| ATOM | 1869 | NE2 | HIS | A | 249 | 23.110 | 45.988 | 125.128 | 1.00 | 23.96 | A |
| ATOM | 1870 | C | HIS | A | 249 | 27.087 | 45.037 | 123.682 | 1.00 | 20.12 | A |
| ATOM | 1871 | O | HIS | A | 249 | 26.687 | 46.133 | 123.261 | 1.00 | 17.34 | A |
| ATOM | 1872 | N | GLY | A | 250 | 28.045 | 44.908 | 124.599 | 1.00 | 18.18 | A |
| ATOM | 1873 | CA | GLY | A | 250 | 28.679 | 46.074 | 125.196 | 1.00 | 21.10 | A |
| ATOM | 1874 | C | GLY | A | 250 | 29.815 | 46.741 | 124.427 | 1.00 | 21.47 | A |
| ATOM | 1875 | O | GLY | A | 250 | 30.439 | 47.677 | 124.938 | 1.00 | 21.77 | A |
| ATOM | 1876 | N | ALA | A | 251 | 30.087 | 46.286 | 123.206 | 1.00 | 19.97 | A |
| ATOM | 1877 | CA | ALA | A | 251 | 31.160 | 46.869 | 122.407 | 1.00 | 20.87 | A |
| ATOM | 1878 | CB | ALA | A | 251 | 31.528 | 45.932 | 121.257 | 1.00 | 21.00 | A |
| ATOM | 1879 | C | ALA | A | 251 | 30.785 | 48.252 | 121.858 | 1.00 | 21.86 | A |
| ATOM | 1880 | O | ALA | A | 251 | 31.551 | 49.209 | 121.990 | 1.00 | 20.74 | A |
| ATOM | 1881 | N | ILE | A | 252 | 29.611 | 48.350 | 121.242 | 1.00 | 20.93 | A |
| ATOM | 1882 | CA | ILE | A | 252 | 29.147 | 49.615 | 120.667 | 1.00 | 22.07 | A |
| ATOM | 1883 | CB | ILE | A | 252 | 29.434 | 49.698 | 119.155 | 1.00 | 24.82 | A |
| ATOM | 1884 | CG2 | ILE | A | 252 | 29.122 | 51.102 | 118.649 | 1.00 | 25.36 | A |
| ATOM | 1885 | CG1 | ILE | A | 252 | 30.889 | 49.343 | 118.861 | 1.00 | 26.65 | A |
| ATOM | 1886 | CD1 | ILE | A | 252 | 31.154 | 49.143 | 117.378 | 1.00 | 29.75 | A |
| ATOM | 1887 | C | ILE | A | 252 | 27.636 | 49.709 | 120.814 | 1.00 | 20.47 | A |
| ATOM | 1888 | O | ILE | A | 252 | 26.922 | 48.788 | 120.440 | 1.00 | 19.94 | A |
| ATOM | 1889 | N | GLY | A | 253 | 27.143 | 50.826 | 121.336 | 1.00 | 18.99 | A |
| ATOM | 1890 | CA | GLY | A | 253 | 25.709 | 50.958 | 121.488 | 1.00 | 18.83 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 1891 | C | GLY | A | 253 | 25.288 | 52.292 | 122.059 | 1.00 | 18.02 | A |
| ATOM | 1892 | O | GLY | A | 253 | 26.093 | 53.220 | 122.166 | 1.00 | 16.78 | A |
| ATOM | 1893 | N | GLY | A | 254 | 24.019 | 52.378 | 122.429 | 1.00 | 18.04 | A |
| ATOM | 1894 | CA | GLY | A | 254 | 23.503 | 53.610 | 122.981 | 1.00 | 19.32 | A |
| ATOM | 1895 | C | GLY | A | 254 | 22.028 | 53.515 | 123.295 | 1.00 | 19.30 | A |
| ATOM | 1896 | O | GLY | A | 254 | 21.379 | 52.497 | 123.029 | 1.00 | 18.05 | A |
| ATOM | 1897 | N | LEU | A | 255 | 21.510 | 54.587 | 123.885 | 1.00 | 18.15 | A |
| ATOM | 1898 | CA | LEU | A | 255 | 20.107 | 54.686 | 124.251 | 1.00 | 17.89 | A |
| ATOM | 1899 | CB | LEU | A | 255 | 19.909 | 54.384 | 125.734 | 1.00 | 19.68 | A |
| ATOM | 1900 | CG | LEU | A | 255 | 20.124 | 52.976 | 126.283 | 1.00 | 23.45 | A |
| ATOM | 1901 | CD1 | LEU | A | 255 | 19.989 | 53.011 | 127.798 | 1.00 | 23.78 | A |
| ATOM | 1902 | CD2 | LEU | A | 255 | 19.114 | 52.020 | 125.679 | 1.00 | 23.72 | A |
| ATOM | 1903 | C | LEU | A | 255 | 19.653 | 56.112 | 124.006 | 1.00 | 18.61 | A |
| ATOM | 1904 | O | LEU | A | 255 | 20.425 | 57.053 | 124.198 | 1.00 | 18.26 | A |
| ATOM | 1905 | N | LEU | A | 256 | 18.408 | 56.275 | 123.575 | 1.00 | 17.55 | A |
| ATOM | 1906 | CA | LEU | A | 256 | 17.871 | 57.608 | 123.367 | 1.00 | 17.89 | A |
| ATOM | 1907 | CB | LEU | A | 256 | 16.779 | 57.596 | 122.291 | 1.00 | 17.89 | A |
| ATOM | 1908 | CG | LEU | A | 256 | 16.201 | 58.956 | 121.868 | 1.00 | 19.06 | A |
| ATOM | 1909 | CD1 | LEU | A | 256 | 17.325 | 59.921 | 121.508 | 1.00 | 19.37 | A |
| ATOM | 1910 | CD2 | LEU | A | 256 | 15.260 | 58.763 | 120.680 | 1.00 | 17.30 | A |
| ATOM | 1911 | C | LEU | A | 256 | 17.297 | 57.972 | 124.733 | 1.00 | 17.61 | A |
| ATOM | 1912 | O | LEU | A | 256 | 16.453 | 57.262 | 125.276 | 1.00 | 17.82 | A |
| ATOM | 1913 | N | ARG | A | 257 | 17.765 | 59.076 | 125.296 | 1.00 | 17.36 | A |
| ATOM | 1914 | CA | ARG | A | 257 | 17.319 | 59.491 | 126.617 | 1.00 | 16.80 | A |
| ATOM | 1915 | CB | ARG | A | 257 | 18.474 | 59.343 | 127.609 | 1.00 | 17.15 | A |
| ATOM | 1916 | CG | ARG | A | 257 | 19.105 | 57.958 | 127.670 | 1.00 | 18.55 | A |
| ATOM | 1917 | CD | ARG | A | 257 | 18.355 | 57.031 | 128.616 | 1.00 | 17.31 | A |
| ATOM | 1918 | NE | ARG | A | 257 | 17.311 | 56.261 | 127.945 | 1.00 | 17.17 | A |
| ATOM | 1919 | CZ | ARG | A | 257 | 16.626 | 55.279 | 128.525 | 1.00 | 16.27 | A |
| ATOM | 1920 | NH1 | ARG | A | 257 | 16.871 | 54.952 | 129.790 | 1.00 | 13.61 | A |
| ATOM | 1921 | NH2 | ARG | A | 257 | 15.722 | 54.600 | 127.833 | 1.00 | 16.69 | A |
| ATOM | 1922 | C | ARG | A | 257 | 16.852 | 60.940 | 126.624 | 1.00 | 17.15 | A |
| ATOM | 1923 | O | ARG | A | 257 | 16.933 | 61.637 | 125.612 | 1.00 | 16.73 | A |
| ATOM | 1924 | N | GLU | A | 258 | 16.381 | 61.390 | 127.782 | 1.00 | 17.18 | A |
| ATOM | 1925 | CA | GLU | A | 258 | 15.913 | 62.757 | 127.926 | 1.00 | 17.36 | A |
| ATOM | 1926 | CB | GLU | A | 258 | 15.210 | 62.911 | 129.283 | 1.00 | 20.05 | A |
| ATOM | 1927 | CG | GLU | A | 258 | 14.011 | 61.956 | 129.408 | 1.00 | 22.85 | A |
| ATOM | 1928 | CD | GLU | A | 258 | 13.427 | 61.842 | 130.811 | 1.00 | 25.37 | A |
| ATOM | 1929 | OE1 | GLU | A | 258 | 12.878 | 60.761 | 131.128 | 1.00 | 19.60 | A |
| ATOM | 1930 | OE2 | GLU | A | 258 | 13.497 | 62.819 | 131.590 | 1.00 | 24.69 | A |
| ATOM | 1931 | C | GLU | A | 258 | 17.074 | 63.743 | 127.755 | 1.00 | 16.92 | A |
| ATOM | 1932 | O | GLU | A | 258 | 16.857 | 64.935 | 127.509 | 1.00 | 17.03 | A |
| ATOM | 1933 | N | VAL | A | 259 | 18.304 | 63.238 | 127.858 | 1.00 | 16.14 | A |
| ATOM | 1934 | CA | VAL | A | 259 | 19.492 | 64.066 | 127.679 | 1.00 | 16.37 | A |
| ATOM | 1935 | CB | VAL | A | 259 | 20.598 | 63.720 | 128.707 | 1.00 | 16.27 | A |
| ATOM | 1936 | CG1 | VAL | A | 259 | 20.035 | 63.814 | 130.117 | 1.00 | 18.16 | A |
| ATOM | 1937 | CG2 | VAL | A | 259 | 21.158 | 62.319 | 128.428 | 1.00 | 18.20 | A |
| ATOM | 1938 | C | VAL | A | 259 | 20.072 | 63.891 | 126.276 | 1.00 | 15.70 | A |
| ATOM | 1939 | O | VAL | A | 259 | 21.175 | 64.360 | 125.984 | 1.00 | 13.21 | A |
| ATOM | 1940 | N | GLY | A | 260 | 19.323 | 63.210 | 125.411 | 1.00 | 17.11 | A |
| ATOM | 1941 | CA | GLY | A | 260 | 19.779 | 62.983 | 124.052 | 1.00 | 16.11 | A |
| ATOM | 1942 | C | GLY | A | 260 | 20.218 | 61.545 | 123.847 | 1.00 | 16.55 | A |
| ATOM | 1943 | O | GLY | A | 260 | 19.886 | 60.674 | 124.644 | 1.00 | 17.86 | A |
| ATOM | 1944 | N | LEU | A | 261 | 20.968 | 61.294 | 122.781 | 1.00 | 15.96 | A |
| ATOM | 1945 | CA | LEU | A | 261 | 21.442 | 59.946 | 122.485 | 1.00 | 18.55 | A |
| ATOM | 1946 | CB | LEU | A | 261 | 21.558 | 59.750 | 120.967 | 1.00 | 20.11 | A |
| ATOM | 1947 | CG | LEU | A | 261 | 22.175 | 58.437 | 120.472 | 1.00 | 20.59 | A |
| ATOM | 1948 | CD1 | LEU | A | 261 | 21.420 | 57.265 | 121.058 | 1.00 | 21.27 | A |
| ATOM | 1949 | CD2 | LEU | A | 261 | 22.126 | 58.391 | 118.943 | 1.00 | 21.87 | A |
| ATOM | 1950 | C | LEU | A | 261 | 22.794 | 59.680 | 123.143 | 1.00 | 19.66 | A |
| ATOM | 1951 | O | LEU | A | 261 | 23.817 | 60.224 | 122.730 | 1.00 | 21.17 | A |
| ATOM | 1952 | N | THR | A | 262 | 22.788 | 58.852 | 124.176 | 1.00 | 19.32 | A |
| ATOM | 1953 | CA | THR | A | 262 | 24.016 | 58.513 | 124.875 | 1.00 | 22.73 | A |
| ATOM | 1954 | CB | THR | A | 262 | 23.734 | 58.130 | 126.332 | 1.00 | 22.38 | A |
| ATOM | 1955 | OG1 | THR | A | 262 | 22.958 | 56.927 | 126.367 | 1.00 | 22.08 | A |
| ATOM | 1956 | CG2 | THR | A | 262 | 22.953 | 59.239 | 127.022 | 1.00 | 22.93 | A |
| ATOM | 1957 | C | THR | A | 262 | 24.604 | 57.320 | 124.143 | 1.00 | 23.97 | A |
| ATOM | 1958 | O | THR | A | 262 | 23.877 | 56.588 | 123.464 | 1.00 | 24.96 | A |
| ATOM | 1959 | N | PHE | A | 263 | 25.912 | 57.122 | 124.260 | 1.00 | 22.66 | A |
| ATOM | 1960 | CA | PHE | A | 263 | 26.541 | 56.001 | 123.580 | 1.00 | 23.58 | A |
| ATOM | 1961 | CB | PHE | A | 263 | 26.870 | 56.396 | 122.144 | 1.00 | 23.86 | A |
| ATOM | 1962 | CG | PHE | A | 263 | 27.863 | 57.515 | 122.044 | 1.00 | 24.17 | A |
| ATOM | 1963 | CD1 | PHE | A | 263 | 29.226 | 57.249 | 121.994 | 1.00 | 22.87 | A |
| ATOM | 1964 | CD2 | PHE | A | 263 | 27.432 | 58.840 | 122.026 | 1.00 | 25.32 | A |
| ATOM | 1965 | CE1 | PHE | A | 263 | 30.153 | 58.290 | 121.928 | 1.00 | 26.00 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 1966 | CE2 | PHE | A | 263 | 28.348 | 59.888 | 121.961 | 1.00 | 26.02 | A |
| ATOM | 1967 | CZ | PHE | A | 263 | 29.712 | 59.613 | 121.912 | 1.00 | 25.32 | A |
| ATOM | 1968 | C | PHE | A | 263 | 27.801 | 55.525 | 124.281 | 1.00 | 22.97 | A |
| ATOM | 1969 | O | PHE | A | 263 | 28.412 | 56.253 | 125.067 | 1.00 | 21.66 | A |
| ATOM | 1970 | N | TYR | A | 264 | 28.173 | 54.283 | 123.995 | 1.00 | 22.70 | A |
| ATOM | 1971 | CA | TYR | A | 264 | 29.362 | 53.678 | 124.565 | 1.00 | 21.47 | A |
| ATOM | 1972 | CB | TYR | A | 264 | 28.998 | 52.613 | 125.611 | 1.00 | 21.41 | A |
| ATOM | 1973 | CG | TYR | A | 264 | 28.038 | 51.534 | 125.150 | 1.00 | 21.74 | A |
| ATOM | 1974 | CD1 | TYR | A | 264 | 26.662 | 51.666 | 125.346 | 1.00 | 23.63 | A |
| ATOM | 1975 | CE1 | TYR | A | 264 | 25.775 | 50.647 | 124.971 | 1.00 | 23.76 | A |
| ATOM | 1976 | CD2 | TYR | A | 264 | 28.509 | 50.358 | 124.557 | 1.00 | 23.02 | A |
| ATOM | 1977 | CE2 | TYR | A | 264 | 27.633 | 49.337 | 124.178 | 1.00 | 23.26 | A |
| ATOM | 1978 | CZ | TYR | A | 264 | 26.267 | 49.488 | 124.391 | 1.00 | 23.52 | A |
| ATOM | 1979 | OH | TYR | A | 264 | 25.394 | 48.478 | 124.041 | 1.00 | 21.37 | A |
| ATOM | 1980 | C | TYR | A | 264 | 30.186 | 53.060 | 123.447 | 1.00 | 22.11 | A |
| ATOM | 1981 | O | TYR | A | 264 | 29.648 | 52.648 | 122.418 | 1.00 | 22.24 | A |
| ATOM | 1982 | N | LEU | A | 265 | 31.495 | 53.014 | 123.652 | 1.00 | 23.91 | A |
| ATOM | 1983 | CA | LEU | A | 265 | 32.421 | 52.474 | 122.667 | 1.00 | 26.53 | A |
| ATOM | 1984 | CB | LEU | A | 265 | 32.998 | 53.610 | 121.815 | 1.00 | 28.16 | A |
| ATOM | 1985 | CG | LEU | A | 265 | 32.020 | 54.644 | 121.236 | 1.00 | 32.15 | A |
| ATOM | 1986 | CD1 | LEU | A | 265 | 32.800 | 55.799 | 120.631 | 1.00 | 33.28 | A |
| ATOM | 1987 | CD2 | LEU | A | 265 | 31.120 | 54.003 | 120.189 | 1.00 | 34.40 | A |
| ATOM | 1988 | C | LEU | A | 265 | 33.544 | 51.788 | 123.432 | 1.00 | 26.95 | A |
| ATOM | 1989 | O | LEU | A | 265 | 34.476 | 52.442 | 123.901 | 1.00 | 28.53 | A |
| ATOM | 1990 | N | ASN | A | 266 | 33.455 | 50.470 | 123.566 | 1.00 | 26.30 | A |
| ATOM | 1991 | CA | ASN | A | 266 | 34.473 | 49.731 | 124.292 | 1.00 | 25.13 | A |
| ATOM | 1992 | CB | ASN | A | 266 | 34.018 | 48.296 | 124.530 | 1.00 | 27.85 | A |
| ATOM | 1993 | CG | ASN | A | 266 | 34.746 | 47.651 | 125.683 | 1.00 | 30.74 | A |
| ATOM | 1994 | OD1 | ASN | A | 266 | 34.492 | 47.971 | 126.845 | 1.00 | 33.50 | A |
| ATOM | 1995 | ND2 | ASN | A | 266 | 35.669 | 46.750 | 125.374 | 1.00 | 31.85 | A |
| ATOM | 1996 | C | ASN | A | 266 | 35.826 | 49.712 | 123.580 | 1.00 | 23.31 | A |
| ATOM | 1997 | O | ASN | A | 266 | 35.900 | 49.755 | 122.354 | 1.00 | 20.14 | A |
| ATOM | 1998 | N | LYS | A | 267 | 36.896 | 49.633 | 124.366 | 1.00 | 22.48 | A |
| ATOM | 1999 | CA | LYS | A | 267 | 38.254 | 49.593 | 123.832 | 1.00 | 23.80 | A |
| ATOM | 2000 | CB | LYS | A | 267 | 39.261 | 49.664 | 124.988 | 1.00 | 27.81 | A |
| ATOM | 2001 | CG | LYS | A | 267 | 39.011 | 50.813 | 125.958 | 1.00 | 32.09 | A |
| ATOM | 2002 | CD | LYS | A | 267 | 39.933 | 50.764 | 127.182 | 1.00 | 35.92 | A |
| ATOM | 2003 | CE | LYS | A | 267 | 39.613 | 49.595 | 128.127 | 1.00 | 39.38 | A |
| ATOM | 2004 | NZ | LYS | A | 267 | 40.014 | 48.253 | 127.603 | 1.00 | 40.18 | A |
| ATOM | 2005 | C | LYS | A | 267 | 38.505 | 48.311 | 123.027 | 1.00 | 22.43 | A |
| ATOM | 2006 | O | LYS | A | 267 | 39.444 | 48.232 | 122.234 | 1.00 | 20.97 | A |
| ATOM | 2007 | N | SER | A | 268 | 37.658 | 47.310 | 123.228 | 1.00 | 21.81 | A |
| ATOM | 2008 | CA | SER | A | 268 | 37.817 | 46.029 | 122.545 | 1.00 | 22.21 | A |
| ATOM | 2009 | CB | SER | A | 268 | 37.109 | 44.940 | 123.342 | 1.00 | 24.17 | A |
| ATOM | 2010 | OG | SER | A | 268 | 35.709 | 45.155 | 123.318 | 1.00 | 27.22 | A |
| ATOM | 2011 | C | SER | A | 268 | 37.299 | 45.985 | 121.107 | 1.00 | 21.22 | A |
| ATOM | 2012 | O | SER | A | 268 | 37.464 | 44.974 | 120.421 | 1.00 | 20.98 | A |
| ATOM | 2013 | N | VAL | A | 269 | 36.681 | 47.067 | 120.647 | 1.00 | 19.08 | A |
| ATOM | 2014 | CA | VAL | A | 269 | 36.122 | 47.085 | 119.301 | 1.00 | 19.55 | A |
| ATOM | 2015 | CB | VAL | A | 269 | 35.463 | 48.454 | 118.996 | 1.00 | 18.98 | A |
| ATOM | 2016 | CG1 | VAL | A | 269 | 35.028 | 48.515 | 117.536 | 1.00 | 19.74 | A |
| ATOM | 2017 | CG2 | VAL | A | 269 | 34.260 | 48.652 | 119.902 | 1.00 | 18.22 | A |
| ATOM | 2018 | C | VAL | A | 269 | 37.090 | 46.698 | 118.180 | 1.00 | 19.21 | A |
| ATOM | 2019 | O | VAL | A | 269 | 36.813 | 45.774 | 117.420 | 1.00 | 21.42 | A |
| ATOM | 2020 | N | PRO | A | 270 | 38.235 | 47.391 | 118.057 | 1.00 | 19.54 | A |
| ATOM | 2021 | CD | PRO | A | 270 | 38.711 | 48.550 | 118.833 | 1.00 | 19.24 | A |
| ATOM | 2022 | CA | PRO | A | 270 | 39.186 | 47.047 | 116.995 | 1.00 | 18.50 | A |
| ATOM | 2023 | CB | PRO | A | 270 | 40.388 | 47.929 | 117.321 | 1.00 | 19.89 | A |
| ATOM | 2024 | CG | PRO | A | 270 | 39.743 | 49.149 | 117.915 | 1.00 | 19.70 | A |
| ATOM | 2025 | C | PRO | A | 270 | 39.538 | 45.557 | 116.994 | 1.00 | 19.27 | A |
| ATOM | 2026 | O | PRO | A | 270 | 39.626 | 44.917 | 115.938 | 1.00 | 16.45 | A |
| ATOM | 2027 | N | ASP | A | 271 | 39.734 | 45.007 | 118.187 | 1.00 | 17.58 | A |
| ATOM | 2028 | CA | ASP | A | 271 | 40.071 | 43.600 | 118.332 | 1.00 | 19.43 | A |
| ATOM | 2029 | CB | ASP | A | 271 | 40.500 | 43.321 | 119.785 | 1.00 | 23.68 | A |
| ATOM | 2030 | CG | ASP | A | 271 | 39.756 | 42.157 | 120.413 | 1.00 | 30.76 | A |
| ATOM | 2031 | OD1 | ASP | A | 271 | 38.543 | 42.298 | 120.707 | 1.00 | 36.55 | A |
| ATOM | 2032 | OD2 | ASP | A | 271 | 40.383 | 41.092 | 120.617 | 1.00 | 35.24 | A |
| ATOM | 2033 | C | ASP | A | 271 | 38.924 | 42.670 | 117.919 | 1.00 | 18.78 | A |
| ATOM | 2034 | O | ASP | A | 271 | 39.154 | 41.637 | 117.279 | 1.00 | 18.87 | A |
| ATOM | 2035 | N | ILE | A | 272 | 37.694 | 43.035 | 118.274 | 1.00 | 16.19 | A |
| ATOM | 2036 | CA | ILE | A | 272 | 36.541 | 42.209 | 117.935 | 1.00 | 16.45 | A |
| ATOM | 2037 | CB | ILE | A | 272 | 35.247 | 42.753 | 118.587 | 1.00 | 17.46 | A |
| ATOM | 2038 | CG2 | ILE | A | 272 | 34.056 | 41.880 | 118.200 | 1.00 | 20.28 | A |
| ATOM | 2039 | CG1 | ILE | A | 272 | 35.403 | 42.775 | 120.110 | 1.00 | 19.02 | A |
| ATOM | 2040 | CD1 | ILE | A | 272 | 34.200 | 43.307 | 120.849 | 1.00 | 20.37 | A |

APPENDIX B-continued

*Arachis hypogaea* STS

| ATOM | # | TYPE | RES | | | X | Y | Z | OCC | B | |
|------|---|------|-----|---|-----|--------|--------|---------|------|-------|---|
| ATOM | 2041 | C | ILE | A | 272 | 36.363 | 42.142 | 116.426 | 1.00 | 17.03 | A |
| ATOM | 2042 | O | ILE | A | 272 | 36.192 | 41.060 | 115.856 | 1.00 | 15.04 | A |
| ATOM | 2043 | N | ILE | A | 273 | 36.412 | 43.301 | 115.777 | 1.00 | 17.12 | A |
| ATOM | 2044 | CA | ILE | A | 273 | 36.264 | 43.369 | 114.328 | 1.00 | 17.75 | A |
| ATOM | 2045 | CB | ILE | A | 273 | 36.243 | 44.836 | 113.845 | 1.00 | 19.23 | A |
| ATOM | 2046 | CG2 | ILE | A | 273 | 36.289 | 44.892 | 112.329 | 1.00 | 18.88 | A |
| ATOM | 2047 | CG1 | ILE | A | 273 | 34.986 | 45.532 | 114.361 | 1.00 | 19.64 | A |
| ATOM | 2048 | CD1 | ILE | A | 273 | 34.965 | 47.032 | 114.095 | 1.00 | 19.97 | A |
| ATOM | 2049 | C | ILE | A | 273 | 37.389 | 42.636 | 113.597 | 1.00 | 19.28 | A |
| ATOM | 2050 | O | ILE | A | 273 | 37.137 | 41.844 | 112.684 | 1.00 | 18.02 | A |
| ATOM | 2051 | N | SER | A | 274 | 38.631 | 42.888 | 113.996 | 1.00 | 19.59 | A |
| ATOM | 2052 | CA | SER | A | 274 | 39.759 | 42.246 | 113.328 | 1.00 | 21.11 | A |
| ATOM | 2053 | CB | SER | A | 274 | 41.087 | 42.873 | 113.790 | 1.00 | 23.23 | A |
| ATOM | 2054 | OG | SER | A | 274 | 41.285 | 42.719 | 115.183 | 1.00 | 22.56 | A |
| ATOM | 2055 | C | SER | A | 274 | 39.783 | 40.732 | 113.530 | 1.00 | 21.08 | A |
| ATOM | 2056 | O | SER | A | 274 | 40.322 | 39.999 | 112.702 | 1.00 | 21.78 | A |
| ATOM | 2057 | N | GLN | A | 275 | 39.186 | 40.261 | 114.617 | 1.00 | 21.60 | A |
| ATOM | 2058 | CA | GLN | A | 275 | 39.147 | 38.824 | 114.896 | 1.00 | 22.43 | A |
| ATOM | 2059 | CB | GLN | A | 275 | 39.056 | 38.583 | 116.406 | 1.00 | 24.09 | A |
| ATOM | 2060 | CG | GLN | A | 275 | 40.334 | 38.941 | 117.162 | 1.00 | 28.75 | A |
| ATOM | 2061 | CD | GLN | A | 275 | 40.235 | 38.671 | 118.658 | 1.00 | 33.27 | A |
| ATOM | 2062 | OE1 | GLN | A | 275 | 41.170 | 38.958 | 119.411 | 1.00 | 37.52 | A |
| ATOM | 2063 | NE2 | GLN | A | 275 | 39.105 | 38.118 | 119.096 | 1.00 | 31.46 | A |
| ATOM | 2064 | C | GLN | A | 275 | 37.986 | 38.104 | 114.196 | 1.00 | 21.53 | A |
| ATOM | 2065 | O | GLN | A | 275 | 37.927 | 36.872 | 114.178 | 1.00 | 21.17 | A |
| ATOM | 2066 | N | ASN | A | 276 | 37.068 | 38.870 | 113.620 | 1.00 | 19.32 | A |
| ATOM | 2067 | CA | ASN | A | 276 | 35.915 | 38.279 | 112.943 | 1.00 | 19.41 | A |
| ATOM | 2068 | CB | ASN | A | 276 | 34.631 | 38.724 | 113.641 | 1.00 | 20.01 | A |
| ATOM | 2069 | CG | ASN | A | 276 | 34.423 | 38.029 | 114.965 | 1.00 | 20.81 | A |
| ATOM | 2070 | OD1 | ASN | A | 276 | 33.911 | 36.911 | 115.013 | 1.00 | 21.49 | A |
| ATOM | 2071 | ND2 | ASN | A | 276 | 34.839 | 38.677 | 116.051 | 1.00 | 20.50 | A |
| ATOM | 2072 | C | ASN | A | 276 | 35.828 | 38.635 | 111.468 | 1.00 | 19.52 | A |
| ATOM | 2073 | O | ASN | A | 276 | 34.927 | 38.170 | 110.763 | 1.00 | 19.26 | A |
| ATOM | 2074 | N | ILE | A | 277 | 36.763 | 39.457 | 111.002 | 1.00 | 17.49 | A |
| ATOM | 2075 | CA | ILE | A | 277 | 36.756 | 39.895 | 109.613 | 1.00 | 19.10 | A |
| ATOM | 2076 | CB | ILE | A | 277 | 37.721 | 41.093 | 109.429 | 1.00 | 20.08 | A |
| ATOM | 2077 | CG2 | ILE | A | 277 | 39.162 | 40.614 | 109.402 | 1.00 | 21.44 | A |
| ATOM | 2078 | CG1 | ILE | A | 277 | 37.369 | 41.855 | 108.147 | 1.00 | 20.38 | A |
| ATOM | 2079 | CD1 | ILE | A | 277 | 36.025 | 42.526 | 108.204 | 1.00 | 20.97 | A |
| ATOM | 2080 | C | ILE | A | 277 | 37.099 | 38.775 | 108.619 | 1.00 | 19.93 | A |
| ATOM | 2081 | O | ILE | A | 277 | 36.548 | 38.713 | 107.520 | 1.00 | 18.82 | A |
| ATOM | 2082 | N | ASN | A | 278 | 38.005 | 37.884 | 109.002 | 1.00 | 19.09 | A |
| ATOM | 2083 | CA | ASN | A | 278 | 38.374 | 36.795 | 108.116 | 1.00 | 21.07 | A |
| ATOM | 2084 | CB | ASN | A | 278 | 39.536 | 35.994 | 108.715 | 1.00 | 21.91 | A |
| ATOM | 2085 | CG | ASN | A | 278 | 40.884 | 36.662 | 108.491 | 1.00 | 25.15 | A |
| ATOM | 2086 | OD1 | ASN | A | 278 | 41.864 | 36.352 | 109.172 | 1.00 | 29.31 | A |
| ATOM | 2087 | ND2 | ASN | A | 278 | 40.945 | 37.569 | 107.525 | 1.00 | 24.39 | A |
| ATOM | 2088 | C | ASN | A | 278 | 37.183 | 35.883 | 107.832 | 1.00 | 18.75 | A |
| ATOM | 2089 | O | ASN | A | 278 | 36.996 | 35.446 | 106.696 | 1.00 | 20.29 | A |
| ATOM | 2090 | N | ASP | A | 279 | 36.374 | 35.600 | 108.848 | 1.00 | 18.61 | A |
| ATOM | 2091 | CA | ASP | A | 279 | 35.198 | 34.749 | 108.652 | 1.00 | 18.90 | A |
| ATOM | 2092 | CB | ASP | A | 279 | 34.489 | 34.482 | 109.987 | 1.00 | 22.33 | A |
| ATOM | 2093 | CG | ASP | A | 279 | 35.247 | 33.495 | 110.874 | 1.00 | 25.45 | A |
| ATOM | 2094 | OD1 | ASP | A | 279 | 34.914 | 33.395 | 112.074 | 1.00 | 25.88 | A |
| ATOM | 2095 | OD2 | ASP | A | 279 | 36.166 | 32.809 | 110.369 | 1.00 | 26.85 | A |
| ATOM | 2096 | C | ASP | A | 279 | 34.233 | 35.426 | 107.676 | 1.00 | 20.29 | A |
| ATOM | 2097 | O | ASP | A | 279 | 33.655 | 34.770 | 106.808 | 1.00 | 16.75 | A |
| ATOM | 2098 | N | ALA | A | 280 | 34.066 | 36.742 | 107.813 | 1.00 | 17.50 | A |
| ATOM | 2099 | CA | ALA | A | 280 | 33.175 | 37.487 | 106.922 | 1.00 | 17.54 | A |
| ATOM | 2100 | CB | ALA | A | 280 | 33.037 | 38.933 | 107.405 | 1.00 | 16.55 | A |
| ATOM | 2101 | C | ALA | A | 280 | 33.674 | 37.468 | 105.475 | 1.00 | 15.17 | A |
| ATOM | 2102 | O | ALA | A | 280 | 32.896 | 37.246 | 104.545 | 1.00 | 16.87 | A |
| ATOM | 2103 | N | LEU | A | 281 | 34.969 | 37.707 | 105.288 | 1.00 | 14.58 | A |
| ATOM | 2104 | CA | LEU | A | 281 | 35.569 | 37.715 | 103.953 | 1.00 | 14.95 | A |
| ATOM | 2105 | CB | LEU | A | 281 | 37.049 | 38.099 | 104.033 | 1.00 | 14.87 | A |
| ATOM | 2106 | CG | LEU | A | 281 | 37.369 | 39.579 | 104.261 | 1.00 | 13.37 | A |
| ATOM | 2107 | CD1 | LEU | A | 281 | 38.829 | 39.744 | 104.677 | 1.00 | 15.16 | A |
| ATOM | 2108 | CD2 | LEU | A | 281 | 37.082 | 40.346 | 102.981 | 1.00 | 14.81 | A |
| ATOM | 2109 | C | LEU | A | 281 | 35.445 | 36.349 | 103.286 | 1.00 | 16.22 | A |
| ATOM | 2110 | O | LEU | A | 281 | 35.119 | 36.254 | 102.104 | 1.00 | 16.95 | A |
| ATOM | 2111 | N | ASN | A | 282 | 35.712 | 35.301 | 104.060 | 1.00 | 17.34 | A |
| ATOM | 2112 | CA | ASN | A | 282 | 35.641 | 33.924 | 103.582 | 1.00 | 18.01 | A |
| ATOM | 2113 | CB | ASN | A | 282 | 36.099 | 32.970 | 104.687 | 1.00 | 20.09 | A |
| ATOM | 2114 | CG | ASN | A | 282 | 37.607 | 32.909 | 104.825 | 1.00 | 22.43 | A |
| ATOM | 2115 | OD1 | ASN | A | 282 | 38.128 | 32.318 | 105.772 | 1.00 | 23.93 | A |

APPENDIX B-continued

*Arachis hypogaea* STS

| ATOM | # | TYPE | RES | | | X | Y | Z | OCC | B | |
|------|---|------|-----|---|---|---|---|---|-----|---|---|
| ATOM | 2116 | ND2 | ASN | A | 282 | 38.316 | 33.506 | 103.877 | 1.00 | 22.40 | A |
| ATOM | 2117 | C | ASN | A | 282 | 34.233 | 33.533 | 103.140 | 1.00 | 18.34 | A |
| ATOM | 2118 | O | ASN | A | 282 | 34.041 | 32.933 | 102.078 | 1.00 | 17.60 | A |
| ATOM | 2119 | N | LYS | A | 283 | 33.247 | 33.861 | 103.965 | 1.00 | 17.04 | A |
| ATOM | 2120 | CA | LYS | A | 283 | 31.865 | 33.538 | 103.641 | 1.00 | 17.42 | A |
| ATOM | 2121 | CB | LYS | A | 283 | 30.956 | 33.927 | 104.809 | 1.00 | 17.63 | A |
| ATOM | 2122 | CG | LYS | A | 283 | 29.481 | 33.667 | 104.564 | 1.00 | 20.90 | A |
| ATOM | 2123 | CD | LYS | A | 283 | 28.671 | 33.796 | 105.848 | 1.00 | 22.60 | A |
| ATOM | 2124 | CE | LYS | A | 283 | 27.207 | 33.456 | 105.613 | 1.00 | 23.23 | A |
| ATOM | 2125 | NZ | LYS | A | 283 | 26.396 | 33.654 | 106.842 | 1.00 | 21.50 | A |
| ATOM | 2126 | C | LYS | A | 283 | 31.402 | 34.240 | 102.361 | 1.00 | 16.87 | A |
| ATOM | 2127 | O | LYS | A | 283 | 30.646 | 33.681 | 101.572 | 1.00 | 14.25 | A |
| ATOM | 2128 | N | ALA | A | 284 | 31.874 | 35.464 | 102.148 | 1.00 | 16.88 | A |
| ATOM | 2129 | CA | ALA | A | 284 | 31.476 | 36.232 | 100.974 | 1.00 | 17.52 | A |
| ATOM | 2130 | CB | ALA | A | 284 | 31.625 | 37.733 | 101.263 | 1.00 | 17.75 | A |
| ATOM | 2131 | C | ALA | A | 284 | 32.224 | 35.879 | 99.691 | 1.00 | 18.24 | A |
| ATOM | 2132 | O | ALA | A | 284 | 31.629 | 35.844 | 98.607 | 1.00 | 16.71 | A |
| ATOM | 2133 | N | PHE | A | 285 | 33.520 | 35.606 | 99.811 | 1.00 | 17.45 | A |
| ATOM | 2134 | CA | PHE | A | 285 | 34.338 | 35.314 | 98.644 | 1.00 | 18.98 | A |
| ATOM | 2135 | CB | PHE | A | 285 | 35.633 | 36.116 | 98.738 | 1.00 | 18.50 | A |
| ATOM | 2136 | CG | PHE | A | 285 | 35.433 | 37.578 | 98.496 | 1.00 | 16.04 | A |
| ATOM | 2137 | CD1 | PHE | A | 285 | 35.225 | 38.054 | 97.206 | 1.00 | 17.03 | A |
| ATOM | 2138 | CD2 | PHE | A | 285 | 35.378 | 38.470 | 99.559 | 1.00 | 16.70 | A |
| ATOM | 2139 | CE1 | PHE | A | 285 | 34.960 | 39.405 | 96.976 | 1.00 | 15.69 | A |
| ATOM | 2140 | CE2 | PHE | A | 285 | 35.113 | 39.819 | 99.341 | 1.00 | 15.47 | A |
| ATOM | 2141 | CZ | PHE | A | 285 | 34.904 | 40.286 | 98.053 | 1.00 | 15.01 | A |
| ATOM | 2142 | C | PHE | A | 285 | 34.639 | 33.860 | 98.300 | 1.00 | 19.52 | A |
| ATOM | 2143 | O | PHE | A | 285 | 34.928 | 33.565 | 97.144 | 1.00 | 21.87 | A |
| ATOM | 2144 | N | ASP | A | 286 | 34.586 | 32.954 | 99.273 | 1.00 | 21.95 | A |
| ATOM | 2145 | CA | ASP | A | 286 | 34.837 | 31.546 | 98.965 | 1.00 | 20.77 | A |
| ATOM | 2146 | CB | ASP | A | 286 | 34.539 | 30.646 | 100.169 | 1.00 | 23.34 | A |
| ATOM | 2147 | CG | ASP | A | 286 | 35.656 | 30.642 | 101.204 | 1.00 | 24.33 | A |
| ATOM | 2148 | OD1 | ASP | A | 286 | 36.803 | 31.013 | 100.871 | 1.00 | 27.05 | A |
| ATOM | 2149 | OD2 | ASP | A | 286 | 35.382 | 30.247 | 102.359 | 1.00 | 28.19 | A |
| ATOM | 2150 | C | ASP | A | 286 | 33.972 | 31.093 | 97.779 | 1.00 | 22.10 | A |
| ATOM | 2151 | O | ASP | A | 286 | 34.462 | 30.438 | 96.860 | 1.00 | 21.16 | A |
| ATOM | 2152 | N | PRO | A | 287 | 32.671 | 31.436 | 97.786 | 1.00 | 22.48 | A |
| ATOM | 2153 | CD | PRO | A | 287 | 31.932 | 32.149 | 98.842 | 1.00 | 23.33 | A |
| ATOM | 2154 | CA | PRO | A | 287 | 31.765 | 31.049 | 96.696 | 1.00 | 23.96 | A |
| ATOM | 2155 | CB | PRO | A | 287 | 30.428 | 31.661 | 97.120 | 1.00 | 24.38 | A |
| ATOM | 2156 | CG | PRO | A | 287 | 30.520 | 31.683 | 98.613 | 1.00 | 24.07 | A |
| ATOM | 2157 | C | PRO | A | 287 | 32.200 | 31.567 | 95.329 | 1.00 | 22.69 | A |
| ATOM | 2158 | O | PRO | A | 287 | 31.804 | 31.030 | 94.298 | 1.00 | 23.56 | A |
| ATOM | 2159 | N | LEU | A | 288 | 33.012 | 32.617 | 95.324 | 1.00 | 22.92 | A |
| ATOM | 2160 | CA | LEU | A | 288 | 33.473 | 33.217 | 94.077 | 1.00 | 22.67 | A |
| ATOM | 2161 | CB | LEU | A | 288 | 33.445 | 34.740 | 94.201 | 1.00 | 23.12 | A |
| ATOM | 2162 | CG | LEU | A | 288 | 32.092 | 35.359 | 94.544 | 1.00 | 23.50 | A |
| ATOM | 2163 | CD1 | LEU | A | 288 | 32.286 | 36.818 | 94.917 | 1.00 | 24.46 | A |
| ATOM | 2164 | CD2 | LEU | A | 288 | 31.147 | 35.227 | 93.357 | 1.00 | 24.22 | A |
| ATOM | 2165 | C | LEU | A | 288 | 34.875 | 32.772 | 93.682 | 1.00 | 22.51 | A |
| ATOM | 2166 | O | LEU | A | 288 | 35.400 | 33.203 | 92.656 | 1.00 | 22.48 | A |
| ATOM | 2167 | N | GLY | A | 289 | 35.483 | 31.923 | 94.506 | 1.00 | 22.66 | A |
| ATOM | 2168 | CA | GLY | A | 289 | 36.819 | 31.445 | 94.214 | 1.00 | 22.32 | A |
| ATOM | 2169 | C | GLY | A | 289 | 37.894 | 32.502 | 94.378 | 1.00 | 23.21 | A |
| ATOM | 2170 | O | GLY | A | 289 | 38.919 | 32.451 | 93.701 | 1.00 | 25.59 | A |
| ATOM | 2171 | N | ILE | A | 290 | 37.668 | 33.454 | 95.281 | 1.00 | 21.89 | A |
| ATOM | 2172 | CA | ILE | A | 290 | 38.628 | 34.527 | 95.536 | 1.00 | 21.83 | A |
| ATOM | 2173 | CB | ILE | A | 290 | 37.950 | 35.909 | 95.392 | 1.00 | 22.82 | A |
| ATOM | 2174 | CG2 | ILE | A | 290 | 38.870 | 37.006 | 95.899 | 1.00 | 22.10 | A |
| ATOM | 2175 | CG1 | ILE | A | 290 | 37.565 | 36.135 | 93.929 | 1.00 | 23.68 | A |
| ATOM | 2176 | CD1 | ILE | A | 290 | 36.795 | 37.419 | 93.684 | 1.00 | 26.43 | A |
| ATOM | 2177 | C | ILE | A | 290 | 39.210 | 34.397 | 96.944 | 1.00 | 22.08 | A |
| ATOM | 2178 | O | ILE | A | 290 | 38.467 | 34.401 | 97.924 | 1.00 | 19.27 | A |
| ATOM | 2179 | N | SER | A | 291 | 40.536 | 34.297 | 97.041 | 1.00 | 22.84 | A |
| ATOM | 2180 | CA | SER | A | 291 | 41.196 | 34.150 | 98.339 | 1.00 | 23.66 | A |
| ATOM | 2181 | CB | SER | A | 291 | 41.870 | 32.777 | 98.430 | 1.00 | 23.67 | A |
| ATOM | 2182 | OG | SER | A | 291 | 42.768 | 32.582 | 97.355 | 1.00 | 26.92 | A |
| ATOM | 2183 | C | SER | A | 291 | 42.224 | 35.241 | 98.645 | 1.00 | 23.75 | A |
| ATOM | 2184 | O | SER | A | 291 | 42.541 | 35.491 | 99.811 | 1.00 | 22.93 | A |
| ATOM | 2185 | N | ASP | A | 292 | 42.749 | 35.875 | 97.601 | 1.00 | 21.84 | A |
| ATOM | 2186 | CA | ASP | A | 292 | 43.732 | 36.946 | 97.754 | 1.00 | 21.38 | A |
| ATOM | 2187 | CB | ASP | A | 292 | 44.600 | 37.027 | 96.499 | 1.00 | 23.29 | A |
| ATOM | 2188 | CG | ASP | A | 292 | 45.573 | 38.195 | 96.526 | 1.00 | 25.31 | A |
| ATOM | 2189 | OD1 | ASP | A | 292 | 46.344 | 38.334 | 95.552 | 1.00 | 25.14 | A |
| ATOM | 2190 | OD2 | ASP | A | 292 | 45.568 | 38.968 | 97.507 | 1.00 | 25.25 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 2191 | C | ASP | A | 292 | 42.959 | 38.251 | 97.944 | 1.00 | 21.41 | A |
| ATOM | 2192 | O | ASP | A | 292 | 42.425 | 38.807 | 96.984 | 1.00 | 21.93 | A |
| ATOM | 2193 | N | TYR | A | 293 | 42.905 | 38.739 | 99.177 | 1.00 | 18.89 | A |
| ATOM | 2194 | CA | TYR | A | 293 | 42.154 | 39.956 | 99.463 | 1.00 | 18.84 | A |
| ATOM | 2195 | CB | TYR | A | 293 | 41.693 | 39.932 | 100.924 | 1.00 | 19.73 | A |
| ATOM | 2196 | CG | TYR | A | 293 | 40.867 | 38.694 | 101.219 | 1.00 | 20.84 | A |
| ATOM | 2197 | CD1 | TYR | A | 293 | 39.776 | 38.355 | 100.417 | 1.00 | 20.08 | A |
| ATOM | 2198 | CE1 | TYR | A | 293 | 39.041 | 37.194 | 100.647 | 1.00 | 22.81 | A |
| ATOM | 2199 | CD2 | TYR | A | 293 | 41.199 | 37.841 | 102.268 | 1.00 | 22.83 | A |
| ATOM | 2200 | CE2 | TYR | A | 293 | 40.472 | 36.677 | 102.509 | 1.00 | 22.45 | A |
| ATOM | 2201 | CZ | TYR | A | 293 | 39.398 | 36.359 | 101.695 | 1.00 | 22.48 | A |
| ATOM | 2202 | OH | TYR | A | 293 | 38.694 | 35.198 | 101.921 | 1.00 | 24.63 | A |
| ATOM | 2203 | C | TYR | A | 293 | 42.842 | 41.263 | 99.098 | 1.00 | 19.82 | A |
| ATOM | 2204 | O | TYR | A | 293 | 42.291 | 42.351 | 99.306 | 1.00 | 17.41 | A |
| ATOM | 2205 | N | ASN | A | 294 | 44.047 | 41.166 | 98.538 | 1.00 | 18.72 | A |
| ATOM | 2206 | CA | ASN | A | 294 | 44.733 | 42.360 | 98.075 | 1.00 | 20.17 | A |
| ATOM | 2207 | CB | ASN | A | 294 | 46.251 | 42.222 | 98.206 | 1.00 | 19.86 | A |
| ATOM | 2208 | CG | ASN | A | 294 | 46.758 | 42.686 | 99.550 | 1.00 | 20.29 | A |
| ATOM | 2209 | OD1 | ASN | A | 294 | 46.625 | 43.860 | 99.902 | 1.00 | 18.17 | A |
| ATOM | 2210 | ND2 | ASN | A | 294 | 47.338 | 41.767 | 100.314 | 1.00 | 16.51 | A |
| ATOM | 2211 | C | ASN | A | 294 | 44.364 | 42.526 | 96.603 | 1.00 | 20.20 | A |
| ATOM | 2212 | O | ASN | A | 294 | 44.704 | 43.534 | 95.983 | 1.00 | 22.64 | A |
| ATOM | 2213 | N | SER | A | 295 | 43.661 | 41.535 | 96.052 | 1.00 | 18.20 | A |
| ATOM | 2214 | CA | SER | A | 295 | 43.269 | 41.568 | 94.642 | 1.00 | 17.41 | A |
| ATOM | 2215 | CB | SER | A | 295 | 43.334 | 40.161 | 94.025 | 1.00 | 18.06 | A |
| ATOM | 2216 | OG | SER | A | 295 | 42.218 | 39.371 | 94.403 | 1.00 | 19.73 | A |
| ATOM | 2217 | C | SER | A | 295 | 41.886 | 42.153 | 94.401 | 1.00 | 15.25 | A |
| ATOM | 2218 | O | SER | A | 295 | 41.413 | 42.179 | 93.263 | 1.00 | 16.23 | A |
| ATOM | 2219 | N | ILE | A | 296 | 41.227 | 42.609 | 95.463 | 1.00 | 11.98 | A |
| ATOM | 2220 | CA | ILE | A | 296 | 39.902 | 43.217 | 95.328 | 1.00 | 13.58 | A |
| ATOM | 2221 | CB | ILE | A | 296 | 38.838 | 42.449 | 96.145 | 1.00 | 13.48 | A |
| ATOM | 2222 | CG2 | ILE | A | 296 | 38.699 | 41.018 | 95.600 | 1.00 | 15.53 | A |
| ATOM | 2223 | CG1 | ILE | A | 296 | 39.233 | 42.414 | 97.629 | 1.00 | 11.74 | A |
| ATOM | 2224 | CD1 | ILE | A | 296 | 38.169 | 41.828 | 98.546 | 1.00 | 14.12 | A |
| ATOM | 2225 | C | ILE | A | 296 | 39.992 | 44.638 | 95.867 | 1.00 | 13.88 | A |
| ATOM | 2226 | O | ILE | A | 296 | 40.947 | 44.959 | 96.575 | 1.00 | 15.39 | A |
| ATOM | 2227 | N | PHE | A | 297 | 39.029 | 45.492 | 95.527 | 1.00 | 14.99 | A |
| ATOM | 2228 | CA | PHE | A | 297 | 39.051 | 46.849 | 96.064 | 1.00 | 15.65 | A |
| ATOM | 2229 | CB | PHE | A | 297 | 38.472 | 47.885 | 95.081 | 1.00 | 14.57 | A |
| ATOM | 2230 | CG | PHE | A | 297 | 37.069 | 47.603 | 94.611 | 1.00 | 15.26 | A |
| ATOM | 2231 | CD1 | PHE | A | 297 | 36.843 | 46.812 | 93.487 | 1.00 | 15.33 | A |
| ATOM | 2232 | CD2 | PHE | A | 297 | 35.979 | 48.191 | 95.244 | 1.00 | 15.89 | A |
| ATOM | 2233 | CE1 | PHE | A | 297 | 35.554 | 46.618 | 92.996 | 1.00 | 15.51 | A |
| ATOM | 2234 | CE2 | PHE | A | 297 | 34.684 | 48.005 | 94.764 | 1.00 | 16.37 | A |
| ATOM | 2235 | CZ | PHE | A | 297 | 34.469 | 47.219 | 93.636 | 1.00 | 16.21 | A |
| ATOM | 2236 | C | PHE | A | 297 | 38.294 | 46.866 | 97.383 | 1.00 | 15.79 | A |
| ATOM | 2237 | O | PHE | A | 297 | 37.377 | 46.063 | 97.596 | 1.00 | 15.96 | A |
| ATOM | 2238 | N | TRP | A | 298 | 38.672 | 47.792 | 98.261 | 1.00 | 13.76 | A |
| ATOM | 2239 | CA | TRP | A | 298 | 38.078 | 47.891 | 99.589 | 1.00 | 13.84 | A |
| ATOM | 2240 | CB | TRP | A | 298 | 39.170 | 47.690 | 100.652 | 1.00 | 15.00 | A |
| ATOM | 2241 | CG | TRP | A | 298 | 39.590 | 46.272 | 100.872 | 1.00 | 15.82 | A |
| ATOM | 2242 | CD2 | TRP | A | 298 | 39.394 | 45.499 | 102.066 | 1.00 | 16.38 | A |
| ATOM | 2243 | CE2 | TRP | A | 298 | 39.943 | 44.220 | 101.831 | 1.00 | 16.53 | A |
| ATOM | 2244 | CE3 | TRP | A | 298 | 38.805 | 45.766 | 103.313 | 1.00 | 15.24 | A |
| ATOM | 2245 | CD1 | TRP | A | 298 | 40.232 | 45.454 | 99.986 | 1.00 | 16.86 | A |
| ATOM | 2246 | NE1 | TRP | A | 298 | 40.448 | 44.216 | 100.556 | 1.00 | 16.65 | A |
| ATOM | 2247 | CZ2 | TRP | A | 298 | 39.922 | 43.204 | 102.799 | 1.00 | 16.35 | A |
| ATOM | 2248 | CZ3 | TRP | A | 298 | 38.783 | 44.756 | 104.275 | 1.00 | 17.36 | A |
| ATOM | 2249 | CH2 | TRP | A | 298 | 39.342 | 43.489 | 104.009 | 1.00 | 16.55 | A |
| ATOM | 2250 | C | TRP | A | 298 | 37.343 | 49.181 | 99.931 | 1.00 | 15.44 | A |
| ATOM | 2251 | O | TRP | A | 298 | 37.838 | 50.274 | 99.674 | 1.00 | 15.12 | A |
| ATOM | 2252 | N | ILE | A | 299 | 36.161 | 49.033 | 100.521 | 1.00 | 14.10 | A |
| ATOM | 2253 | CA | ILE | A | 299 | 35.367 | 50.163 | 100.984 | 1.00 | 14.84 | A |
| ATOM | 2254 | CB | ILE | A | 299 | 34.126 | 50.423 | 100.098 | 1.00 | 12.44 | A |
| ATOM | 2255 | CG2 | ILE | A | 299 | 33.252 | 51.511 | 100.741 | 1.00 | 12.82 | A |
| ATOM | 2256 | CG1 | ILE | A | 299 | 34.584 | 50.866 | 98.704 | 1.00 | 11.52 | A |
| ATOM | 2257 | CD1 | ILE | A | 299 | 33.463 | 51.004 | 97.691 | 1.00 | 14.86 | A |
| ATOM | 2258 | C | ILE | A | 299 | 34.930 | 49.777 | 102.390 | 1.00 | 15.35 | A |
| ATOM | 2259 | O | ILE | A | 299 | 34.006 | 48.991 | 102.566 | 1.00 | 18.17 | A |
| ATOM | 2260 | N | ALA | A | 300 | 35.613 | 50.316 | 103.393 | 1.00 | 16.48 | A |
| ATOM | 2261 | CA | ALA | A | 300 | 35.290 | 49.991 | 104.779 | 1.00 | 16.75 | A |
| ATOM | 2262 | CB | ALA | A | 300 | 36.514 | 49.376 | 105.460 | 1.00 | 17.74 | A |
| ATOM | 2263 | C | ALA | A | 300 | 34.808 | 51.191 | 105.583 | 1.00 | 18.52 | A |
| ATOM | 2264 | O | ALA | A | 300 | 35.309 | 52.303 | 105.410 | 1.00 | 17.89 | A |
| ATOM | 2265 | N | HIS | A | 301 | 33.836 | 50.961 | 106.464 | 1.00 | 16.34 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 2266 | CA | HIS | A | 301 | 33.325 | 52.024 | 107.319 | 1.00 | 17.03 | A |
| ATOM | 2267 | CB | HIS | A | 301 | 32.164 | 51.524 | 108.179 | 1.00 | 16.06 | A |
| ATOM | 2268 | CG | HIS | A | 301 | 31.682 | 52.532 | 109.179 | 1.00 | 17.35 | A |
| ATOM | 2269 | CD2 | HIS | A | 301 | 31.646 | 52.501 | 110.533 | 1.00 | 18.74 | A |
| ATOM | 2270 | ND1 | HIS | A | 301 | 31.211 | 53.776 | 108.813 | 1.00 | 18.35 | A |
| ATOM | 2271 | CE1 | HIS | A | 301 | 30.906 | 54.468 | 109.897 | 1.00 | 18.11 | A |
| ATOM | 2272 | NE2 | HIS | A | 301 | 31.160 | 53.718 | 110.955 | 1.00 | 18.22 | A |
| ATOM | 2273 | C | HIS | A | 301 | 34.472 | 52.467 | 108.224 | 1.00 | 17.49 | A |
| ATOM | 2274 | O | HIS | A | 301 | 35.043 | 51.655 | 108.947 | 1.00 | 18.95 | A |
| ATOM | 2275 | N | PRO | A | 302 | 34.834 | 53.760 | 108.184 | 1.00 | 18.79 | A |
| ATOM | 2276 | CD | PRO | A | 302 | 34.297 | 54.826 | 107.317 | 1.00 | 17.58 | A |
| ATOM | 2277 | CA | PRO | A | 302 | 35.927 | 54.261 | 109.022 | 1.00 | 18.96 | A |
| ATOM | 2278 | CB | PRO | A | 302 | 36.359 | 55.527 | 108.287 | 1.00 | 19.58 | A |
| ATOM | 2279 | CG | PRO | A | 302 | 35.052 | 56.068 | 107.800 | 1.00 | 19.28 | A |
| ATOM | 2280 | C | PRO | A | 302 | 35.465 | 54.544 | 110.453 | 1.00 | 19.81 | A |
| ATOM | 2281 | O | PRO | A | 302 | 35.482 | 55.691 | 110.911 | 1.00 | 19.60 | A |
| ATOM | 2282 | N | GLY | A | 303 | 35.044 | 53.497 | 111.155 | 1.00 | 19.20 | A |
| ATOM | 2283 | CA | GLY | A | 303 | 34.582 | 53.671 | 112.521 | 1.00 | 20.12 | A |
| ATOM | 2284 | C | GLY | A | 303 | 35.644 | 54.332 | 113.377 | 1.00 | 23.33 | A |
| ATOM | 2285 | O | GLY | A | 303 | 35.337 | 55.051 | 114.333 | 1.00 | 23.31 | A |
| ATOM | 2286 | N | GLY | A | 304 | 36.903 | 54.092 | 113.019 | 1.00 | 23.07 | A |
| ATOM | 2287 | CA | GLY | A | 304 | 38.011 | 54.668 | 113.757 | 1.00 | 23.38 | A |
| ATOM | 2288 | C | GLY | A | 304 | 39.348 | 54.218 | 113.199 | 1.00 | 23.14 | A |
| ATOM | 2289 | O | GLY | A | 304 | 39.438 | 53.186 | 112.535 | 1.00 | 20.51 | A |
| ATOM | 2290 | N | ARG | A | 305 | 40.387 | 54.999 | 113.467 | 1.00 | 22.81 | A |
| ATOM | 2291 | CA | ARG | A | 305 | 41.737 | 54.697 | 112.997 | 1.00 | 23.64 | A |
| ATOM | 2292 | CB | ARG | A | 305 | 42.710 | 55.725 | 113.576 | 1.00 | 28.06 | A |
| ATOM | 2293 | CG | ARG | A | 305 | 44.174 | 55.458 | 113.274 | 1.00 | 32.94 | A |
| ATOM | 2294 | CD | ARG | A | 305 | 45.033 | 55.993 | 114.403 | 1.00 | 37.33 | A |
| ATOM | 2295 | NE | ARG | A | 305 | 46.429 | 56.179 | 114.021 | 1.00 | 40.67 | A |
| ATOM | 2296 | CZ | ARG | A | 305 | 47.327 | 56.795 | 114.783 | 1.00 | 42.66 | A |
| ATOM | 2297 | NH1 | ARG | A | 305 | 46.971 | 57.280 | 115.965 | 1.00 | 43.64 | A |
| ATOM | 2298 | NH2 | ARG | A | 305 | 48.578 | 56.938 | 114.363 | 1.00 | 45.35 | A |
| ATOM | 2299 | C | ARG | A | 305 | 42.197 | 53.289 | 113.392 | 1.00 | 22.76 | A |
| ATOM | 2300 | O | ARG | A | 305 | 42.684 | 52.522 | 112.556 | 1.00 | 20.99 | A |
| ATOM | 2301 | N | ALA | A | 306 | 42.037 | 52.968 | 114.673 | 1.00 | 20.50 | A |
| ATOM | 2302 | CA | ALA | A | 306 | 42.440 | 51.676 | 115.224 | 1.00 | 20.59 | A |
| ATOM | 2303 | CB | ALA | A | 306 | 42.125 | 51.638 | 116.718 | 1.00 | 21.66 | A |
| ATOM | 2304 | C | ALA | A | 306 | 41.804 | 50.472 | 114.527 | 1.00 | 19.21 | A |
| ATOM | 2305 | O | ALA | A | 306 | 42.460 | 49.452 | 114.330 | 1.00 | 18.90 | A |
| ATOM | 2306 | N | ILE | A | 307 | 40.523 | 50.578 | 114.183 | 1.00 | 19.28 | A |
| ATOM | 2307 | CA | ILE | A | 307 | 39.837 | 49.488 | 113.496 | 1.00 | 17.80 | A |
| ATOM | 2308 | CB | ILE | A | 307 | 38.336 | 49.810 | 113.287 | 1.00 | 19.27 | A |
| ATOM | 2309 | CG2 | ILE | A | 307 | 37.675 | 48.727 | 112.429 | 1.00 | 18.14 | A |
| ATOM | 2310 | CG1 | ILE | A | 307 | 37.639 | 49.907 | 114.644 | 1.00 | 20.87 | A |
| ATOM | 2311 | CD1 | ILE | A | 307 | 36.228 | 50.441 | 114.578 | 1.00 | 22.85 | A |
| ATOM | 2312 | C | ILE | A | 307 | 40.489 | 49.241 | 112.138 | 1.00 | 19.21 | A |
| ATOM | 2313 | O | ILE | A | 307 | 40.796 | 48.102 | 111.782 | 1.00 | 19.01 | A |
| ATOM | 2314 | N | LEU | A | 308 | 40.709 | 50.308 | 111.376 | 1.00 | 17.31 | A |
| ATOM | 2315 | CA | LEU | A | 308 | 41.326 | 50.156 | 110.069 | 1.00 | 18.79 | A |
| ATOM | 2316 | CB | LEU | A | 308 | 41.352 | 51.503 | 109.329 | 1.00 | 16.84 | A |
| ATOM | 2317 | CG | LEU | A | 308 | 39.986 | 52.166 | 109.093 | 1.00 | 16.60 | A |
| ATOM | 2318 | CD1 | LEU | A | 308 | 40.178 | 53.524 | 108.421 | 1.00 | 15.51 | A |
| ATOM | 2319 | CD2 | LEU | A | 308 | 39.109 | 51.256 | 108.237 | 1.00 | 17.66 | A |
| ATOM | 2320 | C | LEU | A | 308 | 42.744 | 49.588 | 110.203 | 1.00 | 17.81 | A |
| ATOM | 2321 | O | LEU | A | 308 | 43.110 | 48.655 | 109.486 | 1.00 | 18.53 | A |
| ATOM | 2322 | N | ASP | A | 309 | 43.535 | 50.134 | 111.124 | 1.00 | 18.08 | A |
| ATOM | 2323 | CA | ASP | A | 309 | 44.900 | 49.648 | 111.317 | 1.00 | 19.43 | A |
| ATOM | 2324 | CB | ASP | A | 309 | 45.591 | 50.381 | 112.476 | 1.00 | 19.58 | A |
| ATOM | 2325 | CG | ASP | A | 309 | 45.864 | 51.850 | 112.176 | 1.00 | 22.23 | A |
| ATOM | 2326 | OD1 | ASP | A | 309 | 45.633 | 52.295 | 111.032 | 1.00 | 20.80 | A |
| ATOM | 2327 | OD2 | ASP | A | 309 | 46.319 | 52.559 | 113.100 | 1.00 | 21.47 | A |
| ATOM | 2328 | C | ASP | A | 309 | 44.924 | 48.147 | 111.607 | 1.00 | 18.66 | A |
| ATOM | 2329 | O | ASP | A | 309 | 45.695 | 47.394 | 110.999 | 1.00 | 19.55 | A |
| ATOM | 2330 | N | GLN | A | 310 | 44.079 | 47.704 | 112.530 | 1.00 | 19.17 | A |
| ATOM | 2331 | CA | GLN | A | 310 | 44.063 | 46.292 | 112.893 | 1.00 | 19.27 | A |
| ATOM | 2332 | CB | GLN | A | 310 | 43.334 | 46.107 | 114.221 | 1.00 | 20.83 | A |
| ATOM | 2333 | CG | GLN | A | 310 | 44.151 | 46.673 | 115.379 | 1.00 | 24.30 | A |
| ATOM | 2334 | CD | GLN | A | 310 | 43.560 | 46.375 | 116.735 | 1.00 | 26.80 | A |
| ATOM | 2335 | OE1 | GLN | A | 310 | 43.182 | 45.239 | 117.026 | 1.00 | 29.98 | A |
| ATOM | 2336 | NE2 | GLN | A | 310 | 43.486 | 47.393 | 117.582 | 1.00 | 28.79 | A |
| ATOM | 2337 | C | GLN | A | 310 | 43.524 | 45.344 | 111.825 | 1.00 | 19.13 | A |
| ATOM | 2338 | O | GLN | A | 310 | 43.979 | 44.207 | 111.727 | 1.00 | 17.24 | A |
| ATOM | 2339 | N | VAL | A | 311 | 42.576 | 45.812 | 111.019 | 1.00 | 17.16 | A |
| ATOM | 2340 | CA | VAL | A | 311 | 42.031 | 44.990 | 109.948 | 1.00 | 17.35 | A |

APPENDIX B-continued

*Arachis hypogaea* STS

| ATOM | # | TYPE | RES | | | X | Y | Z | OCC | B | |
|------|---|------|-----|---|---|---|---|---|-----|---|---|
| ATOM | 2341 | CB | VAL | A | 311 | 40.769 | 45.643 | 109.330 | 1.00 | 17.80 | A |
| ATOM | 2342 | CG1 | VAL | A | 311 | 40.413 | 44.973 | 107.995 | 1.00 | 19.45 | A |
| ATOM | 2343 | CG2 | VAL | A | 311 | 39.606 | 45.506 | 110.299 | 1.00 | 16.82 | A |
| ATOM | 2344 | C | VAL | A | 311 | 43.115 | 44.799 | 108.881 | 1.00 | 18.13 | A |
| ATOM | 2345 | O | VAL | A | 311 | 43.300 | 43.690 | 108.370 | 1.00 | 15.50 | A |
| ATOM | 2346 | N | GLU | A | 312 | 43.841 | 45.872 | 108.559 | 1.00 | 18.03 | A |
| ATOM | 2347 | CA | GLU | A | 312 | 44.923 | 45.801 | 107.572 | 1.00 | 20.30 | A |
| ATOM | 2348 | CB | GLU | A | 312 | 45.571 | 47.176 | 107.369 | 1.00 | 22.51 | A |
| ATOM | 2349 | CG | GLU | A | 312 | 44.802 | 48.102 | 106.456 | 1.00 | 27.98 | A |
| ATOM | 2350 | CD | GLU | A | 312 | 45.431 | 49.483 | 106.368 | 1.00 | 30.36 | A |
| ATOM | 2351 | OE1 | GLU | A | 312 | 46.632 | 49.578 | 106.053 | 1.00 | 32.69 | A |
| ATOM | 2352 | OE2 | GLU | A | 312 | 44.721 | 50.477 | 106.614 | 1.00 | 37.60 | A |
| ATOM | 2353 | C | GLU | A | 312 | 45.998 | 44.820 | 108.034 | 1.00 | 19.51 | A |
| ATOM | 2354 | O | GLU | A | 312 | 46.588 | 44.095 | 107.230 | 1.00 | 18.40 | A |
| ATOM | 2355 | N | GLN | A | 313 | 46.261 | 44.820 | 109.336 | 1.00 | 21.42 | A |
| ATOM | 2356 | CA | GLN | A | 313 | 47.255 | 43.932 | 109.919 | 1.00 | 22.77 | A |
| ATOM | 2357 | CB | GLN | A | 313 | 47.501 | 44.318 | 111.378 | 1.00 | 24.05 | A |
| ATOM | 2358 | CG | GLN | A | 313 | 48.585 | 45.356 | 111.572 | 1.00 | 30.88 | A |
| ATOM | 2359 | CD | GLN | A | 313 | 49.975 | 44.748 | 111.512 | 1.00 | 35.25 | A |
| ATOM | 2360 | OE1 | GLN | A | 313 | 50.409 | 44.255 | 110.473 | 1.00 | 36.85 | A |
| ATOM | 2361 | NE2 | GLN | A | 313 | 50.677 | 44.769 | 112.639 | 1.00 | 40.09 | A |
| ATOM | 2362 | C | GLN | A | 313 | 46.818 | 42.472 | 109.837 | 1.00 | 21.31 | A |
| ATOM | 2363 | O | GLN | A | 313 | 47.577 | 41.608 | 109.399 | 1.00 | 22.70 | A |
| ATOM | 2364 | N | LYS | A | 314 | 45.585 | 42.208 | 110.249 | 1.00 | 21.15 | A |
| ATOM | 2365 | CA | LYS | A | 314 | 45.040 | 40.855 | 110.236 | 1.00 | 20.71 | A |
| ATOM | 2366 | CB | LYS | A | 314 | 43.665 | 40.836 | 110.904 | 1.00 | 20.52 | A |
| ATOM | 2367 | CG | LYS | A | 314 | 43.101 | 39.443 | 111.099 | 1.00 | 22.86 | A |
| ATOM | 2368 | CD | LYS | A | 314 | 43.948 | 38.650 | 112.092 | 1.00 | 26.70 | A |
| ATOM | 2369 | CE | LYS | A | 314 | 43.390 | 37.253 | 112.316 | 1.00 | 28.35 | A |
| ATOM | 2370 | NZ | LYS | A | 314 | 44.240 | 36.482 | 113.266 | 1.00 | 30.58 | A |
| ATOM | 2371 | C | LYS | A | 314 | 44.915 | 40.275 | 108.834 | 1.00 | 21.15 | A |
| ATOM | 2372 | O | LYS | A | 314 | 45.290 | 39.132 | 108.596 | 1.00 | 19.91 | A |
| ATOM | 2373 | N | VAL | A | 315 | 44.388 | 41.062 | 107.902 | 1.00 | 20.16 | A |
| ATOM | 2374 | CA | VAL | A | 315 | 44.207 | 40.589 | 106.538 | 1.00 | 18.60 | A |
| ATOM | 2375 | CB | VAL | A | 315 | 43.032 | 41.338 | 105.847 | 1.00 | 17.87 | A |
| ATOM | 2376 | CG1 | VAL | A | 315 | 42.788 | 40.768 | 104.465 | 1.00 | 16.87 | A |
| ATOM | 2377 | CG2 | VAL | A | 315 | 41.760 | 41.215 | 106.693 | 1.00 | 16.04 | A |
| ATOM | 2378 | C | VAL | A | 315 | 45.476 | 40.736 | 105.699 | 1.00 | 19.02 | A |
| ATOM | 2379 | O | VAL | A | 315 | 45.562 | 40.199 | 104.595 | 1.00 | 18.12 | A |
| ATOM | 2380 | N | ASN | A | 316 | 46.461 | 41.456 | 106.235 | 1.00 | 19.03 | A |
| ATOM | 2381 | CA | ASN | A | 316 | 47.733 | 41.683 | 105.548 | 1.00 | 17.21 | A |
| ATOM | 2382 | CB | ASN | A | 316 | 48.421 | 40.338 | 105.251 | 1.00 | 17.36 | A |
| ATOM | 2383 | CG | ASN | A | 316 | 49.882 | 40.499 | 104.883 | 1.00 | 18.38 | A |
| ATOM | 2384 | OD1 | ASN | A | 316 | 50.580 | 41.357 | 105.430 | 1.00 | 16.26 | A |
| ATOM | 2385 | ND2 | ASN | A | 316 | 50.360 | 39.665 | 103.964 | 1.00 | 20.02 | A |
| ATOM | 2386 | C | ASN | A | 316 | 47.535 | 42.481 | 104.255 | 1.00 | 16.62 | A |
| ATOM | 2387 | O | ASN | A | 316 | 48.041 | 42.110 | 103.192 | 1.00 | 16.59 | A |
| ATOM | 2388 | N | LEU | A | 317 | 46.811 | 43.593 | 104.362 | 1.00 | 15.63 | A |
| ATOM | 2389 | CA | LEU | A | 317 | 46.522 | 44.447 | 103.212 | 1.00 | 17.20 | A |
| ATOM | 2390 | CB | LEU | A | 317 | 45.210 | 45.212 | 103.441 | 1.00 | 16.66 | A |
| ATOM | 2391 | CG | LEU | A | 317 | 43.936 | 44.404 | 103.701 | 1.00 | 18.52 | A |
| ATOM | 2392 | CD1 | LEU | A | 317 | 42.778 | 45.353 | 104.044 | 1.00 | 17.08 | A |
| ATOM | 2393 | CD2 | LEU | A | 317 | 43.601 | 43.585 | 102.470 | 1.00 | 17.68 | A |
| ATOM | 2394 | C | LEU | A | 317 | 47.609 | 45.467 | 102.918 | 1.00 | 17.33 | A |
| ATOM | 2395 | O | LEU | A | 317 | 48.164 | 46.074 | 103.836 | 1.00 | 17.14 | A |
| ATOM | 2396 | N | LYS | A | 318 | 47.906 | 45.660 | 101.637 | 1.00 | 16.70 | A |
| ATOM | 2397 | CA | LYS | A | 318 | 48.881 | 46.665 | 101.243 | 1.00 | 17.06 | A |
| ATOM | 2398 | CB | LYS | A | 318 | 49.074 | 46.657 | 99.727 | 1.00 | 17.35 | A |
| ATOM | 2399 | CG | LYS | A | 318 | 49.847 | 45.446 | 99.211 | 1.00 | 18.37 | A |
| ATOM | 2400 | CD | LYS | A | 318 | 49.921 | 45.426 | 97.698 | 1.00 | 21.60 | A |
| ATOM | 2401 | CE | LYS | A | 318 | 48.542 | 45.255 | 97.074 | 1.00 | 24.87 | A |
| ATOM | 2402 | NZ | LYS | A | 318 | 48.600 | 45.204 | 95.581 | 1.00 | 27.70 | A |
| ATOM | 2403 | C | LYS | A | 318 | 48.261 | 47.987 | 101.694 | 1.00 | 18.31 | A |
| ATOM | 2404 | O | LYS | A | 318 | 47.041 | 48.155 | 101.637 | 1.00 | 18.82 | A |
| ATOM | 2405 | N | PRO | A | 319 | 49.087 | 48.939 | 102.149 | 1.00 | 17.96 | A |
| ATOM | 2406 | CD | PRO | A | 319 | 50.558 | 48.856 | 102.225 | 1.00 | 19.64 | A |
| ATOM | 2407 | CA | PRO | A | 319 | 48.625 | 50.249 | 102.621 | 1.00 | 18.88 | A |
| ATOM | 2408 | CB | PRO | A | 319 | 49.929 | 51.020 | 102.821 | 1.00 | 20.93 | A |
| ATOM | 2409 | CG | PRO | A | 319 | 50.885 | 49.952 | 103.210 | 1.00 | 19.51 | A |
| ATOM | 2410 | C | PRO | A | 319 | 47.658 | 51.003 | 101.712 | 1.00 | 19.97 | A |
| ATOM | 2411 | O | PRO | A | 319 | 46.757 | 51.691 | 102.195 | 1.00 | 18.40 | A |
| ATOM | 2412 | N | GLU | A | 320 | 47.843 | 50.883 | 100.401 | 1.00 | 21.10 | A |
| ATOM | 2413 | CA | GLU | A | 320 | 46.979 | 51.588 | 99.463 | 1.00 | 22.71 | A |
| ATOM | 2414 | CB | GLU | A | 320 | 47.555 | 51.508 | 98.044 | 1.00 | 24.81 | A |
| ATOM | 2415 | CG | GLU | A | 320 | 48.939 | 52.155 | 97.890 | 1.00 | 33.10 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 2416 | CD | GLU | A | 320 | 48.985 | 53.612 | 98.339 | 1.00 | 35.66 | A |
| ATOM | 2417 | OE1 | GLU | A | 320 | 48.827 | 53.883 | 99.548 | 1.00 | 39.88 | A |
| ATOM | 2418 | OE2 | GLU | A | 320 | 49.184 | 54.495 | 97.479 | 1.00 | 40.62 | A |
| ATOM | 2419 | C | GLU | A | 320 | 45.531 | 51.106 | 99.464 | 1.00 | 20.57 | A |
| ATOM | 2420 | O | GLU | A | 320 | 44.631 | 51.859 | 99.105 | 1.00 | 18.61 | A |
| ATOM | 2421 | N | LYS | A | 321 | 45.300 | 49.863 | 99.874 | 1.00 | 18.41 | A |
| ATOM | 2422 | CA | LYS | A | 321 | 43.941 | 49.318 | 99.901 | 1.00 | 17.42 | A |
| ATOM | 2423 | CB | LYS | A | 321 | 43.957 | 47.914 | 100.525 | 1.00 | 18.91 | A |
| ATOM | 2424 | CG | LYS | A | 321 | 44.603 | 46.871 | 99.627 | 1.00 | 18.63 | A |
| ATOM | 2425 | CD | LYS | A | 321 | 43.749 | 46.700 | 98.385 | 1.00 | 23.06 | A |
| ATOM | 2426 | CE | LYS | A | 321 | 44.484 | 46.048 | 97.247 | 1.00 | 25.54 | A |
| ATOM | 2427 | NZ | LYS | A | 321 | 43.617 | 46.071 | 96.032 | 1.00 | 22.67 | A |
| ATOM | 2428 | C | LYS | A | 321 | 42.941 | 50.216 | 100.645 | 1.00 | 18.06 | A |
| ATOM | 2429 | O | LYS | A | 321 | 41.819 | 50.436 | 100.176 | 1.00 | 14.96 | A |
| ATOM | 2430 | N | MET | A | 322 | 43.352 | 50.736 | 101.800 | 1.00 | 17.37 | A |
| ATOM | 2431 | CA | MET | A | 322 | 42.496 | 51.606 | 102.613 | 1.00 | 16.72 | A |
| ATOM | 2432 | CB | MET | A | 322 | 42.793 | 51.380 | 104.097 | 1.00 | 18.06 | A |
| ATOM | 2433 | CG | MET | A | 322 | 42.387 | 50.017 | 104.612 | 1.00 | 21.77 | A |
| ATOM | 2434 | SD | MET | A | 322 | 40.608 | 49.856 | 104.615 | 1.00 | 26.83 | A |
| ATOM | 2435 | CE | MET | A | 322 | 40.379 | 48.447 | 105.741 | 1.00 | 26.99 | A |
| ATOM | 2436 | C | MET | A | 322 | 42.652 | 53.099 | 102.313 | 1.00 | 17.42 | A |
| ATOM | 2437 | O | MET | A | 322 | 42.136 | 53.940 | 103.055 | 1.00 | 14.58 | A |
| ATOM | 2438 | N | LYS | A | 323 | 43.353 | 53.439 | 101.237 | 1.00 | 16.80 | A |
| ATOM | 2439 | CA | LYS | A | 323 | 43.570 | 54.846 | 100.923 | 1.00 | 18.31 | A |
| ATOM | 2440 | CB | LYS | A | 323 | 44.413 | 54.994 | 99.654 | 1.00 | 20.83 | A |
| ATOM | 2441 | CG | LYS | A | 323 | 44.660 | 56.440 | 99.277 | 1.00 | 22.34 | A |
| ATOM | 2442 | CD | LYS | A | 323 | 45.599 | 56.576 | 98.090 | 1.00 | 25.20 | A |
| ATOM | 2443 | CE | LYS | A | 323 | 45.679 | 58.028 | 97.661 | 1.00 | 27.32 | A |
| ATOM | 2444 | NZ | LYS | A | 323 | 45.942 | 58.916 | 98.833 | 1.00 | 27.74 | A |
| ATOM | 2445 | C | LYS | A | 323 | 42.291 | 55.668 | 100.788 | 1.00 | 18.02 | A |
| ATOM | 2446 | O | LYS | A | 323 | 42.161 | 56.717 | 101.423 | 1.00 | 16.95 | A |
| ATOM | 2447 | N | ALA | A | 324 | 41.347 | 55.207 | 99.970 | 1.00 | 17.17 | A |
| ATOM | 2448 | CA | ALA | A | 324 | 40.094 | 55.946 | 99.784 | 1.00 | 16.35 | A |
| ATOM | 2449 | CB | ALA | A | 324 | 39.206 | 55.241 | 98.752 | 1.00 | 16.45 | A |
| ATOM | 2450 | C | ALA | A | 324 | 39.359 | 56.070 | 101.116 | 1.00 | 16.75 | A |
| ATOM | 2451 | O | ALA | A | 324 | 38.813 | 57.127 | 101.456 | 1.00 | 14.58 | A |
| ATOM | 2452 | N | THR | A | 325 | 39.358 | 54.984 | 101.876 | 1.00 | 14.25 | A |
| ATOM | 2453 | CA | THR | A | 325 | 38.699 | 54.969 | 103.174 | 1.00 | 14.58 | A |
| ATOM | 2454 | CB | THR | A | 325 | 38.752 | 53.568 | 103.792 | 1.00 | 15.15 | A |
| ATOM | 2455 | OG1 | THR | A | 325 | 37.986 | 52.670 | 102.974 | 1.00 | 15.01 | A |
| ATOM | 2456 | CG2 | THR | A | 325 | 38.181 | 53.589 | 105.205 | 1.00 | 13.11 | A |
| ATOM | 2457 | C | THR | A | 325 | 39.314 | 55.967 | 104.162 | 1.00 | 14.64 | A |
| ATOM | 2458 | O | THR | A | 325 | 38.601 | 56.719 | 104.820 | 1.00 | 14.11 | A |
| ATOM | 2459 | N | ARG | A | 326 | 40.636 | 55.977 | 104.263 | 1.00 | 15.97 | A |
| ATOM | 2460 | CA | ARG | A | 326 | 41.298 | 56.883 | 105.194 | 1.00 | 14.76 | A |
| ATOM | 2461 | CB | ARG | A | 326 | 42.766 | 56.485 | 105.367 | 1.00 | 17.17 | A |
| ATOM | 2462 | CG | ARG | A | 326 | 42.970 | 55.120 | 106.039 | 1.00 | 19.48 | A |
| ATOM | 2463 | CD | ARG | A | 326 | 44.462 | 54.809 | 106.181 | 1.00 | 21.00 | A |
| ATOM | 2464 | NE | ARG | A | 326 | 44.729 | 53.505 | 106.789 | 1.00 | 22.68 | A |
| ATOM | 2465 | CZ | ARG | A | 326 | 44.655 | 53.237 | 108.091 | 1.00 | 23.59 | A |
| ATOM | 2466 | NH1 | ARG | A | 326 | 44.314 | 54.181 | 108.960 | 1.00 | 19.97 | A |
| ATOM | 2467 | NH2 | ARG | A | 326 | 44.947 | 52.018 | 108.529 | 1.00 | 21.31 | A |
| ATOM | 2468 | C | ARG | A | 326 | 41.199 | 58.343 | 104.763 | 1.00 | 15.95 | A |
| ATOM | 2469 | O | ARG | A | 326 | 41.204 | 59.244 | 105.607 | 1.00 | 15.73 | A |
| ATOM | 2470 | N | ASP | A | 327 | 41.116 | 58.586 | 103.458 | 1.00 | 14.52 | A |
| ATOM | 2471 | CA | ASP | A | 327 | 41.015 | 59.965 | 102.974 | 1.00 | 16.76 | A |
| ATOM | 2472 | CB | ASP | A | 327 | 41.272 | 60.025 | 101.463 | 1.00 | 17.65 | A |
| ATOM | 2473 | CG | ASP | A | 327 | 42.758 | 59.881 | 101.119 | 1.00 | 22.23 | A |
| ATOM | 2474 | OD1 | ASP | A | 327 | 43.584 | 59.866 | 102.059 | 1.00 | 22.40 | A |
| ATOM | 2475 | OD2 | ASP | A | 327 | 43.105 | 59.789 | 99.917 | 1.00 | 22.97 | A |
| ATOM | 2476 | C | ASP | A | 327 | 39.660 | 60.582 | 103.331 | 1.00 | 15.90 | A |
| ATOM | 2477 | O | ASP | A | 327 | 39.570 | 61.782 | 103.623 | 1.00 | 16.46 | A |
| ATOM | 2478 | N | VAL | A | 328 | 38.610 | 59.767 | 103.317 | 1.00 | 14.20 | A |
| ATOM | 2479 | CA | VAL | A | 328 | 37.278 | 60.247 | 103.685 | 1.00 | 12.95 | A |
| ATOM | 2480 | CB | VAL | A | 328 | 36.187 | 59.206 | 103.338 | 1.00 | 11.54 | A |
| ATOM | 2481 | CG1 | VAL | A | 328 | 34.883 | 59.551 | 104.045 | 1.00 | 13.59 | A |
| ATOM | 2482 | CG2 | VAL | A | 328 | 35.964 | 59.185 | 101.824 | 1.00 | 12.86 | A |
| ATOM | 2483 | C | VAL | A | 328 | 37.281 | 60.513 | 105.188 | 1.00 | 13.33 | A |
| ATOM | 2484 | O | VAL | A | 328 | 36.744 | 61.519 | 105.660 | 1.00 | 13.72 | A |
| ATOM | 2485 | N | LEU | A | 329 | 37.899 | 59.612 | 105.942 | 1.00 | 13.61 | A |
| ATOM | 2486 | CA | LEU | A | 329 | 37.980 | 59.794 | 107.380 | 1.00 | 15.20 | A |
| ATOM | 2487 | CB | LEU | A | 329 | 38.674 | 58.594 | 108.028 | 1.00 | 18.20 | A |
| ATOM | 2488 | CG | LEU | A | 329 | 38.996 | 58.680 | 109.524 | 1.00 | 20.07 | A |
| ATOM | 2489 | CD1 | LEU | A | 329 | 37.723 | 58.841 | 110.346 | 1.00 | 20.82 | A |
| ATOM | 2490 | CD2 | LEU | A | 329 | 39.742 | 57.416 | 109.938 | 1.00 | 21.93 | A |

APPENDIX B-continued

*Arachis hypogaea* STS

| ATOM | # | TYPE | RES | | | X | Y | Z | OCC | B | |
|------|---|------|-----|---|-----|--------|--------|---------|------|-------|---|
| ATOM | 2491 | C | LEU | A | 329 | 38.761 | 61.081 | 107.684 | 1.00 | 15.58 | A |
| ATOM | 2492 | O | LEU | A | 329 | 38.367 | 61.858 | 108.543 | 1.00 | 16.85 | A |
| ATOM | 2493 | N | SER | A | 330 | 39.859 | 61.307 | 106.974 | 1.00 | 15.16 | A |
| ATOM | 2494 | CA | SER | A | 330 | 40.663 | 62.507 | 107.208 | 1.00 | 18.06 | A |
| ATOM | 2495 | CB | SER | A | 330 | 41.946 | 62.489 | 106.371 | 1.00 | 19.28 | A |
| ATOM | 2496 | OG | SER | A | 330 | 42.770 | 61.393 | 106.713 | 1.00 | 25.07 | A |
| ATOM | 2497 | C | SER | A | 330 | 39.933 | 63.800 | 106.901 | 1.00 | 16.71 | A |
| ATOM | 2498 | O | SER | A | 330 | 40.085 | 64.787 | 107.620 | 1.00 | 17.70 | A |
| ATOM | 2499 | N | ASN | A | 331 | 39.146 | 63.791 | 105.832 | 1.00 | 17.19 | A |
| ATOM | 2500 | CA | ASN | A | 331 | 38.434 | 64.984 | 105.390 | 1.00 | 18.16 | A |
| ATOM | 2501 | CB | ASN | A | 331 | 38.402 | 65.014 | 103.858 | 1.00 | 20.73 | A |
| ATOM | 2502 | CG | ASN | A | 331 | 39.792 | 65.061 | 103.251 | 1.00 | 28.36 | A |
| ATOM | 2503 | OD1 | ASN | A | 331 | 40.259 | 64.090 | 102.651 | 1.00 | 30.89 | A |
| ATOM | 2504 | ND2 | ASN | A | 331 | 40.465 | 66.191 | 103.413 | 1.00 | 27.88 | A |
| ATOM | 2505 | C | ASN | A | 331 | 37.019 | 65.203 | 105.917 | 1.00 | 17.12 | A |
| ATOM | 2506 | O | ASN | A | 331 | 36.514 | 66.329 | 105.874 | 1.00 | 14.65 | A |
| ATOM | 2507 | N | TYR | A | 332 | 36.382 | 64.152 | 106.422 | 1.00 | 14.10 | A |
| ATOM | 2508 | CA | TYR | A | 332 | 35.011 | 64.284 | 106.902 | 1.00 | 15.56 | A |
| ATOM | 2509 | CB | TYR | A | 332 | 34.056 | 63.599 | 105.919 | 1.00 | 15.57 | A |
| ATOM | 2510 | CG | TYR | A | 332 | 34.102 | 64.155 | 104.522 | 1.00 | 16.22 | A |
| ATOM | 2511 | CD1 | TYR | A | 332 | 33.342 | 65.269 | 104.165 | 1.00 | 17.52 | A |
| ATOM | 2512 | CE1 | TYR | A | 332 | 33.378 | 65.773 | 102.865 | 1.00 | 19.70 | A |
| ATOM | 2513 | CD2 | TYR | A | 332 | 34.901 | 63.562 | 103.547 | 1.00 | 17.03 | A |
| ATOM | 2514 | CE2 | TYR | A | 332 | 34.945 | 64.055 | 102.254 | 1.00 | 18.80 | A |
| ATOM | 2515 | CZ | TYR | A | 332 | 34.183 | 65.155 | 101.919 | 1.00 | 20.10 | A |
| ATOM | 2516 | OH | TYR | A | 332 | 34.234 | 65.629 | 100.633 | 1.00 | 22.65 | A |
| ATOM | 2517 | C | TYR | A | 332 | 34.732 | 63.728 | 108.285 | 1.00 | 14.80 | A |
| ATOM | 2518 | O | TYR | A | 332 | 33.714 | 64.056 | 108.887 | 1.00 | 13.27 | A |
| ATOM | 2519 | N | GLY | A | 333 | 35.618 | 62.880 | 108.792 | 1.00 | 16.28 | A |
| ATOM | 2520 | CA | GLY | A | 333 | 35.371 | 62.290 | 110.090 | 1.00 | 16.15 | A |
| ATOM | 2521 | C | GLY | A | 333 | 34.397 | 61.131 | 109.935 | 1.00 | 18.11 | A |
| ATOM | 2522 | O | GLY | A | 333 | 34.141 | 60.682 | 108.819 | 1.00 | 17.58 | A |
| ATOM | 2523 | N | ASN | A | 334 | 33.848 | 60.660 | 111.051 | 1.00 | 17.54 | A |
| ATOM | 2524 | CA | ASN | A | 334 | 32.908 | 59.540 | 111.053 | 1.00 | 18.71 | A |
| ATOM | 2525 | CB | ASN | A | 334 | 33.058 | 58.749 | 112.361 | 1.00 | 17.01 | A |
| ATOM | 2526 | CG | ASN | A | 334 | 32.251 | 57.462 | 112.370 | 1.00 | 21.08 | A |
| ATOM | 2527 | OD1 | ASN | A | 334 | 31.230 | 57.342 | 111.691 | 1.00 | 21.26 | A |
| ATOM | 2528 | ND2 | ASN | A | 334 | 32.700 | 56.493 | 113.160 | 1.00 | 19.04 | A |
| ATOM | 2529 | C | ASN | A | 334 | 31.459 | 60.008 | 110.898 | 1.00 | 16.98 | A |
| ATOM | 2530 | O | ASN | A | 334 | 30.834 | 60.434 | 111.867 | 1.00 | 16.99 | A |
| ATOM | 2531 | N | MET | A | 335 | 30.931 | 59.911 | 109.678 | 1.00 | 16.95 | A |
| ATOM | 2532 | CA | MET | A | 335 | 29.559 | 60.317 | 109.381 | 1.00 | 17.01 | A |
| ATOM | 2533 | CB | MET | A | 335 | 29.506 | 60.953 | 107.986 | 1.00 | 15.24 | A |
| ATOM | 2534 | CG | MET | A | 335 | 30.446 | 62.147 | 107.832 | 1.00 | 13.35 | A |
| ATOM | 2535 | SD | MET | A | 335 | 30.472 | 62.793 | 106.156 | 1.00 | 14.73 | A |
| ATOM | 2536 | CE | MET | A | 335 | 31.510 | 61.522 | 105.336 | 1.00 | 11.91 | A |
| ATOM | 2537 | C | MET | A | 335 | 28.552 | 59.160 | 109.469 | 1.00 | 18.59 | A |
| ATOM | 2538 | O | MET | A | 335 | 27.514 | 59.167 | 108.806 | 1.00 | 17.45 | A |
| ATOM | 2539 | N | SER | A | 336 | 28.860 | 58.170 | 110.299 | 1.00 | 16.90 | A |
| ATOM | 2540 | CA | SER | A | 336 | 27.984 | 57.015 | 110.470 | 1.00 | 17.61 | A |
| ATOM | 2541 | CB | SER | A | 336 | 26.719 | 57.421 | 111.241 | 1.00 | 19.09 | A |
| ATOM | 2542 | OG | SER | A | 336 | 25.946 | 56.279 | 111.582 | 1.00 | 22.75 | A |
| ATOM | 2543 | C | SER | A | 336 | 27.602 | 56.337 | 109.144 | 1.00 | 16.31 | A |
| ATOM | 2544 | O | SER | A | 336 | 28.465 | 56.038 | 108.324 | 1.00 | 15.30 | A |
| ATOM | 2545 | N | SER | A | 337 | 26.313 | 56.103 | 108.925 | 1.00 | 17.61 | A |
| ATOM | 2546 | CA | SER | A | 337 | 25.875 | 55.419 | 107.708 | 1.00 | 18.36 | A |
| ATOM | 2547 | CB | SER | A | 337 | 24.351 | 55.237 | 107.722 | 1.00 | 20.03 | A |
| ATOM | 2548 | OG | SER | A | 337 | 23.682 | 56.467 | 107.520 | 1.00 | 23.69 | A |
| ATOM | 2549 | C | SER | A | 337 | 26.295 | 56.038 | 106.367 | 1.00 | 18.79 | A |
| ATOM | 2550 | O | SER | A | 337 | 26.441 | 55.320 | 105.378 | 1.00 | 19.51 | A |
| ATOM | 2551 | N | ALA | A | 338 | 26.499 | 57.352 | 106.319 | 1.00 | 16.65 | A |
| ATOM | 2552 | CA | ALA | A | 338 | 26.879 | 57.996 | 105.059 | 1.00 | 15.68 | A |
| ATOM | 2553 | CB | ALA | A | 338 | 26.664 | 59.499 | 105.162 | 1.00 | 15.38 | A |
| ATOM | 2554 | C | ALA | A | 338 | 28.313 | 57.703 | 104.595 | 1.00 | 16.86 | A |
| ATOM | 2555 | O | ALA | A | 338 | 28.601 | 57.725 | 103.396 | 1.00 | 14.14 | A |
| ATOM | 2556 | N | CYS | A | 339 | 29.205 | 57.409 | 105.540 | 1.00 | 17.12 | A |
| ATOM | 2557 | CA | CYS | A | 339 | 30.611 | 57.142 | 105.222 | 1.00 | 18.43 | A |
| ATOM | 2558 | CB | CYS | A | 339 | 31.313 | 56.504 | 106.420 | 1.00 | 20.52 | A |
| ATOM | 2559 | SG | CYS | A | 339 | 31.572 | 57.633 | 107.785 | 1.00 | 28.72 | A |
| ATOM | 2560 | C | CYS | A | 339 | 30.936 | 56.309 | 103.994 | 1.00 | 17.20 | A |
| ATOM | 2561 | O | CYS | A | 339 | 31.583 | 56.789 | 103.068 | 1.00 | 16.64 | A |
| ATOM | 2562 | N | VAL | A | 340 | 30.507 | 55.052 | 103.986 | 1.00 | 15.01 | A |
| ATOM | 2563 | CA | VAL | A | 340 | 30.824 | 54.181 | 102.865 | 1.00 | 15.41 | A |
| ATOM | 2564 | CB | VAL | A | 340 | 30.187 | 52.785 | 103.054 | 1.00 | 15.58 | A |
| ATOM | 2565 | CG1 | VAL | A | 340 | 30.751 | 52.143 | 104.320 | 1.00 | 17.48 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 2566 | CG2 | VAL | A | 340 | 28.678 | 52.900 | 103.154 | 1.00 | 14.74 | A |
| ATOM | 2567 | C | VAL | A | 340 | 30.449 | 54.741 | 101.493 | 1.00 | 13.89 | A |
| ATOM | 2568 | O | VAL | A | 340 | 31.066 | 54.385 | 100.495 | 1.00 | 15.42 | A |
| ATOM | 2569 | N | PHE | A | 341 | 29.456 | 55.623 | 101.441 | 1.00 | 13.57 | A |
| ATOM | 2570 | CA | PHE | A | 341 | 29.042 | 56.194 | 100.161 | 1.00 | 12.42 | A |
| ATOM | 2571 | CB | PHE | A | 341 | 27.574 | 56.622 | 100.232 | 1.00 | 12.79 | A |
| ATOM | 2572 | CG | PHE | A | 341 | 26.655 | 55.482 | 100.543 | 1.00 | 13.77 | A |
| ATOM | 2573 | CD1 | PHE | A | 341 | 26.541 | 54.414 | 99.661 | 1.00 | 16.75 | A |
| ATOM | 2574 | CD2 | PHE | A | 341 | 25.992 | 55.417 | 101.763 | 1.00 | 17.19 | A |
| ATOM | 2575 | CE1 | PHE | A | 341 | 25.788 | 53.287 | 99.992 | 1.00 | 17.00 | A |
| ATOM | 2576 | CE2 | PHE | A | 341 | 25.234 | 54.291 | 102.108 | 1.00 | 18.62 | A |
| ATOM | 2577 | CZ | PHE | A | 341 | 25.137 | 53.224 | 101.216 | 1.00 | 18.80 | A |
| ATOM | 2578 | C | PHE | A | 341 | 29.957 | 57.334 | 99.732 | 1.00 | 13.00 | A |
| ATOM | 2579 | O | PHE | A | 341 | 30.159 | 57.550 | 98.537 | 1.00 | 13.53 | A |
| ATOM | 2580 | N | PHE | A | 342 | 30.524 | 58.056 | 100.698 | 1.00 | 13.71 | A |
| ATOM | 2581 | CA | PHE | A | 342 | 31.476 | 59.116 | 100.361 | 1.00 | 13.53 | A |
| ATOM | 2582 | CB | PHE | A | 342 | 31.854 | 59.952 | 101.592 | 1.00 | 13.59 | A |
| ATOM | 2583 | CG | PHE | A | 342 | 30.880 | 61.058 | 101.907 | 1.00 | 14.46 | A |
| ATOM | 2584 | CD1 | PHE | A | 342 | 29.606 | 60.776 | 102.386 | 1.00 | 12.57 | A |
| ATOM | 2585 | CD2 | PHE | A | 342 | 31.254 | 62.388 | 101.738 | 1.00 | 17.01 | A |
| ATOM | 2586 | CE1 | PHE | A | 342 | 28.708 | 61.813 | 102.702 | 1.00 | 15.37 | A |
| ATOM | 2587 | CE2 | PHE | A | 342 | 30.369 | 63.429 | 102.047 | 1.00 | 15.22 | A |
| ATOM | 2588 | CZ | PHE | A | 342 | 29.097 | 63.140 | 102.531 | 1.00 | 14.23 | A |
| ATOM | 2589 | C | PHE | A | 342 | 32.731 | 58.410 | 99.836 | 1.00 | 12.98 | A |
| ATOM | 2590 | O | PHE | A | 342 | 33.405 | 58.895 | 98.932 | 1.00 | 11.91 | A |
| ATOM | 2591 | N | ILE | A | 343 | 33.033 | 57.248 | 100.412 | 1.00 | 12.62 | A |
| ATOM | 2592 | CA | ILE | A | 343 | 34.201 | 56.473 | 100.011 | 1.00 | 13.59 | A |
| ATOM | 2593 | CB | ILE | A | 343 | 34.500 | 55.344 | 101.038 | 1.00 | 12.49 | A |
| ATOM | 2594 | CG2 | ILE | A | 343 | 35.671 | 54.512 | 100.561 | 1.00 | 12.36 | A |
| ATOM | 2595 | CG1 | ILE | A | 343 | 34.814 | 55.964 | 102.412 | 1.00 | 14.83 | A |
| ATOM | 2596 | CD1 | ILE | A | 343 | 34.874 | 54.980 | 103.572 | 1.00 | 13.14 | A |
| ATOM | 2597 | C | ILE | A | 343 | 33.962 | 55.868 | 98.627 | 1.00 | 13.20 | A |
| ATOM | 2598 | O | ILE | A | 343 | 34.832 | 55.911 | 97.764 | 1.00 | 13.62 | A |
| ATOM | 2599 | N | MET | A | 344 | 32.782 | 55.293 | 98.427 | 1.00 | 13.40 | A |
| ATOM | 2600 | CA | MET | A | 344 | 32.427 | 54.721 | 97.131 | 1.00 | 13.12 | A |
| ATOM | 2601 | CB | MET | A | 344 | 31.003 | 54.157 | 97.188 | 1.00 | 14.23 | A |
| ATOM | 2602 | CG | MET | A | 344 | 30.511 | 53.546 | 95.877 | 1.00 | 16.48 | A |
| ATOM | 2603 | SD | MET | A | 344 | 28.804 | 52.931 | 95.975 | 1.00 | 17.54 | A |
| ATOM | 2604 | CE | MET | A | 344 | 29.016 | 51.477 | 97.056 | 1.00 | 17.01 | A |
| ATOM | 2605 | C | MET | A | 344 | 32.506 | 55.817 | 96.060 | 1.00 | 11.32 | A |
| ATOM | 2606 | O | MET | A | 344 | 33.005 | 55.599 | 94.959 | 1.00 | 10.54 | A |
| ATOM | 2607 | N | ASP | A | 345 | 32.025 | 57.008 | 96.399 | 1.00 | 12.42 | A |
| ATOM | 2608 | CA | ASP | A | 345 | 32.021 | 58.121 | 95.445 | 1.00 | 13.38 | A |
| ATOM | 2609 | CB | ASP | A | 345 | 31.203 | 59.298 | 96.006 | 1.00 | 11.94 | A |
| ATOM | 2610 | CG | ASP | A | 345 | 30.908 | 60.365 | 94.957 | 1.00 | 19.30 | A |
| ATOM | 2611 | OD1 | ASP | A | 345 | 30.675 | 60.005 | 93.781 | 1.00 | 17.49 | A |
| ATOM | 2612 | OD2 | ASP | A | 345 | 30.896 | 61.566 | 95.313 | 1.00 | 22.09 | A |
| ATOM | 2613 | C | ASP | A | 345 | 33.442 | 58.557 | 95.108 | 1.00 | 12.01 | A |
| ATOM | 2614 | O | ASP | A | 345 | 33.761 | 58.776 | 93.943 | 1.00 | 11.34 | A |
| ATOM | 2615 | N | LEU | A | 346 | 34.291 | 58.669 | 96.126 | 1.00 | 11.80 | A |
| ATOM | 2616 | CA | LEU | A | 346 | 35.687 | 59.055 | 95.932 | 1.00 | 12.85 | A |
| ATOM | 2617 | CB | LEU | A | 346 | 36.409 | 59.176 | 97.274 | 1.00 | 12.43 | A |
| ATOM | 2618 | CG | LEU | A | 346 | 37.879 | 59.603 | 97.208 | 1.00 | 14.56 | A |
| ATOM | 2619 | CD1 | LEU | A | 346 | 37.981 | 60.981 | 96.550 | 1.00 | 16.43 | A |
| ATOM | 2620 | CD2 | LEU | A | 346 | 38.462 | 59.650 | 98.612 | 1.00 | 14.89 | A |
| ATOM | 2621 | C | LEU | A | 346 | 36.413 | 58.012 | 95.097 | 1.00 | 12.74 | A |
| ATOM | 2622 | O | LEU | A | 346 | 37.178 | 58.348 | 94.199 | 1.00 | 12.63 | A |
| ATOM | 2623 | N | MET | A | 347 | 36.172 | 56.741 | 95.402 | 1.00 | 11.90 | A |
| ATOM | 2624 | CA | MET | A | 347 | 36.832 | 55.667 | 94.675 | 1.00 | 13.12 | A |
| ATOM | 2625 | CB | MET | A | 347 | 36.423 | 54.298 | 95.223 | 1.00 | 15.14 | A |
| ATOM | 2626 | CG | MET | A | 347 | 37.188 | 53.175 | 94.563 | 1.00 | 13.55 | A |
| ATOM | 2627 | SD | MET | A | 347 | 36.836 | 51.538 | 95.229 | 1.00 | 18.57 | A |
| ATOM | 2628 | CE | MET | A | 347 | 37.681 | 51.612 | 96.825 | 1.00 | 16.80 | A |
| ATOM | 2629 | C | MET | A | 347 | 36.533 | 55.698 | 93.185 | 1.00 | 13.68 | A |
| ATOM | 2630 | O | MET | A | 347 | 37.449 | 55.649 | 92.371 | 1.00 | 13.15 | A |
| ATOM | 2631 | N | ARG | A | 348 | 35.258 | 55.767 | 92.816 | 1.00 | 13.41 | A |
| ATOM | 2632 | CA | ARG | A | 348 | 34.940 | 55.795 | 91.398 | 1.00 | 13.56 | A |
| ATOM | 2633 | CB | ARG | A | 348 | 33.434 | 55.614 | 91.175 | 1.00 | 14.13 | A |
| ATOM | 2634 | CG | ARG | A | 348 | 32.567 | 56.688 | 91.771 | 1.00 | 16.43 | A |
| ATOM | 2635 | CD | ARG | A | 348 | 31.890 | 57.508 | 90.683 | 1.00 | 15.10 | A |
| ATOM | 2636 | NE | ARG | A | 348 | 30.971 | 58.478 | 91.263 | 1.00 | 17.74 | A |
| ATOM | 2637 | CZ | ARG | A | 348 | 29.944 | 59.021 | 90.614 | 1.00 | 19.42 | A |
| ATOM | 2638 | NH1 | ARG | A | 348 | 29.692 | 58.693 | 89.350 | 1.00 | 17.83 | A |
| ATOM | 2639 | NH2 | ARG | A | 348 | 29.161 | 59.883 | 91.236 | 1.00 | 18.56 | A |
| ATOM | 2640 | C | ARG | A | 348 | 35.440 | 57.076 | 90.733 | 1.00 | 13.82 | A |

APPENDIX B-continued

*Arachis hypogaea* STS

| ATOM | # | TYPE | RES | | | X | Y | Z | OCC | B | |
|---|---|---|---|---|---|---|---|---|---|---|---|
| ATOM | 2641 | O | ARG | A | 348 | 35.909 | 57.042 | 89.596 | 1.00 | 12.96 | A |
| ATOM | 2642 | N | LYS | A | 349 | 35.352 | 58.202 | 91.436 | 1.00 | 14.40 | A |
| ATOM | 2643 | CA | LYS | A | 349 | 35.815 | 59.463 | 90.866 | 1.00 | 16.03 | A |
| ATOM | 2644 | CB | LYS | A | 349 | 35.438 | 60.639 | 91.779 | 1.00 | 19.29 | A |
| ATOM | 2645 | CG | LYS | A | 349 | 33.987 | 61.107 | 91.627 | 1.00 | 22.73 | A |
| ATOM | 2646 | CD | LYS | A | 349 | 33.657 | 62.225 | 92.615 | 1.00 | 25.81 | A |
| ATOM | 2647 | CE | LYS | A | 349 | 32.356 | 62.941 | 92.264 | 1.00 | 28.02 | A |
| ATOM | 2648 | NZ | LYS | A | 349 | 31.184 | 62.031 | 92.147 | 1.00 | 29.68 | A |
| ATOM | 2649 | C | LYS | A | 349 | 37.325 | 59.441 | 90.624 | 1.00 | 16.60 | A |
| ATOM | 2650 | O | LYS | A | 349 | 37.803 | 59.892 | 89.583 | 1.00 | 15.58 | A |
| ATOM | 2651 | N | ARG | A | 350 | 38.080 | 58.917 | 91.582 | 1.00 | 16.64 | A |
| ATOM | 2652 | CA | ARG | A | 350 | 39.527 | 58.845 | 91.430 | 1.00 | 16.97 | A |
| ATOM | 2653 | CB | ARG | A | 350 | 40.191 | 58.429 | 92.738 | 1.00 | 19.36 | A |
| ATOM | 2654 | CG | ARG | A | 350 | 40.260 | 59.531 | 93.768 | 1.00 | 23.11 | A |
| ATOM | 2655 | CD | ARG | A | 350 | 41.012 | 59.072 | 95.001 | 1.00 | 25.31 | A |
| ATOM | 2656 | NE | ARG | A | 350 | 41.301 | 60.187 | 95.897 | 1.00 | 26.05 | A |
| ATOM | 2657 | CZ | ARG | A | 350 | 41.851 | 60.050 | 97.096 | 1.00 | 25.60 | A |
| ATOM | 2658 | NH1 | ARG | A | 350 | 42.174 | 58.842 | 97.540 | 1.00 | 24.33 | A |
| ATOM | 2659 | NH2 | ARG | A | 350 | 42.070 | 61.118 | 97.851 | 1.00 | 27.53 | A |
| ATOM | 2660 | C | ARG | A | 350 | 39.921 | 57.863 | 90.342 | 1.00 | 16.79 | A |
| ATOM | 2661 | O | ARG | A | 350 | 40.840 | 58.132 | 89.574 | 1.00 | 15.18 | A |
| ATOM | 2662 | N | SER | A | 351 | 39.237 | 56.723 | 90.276 | 1.00 | 15.93 | A |
| ATOM | 2663 | CA | SER | A | 351 | 39.559 | 55.731 | 89.257 | 1.00 | 15.20 | A |
| ATOM | 2664 | CB | SER | A | 351 | 38.727 | 54.462 | 89.468 | 1.00 | 16.39 | A |
| ATOM | 2665 | OG | SER | A | 351 | 39.017 | 53.893 | 90.735 | 1.00 | 14.41 | A |
| ATOM | 2666 | C | SER | A | 351 | 39.316 | 56.319 | 87.863 | 1.00 | 15.10 | A |
| ATOM | 2667 | O | SER | A | 351 | 40.113 | 56.122 | 86.946 | 1.00 | 13.78 | A |
| ATOM | 2668 | N | LEU | A | 352 | 38.221 | 57.056 | 87.716 | 1.00 | 16.59 | A |
| ATOM | 2669 | CA | LEU | A | 352 | 37.897 | 57.692 | 86.444 | 1.00 | 18.06 | A |
| ATOM | 2670 | CB | LEU | A | 352 | 36.540 | 58.389 | 86.541 | 1.00 | 19.15 | A |
| ATOM | 2671 | CG | LEU | A | 352 | 35.292 | 57.505 | 86.519 | 1.00 | 19.76 | A |
| ATOM | 2672 | CD1 | LEU | A | 352 | 34.098 | 58.301 | 87.018 | 1.00 | 21.28 | A |
| ATOM | 2673 | CD2 | LEU | A | 352 | 35.053 | 56.988 | 85.112 | 1.00 | 21.19 | A |
| ATOM | 2674 | C | LEU | A | 352 | 38.969 | 58.725 | 86.097 | 1.00 | 19.07 | A |
| ATOM | 2675 | O | LEU | A | 352 | 39.462 | 58.779 | 84.968 | 1.00 | 17.65 | A |
| ATOM | 2676 | N | GLU | A | 353 | 39.322 | 59.540 | 87.086 | 1.00 | 19.59 | A |
| ATOM | 2677 | CA | GLU | A | 353 | 40.320 | 60.594 | 86.921 | 1.00 | 20.60 | A |
| ATOM | 2678 | CB | GLU | A | 353 | 40.422 | 61.400 | 88.218 | 1.00 | 23.38 | A |
| ATOM | 2679 | CG | GLU | A | 353 | 41.485 | 62.485 | 88.211 | 1.00 | 27.60 | A |
| ATOM | 2680 | CD | GLU | A | 353 | 41.544 | 63.238 | 89.530 | 1.00 | 29.84 | A |
| ATOM | 2681 | OE1 | GLU | A | 353 | 41.839 | 62.606 | 90.570 | 1.00 | 31.36 | A |
| ATOM | 2682 | OE2 | GLU | A | 353 | 41.290 | 64.460 | 89.525 | 1.00 | 32.62 | A |
| ATOM | 2683 | C | GLU | A | 353 | 41.700 | 60.070 | 86.532 | 1.00 | 20.58 | A |
| ATOM | 2684 | O | GLU | A | 353 | 42.410 | 60.696 | 85.739 | 1.00 | 18.53 | A |
| ATOM | 2685 | N | GLU | A | 354 | 42.075 | 58.919 | 87.089 | 1.00 | 19.90 | A |
| ATOM | 2686 | CA | GLU | A | 354 | 43.379 | 58.318 | 86.823 | 1.00 | 20.37 | A |
| ATOM | 2687 | CB | GLU | A | 354 | 43.824 | 57.507 | 88.052 | 1.00 | 24.66 | A |
| ATOM | 2688 | CG | GLU | A | 354 | 43.839 | 58.333 | 89.339 | 1.00 | 27.87 | A |
| ATOM | 2689 | CD | GLU | A | 354 | 43.942 | 57.486 | 90.598 | 1.00 | 31.64 | A |
| ATOM | 2690 | OE1 | GLU | A | 354 | 43.427 | 56.346 | 90.602 | 1.00 | 31.88 | A |
| ATOM | 2691 | OE2 | GLU | A | 354 | 44.518 | 57.972 | 91.595 | 1.00 | 32.79 | A |
| ATOM | 2692 | C | GLU | A | 354 | 43.396 | 57.437 | 85.574 | 1.00 | 21.48 | A |
| ATOM | 2693 | O | GLU | A | 354 | 44.415 | 56.819 | 85.253 | 1.00 | 19.63 | A |
| ATOM | 2694 | N | GLY | A | 355 | 42.268 | 57.390 | 84.872 | 1.00 | 19.45 | A |
| ATOM | 2695 | CA | GLY | A | 355 | 42.166 | 56.588 | 83.664 | 1.00 | 21.36 | A |
| ATOM | 2696 | C | GLY | A | 355 | 42.349 | 55.093 | 83.868 | 1.00 | 21.53 | A |
| ATOM | 2697 | O | GLY | A | 355 | 42.909 | 54.419 | 83.010 | 1.00 | 21.87 | A |
| ATOM | 2698 | N | LEU | A | 356 | 41.869 | 54.569 | 84.992 | 1.00 | 20.13 | A |
| ATOM | 2699 | CA | LEU | A | 356 | 42.001 | 53.141 | 85.289 | 1.00 | 20.12 | A |
| ATOM | 2700 | CB | LEU | A | 356 | 41.774 | 52.898 | 86.783 | 1.00 | 20.13 | A |
| ATOM | 2701 | CG | LEU | A | 356 | 42.667 | 53.735 | 87.711 | 1.00 | 19.29 | A |
| ATOM | 2702 | CD1 | LEU | A | 356 | 42.382 | 53.378 | 89.163 | 1.00 | 19.65 | A |
| ATOM | 2703 | CD2 | LEU | A | 356 | 44.129 | 53.492 | 87.381 | 1.00 | 19.63 | A |
| ATOM | 2704 | C | LEU | A | 356 | 41.042 | 52.287 | 84.460 | 1.00 | 20.67 | A |
| ATOM | 2705 | O | LEU | A | 356 | 40.156 | 52.817 | 83.785 | 1.00 | 18.66 | A |
| ATOM | 2706 | N | LYS | A | 357 | 41.218 | 50.966 | 84.523 | 1.00 | 19.35 | A |
| ATOM | 2707 | CA | LYS | A | 357 | 40.398 | 50.030 | 83.754 | 1.00 | 19.96 | A |
| ATOM | 2708 | CB | LYS | A | 357 | 41.085 | 48.663 | 83.692 | 1.00 | 23.34 | A |
| ATOM | 2709 | CG | LYS | A | 357 | 42.598 | 48.754 | 83.565 | 1.00 | 30.70 | A |
| ATOM | 2710 | CD | LYS | A | 357 | 43.246 | 47.382 | 83.544 | 1.00 | 33.70 | A |
| ATOM | 2711 | CE | LYS | A | 357 | 42.888 | 46.623 | 82.278 | 1.00 | 36.65 | A |
| ATOM | 2712 | NZ | LYS | A | 357 | 43.583 | 45.304 | 82.212 | 1.00 | 38.22 | A |
| ATOM | 2713 | C | LYS | A | 357 | 38.979 | 49.843 | 84.276 | 1.00 | 18.13 | A |
| ATOM | 2714 | O | LYS | A | 357 | 38.084 | 49.476 | 83.517 | 1.00 | 18.43 | A |
| ATOM | 2715 | N | THR | A | 358 | 38.771 | 50.068 | 85.569 | 1.00 | 15.16 | A |

APPENDIX B-continued

*Arachis hypogaea* STS

| ATOM | # | TYPE | RES | | | X | Y | Z | OCC | B | |
|------|---|------|-----|---|---|---|---|---|-----|---|---|
| ATOM | 2716 | CA | THR | A | 358 | 37.442 | 49.918 | 86.150 | 1.00 | 14.31 | A |
| ATOM | 2717 | CB | THR | A | 358 | 37.243 | 48.550 | 86.838 | 1.00 | 14.13 | A |
| ATOM | 2718 | OG1 | THR | A | 358 | 37.870 | 48.575 | 88.131 | 1.00 | 15.36 | A |
| ATOM | 2719 | CG2 | THR | A | 358 | 37.830 | 47.424 | 85.995 | 1.00 | 14.35 | A |
| ATOM | 2720 | C | THR | A | 358 | 37.218 | 50.970 | 87.218 | 1.00 | 14.15 | A |
| ATOM | 2721 | O | THR | A | 358 | 38.165 | 51.593 | 87.689 | 1.00 | 15.99 | A |
| ATOM | 2722 | N | THR | A | 359 | 35.963 | 51.132 | 87.620 | 1.00 | 13.93 | A |
| ATOM | 2723 | CA | THR | A | 359 | 35.594 | 52.101 | 88.645 | 1.00 | 14.78 | A |
| ATOM | 2724 | CB | THR | A | 359 | 34.074 | 52.257 | 88.732 | 1.00 | 17.18 | A |
| ATOM | 2725 | OG1 | THR | A | 359 | 33.472 | 50.957 | 88.692 | 1.00 | 16.70 | A |
| ATOM | 2726 | CG2 | THR | A | 359 | 33.544 | 53.102 | 87.570 | 1.00 | 18.46 | A |
| ATOM | 2727 | C | THR | A | 359 | 36.095 | 51.664 | 90.015 | 1.00 | 14.99 | A |
| ATOM | 2728 | O | THR | A | 359 | 36.123 | 52.459 | 90.949 | 1.00 | 14.02 | A |
| ATOM | 2729 | N | GLY | A | 360 | 36.478 | 50.395 | 90.128 | 1.00 | 13.30 | A |
| ATOM | 2730 | CA | GLY | A | 360 | 36.970 | 49.879 | 91.392 | 1.00 | 14.14 | A |
| ATOM | 2731 | C | GLY | A | 360 | 38.486 | 49.805 | 91.423 | 1.00 | 14.17 | A |
| ATOM | 2732 | O | GLY | A | 360 | 39.066 | 48.736 | 91.628 | 1.00 | 13.42 | A |
| ATOM | 2733 | N | GLU | A | 361 | 39.131 | 50.947 | 91.214 | 1.00 | 14.93 | A |
| ATOM | 2734 | CA | GLU | A | 361 | 40.590 | 51.025 | 91.214 | 1.00 | 16.26 | A |
| ATOM | 2735 | CB | GLU | A | 361 | 41.131 | 50.779 | 92.633 | 1.00 | 16.95 | A |
| ATOM | 2736 | CG | GLU | A | 361 | 40.426 | 51.624 | 93.709 | 1.00 | 21.62 | A |
| ATOM | 2737 | CD | GLU | A | 361 | 41.057 | 51.514 | 95.098 | 1.00 | 23.55 | A |
| ATOM | 2738 | OE1 | GLU | A | 361 | 41.466 | 50.403 | 95.497 | 1.00 | 24.80 | A |
| ATOM | 2739 | OE2 | GLU | A | 361 | 41.124 | 52.544 | 95.804 | 1.00 | 24.47 | A |
| ATOM | 2740 | C | GLU | A | 361 | 41.229 | 50.052 | 90.210 | 1.00 | 15.01 | A |
| ATOM | 2741 | O | GLU | A | 361 | 42.313 | 49.512 | 90.437 | 1.00 | 14.46 | A |
| ATOM | 2742 | N | GLY | A | 362 | 40.550 | 49.841 | 89.089 | 1.00 | 13.08 | A |
| ATOM | 2743 | CA | GLY | A | 362 | 41.071 | 48.955 | 88.066 | 1.00 | 16.80 | A |
| ATOM | 2744 | C | GLY | A | 362 | 40.894 | 47.472 | 88.342 | 1.00 | 17.02 | A |
| ATOM | 2745 | O | GLY | A | 362 | 41.318 | 46.641 | 87.539 | 1.00 | 18.60 | A |
| ATOM | 2746 | N | LEU | A | 363 | 40.281 | 47.134 | 89.473 | 1.00 | 17.18 | A |
| ATOM | 2747 | CA | LEU | A | 363 | 40.051 | 45.740 | 89.827 | 1.00 | 18.00 | A |
| ATOM | 2748 | CB | LEU | A | 363 | 40.383 | 45.514 | 91.307 | 1.00 | 19.02 | A |
| ATOM | 2749 | CG | LEU | A | 363 | 41.826 | 45.853 | 91.697 | 1.00 | 19.57 | A |
| ATOM | 2750 | CD1 | LEU | A | 363 | 42.048 | 45.584 | 93.180 | 1.00 | 20.85 | A |
| ATOM | 2751 | CD2 | LEU | A | 363 | 42.781 | 45.022 | 90.863 | 1.00 | 22.14 | A |
| ATOM | 2752 | C | LEU | A | 363 | 38.590 | 45.367 | 89.541 | 1.00 | 17.57 | A |
| ATOM | 2753 | O | LEU | A | 363 | 37.718 | 46.238 | 89.508 | 1.00 | 17.19 | A |
| ATOM | 2754 | N | ASP | A | 364 | 38.323 | 44.079 | 89.332 | 1.00 | 17.36 | A |
| ATOM | 2755 | CA | ASP | A | 364 | 36.961 | 43.629 | 89.030 | 1.00 | 17.54 | A |
| ATOM | 2756 | CB | ASP | A | 364 | 36.985 | 42.329 | 88.214 | 1.00 | 21.31 | A |
| ATOM | 2757 | CG | ASP | A | 364 | 37.599 | 42.504 | 86.835 | 1.00 | 24.11 | A |
| ATOM | 2758 | OD1 | ASP | A | 364 | 37.602 | 43.638 | 86.305 | 1.00 | 23.48 | A |
| ATOM | 2759 | OD2 | ASP | A | 364 | 38.064 | 41.487 | 86.272 | 1.00 | 25.37 | A |
| ATOM | 2760 | C | ASP | A | 364 | 36.027 | 43.418 | 90.226 | 1.00 | 17.38 | A |
| ATOM | 2761 | O | ASP | A | 364 | 34.835 | 43.728 | 90.143 | 1.00 | 15.70 | A |
| ATOM | 2762 | N | TRP | A | 365 | 36.542 | 42.870 | 91.324 | 1.00 | 14.37 | A |
| ATOM | 2763 | CA | TRP | A | 365 | 35.699 | 42.634 | 92.491 | 1.00 | 16.23 | A |
| ATOM | 2764 | CB | TRP | A | 365 | 35.699 | 41.148 | 92.877 | 1.00 | 19.04 | A |
| ATOM | 2765 | CG | TRP | A | 365 | 35.319 | 40.238 | 91.760 | 1.00 | 22.12 | A |
| ATOM | 2766 | CD2 | TRP | A | 365 | 34.027 | 39.675 | 91.515 | 1.00 | 23.55 | A |
| ATOM | 2767 | CE2 | TRP | A | 365 | 34.123 | 38.908 | 90.331 | 1.00 | 25.41 | A |
| ATOM | 2768 | CE3 | TRP | A | 365 | 32.795 | 39.745 | 92.179 | 1.00 | 22.91 | A |
| ATOM | 2769 | CD1 | TRP | A | 365 | 36.126 | 39.803 | 90.750 | 1.00 | 23.60 | A |
| ATOM | 2770 | NE1 | TRP | A | 365 | 35.415 | 39.003 | 89.886 | 1.00 | 24.40 | A |
| ATOM | 2771 | CZ2 | TRP | A | 365 | 33.031 | 38.214 | 89.794 | 1.00 | 25.90 | A |
| ATOM | 2772 | CZ3 | TRP | A | 365 | 31.707 | 39.054 | 91.645 | 1.00 | 25.49 | A |
| ATOM | 2773 | CH2 | TRP | A | 365 | 31.835 | 38.299 | 90.464 | 1.00 | 28.06 | A |
| ATOM | 2774 | C | TRP | A | 365 | 36.131 | 43.449 | 93.704 | 1.00 | 13.48 | A |
| ATOM | 2775 | O | TRP | A | 365 | 37.304 | 43.791 | 93.849 | 1.00 | 16.37 | A |
| ATOM | 2776 | N | GLY | A | 366 | 35.170 | 43.735 | 94.575 | 1.00 | 14.49 | A |
| ATOM | 2777 | CA | GLY | A | 366 | 35.452 | 44.497 | 95.774 | 1.00 | 15.11 | A |
| ATOM | 2778 | C | GLY | A | 366 | 34.515 | 44.126 | 96.907 | 1.00 | 14.59 | A |
| ATOM | 2779 | O | GLY | A | 366 | 33.565 | 43.361 | 96.732 | 1.00 | 16.03 | A |
| ATOM | 2780 | N | VAL | A | 367 | 34.791 | 44.674 | 98.082 | 1.00 | 14.23 | A |
| ATOM | 2781 | CA | VAL | A | 367 | 33.981 | 44.422 | 99.258 | 1.00 | 12.28 | A |
| ATOM | 2782 | CB | VAL | A | 367 | 34.721 | 43.482 | 100.248 | 1.00 | 12.07 | A |
| ATOM | 2783 | CG1 | VAL | A | 367 | 35.988 | 44.156 | 100.753 | 1.00 | 13.16 | A |
| ATOM | 2784 | CG2 | VAL | A | 367 | 33.820 | 43.111 | 101.406 | 1.00 | 10.94 | A |
| ATOM | 2785 | C | VAL | A | 367 | 33.705 | 45.749 | 99.957 | 1.00 | 11.97 | A |
| ATOM | 2786 | O | VAL | A | 367 | 34.550 | 46.650 | 99.961 | 1.00 | 13.50 | A |
| ATOM | 2787 | N | LEU | A | 368 | 32.510 | 45.864 | 100.521 | 1.00 | 13.10 | A |
| ATOM | 2788 | CA | LEU | A | 368 | 32.103 | 47.049 | 101.273 | 1.00 | 14.05 | A |
| ATOM | 2789 | CB | LEU | A | 368 | 30.920 | 47.755 | 100.581 | 1.00 | 13.70 | A |
| ATOM | 2790 | CG | LEU | A | 368 | 30.298 | 48.978 | 101.269 | 1.00 | 12.89 | A |

APPENDIX B-continued

*Arachis hypogaea* STS

| ATOM | # | TYPE | RES | | | X | Y | Z | OCC | B | |
|------|---|------|-----|---|---|---|---|---|-----|---|---|
| ATOM | 2791 | CD1 | LEU | A | 368 | 29.573 | 49.875 | 100.259 | 1.00 | 13.87 | A |
| ATOM | 2792 | CD2 | LEU | A | 368 | 29.340 | 48.498 | 102.343 | 1.00 | 16.70 | A |
| ATOM | 2793 | C | LEU | A | 368 | 31.710 | 46.526 | 102.652 | 1.00 | 14.47 | A |
| ATOM | 2794 | O | LEU | A | 368 | 30.937 | 45.564 | 102.760 | 1.00 | 15.42 | A |
| ATOM | 2795 | N | PHE | A | 369 | 32.271 | 47.136 | 103.697 | 1.00 | 15.36 | A |
| ATOM | 2796 | CA | PHE | A | 369 | 32.017 | 46.735 | 105.081 | 1.00 | 15.36 | A |
| ATOM | 2797 | CB | PHE | A | 369 | 33.328 | 46.375 | 105.795 | 1.00 | 17.30 | A |
| ATOM | 2798 | CG | PHE | A | 369 | 33.837 | 44.996 | 105.504 | 1.00 | 16.57 | A |
| ATOM | 2799 | CD1 | PHE | A | 369 | 33.112 | 43.875 | 105.897 | 1.00 | 17.75 | A |
| ATOM | 2800 | CD2 | PHE | A | 369 | 35.048 | 44.817 | 104.849 | 1.00 | 15.72 | A |
| ATOM | 2801 | CE1 | PHE | A | 369 | 33.593 | 42.587 | 105.637 | 1.00 | 18.32 | A |
| ATOM | 2802 | CE2 | PHE | A | 369 | 35.540 | 43.533 | 104.581 | 1.00 | 18.65 | A |
| ATOM | 2803 | CZ | PHE | A | 369 | 34.807 | 42.415 | 104.978 | 1.00 | 17.23 | A |
| ATOM | 2804 | C | PHE | A | 369 | 31.337 | 47.787 | 105.946 | 1.00 | 17.12 | A |
| ATOM | 2805 | O | PHE | A | 369 | 31.725 | 48.964 | 105.952 | 1.00 | 15.30 | A |
| ATOM | 2806 | N | GLY | A | 370 | 30.329 | 47.345 | 106.688 | 1.00 | 16.03 | A |
| ATOM | 2807 | CA | GLY | A | 370 | 29.650 | 48.217 | 107.623 | 1.00 | 15.32 | A |
| ATOM | 2808 | C | GLY | A | 370 | 29.907 | 47.618 | 109.002 | 1.00 | 15.98 | A |
| ATOM | 2809 | O | GLY | A | 370 | 29.788 | 46.397 | 109.160 | 1.00 | 15.42 | A |
| ATOM | 2810 | N | PHE | A | 371 | 30.267 | 48.446 | 109.986 | 1.00 | 15.18 | A |
| ATOM | 2811 | CA | PHE | A | 371 | 30.519 | 47.969 | 111.356 | 1.00 | 16.88 | A |
| ATOM | 2812 | CB | PHE | A | 371 | 31.994 | 48.167 | 111.748 | 1.00 | 16.02 | A |
| ATOM | 2813 | CG | PHE | A | 371 | 32.980 | 47.576 | 110.776 | 1.00 | 18.36 | A |
| ATOM | 2814 | CD1 | PHE | A | 371 | 33.002 | 46.202 | 110.522 | 1.00 | 19.96 | A |
| ATOM | 2815 | CD2 | PHE | A | 371 | 33.899 | 48.393 | 110.122 | 1.00 | 19.62 | A |
| ATOM | 2816 | CE1 | PHE | A | 371 | 33.925 | 45.655 | 109.631 | 1.00 | 20.17 | A |
| ATOM | 2817 | CE2 | PHE | A | 371 | 34.827 | 47.859 | 109.229 | 1.00 | 20.30 | A |
| ATOM | 2818 | CZ | PHE | A | 371 | 34.842 | 46.484 | 108.982 | 1.00 | 21.44 | A |
| ATOM | 2819 | C | PHE | A | 371 | 29.643 | 48.749 | 112.345 | 1.00 | 17.73 | A |
| ATOM | 2820 | O | PHE | A | 371 | 29.607 | 49.986 | 112.311 | 1.00 | 20.57 | A |
| ATOM | 2821 | N | GLY | A | 372 | 28.959 | 48.037 | 113.235 | 1.00 | 17.64 | A |
| ATOM | 2822 | CA | GLY | A | 372 | 28.095 | 48.706 | 114.193 | 1.00 | 18.38 | A |
| ATOM | 2823 | C | GLY | A | 372 | 27.792 | 47.924 | 115.461 | 1.00 | 18.00 | A |
| ATOM | 2824 | O | GLY | A | 372 | 28.347 | 46.860 | 115.687 | 1.00 | 16.36 | A |
| ATOM | 2825 | N | PRO | A | 373 | 26.887 | 48.432 | 116.305 | 1.00 | 20.27 | A |
| ATOM | 2826 | CD | PRO | A | 373 | 26.146 | 49.670 | 116.005 | 1.00 | 21.14 | A |
| ATOM | 2827 | CA | PRO | A | 373 | 26.444 | 47.861 | 117.588 | 1.00 | 22.67 | A |
| ATOM | 2828 | CB | PRO | A | 373 | 25.456 | 48.913 | 118.104 | 1.00 | 24.87 | A |
| ATOM | 2829 | CG | PRO | A | 373 | 25.821 | 50.173 | 117.373 | 1.00 | 23.22 | A |
| ATOM | 2830 | C | PRO | A | 373 | 25.753 | 46.484 | 117.592 | 1.00 | 23.21 | A |
| ATOM | 2831 | O | PRO | A | 373 | 25.010 | 46.202 | 116.641 | 1.00 | 22.66 | A |
| ATOM | 2832 | N | GLY | A | 374 | 26.016 | 45.617 | 118.597 | 1.00 | 23.17 | A |
| ATOM | 2833 | CA | GLY | A | 374 | 25.178 | 44.436 | 118.666 | 1.00 | 25.29 | A |
| ATOM | 2834 | C | GLY | A | 374 | 26.141 | 43.404 | 119.175 | 1.00 | 23.83 | A |
| ATOM | 2835 | O | GLY | A | 374 | 25.862 | 42.558 | 120.092 | 1.00 | 25.91 | A |
| ATOM | 2836 | N | LEU | A | 375 | 27.563 | 43.367 | 118.304 | 1.00 | 24.44 | A |
| ATOM | 2837 | CA | LEU | A | 375 | 28.323 | 43.906 | 117.199 | 1.00 | 23.26 | A |
| ATOM | 2838 | CB | LEU | A | 375 | 29.771 | 44.208 | 117.541 | 1.00 | 23.81 | A |
| ATOM | 2839 | CG | LEU | A | 375 | 30.492 | 44.899 | 116.384 | 1.00 | 25.97 | A |
| ATOM | 2840 | CD1 | LEU | A | 375 | 31.706 | 45.711 | 116.830 | 1.00 | 27.70 | A |
| ATOM | 2841 | CD2 | LEU | A | 375 | 31.005 | 43.917 | 115.329 | 1.00 | 25.62 | A |
| ATOM | 2842 | C | LEU | A | 375 | 28.226 | 43.150 | 115.907 | 1.00 | 21.89 | A |
| ATOM | 2843 | O | LEU | A | 375 | 28.728 | 42.015 | 115.805 | 1.00 | 23.04 | A |
| ATOM | 2844 | N | THR | A | 376 | 27.598 | 43.904 | 115.007 | 1.00 | 22.34 | A |
| ATOM | 2845 | CA | THR | A | 376 | 27.220 | 43.607 | 113.645 | 1.00 | 19.04 | A |
| ATOM | 2846 | CB | THR | A | 376 | 25.952 | 44.396 | 113.271 | 1.00 | 19.55 | A |
| ATOM | 2847 | OG1 | THR | A | 376 | 24.994 | 44.305 | 114.330 | 1.00 | 18.35 | A |
| ATOM | 2848 | CG2 | THR | A | 376 | 25.352 | 43.860 | 111.974 | 1.00 | 19.52 | A |
| ATOM | 2849 | C | THR | A | 376 | 28.241 | 44.005 | 112.607 | 1.00 | 18.79 | A |
| ATOM | 2850 | O | THR | A | 376 | 28.837 | 45.093 | 112.662 | 1.00 | 17.92 | A |
| ATOM | 2851 | N | ILE | A | 377 | 28.406 | 43.115 | 111.641 | 1.00 | 17.26 | A |
| ATOM | 2852 | CA | ILE | A | 377 | 29.277 | 43.347 | 110.513 | 1.00 | 17.21 | A |
| ATOM | 2853 | CB | ILE | A | 377 | 30.458 | 42.354 | 110.473 | 1.00 | 16.53 | A |
| ATOM | 2854 | CG2 | ILE | A | 377 | 31.241 | 42.543 | 109.184 | 1.00 | 16.65 | A |
| ATOM | 2855 | CG1 | ILE | A | 377 | 31.367 | 42.561 | 111.686 | 1.00 | 18.63 | A |
| ATOM | 2856 | CD1 | ILE | A | 377 | 32.527 | 41.576 | 111.751 | 1.00 | 21.55 | A |
| ATOM | 2857 | C | ILE | A | 377 | 28.400 | 43.096 | 109.290 | 1.00 | 17.23 | A |
| ATOM | 2858 | O | ILE | A | 377 | 27.761 | 42.050 | 109.189 | 1.00 | 17.27 | A |
| ATOM | 2859 | N | GLU | A | 378 | 28.337 | 44.072 | 108.393 | 1.00 | 15.61 | A |
| ATOM | 2860 | CA | GLU | A | 378 | 27.576 | 43.934 | 107.155 | 1.00 | 16.65 | A |
| ATOM | 2861 | CB | GLU | A | 378 | 26.732 | 45.188 | 106.873 | 1.00 | 16.43 | A |
| ATOM | 2862 | CG | GLU | A | 378 | 25.547 | 45.389 | 107.813 | 1.00 | 20.23 | A |
| ATOM | 2863 | CD | GLU | A | 378 | 24.203 | 44.968 | 107.214 | 1.00 | 21.67 | A |
| ATOM | 2864 | OE1 | GLU | A | 378 | 24.176 | 44.331 | 106.137 | 1.00 | 21.94 | A |
| ATOM | 2865 | OE2 | GLU | A | 378 | 23.163 | 45.277 | 107.834 | 1.00 | 23.26 | A |

APPENDIX B-continued

*Arachis hypogaea* STS

| ATOM | # | TYPE | RES | | | X | Y | Z | OCC | B | |
|------|---|------|-----|---|---|---|---|---|-----|---|---|
| ATOM | 2866 | C | GLU | A | 378 | 28.641 | 43.785 | 106.078 | 1.00 | 15.61 | A |
| ATOM | 2867 | O | GLU | A | 378 | 29.575 | 44.595 | 106.009 | 1.00 | 16.34 | A |
| ATOM | 2868 | N | THR | A | 379 | 28.523 | 42.743 | 105.259 | 1.00 | 16.22 | A |
| ATOM | 2869 | CA | THR | A | 379 | 29.494 | 42.504 | 104.194 | 1.00 | 15.92 | A |
| ATOM | 2870 | CB | THR | A | 379 | 30.224 | 41.159 | 104.378 | 1.00 | 18.24 | A |
| ATOM | 2871 | OG1 | THR | A | 379 | 30.715 | 41.052 | 105.720 | 1.00 | 18.54 | A |
| ATOM | 2872 | CG2 | THR | A | 379 | 31.390 | 41.063 | 103.404 | 1.00 | 17.22 | A |
| ATOM | 2873 | C | THR | A | 379 | 28.817 | 42.460 | 102.832 | 1.00 | 16.86 | A |
| ATOM | 2874 | O | THR | A | 379 | 28.045 | 41.533 | 102.540 | 1.00 | 16.09 | A |
| ATOM | 2875 | N | VAL | A | 380 | 29.112 | 43.450 | 101.997 | 1.00 | 12.76 | A |
| ATOM | 2876 | CA | VAL | A | 380 | 28.534 | 43.513 | 100.655 | 1.00 | 13.53 | A |
| ATOM | 2877 | CB | VAL | A | 380 | 27.864 | 44.885 | 100.401 | 1.00 | 13.13 | A |
| ATOM | 2878 | CG1 | VAL | A | 380 | 27.209 | 44.906 | 99.009 | 1.00 | 14.37 | A |
| ATOM | 2879 | CG2 | VAL | A | 380 | 26.844 | 45.171 | 101.483 | 1.00 | 14.22 | A |
| ATOM | 2880 | C | VAL | A | 380 | 29.620 | 43.299 | 99.597 | 1.00 | 14.42 | A |
| ATOM | 2881 | O | VAL | A | 380 | 30.661 | 43.958 | 99.619 | 1.00 | 13.41 | A |
| ATOM | 2882 | N | VAL | A | 381 | 29.397 | 42.362 | 98.679 | 1.00 | 14.62 | A |
| ATOM | 2883 | CA | VAL | A | 381 | 30.374 | 42.131 | 97.618 | 1.00 | 12.94 | A |
| ATOM | 2884 | CB | VAL | A | 381 | 30.424 | 40.663 | 97.169 | 1.00 | 13.15 | A |
| ATOM | 2885 | CG1 | VAL | A | 381 | 31.315 | 40.537 | 95.932 | 1.00 | 11.65 | A |
| ATOM | 2886 | CG2 | VAL | A | 381 | 30.962 | 39.795 | 98.298 | 1.00 | 12.83 | A |
| ATOM | 2887 | C | VAL | A | 381 | 29.962 | 42.987 | 96.439 | 1.00 | 15.10 | A |
| ATOM | 2888 | O | VAL | A | 381 | 28.787 | 43.033 | 96.082 | 1.00 | 15.48 | A |
| ATOM | 2889 | N | LEU | A | 382 | 30.935 | 43.665 | 95.841 | 1.00 | 15.57 | A |
| ATOM | 2890 | CA | LEU | A | 382 | 30.678 | 44.540 | 94.707 | 1.00 | 15.16 | A |
| ATOM | 2891 | CB | LEU | A | 382 | 31.110 | 45.971 | 95.047 | 1.00 | 14.71 | A |
| ATOM | 2892 | CG | LEU | A | 382 | 30.478 | 46.644 | 96.269 | 1.00 | 15.25 | A |
| ATOM | 2893 | CD1 | LEU | A | 382 | 31.191 | 47.967 | 96.546 | 1.00 | 16.34 | A |
| ATOM | 2894 | CD2 | LEU | A | 382 | 28.999 | 46.872 | 96.024 | 1.00 | 16.09 | A |
| ATOM | 2895 | C | LEU | A | 382 | 31.417 | 44.114 | 93.445 | 1.00 | 16.18 | A |
| ATOM | 2896 | O | LEU | A | 382 | 32.433 | 43.423 | 93.485 | 1.00 | 15.42 | A |
| ATOM | 2897 | N | ARG | A | 383 | 30.893 | 44.561 | 92.313 | 1.00 | 16.91 | A |
| ATOM | 2898 | CA | ARG | A | 383 | 31.504 | 44.283 | 91.039 | 1.00 | 18.58 | A |
| ATOM | 2899 | CB | ARG | A | 383 | 30.560 | 43.438 | 90.187 | 1.00 | 23.70 | A |
| ATOM | 2900 | CG | ARG | A | 383 | 31.212 | 42.230 | 89.552 | 1.00 | 29.01 | A |
| ATOM | 2901 | CD | ARG | A | 383 | 32.112 | 42.639 | 88.406 | 1.00 | 34.91 | A |
| ATOM | 2902 | NE | ARG | A | 383 | 32.578 | 41.484 | 87.646 | 1.00 | 38.99 | A |
| ATOM | 2903 | CZ | ARG | A | 383 | 33.297 | 41.570 | 86.532 | 1.00 | 41.42 | A |
| ATOM | 2904 | NH1 | ARG | A | 383 | 33.631 | 42.760 | 86.047 | 1.00 | 42.61 | A |
| ATOM | 2905 | NH2 | ARG | A | 383 | 33.688 | 40.468 | 85.906 | 1.00 | 42.22 | A |
| ATOM | 2906 | C | ARG | A | 383 | 31.709 | 45.663 | 90.425 | 1.00 | 18.51 | A |
| ATOM | 2907 | O | ARG | A | 383 | 30.798 | 46.493 | 90.441 | 1.00 | 18.35 | A |
| ATOM | 2908 | N | SER | A | 384 | 32.908 | 45.918 | 89.916 | 1.00 | 17.71 | A |
| ATOM | 2909 | CA | SER | A | 384 | 33.221 | 47.205 | 89.305 | 1.00 | 17.18 | A |
| ATOM | 2910 | CB | SER | A | 384 | 34.737 | 47.429 | 89.301 | 1.00 | 16.78 | A |
| ATOM | 2911 | OG | SER | A | 384 | 35.377 | 46.504 | 88.434 | 1.00 | 19.20 | A |
| ATOM | 2912 | C | SER | A | 384 | 32.704 | 47.244 | 87.873 | 1.00 | 16.69 | A |
| ATOM | 2913 | O | SER | A | 384 | 32.259 | 46.231 | 87.333 | 1.00 | 14.89 | A |
| ATOM | 2914 | N | VAL | A | 385 | 32.763 | 48.422 | 87.266 | 1.00 | 16.95 | A |
| ATOM | 2915 | CA | VAL | A | 385 | 32.318 | 48.602 | 85.892 | 1.00 | 18.01 | A |
| ATOM | 2916 | CB | VAL | A | 385 | 31.210 | 49.679 | 85.807 | 1.00 | 19.03 | A |
| ATOM | 2917 | CG1 | VAL | A | 385 | 30.892 | 49.986 | 84.356 | 1.00 | 19.61 | A |
| ATOM | 2918 | CG2 | VAL | A | 385 | 29.968 | 49.200 | 86.538 | 1.00 | 19.12 | A |
| ATOM | 2919 | C | VAL | A | 385 | 33.503 | 49.047 | 85.034 | 1.00 | 19.45 | A |
| ATOM | 2920 | O | VAL | A | 385 | 34.277 | 49.916 | 85.437 | 1.00 | 18.07 | A |
| ATOM | 2921 | N | ALA | A | 386 | 33.637 | 48.448 | 83.853 | 1.00 | 18.41 | A |
| ATOM | 2922 | CA | ALA | A | 386 | 34.719 | 48.783 | 82.937 | 1.00 | 19.71 | A |
| ATOM | 2923 | CB | ALA | A | 386 | 34.692 | 47.833 | 81.736 | 1.00 | 21.24 | A |
| ATOM | 2924 | C | ALA | A | 386 | 34.633 | 50.237 | 82.459 | 1.00 | 20.60 | A |
| ATOM | 2925 | O | ALA | A | 386 | 33.573 | 50.698 | 82.038 | 1.00 | 19.64 | A |
| ATOM | 2926 | N | ILE | A | 387 | 35.757 | 50.949 | 82.530 | 1.00 | 20.08 | A |
| ATOM | 2927 | CA | ILE | A | 387 | 35.832 | 52.344 | 82.093 | 1.00 | 21.90 | A |
| ATOM | 2928 | CB | ILE | A | 387 | 35.864 | 53.324 | 83.293 | 1.00 | 20.45 | A |
| ATOM | 2929 | CG2 | ILE | A | 387 | 34.507 | 53.353 | 83.977 | 1.00 | 20.07 | A |
| ATOM | 2930 | CG1 | ILE | A | 387 | 36.969 | 52.923 | 84.274 | 1.00 | 20.21 | A |
| ATOM | 2931 | CD1 | ILE | A | 387 | 37.124 | 53.867 | 85.451 | 1.00 | 17.62 | A |
| ATOM | 2932 | C | ILE | A | 387 | 37.076 | 52.591 | 81.233 | 1.00 | 23.48 | A |
| ATOM | 2933 | O | ILE | A | 387 | 37.190 | 53.699 | 80.664 | 1.00 | 24.34 | A |
| ATOM | 2934 | OXT | ILE | A | 387 | 37.929 | 51.679 | 81.143 | 1.00 | 24.25 | A |

APPENDIX C

18xCHS Mutant

| ATOM | # | TYPE | RES | | | X | Y | Z | OCC | B | |
|------|---|------|-----|---|---|---|---|---|-----|---|---|
| ATOM | 1 | CB | VAL | A | 2 | −13.230 | 29.022 | 69.882 | 1.00 | 30.61 | A |
| ATOM | 2 | CG1 | VAL | A | 2 | −12.890 | 29.579 | 71.256 | 1.00 | 31.32 | A |
| ATOM | 3 | CG2 | VAL | A | 2 | −13.703 | 27.583 | 69.999 | 1.00 | 31.29 | A |
| ATOM | 4 | C | VAL | A | 2 | −14.560 | 29.365 | 67.801 | 1.00 | 29.09 | A |
| ATOM | 5 | O | VAL | A | 2 | −15.501 | 28.610 | 67.557 | 1.00 | 29.96 | A |
| ATOM | 6 | N | VAL | A | 2 | −15.591 | 29.845 | 70.002 | 1.00 | 30.39 | A |
| ATOM | 7 | CA | VAL | A | 2 | −14.326 | 29.883 | 69.216 | 1.00 | 29.93 | A |
| ATOM | 8 | N | SER | A | 3 | −13.700 | 29.774 | 66.873 | 1.00 | 27.49 | A |
| ATOM | 9 | CA | SER | A | 3 | −13.814 | 29.352 | 65.482 | 1.00 | 25.81 | A |
| ATOM | 10 | CB | SER | A | 3 | −13.481 | 30.514 | 64.548 | 1.00 | 25.39 | A |
| ATOM | 11 | OG | SER | A | 3 | −12.104 | 30.840 | 64.623 | 1.00 | 24.75 | A |
| ATOM | 12 | C | SER | A | 3 | −12.866 | 28.195 | 65.190 | 1.00 | 25.08 | A |
| ATOM | 13 | O | SER | A | 3 | −11.910 | 27.961 | 65.931 | 1.00 | 24.70 | A |
| ATOM | 14 | N | VAL | A | 4 | −13.134 | 27.478 | 64.102 | 1.00 | 24.03 | A |
| ATOM | 15 | CA | VAL | A | 4 | −12.298 | 26.352 | 63.704 | 1.00 | 23.31 | A |
| ATOM | 16 | CB | VAL | A | 4 | −12.904 | 25.609 | 62.491 | 1.00 | 23.50 | A |
| ATOM | 17 | CG1 | VAL | A | 4 | −11.986 | 24.474 | 62.058 | 1.00 | 23.11 | A |
| ATOM | 18 | CG2 | VAL | A | 4 | −14.275 | 25.069 | 62.848 | 1.00 | 23.81 | A |
| ATOM | 19 | C | VAL | A | 4 | −10.895 | 26.833 | 63.338 | 1.00 | 22.89 | A |
| ATOM | 20 | O | VAL | A | 4 | −9.910 | 26.129 | 63.557 | 1.00 | 22.82 | A |
| ATOM | 21 | N | SER | A | 5 | −10.813 | 28.037 | 62.778 | 1.00 | 22.60 | A |
| ATOM | 22 | CA | SER | A | 5 | −9.529 | 28.613 | 62.383 | 1.00 | 22.06 | A |
| ATOM | 23 | CB | SER | A | 5 | −9.742 | 29.969 | 61.704 | 1.00 | 21.99 | A |
| ATOM | 24 | OG | SER | A | 5 | −8.505 | 30.545 | 61.320 | 1.00 | 22.10 | A |
| ATOM | 25 | C | SER | A | 5 | −8.610 | 28.788 | 63.587 | 1.00 | 21.94 | A |
| ATOM | 26 | O | SER | A | 5 | −7.435 | 28.423 | 63.542 | 1.00 | 22.12 | A |
| ATOM | 27 | N | GLU | A | 6 | −9.151 | 29.345 | 64.665 | 1.00 | 21.69 | A |
| ATOM | 28 | CA | GLU | A | 6 | −8.372 | 29.572 | 65.875 | 1.00 | 21.71 | A |
| ATOM | 29 | CB | GLU | A | 6 | −9.195 | 30.387 | 66.879 | 1.00 | 23.91 | A |
| ATOM | 30 | CG | GLU | A | 6 | −8.390 | 30.969 | 68.040 | 1.00 | 28.22 | A |
| ATOM | 31 | CD | GLU | A | 6 | −7.384 | 32.032 | 67.608 | 1.00 | 30.05 | A |
| ATOM | 32 | OE1 | GLU | A | 6 | −6.670 | 32.566 | 68.486 | 1.00 | 31.96 | A |
| ATOM | 33 | OE2 | GLU | A | 6 | −7.302 | 32.340 | 66.399 | 1.00 | 32.23 | A |
| ATOM | 34 | C | GLU | A | 6 | −7.945 | 28.234 | 66.488 | 1.00 | 20.55 | A |
| ATOM | 35 | O | GLU | A | 6 | −6.842 | 28.109 | 67.019 | 1.00 | 19.81 | A |
| ATOM | 36 | N | ILE | A | 7 | −8.820 | 27.235 | 66.402 | 1.00 | 18.95 | A |
| ATOM | 37 | CA | ILE | A | 7 | −8.522 | 25.909 | 66.937 | 1.00 | 17.56 | A |
| ATOM | 38 | CB | ILE | A | 7 | −9.766 | 24.987 | 66.864 | 1.00 | 17.72 | A |
| ATOM | 39 | CG2 | ILE | A | 7 | −9.396 | 23.560 | 67.269 | 1.00 | 17.42 | A |
| ATOM | 40 | CG1 | ILE | A | 7 | −10.863 | 25.532 | 67.784 | 1.00 | 17.63 | A |
| ATOM | 41 | CD1 | ILE | A | 7 | −12.178 | 24.790 | 67.693 | 1.00 | 17.98 | A |
| ATOM | 42 | C | ILE | A | 7 | −7.367 | 25.263 | 66.169 | 1.00 | 16.69 | A |
| ATOM | 43 | O | ILE | A | 7 | −6.415 | 24.767 | 66.773 | 1.00 | 16.31 | A |
| ATOM | 44 | N | ARG | A | 8 | −7.450 | 25.283 | 64.839 | 1.00 | 15.59 | A |
| ATOM | 45 | CA | ARG | A | 8 | −6.411 | 24.697 | 63.984 | 1.00 | 15.15 | A |
| ATOM | 46 | CB | ARG | A | 8 | −6.803 | 24.836 | 62.506 | 1.00 | 14.73 | A |
| ATOM | 47 | CG | ARG | A | 8 | −5.829 | 24.202 | 61.507 | 1.00 | 13.64 | A |
| ATOM | 48 | CD | ARG | A | 8 | −6.090 | 22.708 | 61.297 | 1.00 | 13.58 | A |
| ATOM | 49 | NE | ARG | A | 8 | −5.526 | 21.844 | 62.336 | 1.00 | 12.35 | A |
| ATOM | 50 | CZ | ARG | A | 8 | −4.284 | 21.358 | 62.326 | 1.00 | 13.34 | A |
| ATOM | 51 | NH1 | ARG | A | 8 | −3.453 | 21.644 | 61.327 | 1.00 | 12.64 | A |
| ATOM | 52 | NH2 | ARG | A | 8 | −3.870 | 20.578 | 63.319 | 1.00 | 12.49 | A |
| ATOM | 53 | C | ARG | A | 8 | −5.048 | 25.359 | 64.211 | 1.00 | 15.17 | A |
| ATOM | 54 | O | ARG | A | 8 | −4.027 | 24.678 | 64.286 | 1.00 | 14.78 | A |
| ATOM | 55 | N | LYS | A | 9 | −5.034 | 26.687 | 64.320 | 1.00 | 15.05 | A |
| ATOM | 56 | CA | LYS | A | 9 | −3.781 | 27.418 | 64.528 | 1.00 | 15.25 | A |
| ATOM | 57 | CB | LYS | A | 9 | −4.039 | 28.932 | 64.545 | 1.00 | 14.94 | A |
| ATOM | 58 | CG | LYS | A | 9 | −4.332 | 29.532 | 63.178 | 1.00 | 15.21 | A |
| ATOM | 59 | CD | LYS | A | 9 | −4.522 | 31.041 | 63.280 | 1.00 | 16.42 | A |
| ATOM | 60 | CE | LYS | A | 9 | −4.697 | 31.688 | 61.910 | 1.00 | 16.68 | A |
| ATOM | 61 | NZ | LYS | A | 9 | −4.801 | 33.172 | 62.035 | 1.00 | 17.12 | A |
| ATOM | 62 | C | LYS | A | 9 | −3.037 | 27.028 | 65.799 | 1.00 | 15.06 | A |
| ATOM | 63 | O | LYS | A | 9 | −1.804 | 27.007 | 65.822 | 1.00 | 15.26 | A |
| ATOM | 64 | N | ALA | A | 10 | −3.789 | 26.718 | 66.852 | 1.00 | 15.12 | A |
| ATOM | 65 | CA | ALA | A | 10 | −3.206 | 26.349 | 68.141 | 1.00 | 14.75 | A |
| ATOM | 66 | CB | ALA | A | 10 | −4.121 | 26.830 | 69.267 | 1.00 | 15.94 | A |
| ATOM | 67 | C | ALA | A | 10 | −2.979 | 24.848 | 68.268 | 1.00 | 14.60 | A |
| ATOM | 68 | O | ALA | A | 10 | −2.392 | 24.380 | 69.248 | 1.00 | 14.85 | A |
| ATOM | 69 | N | GLN | A | 11 | −3.426 | 24.099 | 67.267 | 1.00 | 13.64 | A |
| ATOM | 70 | CA | GLN | A | 11 | −3.308 | 22.644 | 67.278 | 1.00 | 13.50 | A |
| ATOM | 71 | CB | GLN | A | 11 | −4.549 | 22.038 | 66.608 | 1.00 | 12.91 | A |
| ATOM | 72 | CG | GLN | A | 11 | −4.852 | 20.588 | 66.973 | 1.00 | 13.41 | A |
| ATOM | 73 | CD | GLN | A | 11 | −6.114 | 20.076 | 66.292 | 1.00 | 13.72 | A |
| ATOM | 74 | OE1 | GLN | A | 11 | −6.101 | 19.746 | 65.106 | 1.00 | 14.06 | A |
| ATOM | 75 | NE2 | GLN | A | 11 | −7.214 | 20.031 | 67.036 | 1.00 | 11.82 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 76 | C | GLN | A | 11 | −2.048 | 22.072 | 66.611 | 1.00 | 13.38 | A |
| ATOM | 77 | O | GLN | A | 11 | −1.550 | 21.025 | 67.032 | 1.00 | 13.66 | A |
| ATOM | 78 | N | ARG | A | 12 | −1.531 | 22.752 | 65.589 | 1.00 | 13.00 | A |
| ATOM | 79 | CA | ARG | A | 12 | −0.364 | 22.256 | 64.850 | 1.00 | 12.85 | A |
| ATOM | 80 | CB | ARG | A | 12 | −0.338 | 22.881 | 63.442 | 1.00 | 12.22 | A |
| ATOM | 81 | CG | ARG | A | 12 | −0.209 | 24.409 | 63.409 | 1.00 | 12.52 | A |
| ATOM | 82 | CD | ARG | A | 12 | 0.264 | 24.892 | 62.036 | 1.00 | 13.75 | A |
| ATOM | 83 | NE | ARG | A | 12 | −0.672 | 24.561 | 60.957 | 1.00 | 14.03 | A |
| ATOM | 84 | CZ | ARG | A | 12 | −1.757 | 25.271 | 60.657 | 1.00 | 14.40 | A |
| ATOM | 85 | NH1 | ARG | A | 12 | −2.052 | 26.364 | 61.353 | 1.00 | 14.54 | A |
| ATOM | 86 | NH2 | ARG | A | 12 | −2.549 | 24.892 | 59.659 | 1.00 | 13.01 | A |
| ATOM | 87 | C | ARG | A | 12 | 1.022 | 22.425 | 65.489 | 1.00 | 13.09 | A |
| ATOM | 88 | O | ARG | A | 12 | 1.246 | 23.329 | 66.296 | 1.00 | 13.33 | A |
| ATOM | 89 | N | ALA | A | 13 | 1.950 | 21.541 | 65.116 | 1.00 | 13.02 | A |
| ATOM | 90 | CA | ALA | A | 13 | 3.333 | 21.606 | 65.607 | 1.00 | 13.42 | A |
| ATOM | 91 | CB | ALA | A | 13 | 3.973 | 20.214 | 65.580 | 1.00 | 13.07 | A |
| ATOM | 92 | C | ALA | A | 13 | 4.078 | 22.552 | 64.657 | 1.00 | 14.07 | A |
| ATOM | 93 | O | ALA | A | 13 | 3.503 | 22.988 | 63.662 | 1.00 | 13.68 | A |
| ATOM | 94 | N | GLU | A | 14 | 5.342 | 22.870 | 64.938 | 1.00 | 15.31 | A |
| ATOM | 95 | CA | GLU | A | 14 | 6.072 | 23.788 | 64.055 | 1.00 | 16.79 | A |
| ATOM | 96 | CB | GLU | A | 14 | 6.634 | 24.983 | 64.844 | 1.00 | 19.19 | A |
| ATOM | 97 | CG | GLU | A | 14 | 7.664 | 25.800 | 64.043 | 1.00 | 22.25 | A |
| ATOM | 98 | CD | GLU | A | 14 | 7.866 | 27.218 | 64.565 | 1.00 | 24.73 | A |
| ATOM | 99 | OE1 | GLU | A | 14 | 8.977 | 27.766 | 64.379 | 1.00 | 26.12 | A |
| ATOM | 100 | OE2 | GLU | A | 14 | 6.916 | 27.794 | 65.144 | 1.00 | 25.41 | A |
| ATOM | 101 | C | GLU | A | 14 | 7.190 | 23.226 | 63.180 | 1.00 | 16.32 | A |
| ATOM | 102 | O | GLU | A | 14 | 7.170 | 23.420 | 61.964 | 1.00 | 16.46 | A |
| ATOM | 103 | N | GLY | A | 15 | 8.162 | 22.548 | 63.787 | 1.00 | 15.23 | A |
| ATOM | 104 | CA | GLY | A | 15 | 9.282 | 22.024 | 63.019 | 1.00 | 14.11 | A |
| ATOM | 105 | C | GLY | A | 15 | 9.151 | 20.637 | 62.408 | 1.00 | 13.41 | A |
| ATOM | 106 | O | GLY | A | 15 | 8.109 | 19.999 | 62.521 | 1.00 | 12.54 | A |
| ATOM | 107 | N | PRO | A | 16 | 10.216 | 20.142 | 61.755 | 1.00 | 12.96 | A |
| ATOM | 108 | CD | PRO | A | 16 | 11.490 | 20.849 | 61.524 | 1.00 | 13.60 | A |
| ATOM | 109 | CA | PRO | A | 16 | 10.229 | 18.821 | 61.116 | 1.00 | 13.35 | A |
| ATOM | 110 | CB | PRO | A | 16 | 11.467 | 18.892 | 60.224 | 1.00 | 13.76 | A |
| ATOM | 111 | CG | PRO | A | 16 | 12.407 | 19.735 | 61.052 | 1.00 | 14.19 | A |
| ATOM | 112 | C | PRO | A | 16 | 10.298 | 17.666 | 62.115 | 1.00 | 13.11 | A |
| ATOM | 113 | O | PRO | A | 16 | 10.893 | 17.800 | 63.188 | 1.00 | 13.04 | A |
| ATOM | 114 | N | ALA | A | 17 | 9.685 | 16.540 | 61.759 | 1.00 | 11.96 | A |
| ATOM | 115 | CA | ALA | A | 17 | 9.686 | 15.355 | 62.614 | 1.00 | 12.09 | A |
| ATOM | 116 | CB | ALA | A | 17 | 8.824 | 14.262 | 61.993 | 1.00 | 11.81 | A |
| ATOM | 117 | C | ALA | A | 17 | 11.119 | 14.862 | 62.794 | 1.00 | 11.94 | A |
| ATOM | 118 | O | ALA | A | 17 | 11.883 | 14.766 | 61.826 | 1.00 | 11.18 | A |
| ATOM | 119 | N | THR | A | 18 | 11.480 | 14.543 | 64.035 | 1.00 | 11.49 | A |
| ATOM | 120 | CA | THR | A | 18 | 12.834 | 14.098 | 64.338 | 1.00 | 11.65 | A |
| ATOM | 121 | CB | THR | A | 18 | 13.589 | 15.190 | 65.134 | 1.00 | 13.41 | A |
| ATOM | 122 | OG1 | THR | A | 18 | 13.434 | 16.457 | 64.478 | 1.00 | 13.74 | A |
| ATOM | 123 | CG2 | THR | A | 18 | 15.072 | 14.866 | 65.228 | 1.00 | 14.06 | A |
| ATOM | 124 | C | THR | A | 18 | 12.850 | 12.803 | 65.156 | 1.00 | 11.14 | A |
| ATOM | 125 | O | THR | A | 18 | 12.000 | 12.597 | 66.023 | 1.00 | 11.01 | A |
| ATOM | 126 | N | ILE | A | 19 | 13.810 | 11.931 | 64.860 | 1.00 | 10.75 | A |
| ATOM | 127 | CA | ILE | A | 19 | 13.967 | 10.680 | 65.594 | 1.00 | 10.47 | A |
| ATOM | 128 | CB | ILE | A | 19 | 14.722 | 9.634 | 64.757 | 1.00 | 10.60 | A |
| ATOM | 129 | CG2 | ILE | A | 19 | 14.941 | 8.371 | 65.587 | 1.00 | 9.37 | A |
| ATOM | 130 | CG1 | ILE | A | 19 | 13.924 | 9.327 | 63.483 | 1.00 | 10.89 | A |
| ATOM | 131 | CD1 | ILE | A | 19 | 14.571 | 8.260 | 62.584 | 1.00 | 12.28 | A |
| ATOM | 132 | C | ILE | A | 19 | 14.776 | 11.034 | 66.841 | 1.00 | 10.68 | A |
| ATOM | 133 | O | ILE | A | 19 | 15.886 | 11.560 | 66.735 | 1.00 | 11.42 | A |
| ATOM | 134 | N | LEU | A | 20 | 14.218 | 10.745 | 68.014 | 1.00 | 10.93 | A |
| ATOM | 135 | CA | LEU | A | 20 | 14.850 | 11.093 | 69.287 | 1.00 | 11.54 | A |
| ATOM | 136 | CB | LEU | A | 20 | 13.823 | 11.805 | 70.177 | 1.00 | 12.05 | A |
| ATOM | 137 | CG | LEU | A | 20 | 13.140 | 13.028 | 69.555 | 1.00 | 12.25 | A |
| ATOM | 138 | CD1 | LEU | A | 20 | 11.991 | 13.478 | 70.431 | 1.00 | 12.71 | A |
| ATOM | 139 | CD2 | LEU | A | 20 | 14.156 | 14.157 | 69.371 | 1.00 | 13.13 | A |
| ATOM | 140 | C | LEU | A | 20 | 15.474 | 9.943 | 70.072 | 1.00 | 11.49 | A |
| ATOM | 141 | O | LEU | A | 20 | 16.197 | 10.177 | 71.044 | 1.00 | 12.18 | A |
| ATOM | 142 | N | ALA | A | 21 | 15.194 | 8.711 | 69.659 | 1.00 | 10.73 | A |
| ATOM | 143 | CA | ALA | A | 21 | 15.731 | 7.532 | 70.338 | 1.00 | 10.18 | A |
| ATOM | 144 | CB | ALA | A | 21 | 15.087 | 7.387 | 71.720 | 1.00 | 10.22 | A |
| ATOM | 145 | C | ALA | A | 21 | 15.456 | 6.286 | 69.501 | 1.00 | 10.69 | A |
| ATOM | 146 | O | ALA | A | 21 | 14.472 | 6.242 | 68.757 | 1.00 | 10.07 | A |
| ATOM | 147 | N | ILE | A | 22 | 16.329 | 5.286 | 69.622 | 1.00 | 10.11 | A |
| ATOM | 148 | CA | ILE | A | 22 | 16.191 | 4.028 | 68.885 | 1.00 | 10.87 | A |
| ATOM | 149 | CB | ILE | A | 22 | 17.101 | 3.990 | 67.624 | 1.00 | 11.25 | A |
| ATOM | 150 | CG2 | ILE | A | 22 | 16.805 | 2.740 | 66.807 | 1.00 | 10.74 | A |

APPENDIX C-continued

18xCHS Mutant

| ATOM | # | TYPE | RES | | | X | Y | Z | OCC | B | |
|------|---|------|-----|---|----|--------|---------|--------|------|-------|---|
| ATOM | 151 | CG1 | ILE | A | 22 | 16.889 | 5.242 | 66.765 | 1.00 | 11.30 | A |
| ATOM | 152 | CD1 | ILE | A | 22 | 17.864 | 5.344 | 65.615 | 1.00 | 10.46 | A |
| ATOM | 153 | C | ILE | A | 22 | 16.602 | 2.850 | 69.766 | 1.00 | 11.38 | A |
| ATOM | 154 | O | ILE | A | 22 | 17.647 | 2.898 | 70.415 | 1.00 | 11.77 | A |
| ATOM | 155 | N | GLY | A | 23 | 15.778 | 1.802 | 69.781 | 1.00 | 11.30 | A |
| ATOM | 156 | CA | GLY | A | 23 | 16.072 | 0.607 | 70.560 | 1.00 | 11.51 | A |
| ATOM | 157 | C | GLY | A | 23 | 15.733 | −0.646 | 69.760 | 1.00 | 12.11 | A |
| ATOM | 158 | O | GLY | A | 23 | 14.801 | −0.614 | 68.952 | 1.00 | 11.93 | A |
| ATOM | 159 | N | THR | A | 24 | 16.482 | −1.734 | 69.961 | 1.00 | 11.78 | A |
| ATOM | 160 | CA | THR | A | 24 | 16.244 | −2.990 | 69.239 | 1.00 | 11.90 | A |
| ATOM | 161 | CB | THR | A | 24 | 17.278 | −3.209 | 68.094 | 1.00 | 12.22 | A |
| ATOM | 162 | OG1 | THR | A | 24 | 18.587 | −3.407 | 68.649 | 1.00 | 13.40 | A |
| ATOM | 163 | CG2 | THR | A | 24 | 17.307 | −2.010 | 67.160 | 1.00 | 12.77 | A |
| ATOM | 164 | C | THR | A | 24 | 16.280 | −4.234 | 70.140 | 1.00 | 11.99 | A |
| ATOM | 165 | O | THR | A | 24 | 16.812 | −4.199 | 71.258 | 1.00 | 12.20 | A |
| ATOM | 166 | N | ALA | A | 25 | 15.713 | −5.333 | 69.643 | 1.00 | 11.68 | A |
| ATOM | 167 | CA | ALA | A | 25 | 15.682 | −6.596 | 70.380 | 1.00 | 11.37 | A |
| ATOM | 168 | CB | ALA | A | 25 | 14.534 | −6.579 | 71.390 | 1.00 | 11.43 | A |
| ATOM | 169 | C | ALA | A | 25 | 15.528 | −7.799 | 69.439 | 1.00 | 12.04 | A |
| ATOM | 170 | O | ALA | A | 25 | 14.978 | −7.670 | 68.345 | 1.00 | 10.87 | A |
| ATOM | 171 | N | ASN | A | 26 | 16.020 | −8.964 | 69.868 | 1.00 | 12.29 | A |
| ATOM | 172 | CA | ASN | A | 26 | 15.916 | −10.194 | 69.074 | 1.00 | 12.75 | A |
| ATOM | 173 | CB | ASN | A | 26 | 17.198 | −10.467 | 68.259 | 1.00 | 13.20 | A |
| ATOM | 174 | CG | ASN | A | 26 | 17.652 | −9.276 | 67.425 | 1.00 | 13.62 | A |
| ATOM | 175 | OD1 | ASN | A | 26 | 18.349 | −8.385 | 67.919 | 1.00 | 13.50 | A |
| ATOM | 176 | ND2 | ASN | A | 26 | 17.272 | −9.265 | 66.145 | 1.00 | 11.58 | A |
| ATOM | 177 | C | ASN | A | 26 | 15.689 | −11.396 | 69.992 | 1.00 | 13.37 | A |
| ATOM | 178 | O | ASN | A | 26 | 16.054 | −11.366 | 71.173 | 1.00 | 13.18 | A |
| ATOM | 179 | N | PRO | A | 27 | 15.084 | −12.474 | 69.465 | 1.00 | 14.48 | A |
| ATOM | 180 | CD | PRO | A | 27 | 14.417 | −12.626 | 68.157 | 1.00 | 14.37 | A |
| ATOM | 181 | CA | PRO | A | 27 | 14.856 | −13.652 | 70.309 | 1.00 | 15.55 | A |
| ATOM | 182 | CB | PRO | A | 27 | 14.166 | −14.631 | 69.355 | 1.00 | 15.65 | A |
| ATOM | 183 | CG | PRO | A | 27 | 13.383 | −13.707 | 68.445 | 1.00 | 14.59 | A |
| ATOM | 184 | C | PRO | A | 27 | 16.203 | −14.176 | 70.820 | 1.00 | 16.73 | A |
| ATOM | 185 | O | PRO | A | 27 | 17.239 | −13.968 | 70.185 | 1.00 | 16.65 | A |
| ATOM | 186 | N | ALA | A | 28 | 16.182 | −14.861 | 71.958 | 1.00 | 18.08 | A |
| ATOM | 187 | CA | ALA | A | 28 | 17.402 | −15.387 | 72.565 | 1.00 | 19.92 | A |
| ATOM | 188 | CB | ALA | A | 28 | 17.091 | −15.886 | 73.983 | 1.00 | 20.22 | A |
| ATOM | 189 | C | ALA | A | 28 | 18.122 | −16.483 | 71.771 | 1.00 | 20.71 | A |
| ATOM | 190 | O | ALA | A | 28 | 19.338 | −16.634 | 71.882 | 1.00 | 22.24 | A |
| ATOM | 191 | N | ASN | A | 29 | 17.384 | −17.239 | 70.965 | 1.00 | 21.91 | A |
| ATOM | 192 | CA | ASN | A | 29 | 17.969 | −18.329 | 70.179 | 1.00 | 22.53 | A |
| ATOM | 193 | CB | ASN | A | 29 | 16.853 | −19.300 | 69.770 | 1.00 | 23.29 | A |
| ATOM | 194 | CG | ASN | A | 29 | 17.360 | −20.471 | 68.954 | 1.00 | 24.78 | A |
| ATOM | 195 | OD1 | ASN | A | 29 | 18.351 | −21.106 | 69.311 | 1.00 | 25.80 | A |
| ATOM | 196 | ND2 | ASN | A | 29 | 16.669 | −20.777 | 67.857 | 1.00 | 24.60 | A |
| ATOM | 197 | C | ASN | A | 29 | 18.756 | −17.870 | 68.940 | 1.00 | 22.49 | A |
| ATOM | 198 | O | ASN | A | 29 | 18.163 | −17.478 | 67.941 | 1.00 | 22.38 | A |
| ATOM | 199 | N | CYS | A | 30 | 20.088 | −17.930 | 69.013 | 1.00 | 22.40 | A |
| ATOM | 200 | CA | CYS | A | 30 | 20.963 | −17.534 | 67.901 | 1.00 | 23.15 | A |
| ATOM | 201 | CB | CYS | A | 30 | 22.263 | −16.912 | 68.436 | 1.00 | 23.31 | A |
| ATOM | 202 | SG | CYS | A | 30 | 23.478 | −16.418 | 67.155 | 1.00 | 25.62 | A |
| ATOM | 203 | C | CYS | A | 30 | 21.297 | −18.737 | 67.012 | 1.00 | 23.29 | A |
| ATOM | 204 | O | CYS | A | 30 | 21.769 | −19.768 | 67.496 | 1.00 | 23.46 | A |
| ATOM | 205 | N | VAL | A | 31 | 21.068 | −18.590 | 65.709 | 1.00 | 22.78 | A |
| ATOM | 206 | CA | VAL | A | 31 | 21.307 | −19.667 | 64.751 | 1.00 | 22.63 | A |
| ATOM | 207 | CB | VAL | A | 31 | 20.012 | −19.961 | 63.950 | 1.00 | 22.87 | A |
| ATOM | 208 | CG1 | VAL | A | 31 | 20.196 | −21.191 | 63.072 | 1.00 | 22.78 | A |
| ATOM | 209 | CG2 | VAL | A | 31 | 18.840 | −20.144 | 64.907 | 1.00 | 23.17 | A |
| ATOM | 210 | C | VAL | A | 31 | 22.435 | −19.359 | 63.757 | 1.00 | 22.49 | A |
| ATOM | 211 | O | VAL | A | 31 | 22.312 | −18.452 | 62.932 | 1.00 | 21.48 | A |
| ATOM | 212 | N | GLU | A | 32 | 23.528 | −20.121 | 63.832 | 1.00 | 22.05 | A |
| ATOM | 213 | CA | GLU | A | 32 | 24.663 | −19.925 | 62.925 | 1.00 | 22.03 | A |
| ATOM | 214 | CB | GLU | A | 32 | 25.879 | −20.715 | 63.414 | 1.00 | 23.60 | A |
| ATOM | 215 | CG | GLU | A | 32 | 26.500 | −20.173 | 64.690 | 1.00 | 25.06 | A |
| ATOM | 216 | CD | GLU | A | 32 | 27.024 | −18.765 | 64.517 | 1.00 | 26.01 | A |
| ATOM | 217 | OE1 | GLU | A | 32 | 27.738 | −18.520 | 63.521 | 1.00 | 27.39 | A |
| ATOM | 218 | OE2 | GLU | A | 32 | 26.732 | −17.904 | 65.375 | 1.00 | 26.48 | A |
| ATOM | 219 | C | GLU | A | 32 | 24.310 | −20.366 | 61.508 | 1.00 | 21.46 | A |
| ATOM | 220 | O | GLU | A | 32 | 23.741 | −21.435 | 61.311 | 1.00 | 20.95 | A |
| ATOM | 221 | N | GLN | A | 33 | 24.672 | −19.552 | 60.521 | 1.00 | 20.88 | A |
| ATOM | 222 | CA | GLN | A | 33 | 24.360 | −19.853 | 59.127 | 1.00 | 20.56 | A |
| ATOM | 223 | CB | GLN | A | 33 | 24.497 | −18.589 | 58.272 | 1.00 | 20.04 | A |
| ATOM | 224 | CG | GLN | A | 33 | 23.983 | −18.751 | 56.845 | 1.00 | 18.89 | A |
| ATOM | 225 | CD | GLN | A | 33 | 22.468 | −18.680 | 56.751 | 1.00 | 18.59 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 226 | OE1 | GLN | A | 33 | 21.751 | −19.243 | 57.581 | 1.00 | 17.31 | A |
| ATOM | 227 | NE2 | GLN | A | 33 | 21.972 | −17.988 | 55.726 | 1.00 | 17.55 | A |
| ATOM | 228 | C | GLN | A | 33 | 25.184 | −20.974 | 58.488 | 1.00 | 20.69 | A |
| ATOM | 229 | O | GLN | A | 33 | 24.650 | −21.768 | 57.716 | 1.00 | 20.26 | A |
| ATOM | 230 | N | SER | A | 34 | 26.475 | −21.044 | 58.801 | 1.00 | 21.34 | A |
| ATOM | 231 | CA | SER | A | 34 | 27.331 | −22.068 | 58.201 | 1.00 | 22.30 | A |
| ATOM | 232 | CB | SER | A | 34 | 28.770 | −21.955 | 58.732 | 1.00 | 21.91 | A |
| ATOM | 233 | OG | SER | A | 34 | 28.835 | −22.155 | 60.128 | 1.00 | 22.81 | A |
| ATOM | 234 | C | SER | A | 34 | 26.822 | −23.497 | 58.383 | 1.00 | 22.37 | A |
| ATOM | 235 | O | SER | A | 34 | 27.007 | −24.340 | 57.503 | 1.00 | 23.51 | A |
| ATOM | 236 | N | THR | A | 35 | 26.172 | −23.772 | 59.507 | 1.00 | 22.43 | A |
| ATOM | 237 | CA | THR | A | 35 | 25.659 | −25.113 | 59.765 | 1.00 | 21.81 | A |
| ATOM | 238 | CB | THR | A | 35 | 26.132 | −25.621 | 61.136 | 1.00 | 22.18 | A |
| ATOM | 239 | OG1 | THR | A | 35 | 25.700 | −24.714 | 62.159 | 1.00 | 23.03 | A |
| ATOM | 240 | CG2 | THR | A | 35 | 27.651 | −25.725 | 61.165 | 1.00 | 22.82 | A |
| ATOM | 241 | C | THR | A | 35 | 24.133 | −25.229 | 59.708 | 1.00 | 21.18 | A |
| ATOM | 242 | O | THR | A | 35 | 23.577 | −26.273 | 60.056 | 1.00 | 21.01 | A |
| ATOM | 243 | N | TYR | A | 36 | 23.452 | −24.174 | 59.265 | 1.00 | 19.84 | A |
| ATOM | 244 | CA | TYR | A | 36 | 21.991 | −24.210 | 59.196 | 1.00 | 18.75 | A |
| ATOM | 245 | CB | TYR | A | 36 | 21.429 | −22.843 | 58.775 | 1.00 | 17.52 | A |
| ATOM | 246 | CG | TYR | A | 36 | 19.928 | −22.721 | 58.962 | 1.00 | 16.96 | A |
| ATOM | 247 | CD1 | TYR | A | 36 | 19.346 | −22.898 | 60.220 | 1.00 | 16.53 | A |
| ATOM | 248 | CE1 | TYR | A | 36 | 17.964 | −22.800 | 60.397 | 1.00 | 16.76 | A |
| ATOM | 249 | CD2 | TYR | A | 36 | 19.088 | −22.440 | 57.881 | 1.00 | 16.21 | A |
| ATOM | 250 | CE2 | TYR | A | 36 | 17.705 | −22.340 | 58.047 | 1.00 | 15.96 | A |
| ATOM | 251 | CZ | TYR | A | 36 | 17.149 | −22.522 | 59.305 | 1.00 | 16.90 | A |
| ATOM | 252 | OH | TYR | A | 36 | 15.780 | −22.438 | 59.472 | 1.00 | 16.69 | A |
| ATOM | 253 | C | TYR | A | 36 | 21.465 | −25.294 | 58.256 | 1.00 | 18.74 | A |
| ATOM | 254 | O | TYR | A | 36 | 20.475 | −25.955 | 58.566 | 1.00 | 19.06 | A |
| ATOM | 255 | N | PRO | A | 37 | 22.111 | −25.489 | 57.090 | 1.00 | 18.99 | A |
| ATOM | 256 | CD | PRO | A | 37 | 23.208 | −24.717 | 56.474 | 1.00 | 18.75 | A |
| ATOM | 257 | CA | PRO | A | 37 | 21.627 | −26.525 | 56.169 | 1.00 | 18.98 | A |
| ATOM | 258 | CB | PRO | A | 37 | 22.706 | −26.551 | 55.091 | 1.00 | 19.26 | A |
| ATOM | 259 | CG | PRO | A | 37 | 23.097 | −25.105 | 55.005 | 1.00 | 18.64 | A |
| ATOM | 260 | C | PRO | A | 37 | 21.424 | −27.887 | 56.838 | 1.00 | 19.27 | A |
| ATOM | 261 | O | PRO | A | 37 | 20.387 | −28.525 | 56.653 | 1.00 | 18.41 | A |
| ATOM | 262 | N | ASP | A | 38 | 22.406 | −28.331 | 57.617 | 1.00 | 19.51 | A |
| ATOM | 263 | CA | ASP | A | 38 | 22.283 | −29.618 | 58.303 | 1.00 | 20.18 | A |
| ATOM | 264 | CB | ASP | A | 38 | 23.582 | −29.976 | 59.040 | 1.00 | 20.94 | A |
| ATOM | 265 | CG | ASP | A | 38 | 24.691 | −30.417 | 58.097 | 1.00 | 22.36 | A |
| ATOM | 266 | OD1 | ASP | A | 38 | 24.381 | −31.017 | 57.043 | 1.00 | 22.82 | A |
| ATOM | 267 | OD2 | ASP | A | 38 | 25.877 | −30.186 | 58.417 | 1.00 | 23.40 | A |
| ATOM | 268 | C | ASP | A | 38 | 21.125 | −29.599 | 59.300 | 1.00 | 19.89 | A |
| ATOM | 269 | O | ASP | A | 38 | 20.365 | −30.565 | 59.407 | 1.00 | 19.55 | A |
| ATOM | 270 | N | PHE | A | 39 | 20.991 | −28.492 | 60.022 | 1.00 | 19.50 | A |
| ATOM | 271 | CA | PHE | A | 39 | 19.934 | −28.340 | 61.021 | 1.00 | 19.62 | A |
| ATOM | 272 | CB | PHE | A | 39 | 20.163 | −27.057 | 61.823 | 1.00 | 21.89 | A |
| ATOM | 273 | CG | PHE | A | 39 | 19.139 | −26.822 | 62.892 | 1.00 | 24.15 | A |
| ATOM | 274 | CD1 | PHE | A | 39 | 19.106 | −27.622 | 64.031 | 1.00 | 25.06 | A |
| ATOM | 275 | CD2 | PHE | A | 39 | 18.193 | −25.813 | 62.753 | 1.00 | 25.47 | A |
| ATOM | 276 | CE1 | PHE | A | 39 | 18.145 | −27.423 | 65.019 | 1.00 | 26.34 | A |
| ATOM | 277 | CE2 | PHE | A | 39 | 17.221 | −25.603 | 63.737 | 1.00 | 26.52 | A |
| ATOM | 278 | CZ | PHE | A | 39 | 17.198 | −26.410 | 64.871 | 1.00 | 27.00 | A |
| ATOM | 279 | C | PHE | A | 39 | 18.535 | −28.307 | 60.400 | 1.00 | 18.72 | A |
| ATOM | 280 | O | PHE | A | 39 | 17.628 | −29.011 | 60.852 | 1.00 | 18.17 | A |
| ATOM | 281 | N | TYR | A | 40 | 18.365 | −27.484 | 59.371 | 1.00 | 17.64 | A |
| ATOM | 282 | CA | TYR | A | 40 | 17.080 | −27.345 | 58.691 | 1.00 | 17.02 | A |
| ATOM | 283 | CB | TYR | A | 40 | 17.177 | −26.240 | 57.630 | 1.00 | 16.06 | A |
| ATOM | 284 | CG | TYR | A | 40 | 15.923 | −26.045 | 56.794 | 1.00 | 14.59 | A |
| ATOM | 285 | CD1 | TYR | A | 40 | 14.742 | −25.572 | 57.361 | 1.00 | 14.51 | A |
| ATOM | 286 | CE1 | TYR | A | 40 | 13.595 | −25.367 | 56.585 | 1.00 | 14.11 | A |
| ATOM | 287 | CD2 | TYR | A | 40 | 15.933 | −26.317 | 55.430 | 1.00 | 14.81 | A |
| ATOM | 288 | CE2 | TYR | A | 40 | 14.799 | −26.122 | 54.646 | 1.00 | 14.21 | A |
| ATOM | 289 | CZ | TYR | A | 40 | 13.635 | −25.645 | 55.227 | 1.00 | 14.27 | A |
| ATOM | 290 | OH | TYR | A | 40 | 12.528 | −25.435 | 54.440 | 1.00 | 13.60 | A |
| ATOM | 291 | C | TYR | A | 40 | 16.591 | −28.647 | 58.050 | 1.00 | 17.25 | A |
| ATOM | 292 | O | TYR | A | 40 | 15.422 | −29.004 | 58.178 | 1.00 | 17.01 | A |
| ATOM | 293 | N | PHE | A | 41 | 17.471 | −29.363 | 57.358 | 1.00 | 18.01 | A |
| ATOM | 294 | CA | PHE | A | 41 | 17.044 | −30.607 | 56.725 | 1.00 | 18.83 | A |
| ATOM | 295 | CB | PHE | A | 41 | 18.051 | −31.035 | 55.654 | 1.00 | 18.25 | A |
| ATOM | 296 | CG | PHE | A | 41 | 17.815 | −30.374 | 54.325 | 1.00 | 18.43 | A |
| ATOM | 297 | CD1 | PHE | A | 41 | 18.015 | −29.006 | 54.170 | 1.00 | 17.48 | A |
| ATOM | 298 | CD2 | PHE | A | 41 | 17.312 | −31.104 | 53.250 | 1.00 | 17.95 | A |
| ATOM | 299 | CE1 | PHE | A | 41 | 17.713 | −28.369 | 52.966 | 1.00 | 17.59 | A |
| ATOM | 300 | CE2 | PHE | A | 41 | 17.006 | −30.478 | 52.046 | 1.00 | 18.17 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 301 | CZ | PHE | A | 41 | 17.206 | −29.104 | 51.904 | 1.00 | 18.05 | A |
| ATOM | 302 | C | PHE | A | 41 | 16.766 | −31.745 | 57.705 | 1.00 | 19.60 | A |
| ATOM | 303 | O | PHE | A | 41 | 16.048 | −32.690 | 57.377 | 1.00 | 19.06 | A |
| ATOM | 304 | N | LYS | A | 42 | 17.314 | −31.649 | 58.912 | 1.00 | 20.78 | A |
| ATOM | 305 | CA | LYS | A | 42 | 17.079 | −32.678 | 59.927 | 1.00 | 22.23 | A |
| ATOM | 306 | CB | LYS | A | 42 | 18.174 | −32.647 | 60.996 | 1.00 | 23.48 | A |
| ATOM | 307 | CG | LYS | A | 42 | 17.972 | −33.680 | 62.096 | 1.00 | 25.67 | A |
| ATOM | 308 | CD | LYS | A | 42 | 18.923 | −33.467 | 63.262 | 1.00 | 27.51 | A |
| ATOM | 309 | CE | LYS | A | 42 | 18.621 | −32.169 | 63.993 | 1.00 | 29.25 | A |
| ATOM | 310 | NZ | LYS | A | 42 | 19.511 | −31.974 | 65.173 | 1.00 | 30.49 | A |
| ATOM | 311 | C | LYS | A | 42 | 15.724 | −32.465 | 60.608 | 1.00 | 22.35 | A |
| ATOM | 312 | O | LYS | A | 42 | 14.909 | −33.386 | 60.697 | 1.00 | 22.15 | A |
| ATOM | 313 | N | ILE | A | 43 | 15.485 | −31.246 | 61.085 | 1.00 | 22.66 | A |
| ATOM | 314 | CA | ILE | A | 43 | 14.233 | −30.932 | 61.772 | 1.00 | 22.68 | A |
| ATOM | 315 | CB | ILE | A | 43 | 14.269 | −29.502 | 62.372 | 1.00 | 22.71 | A |
| ATOM | 316 | CG2 | ILE | A | 43 | 14.054 | −28.462 | 61.282 | 1.00 | 21.97 | A |
| ATOM | 317 | CG1 | ILE | A | 43 | 13.190 | −29.364 | 63.446 | 1.00 | 23.48 | A |
| ATOM | 318 | CD1 | ILE | A | 43 | 13.366 | −30.310 | 64.624 | 1.00 | 23.50 | A |
| ATOM | 319 | C | ILE | A | 43 | 12.999 | −31.082 | 60.874 | 1.00 | 22.84 | A |
| ATOM | 320 | O | ILE | A | 43 | 11.891 | −31.309 | 61.366 | 1.00 | 22.92 | A |
| ATOM | 321 | N | THR | A | 44 | 13.184 | −30.960 | 59.562 | 1.00 | 22.55 | A |
| ATOM | 322 | CA | THR | A | 44 | 12.065 | −31.104 | 58.637 | 1.00 | 22.54 | A |
| ATOM | 323 | CB | THR | A | 44 | 12.152 | −30.097 | 57.459 | 1.00 | 22.72 | A |
| ATOM | 324 | OG1 | THR | A | 44 | 13.371 | −30.303 | 56.730 | 1.00 | 22.37 | A |
| ATOM | 325 | CG2 | THR | A | 44 | 12.098 | −28.665 | 57.977 | 1.00 | 22.10 | A |
| ATOM | 326 | C | THR | A | 44 | 12.014 | −32.519 | 58.071 | 1.00 | 23.10 | A |
| ATOM | 327 | O | THR | A | 44 | 11.202 | −32.820 | 57.191 | 1.00 | 23.58 | A |
| ATOM | 328 | N | ASN | A | 45 | 12.887 | −33.383 | 58.584 | 1.00 | 23.35 | A |
| ATOM | 329 | CA | ASN | A | 45 | 12.960 | −34.775 | 58.147 | 1.00 | 23.44 | A |
| ATOM | 330 | CB | ASN | A | 45 | 11.737 | −35.544 | 58.664 | 1.00 | 24.41 | A |
| ATOM | 331 | CG | ASN | A | 45 | 11.514 | −35.346 | 60.161 | 1.00 | 25.94 | A |
| ATOM | 332 | OD1 | ASN | A | 45 | 12.443 | −35.452 | 60.959 | 1.00 | 26.60 | A |
| ATOM | 333 | ND2 | ASN | A | 45 | 10.277 | −35.062 | 60.544 | 1.00 | 26.55 | A |
| ATOM | 334 | C | ASN | A | 45 | 13.051 | −34.877 | 56.621 | 1.00 | 23.02 | A |
| ATOM | 335 | O | ASN | A | 45 | 12.304 | −35.623 | 55.990 | 1.00 | 22.54 | A |
| ATOM | 336 | N | SER | A | 46 | 13.990 | −34.133 | 56.041 | 1.00 | 22.98 | A |
| ATOM | 337 | CA | SER | A | 46 | 14.178 | −34.115 | 54.593 | 1.00 | 23.29 | A |
| ATOM | 338 | CB | SER | A | 46 | 13.839 | −32.723 | 54.056 | 1.00 | 23.17 | A |
| ATOM | 339 | OG | SER | A | 46 | 12.593 | −32.267 | 54.556 | 1.00 | 23.57 | A |
| ATOM | 340 | C | SER | A | 46 | 15.606 | −34.483 | 54.164 | 1.00 | 23.38 | A |
| ATOM | 341 | O | SER | A | 46 | 16.051 | −34.091 | 53.086 | 1.00 | 22.63 | A |
| ATOM | 342 | N | GLU | A | 47 | 16.314 | −35.241 | 54.995 | 1.00 | 23.79 | A |
| ATOM | 343 | CA | GLU | A | 47 | 17.693 | −35.618 | 54.687 | 1.00 | 24.63 | A |
| ATOM | 344 | CB | GLU | A | 47 | 18.342 | −36.266 | 55.912 | 1.00 | 25.51 | A |
| ATOM | 345 | CG | GLU | A | 47 | 18.434 | −35.310 | 57.089 | 1.00 | 28.07 | A |
| ATOM | 346 | CD | GLU | A | 47 | 19.244 | −35.856 | 58.236 | 1.00 | 29.80 | A |
| ATOM | 347 | OE1 | GLU | A | 47 | 18.831 | −36.878 | 58.824 | 1.00 | 31.27 | A |
| ATOM | 348 | OE2 | GLU | A | 47 | 20.297 | −35.260 | 58.550 | 1.00 | 30.37 | A |
| ATOM | 349 | C | GLU | A | 47 | 17.878 | −36.510 | 53.464 | 1.00 | 24.72 | A |
| ATOM | 350 | O | GLU | A | 47 | 18.999 | −36.670 | 52.974 | 1.00 | 24.73 | A |
| ATOM | 351 | N | HIS | A | 48 | 16.792 | −37.087 | 52.963 | 1.00 | 24.76 | A |
| ATOM | 352 | CA | HIS | A | 48 | 16.893 | −37.940 | 51.785 | 1.00 | 24.97 | A |
| ATOM | 353 | CB | HIS | A | 48 | 15.765 | −38.978 | 51.764 | 1.00 | 24.66 | A |
| ATOM | 354 | CG | HIS | A | 48 | 14.401 | −38.396 | 51.952 | 1.00 | 24.86 | A |
| ATOM | 355 | CD2 | HIS | A | 48 | 13.382 | −38.213 | 51.079 | 1.00 | 24.69 | A |
| ATOM | 356 | ND1 | HIS | A | 48 | 13.956 | −37.919 | 53.166 | 1.00 | 25.06 | A |
| ATOM | 357 | CE1 | HIS | A | 48 | 12.721 | −37.468 | 53.033 | 1.00 | 24.93 | A |
| ATOM | 358 | NE2 | HIS | A | 48 | 12.350 | −37.635 | 51.777 | 1.00 | 24.70 | A |
| ATOM | 359 | C | HIS | A | 48 | 16.870 | −37.111 | 50.502 | 1.00 | 25.02 | A |
| ATOM | 360 | O | HIS | A | 48 | 17.084 | −37.637 | 49.411 | 1.00 | 24.86 | A |
| ATOM | 361 | N | LYS | A | 49 | 16.609 | −35.814 | 50.634 | 1.00 | 25.23 | A |
| ATOM | 362 | CA | LYS | A | 49 | 16.588 | −34.927 | 49.472 | 1.00 | 25.72 | A |
| ATOM | 363 | CB | LYS | A | 49 | 15.576 | −33.800 | 49.680 | 1.00 | 26.92 | A |
| ATOM | 364 | CG | LYS | A | 49 | 14.147 | −34.284 | 49.886 | 1.00 | 28.26 | A |
| ATOM | 365 | CD | LYS | A | 49 | 13.175 | −33.119 | 49.924 | 1.00 | 30.09 | A |
| ATOM | 366 | CE | LYS | A | 49 | 11.739 | −33.597 | 50.099 | 1.00 | 31.30 | A |
| ATOM | 367 | NZ | LYS | A | 49 | 10.776 | −32.457 | 50.099 | 1.00 | 31.83 | A |
| ATOM | 368 | C | LYS | A | 49 | 17.993 | −34.356 | 49.298 | 1.00 | 25.62 | A |
| ATOM | 369 | O | LYS | A | 49 | 18.215 | −33.150 | 49.423 | 1.00 | 25.21 | A |
| ATOM | 370 | N | THR | A | 50 | 18.936 | −35.247 | 49.005 | 1.00 | 25.27 | A |
| ATOM | 371 | CA | THR | A | 50 | 20.344 | −34.901 | 48.840 | 1.00 | 25.11 | A |
| ATOM | 372 | CB | THR | A | 50 | 21.147 | −36.142 | 48.410 | 1.00 | 25.28 | A |
| ATOM | 373 | OG1 | THR | A | 50 | 20.640 | −36.633 | 47.164 | 1.00 | 25.79 | A |
| ATOM | 374 | CG2 | THR | A | 50 | 21.018 | −37.238 | 49.459 | 1.00 | 25.39 | A |
| ATOM | 375 | C | THR | A | 50 | 20.662 | −33.751 | 47.882 | 1.00 | 25.05 | A |

APPENDIX C-continued

18xCHS Mutant

| ATOM | # | TYPE | RES | | | X | Y | Z | OCC | B | |
|------|---|------|-----|---|----|--------|---------|--------|------|-------|---|
| ATOM | 376 | O | THR | A | 50 | 21.462 | −32.875 | 48.211 | 1.00 | 24.58 | A |
| ATOM | 377 | N | GLU | A | 51 | 20.054 | −33.758 | 46.700 | 1.00 | 24.67 | A |
| ATOM | 378 | CA | GLU | A | 51 | 20.294 | −32.703 | 45.721 | 1.00 | 24.81 | A |
| ATOM | 379 | CB | GLU | A | 51 | 19.676 | −33.083 | 44.374 | 1.00 | 25.94 | A |
| ATOM | 380 | CG | GLU | A | 51 | 19.663 | −31.964 | 43.338 | 1.00 | 27.31 | A |
| ATOM | 381 | CD | GLU | A | 51 | 20.991 | −31.243 | 43.233 | 1.00 | 28.46 | A |
| ATOM | 382 | OE1 | GLU | A | 51 | 22.039 | −31.924 | 43.231 | 1.00 | 29.16 | A |
| ATOM | 383 | OE2 | GLU | A | 51 | 20.986 | −29.994 | 43.145 | 1.00 | 28.42 | A |
| ATOM | 384 | C | GLU | A | 51 | 19.729 | −31.365 | 46.195 | 1.00 | 24.29 | A |
| ATOM | 385 | O | GLU | A | 51 | 20.385 | −30.328 | 46.083 | 1.00 | 23.82 | A |
| ATOM | 386 | N | LEU | A | 52 | 18.511 | −31.394 | 46.725 | 1.00 | 23.31 | A |
| ATOM | 387 | CA | LEU | A | 52 | 17.874 | −30.180 | 47.222 | 1.00 | 22.68 | A |
| ATOM | 388 | CB | LEU | A | 52 | 16.477 | −30.508 | 47.767 | 1.00 | 22.59 | A |
| ATOM | 389 | CG | LEU | A | 52 | 15.576 | −29.339 | 48.178 | 1.00 | 22.20 | A |
| ATOM | 390 | CD1 | LEU | A | 52 | 15.415 | −28.367 | 47.016 | 1.00 | 22.61 | A |
| ATOM | 391 | CD2 | LEU | A | 52 | 14.221 | −29.876 | 48.612 | 1.00 | 22.03 | A |
| ATOM | 392 | C | LEU | A | 52 | 18.739 | −29.559 | 48.321 | 1.00 | 22.60 | A |
| ATOM | 393 | O | LEU | A | 52 | 18.904 | −28.340 | 48.380 | 1.00 | 22.40 | A |
| ATOM | 394 | N | LYS | A | 53 | 19.299 | −30.401 | 49.185 | 1.00 | 22.30 | A |
| ATOM | 395 | CA | LYS | A | 53 | 20.146 | −29.916 | 50.268 | 1.00 | 22.67 | A |
| ATOM | 396 | CB | LYS | A | 53 | 20.554 | −31.067 | 51.193 | 1.00 | 22.70 | A |
| ATOM | 397 | CG | LYS | A | 53 | 21.340 | −30.614 | 52.422 | 1.00 | 23.68 | A |
| ATOM | 398 | CD | LYS | A | 53 | 21.711 | −31.786 | 53.316 | 1.00 | 24.89 | A |
| ATOM | 399 | CE | LYS | A | 53 | 22.373 | −31.312 | 54.597 | 1.00 | 25.28 | A |
| ATOM | 400 | NZ | LYS | A | 53 | 22.726 | −32.448 | 55.491 | 1.00 | 26.32 | A |
| ATOM | 401 | C | LYS | A | 53 | 21.401 | −29.225 | 49.734 | 1.00 | 22.70 | A |
| ATOM | 402 | O | LYS | A | 53 | 21.884 | −28.267 | 50.336 | 1.00 | 22.36 | A |
| ATOM | 403 | N | GLU | A | 54 | 21.933 | −29.716 | 48.615 | 1.00 | 23.17 | A |
| ATOM | 404 | CA | GLU | A | 54 | 23.129 | −29.112 | 48.025 | 1.00 | 23.50 | A |
| ATOM | 405 | CB | GLU | A | 54 | 23.615 | −29.912 | 46.807 | 1.00 | 24.90 | A |
| ATOM | 406 | CG | GLU | A | 54 | 23.970 | −31.367 | 47.092 | 1.00 | 27.49 | A |
| ATOM | 407 | CD | GLU | A | 54 | 24.723 | −32.028 | 45.943 | 1.00 | 28.58 | A |
| ATOM | 408 | OE1 | GLU | A | 54 | 24.314 | −31.860 | 44.773 | 1.00 | 29.73 | A |
| ATOM | 409 | OE2 | GLU | A | 54 | 25.723 | −32.724 | 46.214 | 1.00 | 29.34 | A |
| ATOM | 410 | C | GLU | A | 54 | 22.793 | −27.691 | 47.591 | 1.00 | 22.71 | A |
| ATOM | 411 | O | GLU | A | 54 | 23.573 | −26.762 | 47.814 | 1.00 | 22.66 | A |
| ATOM | 412 | N | LYS | A | 55 | 21.629 | −27.533 | 46.964 | 1.00 | 21.69 | A |
| ATOM | 413 | CA | LYS | A | 55 | 21.178 | −26.225 | 46.506 | 1.00 | 21.03 | A |
| ATOM | 414 | CB | LYS | A | 55 | 19.819 | −26.330 | 45.801 | 1.00 | 20.58 | A |
| ATOM | 415 | CG | LYS | A | 55 | 19.849 | −26.920 | 44.399 | 1.00 | 21.67 | A |
| ATOM | 416 | CD | LYS | A | 55 | 18.472 | −26.811 | 43.746 | 1.00 | 22.06 | A |
| ATOM | 417 | CE | LYS | A | 55 | 18.490 | −27.256 | 42.290 | 1.00 | 22.95 | A |
| ATOM | 418 | NZ | LYS | A | 55 | 18.862 | −28.692 | 42.156 | 1.00 | 23.21 | A |
| ATOM | 419 | C | LYS | A | 55 | 21.049 | −25.260 | 47.684 | 1.00 | 20.45 | A |
| ATOM | 420 | O | LYS | A | 55 | 21.441 | −24.097 | 47.588 | 1.00 | 19.89 | A |
| ATOM | 421 | N | PHE | A | 56 | 20.498 | −25.748 | 48.794 | 1.00 | 19.90 | A |
| ATOM | 422 | CA | PHE | A | 56 | 20.309 | −24.914 | 49.976 | 1.00 | 19.76 | A |
| ATOM | 423 | CB | PHE | A | 56 | 19.436 | −25.638 | 51.009 | 1.00 | 19.84 | A |
| ATOM | 424 | CG | PHE | A | 56 | 18.945 | −24.743 | 52.119 | 1.00 | 19.88 | A |
| ATOM | 425 | CD1 | PHE | A | 56 | 18.160 | −23.628 | 51.833 | 1.00 | 19.11 | A |
| ATOM | 426 | CD2 | PHE | A | 56 | 19.283 | −25.003 | 53.444 | 1.00 | 19.71 | A |
| ATOM | 427 | CE1 | PHE | A | 56 | 17.718 | −22.782 | 52.853 | 1.00 | 19.68 | A |
| ATOM | 428 | CE2 | PHE | A | 56 | 18.848 | −24.165 | 54.473 | 1.00 | 19.76 | A |
| ATOM | 429 | CZ | PHE | A | 56 | 18.064 | −23.052 | 54.177 | 1.00 | 19.57 | A |
| ATOM | 430 | C | PHE | A | 56 | 21.648 | −24.509 | 50.599 | 1.00 | 20.08 | A |
| ATOM | 431 | O | PHE | A | 56 | 21.786 | −23.399 | 51.114 | 1.00 | 19.29 | A |
| ATOM | 432 | N | GLN | A | 57 | 22.633 | −25.404 | 50.544 | 1.00 | 20.33 | A |
| ATOM | 433 | CA | GLN | A | 57 | 23.957 | −25.102 | 51.084 | 1.00 | 21.34 | A |
| ATOM | 434 | CB | GLN | A | 57 | 24.883 | −26.318 | 50.958 | 1.00 | 21.90 | A |
| ATOM | 435 | CG | GLN | A | 57 | 26.264 | −26.129 | 51.590 | 1.00 | 22.72 | A |
| ATOM | 436 | CD | GLN | A | 57 | 26.206 | −25.936 | 53.094 | 1.00 | 23.02 | A |
| ATOM | 437 | OE1 | GLN | A | 57 | 25.666 | −26.776 | 53.818 | 1.00 | 23.90 | A |
| ATOM | 438 | NE2 | GLN | A | 57 | 26.766 | −24.830 | 53.573 | 1.00 | 22.69 | A |
| ATOM | 439 | C | GLN | A | 57 | 24.543 | −23.924 | 50.300 | 1.00 | 21.43 | A |
| ATOM | 440 | O | GLN | A | 57 | 25.161 | −23.026 | 50.880 | 1.00 | 21.65 | A |
| ATOM | 441 | N | ARG | A | 58 | 24.344 | −23.933 | 48.982 | 1.00 | 21.69 | A |
| ATOM | 442 | CA | ARG | A | 58 | 24.840 | −22.857 | 48.128 | 1.00 | 22.25 | A |
| ATOM | 443 | CB | ARG | A | 58 | 24.633 | −23.184 | 46.645 | 1.00 | 23.45 | A |
| ATOM | 444 | CG | ARG | A | 58 | 25.478 | −24.334 | 46.108 | 1.00 | 27.13 | A |
| ATOM | 445 | CD | ARG | A | 58 | 25.592 | −24.237 | 44.587 | 1.00 | 28.97 | A |
| ATOM | 446 | NE | ARG | A | 58 | 26.291 | −25.374 | 43.994 | 1.00 | 31.10 | A |
| ATOM | 447 | CZ | ARG | A | 58 | 25.779 | −26.596 | 43.878 | 1.00 | 31.73 | A |
| ATOM | 448 | NH1 | ARG | A | 58 | 24.551 | −26.851 | 44.316 | 1.00 | 30.89 | A |
| ATOM | 449 | NH2 | ARG | A | 58 | 26.495 | −27.563 | 43.317 | 1.00 | 31.70 | A |
| ATOM | 450 | C | ARG | A | 58 | 24.130 | −21.544 | 48.451 | 1.00 | 21.39 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 451 | O | ARG | A | 58 | 24.758 | −20.487 | 48.489 | 1.00 | 21.08 | A |
| ATOM | 452 | N | MET | A | 59 | 22.820 | −21.616 | 48.667 | 1.00 | 20.52 | A |
| ATOM | 453 | CA | MET | A | 59 | 22.037 | −20.433 | 49.004 | 1.00 | 20.06 | A |
| ATOM | 454 | CB | MET | A | 59 | 20.560 | −20.801 | 49.198 | 1.00 | 19.96 | A |
| ATOM | 455 | CG | MET | A | 59 | 19.825 | −21.168 | 47.908 | 1.00 | 20.74 | A |
| ATOM | 456 | SD | MET | A | 59 | 18.084 | −21.605 | 48.175 | 1.00 | 20.50 | A |
| ATOM | 457 | CE | MET | A | 59 | 17.663 | −22.339 | 46.587 | 1.00 | 21.29 | A |
| ATOM | 458 | C | MET | A | 59 | 22.586 | −19.807 | 50.285 | 1.00 | 20.21 | A |
| ATOM | 459 | O | MET | A | 59 | 22.811 | −18.595 | 50.348 | 1.00 | 19.35 | A |
| ATOM | 460 | N | CYS | A | 60 | 22.814 | −20.638 | 51.298 | 1.00 | 19.75 | A |
| ATOM | 461 | CA | CYS | A | 60 | 23.336 | −20.152 | 52.571 | 1.00 | 20.27 | A |
| ATOM | 462 | CB | CYS | A | 60 | 23.254 | −21.254 | 53.638 | 1.00 | 19.75 | A |
| ATOM | 463 | SG | CYS | A | 60 | 21.564 | −21.694 | 54.177 | 1.00 | 19.90 | A |
| ATOM | 464 | C | CYS | A | 60 | 24.772 | −19.627 | 52.468 | 1.00 | 20.80 | A |
| ATOM | 465 | O | CYS | A | 60 | 25.109 | −18.616 | 53.085 | 1.00 | 20.42 | A |
| ATOM | 466 | N | ASP | A | 61 | 25.618 | −20.301 | 51.689 | 1.00 | 21.26 | A |
| ATOM | 467 | CA | ASP | A | 61 | 27.008 | −19.865 | 51.542 | 1.00 | 22.02 | A |
| ATOM | 468 | CB | ASP | A | 61 | 27.826 | −20.878 | 50.729 | 1.00 | 22.21 | A |
| ATOM | 469 | CG | ASP | A | 61 | 28.014 | −22.201 | 51.445 | 1.00 | 23.21 | A |
| ATOM | 470 | OD1 | ASP | A | 61 | 27.908 | −22.240 | 52.692 | 1.00 | 21.87 | A |
| ATOM | 471 | OD2 | ASP | A | 61 | 28.290 | −23.203 | 50.747 | 1.00 | 23.65 | A |
| ATOM | 472 | C | ASP | A | 61 | 27.161 | −18.498 | 50.875 | 1.00 | 22.10 | A |
| ATOM | 473 | O | ASP | A | 61 | 28.122 | −17.778 | 51.145 | 1.00 | 22.14 | A |
| ATOM | 474 | N | LYS | A | 62 | 26.224 | −18.143 | 50.004 | 1.00 | 22.31 | A |
| ATOM | 475 | CA | LYS | A | 62 | 26.307 | −16.871 | 49.294 | 1.00 | 22.65 | A |
| ATOM | 476 | CB | LYS | A | 62 | 26.114 | −17.110 | 47.797 | 1.00 | 23.96 | A |
| ATOM | 477 | CG | LYS | A | 62 | 27.022 | −18.201 | 47.241 | 1.00 | 25.71 | A |
| ATOM | 478 | CD | LYS | A | 62 | 27.053 | −18.181 | 45.729 | 1.00 | 28.01 | A |
| ATOM | 479 | CE | LYS | A | 62 | 27.778 | −16.951 | 45.218 | 1.00 | 29.31 | A |
| ATOM | 480 | NZ | LYS | A | 62 | 29.179 | −16.906 | 45.723 | 1.00 | 30.60 | A |
| ATOM | 481 | C | LYS | A | 62 | 25.331 | −15.796 | 49.768 | 1.00 | 22.01 | A |
| ATOM | 482 | O | LYS | A | 62 | 25.206 | −14.746 | 49.135 | 1.00 | 21.84 | A |
| ATOM | 483 | N | SER | A | 63 | 24.660 | −16.052 | 50.886 | 1.00 | 20.99 | A |
| ATOM | 484 | CA | SER | A | 63 | 23.688 | −15.112 | 51.438 | 1.00 | 20.43 | A |
| ATOM | 485 | CB | SER | A | 63 | 22.798 | −15.830 | 52.452 | 1.00 | 19.65 | A |
| ATOM | 486 | OG | SER | A | 63 | 23.572 | −16.299 | 53.544 | 1.00 | 19.58 | A |
| ATOM | 487 | C | SER | A | 63 | 24.326 | −13.903 | 52.118 | 1.00 | 20.52 | A |
| ATOM | 488 | O | SER | A | 63 | 23.685 | −12.861 | 52.274 | 1.00 | 20.08 | A |
| ATOM | 489 | N | MET | A | 64 | 25.584 | −14.051 | 52.523 | 1.00 | 20.87 | A |
| ATOM | 490 | CA | MET | A | 64 | 26.315 | −12.990 | 53.212 | 1.00 | 21.59 | A |
| ATOM | 491 | CB | MET | A | 64 | 26.284 | −11.685 | 52.405 | 1.00 | 23.35 | A |
| ATOM | 492 | CG | MET | A | 64 | 26.926 | −11.785 | 51.024 | 1.00 | 25.55 | A |
| ATOM | 493 | SD | MET | A | 64 | 28.605 | −12.454 | 51.053 | 1.00 | 29.17 | A |
| ATOM | 494 | CE | MET | A | 64 | 28.299 | −14.085 | 50.424 | 1.00 | 28.30 | A |
| ATOM | 495 | C | MET | A | 64 | 25.730 | −12.762 | 54.606 | 1.00 | 21.04 | A |
| ATOM | 496 | O | MET | A | 64 | 25.831 | −11.671 | 55.175 | 1.00 | 20.22 | A |
| ATOM | 497 | N | ILE | A | 65 | 25.114 | −13.811 | 55.144 | 1.00 | 20.43 | A |
| ATOM | 498 | CA | ILE | A | 65 | 24.523 | −13.785 | 56.478 | 1.00 | 19.58 | A |
| ATOM | 499 | CB | ILE | A | 65 | 23.059 | −14.294 | 56.457 | 1.00 | 18.89 | A |
| ATOM | 500 | CG2 | ILE | A | 65 | 22.542 | −14.457 | 57.875 | 1.00 | 18.15 | A |
| ATOM | 501 | CG1 | ILE | A | 65 | 22.176 | −13.322 | 55.668 | 1.00 | 18.42 | A |
| ATOM | 502 | CD1 | ILE | A | 65 | 20.726 | −13.775 | 55.516 | 1.00 | 17.96 | A |
| ATOM | 503 | C | ILE | A | 65 | 25.344 | −14.718 | 57.362 | 1.00 | 19.92 | A |
| ATOM | 504 | O | ILE | A | 65 | 25.572 | −15.871 | 56.999 | 1.00 | 20.12 | A |
| ATOM | 505 | N | LYS | A | 66 | 25.794 | −14.225 | 58.513 | 1.00 | 19.96 | A |
| ATOM | 506 | CA | LYS | A | 66 | 26.584 | −15.047 | 59.426 | 1.00 | 20.16 | A |
| ATOM | 507 | CB | LYS | A | 66 | 27.604 | −14.186 | 60.175 | 1.00 | 21.74 | A |
| ATOM | 508 | CG | LYS | A | 66 | 28.575 | −13.467 | 59.257 | 1.00 | 24.36 | A |
| ATOM | 509 | CD | LYS | A | 66 | 29.645 | −12.710 | 60.029 | 1.00 | 25.33 | A |
| ATOM | 510 | CE | LYS | A | 66 | 30.637 | −13.655 | 60.689 | 1.00 | 26.98 | A |
| ATOM | 511 | NZ | LYS | A | 66 | 31.829 | −12.917 | 61.209 | 1.00 | 26.99 | A |
| ATOM | 512 | C | LYS | A | 66 | 25.696 | −15.782 | 60.431 | 1.00 | 19.49 | A |
| ATOM | 513 | O | LYS | A | 66 | 25.986 | −16.918 | 60.812 | 1.00 | 18.64 | A |
| ATOM | 514 | N | ARG | A | 67 | 24.622 | −15.126 | 60.861 | 1.00 | 18.51 | A |
| ATOM | 515 | CA | ARG | A | 67 | 23.691 | −15.726 | 61.810 | 1.00 | 18.88 | A |
| ATOM | 516 | CB | ARG | A | 67 | 24.349 | −15.877 | 63.187 | 1.00 | 20.52 | A |
| ATOM | 517 | CG | ARG | A | 67 | 25.004 | −14.622 | 63.746 | 1.00 | 23.68 | A |
| ATOM | 518 | CD | ARG | A | 67 | 25.877 | −14.994 | 64.946 | 1.00 | 26.21 | A |
| ATOM | 519 | NE | ARG | A | 67 | 26.647 | −13.871 | 65.476 | 1.00 | 28.84 | A |
| ATOM | 520 | CZ | ARG | A | 67 | 27.641 | −13.264 | 64.833 | 1.00 | 29.97 | A |
| ATOM | 521 | NH1 | ARG | A | 67 | 27.999 | −13.664 | 63.621 | 1.00 | 30.84 | A |
| ATOM | 522 | NH2 | ARG | A | 67 | 28.286 | −12.257 | 65.410 | 1.00 | 30.56 | A |
| ATOM | 523 | C | ARG | A | 67 | 22.385 | −14.950 | 61.939 | 1.00 | 17.34 | A |
| ATOM | 524 | O | ARG | A | 67 | 22.300 | −13.788 | 61.540 | 1.00 | 17.53 | A |
| ATOM | 525 | N | ARG | A | 68 | 21.373 | −15.612 | 62.494 | 1.00 | 15.84 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 526 | CA | ARG | A | 68 | 20.048 | −15.030 | 62.690 | 1.00 | 15.12 | A |
| ATOM | 527 | CB | ARG | A | 68 | 19.090 | −15.512 | 61.595 | 1.00 | 15.02 | A |
| ATOM | 528 | CG | ARG | A | 68 | 19.435 | −15.049 | 60.182 | 1.00 | 15.37 | A |
| ATOM | 529 | CD | ARG | A | 68 | 18.539 | −15.737 | 59.159 | 1.00 | 15.36 | A |
| ATOM | 530 | NE | ARG | A | 68 | 18.998 | −17.087 | 58.835 | 1.00 | 15.15 | A |
| ATOM | 531 | CZ | ARG | A | 68 | 18.294 | −17.961 | 58.118 | 1.00 | 16.53 | A |
| ATOM | 532 | NH1 | ARG | A | 68 | 17.092 | −17.632 | 57.656 | 1.00 | 14.86 | A |
| ATOM | 533 | NH2 | ARG | A | 68 | 18.797 | −19.160 | 57.842 | 1.00 | 15.79 | A |
| ATOM | 534 | C | ARG | A | 68 | 19.481 | −15.459 | 64.047 | 1.00 | 15.54 | A |
| ATOM | 535 | O | ARG | A | 68 | 19.968 | −16.408 | 64.661 | 1.00 | 15.15 | A |
| ATOM | 536 | N | TYR | A | 69 | 18.445 | −14.762 | 64.503 | 1.00 | 14.96 | A |
| ATOM | 537 | CA | TYR | A | 69 | 17.798 | −15.088 | 65.770 | 1.00 | 15.18 | A |
| ATOM | 538 | CB | TYR | A | 69 | 17.811 | −13.869 | 66.701 | 1.00 | 15.19 | A |
| ATOM | 539 | CG | TYR | A | 69 | 19.222 | −13.407 | 67.003 | 1.00 | 15.86 | A |
| ATOM | 540 | CD1 | TYR | A | 69 | 19.938 | −12.641 | 66.081 | 1.00 | 15.86 | A |
| ATOM | 541 | CE1 | TYR | A | 69 | 21.279 | −12.307 | 66.304 | 1.00 | 16.29 | A |
| ATOM | 542 | CD2 | TYR | A | 69 | 19.876 | −13.821 | 68.163 | 1.00 | 16.01 | A |
| ATOM | 543 | CE2 | TYR | A | 69 | 21.213 | −13.498 | 68.394 | 1.00 | 16.51 | A |
| ATOM | 544 | CZ | TYR | A | 69 | 21.909 | −12.745 | 67.462 | 1.00 | 16.56 | A |
| ATOM | 545 | OH | TYR | A | 69 | 23.243 | −12.456 | 67.670 | 1.00 | 17.13 | A |
| ATOM | 546 | C | TYR | A | 69 | 16.377 | −15.533 | 65.459 | 1.00 | 15.75 | A |
| ATOM | 547 | O | TYR | A | 69 | 15.668 | −14.878 | 64.692 | 1.00 | 15.23 | A |
| ATOM | 548 | N | MET | A | 70 | 15.965 | −16.655 | 66.040 | 1.00 | 15.97 | A |
| ATOM | 549 | CA | MET | A | 70 | 14.631 | −17.191 | 65.775 | 1.00 | 17.00 | A |
| ATOM | 550 | CB | MET | A | 70 | 14.731 | −18.369 | 64.796 | 1.00 | 18.13 | A |
| ATOM | 551 | CG | MET | A | 70 | 15.216 | −18.019 | 63.389 | 1.00 | 20.30 | A |
| ATOM | 552 | SD | MET | A | 70 | 15.414 | −19.496 | 62.341 | 1.00 | 23.91 | A |
| ATOM | 553 | CE | MET | A | 70 | 16.362 | −18.809 | 60.972 | 1.00 | 22.14 | A |
| ATOM | 554 | C | MET | A | 70 | 13.857 | −17.654 | 67.007 | 1.00 | 16.77 | A |
| ATOM | 555 | O | MET | A | 70 | 14.386 | −18.385 | 67.844 | 1.00 | 17.33 | A |
| ATOM | 556 | N | TYR | A | 71 | 12.598 | −17.231 | 67.099 | 1.00 | 16.96 | A |
| ATOM | 557 | CA | TYR | A | 71 | 11.713 | −17.629 | 68.193 | 1.00 | 17.37 | A |
| ATOM | 558 | CB | TYR | A | 71 | 10.377 | −16.878 | 68.096 | 1.00 | 17.57 | A |
| ATOM | 559 | CG | TYR | A | 71 | 9.219 | −17.560 | 68.802 | 1.00 | 18.29 | A |
| ATOM | 560 | CD1 | TYR | A | 71 | 9.065 | −17.475 | 70.185 | 1.00 | 18.60 | A |
| ATOM | 561 | CE1 | TYR | A | 71 | 8.012 | −18.126 | 70.835 | 1.00 | 19.20 | A |
| ATOM | 562 | CD2 | TYR | A | 71 | 8.291 | −18.311 | 68.083 | 1.00 | 18.96 | A |
| ATOM | 563 | CE2 | TYR | A | 71 | 7.238 | −18.963 | 68.719 | 1.00 | 19.52 | A |
| ATOM | 564 | CZ | TYR | A | 71 | 7.103 | −18.868 | 70.093 | 1.00 | 19.82 | A |
| ATOM | 565 | OH | TYR | A | 71 | 6.056 | −19.511 | 70.718 | 1.00 | 19.82 | A |
| ATOM | 566 | C | TYR | A | 71 | 11.462 | −19.135 | 68.079 | 1.00 | 17.45 | A |
| ATOM | 567 | O | TYR | A | 71 | 11.358 | −19.842 | 69.085 | 1.00 | 16.85 | A |
| ATOM | 568 | N | LEU | A | 72 | 11.348 | −19.613 | 66.843 | 1.00 | 17.94 | A |
| ATOM | 569 | CA | LEU | A | 72 | 11.124 | −21.032 | 66.586 | 1.00 | 18.87 | A |
| ATOM | 570 | CB | LEU | A | 72 | 10.858 | −21.288 | 65.098 | 1.00 | 19.09 | A |
| ATOM | 571 | CG | LEU | A | 72 | 9.483 | −20.991 | 64.499 | 1.00 | 19.52 | A |
| ATOM | 572 | CD1 | LEU | A | 72 | 9.514 | −21.350 | 63.019 | 1.00 | 19.49 | A |
| ATOM | 573 | CD2 | LEU | A | 72 | 8.404 | −21.791 | 65.213 | 1.00 | 19.42 | A |
| ATOM | 574 | C | LEU | A | 72 | 12.352 | −21.831 | 66.997 | 1.00 | 18.91 | A |
| ATOM | 575 | O | LEU | A | 72 | 13.458 | −21.568 | 66.528 | 1.00 | 19.47 | A |
| ATOM | 576 | N | THR | A | 73 | 12.152 | −22.808 | 67.871 | 1.00 | 19.15 | A |
| ATOM | 577 | CA | THR | A | 73 | 13.247 | −23.651 | 68.336 | 1.00 | 19.69 | A |
| ATOM | 578 | CB | THR | A | 73 | 13.379 | −23.592 | 69.863 | 1.00 | 19.91 | A |
| ATOM | 579 | OG1 | THR | A | 73 | 12.153 | −24.037 | 70.457 | 1.00 | 20.02 | A |
| ATOM | 580 | CG2 | THR | A | 73 | 13.679 | −22.176 | 70.321 | 1.00 | 19.67 | A |
| ATOM | 581 | C | THR | A | 73 | 12.955 | −25.093 | 67.946 | 1.00 | 20.34 | A |
| ATOM | 582 | O | THR | A | 73 | 11.850 | −25.416 | 67.509 | 1.00 | 19.94 | A |
| ATOM | 583 | N | GLU | A | 74 | 13.945 | −25.963 | 68.101 | 1.00 | 20.84 | A |
| ATOM | 584 | CA | GLU | A | 74 | 13.747 | −27.364 | 67.775 | 1.00 | 21.72 | A |
| ATOM | 585 | CB | GLU | A | 74 | 15.055 | −28.140 | 67.970 | 1.00 | 22.75 | A |
| ATOM | 586 | CG | GLU | A | 74 | 14.904 | −29.649 | 67.901 | 1.00 | 24.21 | A |
| ATOM | 587 | CD | GLU | A | 74 | 16.228 | −30.359 | 67.729 | 1.00 | 25.53 | A |
| ATOM | 588 | OE1 | GLU | A | 74 | 17.232 | −29.907 | 68.322 | 1.00 | 25.87 | A |
| ATOM | 589 | OE2 | GLU | A | 74 | 16.263 | −31.378 | 67.003 | 1.00 | 26.84 | A |
| ATOM | 590 | C | GLU | A | 74 | 12.629 | −27.968 | 68.632 | 1.00 | 21.92 | A |
| ATOM | 591 | O | GLU | A | 74 | 11.862 | −28.803 | 68.153 | 1.00 | 21.27 | A |
| ATOM | 592 | N | GLU | A | 75 | 12.520 | −27.538 | 69.888 | 1.00 | 22.05 | A |
| ATOM | 593 | CA | GLU | A | 75 | 11.481 | −28.073 | 70.769 | 1.00 | 22.84 | A |
| ATOM | 594 | CB | GLU | A | 75 | 11.667 | −27.583 | 72.209 | 1.00 | 24.92 | A |
| ATOM | 595 | CG | GLU | A | 75 | 13.096 | −27.606 | 72.704 | 1.00 | 27.52 | A |
| ATOM | 596 | CD | GLU | A | 75 | 13.837 | −26.334 | 72.354 | 1.00 | 29.08 | A |
| ATOM | 597 | OE1 | GLU | A | 75 | 13.446 | −25.259 | 72.867 | 1.00 | 30.76 | A |
| ATOM | 598 | OE2 | GLU | A | 75 | 14.803 | −26.403 | 71.567 | 1.00 | 30.32 | A |
| ATOM | 599 | C | GLU | A | 75 | 10.086 | −27.682 | 70.296 | 1.00 | 22.09 | A |
| ATOM | 600 | O | GLU | A | 75 | 9.157 | −28.493 | 70.327 | 1.00 | 21.65 | A |

APPENDIX C-continued

18xCHS Mutant

| ATOM | # | TYPE | RES | | | X | Y | Z | OCC | B | |
|------|---|------|-----|---|---|---|---|---|-----|---|---|
| ATOM | 601 | N | ILE | A | 76 | 9.937 | −26.432 | 69.869 | 1.00 | 21.20 | A |
| ATOM | 602 | CA | ILE | A | 76 | 8.648 | −25.953 | 69.388 | 1.00 | 20.72 | A |
| ATOM | 603 | CB | ILE | A | 76 | 8.677 | −24.424 | 69.138 | 1.00 | 20.85 | A |
| ATOM | 604 | CG2 | ILE | A | 76 | 7.408 | −23.981 | 68.404 | 1.00 | 20.95 | A |
| ATOM | 605 | CG1 | ILE | A | 76 | 8.814 | −23.689 | 70.476 | 1.00 | 21.17 | A |
| ATOM | 606 | CD1 | ILE | A | 76 | 8.900 | −22.178 | 70.356 | 1.00 | 21.73 | A |
| ATOM | 607 | C | ILE | A | 76 | 8.288 | −26.677 | 68.094 | 1.00 | 20.27 | A |
| ATOM | 608 | O | ILE | A | 76 | 7.169 | −27.165 | 67.939 | 1.00 | 19.16 | A |
| ATOM | 609 | N | LEU | A | 77 | 9.243 | −26.757 | 67.173 | 1.00 | 20.41 | A |
| ATOM | 610 | CA | LEU | A | 77 | 8.992 | −27.427 | 65.904 | 1.00 | 21.09 | A |
| ATOM | 611 | CB | LEU | A | 77 | 10.233 | −27.365 | 65.008 | 1.00 | 20.90 | A |
| ATOM | 612 | CG | LEU | A | 77 | 10.516 | −25.973 | 64.424 | 1.00 | 20.93 | A |
| ATOM | 613 | CD1 | LEU | A | 77 | 11.852 | −25.962 | 63.711 | 1.00 | 21.04 | A |
| ATOM | 614 | CD2 | LEU | A | 77 | 9.395 | −25.587 | 63.467 | 1.00 | 20.50 | A |
| ATOM | 615 | C | LEU | A | 77 | 8.557 | −28.872 | 66.114 | 1.00 | 21.87 | A |
| ATOM | 616 | O | LEU | A | 77 | 7.678 | −29.367 | 65.409 | 1.00 | 22.38 | A |
| ATOM | 617 | N | LYS | A | 78 | 9.150 | −29.546 | 67.095 | 1.00 | 22.54 | A |
| ATOM | 618 | CA | LYS | A | 78 | 8.785 | −30.933 | 67.354 | 1.00 | 23.21 | A |
| ATOM | 619 | CB | LYS | A | 78 | 9.792 | −31.577 | 68.320 | 1.00 | 24.36 | A |
| ATOM | 620 | CG | LYS | A | 78 | 11.206 | −31.602 | 67.746 | 1.00 | 26.62 | A |
| ATOM | 621 | CD | LYS | A | 78 | 12.031 | −32.799 | 68.203 | 1.00 | 28.49 | A |
| ATOM | 622 | CE | LYS | A | 78 | 12.481 | −32.672 | 69.644 | 1.00 | 29.78 | A |
| ATOM | 623 | NZ | LYS | A | 78 | 13.422 | −33.776 | 70.010 | 1.00 | 30.83 | A |
| ATOM | 624 | C | LYS | A | 78 | 7.355 | −31.090 | 67.871 | 1.00 | 22.73 | A |
| ATOM | 625 | O | LYS | A | 78 | 6.767 | −32.162 | 67.753 | 1.00 | 23.44 | A |
| ATOM | 626 | N | GLU | A | 79 | 6.788 | −30.017 | 68.417 | 1.00 | 22.50 | A |
| ATOM | 627 | CA | GLU | A | 79 | 5.418 | −30.042 | 68.940 | 1.00 | 22.20 | A |
| ATOM | 628 | CB | GLU | A | 79 | 5.274 | −29.037 | 70.094 | 1.00 | 24.23 | A |
| ATOM | 629 | CG | GLU | A | 79 | 6.191 | −29.276 | 71.295 | 1.00 | 27.11 | A |
| ATOM | 630 | CD | GLU | A | 79 | 6.244 | −28.080 | 72.247 | 1.00 | 29.29 | A |
| ATOM | 631 | OE1 | GLU | A | 79 | 5.173 | −27.543 | 72.598 | 1.00 | 31.41 | A |
| ATOM | 632 | OE2 | GLU | A | 79 | 7.357 | −27.678 | 72.655 | 1.00 | 30.28 | A |
| ATOM | 633 | C | GLU | A | 79 | 4.380 | −29.695 | 67.859 | 1.00 | 20.87 | A |
| ATOM | 634 | O | GLU | A | 79 | 3.180 | −29.910 | 68.046 | 1.00 | 20.47 | A |
| ATOM | 635 | N | ASN | A | 80 | 4.843 | −29.158 | 66.734 | 1.00 | 18.83 | A |
| ATOM | 636 | CA | ASN | A | 80 | 3.946 | −28.749 | 65.648 | 1.00 | 17.98 | A |
| ATOM | 637 | CB | ASN | A | 80 | 4.013 | −27.229 | 65.498 | 1.00 | 17.92 | A |
| ATOM | 638 | CG | ASN | A | 80 | 3.591 | −26.503 | 66.761 | 1.00 | 18.10 | A |
| ATOM | 639 | OD1 | ASN | A | 80 | 2.407 | −26.251 | 66.978 | 1.00 | 17.75 | A |
| ATOM | 640 | ND2 | ASN | A | 80 | 4.562 | −26.178 | 67.612 | 1.00 | 17.68 | A |
| ATOM | 641 | C | ASN | A | 80 | 4.319 | −29.421 | 64.328 | 1.00 | 16.94 | A |
| ATOM | 642 | O | ASN | A | 80 | 4.901 | −28.797 | 63.442 | 1.00 | 16.43 | A |
| ATOM | 643 | N | PRO | A | 81 | 3.961 | −30.703 | 64.172 | 1.00 | 16.48 | A |
| ATOM | 644 | CD | PRO | A | 81 | 3.181 | −31.528 | 65.108 | 1.00 | 16.60 | A |
| ATOM | 645 | CA | PRO | A | 81 | 4.281 | −31.448 | 62.949 | 1.00 | 16.06 | A |
| ATOM | 646 | CB | PRO | A | 81 | 3.647 | −32.826 | 63.200 | 1.00 | 16.19 | A |
| ATOM | 647 | CG | PRO | A | 81 | 2.576 | −32.556 | 64.195 | 1.00 | 17.80 | A |
| ATOM | 648 | C | PRO | A | 81 | 3.895 | −30.837 | 61.598 | 1.00 | 15.44 | A |
| ATOM | 649 | O | PRO | A | 81 | 4.656 | −30.956 | 60.635 | 1.00 | 14.88 | A |
| ATOM | 650 | N | ASN | A | 82 | 2.740 | −30.180 | 61.512 | 1.00 | 14.66 | A |
| ATOM | 651 | CA | ASN | A | 82 | 2.334 | −29.578 | 60.241 | 1.00 | 14.83 | A |
| ATOM | 652 | CB | ASN | A | 82 | 0.833 | −29.240 | 60.252 | 1.00 | 14.58 | A |
| ATOM | 653 | CG | ASN | A | 82 | −0.039 | −30.447 | 59.932 | 1.00 | 15.49 | A |
| ATOM | 654 | OD1 | ASN | A | 82 | −1.277 | −30.345 | 59.864 | 1.00 | 15.62 | A |
| ATOM | 655 | ND2 | ASN | A | 82 | 0.598 | −31.595 | 59.729 | 1.00 | 14.09 | A |
| ATOM | 656 | C | ASN | A | 82 | 3.160 | −28.337 | 59.877 | 1.00 | 14.64 | A |
| ATOM | 657 | O | ASN | A | 82 | 3.217 | −27.939 | 58.714 | 1.00 | 14.35 | A |
| ATOM | 658 | N | VAL | A | 83 | 3.805 | −27.728 | 60.866 | 1.00 | 14.89 | A |
| ATOM | 659 | CA | VAL | A | 83 | 4.637 | −26.556 | 60.596 | 1.00 | 15.18 | A |
| ATOM | 660 | CB | VAL | A | 83 | 5.025 | −25.821 | 61.910 | 1.00 | 14.86 | A |
| ATOM | 661 | CG1 | VAL | A | 83 | 6.039 | −24.718 | 61.621 | 1.00 | 15.10 | A |
| ATOM | 662 | CG2 | VAL | A | 83 | 3.783 | −25.221 | 62.552 | 1.00 | 14.94 | A |
| ATOM | 663 | C | VAL | A | 83 | 5.909 | −26.987 | 59.857 | 1.00 | 15.64 | A |
| ATOM | 664 | O | VAL | A | 83 | 6.543 | −26.183 | 59.162 | 1.00 | 15.69 | A |
| ATOM | 665 | N | CYS | A | 84 | 6.270 | −28.260 | 59.995 | 1.00 | 15.13 | A |
| ATOM | 666 | CA | CYS | A | 84 | 7.465 | −28.790 | 59.341 | 1.00 | 16.08 | A |
| ATOM | 667 | CB | CYS | A | 84 | 8.022 | −29.967 | 60.147 | 1.00 | 16.89 | A |
| ATOM | 668 | SG | CYS | A | 84 | 8.593 | −29.490 | 61.809 | 1.00 | 20.29 | A |
| ATOM | 669 | C | CYS | A | 84 | 7.242 | −29.216 | 57.889 | 1.00 | 15.77 | A |
| ATOM | 670 | O | CYS | A | 84 | 8.199 | −29.479 | 57.164 | 1.00 | 15.77 | A |
| ATOM | 671 | N | GLU | A | 85 | 5.983 | −29.294 | 57.470 | 1.00 | 15.87 | A |
| ATOM | 672 | CA | GLU | A | 85 | 5.658 | −29.675 | 56.098 | 1.00 | 16.07 | A |
| ATOM | 673 | CB | GLU | A | 85 | 4.262 | −30.308 | 56.032 | 1.00 | 16.42 | A |
| ATOM | 674 | CG | GLU | A | 85 | 4.131 | −31.593 | 56.834 | 1.00 | 16.57 | A |
| ATOM | 675 | CD | GLU | A | 85 | 4.986 | −32.721 | 56.280 | 1.00 | 17.93 | A |

APPENDIX C-continued

18xCHS Mutant

| ATOM | # | TYPE | RES | | | X | Y | Z | OCC | B | |
|------|---|------|-----|---|---|---|---|---|-----|---|---|
| ATOM | 676 | OE1 | GLU | A | 85 | 5.562 | −33.478 | 57.087 | 1.00 | 17.45 | A |
| ATOM | 677 | OE2 | GLU | A | 85 | 5.075 | −32.860 | 55.041 | 1.00 | 18.39 | A |
| ATOM | 678 | C | GLU | A | 85 | 5.699 | −28.430 | 55.222 | 1.00 | 16.50 | A |
| ATOM | 679 | O | GLU | A | 85 | 5.616 | −27.316 | 55.727 | 1.00 | 15.38 | A |
| ATOM | 680 | N | TYR | A | 86 | 5.830 | −28.612 | 53.910 | 1.00 | 17.34 | A |
| ATOM | 681 | CA | TYR | A | 86 | 5.874 | −27.460 | 53.018 | 1.00 | 18.46 | A |
| ATOM | 682 | CB | TYR | A | 86 | 6.224 | −27.887 | 51.582 | 1.00 | 19.38 | A |
| ATOM | 683 | CG | TYR | A | 86 | 6.095 | −26.761 | 50.585 | 1.00 | 20.22 | A |
| ATOM | 684 | CD1 | TYR | A | 86 | 6.856 | −25.597 | 50.716 | 1.00 | 21.14 | A |
| ATOM | 685 | CE1 | TYR | A | 86 | 6.676 | −24.519 | 49.855 | 1.00 | 22.27 | A |
| ATOM | 686 | CD2 | TYR | A | 86 | 5.155 | −26.821 | 49.555 | 1.00 | 21.48 | A |
| ATOM | 687 | CE2 | TYR | A | 86 | 4.967 | −25.748 | 48.686 | 1.00 | 22.12 | A |
| ATOM | 688 | CZ | TYR | A | 86 | 5.727 | −24.600 | 48.845 | 1.00 | 22.64 | A |
| ATOM | 689 | OH | TYR | A | 86 | 5.517 | −23.521 | 48.020 | 1.00 | 23.89 | A |
| ATOM | 690 | C | TYR | A | 86 | 4.544 | −26.712 | 53.019 | 1.00 | 18.72 | A |
| ATOM | 691 | O | TYR | A | 86 | 4.518 | −25.482 | 53.102 | 1.00 | 18.89 | A |
| ATOM | 692 | N | MET | A | 87 | 3.441 | −27.449 | 52.943 | 1.00 | 18.63 | A |
| ATOM | 693 | CA | MET | A | 87 | 2.128 | −26.818 | 52.912 | 1.00 | 19.97 | A |
| ATOM | 694 | CB | MET | A | 87 | 1.734 | −26.542 | 51.463 | 1.00 | 22.09 | A |
| ATOM | 695 | CG | MET | A | 87 | 0.665 | −25.497 | 51.318 | 1.00 | 24.97 | A |
| ATOM | 696 | SD | MET | A | 87 | 1.405 | −23.880 | 51.450 | 1.00 | 30.11 | A |
| ATOM | 697 | CE | MET | A | 87 | 1.541 | −23.463 | 49.721 | 1.00 | 27.15 | A |
| ATOM | 698 | C | MET | A | 87 | 1.020 | −27.639 | 53.574 | 1.00 | 19.37 | A |
| ATOM | 699 | O | MET | A | 87 | 0.199 | −28.245 | 52.884 | 1.00 | 20.41 | A |
| ATOM | 700 | N | ALA | A | 88 | 0.989 | −27.654 | 54.903 | 1.00 | 18.05 | A |
| ATOM | 701 | CA | ALA | A | 88 | −0.033 | −28.402 | 55.642 | 1.00 | 17.23 | A |
| ATOM | 702 | CB | ALA | A | 88 | 0.624 | −29.521 | 56.451 | 1.00 | 17.03 | A |
| ATOM | 703 | C | ALA | A | 88 | −0.797 | −27.453 | 56.576 | 1.00 | 16.29 | A |
| ATOM | 704 | O | ALA | A | 88 | −0.274 | −26.407 | 56.952 | 1.00 | 16.42 | A |
| ATOM | 705 | N | PRO | A | 89 | −2.043 | −27.808 | 56.956 | 1.00 | 15.67 | A |
| ATOM | 706 | CD | PRO | A | 89 | −2.741 | −29.042 | 56.551 | 1.00 | 15.28 | A |
| ATOM | 707 | CA | PRO | A | 89 | −2.894 | −26.998 | 57.846 | 1.00 | 15.05 | A |
| ATOM | 708 | CB | PRO | A | 89 | −4.104 | −27.900 | 58.083 | 1.00 | 15.61 | A |
| ATOM | 709 | CG | PRO | A | 89 | −4.184 | −28.697 | 56.819 | 1.00 | 15.58 | A |
| ATOM | 710 | C | PRO | A | 89 | −2.178 | −26.655 | 59.154 | 1.00 | 14.67 | A |
| ATOM | 711 | O | PRO | A | 89 | −1.999 | −27.523 | 60.008 | 1.00 | 14.71 | A |
| ATOM | 712 | N | SER | A | 90 | −1.792 | −25.391 | 59.321 | 1.00 | 13.74 | A |
| ATOM | 713 | CA | SER | A | 90 | −1.061 | −24.990 | 60.526 | 1.00 | 13.11 | A |
| ATOM | 714 | CB | SER | A | 90 | 0.427 | −25.292 | 60.326 | 1.00 | 13.29 | A |
| ATOM | 715 | OG | SER | A | 90 | 0.922 | −24.652 | 59.149 | 1.00 | 13.45 | A |
| ATOM | 716 | C | SER | A | 90 | −1.219 | −23.527 | 60.950 | 1.00 | 13.09 | A |
| ATOM | 717 | O | SER | A | 90 | −0.528 | −23.066 | 61.866 | 1.00 | 12.71 | A |
| ATOM | 718 | N | LEU | A | 91 | −2.125 | −22.792 | 60.309 | 1.00 | 12.11 | A |
| ATOM | 719 | CA | LEU | A | 91 | −2.308 | −21.386 | 60.669 | 1.00 | 11.80 | A |
| ATOM | 720 | CB | LEU | A | 91 | −3.361 | −20.725 | 59.770 | 1.00 | 11.33 | A |
| ATOM | 721 | CG | LEU | A | 91 | −3.691 | −19.275 | 60.146 | 1.00 | 11.28 | A |
| ATOM | 722 | CD1 | LEU | A | 91 | −2.489 | −18.391 | 59.860 | 1.00 | 10.89 | A |
| ATOM | 723 | CD2 | LEU | A | 91 | −4.913 | −18.792 | 59.357 | 1.00 | 10.27 | A |
| ATOM | 724 | C | LEU | A | 91 | −2.697 | −21.164 | 62.131 | 1.00 | 11.83 | A |
| ATOM | 725 | O | LEU | A | 91 | −2.109 | −20.321 | 62.809 | 1.00 | 11.61 | A |
| ATOM | 726 | N | ASP | A | 92 | −3.680 | −21.917 | 62.622 | 1.00 | 12.12 | A |
| ATOM | 727 | CA | ASP | A | 92 | −4.134 | −21.745 | 64.001 | 1.00 | 12.34 | A |
| ATOM | 728 | CB | ASP | A | 92 | −5.233 | −22.771 | 64.340 | 1.00 | 12.99 | A |
| ATOM | 729 | CG | ASP | A | 92 | −6.524 | −22.550 | 63.536 | 1.00 | 14.23 | A |
| ATOM | 730 | OD1 | ASP | A | 92 | −6.606 | −21.569 | 62.768 | 1.00 | 14.04 | A |
| ATOM | 731 | OD2 | ASP | A | 92 | −7.468 | −23.362 | 63.677 | 1.00 | 15.03 | A |
| ATOM | 732 | C | ASP | A | 92 | −2.996 | −21.823 | 65.022 | 1.00 | 12.28 | A |
| ATOM | 733 | O | ASP | A | 92 | −2.963 | −21.045 | 65.980 | 1.00 | 12.39 | A |
| ATOM | 734 | N | ALA | A | 93 | −2.060 | −22.747 | 64.820 | 1.00 | 11.80 | A |
| ATOM | 735 | CA | ALA | A | 93 | −0.931 | −22.884 | 65.737 | 1.00 | 11.93 | A |
| ATOM | 736 | CB | ALA | A | 93 | −0.177 | −24.187 | 65.462 | 1.00 | 12.38 | A |
| ATOM | 737 | C | ALA | A | 93 | 0.010 | −21.685 | 65.601 | 1.00 | 12.01 | A |
| ATOM | 738 | O | ALA | A | 93 | 0.526 | −21.175 | 66.599 | 1.00 | 11.34 | A |
| ATOM | 739 | N | ARG | A | 94 | 0.234 | −21.237 | 64.366 | 1.00 | 11.55 | A |
| ATOM | 740 | CA | ARG | A | 94 | 1.102 | −20.084 | 64.120 | 1.00 | 11.09 | A |
| ATOM | 741 | CB | ARG | A | 94 | 1.325 | −19.893 | 62.605 | 1.00 | 10.46 | A |
| ATOM | 742 | CG | ARG | A | 94 | 2.047 | −21.056 | 61.875 | 1.00 | 10.01 | A |
| ATOM | 743 | CD | ARG | A | 94 | 1.938 | −20.890 | 60.346 | 1.00 | 10.88 | A |
| ATOM | 744 | NE | ARG | A | 94 | 2.397 | −22.036 | 59.544 | 1.00 | 11.13 | A |
| ATOM | 745 | CZ | ARG | A | 94 | 3.660 | −22.262 | 59.184 | 1.00 | 12.04 | A |
| ATOM | 746 | NH1 | ARG | A | 94 | 4.622 | −21.427 | 59.553 | 1.00 | 11.41 | A |
| ATOM | 747 | NH2 | ARG | A | 94 | 3.962 | −23.309 | 58.420 | 1.00 | 10.17 | A |
| ATOM | 748 | C | ARG | A | 94 | 0.484 | −18.807 | 64.728 | 1.00 | 11.74 | A |
| ATOM | 749 | O | ARG | A | 94 | 1.201 | −17.938 | 65.236 | 1.00 | 12.18 | A |
| ATOM | 750 | N | GLN | A | 95 | −0.843 | −18.699 | 64.692 | 1.00 | 11.95 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 751 | CA | GLN | A | 95 | −1.524 | −17.524 | 65.243 | 1.00 | 12.30 | A |
| ATOM | 752 | CB | GLN | A | 95 | −3.039 | −17.590 | 64.973 | 1.00 | 12.64 | A |
| ATOM | 753 | CG | GLN | A | 95 | −3.438 | −17.531 | 63.488 | 1.00 | 12.78 | A |
| ATOM | 754 | CD | GLN | A | 95 | −3.080 | −16.212 | 62.812 | 1.00 | 13.00 | A |
| ATOM | 755 | OE1 | GLN | A | 95 | −1.934 | −15.765 | 62.861 | 1.00 | 11.99 | A |
| ATOM | 756 | NE2 | GLN | A | 95 | −4.067 | −15.587 | 62.170 | 1.00 | 12.04 | A |
| ATOM | 757 | C | GLN | A | 95 | −1.275 | −17.390 | 66.745 | 1.00 | 12.26 | A |
| ATOM | 758 | O | GLN | A | 95 | −1.037 | −16.287 | 67.243 | 1.00 | 11.48 | A |
| ATOM | 759 | N | ALA | A | 96 | −1.324 | −18.511 | 67.463 | 1.00 | 12.75 | A |
| ATOM | 760 | CA | ALA | A | 96 | −1.099 | −18.502 | 68.908 | 1.00 | 12.75 | A |
| ATOM | 761 | CB | ALA | A | 96 | −1.407 | −19.883 | 69.503 | 1.00 | 12.71 | A |
| ATOM | 762 | C | ALA | A | 96 | 0.331 | −18.085 | 69.244 | 1.00 | 12.95 | A |
| ATOM | 763 | O | ALA | A | 96 | 0.563 | −17.420 | 70.260 | 1.00 | 13.08 | A |
| ATOM | 764 | N | MET | A | 97 | 1.284 | −18.462 | 68.389 | 1.00 | 12.73 | A |
| ATOM | 765 | CA | MET | A | 97 | 2.691 | −18.112 | 68.596 | 1.00 | 12.42 | A |
| ATOM | 766 | CB | MET | A | 97 | 3.597 | −18.849 | 67.596 | 1.00 | 12.18 | A |
| ATOM | 767 | CG | MET | A | 97 | 3.612 | −20.371 | 67.718 | 1.00 | 11.76 | A |
| ATOM | 768 | SD | MET | A | 97 | 4.617 | −21.149 | 66.408 | 1.00 | 13.63 | A |
| ATOM | 769 | CE | MET | A | 97 | 4.109 | −22.880 | 66.555 | 1.00 | 12.10 | A |
| ATOM | 770 | C | MET | A | 97 | 2.899 | −16.609 | 68.423 | 1.00 | 12.57 | A |
| ATOM | 771 | O | MET | A | 97 | 3.570 | −15.962 | 69.236 | 1.00 | 12.06 | A |
| ATOM | 772 | N | LEU | A | 98 | 2.328 | −16.062 | 67.354 | 1.00 | 11.79 | A |
| ATOM | 773 | CA | LEU | A | 98 | 2.452 | −14.634 | 67.063 | 1.00 | 12.16 | A |
| ATOM | 774 | CB | LEU | A | 98 | 1.854 | −14.324 | 65.684 | 1.00 | 11.36 | A |
| ATOM | 775 | CG | LEU | A | 98 | 2.512 | −15.031 | 64.496 | 1.00 | 12.62 | A |
| ATOM | 776 | CD1 | LEU | A | 98 | 1.679 | −14.830 | 63.227 | 1.00 | 12.76 | A |
| ATOM | 777 | CD2 | LEU | A | 98 | 3.921 | −14.487 | 64.305 | 1.00 | 12.17 | A |
| ATOM | 778 | C | LEU | A | 98 | 1.763 | −13.770 | 68.111 | 1.00 | 11.92 | A |
| ATOM | 779 | O | LEU | A | 98 | 2.257 | −12.695 | 68.460 | 1.00 | 12.04 | A |
| ATOM | 780 | N | ALA | A | 99 | 0.621 | −14.237 | 68.606 | 1.00 | 12.12 | A |
| ATOM | 781 | CA | ALA | A | 99 | −0.144 | −13.492 | 69.602 | 1.00 | 12.56 | A |
| ATOM | 782 | CB | ALA | A | 99 | −1.389 | −14.288 | 70.020 | 1.00 | 12.39 | A |
| ATOM | 783 | C | ALA | A | 99 | 0.695 | −13.155 | 70.827 | 1.00 | 13.30 | A |
| ATOM | 784 | O | ALA | A | 99 | 0.474 | −12.132 | 71.475 | 1.00 | 12.88 | A |
| ATOM | 785 | N | MET | A | 100 | 1.660 | −14.016 | 71.134 | 1.00 | 14.50 | A |
| ATOM | 786 | CA | MET | A | 100 | 2.537 | −13.818 | 72.285 | 1.00 | 15.61 | A |
| ATOM | 787 | CB | MET | A | 100 | 2.832 | −15.168 | 72.952 | 1.00 | 17.98 | A |
| ATOM | 788 | CG | MET | A | 100 | 3.608 | −15.105 | 74.281 | 1.00 | 21.83 | A |
| ATOM | 789 | SD | MET | A | 100 | 5.365 | −14.630 | 74.196 | 1.00 | 26.83 | A |
| ATOM | 790 | CE | MET | A | 100 | 6.114 | −16.169 | 73.669 | 1.00 | 24.50 | A |
| ATOM | 791 | C | MET | A | 100 | 3.862 | −13.135 | 71.932 | 1.00 | 15.20 | A |
| ATOM | 792 | O | MET | A | 100 | 4.217 | −12.113 | 72.520 | 1.00 | 15.12 | A |
| ATOM | 793 | N | GLU | A | 101 | 4.577 | −13.687 | 70.958 | 1.00 | 13.89 | A |
| ATOM | 794 | CA | GLU | A | 101 | 5.890 | −13.163 | 70.586 | 1.00 | 13.45 | A |
| ATOM | 795 | CB | GLU | A | 101 | 6.616 | −14.187 | 69.713 | 1.00 | 13.61 | A |
| ATOM | 796 | CG | GLU | A | 101 | 8.094 | −13.880 | 69.475 | 1.00 | 13.97 | A |
| ATOM | 797 | CD | GLU | A | 101 | 8.942 | −13.936 | 70.741 | 1.00 | 14.80 | A |
| ATOM | 798 | OE1 | GLU | A | 101 | 8.422 | −14.335 | 71.808 | 1.00 | 15.03 | A |
| ATOM | 799 | OE2 | GLU | A | 101 | 10.143 | −13.584 | 70.666 | 1.00 | 14.42 | A |
| ATOM | 800 | C | GLU | A | 101 | 5.980 | −11.778 | 69.933 | 1.00 | 13.03 | A |
| ATOM | 801 | O | GLU | A | 101 | 6.860 | −10.993 | 70.286 | 1.00 | 11.63 | A |
| ATOM | 802 | N | VAL | A | 102 | 5.097 | −11.469 | 68.985 | 1.00 | 12.32 | A |
| ATOM | 803 | CA | VAL | A | 102 | 5.160 | −10.161 | 68.340 | 1.00 | 12.06 | A |
| ATOM | 804 | CB | VAL | A | 102 | 4.054 | −10.002 | 67.271 | 1.00 | 12.10 | A |
| ATOM | 805 | CG1 | VAL | A | 102 | 4.043 | −8.579 | 66.730 | 1.00 | 12.24 | A |
| ATOM | 806 | CG2 | VAL | A | 102 | 4.312 | −10.982 | 66.120 | 1.00 | 12.82 | A |
| ATOM | 807 | C | VAL | A | 102 | 5.071 | −9.035 | 69.378 | 1.00 | 12.40 | A |
| ATOM | 808 | O | VAL | A | 102 | 5.911 | −8.135 | 69.388 | 1.00 | 12.03 | A |
| ATOM | 809 | N | PRO | A | 103 | 4.061 | −9.072 | 70.268 | 1.00 | 12.59 | A |
| ATOM | 810 | CD | PRO | A | 103 | 2.862 | −9.928 | 70.270 | 1.00 | 12.42 | A |
| ATOM | 811 | CA | PRO | A | 103 | 3.942 | −8.020 | 71.284 | 1.00 | 12.41 | A |
| ATOM | 812 | CB | PRO | A | 103 | 2.585 | −8.312 | 71.931 | 1.00 | 13.58 | A |
| ATOM | 813 | CG | PRO | A | 103 | 1.819 | −9.000 | 70.828 | 1.00 | 13.22 | A |
| ATOM | 814 | C | PRO | A | 103 | 5.085 | −8.056 | 72.312 | 1.00 | 12.46 | A |
| ATOM | 815 | O | PRO | A | 103 | 5.570 | −7.008 | 72.748 | 1.00 | 11.92 | A |
| ATOM | 816 | N | ARG | A | 104 | 5.512 | −9.256 | 72.705 | 1.00 | 12.35 | A |
| ATOM | 817 | CA | ARG | A | 104 | 6.593 | −9.376 | 73.691 | 1.00 | 12.83 | A |
| ATOM | 818 | CB | ARG | A | 104 | 6.830 | −10.841 | 74.073 | 1.00 | 13.38 | A |
| ATOM | 819 | CG | ARG | A | 104 | 7.824 | −11.005 | 75.233 | 1.00 | 14.51 | A |
| ATOM | 820 | CD | ARG | A | 104 | 8.463 | −12.393 | 75.252 | 1.00 | 15.96 | A |
| ATOM | 821 | NE | ARG | A | 104 | 9.362 | −12.594 | 74.116 | 1.00 | 17.99 | A |
| ATOM | 822 | CZ | ARG | A | 104 | 10.561 | −12.031 | 73.994 | 1.00 | 19.06 | A |
| ATOM | 823 | NH1 | ARG | A | 104 | 11.025 | −11.228 | 74.946 | 1.00 | 19.58 | A |
| ATOM | 824 | NH2 | ARG | A | 104 | 11.295 | −12.260 | 72.911 | 1.00 | 19.03 | A |
| ATOM | 825 | C | ARG | A | 104 | 7.907 | −8.789 | 73.179 | 1.00 | 12.54 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 826 | O | ARG | A | 104 | 8.559 | −8.002 | 73.867 | 1.00 | 12.97 | A |
| ATOM | 827 | N | LEU | A | 105 | 8.297 | −9.190 | 71.972 | 1.00 | 12.55 | A |
| ATOM | 828 | CA | LEU | A | 105 | 9.532 | −8.722 | 71.356 | 1.00 | 12.96 | A |
| ATOM | 829 | CB | LEU | A | 105 | 9.768 | −9.491 | 70.047 | 1.00 | 13.70 | A |
| ATOM | 830 | CG | LEU | A | 105 | 11.113 | −9.417 | 69.327 | 1.00 | 15.14 | A |
| ATOM | 831 | CD1 | LEU | A | 105 | 12.227 | −9.949 | 70.231 | 1.00 | 14.66 | A |
| ATOM | 832 | CD2 | LEU | A | 105 | 11.028 | −10.247 | 68.034 | 1.00 | 14.82 | A |
| ATOM | 833 | C | LEU | A | 105 | 9.454 | −7.219 | 71.094 | 1.00 | 12.85 | A |
| ATOM | 834 | O | LEU | A | 105 | 10.436 | −6.494 | 71.271 | 1.00 | 12.86 | A |
| ATOM | 835 | N | GLY | A | 106 | 8.278 | −6.754 | 70.675 | 1.00 | 12.06 | A |
| ATOM | 836 | CA | GLY | A | 106 | 8.086 | −5.337 | 70.412 | 1.00 | 11.77 | A |
| ATOM | 837 | C | GLY | A | 106 | 8.215 | −4.504 | 71.675 | 1.00 | 11.78 | A |
| ATOM | 838 | O | GLY | A | 106 | 8.767 | −3.405 | 71.648 | 1.00 | 11.19 | A |
| ATOM | 839 | N | LYS | A | 107 | 7.710 | −5.025 | 72.790 | 1.00 | 11.65 | A |
| ATOM | 840 | CA | LYS | A | 107 | 7.800 | −4.312 | 74.060 | 1.00 | 12.93 | A |
| ATOM | 841 | CB | LYS | A | 107 | 6.993 | −5.029 | 75.145 | 1.00 | 14.06 | A |
| ATOM | 842 | CG | LYS | A | 107 | 6.987 | −4.280 | 76.465 | 1.00 | 15.87 | A |
| ATOM | 843 | CD | LYS | A | 107 | 7.048 | −5.223 | 77.649 | 1.00 | 17.85 | A |
| ATOM | 844 | CE | LYS | A | 107 | 7.068 | −4.444 | 78.954 | 1.00 | 19.08 | A |
| ATOM | 845 | NZ | LYS | A | 107 | 7.304 | −5.335 | 80.128 | 1.00 | 21.55 | A |
| ATOM | 846 | C | LYS | A | 107 | 9.255 | −4.203 | 74.520 | 1.00 | 13.01 | A |
| ATOM | 847 | O | LYS | A | 107 | 9.664 | −3.180 | 75.067 | 1.00 | 13.04 | A |
| ATOM | 848 | N | GLU | A | 108 | 10.034 | −5.260 | 74.302 | 1.00 | 13.42 | A |
| ATOM | 849 | CA | GLU | A | 108 | 11.441 | −5.264 | 74.702 | 1.00 | 13.99 | A |
| ATOM | 850 | CB | GLU | A | 108 | 12.081 | −6.618 | 74.360 | 1.00 | 15.13 | A |
| ATOM | 851 | CG | GLU | A | 108 | 13.507 | −6.782 | 74.851 | 1.00 | 16.71 | A |
| ATOM | 852 | CD | GLU | A | 108 | 14.044 | −8.195 | 74.660 | 1.00 | 17.86 | A |
| ATOM | 853 | OE1 | GLU | A | 108 | 15.250 | −8.408 | 74.910 | 1.00 | 18.93 | A |
| ATOM | 854 | OE2 | GLU | A | 108 | 13.265 | −9.088 | 74.267 | 1.00 | 16.99 | A |
| ATOM | 855 | C | GLU | A | 108 | 12.208 | −4.122 | 74.019 | 1.00 | 13.77 | A |
| ATOM | 856 | O | GLU | A | 108 | 13.015 | −3.433 | 74.651 | 1.00 | 13.37 | A |
| ATOM | 857 | N | ALA | A | 109 | 11.954 | −3.922 | 72.728 | 1.00 | 12.99 | A |
| ATOM | 858 | CA | ALA | A | 109 | 12.618 | −2.855 | 71.981 | 1.00 | 12.44 | A |
| ATOM | 859 | CB | ALA | A | 109 | 12.370 | −3.027 | 70.494 | 1.00 | 11.96 | A |
| ATOM | 860 | C | ALA | A | 109 | 12.105 | −1.491 | 72.440 | 1.00 | 12.31 | A |
| ATOM | 861 | O | ALA | A | 109 | 12.881 | −0.543 | 72.595 | 1.00 | 11.79 | A |
| ATOM | 862 | N | ALA | A | 110 | 10.796 | −1.400 | 72.657 | 1.00 | 11.92 | A |
| ATOM | 863 | CA | ALA | A | 110 | 10.170 | −0.154 | 73.093 | 1.00 | 12.92 | A |
| ATOM | 864 | CB | ALA | A | 110 | 8.655 | −0.335 | 73.173 | 1.00 | 12.53 | A |
| ATOM | 865 | C | ALA | A | 110 | 10.712 | 0.332 | 74.440 | 1.00 | 13.13 | A |
| ATOM | 866 | O | ALA | A | 110 | 10.938 | 1.528 | 74.632 | 1.00 | 13.01 | A |
| ATOM | 867 | N | VAL | A | 111 | 10.923 | −0.592 | 75.371 | 1.00 | 13.59 | A |
| ATOM | 868 | CA | VAL | A | 111 | 11.442 | −0.219 | 76.683 | 1.00 | 14.30 | A |
| ATOM | 869 | CB | VAL | A | 111 | 11.512 | −1.445 | 77.632 | 1.00 | 14.16 | A |
| ATOM | 870 | CG1 | VAL | A | 111 | 12.249 | −1.073 | 78.921 | 1.00 | 14.90 | A |
| ATOM | 871 | CG2 | VAL | A | 111 | 10.102 | −1.915 | 77.972 | 1.00 | 14.85 | A |
| ATOM | 872 | C | VAL | A | 111 | 12.830 | 0.412 | 76.549 | 1.00 | 14.57 | A |
| ATOM | 873 | O | VAL | A | 111 | 13.140 | 1.393 | 77.232 | 1.00 | 14.48 | A |
| ATOM | 874 | N | LYS | A | 112 | 13.655 | −0.140 | 75.660 | 1.00 | 14.33 | A |
| ATOM | 875 | CA | LYS | A | 112 | 15.003 | 0.382 | 75.439 | 1.00 | 14.52 | A |
| ATOM | 876 | CB | LYS | A | 112 | 15.803 | −0.550 | 74.522 | 1.00 | 15.84 | A |
| ATOM | 877 | CG | LYS | A | 112 | 16.113 | −1.911 | 75.118 | 1.00 | 17.43 | A |
| ATOM | 878 | CD | LYS | A | 112 | 16.934 | −2.747 | 74.147 | 1.00 | 18.69 | A |
| ATOM | 879 | CE | LYS | A | 112 | 17.182 | −4.137 | 74.687 | 1.00 | 19.96 | A |
| ATOM | 880 | NZ | LYS | A | 112 | 17.933 | −4.976 | 73.708 | 1.00 | 20.59 | A |
| ATOM | 881 | C | LYS | A | 112 | 14.973 | 1.783 | 74.829 | 1.00 | 14.19 | A |
| ATOM | 882 | O | LYS | A | 112 | 15.771 | 2.645 | 75.198 | 1.00 | 13.66 | A |
| ATOM | 883 | N | ALA | A | 113 | 14.054 | 2.008 | 73.894 | 1.00 | 13.82 | A |
| ATOM | 884 | CA | ALA | A | 113 | 13.935 | 3.316 | 73.252 | 1.00 | 13.94 | A |
| ATOM | 885 | CB | ALA | A | 113 | 12.985 | 3.227 | 72.039 | 1.00 | 13.86 | A |
| ATOM | 886 | C | ALA | A | 113 | 13.443 | 4.384 | 74.235 | 1.00 | 13.81 | A |
| ATOM | 887 | O | ALA | A | 113 | 13.923 | 5.519 | 74.228 | 1.00 | 13.80 | A |
| ATOM | 888 | N | ILE | A | 114 | 12.492 | 4.014 | 75.085 | 1.00 | 13.62 | A |
| ATOM | 889 | CA | ILE | A | 114 | 11.939 | 4.938 | 76.067 | 1.00 | 14.81 | A |
| ATOM | 890 | CB | ILE | A | 114 | 10.690 | 4.325 | 76.751 | 1.00 | 14.96 | A |
| ATOM | 891 | CG2 | ILE | A | 114 | 10.205 | 5.229 | 77.874 | 1.00 | 15.35 | A |
| ATOM | 892 | CG1 | ILE | A | 114 | 9.592 | 4.106 | 75.702 | 1.00 | 15.11 | A |
| ATOM | 893 | CD1 | ILE | A | 114 | 8.359 | 3.358 | 76.211 | 1.00 | 14.83 | A |
| ATOM | 894 | C | ILE | A | 114 | 12.993 | 5.301 | 77.118 | 1.00 | 15.14 | A |
| ATOM | 895 | O | ILE | A | 114 | 13.031 | 6.430 | 77.607 | 1.00 | 14.81 | A |
| ATOM | 896 | N | LYS | A | 115 | 13.851 | 4.341 | 77.452 | 1.00 | 15.95 | A |
| ATOM | 897 | CA | LYS | A | 115 | 14.915 | 4.572 | 78.427 | 1.00 | 17.10 | A |
| ATOM | 898 | CB | LYS | A | 115 | 15.664 | 3.264 | 78.723 | 1.00 | 18.03 | A |
| ATOM | 899 | CG | LYS | A | 115 | 16.793 | 3.422 | 79.732 | 1.00 | 20.46 | A |
| ATOM | 900 | CD | LYS | A | 115 | 17.665 | 2.176 | 79.815 | 1.00 | 22.06 | A |

APPENDIX C-continued

18xCHS Mutant

| ATOM | # | TYPE | RES | | | X | Y | Z | OCC | B | |
|------|---|------|-----|---|---|---|---|---|-----|---|---|
| ATOM | 901 | CE | LYS | A | 115 | 18.867 | 2.413 | 80.730 | 1.00 | 24.19 | A |
| ATOM | 902 | NZ | LYS | A | 115 | 19.768 | 1.230 | 80.814 | 1.00 | 24.53 | A |
| ATOM | 903 | C | LYS | A | 115 | 15.896 | 5.615 | 77.882 | 1.00 | 16.58 | A |
| ATOM | 904 | O | LYS | A | 115 | 16.293 | 6.536 | 78.596 | 1.00 | 16.08 | A |
| ATOM | 905 | N | GLU | A | 116 | 16.282 | 5.470 | 76.615 | 1.00 | 15.74 | A |
| ATOM | 906 | CA | GLU | A | 116 | 17.209 | 6.413 | 75.989 | 1.00 | 15.99 | A |
| ATOM | 907 | CB | GLU | A | 116 | 17.559 | 5.973 | 74.563 | 1.00 | 15.39 | A |
| ATOM | 908 | CG | GLU | A | 116 | 18.606 | 6.860 | 73.895 | 1.00 | 16.97 | A |
| ATOM | 909 | CD | GLU | A | 116 | 18.736 | 6.634 | 72.392 | 1.00 | 17.20 | A |
| ATOM | 910 | OE1 | GLU | A | 116 | 18.375 | 5.542 | 71.907 | 1.00 | 16.77 | A |
| ATOM | 911 | OE2 | GLU | A | 116 | 19.219 | 7.553 | 71.694 | 1.00 | 17.90 | A |
| ATOM | 912 | C | GLU | A | 116 | 16.576 | 7.807 | 75.935 | 1.00 | 16.26 | A |
| ATOM | 913 | O | GLU | A | 116 | 17.223 | 8.811 | 76.250 | 1.00 | 15.55 | A |
| ATOM | 914 | N | TRP | A | 117 | 15.312 | 7.853 | 75.520 | 1.00 | 16.06 | A |
| ATOM | 915 | CA | TRP | A | 117 | 14.561 | 9.102 | 75.424 | 1.00 | 16.63 | A |
| ATOM | 916 | CB | TRP | A | 117 | 13.113 | 8.792 | 75.026 | 1.00 | 15.45 | A |
| ATOM | 917 | CG | TRP | A | 117 | 12.222 | 9.992 | 74.851 | 1.00 | 15.18 | A |
| ATOM | 918 | CD2 | TRP | A | 117 | 10.815 | 10.061 | 75.130 | 1.00 | 14.59 | A |
| ATOM | 919 | CE2 | TRP | A | 117 | 10.372 | 11.344 | 74.735 | 1.00 | 14.57 | A |
| ATOM | 920 | CE3 | TRP | A | 117 | 9.885 | 9.162 | 75.672 | 1.00 | 14.93 | A |
| ATOM | 921 | CD1 | TRP | A | 117 | 12.565 | 11.204 | 74.320 | 1.00 | 14.39 | A |
| ATOM | 922 | NE1 | TRP | A | 117 | 11.459 | 12.019 | 74.246 | 1.00 | 14.28 | A |
| ATOM | 923 | CZ2 | TRP | A | 117 | 9.038 | 11.752 | 74.864 | 1.00 | 14.45 | A |
| ATOM | 924 | CZ3 | TRP | A | 117 | 8.555 | 9.569 | 75.801 | 1.00 | 14.58 | A |
| ATOM | 925 | CH2 | TRP | A | 117 | 8.147 | 10.852 | 75.397 | 1.00 | 14.55 | A |
| ATOM | 926 | C | TRP | A | 117 | 14.615 | 9.836 | 76.765 | 1.00 | 17.46 | A |
| ATOM | 927 | O | TRP | A | 117 | 14.919 | 11.026 | 76.812 | 1.00 | 17.93 | A |
| ATOM | 928 | N | GLY | A | 118 | 14.322 | 9.120 | 77.848 | 1.00 | 18.47 | A |
| ATOM | 929 | CA | GLY | A | 118 | 14.375 | 9.713 | 79.175 | 1.00 | 19.45 | A |
| ATOM | 930 | C | GLY | A | 118 | 13.121 | 10.377 | 79.724 | 1.00 | 20.29 | A |
| ATOM | 931 | O | GLY | A | 118 | 13.110 | 10.800 | 80.883 | 1.00 | 20.22 | A |
| ATOM | 932 | N | GLN | A | 119 | 12.066 | 10.469 | 78.918 | 1.00 | 20.22 | A |
| ATOM | 933 | CA | GLN | A | 119 | 10.825 | 11.100 | 79.363 | 1.00 | 20.78 | A |
| ATOM | 934 | CB | GLN | A | 119 | 10.282 | 12.014 | 78.257 | 1.00 | 21.39 | A |
| ATOM | 935 | CG | GLN | A | 119 | 11.219 | 13.173 | 77.913 | 1.00 | 23.09 | A |
| ATOM | 936 | CD | GLN | A | 119 | 11.655 | 13.958 | 79.146 | 1.00 | 23.77 | A |
| ATOM | 937 | OE1 | GLN | A | 119 | 10.824 | 14.468 | 79.899 | 1.00 | 24.98 | A |
| ATOM | 938 | NE2 | GLN | A | 119 | 12.962 | 14.050 | 79.357 | 1.00 | 24.40 | A |
| ATOM | 939 | C | GLN | A | 119 | 9.763 | 10.079 | 79.782 | 1.00 | 20.88 | A |
| ATOM | 940 | O | GLN | A | 119 | 9.859 | 8.903 | 79.443 | 1.00 | 20.86 | A |
| ATOM | 941 | N | PRO | A | 120 | 8.733 | 10.524 | 80.525 | 1.00 | 21.16 | A |
| ATOM | 942 | CD | PRO | A | 120 | 8.517 | 11.921 | 80.939 | 1.00 | 21.29 | A |
| ATOM | 943 | CA | PRO | A | 120 | 7.641 | 9.667 | 81.008 | 1.00 | 21.57 | A |
| ATOM | 944 | CB | PRO | A | 120 | 6.746 | 10.643 | 81.772 | 1.00 | 21.80 | A |
| ATOM | 945 | CG | PRO | A | 120 | 7.677 | 11.753 | 82.165 | 1.00 | 22.42 | A |
| ATOM | 946 | C | PRO | A | 120 | 6.877 | 8.983 | 79.873 | 1.00 | 21.27 | A |
| ATOM | 947 | O | PRO | A | 120 | 6.608 | 9.607 | 78.851 | 1.00 | 21.61 | A |
| ATOM | 948 | N | LYS | A | 121 | 6.519 | 7.714 | 80.056 | 1.00 | 21.35 | A |
| ATOM | 949 | CA | LYS | A | 121 | 5.777 | 6.977 | 79.029 | 1.00 | 21.42 | A |
| ATOM | 950 | CB | LYS | A | 121 | 5.623 | 5.501 | 79.421 | 1.00 | 22.56 | A |
| ATOM | 951 | CG | LYS | A | 121 | 4.759 | 5.288 | 80.654 | 1.00 | 25.13 | A |
| ATOM | 952 | CD | LYS | A | 121 | 4.399 | 3.822 | 80.900 | 1.00 | 26.18 | A |
| ATOM | 953 | CE | LYS | A | 121 | 5.619 | 2.984 | 81.222 | 1.00 | 27.36 | A |
| ATOM | 954 | NZ | LYS | A | 121 | 5.225 | 1.655 | 81.786 | 1.00 | 28.12 | A |
| ATOM | 955 | C | LYS | A | 121 | 4.392 | 7.595 | 78.840 | 1.00 | 20.94 | A |
| ATOM | 956 | O | LYS | A | 121 | 3.762 | 7.429 | 77.791 | 1.00 | 20.02 | A |
| ATOM | 957 | N | SER | A | 122 | 3.928 | 8.309 | 79.863 | 1.00 | 19.98 | A |
| ATOM | 958 | CA | SER | A | 122 | 2.621 | 8.956 | 79.836 | 1.00 | 19.81 | A |
| ATOM | 959 | CB | SER | A | 122 | 2.252 | 9.457 | 81.236 | 1.00 | 20.86 | A |
| ATOM | 960 | OG | SER | A | 122 | 3.131 | 10.488 | 81.656 | 1.00 | 20.86 | A |
| ATOM | 961 | C | SER | A | 122 | 2.580 | 10.121 | 78.856 | 1.00 | 19.21 | A |
| ATOM | 962 | O | SER | A | 122 | 1.508 | 10.633 | 78.533 | 1.00 | 19.72 | A |
| ATOM | 963 | N | LYS | A | 123 | 3.748 | 10.540 | 78.380 | 1.00 | 18.76 | A |
| ATOM | 964 | CA | LYS | A | 123 | 3.819 | 11.646 | 77.435 | 1.00 | 17.51 | A |
| ATOM | 965 | CB | LYS | A | 123 | 5.069 | 12.486 | 77.715 | 1.00 | 19.70 | A |
| ATOM | 966 | CG | LYS | A | 123 | 5.096 | 13.004 | 79.157 | 1.00 | 21.88 | A |
| ATOM | 967 | CD | LYS | A | 123 | 6.289 | 13.894 | 79.465 | 1.00 | 24.26 | A |
| ATOM | 968 | CE | LYS | A | 123 | 6.204 | 15.233 | 78.751 | 1.00 | 25.53 | A |
| ATOM | 969 | NZ | LYS | A | 123 | 7.195 | 16.202 | 79.318 | 1.00 | 26.85 | A |
| ATOM | 970 | C | LYS | A | 123 | 3.782 | 11.179 | 75.975 | 1.00 | 16.02 | A |
| ATOM | 971 | O | LYS | A | 123 | 3.874 | 11.990 | 75.056 | 1.00 | 15.29 | A |
| ATOM | 972 | N | ILE | A | 124 | 3.649 | 9.871 | 75.767 | 1.00 | 14.24 | A |
| ATOM | 973 | CA | ILE | A | 124 | 3.551 | 9.326 | 74.413 | 1.00 | 13.14 | A |
| ATOM | 974 | CB | ILE | A | 124 | 3.949 | 7.828 | 74.370 | 1.00 | 13.63 | A |
| ATOM | 975 | CG2 | ILE | A | 124 | 3.612 | 7.235 | 73.000 | 1.00 | 13.42 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 976 | CG1 | ILE | A | 124 | 5.451 | 7.685 | 74.668 | 1.00 | 13.73 | A |
| ATOM | 977 | CD1 | ILE | A | 124 | 5.932 | 6.250 | 74.850 | 1.00 | 14.46 | A |
| ATOM | 978 | C | ILE | A | 124 | 2.084 | 9.503 | 74.016 | 1.00 | 12.41 | A |
| ATOM | 979 | O | ILE | A | 124 | 1.184 | 9.010 | 74.695 | 1.00 | 12.34 | A |
| ATOM | 980 | N | THR | A | 125 | 1.853 | 10.219 | 72.922 | 1.00 | 11.64 | A |
| ATOM | 981 | CA | THR | A | 125 | 0.499 | 10.515 | 72.451 | 1.00 | 10.75 | A |
| ATOM | 982 | CB | THR | A | 125 | 0.409 | 11.975 | 71.989 | 1.00 | 9.91 | A |
| ATOM | 983 | OG1 | THR | A | 125 | 1.357 | 12.196 | 70.937 | 1.00 | 10.98 | A |
| ATOM | 984 | CG2 | THR | A | 125 | 0.714 | 12.921 | 73.147 | 1.00 | 10.30 | A |
| ATOM | 985 | C | THR | A | 125 | −0.030 | 9.639 | 71.313 | 1.00 | 10.65 | A |
| ATOM | 986 | O | THR | A | 125 | −1.249 | 9.502 | 71.150 | 1.00 | 10.36 | A |
| ATOM | 987 | N | HIS | A | 126 | 0.877 | 9.078 | 70.516 | 1.00 | 10.15 | A |
| ATOM | 988 | CA | HIS | A | 126 | 0.494 | 8.223 | 69.389 | 1.00 | 9.76 | A |
| ATOM | 989 | CB | HIS | A | 126 | 0.735 | 8.936 | 68.047 | 1.00 | 9.29 | A |
| ATOM | 990 | CG | HIS | A | 126 | −0.054 | 10.195 | 67.858 | 1.00 | 9.51 | A |
| ATOM | 991 | CD2 | HIS | A | 126 | −1.047 | 10.498 | 66.987 | 1.00 | 10.73 | A |
| ATOM | 992 | ND1 | HIS | A | 126 | 0.185 | 11.346 | 68.580 | 1.00 | 9.94 | A |
| ATOM | 993 | CE1 | HIS | A | 126 | −0.624 | 12.303 | 68.159 | 1.00 | 10.59 | A |
| ATOM | 994 | NE2 | HIS | A | 126 | −1.381 | 11.815 | 67.193 | 1.00 | 10.64 | A |
| ATOM | 995 | C | HIS | A | 126 | 1.329 | 6.935 | 69.390 | 1.00 | 9.52 | A |
| ATOM | 996 | O | HIS | A | 126 | 2.463 | 6.926 | 69.870 | 1.00 | 9.39 | A |
| ATOM | 997 | N | LEU | A | 127 | 0.770 | 5.865 | 68.826 | 1.00 | 8.68 | A |
| ATOM | 998 | CA | LEU | A | 127 | 1.457 | 4.577 | 68.741 | 1.00 | 8.66 | A |
| ATOM | 999 | CB | LEU | A | 127 | 0.943 | 3.615 | 69.820 | 1.00 | 8.64 | A |
| ATOM | 1000 | CG | LEU | A | 127 | 1.448 | 2.167 | 69.722 | 1.00 | 9.47 | A |
| ATOM | 1001 | CD1 | LEU | A | 127 | 2.954 | 2.119 | 69.949 | 1.00 | 9.18 | A |
| ATOM | 1002 | CD2 | LEU | A | 127 | 0.728 | 1.298 | 70.748 | 1.00 | 9.28 | A |
| ATOM | 1003 | C | LEU | A | 127 | 1.243 | 3.927 | 67.379 | 1.00 | 8.85 | A |
| ATOM | 1004 | O | LEU | A | 127 | 0.107 | 3.737 | 66.956 | 1.00 | 7.92 | A |
| ATOM | 1005 | N | ILE | A | 128 | 2.339 | 3.580 | 66.710 | 1.00 | 8.63 | A |
| ATOM | 1006 | CA | ILE | A | 128 | 2.280 | 2.921 | 65.407 | 1.00 | 8.91 | A |
| ATOM | 1007 | CB | ILE | A | 128 | 3.054 | 3.717 | 64.324 | 1.00 | 8.76 | A |
| ATOM | 1008 | CG2 | ILE | A | 128 | 3.053 | 2.942 | 63.007 | 1.00 | 9.37 | A |
| ATOM | 1009 | CG1 | ILE | A | 128 | 2.436 | 5.110 | 64.144 | 1.00 | 8.68 | A |
| ATOM | 1010 | CD1 | ILE | A | 128 | 3.161 | 5.984 | 63.137 | 1.00 | 8.20 | A |
| ATOM | 1011 | C | ILE | A | 128 | 2.950 | 1.551 | 65.541 | 1.00 | 9.26 | A |
| ATOM | 1012 | O | ILE | A | 128 | 4.142 | 1.477 | 65.847 | 1.00 | 9.52 | A |
| ATOM | 1013 | N | VAL | A | 129 | 2.195 | 0.475 | 65.329 | 1.00 | 9.33 | A |
| ATOM | 1014 | CA | VAL | A | 129 | 2.768 | −0.872 | 65.408 | 1.00 | 9.83 | A |
| ATOM | 1015 | CB | VAL | A | 129 | 2.095 | −1.728 | 66.500 | 1.00 | 9.91 | A |
| ATOM | 1016 | CG1 | VAL | A | 129 | 2.655 | −3.151 | 66.465 | 1.00 | 9.78 | A |
| ATOM | 1017 | CG2 | VAL | A | 129 | 2.342 | −1.099 | 67.873 | 1.00 | 8.95 | A |
| ATOM | 1018 | C | VAL | A | 129 | 2.621 | −1.571 | 64.063 | 1.00 | 10.19 | A |
| ATOM | 1019 | O | VAL | A | 129 | 1.524 | −1.638 | 63.504 | 1.00 | 10.94 | A |
| ATOM | 1020 | N | CYS | A | 130 | 3.739 | −2.089 | 63.561 | 1.00 | 10.12 | A |
| ATOM | 1021 | CA | CYS | A | 130 | 3.803 | −2.765 | 62.268 | 1.00 | 10.10 | A |
| ATOM | 1022 | CB | CYS | A | 130 | 4.696 | −1.946 | 61.328 | 1.00 | 10.57 | A |
| ATOM | 1023 | SG | CYS | A | 130 | 5.174 | −2.737 | 59.758 | 1.00 | 12.03 | A |
| ATOM | 1024 | C | CYS | A | 130 | 4.343 | −4.194 | 62.363 | 1.00 | 9.44 | A |
| ATOM | 1025 | O | CYS | A | 130 | 5.309 | −4.455 | 63.078 | 1.00 | 9.20 | A |
| ATOM | 1026 | N | SER | A | 131 | 3.702 | −5.109 | 61.641 | 1.00 | 8.71 | A |
| ATOM | 1027 | CA | SER | A | 131 | 4.117 | −6.516 | 61.579 | 1.00 | 9.13 | A |
| ATOM | 1028 | CB | SER | A | 131 | 3.590 | −7.297 | 62.788 | 1.00 | 9.14 | A |
| ATOM | 1029 | OG | SER | A | 131 | 4.170 | −8.592 | 62.834 | 1.00 | 8.81 | A |
| ATOM | 1030 | C | SER | A | 131 | 3.535 | −7.098 | 60.293 | 1.00 | 9.18 | A |
| ATOM | 1031 | O | SER | A | 131 | 2.451 | −6.699 | 59.878 | 1.00 | 9.08 | A |
| ATOM | 1032 | N | THR | A | 132 | 4.246 | −8.028 | 59.655 | 1.00 | 10.48 | A |
| ATOM | 1033 | CA | THR | A | 132 | 3.754 | −8.620 | 58.411 | 1.00 | 10.93 | A |
| ATOM | 1034 | CB | THR | A | 132 | 4.689 | −9.774 | 57.941 | 1.00 | 11.08 | A |
| ATOM | 1035 | OG1 | THR | A | 132 | 5.988 | −9.232 | 57.654 | 1.00 | 10.58 | A |
| ATOM | 1036 | CG2 | THR | A | 132 | 4.150 | −10.437 | 56.675 | 1.00 | 11.82 | A |
| ATOM | 1037 | C | THR | A | 132 | 2.294 | −9.089 | 58.544 | 1.00 | 11.41 | A |
| ATOM | 1038 | O | THR | A | 132 | 1.505 | −8.928 | 57.607 | 1.00 | 11.93 | A |
| ATOM | 1039 | N | THR | A | 133 | 1.928 | −9.647 | 59.701 | 1.00 | 11.44 | A |
| ATOM | 1040 | CA | THR | A | 133 | 0.541 | −10.075 | 59.960 | 1.00 | 11.06 | A |
| ATOM | 1041 | CB | THR | A | 133 | 0.301 | −11.586 | 59.681 | 1.00 | 12.44 | A |
| ATOM | 1042 | OG1 | THR | A | 133 | 0.982 | −12.371 | 60.675 | 1.00 | 12.81 | A |
| ATOM | 1043 | CG2 | THR | A | 133 | 0.798 | −11.975 | 58.292 | 1.00 | 12.09 | A |
| ATOM | 1044 | C | THR | A | 133 | 0.171 | −9.867 | 61.432 | 1.00 | 11.34 | A |
| ATOM | 1045 | O | THR | A | 133 | 1.038 | −9.591 | 62.262 | 1.00 | 10.26 | A |
| ATOM | 1046 | N | THR | A | 134 | −1.121 | −9.972 | 61.741 | 1.00 | 10.39 | A |
| ATOM | 1047 | CA | THR | A | 134 | −1.599 | −9.886 | 63.127 | 1.00 | 10.86 | A |
| ATOM | 1048 | CB | THR | A | 134 | −2.151 | −8.478 | 63.490 | 1.00 | 10.72 | A |
| ATOM | 1049 | OG1 | THR | A | 134 | −2.068 | −8.297 | 64.913 | 1.00 | 10.97 | A |
| ATOM | 1050 | CG2 | THR | A | 134 | −3.595 | −8.310 | 63.049 | 1.00 | 9.79 | A |

APPENDIX C-continued

18xCHS Mutant

| ATOM | # | TYPE | RES | | | X | Y | Z | OCC | B | |
|------|---|------|-----|---|---|---|---|---|-----|---|---|
| ATOM | 1051 | C | THR | A | 134 | −2.681 | −10.973 | 63.214 | 1.00 | 10.76 | A |
| ATOM | 1052 | O | THR | A | 134 | −3.493 | −11.124 | 62.307 | 1.00 | 10.88 | A |
| ATOM | 1053 | N | PRO | A | 135 | −2.696 | −11.753 | 64.305 | 1.00 | 10.68 | A |
| ATOM | 1054 | CD | PRO | A | 135 | −1.766 | −11.689 | 65.450 | 1.00 | 10.93 | A |
| ATOM | 1055 | CA | PRO | A | 135 | −3.665 | −12.840 | 64.483 | 1.00 | 11.06 | A |
| ATOM | 1056 | CB | PRO | A | 135 | −2.969 | −13.736 | 65.502 | 1.00 | 10.76 | A |
| ATOM | 1057 | CG | PRO | A | 135 | −2.338 | −12.722 | 66.415 | 1.00 | 10.45 | A |
| ATOM | 1058 | C | PRO | A | 135 | −5.105 | −12.568 | 64.890 | 1.00 | 11.42 | A |
| ATOM | 1059 | O | PRO | A | 135 | −5.999 | −13.341 | 64.538 | 1.00 | 11.28 | A |
| ATOM | 1060 | N | ASP | A | 136 | −5.352 | −11.481 | 65.608 | 1.00 | 11.37 | A |
| ATOM | 1061 | CA | ASP | A | 136 | −6.704 | −11.235 | 66.091 | 1.00 | 12.18 | A |
| ATOM | 1062 | CB | ASP | A | 136 | −6.774 | −11.593 | 67.587 | 1.00 | 13.43 | A |
| ATOM | 1063 | CG | ASP | A | 136 | −6.122 | −12.935 | 67.916 | 1.00 | 14.45 | A |
| ATOM | 1064 | OD1 | ASP | A | 136 | −5.193 | −12.973 | 68.762 | 1.00 | 13.87 | A |
| ATOM | 1065 | OD2 | ASP | A | 136 | −6.544 | −13.955 | 67.343 | 1.00 | 14.97 | A |
| ATOM | 1066 | C | ASP | A | 136 | −7.199 | −9.802 | 65.942 | 1.00 | 12.49 | A |
| ATOM | 1067 | O | ASP | A | 136 | −6.625 | −8.983 | 65.225 | 1.00 | 12.60 | A |
| ATOM | 1068 | N | LEU | A | 137 | −8.310 | −9.546 | 66.627 | 1.00 | 12.88 | A |
| ATOM | 1069 | CA | LEU | A | 137 | −8.924 | −8.230 | 66.740 | 1.00 | 13.15 | A |
| ATOM | 1070 | CB | LEU | A | 137 | −10.244 | −8.126 | 65.967 | 1.00 | 13.24 | A |
| ATOM | 1071 | CG | LEU | A | 137 | −10.145 | −7.967 | 64.450 | 1.00 | 13.68 | A |
| ATOM | 1072 | CD1 | LEU | A | 137 | −10.283 | −9.326 | 63.798 | 1.00 | 14.40 | A |
| ATOM | 1073 | CD2 | LEU | A | 137 | −11.235 | −7.023 | 63.957 | 1.00 | 14.51 | A |
| ATOM | 1074 | C | LEU | A | 137 | −9.212 | −8.202 | 68.231 | 1.00 | 13.21 | A |
| ATOM | 1075 | O | LEU | A | 137 | −9.906 | −9.080 | 68.741 | 1.00 | 13.93 | A |
| ATOM | 1076 | N | PRO | A | 138 | −8.660 | −7.225 | 68.963 | 1.00 | 13.99 | A |
| ATOM | 1077 | CD | PRO | A | 138 | −8.996 | −7.174 | 70.396 | 1.00 | 14.42 | A |
| ATOM | 1078 | CA | PRO | A | 138 | −7.780 | −6.107 | 68.602 | 1.00 | 13.83 | A |
| ATOM | 1079 | CB | PRO | A | 138 | −7.565 | −5.401 | 69.941 | 1.00 | 14.52 | A |
| ATOM | 1080 | CG | PRO | A | 138 | −8.802 | −5.728 | 70.705 | 1.00 | 14.81 | A |
| ATOM | 1081 | C | PRO | A | 138 | −6.444 | −6.511 | 67.956 | 1.00 | 14.18 | A |
| ATOM | 1082 | O | PRO | A | 138 | −5.955 | −7.621 | 68.166 | 1.00 | 13.48 | A |
| ATOM | 1083 | N | GLY | A | 139 | −5.872 | −5.598 | 67.170 | 1.00 | 13.47 | A |
| ATOM | 1084 | CA | GLY | A | 139 | −4.596 | −5.841 | 66.515 | 1.00 | 13.68 | A |
| ATOM | 1085 | C | GLY | A | 139 | −3.441 | −5.742 | 67.504 | 1.00 | 13.10 | A |
| ATOM | 1086 | O | GLY | A | 139 | −3.664 | −5.427 | 68.668 | 1.00 | 13.23 | A |
| ATOM | 1087 | N | ALA | A | 140 | −2.212 | −5.995 | 67.056 | 1.00 | 12.38 | A |
| ATOM | 1088 | CA | ALA | A | 140 | −1.056 | −5.938 | 67.961 | 1.00 | 12.40 | A |
| ATOM | 1089 | CB | ALA | A | 140 | 0.216 | −6.393 | 67.236 | 1.00 | 10.91 | A |
| ATOM | 1090 | C | ALA | A | 140 | −0.823 | −4.568 | 68.611 | 1.00 | 12.51 | A |
| ATOM | 1091 | O | ALA | A | 140 | −0.152 | −4.483 | 69.643 | 1.00 | 12.15 | A |
| ATOM | 1092 | N | ASP | A | 141 | −1.359 | −3.499 | 68.024 | 1.00 | 12.33 | A |
| ATOM | 1093 | CA | ASP | A | 141 | −1.191 | −2.173 | 68.622 | 1.00 | 12.63 | A |
| ATOM | 1094 | CB | ASP | A | 141 | −1.785 | −1.081 | 67.724 | 1.00 | 13.06 | A |
| ATOM | 1095 | CG | ASP | A | 141 | −3.207 | −1.384 | 67.287 | 1.00 | 13.39 | A |
| ATOM | 1096 | OD1 | ASP | A | 141 | −3.413 | −2.385 | 66.564 | 1.00 | 13.50 | A |
| ATOM | 1097 | OD2 | ASP | A | 141 | −4.119 | −0.618 | 67.661 | 1.00 | 13.61 | A |
| ATOM | 1098 | C | ASP | A | 141 | −1.856 | −2.140 | 70.000 | 1.00 | 12.86 | A |
| ATOM | 1099 | O | ASP | A | 141 | −1.319 | −1.562 | 70.948 | 1.00 | 12.35 | A |
| ATOM | 1100 | N | TYR | A | 142 | −3.022 | −2.774 | 70.110 | 1.00 | 13.35 | A |
| ATOM | 1101 | CA | TYR | A | 142 | −3.747 | −2.836 | 71.377 | 1.00 | 13.60 | A |
| ATOM | 1102 | CB | TYR | A | 142 | −5.090 | −3.549 | 71.182 | 1.00 | 14.21 | A |
| ATOM | 1103 | CG | TYR | A | 142 | −5.781 | −3.900 | 72.478 | 1.00 | 15.51 | A |
| ATOM | 1104 | CD1 | TYR | A | 142 | −6.503 | −2.943 | 73.193 | 1.00 | 15.93 | A |
| ATOM | 1105 | CE1 | TYR | A | 142 | −7.110 | −3.262 | 74.411 | 1.00 | 17.60 | A |
| ATOM | 1106 | CD2 | TYR | A | 142 | −5.680 | −5.184 | 73.012 | 1.00 | 16.59 | A |
| ATOM | 1107 | CE2 | TYR | A | 142 | −6.275 | −5.509 | 74.224 | 1.00 | 17.58 | A |
| ATOM | 1108 | CZ | TYR | A | 142 | −6.988 | −4.549 | 74.917 | 1.00 | 18.62 | A |
| ATOM | 1109 | OH | TYR | A | 142 | −7.587 | −4.890 | 76.112 | 1.00 | 20.44 | A |
| ATOM | 1110 | C | TYR | A | 142 | −2.932 | −3.584 | 72.441 | 1.00 | 13.98 | A |
| ATOM | 1111 | O | TYR | A | 142 | −2.773 | −3.109 | 73.572 | 1.00 | 13.20 | A |
| ATOM | 1112 | N | GLN | A | 143 | −2.420 | −4.757 | 72.080 | 1.00 | 14.49 | A |
| ATOM | 1113 | CA | GLN | A | 143 | −1.635 | −5.551 | 73.023 | 1.00 | 15.02 | A |
| ATOM | 1114 | CB | GLN | A | 143 | −1.239 | −6.896 | 72.403 | 1.00 | 16.02 | A |
| ATOM | 1115 | CG | GLN | A | 143 | −2.406 | −7.861 | 72.183 | 1.00 | 17.48 | A |
| ATOM | 1116 | CD | GLN | A | 143 | −3.193 | −8.148 | 73.455 | 1.00 | 18.91 | A |
| ATOM | 1117 | OE1 | GLN | A | 143 | −2.621 | −8.294 | 74.539 | 1.00 | 18.85 | A |
| ATOM | 1118 | NE2 | GLN | A | 143 | −4.515 | −8.246 | 73.324 | 1.00 | 20.56 | A |
| ATOM | 1119 | C | GLN | A | 143 | −0.385 | −4.824 | 73.518 | 1.00 | 15.31 | A |
| ATOM | 1120 | O | GLN | A | 143 | −0.047 | −4.908 | 74.703 | 1.00 | 15.22 | A |
| ATOM | 1121 | N | LEU | A | 144 | 0.303 | −4.113 | 72.626 | 1.00 | 14.97 | A |
| ATOM | 1122 | CA | LEU | A | 144 | 1.506 | −3.385 | 73.032 | 1.00 | 15.35 | A |
| ATOM | 1123 | CB | LEU | A | 144 | 2.189 | −2.716 | 71.832 | 1.00 | 16.16 | A |
| ATOM | 1124 | CG | LEU | A | 144 | 3.669 | −3.050 | 71.600 | 1.00 | 17.50 | A |
| ATOM | 1125 | CD1 | LEU | A | 144 | 4.321 | −1.918 | 70.822 | 1.00 | 18.53 | A |

APPENDIX C-continued

18xCHS Mutant

| ATOM | # | TYPE | RES | | | X | Y | Z | OCC | B | |
|------|---|------|-----|---|-----|--------|--------|--------|------|-------|---|
| ATOM | 1126 | CD2 | LEU | A | 144 | 4.399 | −3.242 | 72.926 | 1.00 | 18.13 | A |
| ATOM | 1127 | C | LEU | A | 144 | 1.150 | −2.317 | 74.061 | 1.00 | 15.11 | A |
| ATOM | 1128 | O | LEU | A | 144 | 1.880 | −2.110 | 75.030 | 1.00 | 14.55 | A |
| ATOM | 1129 | N | THR | A | 145 | 0.030 | −1.635 | 73.838 | 1.00 | 14.64 | A |
| ATOM | 1130 | CA | THR | A | 145 | −0.442 | −0.599 | 74.752 | 1.00 | 15.04 | A |
| ATOM | 1131 | CB | THR | A | 145 | −1.769 | 0.018 | 74.258 | 1.00 | 15.52 | A |
| ATOM | 1132 | OG1 | THR | A | 145 | −1.544 | 0.707 | 73.023 | 1.00 | 15.30 | A |
| ATOM | 1133 | CG2 | THR | A | 145 | −2.325 | 0.993 | 75.288 | 1.00 | 15.63 | A |
| ATOM | 1134 | C | THR | A | 145 | −0.678 | −1.215 | 76.130 | 1.00 | 15.20 | A |
| ATOM | 1135 | O | THR | A | 145 | −0.310 | −0.640 | 77.156 | 1.00 | 14.90 | A |
| ATOM | 1136 | N | LYS | A | 146 | −1.296 | −2.392 | 76.138 | 1.00 | 15.71 | A |
| ATOM | 1137 | CA | LYS | A | 146 | −1.587 | −3.116 | 77.374 | 1.00 | 16.56 | A |
| ATOM | 1138 | CB | LYS | A | 146 | −2.469 | −4.325 | 77.054 | 1.00 | 17.61 | A |
| ATOM | 1139 | CG | LYS | A | 146 | −2.785 | −5.242 | 78.232 | 1.00 | 19.39 | A |
| ATOM | 1140 | CD | LYS | A | 146 | −3.567 | −6.463 | 77.745 | 1.00 | 21.39 | A |
| ATOM | 1141 | CE | LYS | A | 146 | −3.488 | −7.618 | 78.725 | 1.00 | 22.15 | A |
| ATOM | 1142 | NZ | LYS | A | 146 | −4.011 | −8.877 | 78.116 | 1.00 | 23.90 | A |
| ATOM | 1143 | C | LYS | A | 146 | −0.302 | −3.569 | 78.083 | 1.00 | 16.40 | A |
| ATOM | 1144 | O | LYS | A | 146 | −0.176 | −3.421 | 79.302 | 1.00 | 16.41 | A |
| ATOM | 1145 | N | LEU | A | 147 | 0.654 | −4.102 | 77.322 | 1.00 | 16.28 | A |
| ATOM | 1146 | CA | LEU | A | 147 | 1.912 | −4.579 | 77.901 | 1.00 | 16.03 | A |
| ATOM | 1147 | CB | LEU | A | 147 | 2.717 | −5.387 | 76.872 | 1.00 | 16.79 | A |
| ATOM | 1148 | CG | LEU | A | 147 | 2.089 | −6.628 | 76.224 | 1.00 | 17.91 | A |
| ATOM | 1149 | CD1 | LEU | A | 147 | 3.145 | −7.359 | 75.409 | 1.00 | 18.58 | A |
| ATOM | 1150 | CD2 | LEU | A | 147 | 1.520 | −7.551 | 77.277 | 1.00 | 19.05 | A |
| ATOM | 1151 | C | LEU | A | 147 | 2.789 | −3.449 | 78.446 | 1.00 | 15.74 | A |
| ATOM | 1152 | O | LEU | A | 147 | 3.477 | −3.622 | 79.456 | 1.00 | 15.01 | A |
| ATOM | 1153 | N | LEU | A | 148 | 2.765 | −2.297 | 77.780 | 1.00 | 14.59 | A |
| ATOM | 1154 | CA | LEU | A | 148 | 3.567 | −1.149 | 78.202 | 1.00 | 14.85 | A |
| ATOM | 1155 | CB | LEU | A | 148 | 3.913 | −0.261 | 76.998 | 1.00 | 14.25 | A |
| ATOM | 1156 | CG | LEU | A | 148 | 4.991 | −0.710 | 76.017 | 1.00 | 14.59 | A |
| ATOM | 1157 | CD1 | LEU | A | 148 | 4.989 | 0.201 | 74.790 | 1.00 | 14.37 | A |
| ATOM | 1158 | CD2 | LEU | A | 148 | 6.349 | −0.680 | 76.712 | 1.00 | 15.53 | A |
| ATOM | 1159 | C | LEU | A | 148 | 2.877 | −0.289 | 79.257 | 1.00 | 14.60 | A |
| ATOM | 1160 | O | LEU | A | 148 | 3.535 | 0.459 | 79.981 | 1.00 | 14.89 | A |
| ATOM | 1161 | N | GLY | A | 149 | 1.554 | −0.381 | 79.336 | 1.00 | 14.31 | A |
| ATOM | 1162 | CA | GLY | A | 149 | 0.822 | 0.426 | 80.295 | 1.00 | 14.76 | A |
| ATOM | 1163 | C | GLY | A | 149 | 0.754 | 1.885 | 79.867 | 1.00 | 15.29 | A |
| ATOM | 1164 | O | GLY | A | 149 | 0.838 | 2.792 | 80.696 | 1.00 | 15.01 | A |
| ATOM | 1165 | N | LEU | A | 150 | 0.618 | 2.123 | 78.565 | 1.00 | 15.01 | A |
| ATOM | 1166 | CA | LEU | A | 150 | 0.522 | 3.490 | 78.058 | 1.00 | 14.43 | A |
| ATOM | 1167 | CB | LEU | A | 150 | 0.665 | 3.500 | 76.530 | 1.00 | 14.29 | A |
| ATOM | 1168 | CG | LEU | A | 150 | 1.962 | 2.940 | 75.928 | 1.00 | 14.95 | A |
| ATOM | 1169 | CD1 | LEU | A | 150 | 1.852 | 2.932 | 74.401 | 1.00 | 15.08 | A |
| ATOM | 1170 | CD2 | LEU | A | 150 | 3.157 | 3.773 | 76.374 | 1.00 | 14.06 | A |
| ATOM | 1171 | C | LEU | A | 150 | −0.851 | 4.041 | 78.451 | 1.00 | 14.48 | A |
| ATOM | 1172 | O | LEU | A | 150 | −1.729 | 3.278 | 78.853 | 1.00 | 14.49 | A |
| ATOM | 1173 | N | ARG | A | 151 | −1.043 | 5.356 | 78.348 | 1.00 | 14.75 | A |
| ATOM | 1174 | CA | ARG | A | 151 | −2.343 | 5.942 | 78.686 | 1.00 | 15.18 | A |
| ATOM | 1175 | CB | ARG | A | 151 | −2.363 | 7.447 | 78.418 | 1.00 | 16.74 | A |
| ATOM | 1176 | CG | ARG | A | 151 | −1.317 | 8.281 | 79.141 | 1.00 | 20.10 | A |
| ATOM | 1177 | CD | ARG | A | 151 | −1.614 | 8.453 | 80.619 | 1.00 | 22.50 | A |
| ATOM | 1178 | NE | ARG | A | 151 | −1.242 | 7.285 | 81.409 | 1.00 | 25.48 | A |
| ATOM | 1179 | CZ | ARG | A | 151 | −0.889 | 7.345 | 82.690 | 1.00 | 26.63 | A |
| ATOM | 1180 | NH1 | ARG | A | 151 | −0.863 | 8.517 | 83.315 | 1.00 | 27.54 | A |
| ATOM | 1181 | NH2 | ARG | A | 151 | −0.554 | 6.240 | 83.345 | 1.00 | 27.39 | A |
| ATOM | 1182 | C | ARG | A | 151 | −3.376 | 5.285 | 77.767 | 1.00 | 14.81 | A |
| ATOM | 1183 | O | ARG | A | 151 | −3.086 | 5.017 | 76.597 | 1.00 | 14.19 | A |
| ATOM | 1184 | N | PRO | A | 152 | −4.594 | 5.026 | 78.276 | 1.00 | 14.13 | A |
| ATOM | 1185 | CD | PRO | A | 152 | −5.080 | 5.236 | 79.652 | 1.00 | 14.92 | A |
| ATOM | 1186 | CA | PRO | A | 152 | −5.626 | 4.397 | 77.440 | 1.00 | 13.82 | A |
| ATOM | 1187 | CB | PRO | A | 152 | −6.768 | 4.139 | 78.427 | 1.00 | 14.60 | A |
| ATOM | 1188 | CG | PRO | A | 152 | −6.581 | 5.212 | 79.469 | 1.00 | 15.28 | A |
| ATOM | 1189 | C | PRO | A | 152 | −6.063 | 5.243 | 76.244 | 1.00 | 13.54 | A |
| ATOM | 1190 | O | PRO | A | 152 | −6.637 | 4.718 | 75.285 | 1.00 | 13.02 | A |
| ATOM | 1191 | N | TYR | A | 153 | −5.782 | 6.543 | 76.296 | 1.00 | 12.81 | A |
| ATOM | 1192 | CA | TYR | A | 153 | −6.160 | 7.447 | 75.215 | 1.00 | 12.98 | A |
| ATOM | 1193 | CB | TYR | A | 153 | −6.697 | 8.760 | 75.799 | 1.00 | 13.85 | A |
| ATOM | 1194 | CG | TYR | A | 153 | −5.834 | 9.362 | 76.879 | 1.00 | 15.46 | A |
| ATOM | 1195 | CD1 | TYR | A | 153 | −4.728 | 10.150 | 76.559 | 1.00 | 15.67 | A |
| ATOM | 1196 | CE1 | TYR | A | 153 | −3.933 | 10.713 | 77.558 | 1.00 | 16.87 | A |
| ATOM | 1197 | CD2 | TYR | A | 153 | −6.124 | 9.145 | 78.228 | 1.00 | 15.87 | A |
| ATOM | 1198 | CE2 | TYR | A | 153 | −5.335 | 9.700 | 79.233 | 1.00 | 16.78 | A |
| ATOM | 1199 | CZ | TYR | A | 153 | −4.243 | 10.484 | 78.892 | 1.00 | 16.94 | A |
| ATOM | 1200 | OH | TYR | A | 153 | −3.466 | 11.045 | 79.887 | 1.00 | 18.20 | A |

APPENDIX C-continued

18xCHS Mutant

| ATOM | # | TYPE | RES | | | X | Y | Z | OCC | B | |
|------|---|------|-----|---|---|---|---|---|-----|---|---|
| ATOM | 1201 | C | TYR | A | 153 | −5.046 | 7.714 | 74.198 | 1.00 | 12.40 | A |
| ATOM | 1202 | O | TYR | A | 153 | −5.072 | 8.707 | 73.471 | 1.00 | 11.41 | A |
| ATOM | 1203 | N | VAL | A | 154 | −4.061 | 6.822 | 74.157 | 1.00 | 11.87 | A |
| ATOM | 1204 | CA | VAL | A | 154 | −2.980 | 6.940 | 73.185 | 1.00 | 11.77 | A |
| ATOM | 1205 | CB | VAL | A | 154 | −1.853 | 5.908 | 73.489 | 1.00 | 11.94 | A |
| ATOM | 1206 | CG1 | VAL | A | 154 | −2.405 | 4.491 | 73.415 | 1.00 | 11.75 | A |
| ATOM | 1207 | CG2 | VAL | A | 154 | −0.689 | 6.092 | 72.525 | 1.00 | 11.07 | A |
| ATOM | 1208 | C | VAL | A | 154 | −3.648 | 6.625 | 71.837 | 1.00 | 11.61 | A |
| ATOM | 1209 | O | VAL | A | 154 | −4.427 | 5.677 | 71.746 | 1.00 | 11.48 | A |
| ATOM | 1210 | N | LYS | A | 155 | −3.372 | 7.434 | 70.815 | 1.00 | 11.04 | A |
| ATOM | 1211 | CA | LYS | A | 155 | −3.958 | 7.240 | 69.488 | 1.00 | 11.52 | A |
| ATOM | 1212 | CB | LYS | A | 155 | −4.021 | 8.579 | 68.744 | 1.00 | 12.00 | A |
| ATOM | 1213 | CG | LYS | A | 155 | −5.109 | 9.511 | 69.281 | 1.00 | 13.78 | A |
| ATOM | 1214 | CD | LYS | A | 155 | −5.049 | 10.889 | 68.638 | 1.00 | 14.84 | A |
| ATOM | 1215 | CE | LYS | A | 155 | −4.098 | 11.811 | 69.373 | 1.00 | 16.12 | A |
| ATOM | 1216 | NZ | LYS | A | 155 | −4.651 | 12.234 | 70.700 | 1.00 | 17.06 | A |
| ATOM | 1217 | C | LYS | A | 155 | −3.144 | 6.219 | 68.705 | 1.00 | 10.94 | A |
| ATOM | 1218 | O | LYS | A | 155 | −1.993 | 6.472 | 68.349 | 1.00 | 10.07 | A |
| ATOM | 1219 | N | ARG | A | 156 | −3.771 | 5.077 | 68.422 | 1.00 | 10.42 | A |
| ATOM | 1220 | CA | ARG | A | 156 | −3.118 | 3.956 | 67.748 | 1.00 | 10.30 | A |
| ATOM | 1221 | CB | ARG | A | 156 | −3.463 | 2.660 | 68.492 | 1.00 | 10.46 | A |
| ATOM | 1222 | CG | ARG | A | 156 | −3.114 | 2.635 | 69.984 | 1.00 | 12.15 | A |
| ATOM | 1223 | CD | ARG | A | 156 | −3.773 | 1.430 | 70.673 | 1.00 | 11.65 | A |
| ATOM | 1224 | NE | ARG | A | 156 | −5.153 | 1.718 | 71.061 | 1.00 | 13.59 | A |
| ATOM | 1225 | CZ | ARG | A | 156 | −6.222 | 1.026 | 70.670 | 1.00 | 13.73 | A |
| ATOM | 1226 | NH1 | ARG | A | 156 | −6.092 | −0.017 | 69.860 | 1.00 | 13.14 | A |
| ATOM | 1227 | NH2 | ARG | A | 156 | −7.429 | 1.377 | 71.101 | 1.00 | 12.93 | A |
| ATOM | 1228 | C | ARG | A | 156 | −3.435 | 3.718 | 66.271 | 1.00 | 10.47 | A |
| ATOM | 1229 | O | ARG | A | 156 | −4.520 | 4.034 | 65.794 | 1.00 | 10.65 | A |
| ATOM | 1230 | N | VAL | A | 157 | −2.470 | 3.128 | 65.569 | 1.00 | 10.08 | A |
| ATOM | 1231 | CA | VAL | A | 157 | −2.629 | 2.742 | 64.166 | 1.00 | 10.38 | A |
| ATOM | 1232 | CB | VAL | A | 157 | −2.160 | 3.834 | 63.181 | 1.00 | 10.90 | A |
| ATOM | 1233 | CG1 | VAL | A | 157 | −0.714 | 4.156 | 63.410 | 1.00 | 13.08 | A |
| ATOM | 1234 | CG2 | VAL | A | 157 | −2.374 | 3.352 | 61.739 | 1.00 | 12.71 | A |
| ATOM | 1235 | C | VAL | A | 157 | −1.793 | 1.484 | 63.939 | 1.00 | 9.54 | A |
| ATOM | 1236 | O | VAL | A | 157 | −0.603 | 1.456 | 64.257 | 1.00 | 8.67 | A |
| ATOM | 1237 | N | GLY | A | 158 | −2.431 | 0.440 | 63.414 | 1.00 | 8.62 | A |
| ATOM | 1238 | CA | GLY | A | 158 | −1.725 | −0.801 | 63.145 | 1.00 | 8.95 | A |
| ATOM | 1239 | C | GLY | A | 158 | −1.474 | −0.920 | 61.655 | 1.00 | 9.11 | A |
| ATOM | 1240 | O | GLY | A | 158 | −2.377 | −0.660 | 60.861 | 1.00 | 9.18 | A |
| ATOM | 1241 | N | VAL | A | 159 | −0.252 | −1.297 | 61.280 | 1.00 | 8.82 | A |
| ATOM | 1242 | CA | VAL | A | 159 | 0.139 | −1.446 | 59.876 | 1.00 | 9.27 | A |
| ATOM | 1243 | CB | VAL | A | 159 | 1.383 | −0.578 | 59.566 | 1.00 | 10.03 | A |
| ATOM | 1244 | CG1 | VAL | A | 159 | 1.821 | −0.763 | 58.120 | 1.00 | 9.90 | A |
| ATOM | 1245 | CG2 | VAL | A | 159 | 1.060 | 0.890 | 59.848 | 1.00 | 8.75 | A |
| ATOM | 1246 | C | VAL | A | 159 | 0.449 | −2.918 | 59.622 | 1.00 | 9.42 | A |
| ATOM | 1247 | O | VAL | A | 159 | 1.541 | −3.403 | 59.937 | 1.00 | 8.94 | A |
| ATOM | 1248 | N | PHE | A | 160 | −0.523 | −3.620 | 59.048 | 1.00 | 9.07 | A |
| ATOM | 1249 | CA | PHE | A | 160 | −0.401 | −5.049 | 58.793 | 1.00 | 9.95 | A |
| ATOM | 1250 | CB | PHE | A | 160 | −1.476 | −5.787 | 59.607 | 1.00 | 9.65 | A |
| ATOM | 1251 | CG | PHE | A | 160 | −1.534 | −5.354 | 61.057 | 1.00 | 10.47 | A |
| ATOM | 1252 | CD1 | PHE | A | 160 | −0.428 | −5.519 | 61.889 | 1.00 | 10.51 | A |
| ATOM | 1253 | CD2 | PHE | A | 160 | −2.679 | −4.757 | 61.577 | 1.00 | 10.31 | A |
| ATOM | 1254 | CE1 | PHE | A | 160 | −0.462 | −5.091 | 63.226 | 1.00 | 10.88 | A |
| ATOM | 1255 | CE2 | PHE | A | 160 | −2.726 | −4.325 | 62.913 | 1.00 | 11.26 | A |
| ATOM | 1256 | CZ | PHE | A | 160 | −1.618 | −4.491 | 63.735 | 1.00 | 10.62 | A |
| ATOM | 1257 | C | PHE | A | 160 | −0.506 | −5.439 | 57.320 | 1.00 | 10.38 | A |
| ATOM | 1258 | O | PHE | A | 160 | −1.192 | −4.787 | 56.530 | 1.00 | 10.36 | A |
| ATOM | 1259 | N | GLN | A | 161 | 0.179 | −6.527 | 56.981 | 1.00 | 10.62 | A |
| ATOM | 1260 | CA | GLN | A | 161 | 0.230 | −7.076 | 55.634 | 1.00 | 11.79 | A |
| ATOM | 1261 | CB | GLN | A | 161 | −1.117 | −7.743 | 55.272 | 1.00 | 11.33 | A |
| ATOM | 1262 | CG | GLN | A | 161 | −1.311 | −9.055 | 56.058 | 1.00 | 12.18 | A |
| ATOM | 1263 | CD | GLN | A | 161 | −2.598 | −9.818 | 55.754 | 1.00 | 12.20 | A |
| ATOM | 1264 | OE1 | GLN | A | 161 | −3.381 | −10.113 | 56.662 | 1.00 | 11.95 | A |
| ATOM | 1265 | NE2 | GLN | A | 161 | −2.810 | −10.161 | 54.487 | 1.00 | 12.09 | A |
| ATOM | 1266 | C | GLN | A | 161 | 0.704 | −6.102 | 54.554 | 1.00 | 12.04 | A |
| ATOM | 1267 | O | GLN | A | 161 | 0.215 | −6.114 | 53.421 | 1.00 | 13.06 | A |
| ATOM | 1268 | N | HIS | A | 162 | 1.667 | −5.256 | 54.922 | 1.00 | 11.82 | A |
| ATOM | 1269 | CA | HIS | A | 162 | 2.279 | −4.330 | 53.975 | 1.00 | 12.08 | A |
| ATOM | 1270 | CB | HIS | A | 162 | 2.552 | −2.962 | 54.619 | 1.00 | 11.69 | A |
| ATOM | 1271 | CG | HIS | A | 162 | 1.307 | −2.154 | 54.852 | 1.00 | 10.82 | A |
| ATOM | 1272 | CD2 | HIS | A | 162 | 0.161 | −2.456 | 55.507 | 1.00 | 9.91 | A |
| ATOM | 1273 | ND1 | HIS | A | 162 | 1.142 | −0.874 | 54.366 | 1.00 | 12.15 | A |
| ATOM | 1274 | CE1 | HIS | A | 162 | −0.051 | −0.422 | 54.711 | 1.00 | 9.94 | A |
| ATOM | 1275 | NE2 | HIS | A | 162 | −0.667 | −1.363 | 55.405 | 1.00 | 11.67 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 1276 | C | HIS | A | 162 | 3.575 | −5.021 | 53.539 | 1.00 | 12.51 | A |
| ATOM | 1277 | O | HIS | A | 162 | 3.854 | −5.127 | 52.348 | 1.00 | 14.03 | A |
| ATOM | 1278 | N | GLY | A | 163 | 4.361 | −5.507 | 54.497 | 1.00 | 12.09 | A |
| ATOM | 1279 | CA | GLY | A | 163 | 5.570 | −6.229 | 54.130 | 1.00 | 12.81 | A |
| ATOM | 1280 | C | GLY | A | 163 | 6.937 | −5.602 | 54.325 | 1.00 | 12.93 | A |
| ATOM | 1281 | O | GLY | A | 163 | 7.122 | −4.713 | 55.159 | 1.00 | 13.11 | A |
| ATOM | 1282 | N | CYS | A | 164 | 7.898 | −6.079 | 53.533 | 1.00 | 12.87 | A |
| ATOM | 1283 | CA | CYS | A | 164 | 9.285 | −5.630 | 53.608 | 1.00 | 12.88 | A |
| ATOM | 1284 | CB | CYS | A | 164 | 10.145 | −6.435 | 52.621 | 1.00 | 14.32 | A |
| ATOM | 1285 | SG | CYS | A | 164 | 10.567 | −8.126 | 53.171 | 1.00 | 18.21 | A |
| ATOM | 1286 | C | CYS | A | 164 | 9.565 | −4.137 | 53.419 | 1.00 | 12.07 | A |
| ATOM | 1287 | O | CYS | A | 164 | 10.611 | −3.655 | 53.851 | 1.00 | 12.09 | A |
| ATOM | 1288 | N | PHE | A | 165 | 8.656 | −3.402 | 52.787 | 1.00 | 11.32 | A |
| ATOM | 1289 | CA | PHE | A | 165 | 8.881 | −1.970 | 52.579 | 1.00 | 11.97 | A |
| ATOM | 1290 | CB | PHE | A | 165 | 8.268 | −1.529 | 51.239 | 1.00 | 12.38 | A |
| ATOM | 1291 | CG | PHE | A | 165 | 6.761 | −1.608 | 51.194 | 1.00 | 12.73 | A |
| ATOM | 1292 | CD1 | PHE | A | 165 | 5.977 | −0.679 | 51.878 | 1.00 | 12.91 | A |
| ATOM | 1293 | CD2 | PHE | A | 165 | 6.126 | −2.624 | 50.487 | 1.00 | 12.52 | A |
| ATOM | 1294 | CE1 | PHE | A | 165 | 4.582 | −0.763 | 51.865 | 1.00 | 12.61 | A |
| ATOM | 1295 | CE2 | PHE | A | 165 | 4.727 | −2.719 | 50.466 | 1.00 | 12.91 | A |
| ATOM | 1296 | CZ | PHE | A | 165 | 3.955 | −1.785 | 51.160 | 1.00 | 12.54 | A |
| ATOM | 1297 | C | PHE | A | 165 | 8.327 | −1.090 | 53.711 | 1.00 | 11.55 | A |
| ATOM | 1298 | O | PHE | A | 165 | 8.591 | 0.116 | 53.755 | 1.00 | 10.90 | A |
| ATOM | 1299 | N | ALA | A | 166 | 7.597 | −1.705 | 54.640 | 1.00 | 11.47 | A |
| ATOM | 1300 | CA | ALA | A | 166 | 6.951 | −0.987 | 55.742 | 1.00 | 10.36 | A |
| ATOM | 1301 | CB | ALA | A | 166 | 6.055 | −1.944 | 56.520 | 1.00 | 10.05 | A |
| ATOM | 1302 | C | ALA | A | 166 | 7.832 | −0.201 | 56.716 | 1.00 | 10.76 | A |
| ATOM | 1303 | O | ALA | A | 166 | 7.311 | 0.568 | 57.541 | 1.00 | 10.61 | A |
| ATOM | 1304 | N | GLY | A | 167 | 9.142 | −0.404 | 56.660 | 1.00 | 10.33 | A |
| ATOM | 1305 | CA | GLY | A | 167 | 10.025 | 0.363 | 57.525 | 1.00 | 10.23 | A |
| ATOM | 1306 | C | GLY | A | 167 | 9.945 | 1.808 | 57.056 | 1.00 | 10.55 | A |
| ATOM | 1307 | O | GLY | A | 167 | 10.031 | 2.757 | 57.844 | 1.00 | 9.84 | A |
| ATOM | 1308 | N | GLY | A | 168 | 9.779 | 1.982 | 55.749 | 1.00 | 9.79 | A |
| ATOM | 1309 | CA | GLY | A | 168 | 9.650 | 3.319 | 55.205 | 1.00 | 10.50 | A |
| ATOM | 1310 | C | GLY | A | 168 | 8.246 | 3.849 | 55.466 | 1.00 | 9.99 | A |
| ATOM | 1311 | O | GLY | A | 168 | 8.057 | 5.036 | 55.733 | 1.00 | 10.63 | A |
| ATOM | 1312 | N | THR | A | 169 | 7.260 | 2.957 | 55.392 | 1.00 | 9.91 | A |
| ATOM | 1313 | CA | THR | A | 169 | 5.853 | 3.307 | 55.615 | 1.00 | 8.80 | A |
| ATOM | 1314 | CB | THR | A | 169 | 4.939 | 2.060 | 55.439 | 1.00 | 9.40 | A |
| ATOM | 1315 | OG1 | THR | A | 169 | 5.186 | 1.457 | 54.163 | 1.00 | 10.04 | A |
| ATOM | 1316 | CG2 | THR | A | 169 | 3.468 | 2.454 | 55.521 | 1.00 | 9.30 | A |
| ATOM | 1317 | C | THR | A | 169 | 5.590 | 3.898 | 57.006 | 1.00 | 8.76 | A |
| ATOM | 1318 | O | THR | A | 169 | 4.865 | 4.896 | 57.144 | 1.00 | 7.14 | A |
| ATOM | 1319 | N | VAL | A | 170 | 6.157 | 3.288 | 58.046 | 1.00 | 7.94 | A |
| ATOM | 1320 | CA | VAL | A | 170 | 5.925 | 3.804 | 59.391 | 1.00 | 7.96 | A |
| ATOM | 1321 | CB | VAL | A | 170 | 6.391 | 2.818 | 60.492 | 1.00 | 8.12 | A |
| ATOM | 1322 | CG1 | VAL | A | 170 | 5.595 | 1.516 | 60.377 | 1.00 | 8.51 | A |
| ATOM | 1323 | CG2 | VAL | A | 170 | 7.894 | 2.571 | 60.387 | 1.00 | 8.83 | A |
| ATOM | 1324 | C | VAL | A | 170 | 6.599 | 5.153 | 59.615 | 1.00 | 8.27 | A |
| ATOM | 1325 | O | VAL | A | 170 | 6.121 | 5.958 | 60.411 | 1.00 | 8.24 | A |
| ATOM | 1326 | N | LEU | A | 171 | 7.706 | 5.401 | 58.919 | 1.00 | 8.82 | A |
| ATOM | 1327 | CA | LEU | A | 171 | 8.398 | 6.680 | 59.059 | 1.00 | 9.31 | A |
| ATOM | 1328 | CB | LEU | A | 171 | 9.798 | 6.610 | 58.438 | 1.00 | 9.00 | A |
| ATOM | 1329 | CG | LEU | A | 171 | 10.849 | 5.863 | 59.275 | 1.00 | 9.38 | A |
| ATOM | 1330 | CD1 | LEU | A | 171 | 12.115 | 5.666 | 58.461 | 1.00 | 10.01 | A |
| ATOM | 1331 | CD2 | LEU | A | 171 | 11.155 | 6.668 | 60.549 | 1.00 | 10.13 | A |
| ATOM | 1332 | C | LEU | A | 171 | 7.559 | 7.756 | 58.371 | 1.00 | 9.34 | A |
| ATOM | 1333 | O | LEU | A | 171 | 7.412 | 8.868 | 58.886 | 1.00 | 9.70 | A |
| ATOM | 1334 | N | ARG | A | 172 | 7.006 | 7.411 | 57.208 | 1.00 | 9.62 | A |
| ATOM | 1335 | CA | ARG | A | 172 | 6.155 | 8.319 | 56.435 | 1.00 | 9.46 | A |
| ATOM | 1336 | CB | ARG | A | 172 | 5.757 | 7.647 | 55.106 | 1.00 | 10.16 | A |
| ATOM | 1337 | CG | ARG | A | 172 | 4.732 | 8.408 | 54.269 | 1.00 | 10.70 | A |
| ATOM | 1338 | CD | ARG | A | 172 | 4.768 | 7.971 | 52.792 | 1.00 | 10.81 | A |
| ATOM | 1339 | NE | ARG | A | 172 | 4.534 | 6.538 | 52.581 | 1.00 | 10.35 | A |
| ATOM | 1340 | CZ | ARG | A | 172 | 3.341 | 5.948 | 52.574 | 1.00 | 10.72 | A |
| ATOM | 1341 | NH1 | ARG | A | 172 | 2.232 | 6.652 | 52.772 | 1.00 | 10.58 | A |
| ATOM | 1342 | NH2 | ARG | A | 172 | 3.251 | 4.641 | 52.336 | 1.00 | 10.24 | A |
| ATOM | 1343 | C | ARG | A | 172 | 4.906 | 8.703 | 57.246 | 1.00 | 9.67 | A |
| ATOM | 1344 | O | ARG | A | 172 | 4.491 | 9.864 | 57.251 | 1.00 | 8.96 | A |
| ATOM | 1345 | N | LEU | A | 173 | 4.315 | 7.735 | 57.943 | 1.00 | 9.66 | A |
| ATOM | 1346 | CA | LEU | A | 173 | 3.135 | 8.015 | 58.759 | 1.00 | 9.61 | A |
| ATOM | 1347 | CB | LEU | A | 173 | 2.469 | 6.714 | 59.221 | 1.00 | 10.65 | A |
| ATOM | 1348 | CG | LEU | A | 173 | 1.700 | 5.893 | 58.180 | 1.00 | 10.70 | A |
| ATOM | 1349 | CD1 | LEU | A | 173 | 1.374 | 4.522 | 58.764 | 1.00 | 10.48 | A |
| ATOM | 1350 | CD2 | LEU | A | 173 | 0.422 | 6.630 | 57.766 | 1.00 | 10.97 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 1351 | C | LEU | A | 173 | 3.514 | 8.846 | 59.985 | 1.00 | 10.02 | A |
| ATOM | 1352 | O | LEU | A | 173 | 2.838 | 9.819 | 60.314 | 1.00 | 8.14 | A |
| ATOM | 1353 | N | ALA | A | 174 | 4.589 | 8.452 | 60.667 | 1.00 | 9.18 | A |
| ATOM | 1354 | CA | ALA | A | 174 | 5.031 | 9.177 | 61.858 | 1.00 | 9.26 | A |
| ATOM | 1355 | CB | ALA | A | 174 | 6.273 | 8.507 | 62.453 | 1.00 | 8.76 | A |
| ATOM | 1356 | C | ALA | A | 174 | 5.331 | 10.640 | 61.533 | 1.00 | 9.47 | A |
| ATOM | 1357 | O | ALA | A | 174 | 5.117 | 11.530 | 62.362 | 1.00 | 9.93 | A |
| ATOM | 1358 | N | LYS | A | 175 | 5.833 | 10.889 | 60.330 | 1.00 | 9.17 | A |
| ATOM | 1359 | CA | LYS | A | 175 | 6.160 | 12.252 | 59.925 | 1.00 | 9.55 | A |
| ATOM | 1360 | CB | LYS | A | 175 | 6.749 | 12.262 | 58.509 | 1.00 | 9.91 | A |
| ATOM | 1361 | CG | LYS | A | 175 | 7.144 | 13.652 | 58.009 | 1.00 | 10.71 | A |
| ATOM | 1362 | CD | LYS | A | 175 | 7.661 | 13.602 | 56.573 | 1.00 | 11.77 | A |
| ATOM | 1363 | CE | LYS | A | 175 | 8.152 | 14.967 | 56.104 | 1.00 | 11.36 | A |
| ATOM | 1364 | NZ | LYS | A | 175 | 7.064 | 15.983 | 56.022 | 1.00 | 12.68 | A |
| ATOM | 1365 | C | LYS | A | 175 | 4.932 | 13.167 | 59.986 | 1.00 | 9.54 | A |
| ATOM | 1366 | O | LYS | A | 175 | 4.990 | 14.252 | 60.561 | 1.00 | 9.61 | A |
| ATOM | 1367 | N | ASP | A | 176 | 3.816 | 12.733 | 59.409 | 1.00 | 9.94 | A |
| ATOM | 1368 | CA | ASP | A | 176 | 2.611 | 13.563 | 59.437 | 1.00 | 10.35 | A |
| ATOM | 1369 | CB | ASP | A | 176 | 1.577 | 13.062 | 58.422 | 1.00 | 10.89 | A |
| ATOM | 1370 | CG | ASP | A | 176 | 1.986 | 13.336 | 56.984 | 1.00 | 11.89 | A |
| ATOM | 1371 | OD1 | ASP | A | 176 | 2.750 | 14.301 | 56.755 | 1.00 | 12.55 | A |
| ATOM | 1372 | OD2 | ASP | A | 176 | 1.526 | 12.600 | 56.084 | 1.00 | 12.25 | A |
| ATOM | 1373 | C | ASP | A | 176 | 1.953 | 13.658 | 60.816 | 1.00 | 10.80 | A |
| ATOM | 1374 | O | ASP | A | 176 | 1.484 | 14.729 | 61.206 | 1.00 | 11.51 | A |
| ATOM | 1375 | N | LEU | A | 177 | 1.913 | 12.558 | 61.563 | 1.00 | 10.38 | A |
| ATOM | 1376 | CA | LEU | A | 177 | 1.278 | 12.595 | 62.882 | 1.00 | 10.56 | A |
| ATOM | 1377 | CB | LEU | A | 177 | 1.206 | 11.190 | 63.502 | 1.00 | 11.79 | A |
| ATOM | 1378 | CG | LEU | A | 177 | 0.639 | 9.991 | 62.725 | 1.00 | 14.19 | A |
| ATOM | 1379 | CD1 | LEU | A | 177 | 0.109 | 8.979 | 63.738 | 1.00 | 13.55 | A |
| ATOM | 1380 | CD2 | LEU | A | 177 | −0.469 | 10.405 | 61.769 | 1.00 | 13.39 | A |
| ATOM | 1381 | C | LEU | A | 177 | 2.012 | 13.535 | 63.845 | 1.00 | 10.13 | A |
| ATOM | 1382 | O | LEU | A | 177 | 1.381 | 14.256 | 64.613 | 1.00 | 10.07 | A |
| ATOM | 1383 | N | ALA | A | 178 | 3.343 | 13.532 | 63.798 | 1.00 | 9.17 | A |
| ATOM | 1384 | CA | ALA | A | 178 | 4.132 | 14.387 | 64.684 | 1.00 | 9.84 | A |
| ATOM | 1385 | CB | ALA | A | 178 | 5.565 | 13.867 | 64.768 | 1.00 | 9.65 | A |
| ATOM | 1386 | C | ALA | A | 178 | 4.144 | 15.860 | 64.261 | 1.00 | 9.88 | A |
| ATOM | 1387 | O | ALA | A | 178 | 4.064 | 16.756 | 65.108 | 1.00 | 10.05 | A |
| ATOM | 1388 | N | GLU | A | 179 | 4.243 | 16.111 | 62.958 | 1.00 | 9.81 | A |
| ATOM | 1389 | CA | GLU | A | 179 | 4.286 | 17.479 | 62.447 | 1.00 | 10.22 | A |
| ATOM | 1390 | CB | GLU | A | 179 | 4.834 | 17.488 | 61.005 | 1.00 | 10.39 | A |
| ATOM | 1391 | CG | GLU | A | 179 | 6.363 | 17.310 | 60.920 | 1.00 | 12.08 | A |
| ATOM | 1392 | CD | GLU | A | 179 | 6.887 | 17.099 | 59.495 | 1.00 | 12.59 | A |
| ATOM | 1393 | OE1 | GLU | A | 179 | 6.109 | 17.252 | 58.527 | 1.00 | 13.52 | A |
| ATOM | 1394 | OE2 | GLU | A | 179 | 8.090 | 16.781 | 59.344 | 1.00 | 11.85 | A |
| ATOM | 1395 | C | GLU | A | 179 | 2.954 | 18.241 | 62.507 | 1.00 | 10.38 | A |
| ATOM | 1396 | O | GLU | A | 179 | 2.953 | 19.465 | 62.644 | 1.00 | 10.28 | A |
| ATOM | 1397 | N | ASN | A | 180 | 1.828 | 17.534 | 62.426 | 1.00 | 10.18 | A |
| ATOM | 1398 | CA | ASN | A | 180 | 0.522 | 18.204 | 62.453 | 1.00 | 10.49 | A |
| ATOM | 1399 | CB | ASN | A | 180 | −0.468 | 17.472 | 61.534 | 1.00 | 10.37 | A |
| ATOM | 1400 | CG | ASN | A | 180 | −1.703 | 18.304 | 61.229 | 1.00 | 10.46 | A |
| ATOM | 1401 | OD1 | ASN | A | 180 | −1.591 | 19.448 | 60.787 | 1.00 | 11.09 | A |
| ATOM | 1402 | ND2 | ASN | A | 180 | −2.888 | 17.733 | 61.457 | 1.00 | 10.21 | A |
| ATOM | 1403 | C | ASN | A | 180 | −0.121 | 18.362 | 63.834 | 1.00 | 10.50 | A |
| ATOM | 1404 | O | ASN | A | 180 | −1.202 | 18.945 | 63.944 | 1.00 | 10.62 | A |
| ATOM | 1405 | N | ASN | A | 181 | 0.535 | 17.860 | 64.880 | 1.00 | 10.99 | A |
| ATOM | 1406 | CA | ASN | A | 181 | −0.016 | 17.927 | 66.238 | 1.00 | 11.61 | A |
| ATOM | 1407 | CB | ASN | A | 181 | −0.564 | 16.549 | 66.625 | 1.00 | 10.99 | A |
| ATOM | 1408 | CG | ASN | A | 181 | −1.740 | 16.127 | 65.759 | 1.00 | 11.32 | A |
| ATOM | 1409 | OD1 | ASN | A | 181 | −2.859 | 16.615 | 65.934 | 1.00 | 10.59 | A |
| ATOM | 1410 | ND2 | ASN | A | 181 | −1.489 | 15.227 | 64.808 | 1.00 | 9.52 | A |
| ATOM | 1411 | C | ASN | A | 181 | 0.998 | 18.401 | 67.292 | 1.00 | 11.97 | A |
| ATOM | 1412 | O | ASN | A | 181 | 1.937 | 17.679 | 67.643 | 1.00 | 12.00 | A |
| ATOM | 1413 | N | LYS | A | 182 | 0.795 | 19.614 | 67.798 | 1.00 | 12.75 | A |
| ATOM | 1414 | CA | LYS | A | 182 | 1.696 | 20.206 | 68.789 | 1.00 | 13.47 | A |
| ATOM | 1415 | CB | LYS | A | 182 | 1.196 | 21.599 | 69.184 | 1.00 | 14.26 | A |
| ATOM | 1416 | CG | LYS | A | 182 | 2.079 | 22.332 | 70.192 | 1.00 | 15.00 | A |
| ATOM | 1417 | CD | LYS | A | 182 | 1.552 | 23.747 | 70.417 | 1.00 | 16.14 | A |
| ATOM | 1418 | CE | LYS | A | 182 | 2.521 | 24.601 | 71.221 | 1.00 | 16.60 | A |
| ATOM | 1419 | NZ | LYS | A | 182 | 1.974 | 25.979 | 71.402 | 1.00 | 18.49 | A |
| ATOM | 1420 | C | LYS | A | 182 | 1.856 | 19.357 | 70.044 | 1.00 | 13.44 | A |
| ATOM | 1421 | O | LYS | A | 182 | 0.872 | 18.987 | 70.684 | 1.00 | 13.52 | A |
| ATOM | 1422 | N | GLY | A | 183 | 3.105 | 19.060 | 70.391 | 1.00 | 13.68 | A |
| ATOM | 1423 | CA | GLY | A | 183 | 3.383 | 18.262 | 71.574 | 1.00 | 13.42 | A |
| ATOM | 1424 | C | GLY | A | 183 | 3.351 | 16.758 | 71.360 | 1.00 | 12.95 | A |
| ATOM | 1425 | O | GLY | A | 183 | 3.689 | 15.993 | 72.259 | 1.00 | 13.54 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 1426 | N | ALA | A | 184 | 2.963 | 16.320 | 70.169 | 1.00 | 13.05 | A |
| ATOM | 1427 | CA | ALA | A | 184 | 2.875 | 14.891 | 69.893 | 1.00 | 11.73 | A |
| ATOM | 1428 | CB | ALA | A | 184 | 2.194 | 14.659 | 68.537 | 1.00 | 11.31 | A |
| ATOM | 1429 | C | ALA | A | 184 | 4.218 | 14.167 | 69.930 | 1.00 | 11.28 | A |
| ATOM | 1430 | O | ALA | A | 184 | 5.223 | 14.664 | 69.426 | 1.00 | 11.97 | A |
| ATOM | 1431 | N | ARG | A | 185 | 4.216 | 12.990 | 70.547 | 1.00 | 10.77 | A |
| ATOM | 1432 | CA | ARG | A | 185 | 5.402 | 12.145 | 70.650 | 1.00 | 10.15 | A |
| ATOM | 1433 | CB | ARG | A | 185 | 5.943 | 12.158 | 72.085 | 1.00 | 10.47 | A |
| ATOM | 1434 | CG | ARG | A | 185 | 6.661 | 13.478 | 72.457 | 1.00 | 10.37 | A |
| ATOM | 1435 | CD | ARG | A | 185 | 7.966 | 13.635 | 71.667 | 1.00 | 11.21 | A |
| ATOM | 1436 | NE | ARG | A | 185 | 8.724 | 14.859 | 71.958 | 1.00 | 11.36 | A |
| ATOM | 1437 | CZ | ARG | A | 185 | 8.514 | 16.039 | 71.375 | 1.00 | 11.90 | A |
| ATOM | 1438 | NH1 | ARG | A | 185 | 7.557 | 16.180 | 70.462 | 1.00 | 11.35 | A |
| ATOM | 1439 | NH2 | ARG | A | 185 | 9.287 | 17.078 | 71.676 | 1.00 | 12.08 | A |
| ATOM | 1440 | C | ARG | A | 185 | 4.937 | 10.754 | 70.219 | 1.00 | 9.96 | A |
| ATOM | 1441 | O | ARG | A | 185 | 4.102 | 10.121 | 70.878 | 1.00 | 8.97 | A |
| ATOM | 1442 | N | VAL | A | 186 | 5.477 | 10.297 | 69.093 | 1.00 | 9.29 | A |
| ATOM | 1443 | CA | VAL | A | 186 | 5.083 | 9.024 | 68.499 | 1.00 | 9.31 | A |
| ATOM | 1444 | CB | VAL | A | 186 | 4.918 | 9.190 | 66.966 | 1.00 | 9.15 | A |
| ATOM | 1445 | CG1 | VAL | A | 186 | 4.292 | 7.933 | 66.360 | 1.00 | 9.74 | A |
| ATOM | 1446 | CG2 | VAL | A | 186 | 4.063 | 10.423 | 66.659 | 1.00 | 9.08 | A |
| ATOM | 1447 | C | VAL | A | 186 | 6.026 | 7.852 | 68.742 | 1.00 | 9.11 | A |
| ATOM | 1448 | O | VAL | A | 186 | 7.213 | 7.930 | 68.423 | 1.00 | 8.24 | A |
| ATOM | 1449 | N | LEU | A | 187 | 5.496 | 6.774 | 69.325 | 1.00 | 9.01 | A |
| ATOM | 1450 | CA | LEU | A | 187 | 6.293 | 5.570 | 69.547 | 1.00 | 8.10 | A |
| ATOM | 1451 | CB | LEU | A | 187 | 5.856 | 4.829 | 70.819 | 1.00 | 8.38 | A |
| ATOM | 1452 | CG | LEU | A | 187 | 6.458 | 3.432 | 71.043 | 1.00 | 7.36 | A |
| ATOM | 1453 | CD1 | LEU | A | 187 | 7.982 | 3.520 | 71.124 | 1.00 | 7.26 | A |
| ATOM | 1454 | CD2 | LEU | A | 187 | 5.901 | 2.821 | 72.327 | 1.00 | 6.64 | A |
| ATOM | 1455 | C | LEU | A | 187 | 6.011 | 4.703 | 68.319 | 1.00 | 8.64 | A |
| ATOM | 1456 | O | LEU | A | 187 | 4.852 | 4.408 | 68.021 | 1.00 | 8.42 | A |
| ATOM | 1457 | N | VAL | A | 188 | 7.069 | 4.320 | 67.610 | 1.00 | 8.34 | A |
| ATOM | 1458 | CA | VAL | A | 188 | 6.954 | 3.497 | 66.406 | 1.00 | 8.95 | A |
| ATOM | 1459 | CB | VAL | A | 188 | 7.675 | 4.163 | 65.208 | 1.00 | 8.81 | A |
| ATOM | 1460 | CG1 | VAL | A | 188 | 7.505 | 3.307 | 63.952 | 1.00 | 9.57 | A |
| ATOM | 1461 | CG2 | VAL | A | 188 | 7.127 | 5.563 | 64.983 | 1.00 | 8.73 | A |
| ATOM | 1462 | C | VAL | A | 188 | 7.603 | 2.144 | 66.665 | 1.00 | 9.22 | A |
| ATOM | 1463 | O | VAL | A | 188 | 8.750 | 2.089 | 67.109 | 1.00 | 9.45 | A |
| ATOM | 1464 | N | VAL | A | 189 | 6.876 | 1.059 | 66.389 | 1.00 | 9.29 | A |
| ATOM | 1465 | CA | VAL | A | 189 | 7.403 | −0.286 | 66.609 | 1.00 | 9.54 | A |
| ATOM | 1466 | CB | VAL | A | 189 | 6.771 | −0.938 | 67.876 | 1.00 | 9.93 | A |
| ATOM | 1467 | CG1 | VAL | A | 189 | 7.359 | −2.339 | 68.101 | 1.00 | 10.83 | A |
| ATOM | 1468 | CG2 | VAL | A | 189 | 7.006 | −0.060 | 69.103 | 1.00 | 10.08 | A |
| ATOM | 1469 | C | VAL | A | 189 | 7.180 | −1.250 | 65.437 | 1.00 | 9.89 | A |
| ATOM | 1470 | O | VAL | A | 189 | 6.044 | −1.446 | 64.985 | 1.00 | 9.62 | A |
| ATOM | 1471 | N | CYS | A | 190 | 8.267 | −1.838 | 64.944 | 1.00 | 10.01 | A |
| ATOM | 1472 | CA | CYS | A | 190 | 8.194 | −2.838 | 63.875 | 1.00 | 10.09 | A |
| ATOM | 1473 | CB | CYS | A | 190 | 9.120 | −2.495 | 62.703 | 1.00 | 11.33 | A |
| ATOM | 1474 | SG | CYS | A | 190 | 8.653 | −1.059 | 61.716 | 1.00 | 12.55 | A |
| ATOM | 1475 | C | CYS | A | 190 | 8.680 | −4.130 | 64.530 | 1.00 | 10.56 | A |
| ATOM | 1476 | O | CYS | A | 190 | 9.794 | −4.182 | 65.062 | 1.00 | 9.40 | A |
| ATOM | 1477 | N | SER | A | 191 | 7.847 | −5.165 | 64.498 | 1.00 | 10.19 | A |
| ATOM | 1478 | CA | SER | A | 191 | 8.193 | −6.448 | 65.106 | 1.00 | 10.68 | A |
| ATOM | 1479 | CB | SER | A | 191 | 7.402 | −6.629 | 66.405 | 1.00 | 10.50 | A |
| ATOM | 1480 | OG | SER | A | 191 | 7.696 | −7.867 | 67.016 | 1.00 | 10.11 | A |
| ATOM | 1481 | C | SER | A | 191 | 7.863 | −7.573 | 64.137 | 1.00 | 10.91 | A |
| ATOM | 1482 | O | SER | A | 191 | 6.706 | −7.740 | 63.750 | 1.00 | 10.99 | A |
| ATOM | 1483 | N | GLU | A | 192 | 8.876 | −8.351 | 63.760 | 1.00 | 11.05 | A |
| ATOM | 1484 | CA | GLU | A | 192 | 8.699 | −9.442 | 62.800 | 1.00 | 10.62 | A |
| ATOM | 1485 | CB | GLU | A | 192 | 9.462 | −9.107 | 61.512 | 1.00 | 10.66 | A |
| ATOM | 1486 | CG | GLU | A | 192 | 9.135 | −7.721 | 60.914 | 1.00 | 10.64 | A |
| ATOM | 1487 | CD | GLU | A | 192 | 7.802 | −7.684 | 60.166 | 1.00 | 10.87 | A |
| ATOM | 1488 | OE1 | GLU | A | 192 | 7.109 | −8.719 | 60.125 | 1.00 | 11.53 | A |
| ATOM | 1489 | OE2 | GLU | A | 192 | 7.446 | −6.618 | 59.618 | 1.00 | 10.92 | A |
| ATOM | 1490 | C | GLU | A | 192 | 9.170 | −10.796 | 63.347 | 1.00 | 10.89 | A |
| ATOM | 1491 | O | GLU | A | 192 | 10.285 | −10.917 | 63.847 | 1.00 | 9.91 | A |
| ATOM | 1492 | N | VAL | A | 193 | 8.316 | −11.811 | 63.221 | 1.00 | 11.07 | A |
| ATOM | 1493 | CA | VAL | A | 193 | 8.602 | −13.162 | 63.711 | 1.00 | 11.62 | A |
| ATOM | 1494 | CB | VAL | A | 193 | 7.725 | −13.468 | 64.953 | 1.00 | 11.44 | A |
| ATOM | 1495 | CG1 | VAL | A | 193 | 7.933 | −14.908 | 65.420 | 1.00 | 11.03 | A |
| ATOM | 1496 | CG2 | VAL | A | 193 | 8.074 | −12.489 | 66.077 | 1.00 | 11.56 | A |
| ATOM | 1497 | C | VAL | A | 193 | 8.328 | −14.197 | 62.614 | 1.00 | 12.46 | A |
| ATOM | 1498 | O | VAL | A | 193 | 7.192 | −14.331 | 62.151 | 1.00 | 12.86 | A |
| ATOM | 1499 | N | THR | A | 194 | 9.366 | −14.933 | 62.216 | 1.00 | 12.81 | A |
| ATOM | 1500 | CA | THR | A | 194 | 9.260 | −15.931 | 61.148 | 1.00 | 12.86 | A |

APPENDIX C-continued

18xCHS Mutant

| ATOM | # | TYPE | RES | | | X | Y | Z | OCC | B | |
|------|---|------|-----|---|---|---|---|---|-----|---|---|
| ATOM | 1501 | CB | THR | A | 194 | 10.664 | −16.424 | 60.702 | 1.00 | 13.15 | A |
| ATOM | 1502 | OG1 | THR | A | 194 | 11.370 | −16.975 | 61.822 | 1.00 | 12.89 | A |
| ATOM | 1503 | CG2 | THR | A | 194 | 11.472 | −15.264 | 60.112 | 1.00 | 13.13 | A |
| ATOM | 1504 | C | THR | A | 194 | 8.381 | −17.160 | 61.395 | 1.00 | 13.30 | A |
| ATOM | 1505 | O | THR | A | 194 | 8.258 | −18.017 | 60.519 | 1.00 | 12.89 | A |
| ATOM | 1506 | N | ALA | A | 195 | 7.775 | −17.256 | 62.571 | 1.00 | 13.76 | A |
| ATOM | 1507 | CA | ALA | A | 195 | 6.897 | −18.384 | 62.872 | 1.00 | 14.53 | A |
| ATOM | 1508 | CB | ALA | A | 195 | 6.322 | −18.242 | 64.278 | 1.00 | 15.45 | A |
| ATOM | 1509 | C | ALA | A | 195 | 5.758 | −18.440 | 61.855 | 1.00 | 14.54 | A |
| ATOM | 1510 | O | ALA | A | 195 | 5.173 | −19.498 | 61.612 | 1.00 | 14.97 | A |
| ATOM | 1511 | N | VAL | A | 196 | 5.445 | −17.296 | 61.260 | 1.00 | 14.30 | A |
| ATOM | 1512 | CA | VAL | A | 196 | 4.363 | −17.231 | 60.289 | 1.00 | 14.81 | A |
| ATOM | 1513 | CB | VAL | A | 196 | 3.774 | −15.792 | 60.215 | 1.00 | 14.74 | A |
| ATOM | 1514 | CG1 | VAL | A | 196 | 4.742 | −14.859 | 59.494 | 1.00 | 15.82 | A |
| ATOM | 1515 | CG2 | VAL | A | 196 | 2.412 | −15.816 | 59.525 | 1.00 | 15.91 | A |
| ATOM | 1516 | C | VAL | A | 196 | 4.770 | −17.696 | 58.884 | 1.00 | 14.53 | A |
| ATOM | 1517 | O | VAL | A | 196 | 3.914 | −18.082 | 58.088 | 1.00 | 14.83 | A |
| ATOM | 1518 | N | THR | A | 197 | 6.069 | −17.694 | 58.589 | 1.00 | 14.33 | A |
| ATOM | 1519 | CA | THR | A | 197 | 6.542 | −18.097 | 57.263 | 1.00 | 14.12 | A |
| ATOM | 1520 | CB | THR | A | 197 | 7.393 | −16.975 | 56.603 | 1.00 | 14.84 | A |
| ATOM | 1521 | OG1 | THR | A | 197 | 8.492 | −16.640 | 57.460 | 1.00 | 14.20 | A |
| ATOM | 1522 | CG2 | THR | A | 197 | 6.548 | −15.736 | 56.346 | 1.00 | 14.92 | A |
| ATOM | 1523 | C | THR | A | 197 | 7.361 | −19.392 | 57.184 | 1.00 | 13.95 | A |
| ATOM | 1524 | O | THR | A | 197 | 7.515 | −19.951 | 56.099 | 1.00 | 14.12 | A |
| ATOM | 1525 | N | PHE | A | 198 | 7.891 | −19.868 | 58.309 | 1.00 | 13.34 | A |
| ATOM | 1526 | CA | PHE | A | 198 | 8.705 | −21.089 | 58.295 | 1.00 | 13.23 | A |
| ATOM | 1527 | CB | PHE | A | 198 | 9.239 | −21.393 | 59.706 | 1.00 | 12.64 | A |
| ATOM | 1528 | CG | PHE | A | 198 | 10.107 | −22.633 | 59.782 | 1.00 | 12.39 | A |
| ATOM | 1529 | CD1 | PHE | A | 198 | 9.538 | −23.904 | 59.752 | 1.00 | 12.24 | A |
| ATOM | 1530 | CD2 | PHE | A | 198 | 11.495 | −22.524 | 59.849 | 1.00 | 12.72 | A |
| ATOM | 1531 | CE1 | PHE | A | 198 | 10.336 | −25.054 | 59.783 | 1.00 | 12.32 | A |
| ATOM | 1532 | CE2 | PHE | A | 198 | 12.306 | −23.668 | 59.880 | 1.00 | 12.12 | A |
| ATOM | 1533 | CZ | PHE | A | 198 | 11.720 | −24.936 | 59.846 | 1.00 | 12.30 | A |
| ATOM | 1534 | C | PHE | A | 198 | 7.958 | −22.310 | 57.764 | 1.00 | 13.09 | A |
| ATOM | 1535 | O | PHE | A | 198 | 6.816 | −22.572 | 58.152 | 1.00 | 12.80 | A |
| ATOM | 1536 | N | ARG | A | 199 | 8.609 | −23.060 | 56.877 | 1.00 | 13.29 | A |
| ATOM | 1537 | CA | ARG | A | 199 | 8.012 | −24.275 | 56.323 | 1.00 | 13.07 | A |
| ATOM | 1538 | CB | ARG | A | 199 | 6.925 | −23.922 | 55.293 | 1.00 | 13.33 | A |
| ATOM | 1539 | CG | ARG | A | 199 | 7.405 | −23.140 | 54.078 | 1.00 | 12.99 | A |
| ATOM | 1540 | CD | ARG | A | 199 | 6.224 | −22.551 | 53.305 | 1.00 | 13.81 | A |
| ATOM | 1541 | NE | ARG | A | 199 | 5.473 | −21.575 | 54.101 | 1.00 | 13.90 | A |
| ATOM | 1542 | CZ | ARG | A | 199 | 4.324 | −21.820 | 54.734 | 1.00 | 13.37 | A |
| ATOM | 1543 | NH1 | ARG | A | 199 | 3.757 | −23.020 | 54.682 | 1.00 | 12.59 | A |
| ATOM | 1544 | NH2 | ARG | A | 199 | 3.735 | −20.854 | 55.424 | 1.00 | 12.86 | A |
| ATOM | 1545 | C | ARG | A | 199 | 9.076 | −25.183 | 55.702 | 1.00 | 13.44 | A |
| ATOM | 1546 | O | ARG | A | 199 | 10.198 | −24.749 | 55.446 | 1.00 | 12.86 | A |
| ATOM | 1547 | N | GLY | A | 200 | 8.717 | −26.447 | 55.479 | 1.00 | 14.16 | A |
| ATOM | 1548 | CA | GLY | A | 200 | 9.647 | −27.412 | 54.908 | 1.00 | 14.89 | A |
| ATOM | 1549 | C | GLY | A | 200 | 10.055 | −27.114 | 53.476 | 1.00 | 15.67 | A |
| ATOM | 1550 | O | GLY | A | 200 | 9.433 | −26.282 | 52.820 | 1.00 | 15.33 | A |
| ATOM | 1551 | N | PRO | A | 201 | 11.101 | −27.789 | 52.962 | 1.00 | 16.65 | A |
| ATOM | 1552 | CD | PRO | A | 201 | 11.997 | −28.662 | 53.747 | 1.00 | 16.48 | A |
| ATOM | 1553 | CA | PRO | A | 201 | 11.616 | −27.610 | 51.600 | 1.00 | 17.08 | A |
| ATOM | 1554 | CB | PRO | A | 201 | 13.059 | −28.084 | 51.724 | 1.00 | 16.70 | A |
| ATOM | 1555 | CG | PRO | A | 201 | 12.923 | −29.231 | 52.681 | 1.00 | 17.23 | A |
| ATOM | 1556 | C | PRO | A | 201 | 10.861 | −28.372 | 50.514 | 1.00 | 18.19 | A |
| ATOM | 1557 | O | PRO | A | 201 | 10.369 | −29.475 | 50.748 | 1.00 | 18.52 | A |
| ATOM | 1558 | N | SER | A | 202 | 10.788 | −27.777 | 49.325 | 1.00 | 19.20 | A |
| ATOM | 1559 | CA | SER | A | 202 | 10.112 | −28.381 | 48.171 | 1.00 | 20.83 | A |
| ATOM | 1560 | CB | SER | A | 202 | 8.714 | −27.777 | 48.003 | 1.00 | 20.75 | A |
| ATOM | 1561 | OG | SER | A | 202 | 8.080 | −28.273 | 46.833 | 1.00 | 22.13 | A |
| ATOM | 1562 | C | SER | A | 202 | 10.939 | −28.131 | 46.906 | 1.00 | 21.36 | A |
| ATOM | 1563 | O | SER | A | 202 | 11.276 | −26.988 | 46.601 | 1.00 | 21.26 | A |
| ATOM | 1564 | N | ASP | A | 203 | 11.259 | −29.188 | 46.162 | 1.00 | 22.79 | A |
| ATOM | 1565 | CA | ASP | A | 203 | 12.071 | −29.018 | 44.958 | 1.00 | 24.44 | A |
| ATOM | 1566 | CB | ASP | A | 203 | 12.717 | −30.349 | 44.543 | 1.00 | 25.63 | A |
| ATOM | 1567 | CG | ASP | A | 203 | 11.705 | −31.429 | 44.235 | 1.00 | 27.41 | A |
| ATOM | 1568 | OD1 | ASP | A | 203 | 12.134 | −32.575 | 43.975 | 1.00 | 29.04 | A |
| ATOM | 1569 | OD2 | ASP | A | 203 | 10.490 | −31.143 | 44.249 | 1.00 | 28.72 | A |
| ATOM | 1570 | C | ASP | A | 203 | 11.345 | −28.383 | 43.774 | 1.00 | 24.57 | A |
| ATOM | 1571 | O | ASP | A | 203 | 11.938 | −28.183 | 42.714 | 1.00 | 25.13 | A |
| ATOM | 1572 | N | THR | A | 204 | 10.070 | −28.055 | 43.952 | 1.00 | 24.84 | A |
| ATOM | 1573 | CA | THR | A | 204 | 9.307 | −27.406 | 42.892 | 1.00 | 25.35 | A |
| ATOM | 1574 | CB | THR | A | 204 | 7.995 | −28.171 | 42.574 | 1.00 | 25.57 | A |
| ATOM | 1575 | OG1 | THR | A | 204 | 7.270 | −28.430 | 43.784 | 1.00 | 26.36 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 1576 | CG2 | THR | A | 204 | 8.309 | −29.491 | 41.878 | 1.00 | 25.89 | A |
| ATOM | 1577 | C | THR | A | 204 | 8.980 | −25.962 | 43.290 | 1.00 | 25.30 | A |
| ATOM | 1578 | O | THR | A | 204 | 8.263 | −25.253 | 42.579 | 1.00 | 24.92 | A |
| ATOM | 1579 | N | HIS | A | 205 | 9.520 | −25.533 | 44.429 | 1.00 | 25.03 | A |
| ATOM | 1580 | CA | HIS | A | 205 | 9.308 | −24.175 | 44.924 | 1.00 | 25.38 | A |
| ATOM | 1581 | CB | HIS | A | 205 | 8.244 | −24.166 | 46.026 | 1.00 | 26.03 | A |
| ATOM | 1582 | CG | HIS | A | 205 | 6.916 | −24.699 | 45.585 | 1.00 | 26.52 | A |
| ATOM | 1583 | CD2 | HIS | A | 205 | 5.865 | −24.087 | 44.989 | 1.00 | 27.09 | A |
| ATOM | 1584 | ND1 | HIS | A | 205 | 6.571 | −26.029 | 45.698 | 1.00 | 26.88 | A |
| ATOM | 1585 | CE1 | HIS | A | 205 | 5.366 | −26.214 | 45.189 | 1.00 | 26.94 | A |
| ATOM | 1586 | NE2 | HIS | A | 205 | 4.915 | −25.051 | 44.751 | 1.00 | 27.31 | A |
| ATOM | 1587 | C | HIS | A | 205 | 10.609 | −23.584 | 45.461 | 1.00 | 25.22 | A |
| ATOM | 1588 | O | HIS | A | 205 | 10.719 | −23.267 | 46.643 | 1.00 | 25.50 | A |
| ATOM | 1589 | N | LEU | A | 206 | 11.591 | −23.425 | 44.579 | 1.00 | 24.95 | A |
| ATOM | 1590 | CA | LEU | A | 206 | 12.892 | −22.890 | 44.963 | 1.00 | 24.94 | A |
| ATOM | 1591 | CB | LEU | A | 206 | 13.863 | −22.992 | 43.781 | 1.00 | 24.92 | A |
| ATOM | 1592 | CG | LEU | A | 206 | 14.102 | −24.420 | 43.264 | 1.00 | 25.37 | A |
| ATOM | 1593 | CD1 | LEU | A | 206 | 15.120 | −24.397 | 42.129 | 1.00 | 25.23 | A |
| ATOM | 1594 | CD2 | LEU | A | 206 | 14.591 | −25.313 | 44.404 | 1.00 | 24.70 | A |
| ATOM | 1595 | C | LEU | A | 206 | 12.850 | −21.455 | 45.495 | 1.00 | 25.23 | A |
| ATOM | 1596 | O | LEU | A | 206 | 13.729 | −21.047 | 46.257 | 1.00 | 24.95 | A |
| ATOM | 1597 | N | ASP | A | 207 | 11.832 | −20.690 | 45.104 | 1.00 | 25.29 | A |
| ATOM | 1598 | CA | ASP | A | 207 | 11.709 | −19.317 | 45.583 | 1.00 | 25.66 | A |
| ATOM | 1599 | CB | ASP | A | 207 | 10.656 | −18.548 | 44.775 | 1.00 | 27.12 | A |
| ATOM | 1600 | CG | ASP | A | 207 | 9.299 | −19.231 | 44.768 | 1.00 | 28.64 | A |
| ATOM | 1601 | OD1 | ASP | A | 207 | 8.347 | −18.634 | 44.222 | 1.00 | 29.73 | A |
| ATOM | 1602 | OD2 | ASP | A | 207 | 9.178 | −20.360 | 45.294 | 1.00 | 29.96 | A |
| ATOM | 1603 | C | ASP | A | 207 | 11.341 | −19.309 | 47.065 | 1.00 | 25.27 | A |
| ATOM | 1604 | O | ASP | A | 207 | 11.753 | −18.426 | 47.817 | 1.00 | 25.41 | A |
| ATOM | 1605 | N | SER | A | 208 | 10.567 | −20.301 | 47.486 | 1.00 | 24.29 | A |
| ATOM | 1606 | CA | SER | A | 208 | 10.173 | −20.399 | 48.881 | 1.00 | 23.76 | A |
| ATOM | 1607 | CB | SER | A | 208 | 9.090 | −21.473 | 49.048 | 1.00 | 24.07 | A |
| ATOM | 1608 | OG | SER | A | 208 | 8.686 | −21.592 | 50.400 | 1.00 | 25.22 | A |
| ATOM | 1609 | C | SER | A | 208 | 11.409 | −20.761 | 49.704 | 1.00 | 22.63 | A |
| ATOM | 1610 | O | SER | A | 208 | 11.607 | −20.258 | 50.809 | 1.00 | 22.30 | A |
| ATOM | 1611 | N | LEU | A | 209 | 12.251 | −21.620 | 49.138 | 1.00 | 21.70 | A |
| ATOM | 1612 | CA | LEU | A | 209 | 13.464 | −22.075 | 49.802 | 1.00 | 20.71 | A |
| ATOM | 1613 | CB | LEU | A | 209 | 14.136 | −23.165 | 48.957 | 1.00 | 20.77 | A |
| ATOM | 1614 | CG | LEU | A | 209 | 15.193 | −24.039 | 49.629 | 1.00 | 20.98 | A |
| ATOM | 1615 | CD1 | LEU | A | 209 | 14.554 | −24.802 | 50.786 | 1.00 | 20.75 | A |
| ATOM | 1616 | CD2 | LEU | A | 209 | 15.786 | −25.009 | 48.608 | 1.00 | 20.81 | A |
| ATOM | 1617 | C | LEU | A | 209 | 14.461 | −20.950 | 50.078 | 1.00 | 20.48 | A |
| ATOM | 1618 | O | LEU | A | 209 | 15.090 | −20.924 | 51.139 | 1.00 | 20.50 | A |
| ATOM | 1619 | N | VAL | A | 210 | 14.621 | −20.029 | 49.131 | 1.00 | 19.42 | A |
| ATOM | 1620 | CA | VAL | A | 210 | 15.560 | −18.929 | 49.329 | 1.00 | 19.15 | A |
| ATOM | 1621 | CB | VAL | A | 210 | 15.658 | −18.009 | 48.080 | 1.00 | 19.36 | A |
| ATOM | 1622 | CG1 | VAL | A | 210 | 14.353 | −17.264 | 47.857 | 1.00 | 20.36 | A |
| ATOM | 1623 | CG2 | VAL | A | 210 | 16.806 | −17.025 | 48.251 | 1.00 | 20.35 | A |
| ATOM | 1624 | C | VAL | A | 210 | 15.123 | −18.119 | 50.545 | 1.00 | 18.35 | A |
| ATOM | 1625 | O | VAL | A | 210 | 15.954 | −17.608 | 51.289 | 1.00 | 18.00 | A |
| ATOM | 1626 | N | GLY | A | 211 | 13.812 | −18.016 | 50.742 | 1.00 | 17.76 | A |
| ATOM | 1627 | CA | GLY | A | 211 | 13.288 | −17.295 | 51.888 | 1.00 | 17.42 | A |
| ATOM | 1628 | C | GLY | A | 211 | 13.710 | −17.941 | 53.202 | 1.00 | 16.84 | A |
| ATOM | 1629 | O | GLY | A | 211 | 13.903 | −17.249 | 54.201 | 1.00 | 17.07 | A |
| ATOM | 1630 | N | GLN | A | 212 | 13.855 | −19.265 | 53.207 | 1.00 | 16.19 | A |
| ATOM | 1631 | CA | GLN | A | 212 | 14.267 | −19.979 | 54.415 | 1.00 | 16.19 | A |
| ATOM | 1632 | CB | GLN | A | 212 | 14.053 | −21.491 | 54.250 | 1.00 | 16.68 | A |
| ATOM | 1633 | CG | GLN | A | 212 | 12.614 | −21.917 | 53.927 | 1.00 | 18.07 | A |
| ATOM | 1634 | CD | GLN | A | 212 | 11.600 | −21.436 | 54.954 | 1.00 | 18.95 | A |
| ATOM | 1635 | OE1 | GLN | A | 212 | 11.761 | −21.657 | 56.152 | 1.00 | 19.82 | A |
| ATOM | 1636 | NE2 | GLN | A | 212 | 10.547 | −20.779 | 54.485 | 1.00 | 19.27 | A |
| ATOM | 1637 | C | GLN | A | 212 | 15.741 | −19.702 | 54.741 | 1.00 | 15.86 | A |
| ATOM | 1638 | O | GLN | A | 212 | 16.191 | −19.908 | 55.869 | 1.00 | 15.74 | A |
| ATOM | 1639 | N | ALA | A | 213 | 16.492 | −19.231 | 53.751 | 1.00 | 15.43 | A |
| ATOM | 1640 | CA | ALA | A | 213 | 17.904 | −18.922 | 53.953 | 1.00 | 15.06 | A |
| ATOM | 1641 | CB | ALA | A | 213 | 18.686 | −19.225 | 52.674 | 1.00 | 15.32 | A |
| ATOM | 1642 | C | ALA | A | 213 | 18.137 | −17.463 | 54.365 | 1.00 | 14.68 | A |
| ATOM | 1643 | O | ALA | A | 213 | 19.204 | −17.117 | 54.886 | 1.00 | 14.33 | A |
| ATOM | 1644 | N | LEU | A | 214 | 17.135 | −16.616 | 54.154 | 1.00 | 14.29 | A |
| ATOM | 1645 | CA | LEU | A | 214 | 17.275 | −15.192 | 54.455 | 1.00 | 14.48 | A |
| ATOM | 1646 | CB | LEU | A | 214 | 16.924 | −14.378 | 53.205 | 1.00 | 14.91 | A |
| ATOM | 1647 | CG | LEU | A | 214 | 17.668 | −14.670 | 51.901 | 1.00 | 15.41 | A |
| ATOM | 1648 | CD1 | LEU | A | 214 | 17.042 | −13.844 | 50.774 | 1.00 | 16.41 | A |
| ATOM | 1649 | CD2 | LEU | A | 214 | 19.146 | −14.341 | 52.058 | 1.00 | 16.05 | A |
| ATOM | 1650 | C | LEU | A | 214 | 16.520 | −14.576 | 55.640 | 1.00 | 14.29 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 1651 | O | LEU | A | 214 | 17.082 | -13.739 | 56.351 | 1.00 | 14.63 | A |
| ATOM | 1652 | N | PHE | A | 215 | 15.264 | -14.965 | 55.844 | 1.00 | 13.93 | A |
| ATOM | 1653 | CA | PHE | A | 215 | 14.440 | -14.377 | 56.907 | 1.00 | 13.96 | A |
| ATOM | 1654 | CB | PHE | A | 215 | 12.961 | -14.752 | 56.718 | 1.00 | 15.54 | A |
| ATOM | 1655 | CG | PHE | A | 215 | 12.433 | -14.517 | 55.324 | 1.00 | 17.87 | A |
| ATOM | 1656 | CD1 | PHE | A | 215 | 12.952 | -13.507 | 54.519 | 1.00 | 18.86 | A |
| ATOM | 1657 | CD2 | PHE | A | 215 | 11.395 | -15.302 | 54.826 | 1.00 | 18.79 | A |
| ATOM | 1658 | CE1 | PHE | A | 215 | 12.445 | -13.283 | 53.234 | 1.00 | 19.31 | A |
| ATOM | 1659 | CE2 | PHE | A | 215 | 10.882 | -15.086 | 53.547 | 1.00 | 19.39 | A |
| ATOM | 1660 | CZ | PHE | A | 215 | 11.409 | -14.074 | 52.750 | 1.00 | 19.43 | A |
| ATOM | 1661 | C | PHE | A | 215 | 14.826 | -14.689 | 58.349 | 1.00 | 13.33 | A |
| ATOM | 1662 | O | PHE | A | 215 | 15.054 | -15.847 | 58.704 | 1.00 | 12.97 | A |
| ATOM | 1663 | N | GLY | A | 216 | 14.859 | -13.637 | 59.170 | 1.00 | 12.63 | A |
| ATOM | 1664 | CA | GLY | A | 216 | 15.195 | -13.751 | 60.585 | 1.00 | 12.55 | A |
| ATOM | 1665 | C | GLY | A | 216 | 14.239 | -12.912 | 61.429 | 1.00 | 12.18 | A |
| ATOM | 1666 | O | GLY | A | 216 | 13.452 | -12.136 | 60.873 | 1.00 | 11.45 | A |
| ATOM | 1667 | N | ASP | A | 217 | 14.313 | -13.050 | 62.757 | 1.00 | 11.54 | A |
| ATOM | 1668 | CA | ASP | A | 217 | 13.430 | -12.325 | 63.687 | 1.00 | 11.59 | A |
| ATOM | 1669 | CB | ASP | A | 217 | 12.952 | -13.267 | 64.798 | 1.00 | 11.47 | A |
| ATOM | 1670 | CG | ASP | A | 217 | 12.188 | -14.469 | 64.275 | 1.00 | 12.37 | A |
| ATOM | 1671 | OD1 | ASP | A | 217 | 12.114 | -14.667 | 63.043 | 1.00 | 12.95 | A |
| ATOM | 1672 | OD2 | ASP | A | 217 | 11.665 | -15.227 | 65.112 | 1.00 | 13.04 | A |
| ATOM | 1673 | C | ASP | A | 217 | 14.046 | -11.089 | 64.362 | 1.00 | 11.79 | A |
| ATOM | 1674 | O | ASP | A | 217 | 15.253 | -11.040 | 64.619 | 1.00 | 11.06 | A |
| ATOM | 1675 | N | GLY | A | 218 | 13.196 | -10.109 | 64.681 | 1.00 | 11.39 | A |
| ATOM | 1676 | CA | GLY | A | 218 | 13.666 | -8.899 | 65.338 | 1.00 | 10.97 | A |
| ATOM | 1677 | C | GLY | A | 218 | 12.637 | -7.786 | 65.469 | 1.00 | 11.12 | A |
| ATOM | 1678 | O | GLY | A | 218 | 11.619 | -7.780 | 64.774 | 1.00 | 11.86 | A |
| ATOM | 1679 | N | ALA | A | 219 | 12.894 | -6.850 | 66.379 | 1.00 | 10.90 | A |
| ATOM | 1680 | CA | ALA | A | 219 | 12.010 | -5.702 | 66.587 | 1.00 | 10.79 | A |
| ATOM | 1681 | CB | ALA | A | 219 | 11.083 | -5.943 | 67.792 | 1.00 | 10.28 | A |
| ATOM | 1682 | C | ALA | A | 219 | 12.848 | -4.439 | 66.811 | 1.00 | 10.65 | A |
| ATOM | 1683 | O | ALA | A | 219 | 13.940 | -4.496 | 67.388 | 1.00 | 10.66 | A |
| ATOM | 1684 | N | ALA | A | 220 | 12.333 | -3.309 | 66.337 | 1.00 | 9.85 | A |
| ATOM | 1685 | CA | ALA | A | 220 | 13.002 | -2.019 | 66.486 | 1.00 | 10.37 | A |
| ATOM | 1686 | CB | ALA | A | 220 | 13.677 | -1.616 | 65.172 | 1.00 | 9.86 | A |
| ATOM | 1687 | C | ALA | A | 220 | 11.959 | -0.979 | 66.887 | 1.00 | 10.57 | A |
| ATOM | 1688 | O | ALA | A | 220 | 10.824 | -1.007 | 66.399 | 1.00 | 10.66 | A |
| ATOM | 1689 | N | ALA | A | 221 | 12.339 | -0.068 | 67.781 | 1.00 | 9.94 | A |
| ATOM | 1690 | CA | ALA | A | 221 | 11.419 | 0.963 | 68.246 | 1.00 | 10.32 | A |
| ATOM | 1691 | CB | ALA | A | 221 | 10.959 | 0.653 | 69.680 | 1.00 | 10.35 | A |
| ATOM | 1692 | C | ALA | A | 221 | 12.045 | 2.352 | 68.192 | 1.00 | 10.54 | A |
| ATOM | 1693 | O | ALA | A | 221 | 13.237 | 2.518 | 68.475 | 1.00 | 9.74 | A |
| ATOM | 1694 | N | LEU | A | 222 | 11.223 | 3.341 | 67.840 | 1.00 | 10.56 | A |
| ATOM | 1695 | CA | LEU | A | 222 | 11.664 | 4.731 | 67.735 | 1.00 | 11.43 | A |
| ATOM | 1696 | CB | LEU | A | 222 | 11.676 | 5.180 | 66.269 | 1.00 | 12.57 | A |
| ATOM | 1697 | CG | LEU | A | 222 | 12.161 | 4.265 | 65.151 | 1.00 | 13.60 | A |
| ATOM | 1698 | CD1 | LEU | A | 222 | 11.614 | 4.787 | 63.819 | 1.00 | 13.87 | A |
| ATOM | 1699 | CD2 | LEU | A | 222 | 13.681 | 4.204 | 65.138 | 1.00 | 12.89 | A |
| ATOM | 1700 | C | LEU | A | 222 | 10.704 | 5.672 | 68.459 | 1.00 | 11.56 | A |
| ATOM | 1701 | O | LEU | A | 222 | 9.532 | 5.341 | 68.669 | 1.00 | 12.07 | A |
| ATOM | 1702 | N | ILE | A | 223 | 11.216 | 6.838 | 68.848 | 1.00 | 11.46 | A |
| ATOM | 1703 | CA | ILE | A | 223 | 10.393 | 7.887 | 69.447 | 1.00 | 11.36 | A |
| ATOM | 1704 | CB | ILE | A | 223 | 10.904 | 8.370 | 70.829 | 1.00 | 11.65 | A |
| ATOM | 1705 | CG2 | ILE | A | 223 | 10.178 | 9.655 | 71.223 | 1.00 | 10.99 | A |
| ATOM | 1706 | CG1 | ILE | A | 223 | 10.687 | 7.289 | 71.893 | 1.00 | 11.08 | A |
| ATOM | 1707 | CD1 | ILE | A | 223 | 9.227 | 6.989 | 72.214 | 1.00 | 12.35 | A |
| ATOM | 1708 | C | ILE | A | 223 | 10.588 | 9.011 | 68.435 | 1.00 | 11.23 | A |
| ATOM | 1709 | O | ILE | A | 223 | 11.726 | 9.402 | 68.149 | 1.00 | 11.56 | A |
| ATOM | 1710 | N | VAL | A | 224 | 9.486 | 9.509 | 67.879 | 1.00 | 10.50 | A |
| ATOM | 1711 | CA | VAL | A | 224 | 9.522 | 10.570 | 66.876 | 1.00 | 10.56 | A |
| ATOM | 1712 | CB | VAL | A | 224 | 8.947 | 10.078 | 65.519 | 1.00 | 9.92 | A |
| ATOM | 1713 | CG1 | VAL | A | 224 | 8.933 | 11.223 | 64.499 | 1.00 | 9.91 | A |
| ATOM | 1714 | CG2 | VAL | A | 224 | 9.770 | 8.915 | 64.999 | 1.00 | 9.84 | A |
| ATOM | 1715 | C | VAL | A | 224 | 8.705 | 11.782 | 67.310 | 1.00 | 10.99 | A |
| ATOM | 1716 | O | VAL | A | 224 | 7.578 | 11.644 | 67.789 | 1.00 | 10.91 | A |
| ATOM | 1717 | N | GLY | A | 225 | 9.276 | 12.970 | 67.135 | 1.00 | 11.59 | A |
| ATOM | 1718 | CA | GLY | A | 225 | 8.567 | 14.181 | 67.499 | 1.00 | 11.11 | A |
| ATOM | 1719 | C | GLY | A | 225 | 9.126 | 15.444 | 66.874 | 1.00 | 11.82 | A |
| ATOM | 1720 | O | GLY | A | 225 | 10.297 | 15.500 | 66.488 | 1.00 | 10.35 | A |
| ATOM | 1721 | N | SER | A | 226 | 8.273 | 16.457 | 66.761 | 1.00 | 12.29 | A |
| ATOM | 1722 | CA | SER | A | 226 | 8.676 | 17.755 | 66.230 | 1.00 | 13.04 | A |
| ATOM | 1723 | CB | SER | A | 226 | 7.557 | 18.364 | 65.376 | 1.00 | 13.32 | A |
| ATOM | 1724 | OG | SER | A | 226 | 7.422 | 17.697 | 64.133 | 1.00 | 14.87 | A |
| ATOM | 1725 | C | SER | A | 226 | 8.940 | 18.661 | 67.437 | 1.00 | 13.71 | A |

APPENDIX C-continued

18xCHS Mutant

| ATOM | # | TYPE | RES | | | X | Y | Z | OCC | B | |
|------|---|------|-----|---|---|---|---|---|-----|---|---|
| ATOM | 1726 | O | SER | A | 226 | 8.429 | 18.406 | 68.533 | 1.00 | 13.89 | A |
| ATOM | 1727 | N | ASP | A | 227 | 9.746 | 19.701 | 67.240 | 1.00 | 13.96 | A |
| ATOM | 1728 | CA | ASP | A | 227 | 10.056 | 20.659 | 68.304 | 1.00 | 14.97 | A |
| ATOM | 1729 | CB | ASP | A | 227 | 8.775 | 21.400 | 68.711 | 1.00 | 15.35 | A |
| ATOM | 1730 | CG | ASP | A | 227 | 7.974 | 21.886 | 67.512 | 1.00 | 15.96 | A |
| ATOM | 1731 | OD1 | ASP | A | 227 | 8.588 | 22.393 | 66.551 | 1.00 | 16.70 | A |
| ATOM | 1732 | OD2 | ASP | A | 227 | 6.729 | 21.766 | 67.536 | 1.00 | 17.02 | A |
| ATOM | 1733 | C | ASP | A | 227 | 10.705 | 20.040 | 69.549 | 1.00 | 15.00 | A |
| ATOM | 1734 | O | ASP | A | 227 | 10.144 | 20.093 | 70.646 | 1.00 | 14.00 | A |
| ATOM | 1735 | N | PRO | A | 228 | 11.906 | 19.458 | 69.398 | 1.00 | 15.76 | A |
| ATOM | 1736 | CD | PRO | A | 228 | 12.704 | 19.370 | 68.165 | 1.00 | 16.05 | A |
| ATOM | 1737 | CA | PRO | A | 228 | 12.614 | 18.832 | 70.524 | 1.00 | 16.49 | A |
| ATOM | 1738 | CB | PRO | A | 228 | 13.862 | 18.230 | 69.868 | 1.00 | 16.50 | A |
| ATOM | 1739 | CG | PRO | A | 228 | 13.500 | 18.124 | 68.405 | 1.00 | 17.67 | A |
| ATOM | 1740 | C | PRO | A | 228 | 12.996 | 19.845 | 71.605 | 1.00 | 16.81 | A |
| ATOM | 1741 | O | PRO | A | 228 | 13.345 | 20.982 | 71.296 | 1.00 | 16.80 | A |
| ATOM | 1742 | N | VAL | A | 229 | 12.936 | 19.432 | 72.868 | 1.00 | 17.75 | A |
| ATOM | 1743 | CA | VAL | A | 229 | 13.307 | 20.311 | 73.972 | 1.00 | 18.66 | A |
| ATOM | 1744 | CB | VAL | A | 229 | 12.759 | 19.777 | 75.319 | 1.00 | 18.87 | A |
| ATOM | 1745 | CG1 | VAL | A | 229 | 13.106 | 20.735 | 76.442 | 1.00 | 18.50 | A |
| ATOM | 1746 | CG2 | VAL | A | 229 | 11.252 | 19.587 | 75.231 | 1.00 | 19.24 | A |
| ATOM | 1747 | C | VAL | A | 229 | 14.842 | 20.357 | 74.024 | 1.00 | 19.25 | A |
| ATOM | 1748 | O | VAL | A | 229 | 15.490 | 19.361 | 74.338 | 1.00 | 19.01 | A |
| ATOM | 1749 | N | PRO | A | 230 | 15.440 | 21.516 | 73.703 | 1.00 | 19.93 | A |
| ATOM | 1750 | CD | PRO | A | 230 | 14.785 | 22.779 | 73.322 | 1.00 | 20.33 | A |
| ATOM | 1751 | CA | PRO | A | 230 | 16.898 | 21.673 | 73.713 | 1.00 | 20.52 | A |
| ATOM | 1752 | CB | PRO | A | 230 | 17.082 | 23.173 | 73.500 | 1.00 | 20.70 | A |
| ATOM | 1753 | CG | PRO | A | 230 | 15.912 | 23.527 | 72.641 | 1.00 | 20.85 | A |
| ATOM | 1754 | C | PRO | A | 230 | 17.585 | 21.188 | 74.986 | 1.00 | 21.15 | A |
| ATOM | 1755 | O | PRO | A | 230 | 17.133 | 21.471 | 76.092 | 1.00 | 20.91 | A |
| ATOM | 1756 | N | GLU | A | 231 | 18.677 | 20.450 | 74.807 | 1.00 | 21.72 | A |
| ATOM | 1757 | CA | GLU | A | 231 | 19.474 | 19.921 | 75.914 | 1.00 | 22.87 | A |
| ATOM | 1758 | CB | GLU | A | 231 | 19.977 | 21.072 | 76.790 | 1.00 | 24.06 | A |
| ATOM | 1759 | CG | GLU | A | 231 | 20.632 | 22.204 | 76.014 | 1.00 | 26.41 | A |
| ATOM | 1760 | CD | GLU | A | 231 | 21.929 | 21.795 | 75.342 | 1.00 | 28.22 | A |
| ATOM | 1761 | OE1 | GLU | A | 231 | 22.428 | 22.575 | 74.502 | 1.00 | 29.91 | A |
| ATOM | 1762 | OE2 | GLU | A | 231 | 22.458 | 20.705 | 75.654 | 1.00 | 29.36 | A |
| ATOM | 1763 | C | GLU | A | 231 | 18.778 | 18.879 | 76.792 | 1.00 | 22.51 | A |
| ATOM | 1764 | O | GLU | A | 231 | 19.405 | 18.321 | 77.693 | 1.00 | 23.39 | A |
| ATOM | 1765 | N | ILE | A | 232 | 17.492 | 18.626 | 76.548 | 1.00 | 21.33 | A |
| ATOM | 1766 | CA | ILE | A | 232 | 16.744 | 17.622 | 77.314 | 1.00 | 20.10 | A |
| ATOM | 1767 | CB | ILE | A | 232 | 15.372 | 18.165 | 77.808 | 1.00 | 20.35 | A |
| ATOM | 1768 | CG2 | ILE | A | 232 | 14.505 | 17.021 | 78.323 | 1.00 | 20.81 | A |
| ATOM | 1769 | CG1 | ILE | A | 232 | 15.588 | 19.189 | 78.927 | 1.00 | 20.76 | A |
| ATOM | 1770 | CD1 | ILE | A | 232 | 16.381 | 18.652 | 80.107 | 1.00 | 20.81 | A |
| ATOM | 1771 | C | ILE | A | 232 | 16.511 | 16.406 | 76.418 | 1.00 | 19.24 | A |
| ATOM | 1772 | O | ILE | A | 232 | 16.779 | 15.270 | 76.808 | 1.00 | 18.76 | A |
| ATOM | 1773 | N | GLU | A | 233 | 15.998 | 16.654 | 75.218 | 1.00 | 18.19 | A |
| ATOM | 1774 | CA | GLU | A | 233 | 15.773 | 15.588 | 74.248 | 1.00 | 17.68 | A |
| ATOM | 1775 | CB | GLU | A | 233 | 14.435 | 15.796 | 73.516 | 1.00 | 16.61 | A |
| ATOM | 1776 | CG | GLU | A | 233 | 13.225 | 15.614 | 74.442 | 1.00 | 15.77 | A |
| ATOM | 1777 | CD | GLU | A | 233 | 11.878 | 15.811 | 73.763 | 1.00 | 15.66 | A |
| ATOM | 1778 | OE1 | GLU | A | 233 | 11.663 | 16.888 | 73.164 | 1.00 | 14.98 | A |
| ATOM | 1779 | OE2 | GLU | A | 233 | 11.024 | 14.894 | 73.846 | 1.00 | 13.88 | A |
| ATOM | 1780 | C | GLU | A | 233 | 16.969 | 15.696 | 73.304 | 1.00 | 18.08 | A |
| ATOM | 1781 | O | GLU | A | 233 | 17.581 | 16.763 | 73.202 | 1.00 | 18.12 | A |
| ATOM | 1782 | N | LYS | A | 234 | 17.316 | 14.606 | 72.626 | 1.00 | 18.13 | A |
| ATOM | 1783 | CA | LYS | A | 234 | 18.479 | 14.620 | 71.743 | 1.00 | 18.28 | A |
| ATOM | 1784 | CB | LYS | A | 234 | 19.609 | 13.818 | 72.391 | 1.00 | 19.97 | A |
| ATOM | 1785 | CG | LYS | A | 234 | 20.833 | 13.658 | 71.517 | 1.00 | 22.36 | A |
| ATOM | 1786 | CD | LYS | A | 234 | 21.912 | 12.864 | 72.228 | 1.00 | 24.07 | A |
| ATOM | 1787 | CE | LYS | A | 234 | 23.161 | 12.748 | 71.377 | 1.00 | 24.43 | A |
| ATOM | 1788 | NZ | LYS | A | 234 | 24.241 | 12.063 | 72.132 | 1.00 | 26.13 | A |
| ATOM | 1789 | C | LYS | A | 234 | 18.226 | 14.088 | 70.332 | 1.00 | 17.50 | A |
| ATOM | 1790 | O | LYS | A | 234 | 18.151 | 12.879 | 70.117 | 1.00 | 17.33 | A |
| ATOM | 1791 | N | PRO | A | 235 | 18.103 | 14.995 | 69.349 | 1.00 | 16.44 | A |
| ATOM | 1792 | CD | PRO | A | 235 | 18.018 | 16.454 | 69.532 | 1.00 | 16.79 | A |
| ATOM | 1793 | CA | PRO | A | 235 | 17.861 | 14.628 | 67.948 | 1.00 | 15.90 | A |
| ATOM | 1794 | CB | PRO | A | 235 | 17.822 | 15.983 | 67.244 | 1.00 | 16.17 | A |
| ATOM | 1795 | CG | PRO | A | 235 | 17.250 | 16.890 | 68.297 | 1.00 | 17.19 | A |
| ATOM | 1796 | C | PRO | A | 235 | 18.948 | 13.719 | 67.365 | 1.00 | 15.14 | A |
| ATOM | 1797 | O | PRO | A | 235 | 20.133 | 13.916 | 67.642 | 1.00 | 15.33 | A |
| ATOM | 1798 | N | ILE | A | 236 | 18.540 | 12.739 | 66.559 | 1.00 | 13.84 | A |
| ATOM | 1799 | CA | ILE | A | 236 | 19.475 | 11.815 | 65.914 | 1.00 | 13.10 | A |
| ATOM | 1800 | CB | ILE | A | 236 | 19.117 | 10.335 | 66.217 | 1.00 | 12.82 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 1801 | CG2 | ILE | A | 236 | 20.170 | 9.416 | 65.618 | 1.00 | 13.36 | A |
| ATOM | 1802 | CG1 | ILE | A | 236 | 19.028 | 10.104 | 67.727 | 1.00 | 12.98 | A |
| ATOM | 1803 | CD1 | ILE | A | 236 | 18.623 | 8.689 | 68.107 | 1.00 | 13.32 | A |
| ATOM | 1804 | C | ILE | A | 236 | 19.454 | 12.029 | 64.389 | 1.00 | 12.89 | A |
| ATOM | 1805 | O | ILE | A | 236 | 20.503 | 12.188 | 63.760 | 1.00 | 12.73 | A |
| ATOM | 1806 | N | PHE | A | 237 | 18.254 | 12.019 | 63.808 | 1.00 | 12.93 | A |
| ATOM | 1807 | CA | PHE | A | 237 | 18.052 | 12.233 | 62.372 | 1.00 | 13.23 | A |
| ATOM | 1808 | CB | PHE | A | 237 | 17.878 | 10.894 | 61.631 | 1.00 | 13.29 | A |
| ATOM | 1809 | CG | PHE | A | 237 | 19.118 | 10.037 | 61.594 | 1.00 | 13.07 | A |
| ATOM | 1810 | CD1 | PHE | A | 237 | 20.214 | 10.398 | 60.812 | 1.00 | 13.37 | A |
| ATOM | 1811 | CD2 | PHE | A | 237 | 19.183 | 8.860 | 62.334 | 1.00 | 13.32 | A |
| ATOM | 1812 | CE1 | PHE | A | 237 | 21.359 | 9.594 | 60.769 | 1.00 | 13.12 | A |
| ATOM | 1813 | CE2 | PHE | A | 237 | 20.321 | 8.050 | 62.300 | 1.00 | 13.01 | A |
| ATOM | 1814 | CZ | PHE | A | 237 | 21.411 | 8.418 | 61.515 | 1.00 | 13.20 | A |
| ATOM | 1815 | C | PHE | A | 237 | 16.769 | 13.057 | 62.185 | 1.00 | 13.74 | A |
| ATOM | 1816 | O | PHE | A | 237 | 15.818 | 12.909 | 62.953 | 1.00 | 14.05 | A |
| ATOM | 1817 | N | GLU | A | 238 | 16.744 | 13.917 | 61.170 | 1.00 | 14.11 | A |
| ATOM | 1818 | CA | GLU | A | 238 | 15.558 | 14.728 | 60.873 | 1.00 | 14.73 | A |
| ATOM | 1819 | CB | GLU | A | 238 | 15.917 | 16.213 | 60.718 | 1.00 | 15.82 | A |
| ATOM | 1820 | CG | GLU | A | 238 | 16.429 | 16.918 | 61.958 | 1.00 | 18.71 | A |
| ATOM | 1821 | CD | GLU | A | 238 | 16.434 | 18.438 | 61.794 | 1.00 | 21.33 | A |
| ATOM | 1822 | OE1 | GLU | A | 238 | 17.008 | 18.939 | 60.803 | 1.00 | 22.01 | A |
| ATOM | 1823 | OE2 | GLU | A | 238 | 15.856 | 19.135 | 62.657 | 1.00 | 22.77 | A |
| ATOM | 1824 | C | GLU | A | 238 | 14.963 | 14.251 | 59.548 | 1.00 | 14.20 | A |
| ATOM | 1825 | O | GLU | A | 238 | 15.707 | 13.948 | 58.614 | 1.00 | 13.90 | A |
| ATOM | 1826 | N | MET | A | 239 | 13.638 | 14.180 | 59.456 | 1.00 | 13.86 | A |
| ATOM | 1827 | CA | MET | A | 239 | 13.008 | 13.766 | 58.205 | 1.00 | 14.51 | A |
| ATOM | 1828 | CB | MET | A | 239 | 11.702 | 13.006 | 58.468 | 1.00 | 15.35 | A |
| ATOM | 1829 | CG | MET | A | 239 | 11.940 | 11.583 | 58.970 | 1.00 | 17.08 | A |
| ATOM | 1830 | SD | MET | A | 239 | 10.448 | 10.564 | 59.044 | 1.00 | 19.48 | A |
| ATOM | 1831 | CE | MET | A | 239 | 9.981 | 10.786 | 60.745 | 1.00 | 18.17 | A |
| ATOM | 1832 | C | MET | A | 239 | 12.757 | 15.011 | 57.363 | 1.00 | 14.60 | A |
| ATOM | 1833 | O | MET | A | 239 | 12.329 | 16.047 | 57.884 | 1.00 | 13.98 | A |
| ATOM | 1834 | N | VAL | A | 240 | 13.041 | 14.905 | 56.067 | 1.00 | 14.28 | A |
| ATOM | 1835 | CA | VAL | A | 240 | 12.893 | 16.025 | 55.141 | 1.00 | 15.20 | A |
| ATOM | 1836 | CB | VAL | A | 240 | 14.224 | 16.271 | 54.375 | 1.00 | 15.56 | A |
| ATOM | 1837 | CG1 | VAL | A | 240 | 14.091 | 17.470 | 53.452 | 1.00 | 15.90 | A |
| ATOM | 1838 | CG2 | VAL | A | 240 | 15.366 | 16.479 | 55.363 | 1.00 | 16.93 | A |
| ATOM | 1839 | C | VAL | A | 240 | 11.784 | 15.875 | 54.096 | 1.00 | 15.14 | A |
| ATOM | 1840 | O | VAL | A | 240 | 11.009 | 16.803 | 53.865 | 1.00 | 14.78 | A |
| ATOM | 1841 | N | TRP | A | 241 | 11.715 | 14.706 | 53.466 | 1.00 | 15.48 | A |
| ATOM | 1842 | CA | TRP | A | 241 | 10.740 | 14.462 | 52.405 | 1.00 | 15.48 | A |
| ATOM | 1843 | CB | TRP | A | 241 | 11.309 | 15.035 | 51.104 | 1.00 | 17.25 | A |
| ATOM | 1844 | CG | TRP | A | 241 | 10.446 | 14.908 | 49.891 | 1.00 | 18.55 | A |
| ATOM | 1845 | CD2 | TRP | A | 241 | 10.627 | 13.993 | 48.802 | 1.00 | 19.60 | A |
| ATOM | 1846 | CE2 | TRP | A | 241 | 9.618 | 14.267 | 47.851 | 1.00 | 20.24 | A |
| ATOM | 1847 | CE3 | TRP | A | 241 | 11.544 | 12.968 | 48.536 | 1.00 | 19.96 | A |
| ATOM | 1848 | CD1 | TRP | A | 241 | 9.363 | 15.674 | 49.571 | 1.00 | 19.19 | A |
| ATOM | 1849 | NE1 | TRP | A | 241 | 8.860 | 15.296 | 48.345 | 1.00 | 20.36 | A |
| ATOM | 1850 | CZ2 | TRP | A | 241 | 9.503 | 13.554 | 46.652 | 1.00 | 20.07 | A |
| ATOM | 1851 | CZ3 | TRP | A | 241 | 11.428 | 12.259 | 47.344 | 1.00 | 20.26 | A |
| ATOM | 1852 | CH2 | TRP | A | 241 | 10.414 | 12.559 | 46.417 | 1.00 | 20.45 | A |
| ATOM | 1853 | C | TRP | A | 241 | 10.500 | 12.958 | 52.252 | 1.00 | 15.29 | A |
| ATOM | 1854 | O | TRP | A | 241 | 11.399 | 12.162 | 52.516 | 1.00 | 15.20 | A |
| ATOM | 1855 | N | THR | A | 242 | 9.297 | 12.570 | 51.827 | 1.00 | 14.37 | A |
| ATOM | 1856 | CA | THR | A | 242 | 8.984 | 11.149 | 51.636 | 1.00 | 13.75 | A |
| ATOM | 1857 | CB | THR | A | 242 | 8.150 | 10.563 | 52.815 | 1.00 | 14.23 | A |
| ATOM | 1858 | OG1 | THR | A | 242 | 6.860 | 11.188 | 52.853 | 1.00 | 15.91 | A |
| ATOM | 1859 | CG2 | THR | A | 242 | 8.863 | 10.780 | 54.144 | 1.00 | 13.74 | A |
| ATOM | 1860 | C | THR | A | 242 | 8.207 | 10.878 | 50.350 | 1.00 | 13.35 | A |
| ATOM | 1661 | O | THR | A | 242 | 7.526 | 11.757 | 49.820 | 1.00 | 13.22 | A |
| ATOM | 1862 | N | ALA | A | 243 | 8.310 | 9.648 | 49.856 | 1.00 | 12.74 | A |
| ATOM | 1863 | CA | ALA | A | 243 | 7.607 | 9.244 | 48.646 | 1.00 | 12.52 | A |
| ATOM | 1864 | CB | ALA | A | 243 | 8.379 | 9.702 | 47.410 | 1.00 | 12.73 | A |
| ATOM | 1865 | C | ALA | A | 243 | 7.422 | 7.726 | 48.611 | 1.00 | 12.56 | A |
| ATOM | 1866 | O | ALA | A | 243 | 8.142 | 6.988 | 49.285 | 1.00 | 12.38 | A |
| ATOM | 1867 | N | GLN | A | 244 | 6.430 | 7.276 | 47.848 | 1.00 | 12.33 | A |
| ATOM | 1868 | CA | GLN | A | 244 | 6.158 | 5.850 | 47.681 | 1.00 | 13.23 | A |
| ATOM | 1869 | CB | GLN | A | 244 | 5.005 | 5.372 | 48.581 | 1.00 | 13.07 | A |
| ATOM | 1870 | CG | GLN | A | 244 | 4.761 | 3.860 | 48.475 | 1.00 | 12.26 | A |
| ATOM | 1871 | CD | GLN | A | 244 | 3.457 | 3.383 | 49.114 | 1.00 | 12.34 | A |
| ATOM | 1872 | OE1 | GLN | A | 244 | 2.378 | 3.893 | 48.811 | 1.00 | 12.05 | A |
| ATOM | 1873 | NE2 | GLN | A | 244 | 3.556 | 2.379 | 49.989 | 1.00 | 10.52 | A |
| ATOM | 1874 | C | GLN | A | 244 | 5.753 | 5.660 | 46.225 | 1.00 | 13.65 | A |
| ATOM | 1875 | O | GLN | A | 244 | 4.996 | 6.466 | 45.681 | 1.00 | 13.54 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 1876 | N | THR | A | 245 | 6.260 | 4.611 | 45.588 | 1.00 | 14.00 | A |
| ATOM | 1877 | CA | THR | A | 245 | 5.903 | 4.361 | 44.200 | 1.00 | 14.97 | A |
| ATOM | 1878 | CB | THR | A | 245 | 6.862 | 5.104 | 43.240 | 1.00 | 15.16 | A |
| ATOM | 1879 | OG1 | THR | A | 245 | 6.295 | 5.121 | 41.922 | 1.00 | 16.09 | A |
| ATOM | 1880 | CG2 | THR | A | 245 | 8.222 | 4.418 | 43.201 | 1.00 | 16.31 | A |
| ATOM | 1881 | C | THR | A | 245 | 5.908 | 2.872 | 43.875 | 1.00 | 15.50 | A |
| ATOM | 1882 | O | THR | A | 245 | 6.472 | 2.069 | 44.616 | 1.00 | 15.47 | A |
| ATOM | 1883 | N | ILE | A | 246 | 5.257 | 2.516 | 42.770 | 1.00 | 16.25 | A |
| ATOM | 1884 | CA | ILE | A | 246 | 5.174 | 1.136 | 42.309 | 1.00 | 16.49 | A |
| ATOM | 1885 | CB | ILE | A | 246 | 3.698 | 0.719 | 42.056 | 1.00 | 16.23 | A |
| ATOM | 1886 | CG2 | ILE | A | 246 | 3.636 | −0.679 | 41.456 | 1.00 | 15.84 | A |
| ATOM | 1887 | CG1 | ILE | A | 246 | 2.915 | 0.748 | 43.376 | 1.00 | 15.94 | A |
| ATOM | 1888 | CD1 | ILE | A | 246 | 1.417 | 0.555 | 43.212 | 1.00 | 15.61 | A |
| ATOM | 1889 | C | ILE | A | 246 | 5.960 | 1.046 | 41.001 | 1.00 | 18.27 | A |
| ATOM | 1890 | O | ILE | A | 246 | 5.689 | 1.790 | 40.058 | 1.00 | 17.51 | A |
| ATOM | 1891 | N | ALA | A | 247 | 6.937 | 0.145 | 40.956 | 1.00 | 19.38 | A |
| ATOM | 1892 | CA | ALA | A | 247 | 7.770 | −0.025 | 39.768 | 1.00 | 21.64 | A |
| ATOM | 1893 | CB | ALA | A | 247 | 8.938 | −0.960 | 40.080 | 1.00 | 21.46 | A |
| ATOM | 1894 | C | ALA | A | 247 | 6.971 | −0.566 | 38.584 | 1.00 | 23.14 | A |
| ATOM | 1895 | O | ALA | A | 247 | 6.131 | −1.451 | 38.743 | 1.00 | 23.05 | A |
| ATOM | 1896 | N | PRO | A | 248 | 7.223 | −0.033 | 37.378 | 1.00 | 24.93 | A |
| ATOM | 1897 | CD | PRO | A | 248 | 8.193 | 1.027 | 37.042 | 1.00 | 25.33 | A |
| ATOM | 1898 | CA | PRO | A | 248 | 6.510 | −0.488 | 36.183 | 1.00 | 26.41 | A |
| ATOM | 1899 | CB | PRO | A | 248 | 6.983 | 0.490 | 35.107 | 1.00 | 26.16 | A |
| ATOM | 1900 | CG | PRO | A | 248 | 8.370 | 0.834 | 35.554 | 1.00 | 26.28 | A |
| ATOM | 1901 | C | PRO | A | 248 | 6.835 | −1.945 | 35.847 | 1.00 | 28.02 | A |
| ATOM | 1902 | O | PRO | A | 248 | 7.964 | −2.401 | 36.040 | 1.00 | 28.21 | A |
| ATOM | 1903 | N | ASP | A | 249 | 5.832 | −2.667 | 35.354 | 1.00 | 29.84 | A |
| ATOM | 1904 | CA | ASP | A | 249 | 5.982 | −4.077 | 34.997 | 1.00 | 31.50 | A |
| ATOM | 1905 | CB | ASP | A | 249 | 6.744 | −4.214 | 33.680 | 1.00 | 32.96 | A |
| ATOM | 1906 | CG | ASP | A | 249 | 5.969 | −3.663 | 32.506 | 1.00 | 34.22 | A |
| ATOM | 1907 | OD1 | ASP | A | 249 | 4.816 | −4.104 | 32.299 | 1.00 | 35.29 | A |
| ATOM | 1908 | OD2 | ASP | A | 249 | 6.512 | −2.794 | 31.792 | 1.00 | 35.24 | A |
| ATOM | 1909 | C | ASP | A | 249 | 6.691 | −4.878 | 36.077 | 1.00 | 31.86 | A |
| ATOM | 1910 | O | ASP | A | 249 | 7.796 | −5.379 | 35.867 | 1.00 | 32.42 | A |
| ATOM | 1911 | N | SER | A | 250 | 6.049 | −5.004 | 37.232 | 1.00 | 31.79 | A |
| ATOM | 1912 | CA | SER | A | 250 | 6.629 | −5.747 | 38.338 | 1.00 | 31.71 | A |
| ATOM | 1913 | CB | SER | A | 250 | 7.363 | −4.793 | 39.281 | 1.00 | 31.24 | A |
| ATOM | 1914 | OG | SER | A | 250 | 6.458 | −3.890 | 39.883 | 1.00 | 30.46 | A |
| ATOM | 1915 | C | SER | A | 250 | 5.556 | −6.506 | 39.111 | 1.00 | 31.85 | A |
| ATOM | 1916 | O | SER | A | 250 | 5.839 | −7.133 | 40.129 | 1.00 | 31.15 | A |
| ATOM | 1917 | N | GLU | A | 251 | 4.321 | −6.441 | 38.624 | 1.00 | 32.41 | A |
| ATOM | 1918 | CA | GLU | A | 251 | 3.219 | −7.135 | 39.275 | 1.00 | 32.93 | A |
| ATOM | 1919 | CB | GLU | A | 251 | 1.915 | −6.885 | 38.510 | 1.00 | 34.41 | A |
| ATOM | 1920 | CG | GLU | A | 251 | 0.667 | −7.443 | 39.186 | 1.00 | 36.20 | A |
| ATOM | 1921 | CD | GLU | A | 251 | −0.612 | −7.063 | 38.459 | 1.00 | 37.28 | A |
| ATOM | 1922 | OE1 | GLU | A | 251 | −1.705 | −7.458 | 38.925 | 1.00 | 37.89 | A |
| ATOM | 1923 | OE2 | GLU | A | 251 | −0.525 | −6.368 | 37.421 | 1.00 | 38.05 | A |
| ATOM | 1924 | C | GLU | A | 251 | 3.542 | −8.625 | 39.301 | 1.00 | 32.68 | A |
| ATOM | 1925 | O | GLU | A | 251 | 3.762 | −9.240 | 38.254 | 1.00 | 32.66 | A |
| ATOM | 1926 | N | GLY | A | 252 | 3.595 | −9.196 | 40.501 | 1.00 | 32.04 | A |
| ATOM | 1927 | CA | GLY | A | 252 | 3.901 | −10.609 | 40.637 | 1.00 | 30.95 | A |
| ATOM | 1928 | C | GLY | A | 252 | 5.326 | −10.861 | 41.093 | 1.00 | 30.57 | A |
| ATOM | 1929 | O | GLY | A | 252 | 5.672 | −11.974 | 41.488 | 1.00 | 30.50 | A |
| ATOM | 1930 | N | ALA | A | 253 | 6.159 | −9.827 | 41.045 | 1.00 | 29.95 | A |
| ATOM | 1931 | CA | ALA | A | 253 | 7.553 | −9.955 | 41.454 | 1.00 | 29.30 | A |
| ATOM | 1932 | CB | ALA | A | 253 | 8.253 | −8.608 | 41.344 | 1.00 | 29.04 | A |
| ATOM | 1933 | C | ALA | A | 253 | 7.670 | −10.494 | 42.876 | 1.00 | 29.10 | A |
| ATOM | 1934 | O | ALA | A | 253 | 8.502 | −11.358 | 43.153 | 1.00 | 28.97 | A |
| ATOM | 1935 | N | ILE | A | 254 | 6.833 | −9.977 | 43.772 | 1.00 | 29.05 | A |
| ATOM | 1936 | CA | ILE | A | 254 | 6.827 | −10.404 | 45.169 | 1.00 | 28.75 | A |
| ATOM | 1937 | CB | ILE | A | 254 | 7.611 | −9.424 | 46.070 | 1.00 | 28.87 | A |
| ATOM | 1938 | CG2 | ILE | A | 254 | 7.593 | −9.922 | 47.511 | 1.00 | 29.14 | A |
| ATOM | 1939 | CG1 | ILE | A | 254 | 9.055 | −9.287 | 45.584 | 1.00 | 29.03 | A |
| ATOM | 1940 | CD1 | ILE | A | 254 | 9.901 | −10.528 | 45.803 | 1.00 | 30.14 | A |
| ATOM | 1941 | C | ILE | A | 254 | 5.387 | −10.447 | 45.670 | 1.00 | 28.64 | A |
| ATOM | 1942 | O | ILE | A | 254 | 4.730 | −9.411 | 45.773 | 1.00 | 28.64 | A |
| ATOM | 1943 | N | ASP | A | 255 | 4.895 | −11.639 | 45.989 | 1.00 | 28.26 | A |
| ATOM | 1944 | CA | ASP | A | 255 | 3.525 | −11.762 | 46.471 | 1.00 | 27.70 | A |
| ATOM | 1945 | CB | ASP | A | 255 | 2.598 | −12.163 | 45.322 | 1.00 | 29.83 | A |
| ATOM | 1946 | CG | ASP | A | 255 | 2.660 | −13.643 | 45.016 | 1.00 | 32.19 | A |
| ATOM | 1947 | OD1 | ASP | A | 255 | 2.153 | −14.443 | 45.835 | 1.00 | 33.88 | A |
| ATOM | 1948 | OD2 | ASP | A | 255 | 3.222 | −14.012 | 43.964 | 1.00 | 33.72 | A |
| ATOM | 1949 | C | ASP | A | 255 | 3.401 | −12.778 | 47.600 | 1.00 | 26.17 | A |
| ATOM | 1950 | O | ASP | A | 255 | 4.086 | −13.803 | 47.612 | 1.00 | 26.56 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 1951 | N | GLY | A | 256 | 2.519 | −12.483 | 48.548 | 1.00 | 23.34 | A |
| ATOM | 1952 | CA | GLY | A | 256 | 2.304 | −13.379 | 49.664 | 1.00 | 20.65 | A |
| ATOM | 1953 | C | GLY | A | 256 | 0.831 | −13.708 | 49.807 | 1.00 | 18.54 | A |
| ATOM | 1954 | O | GLY | A | 256 | −0.030 | −12.931 | 49.389 | 1.00 | 17.67 | A |
| ATOM | 1955 | N | HIS | A | 257 | 0.537 | −14.862 | 50.395 | 1.00 | 17.10 | A |
| ATOM | 1956 | CA | HIS | A | 257 | −0.844 | −15.289 | 50.586 | 1.00 | 16.09 | A |
| ATOM | 1957 | CB | HIS | A | 257 | −1.205 | −16.374 | 49.567 | 1.00 | 17.01 | A |
| ATOM | 1958 | CG | HIS | A | 257 | −0.976 | −15.973 | 48.141 | 1.00 | 17.98 | A |
| ATOM | 1959 | CD2 | HIS | A | 257 | −0.126 | −16.458 | 47.204 | 1.00 | 18.47 | A |
| ATOM | 1960 | ND1 | HIS | A | 257 | −1.680 | −14.957 | 47.529 | 1.00 | 18.29 | A |
| ATOM | 1961 | CE1 | HIS | A | 257 | −1.275 | −14.836 | 46.276 | 1.00 | 18.53 | A |
| ATOM | 1962 | NE2 | HIS | A | 257 | −0.332 | −15.734 | 46.054 | 1.00 | 18.65 | A |
| ATOM | 1963 | C | HIS | A | 257 | −1.034 | −15.842 | 51.997 | 1.00 | 15.08 | A |
| ATOM | 1964 | O | HIS | A | 257 | −0.328 | −16.771 | 52.400 | 1.00 | 14.51 | A |
| ATOM | 1965 | N | LEU | A | 258 | −1.981 | −15.274 | 52.744 | 1.00 | 13.67 | A |
| ATOM | 1966 | CA | LEU | A | 258 | −2.269 | −15.735 | 54.104 | 1.00 | 12.94 | A |
| ATOM | 1967 | CB | LEU | A | 258 | −2.743 | −14.565 | 54.973 | 1.00 | 13.79 | A |
| ATOM | 1968 | CG | LEU | A | 258 | −2.864 | −14.775 | 56.490 | 1.00 | 14.04 | A |
| ATOM | 1969 | CD1 | LEU | A | 258 | −3.994 | −15.736 | 56.802 | 1.00 | 15.09 | A |
| ATOM | 1970 | CD2 | LEU | A | 258 | −1.542 | −15.300 | 57.035 | 1.00 | 13.98 | A |
| ATOM | 1971 | C | LEU | A | 258 | −3.369 | −16.789 | 53.972 | 1.00 | 12.65 | A |
| ATOM | 1972 | O | LEU | A | 258 | −4.527 | −16.464 | 53.684 | 1.00 | 11.92 | A |
| ATOM | 1973 | N | ARG | A | 259 | −2.998 | −18.047 | 54.185 | 1.00 | 11.51 | A |
| ATOM | 1974 | CA | ARG | A | 259 | −3.927 | −19.162 | 54.033 | 1.00 | 12.09 | A |
| ATOM | 1975 | CB | ARG | A | 259 | −3.614 | −19.896 | 52.723 | 1.00 | 12.33 | A |
| ATOM | 1976 | CG | ARG | A | 259 | −3.690 | −19.023 | 51.473 | 1.00 | 12.60 | A |
| ATOM | 1977 | CD | ARG | A | 259 | −5.127 | −18.640 | 51.129 | 1.00 | 13.20 | A |
| ATOM | 1978 | NE | ARG | A | 259 | −5.220 | −17.892 | 49.874 | 1.00 | 13.86 | A |
| ATOM | 1979 | CZ | ARG | A | 259 | −5.066 | −16.575 | 49.767 | 1.00 | 14.56 | A |
| ATOM | 1980 | NH1 | ARG | A | 259 | −4.814 | −15.846 | 50.843 | 1.00 | 13.37 | A |
| ATOM | 1981 | NH2 | ARG | A | 259 | −5.163 | −15.987 | 48.580 | 1.00 | 14.20 | A |
| ATOM | 1982 | C | ARG | A | 259 | −3.892 | −20.155 | 55.194 | 1.00 | 12.02 | A |
| ATOM | 1983 | O | ARG | A | 259 | −3.224 | −19.925 | 56.208 | 1.00 | 11.93 | A |
| ATOM | 1984 | N | GLU | A | 260 | −4.608 | −21.266 | 55.032 | 1.00 | 12.07 | A |
| ATOM | 1985 | CA | GLU | A | 260 | −4.677 | −22.293 | 56.067 | 1.00 | 11.81 | A |
| ATOM | 1986 | CB | GLU | A | 260 | −5.658 | −23.401 | 55.638 | 1.00 | 12.66 | A |
| ATOM | 1987 | CG | GLU | A | 260 | −7.136 | −22.962 | 55.733 | 1.00 | 12.50 | A |
| ATOM | 1988 | CD | GLU | A | 260 | −8.119 | −23.909 | 55.037 | 1.00 | 13.49 | A |
| ATOM | 1989 | OE1 | GLU | A | 260 | −8.009 | −25.138 | 55.209 | 1.00 | 13.25 | A |
| ATOM | 1990 | OE2 | GLU | A | 260 | −9.020 | −23.414 | 54.323 | 1.00 | 13.98 | A |
| ATOM | 1991 | C | GLU | A | 260 | −3.314 | −22.877 | 56.433 | 1.00 | 12.29 | A |
| ATOM | 1992 | O | GLU | A | 260 | −3.138 | −23.412 | 57.531 | 1.00 | 12.18 | A |
| ATOM | 1993 | N | ALA | A | 261 | −2.344 | −22.760 | 55.530 | 1.00 | 12.23 | A |
| ATOM | 1994 | CA | ALA | A | 261 | −1.006 | −23.282 | 55.789 | 1.00 | 12.39 | A |
| ATOM | 1995 | CB | ALA | A | 261 | −0.454 | −23.962 | 54.531 | 1.00 | 13.04 | A |
| ATOM | 1996 | C | ALA | A | 261 | −0.047 | −22.180 | 56.255 | 1.00 | 12.98 | A |
| ATOM | 1997 | O | ALA | A | 261 | 1.165 | −22.383 | 56.308 | 1.00 | 12.59 | A |
| ATOM | 1998 | N | GLY | A | 262 | −0.591 | −21.016 | 56.596 | 1.00 | 13.18 | A |
| ATOM | 1999 | CA | GLY | A | 262 | 0.249 | −19.916 | 57.033 | 1.00 | 13.93 | A |
| ATOM | 2000 | C | GLY | A | 262 | 0.495 | −18.934 | 55.902 | 1.00 | 14.52 | A |
| ATOM | 2001 | O | GLY | A | 262 | −0.305 | −18.850 | 54.965 | 1.00 | 14.28 | A |
| ATOM | 2002 | N | LEU | A | 263 | 1.598 | −18.193 | 55.981 | 1.00 | 15.26 | A |
| ATOM | 2003 | CA | LEU | A | 263 | 1.944 | −17.210 | 54.954 | 1.00 | 16.05 | A |
| ATOM | 2004 | CB | LEU | A | 263 | 2.466 | −15.924 | 55.609 | 1.00 | 15.77 | A |
| ATOM | 2005 | CG | LEU | A | 263 | 2.933 | −14.826 | 54.646 | 1.00 | 15.80 | A |
| ATOM | 2006 | CD1 | LEU | A | 263 | 1.737 | −14.294 | 53.861 | 1.00 | 16.55 | A |
| ATOM | 2007 | CD2 | LEU | A | 263 | 3.604 | −13.700 | 55.424 | 1.00 | 15.82 | A |
| ATOM | 2008 | C | LEU | A | 263 | 2.997 | −17.737 | 53.976 | 1.00 | 17.41 | A |
| ATOM | 2009 | O | LEU | A | 263 | 4.087 | −18.131 | 54.388 | 1.00 | 15.70 | A |
| ATOM | 2010 | N | THR | A | 264 | 2.669 | −17.745 | 52.683 | 1.00 | 19.51 | A |
| ATOM | 2011 | CA | THR | A | 264 | 3.604 | −18.203 | 51.652 | 1.00 | 22.55 | A |
| ATOM | 2012 | CB | THR | A | 264 | 3.032 | −19.396 | 50.841 | 1.00 | 22.62 | A |
| ATOM | 2013 | OG1 | THR | A | 264 | 1.814 | −19.005 | 50.193 | 1.00 | 22.53 | A |
| ATOM | 2014 | CG2 | THR | A | 264 | 2.758 | −20.578 | 51.759 | 1.00 | 22.97 | A |
| ATOM | 2015 | C | THR | A | 264 | 3.930 | −17.061 | 50.684 | 1.00 | 25.08 | A |
| ATOM | 2016 | O | THR | A | 264 | 3.152 | −16.116 | 50.553 | 1.00 | 24.86 | A |
| ATOM | 2017 | N | PHE | A | 265 | 5.080 | −17.150 | 50.014 | 1.00 | 27.68 | A |
| ATOM | 2018 | CA | PHE | A | 265 | 5.520 | −16.124 | 49.059 | 1.00 | 30.90 | A |
| ATOM | 2019 | CB | PHE | A | 265 | 6.761 | −15.399 | 49.590 | 1.00 | 31.48 | A |
| ATOM | 2020 | CG | PHE | A | 265 | 6.458 | −14.282 | 50.550 | 1.00 | 31.83 | A |
| ATOM | 2021 | CD1 | PHE | A | 265 | 5.800 | −13.133 | 50.116 | 1.00 | 32.13 | A |
| ATOM | 2022 | CD2 | PHE | A | 265 | 6.851 | −14.364 | 51.882 | 1.00 | 31.97 | A |
| ATOM | 2023 | CE1 | PHE | A | 265 | 5.541 | −12.080 | 50.997 | 1.00 | 31.84 | A |
| ATOM | 2024 | CE2 | PHE | A | 265 | 6.595 | −13.316 | 52.770 | 1.00 | 32.16 | A |
| ATOM | 2025 | CZ | PHE | A | 265 | 5.941 | −12.174 | 52.325 | 1.00 | 31.81 | A |

APPENDIX C-continued

18xCHS Mutant

| ATOM | # | TYPE | RES | | | X | Y | Z | OCC | B | |
|------|---|------|-----|---|---|---|---|---|-----|---|---|
| ATOM | 2026 | C | PHE | A | 265 | 5.844 | −16.701 | 47.679 | 1.00 | 33.06 | A |
| ATOM | 2027 | O | PHE | A | 265 | 6.356 | −17.817 | 47.572 | 1.00 | 33.32 | A |
| ATOM | 2028 | N | HIS | A | 266 | 5.552 | −15.931 | 46.630 | 1.00 | 35.28 | A |
| ATOM | 2029 | CA | HIS | A | 266 | 5.803 | −16.354 | 45.249 | 1.00 | 37.58 | A |
| ATOM | 2030 | CB | HIS | A | 266 | 4.495 | −16.800 | 44.589 | 1.00 | 38.61 | A |
| ATOM | 2031 | CG | HIS | A | 266 | 3.760 | −17.857 | 45.355 | 1.00 | 40.09 | A |
| ATOM | 2032 | CD2 | HIS | A | 266 | 3.407 | −19.120 | 45.018 | 1.00 | 40.75 | A |
| ATOM | 2033 | ND1 | HIS | A | 266 | 3.288 | −17.657 | 46.635 | 1.00 | 40.98 | A |
| ATOM | 2034 | CE1 | HIS | A | 266 | 2.674 | −18.750 | 47.053 | 1.00 | 41.00 | A |
| ATOM | 2035 | NE2 | HIS | A | 266 | 2.732 | −19.653 | 46.090 | 1.00 | 41.36 | A |
| ATOM | 2036 | C | HIS | A | 266 | 6.427 | −15.224 | 44.421 | 1.00 | 38.52 | A |
| ATOM | 2037 | O | HIS | A | 266 | 5.931 | −14.096 | 44.426 | 1.00 | 38.95 | A |
| ATOM | 2038 | N | LEU | A | 267 | 7.503 | −15.533 | 43.699 | 1.00 | 39.31 | A |
| ATOM | 2039 | CA | LEU | A | 267 | 8.197 | −14.531 | 42.889 | 1.00 | 39.61 | A |
| ATOM | 2040 | CB | LEU | A | 267 | 9.705 | −14.576 | 43.174 | 1.00 | 39.95 | A |
| ATOM | 2041 | CG | LEU | A | 267 | 10.194 | −14.308 | 44.603 | 1.00 | 40.58 | A |
| ATOM | 2042 | CD1 | LEU | A | 267 | 9.725 | −15.410 | 45.541 | 1.00 | 40.74 | A |
| ATOM | 2043 | CD2 | LEU | A | 267 | 11.711 | −14.243 | 44.608 | 1.00 | 40.64 | A |
| ATOM | 2044 | C | LEU | A | 267 | 7.975 | −14.660 | 41.381 | 1.00 | 39.65 | A |
| ATOM | 2045 | O | LEU | A | 267 | 7.598 | −15.719 | 40.878 | 1.00 | 39.80 | A |
| ATOM | 2046 | N | ALA | A | 268 | 8.217 | −13.562 | 40.670 | 1.00 | 39.52 | A |
| ATOM | 2047 | CA | ALA | A | 268 | 8.069 | −13.510 | 39.218 | 1.00 | 39.27 | A |
| ATOM | 2048 | CB | ALA | A | 268 | 6.646 | −13.114 | 38.846 | 1.00 | 39.26 | A |
| ATOM | 2049 | C | ALA | A | 268 | 9.062 | −12.486 | 38.673 | 1.00 | 39.03 | A |
| ATOM | 2050 | O | ALA | A | 268 | 8.990 | −11.303 | 39.004 | 1.00 | 39.11 | A |
| ATOM | 2051 | N | GLY | A | 269 | 9.988 | −12.942 | 37.837 | 1.00 | 38.84 | A |
| ATOM | 2052 | CA | GLY | A | 269 | 10.985 | −12.040 | 37.288 | 1.00 | 38.15 | A |
| ATOM | 2053 | C | GLY | A | 269 | 12.158 | −11.931 | 38.247 | 1.00 | 37.50 | A |
| ATOM | 2054 | O | GLY | A | 269 | 12.241 | −12.699 | 39.206 | 1.00 | 37.96 | A |
| ATOM | 2055 | N | ALA | A | 270 | 13.058 | −10.983 | 38.003 | 1.00 | 36.27 | A |
| ATOM | 2056 | CA | ALA | A | 270 | 14.223 | −10.808 | 38.865 | 1.00 | 34.83 | A |
| ATOM | 2057 | CB | ALA | A | 270 | 15.486 | −10.771 | 38.019 | 1.00 | 35.40 | A |
| ATOM | 2058 | C | ALA | A | 270 | 14.130 | −9.547 | 39.724 | 1.00 | 33.76 | A |
| ATOM | 2059 | O | ALA | A | 270 | 14.279 | −8.431 | 39.224 | 1.00 | 33.47 | A |
| ATOM | 2060 | N | VAL | A | 271 | 13.892 | −9.737 | 41.019 | 1.00 | 32.23 | A |
| ATOM | 2061 | CA | VAL | A | 271 | 13.773 | −8.626 | 41.961 | 1.00 | 31.04 | A |
| ATOM | 2062 | CB | VAL | A | 271 | 13.521 | −9.145 | 43.402 | 1.00 | 31.01 | A |
| ATOM | 2063 | CG1 | VAL | A | 271 | 13.626 | −8.003 | 44.404 | 1.00 | 30.77 | A |
| ATOM | 2064 | CG2 | VAL | A | 271 | 12.151 | −9.783 | 43.484 | 1.00 | 31.12 | A |
| ATOM | 2065 | C | VAL | A | 271 | 14.989 | −7.697 | 41.972 | 1.00 | 29.97 | A |
| ATOM | 2066 | O | VAL | A | 271 | 14.841 | −6.479 | 41.883 | 1.00 | 30.03 | A |
| ATOM | 2067 | N | PRO | A | 272 | 16.206 | −8.256 | 42.086 | 1.00 | 29.22 | A |
| ATOM | 2068 | CD | PRO | A | 272 | 16.559 | −9.677 | 42.254 | 1.00 | 28.94 | A |
| ATOM | 2069 | CA | PRO | A | 272 | 17.410 | −7.417 | 42.104 | 1.00 | 28.46 | A |
| ATOM | 2070 | CB | PRO | A | 272 | 18.542 | −8.442 | 42.131 | 1.00 | 28.41 | A |
| ATOM | 2071 | CG | PRO | A | 272 | 17.932 | −9.590 | 42.878 | 1.00 | 28.73 | A |
| ATOM | 2072 | C | PRO | A | 272 | 17.509 | −6.479 | 40.897 | 1.00 | 27.94 | A |
| ATOM | 2073 | O | PRO | A | 272 | 17.907 | −5.323 | 41.032 | 1.00 | 27.50 | A |
| ATOM | 2074 | N | ASP | A | 273 | 17.147 | −6.986 | 39.722 | 1.00 | 27.25 | A |
| ATOM | 2075 | CA | ASP | A | 273 | 17.193 | −6.196 | 38.496 | 1.00 | 26.96 | A |
| ATOM | 2076 | CB | ASP | A | 273 | 16.970 | −7.099 | 37.281 | 1.00 | 27.99 | A |
| ATOM | 2077 | CG | ASP | A | 273 | 18.228 | −7.831 | 36.859 | 1.00 | 29.35 | A |
| ATOM | 2078 | OD1 | ASP | A | 273 | 18.956 | −8.347 | 37.734 | 1.00 | 30.19 | A |
| ATOM | 2079 | OD2 | ASP | A | 273 | 18.488 | −7.899 | 35.642 | 1.00 | 31.21 | A |
| ATOM | 2080 | C | ASP | A | 273 | 16.164 | −5.070 | 38.494 | 1.00 | 26.29 | A |
| ATOM | 2081 | O | ASP | A | 273 | 16.457 | −3.951 | 38.082 | 1.00 | 25.72 | A |
| ATOM | 2082 | N | ILE | A | 274 | 14.954 | −5.368 | 38.952 | 1.00 | 26.11 | A |
| ATOM | 2083 | CA | ILE | A | 274 | 13.899 | −4.363 | 38.990 | 1.00 | 25.68 | A |
| ATOM | 2084 | CB | ILE | A | 274 | 12.561 | −4.987 | 39.440 | 1.00 | 25.78 | A |
| ATOM | 2085 | CG2 | ILE | A | 274 | 11.480 | −3.915 | 39.498 | 1.00 | 25.49 | A |
| ATOM | 2086 | CG1 | ILE | A | 274 | 12.169 | −6.103 | 38.465 | 1.00 | 26.11 | A |
| ATOM | 2087 | CD1 | ILE | A | 274 | 10.946 | −6.901 | 38.866 | 1.00 | 26.62 | A |
| ATOM | 2088 | C | ILE | A | 274 | 14.281 | −3.215 | 39.925 | 1.00 | 25.55 | A |
| ATOM | 2089 | O | ILE | A | 274 | 14.087 | −2.045 | 39.594 | 1.00 | 24.97 | A |
| ATOM | 2090 | N | VAL | A | 275 | 14.838 | −3.550 | 41.086 | 1.00 | 25.89 | A |
| ATOM | 2091 | CA | VAL | A | 275 | 15.249 | −2.530 | 42.048 | 1.00 | 26.31 | A |
| ATOM | 2092 | CB | VAL | A | 275 | 15.736 | −3.164 | 43.380 | 1.00 | 26.56 | A |
| ATOM | 2093 | CG1 | VAL | A | 275 | 16.295 | −2.087 | 44.301 | 1.00 | 26.70 | A |
| ATOM | 2094 | CG2 | VAL | A | 275 | 14.586 | −3.886 | 44.068 | 1.00 | 26.15 | A |
| ATOM | 2095 | C | VAL | A | 275 | 16.371 | −1.657 | 41.482 | 1.00 | 26.97 | A |
| ATOM | 2096 | O | VAL | A | 275 | 16.257 | −0.433 | 41.458 | 1.00 | 27.12 | A |
| ATOM | 2097 | N | SER | A | 276 | 17.442 | −2.289 | 41.006 | 1.00 | 27.37 | A |
| ATOM | 2098 | CA | SER | A | 276 | 18.587 | −1.559 | 40.465 | 1.00 | 28.02 | A |
| ATOM | 2099 | CB | SER | A | 276 | 19.741 | −2.526 | 40.173 | 1.00 | 28.39 | A |
| ATOM | 2100 | OG | SER | A | 276 | 19.374 | −3.502 | 39.214 | 1.00 | 28.82 | A |

APPENDIX C-continued

18xCHS Mutant

| ATOM | # | TYPE | RES | | | X | Y | Z | OCC | B | |
|------|---|------|-----|---|---|---|---|---|-----|---|---|
| ATOM | 2101 | C | SER | A | 276 | 18.286 | −0.729 | 39.218 | 1.00 | 28.31 | A |
| ATOM | 2102 | O | SER | A | 276 | 18.977 | 0.254 | 38.947 | 1.00 | 28.51 | A |
| ATOM | 2103 | N | LYS | A | 277 | 17.265 | −1.116 | 38.461 | 1.00 | 28.38 | A |
| ATOM | 2104 | CA | LYS | A | 277 | 16.901 | −0.379 | 37.255 | 1.00 | 28.77 | A |
| ATOM | 2105 | CB | LYS | A | 277 | 16.196 | −1.298 | 36.255 | 1.00 | 30.10 | A |
| ATOM | 2106 | CG | LYS | A | 277 | 17.077 | −2.408 | 35.702 | 1.00 | 32.06 | A |
| ATOM | 2107 | CD | LYS | A | 277 | 16.333 | −3.237 | 34.667 | 1.00 | 33.51 | A |
| ATOM | 2108 | CE | LYS | A | 277 | 17.151 | −4.443 | 34.229 | 1.00 | 34.41 | A |
| ATOM | 2109 | NZ | LYS | A | 277 | 18.471 | −4.060 | 33.652 | 1.00 | 34.50 | A |
| ATOM | 2110 | C | LYS | A | 277 | 15.998 | 0.814 | 37.556 | 1.00 | 28.23 | A |
| ATOM | 2111 | O | LYS | A | 277 | 15.910 | 1.745 | 36.756 | 1.00 | 28.03 | A |
| ATOM | 2112 | N | ASN | A | 278 | 15.339 | 0.784 | 38.712 | 1.00 | 27.01 | A |
| ATOM | 2113 | CA | ASN | A | 278 | 14.427 | 1.853 | 39.115 | 1.00 | 26.27 | A |
| ATOM | 2114 | CB | ASN | A | 278 | 13.103 | 1.253 | 39.591 | 1.00 | 26.13 | A |
| ATOM | 2115 | CG | ASN | A | 278 | 12.247 | 0.739 | 38.447 | 1.00 | 26.09 | A |
| ATOM | 2116 | OD1 | ASN | A | 278 | 11.588 | 1.516 | 37.752 | 1.00 | 26.66 | A |
| ATOM | 2117 | ND2 | ASN | A | 278 | 12.261 | −0.572 | 38.240 | 1.00 | 25.15 | A |
| ATOM | 2118 | C | ASN | A | 278 | 14.989 | 2.735 | 40.221 | 1.00 | 26.25 | A |
| ATOM | 2119 | O | ASN | A | 278 | 14.376 | 3.738 | 40.591 | 1.00 | 26.18 | A |
| ATOM | 2120 | N | ILE | A | 279 | 16.155 | 2.370 | 40.743 | 1.00 | 25.52 | A |
| ATOM | 2121 | CA | ILE | A | 279 | 16.762 | 3.123 | 41.830 | 1.00 | 25.04 | A |
| ATOM | 2122 | CB | ILE | A | 279 | 17.921 | 2.327 | 42.474 | 1.00 | 25.04 | A |
| ATOM | 2123 | CG2 | ILE | A | 279 | 19.131 | 2.299 | 41.548 | 1.00 | 25.43 | A |
| ATOM | 2124 | CG1 | ILE | A | 279 | 18.284 | 2.951 | 43.820 | 1.00 | 24.74 | A |
| ATOM | 2125 | CD1 | ILE | A | 279 | 17.153 | 2.907 | 44.818 | 1.00 | 24.79 | A |
| ATOM | 2126 | C | ILE | A | 279 | 17.265 | 4.513 | 41.446 | 1.00 | 24.99 | A |
| ATOM | 2127 | O | ILE | A | 279 | 17.085 | 5.468 | 42.204 | 1.00 | 24.98 | A |
| ATOM | 2128 | N | THR | A | 280 | 17.887 | 4.636 | 40.276 | 1.00 | 24.16 | A |
| ATOM | 2129 | CA | THR | A | 280 | 18.406 | 5.927 | 39.846 | 1.00 | 23.97 | A |
| ATOM | 2130 | CB | THR | A | 280 | 19.122 | 5.831 | 38.480 | 1.00 | 23.59 | A |
| ATOM | 2131 | OG1 | THR | A | 280 | 20.213 | 4.907 | 38.573 | 1.00 | 23.27 | A |
| ATOM | 2132 | CG2 | THR | A | 280 | 19.661 | 7.195 | 38.069 | 1.00 | 23.09 | A |
| ATOM | 2133 | C | THR | A | 280 | 17.309 | 6.978 | 39.745 | 1.00 | 24.11 | A |
| ATOM | 2134 | O | THR | A | 280 | 17.489 | 8.109 | 40.197 | 1.00 | 23.96 | A |
| ATOM | 2135 | N | LYS | A | 281 | 16.172 | 6.608 | 39.161 | 1.00 | 24.39 | A |
| ATOM | 2136 | CA | LYS | A | 281 | 15.069 | 7.550 | 39.010 | 1.00 | 24.90 | A |
| ATOM | 2137 | CB | LYS | A | 281 | 13.962 | 6.949 | 38.140 | 1.00 | 26.58 | A |
| ATOM | 2138 | CG | LYS | A | 281 | 13.414 | 5.626 | 38.631 | 1.00 | 28.54 | A |
| ATOM | 2139 | CD | LYS | A | 281 | 12.272 | 5.129 | 37.750 | 1.00 | 30.15 | A |
| ATOM | 2140 | CE | LYS | A | 281 | 11.047 | 6.036 | 37.837 | 1.00 | 31.02 | A |
| ATOM | 2141 | NZ | LYS | A | 281 | 11.308 | 7.427 | 37.359 | 1.00 | 32.08 | A |
| ATOM | 2142 | C | LYS | A | 281 | 14.501 | 7.990 | 40.353 | 1.00 | 24.09 | A |
| ATOM | 2143 | O | LYS | A | 281 | 14.058 | 9.128 | 40.502 | 1.00 | 24.02 | A |
| ATOM | 2144 | N | ALA | A | 282 | 14.509 | 7.092 | 41.331 | 1.00 | 23.31 | A |
| ATOM | 2145 | CA | ALA | A | 282 | 14.004 | 7.434 | 42.658 | 1.00 | 22.44 | A |
| ATOM | 2146 | CB | ALA | A | 282 | 13.877 | 6.176 | 43.517 | 1.00 | 22.10 | A |
| ATOM | 2147 | C | ALA | A | 282 | 14.967 | 8.432 | 43.309 | 1.00 | 22.14 | A |
| ATOM | 2148 | O | ALA | A | 282 | 14.544 | 9.360 | 43.999 | 1.00 | 21.76 | A |
| ATOM | 2149 | N | LEU | A | 283 | 16.264 | 8.240 | 43.074 | 1.00 | 21.91 | A |
| ATOM | 2150 | CA | LEU | A | 283 | 17.298 | 9.119 | 43.627 | 1.00 | 22.25 | A |
| ATOM | 2151 | CB | LEU | A | 283 | 18.681 | 8.487 | 43.466 | 1.00 | 21.95 | A |
| ATOM | 2152 | CG | LEU | A | 283 | 19.137 | 7.434 | 44.471 | 1.00 | 21.65 | A |
| ATOM | 2153 | CD1 | LEU | A | 283 | 20.407 | 6.781 | 43.954 | 1.00 | 21.52 | A |
| ATOM | 2154 | CD2 | LEU | A | 283 | 19.372 | 8.078 | 45.837 | 1.00 | 20.87 | A |
| ATOM | 2155 | C | LEU | A | 283 | 17.324 | 10.498 | 42.977 | 1.00 | 22.77 | A |
| ATOM | 2156 | O | LEU | A | 283 | 17.448 | 11.513 | 43.667 | 1.00 | 22.46 | A |
| ATOM | 2157 | N | VAL | A | 284 | 17.235 | 10.535 | 41.651 | 1.00 | 23.26 | A |
| ATOM | 2158 | CA | VAL | A | 284 | 17.258 | 11.810 | 40.942 | 1.00 | 24.56 | A |
| ATOM | 2159 | CB | VAL | A | 284 | 17.197 | 11.617 | 39.402 | 1.00 | 24.60 | A |
| ATOM | 2160 | CG1 | VAL | A | 284 | 18.434 | 10.888 | 38.922 | 1.00 | 24.22 | A |
| ATOM | 2161 | CG2 | VAL | A | 284 | 15.948 | 10.847 | 39.018 | 1.00 | 25.47 | A |
| ATOM | 2162 | C | VAL | A | 284 | 16.099 | 12.696 | 41.371 | 1.00 | 25.10 | A |
| ATOM | 2163 | O | VAL | A | 284 | 16.268 | 13.896 | 41.576 | 1.00 | 26.07 | A |
| ATOM | 2164 | N | GLU | A | 285 | 14.924 | 12.097 | 41.520 | 1.00 | 25.93 | A |
| ATOM | 2165 | CA | GLU | A | 285 | 13.732 | 12.832 | 41.915 | 1.00 | 26.80 | A |
| ATOM | 2166 | CB | GLU | A | 285 | 12.500 | 11.947 | 41.715 | 1.00 | 28.36 | A |
| ATOM | 2167 | CG | GLU | A | 285 | 11.241 | 12.450 | 42.384 | 1.00 | 31.15 | A |
| ATOM | 2168 | CD | GLU | A | 285 | 10.001 | 11.815 | 41.809 | 1.00 | 32.58 | A |
| ATOM | 2169 | OE1 | GLU | A | 285 | 10.025 | 10.588 | 41.569 | 1.00 | 34.38 | A |
| ATOM | 2170 | OE2 | GLU | A | 285 | 9.000 | 12.538 | 41.599 | 1.00 | 34.22 | A |
| ATOM | 2171 | C | GLU | A | 285 | 13.788 | 13.347 | 43.351 | 1.00 | 26.74 | A |
| ATOM | 2172 | O | GLU | A | 285 | 13.174 | 14.363 | 43.676 | 1.00 | 26.52 | A |
| ATOM | 2173 | N | ALA | A | 286 | 14.534 | 12.655 | 44.205 | 1.00 | 26.28 | A |
| ATOM | 2174 | CA | ALA | A | 286 | 14.651 | 13.057 | 45.602 | 1.00 | 26.53 | A |
| ATOM | 2175 | CB | ALA | A | 286 | 14.821 | 11.821 | 46.477 | 1.00 | 25.97 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 2176 | C | ALA | A | 286 | 15.797 | 14.035 | 45.864 | 1.00 | 26.80 | A |
| ATOM | 2177 | O | ALA | A | 286 | 15.683 | 14.921 | 46.713 | 1.00 | 26.76 | A |
| ATOM | 2178 | N | PHE | A | 287 | 16.894 | 13.884 | 45.127 | 1.00 | 27.08 | A |
| ATOM | 2179 | CA | PHE | A | 287 | 18.062 | 14.733 | 45.329 | 1.00 | 27.56 | A |
| ATOM | 2180 | CB | PHE | A | 287 | 19.294 | 13.848 | 45.536 | 1.00 | 26.16 | A |
| ATOM | 2181 | CG | PHE | A | 287 | 19.300 | 13.142 | 46.860 | 1.00 | 25.16 | A |
| ATOM | 2182 | CD1 | PHE | A | 287 | 19.599 | 13.837 | 48.027 | 1.00 | 24.31 | A |
| ATOM | 2183 | CD2 | PHE | A | 287 | 18.941 | 11.802 | 46.952 | 1.00 | 24.68 | A |
| ATOM | 2184 | CE1 | PHE | A | 287 | 19.538 | 13.210 | 49.270 | 1.00 | 24.57 | A |
| ATOM | 2185 | CE2 | PHE | A | 287 | 18.876 | 11.164 | 48.191 | 1.00 | 24.72 | A |
| ATOM | 2186 | CZ | PHE | A | 287 | 19.174 | 11.872 | 49.353 | 1.00 | 24.05 | A |
| ATOM | 2187 | C | PHE | A | 287 | 18.354 | 15.805 | 44.282 | 1.00 | 29.00 | A |
| ATOM | 2188 | O | PHE | A | 287 | 19.231 | 16.646 | 44.487 | 1.00 | 28.79 | A |
| ATOM | 2189 | N | GLU | A | 288 | 17.636 | 15.781 | 43.164 | 1.00 | 30.59 | A |
| ATOM | 2190 | CA | GLU | A | 288 | 17.845 | 16.801 | 42.138 | 1.00 | 32.44 | A |
| ATOM | 2191 | CB | GLU | A | 288 | 16.899 | 16.581 | 40.954 | 1.00 | 33.45 | A |
| ATOM | 2192 | CG | GLU | A | 288 | 17.114 | 17.546 | 39.799 | 1.00 | 35.64 | A |
| ATOM | 2193 | CD | GLU | A | 288 | 16.158 | 17.296 | 38.646 | 1.00 | 36.73 | A |
| ATOM | 2194 | OE1 | GLU | A | 288 | 14.950 | 17.577 | 38.796 | 1.00 | 37.57 | A |
| ATOM | 2195 | OE2 | GLU | A | 288 | 16.616 | 16.808 | 37.592 | 1.00 | 37.77 | A |
| ATOM | 2196 | C | GLU | A | 288 | 17.588 | 18.176 | 42.761 | 1.00 | 32.65 | A |
| ATOM | 2197 | O | GLU | A | 288 | 18.391 | 19.095 | 42.608 | 1.00 | 33.11 | A |
| ATOM | 2198 | N | PRO | A | 289 | 16.463 | 18.329 | 43.482 | 1.00 | 33.05 | A |
| ATOM | 2199 | CD | PRO | A | 289 | 15.364 | 17.358 | 43.650 | 1.00 | 33.26 | A |
| ATOM | 2200 | CA | PRO | A | 289 | 16.121 | 19.602 | 44.125 | 1.00 | 33.05 | A |
| ATOM | 2201 | CB | PRO | A | 289 | 14.818 | 19.279 | 44.851 | 1.00 | 33.14 | A |
| ATOM | 2202 | CG | PRO | A | 289 | 14.192 | 18.256 | 43.966 | 1.00 | 33.18 | A |
| ATOM | 2203 | C | PRO | A | 289 | 17.196 | 20.118 | 45.083 | 1.00 | 33.10 | A |
| ATOM | 2204 | O | PRO | A | 289 | 17.298 | 21.324 | 45.315 | 1.00 | 33.32 | A |
| ATOM | 2205 | N | LEU | A | 290 | 17.988 | 19.206 | 45.641 | 1.00 | 32.89 | A |
| ATOM | 2206 | CA | LEU | A | 290 | 19.047 | 19.580 | 46.577 | 1.00 | 32.40 | A |
| ATOM | 2207 | CB | LEU | A | 290 | 19.289 | 18.457 | 47.596 | 1.00 | 32.52 | A |
| ATOM | 2208 | CG | LEU | A | 290 | 18.136 | 18.060 | 48.524 | 1.00 | 32.73 | A |
| ATOM | 2209 | CD1 | LEU | A | 290 | 18.595 | 16.961 | 49.469 | 1.00 | 32.65 | A |
| ATOM | 2210 | CD2 | LEU | A | 290 | 17.672 | 19.267 | 49.313 | 1.00 | 32.85 | A |
| ATOM | 2211 | C | LEU | A | 290 | 20.351 | 19.887 | 45.852 | 1.00 | 32.01 | A |
| ATOM | 2212 | O | LEU | A | 290 | 21.323 | 20.330 | 46.468 | 1.00 | 31.92 | A |
| ATOM | 2213 | N | GLY | A | 291 | 20.369 | 19.640 | 44.545 | 1.00 | 31.46 | A |
| ATOM | 2214 | CA | GLY | A | 291 | 21.559 | 19.898 | 43.753 | 1.00 | 30.99 | A |
| ATOM | 2215 | C | GLY | A | 291 | 22.663 | 18.874 | 43.948 | 1.00 | 30.50 | A |
| ATOM | 2216 | O | GLY | A | 291 | 23.839 | 19.169 | 43.726 | 1.00 | 30.55 | A |
| ATOM | 2217 | N | ILE | A | 292 | 22.290 | 17.665 | 44.355 | 1.00 | 29.69 | A |
| ATOM | 2218 | CA | ILE | A | 292 | 23.261 | 16.601 | 44.583 | 1.00 | 29.08 | A |
| ATOM | 2219 | CB | ILE | A | 292 | 23.031 | 15.937 | 45.953 | 1.00 | 29.06 | A |
| ATOM | 2220 | CG2 | ILE | A | 292 | 23.989 | 14.764 | 46.135 | 1.00 | 28.81 | A |
| ATOM | 2221 | CG1 | ILE | A | 292 | 23.224 | 16.973 | 47.066 | 1.00 | 28.76 | A |
| ATOM | 2222 | CD1 | ILE | A | 292 | 22.920 | 16.455 | 48.454 | 1.00 | 28.39 | A |
| ATOM | 2223 | C | ILE | A | 292 | 23.189 | 15.530 | 43.499 | 1.00 | 28.90 | A |
| ATOM | 2224 | O | ILE | A | 292 | 22.140 | 14.926 | 43.282 | 1.00 | 28.79 | A |
| ATOM | 2225 | N | SER | A | 293 | 24.312 | 15.302 | 42.821 | 1.00 | 28.59 | A |
| ATOM | 2226 | CA | SER | A | 293 | 24.381 | 14.304 | 41.756 | 1.00 | 28.30 | A |
| ATOM | 2227 | CB | SER | A | 293 | 24.792 | 14.969 | 40.440 | 1.00 | 28.20 | A |
| ATOM | 2228 | OG | SER | A | 293 | 26.091 | 15.529 | 40.548 | 1.00 | 28.70 | A |
| ATOM | 2229 | C | SER | A | 293 | 25.373 | 13.188 | 42.087 | 1.00 | 27.62 | A |
| ATOM | 2230 | O | SER | A | 293 | 25.332 | 12.119 | 41.485 | 1.00 | 27.89 | A |
| ATOM | 2231 | N | ASP | A | 294 | 26.265 | 13.446 | 43.039 | 1.00 | 27.00 | A |
| ATOM | 2232 | CA | ASP | A | 294 | 27.266 | 12.463 | 43.450 | 1.00 | 26.30 | A |
| ATOM | 2233 | CB | ASP | A | 294 | 28.587 | 13.173 | 43.769 | 1.00 | 27.80 | A |
| ATOM | 2234 | CG | ASP | A | 294 | 29.621 | 12.246 | 44.379 | 1.00 | 28.79 | A |
| ATOM | 2235 | OD1 | ASP | A | 294 | 29.606 | 11.037 | 44.063 | 1.00 | 28.85 | A |
| ATOM | 2236 | OD2 | ASP | A | 294 | 30.459 | 12.735 | 45.168 | 1.00 | 30.27 | A |
| ATOM | 2237 | C | ASP | A | 294 | 26.770 | 11.676 | 44.667 | 1.00 | 25.13 | A |
| ATOM | 2238 | O | ASP | A | 294 | 26.850 | 12.151 | 45.797 | 1.00 | 24.51 | A |
| ATOM | 2239 | N | TYR | A | 295 | 26.276 | 10.465 | 44.424 | 1.00 | 23.98 | A |
| ATOM | 2240 | CA | TYR | A | 295 | 25.727 | 9.628 | 45.487 | 1.00 | 22.92 | A |
| ATOM | 2241 | CB | TYR | A | 295 | 24.901 | 8.504 | 44.861 | 1.00 | 23.20 | A |
| ATOM | 2242 | CG | TYR | A | 295 | 23.850 | 9.050 | 43.922 | 1.00 | 23.56 | A |
| ATOM | 2243 | CD1 | TYR | A | 295 | 22.910 | 9.985 | 44.366 | 1.00 | 24.31 | A |
| ATOM | 2244 | CE1 | TYR | A | 295 | 21.984 | 10.552 | 43.491 | 1.00 | 24.25 | A |
| ATOM | 2245 | CD2 | TYR | A | 295 | 23.833 | 8.690 | 42.573 | 1.00 | 24.63 | A |
| ATOM | 2246 | CE2 | TYR | A | 295 | 22.911 | 9.251 | 41.688 | 1.00 | 24.54 | A |
| ATOM | 2247 | CZ | TYR | A | 295 | 21.992 | 10.182 | 42.153 | 1.00 | 24.93 | A |
| ATOM | 2248 | OH | TYR | A | 295 | 21.095 | 10.752 | 41.279 | 1.00 | 24.87 | A |
| ATOM | 2249 | C | TYR | A | 295 | 26.723 | 9.088 | 46.514 | 1.00 | 22.33 | A |
| ATOM | 2250 | O | TYR | A | 295 | 26.338 | 8.392 | 47.455 | 1.00 | 21.89 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 2251 | N | ASN | A | 296 | 28.001 | 9.407 | 46.339 | 1.00 | 21.23 | A |
| ATOM | 2252 | CA | ASN | A | 296 | 29.011 | 8.999 | 47.306 | 1.00 | 20.36 | A |
| ATOM | 2253 | CB | ASN | A | 296 | 30.383 | 8.844 | 46.641 | 1.00 | 21.14 | A |
| ATOM | 2254 | CG | ASN | A | 296 | 30.596 | 7.460 | 46.052 | 1.00 | 20.97 | A |
| ATOM | 2255 | OD1 | ASN | A | 296 | 30.624 | 6.464 | 46.776 | 1.00 | 21.95 | A |
| ATOM | 2256 | ND2 | ASN | A | 296 | 30.749 | 7.392 | 44.735 | 1.00 | 20.64 | A |
| ATOM | 2257 | C | ASN | A | 296 | 29.073 | 10.104 | 48.359 | 1.00 | 19.68 | A |
| ATOM | 2258 | O | ASN | A | 296 | 29.722 | 9.959 | 49.395 | 1.00 | 19.26 | A |
| ATOM | 2259 | N | SER | A | 297 | 28.373 | 11.206 | 48.089 | 1.00 | 19.05 | A |
| ATOM | 2260 | CA | SER | A | 297 | 28.354 | 12.345 | 49.003 | 1.00 | 18.66 | A |
| ATOM | 2261 | CB | SER | A | 297 | 28.379 | 13.659 | 48.209 | 1.00 | 18.96 | A |
| ATOM | 2262 | OG | SER | A | 297 | 27.200 | 13.833 | 47.438 | 1.00 | 20.75 | A |
| ATOM | 2263 | C | SER | A | 297 | 27.196 | 12.379 | 50.006 | 1.00 | 18.07 | A |
| ATOM | 2264 | O | SER | A | 297 | 26.998 | 13.387 | 50.687 | 1.00 | 17.98 | A |
| ATOM | 2265 | N | ILE | A | 298 | 26.435 | 11.292 | 50.101 | 1.00 | 17.31 | A |
| ATOM | 2266 | CA | ILE | A | 298 | 25.312 | 11.216 | 51.046 | 1.00 | 16.71 | A |
| ATOM | 2267 | CB | ILE | A | 298 | 23.949 | 11.279 | 50.305 | 1.00 | 16.38 | A |
| ATOM | 2268 | CG2 | ILE | A | 298 | 23.849 | 12.575 | 49.504 | 1.00 | 16.94 | A |
| ATOM | 2269 | CG1 | ILE | A | 298 | 23.797 | 10.070 | 49.375 | 1.00 | 16.73 | A |
| ATOM | 2270 | CD1 | ILE | A | 298 | 22.459 | 10.005 | 48.652 | 1.00 | 16.32 | A |
| ATOM | 2271 | C | ILE | A | 298 | 25.392 | 9.891 | 51.814 | 1.00 | 16.04 | A |
| ATOM | 2272 | O | ILE | A | 298 | 26.006 | 8.943 | 51.317 | 1.00 | 16.33 | A |
| ATOM | 2273 | N | PHE | A | 299 | 24.810 | 9.819 | 53.018 | 1.00 | 15.01 | A |
| ATOM | 2274 | CA | PHE | A | 299 | 24.843 | 8.556 | 53.759 | 1.00 | 14.11 | A |
| ATOM | 2275 | CB | PHE | A | 299 | 24.851 | 8.754 | 55.292 | 1.00 | 13.75 | A |
| ATOM | 2276 | CG | PHE | A | 299 | 23.689 | 9.547 | 55.850 | 1.00 | 12.78 | A |
| ATOM | 2277 | CD1 | PHE | A | 299 | 23.713 | 10.939 | 55.852 | 1.00 | 12.57 | A |
| ATOM | 2278 | CD2 | PHE | A | 299 | 22.616 | 8.897 | 56.455 | 1.00 | 12.47 | A |
| ATOM | 2279 | CE1 | PHE | A | 299 | 22.687 | 11.674 | 56.458 | 1.00 | 12.78 | A |
| ATOM | 2280 | CE2 | PHE | A | 299 | 21.583 | 9.620 | 57.064 | 1.00 | 12.49 | A |
| ATOM | 2281 | CZ | PHE | A | 299 | 21.620 | 11.012 | 57.066 | 1.00 | 12.45 | A |
| ATOM | 2282 | C | PHE | A | 299 | 23.698 | 7.645 | 53.311 | 1.00 | 14.17 | A |
| ATOM | 2283 | O | PHE | A | 299 | 22.620 | 8.119 | 52.932 | 1.00 | 14.13 | A |
| ATOM | 2284 | N | TRP | A | 300 | 23.953 | 6.338 | 53.347 | 1.00 | 13.43 | A |
| ATOM | 2285 | CA | TRP | A | 300 | 23.012 | 5.330 | 52.863 | 1.00 | 13.55 | A |
| ATOM | 2286 | CB | TRP | A | 300 | 23.689 | 4.499 | 51.756 | 1.00 | 13.64 | A |
| ATOM | 2287 | CG | TRP | A | 300 | 23.741 | 5.128 | 50.398 | 1.00 | 14.19 | A |
| ATOM | 2288 | CD2 | TRP | A | 300 | 22.917 | 4.794 | 49.275 | 1.00 | 14.07 | A |
| ATOM | 2289 | CE2 | TRP | A | 300 | 23.295 | 5.642 | 48.212 | 1.00 | 14.33 | A |
| ATOM | 2290 | CE3 | TRP | A | 300 | 21.888 | 3.861 | 49.067 | 1.00 | 14.36 | A |
| ATOM | 2291 | CD1 | TRP | A | 300 | 24.568 | 6.134 | 49.981 | 1.00 | 14.12 | A |
| ATOM | 2292 | NE1 | TRP | A | 300 | 24.305 | 6.447 | 48.669 | 1.00 | 14.30 | A |
| ATOM | 2293 | CZ2 | TRP | A | 300 | 22.683 | 5.585 | 46.953 | 1.00 | 14.52 | A |
| ATOM | 2294 | CZ3 | TRP | A | 300 | 21.278 | 3.805 | 47.813 | 1.00 | 14.75 | A |
| ATOM | 2295 | CH2 | TRP | A | 300 | 21.679 | 4.665 | 46.774 | 1.00 | 14.61 | A |
| ATOM | 2296 | C | TRP | A | 300 | 22.394 | 4.327 | 53.840 | 1.00 | 12.97 | A |
| ATOM | 2297 | O | TRP | A | 300 | 23.067 | 3.808 | 54.733 | 1.00 | 13.38 | A |
| ATOM | 2298 | N | ILE | A | 301 | 21.109 | 4.050 | 53.631 | 1.00 | 12.82 | A |
| ATOM | 2299 | CA | ILE | A | 301 | 20.370 | 3.041 | 54.389 | 1.00 | 12.85 | A |
| ATOM | 2300 | CB | ILE | A | 301 | 19.465 | 3.629 | 55.510 | 1.00 | 12.55 | A |
| ATOM | 2301 | CG2 | ILE | A | 301 | 18.614 | 2.508 | 56.122 | 1.00 | 12.29 | A |
| ATOM | 2302 | CG1 | ILE | A | 301 | 20.311 | 4.266 | 56.620 | 1.00 | 12.45 | A |
| ATOM | 2303 | CD1 | ILE | A | 301 | 20.591 | 5.741 | 56.412 | 1.00 | 11.84 | A |
| ATOM | 2304 | C | ILE | A | 301 | 19.471 | 2.341 | 53.356 | 1.00 | 13.12 | A |
| ATOM | 2305 | O | ILE | A | 301 | 18.549 | 2.951 | 52.806 | 1.00 | 13.40 | A |
| ATOM | 2306 | N | ALA | A | 302 | 19.754 | 1.072 | 53.073 | 1.00 | 13.05 | A |
| ATOM | 2307 | CA | ALA | A | 302 | 18.965 | 0.321 | 52.093 | 1.00 | 13.27 | A |
| ATOM | 2308 | CB | ALA | A | 302 | 19.806 | 0.064 | 50.836 | 1.00 | 13.42 | A |
| ATOM | 2309 | C | ALA | A | 302 | 18.462 | −1.006 | 52.658 | 1.00 | 13.08 | A |
| ATOM | 2310 | O | ALA | A | 302 | 19.217 | −1.741 | 53.295 | 1.00 | 13.86 | A |
| ATOM | 2311 | N | HIS | A | 303 | 17.188 | −1.313 | 52.425 | 1.00 | 12.38 | A |
| ATOM | 2312 | CA | HIS | A | 303 | 16.613 | −2.566 | 52.905 | 1.00 | 12.20 | A |
| ATOM | 2313 | CB | HIS | A | 303 | 15.131 | −2.673 | 52.516 | 1.00 | 11.11 | A |
| ATOM | 2314 | CG | HIS | A | 303 | 14.535 | −4.016 | 52.809 | 1.00 | 10.71 | A |
| ATOM | 2315 | CD2 | HIS | A | 303 | 14.074 | −4.986 | 51.983 | 1.00 | 10.88 | A |
| ATOM | 2316 | ND1 | HIS | A | 303 | 14.422 | −4.518 | 54.088 | 1.00 | 11.15 | A |
| ATOM | 2317 | CE1 | HIS | A | 303 | 13.918 | −5.739 | 54.039 | 1.00 | 10.53 | A |
| ATOM | 2318 | NE2 | HIS | A | 303 | 13.699 | −6.047 | 52.773 | 1.00 | 10.34 | A |
| ATOM | 2319 | C | HIS | A | 303 | 17.390 | −3.732 | 52.295 | 1.00 | 12.67 | A |
| ATOM | 2320 | O | HIS | A | 303 | 17.415 | −3.901 | 51.076 | 1.00 | 12.89 | A |
| ATOM | 2321 | N | PRO | A | 304 | 18.033 | −4.558 | 53.137 | 1.00 | 13.61 | A |
| ATOM | 2322 | CD | PRO | A | 304 | 18.161 | −4.439 | 54.602 | 1.00 | 14.16 | A |
| ATOM | 2323 | CA | PRO | A | 304 | 18.808 | −5.698 | 52.638 | 1.00 | 14.34 | A |
| ATOM | 2324 | CB | PRO | A | 304 | 19.786 | −5.950 | 53.774 | 1.00 | 14.36 | A |
| ATOM | 2325 | CG | PRO | A | 304 | 18.916 | −5.711 | 54.973 | 1.00 | 14.60 | A |

APPENDIX C-continued

18xCHS Mutant

| ATOM | # | TYPE | RES | | | X | Y | Z | OCC | B | |
|------|---|------|-----|---|---|---|---|---|-----|---|---|
| ATOM | 2326 | C | PRO | A | 304 | 17.956 | −6.929 | 52.324 | 1.00 | 14.55 | A |
| ATOM | 2327 | O | PRO | A | 304 | 18.096 | −7.965 | 52.972 | 1.00 | 15.04 | A |
| ATOM | 2328 | N | GLY | A | 305 | 17.077 | −6.809 | 51.331 | 1.00 | 14.61 | A |
| ATOM | 2329 | CA | GLY | A | 305 | 16.224 | −7.925 | 50.966 | 1.00 | 14.76 | A |
| ATOM | 2330 | C | GLY | A | 305 | 17.055 | −9.156 | 50.666 | 1.00 | 15.27 | A |
| ATOM | 2331 | O | GLY | A | 305 | 16.671 | −10.275 | 51.006 | 1.00 | 15.14 | A |
| ATOM | 2332 | N | GLY | A | 306 | 18.199 | −8.938 | 50.027 | 1.00 | 15.34 | A |
| ATOM | 2333 | CA | GLY | A | 306 | 19.102 | −10.025 | 49.678 | 1.00 | 16.49 | A |
| ATOM | 2334 | C | GLY | A | 306 | 20.457 | −9.455 | 49.307 | 1.00 | 16.93 | A |
| ATOM | 2335 | O | GLY | A | 306 | 20.564 | −8.249 | 49.082 | 1.00 | 17.30 | A |
| ATOM | 2336 | N | PRO | A | 307 | 21.515 | −10.278 | 49.228 | 1.00 | 17.46 | A |
| ATOM | 2337 | CD | PRO | A | 307 | 21.579 | −11.730 | 49.472 | 1.00 | 18.01 | A |
| ATOM | 2338 | CA | PRO | A | 307 | 22.836 | −9.748 | 48.874 | 1.00 | 18.03 | A |
| ATOM | 2339 | CB | PRO | A | 307 | 23.761 | −10.938 | 49.126 | 1.00 | 18.12 | A |
| ATOM | 2340 | CG | PRO | A | 307 | 22.891 | −12.109 | 48.814 | 1.00 | 18.51 | A |
| ATOM | 2341 | C | PRO | A | 307 | 22.949 | −9.212 | 47.444 | 1.00 | 18.05 | A |
| ATOM | 2342 | O | PRO | A | 307 | 23.710 | −8.272 | 47.184 | 1.00 | 17.85 | A |
| ATOM | 2343 | N | ALA | A | 308 | 22.191 | −9.803 | 46.524 | 1.00 | 17.71 | A |
| ATOM | 2344 | CA | ALA | A | 308 | 22.224 | −9.383 | 45.126 | 1.00 | 18.01 | A |
| ATOM | 2345 | CB | ALA | A | 308 | 21.413 | −10.347 | 44.269 | 1.00 | 18.21 | A |
| ATOM | 2346 | C | ALA | A | 308 | 21.715 | −7.956 | 44.926 | 1.00 | 18.23 | A |
| ATOM | 2347 | O | ALA | A | 308 | 22.236 | −7.219 | 44.085 | 1.00 | 18.16 | A |
| ATOM | 2348 | N | ILE | A | 309 | 20.691 | −7.569 | 45.681 | 1.00 | 17.84 | A |
| ATOM | 2349 | CA | ILE | A | 309 | 20.155 | −6.217 | 45.561 | 1.00 | 17.99 | A |
| ATOM | 2350 | CB | ILE | A | 309 | 18.928 | −6.011 | 46.480 | 1.00 | 18.26 | A |
| ATOM | 2351 | CG2 | ILE | A | 309 | 18.527 | −4.541 | 46.488 | 1.00 | 18.23 | A |
| ATOM | 2352 | CG1 | ILE | A | 309 | 17.771 | −6.893 | 45.999 | 1.00 | 18.73 | A |
| ATOM | 2353 | CD1 | ILE | A | 309 | 16.508 | −6.785 | 46.833 | 1.00 | 19.58 | A |
| ATOM | 2354 | C | ILE | A | 309 | 21.238 | −5.204 | 45.925 | 1.00 | 17.80 | A |
| ATOM | 2355 | O | ILE | A | 309 | 21.412 | −4.191 | 45.243 | 1.00 | 17.95 | A |
| ATOM | 2356 | N | LEU | A | 310 | 21.978 | −5.488 | 46.992 | 1.00 | 17.66 | A |
| ATOM | 2357 | CA | LEU | A | 310 | 23.051 | −4.600 | 47.428 | 1.00 | 17.75 | A |
| ATOM | 2358 | CB | LEU | A | 310 | 23.611 | −5.070 | 48.774 | 1.00 | 17.50 | A |
| ATOM | 2359 | CG | LEU | A | 310 | 22.609 | −5.217 | 49.926 | 1.00 | 17.03 | A |
| ATOM | 2360 | CD1 | LEU | A | 310 | 23.348 | −5.610 | 51.199 | 1.00 | 16.69 | A |
| ATOM | 2361 | CD2 | LEU | A | 310 | 21.863 | −3.908 | 50.138 | 1.00 | 17.12 | A |
| ATOM | 2362 | C | LEU | A | 310 | 24.182 | −4.513 | 46.392 | 1.00 | 18.34 | A |
| ATOM | 2363 | O | LEU | A | 310 | 24.685 | −3.422 | 46.102 | 1.00 | 17.54 | A |
| ATOM | 2364 | N | ASP | A | 311 | 24.578 | −5.655 | 45.832 | 1.00 | 18.40 | A |
| ATOM | 2365 | CA | ASP | A | 311 | 25.645 | −5.673 | 44.829 | 1.00 | 19.39 | A |
| ATOM | 2366 | CB | ASP | A | 311 | 25.973 | −7.107 | 44.384 | 1.00 | 19.51 | A |
| ATOM | 2367 | CG | ASP | A | 311 | 26.604 | −7.945 | 45.483 | 1.00 | 20.61 | A |
| ATOM | 2368 | OD1 | ASP | A | 311 | 27.210 | −7.374 | 46.416 | 1.00 | 20.57 | A |
| ATOM | 2369 | OD2 | ASP | A | 311 | 26.509 | −9.189 | 45.395 | 1.00 | 21.12 | A |
| ATOM | 2370 | C | ASP | A | 311 | 25.273 | −4.860 | 43.588 | 1.00 | 19.57 | A |
| ATOM | 2371 | O | ASP | A | 311 | 26.079 | −4.072 | 43.090 | 1.00 | 19.38 | A |
| ATOM | 2372 | N | GLN | A | 312 | 24.057 | −5.059 | 43.086 | 1.00 | 20.06 | A |
| ATOM | 2373 | CA | GLN | A | 312 | 23.604 | −4.351 | 41.890 | 1.00 | 20.92 | A |
| ATOM | 2374 | CB | GLN | A | 312 | 22.336 | −5.011 | 41.331 | 1.00 | 21.67 | A |
| ATOM | 2375 | CG | GLN | A | 312 | 22.644 | −6.263 | 40.511 | 1.00 | 22.92 | A |
| ATOM | 2376 | CD | GLN | A | 312 | 21.408 | −6.980 | 40.001 | 1.00 | 23.83 | A |
| ATOM | 2377 | OE1 | GLN | A | 312 | 20.503 | −6.365 | 39.435 | 1.00 | 24.46 | A |
| ATOM | 2378 | NE2 | GLN | A | 312 | 21.372 | −8.297 | 40.187 | 1.00 | 24.27 | A |
| ATOM | 2379 | C | GLN | A | 312 | 23.389 | −2.856 | 42.106 | 1.00 | 21.43 | A |
| ATOM | 2380 | O | GLN | A | 312 | 23.610 | −2.054 | 41.193 | 1.00 | 21.12 | A |
| ATOM | 2381 | N | VAL | A | 313 | 22.964 | −2.472 | 43.304 | 1.00 | 21.36 | A |
| ATOM | 2382 | CA | VAL | A | 313 | 22.772 | −1.056 | 43.593 | 1.00 | 22.26 | A |
| ATOM | 2383 | CB | VAL | A | 313 | 22.064 | −0.847 | 44.958 | 1.00 | 21.61 | A |
| ATOM | 2384 | CG1 | VAL | A | 313 | 22.126 | 0.618 | 45.368 | 1.00 | 21.70 | A |
| ATOM | 2385 | CG2 | VAL | A | 313 | 20.610 | −1.280 | 44.856 | 1.00 | 21.27 | A |
| ATOM | 2386 | C | VAL | A | 313 | 24.152 | −0.399 | 43.620 | 1.00 | 22.76 | A |
| ATOM | 2387 | O | VAL | A | 313 | 24.365 | 0.652 | 43.016 | 1.00 | 22.83 | A |
| ATOM | 2388 | N | GLU | A | 314 | 25.090 | −1.044 | 44.306 | 1.00 | 23.89 | A |
| ATOM | 2389 | CA | GLU | A | 314 | 26.452 | −0.539 | 44.423 | 1.00 | 24.82 | A |
| ATOM | 2390 | CB | GLU | A | 314 | 27.285 | −1.490 | 45.290 | 1.00 | 26.33 | A |
| ATOM | 2391 | CG | GLU | A | 314 | 28.633 | −0.930 | 45.720 | 1.00 | 28.97 | A |
| ATOM | 2392 | CD | GLU | A | 314 | 29.345 | −1.809 | 46.737 | 1.00 | 30.11 | A |
| ATOM | 2393 | OE1 | GLU | A | 314 | 28.730 | −2.158 | 47.768 | 1.00 | 30.61 | A |
| ATOM | 2394 | OE2 | GLU | A | 314 | 30.528 | −2.141 | 46.511 | 1.00 | 31.99 | A |
| ATOM | 2395 | C | GLU | A | 314 | 27.107 | −0.370 | 43.046 | 1.00 | 25.07 | A |
| ATOM | 2396 | O | GLU | A | 314 | 27.788 | 0.627 | 42.790 | 1.00 | 24.35 | A |
| ATOM | 2397 | N | GLN | A | 315 | 26.893 | −1.339 | 42.162 | 1.00 | 24.83 | A |
| ATOM | 2398 | CA | GLN | A | 315 | 27.472 | −1.280 | 40.823 | 1.00 | 25.91 | A |
| ATOM | 2399 | CB | GLN | A | 315 | 27.421 | −2.664 | 40.165 | 1.00 | 26.90 | A |
| ATOM | 2400 | CG | GLN | A | 315 | 28.328 | −3.678 | 40.846 | 1.00 | 29.10 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 2401 | CD | GLN | A | 315 | 28.375 | −5.012 | 40.128 | 1.00 | 31.04 | A |
| ATOM | 2402 | OE1 | GLN | A | 315 | 28.733 | −5.083 | 38.949 | 1.00 | 32.27 | A |
| ATOM | 2403 | NE2 | GLN | A | 315 | 28.019 | −6.083 | 40.838 | 1.00 | 31.39 | A |
| ATOM | 2404 | C | GLN | A | 315 | 26.787 | −0.250 | 39.928 | 1.00 | 25.61 | A |
| ATOM | 2405 | O | GLN | A | 315 | 27.448 | 0.453 | 39.166 | 1.00 | 25.64 | A |
| ATOM | 2406 | N | LYS | A | 316 | 25.464 | −0.161 | 40.030 | 1.00 | 25.14 | A |
| ATOM | 2407 | CA | LYS | A | 316 | 24.683 | 0.781 | 39.232 | 1.00 | 25.04 | A |
| ATOM | 2408 | CB | LYS | A | 316 | 23.187 | 0.591 | 39.524 | 1.00 | 26.09 | A |
| ATOM | 2409 | CG | LYS | A | 316 | 22.251 | 1.622 | 38.882 | 1.00 | 26.89 | A |
| ATOM | 2410 | CD | LYS | A | 316 | 21.711 | 1.164 | 37.528 | 1.00 | 27.90 | A |
| ATOM | 2411 | CE | LYS | A | 316 | 22.772 | 1.182 | 36.447 | 1.00 | 28.93 | A |
| ATOM | 2412 | NZ | LYS | A | 316 | 22.266 | 0.658 | 35.140 | 1.00 | 27.99 | A |
| ATOM | 2413 | C | LYS | A | 316 | 25.069 | 2.238 | 39.489 | 1.00 | 24.49 | A |
| ATOM | 2414 | O | LYS | A | 316 | 25.110 | 3.046 | 38.561 | 1.00 | 24.40 | A |
| ATOM | 2415 | N | LEU | A | 317 | 25.361 | 2.571 | 40.744 | 1.00 | 23.79 | A |
| ATOM | 2416 | CA | LEU | A | 317 | 25.712 | 3.941 | 41.112 | 1.00 | 23.24 | A |
| ATOM | 2417 | CB | LEU | A | 317 | 24.917 | 4.344 | 42.356 | 1.00 | 23.11 | A |
| ATOM | 2418 | CG | LEU | A | 317 | 23.407 | 4.110 | 42.247 | 1.00 | 22.79 | A |
| ATOM | 2419 | CD1 | LEU | A | 317 | 22.780 | 4.131 | 43.631 | 1.00 | 22.84 | A |
| ATOM | 2420 | CD2 | LEU | A | 317 | 22.786 | 5.164 | 41.335 | 1.00 | 22.52 | A |
| ATOM | 2421 | C | LEU | A | 317 | 27.204 | 4.175 | 41.361 | 1.00 | 23.10 | A |
| ATOM | 2422 | O | LEU | A | 317 | 27.602 | 5.265 | 41.773 | 1.00 | 23.32 | A |
| ATOM | 2423 | N | ALA | A | 318 | 28.021 | 3.156 | 41.115 | 1.00 | 22.49 | A |
| ATOM | 2424 | CA | ALA | A | 318 | 29.466 | 3.253 | 41.314 | 1.00 | 22.25 | A |
| ATOM | 2425 | CB | ALA | A | 318 | 30.080 | 4.152 | 40.238 | 1.00 | 22.73 | A |
| ATOM | 2426 | C | ALA | A | 318 | 29.823 | 3.781 | 42.705 | 1.00 | 22.10 | A |
| ATOM | 2427 | O | ALA | A | 318 | 30.592 | 4.735 | 42.837 | 1.00 | 21.67 | A |
| ATOM | 2428 | N | LEU | A | 319 | 29.271 | 3.148 | 43.738 | 1.00 | 21.00 | A |
| ATOM | 2429 | CA | LEU | A | 319 | 29.519 | 3.546 | 45.122 | 1.00 | 20.63 | A |
| ATOM | 2430 | CB | LEU | A | 319 | 28.350 | 3.104 | 46.010 | 1.00 | 20.00 | A |
| ATOM | 2431 | CG | LEU | A | 319 | 26.936 | 3.586 | 45.666 | 1.00 | 19.28 | A |
| ATOM | 2432 | CD1 | LEU | A | 319 | 25.935 | 2.999 | 46.661 | 1.00 | 19.38 | A |
| ATOM | 2433 | CD2 | LEU | A | 319 | 26.888 | 5.099 | 45.699 | 1.00 | 18.96 | A |
| ATOM | 2434 | C | LEU | A | 319 | 30.808 | 2.944 | 45.688 | 1.00 | 21.45 | A |
| ATOM | 2435 | O | LEU | A | 319 | 31.163 | 1.814 | 45.366 | 1.00 | 20.80 | A |
| ATOM | 2436 | N | LYS | A | 320 | 31.498 | 3.699 | 46.541 | 1.00 | 21.99 | A |
| ATOM | 2437 | CA | LYS | A | 320 | 32.717 | 3.203 | 47.173 | 1.00 | 23.22 | A |
| ATOM | 2438 | CB | LYS | A | 320 | 33.413 | 4.315 | 47.966 | 1.00 | 24.04 | A |
| ATOM | 2439 | CG | LYS | A | 320 | 33.695 | 5.585 | 47.170 | 1.00 | 26.42 | A |
| ATOM | 2440 | CD | LYS | A | 320 | 34.439 | 6.616 | 48.014 | 1.00 | 27.32 | A |
| ATOM | 2441 | CE | LYS | A | 320 | 34.260 | 8.023 | 47.455 | 1.00 | 28.64 | A |
| ATOM | 2442 | NZ | LYS | A | 320 | 34.606 | 8.111 | 46.002 | 1.00 | 29.29 | A |
| ATOM | 2443 | C | LYS | A | 320 | 32.283 | 2.086 | 48.128 | 1.00 | 23.17 | A |
| ATOM | 2444 | O | LYS | A | 320 | 31.162 | 2.097 | 48.634 | 1.00 | 23.14 | A |
| ATOM | 2445 | N | PRO | A | 321 | 33.167 | 1.114 | 48.392 | 1.00 | 23.18 | A |
| ATOM | 2446 | CD | PRO | A | 321 | 34.535 | 0.975 | 47.858 | 1.00 | 23.17 | A |
| ATOM | 2447 | CA | PRO | A | 321 | 32.842 | −0.001 | 49.291 | 1.00 | 23.00 | A |
| ATOM | 2448 | CB | PRO | A | 321 | 34.174 | −0.738 | 49.416 | 1.00 | 23.25 | A |
| ATOM | 2449 | CG | PRO | A | 321 | 34.812 | −0.495 | 48.077 | 1.00 | 23.67 | A |
| ATOM | 2450 | C | PRO | A | 321 | 32.280 | 0.405 | 50.655 | 1.00 | 22.40 | A |
| ATOM | 2451 | O | PRO | A | 321 | 31.373 | −0.239 | 51.182 | 1.00 | 21.92 | A |
| ATOM | 2452 | N | GLU | A | 322 | 32.813 | 1.482 | 51.214 | 1.00 | 22.04 | A |
| ATOM | 2453 | CA | GLU | A | 322 | 32.391 | 1.954 | 52.528 | 1.00 | 21.71 | A |
| ATOM | 2454 | CB | GLU | A | 322 | 33.316 | 3.088 | 52.988 | 1.00 | 23.36 | A |
| ATOM | 2455 | CG | GLU | A | 322 | 34.795 | 2.845 | 52.720 | 1.00 | 26.98 | A |
| ATOM | 2456 | CD | GLU | A | 322 | 35.132 | 2.879 | 51.241 | 1.00 | 28.13 | A |
| ATOM | 2457 | OE1 | GLU | A | 322 | 34.883 | 3.918 | 50.596 | 1.00 | 30.06 | A |
| ATOM | 2458 | OE2 | GLU | A | 322 | 35.640 | 1.867 | 50.720 | 1.00 | 30.37 | A |
| ATOM | 2459 | C | GLU | A | 322 | 30.934 | 2.429 | 52.631 | 1.00 | 20.23 | A |
| ATOM | 2460 | O | GLU | A | 322 | 30.368 | 2.439 | 53.720 | 1.00 | 19.87 | A |
| ATOM | 2461 | N | LYS | A | 323 | 30.326 | 2.821 | 51.515 | 1.00 | 19.09 | A |
| ATOM | 2462 | CA | LYS | A | 323 | 28.946 | 3.314 | 51.555 | 1.00 | 18.24 | A |
| ATOM | 2463 | CB | LYS | A | 323 | 28.468 | 3.697 | 50.148 | 1.00 | 17.68 | A |
| ATOM | 2464 | CG | LYS | A | 323 | 29.359 | 4.719 | 49.423 | 1.00 | 17.88 | A |
| ATOM | 2465 | CD | LYS | A | 323 | 29.670 | 5.951 | 50.275 | 1.00 | 18.08 | A |
| ATOM | 2466 | CE | LYS | A | 323 | 28.407 | 6.688 | 50.708 | 1.00 | 17.75 | A |
| ATOM | 2467 | NZ | LYS | A | 323 | 28.711 | 7.892 | 51.538 | 1.00 | 18.08 | A |
| ATOM | 2468 | C | LYS | A | 323 | 27.949 | 2.330 | 52.186 | 1.00 | 18.18 | A |
| ATOM | 2469 | O | LYS | A | 323 | 27.091 | 2.727 | 52.980 | 1.00 | 17.44 | A |
| ATOM | 2470 | N | MET | A | 324 | 28.072 | 1.050 | 51.843 | 1.00 | 17.79 | A |
| ATOM | 2471 | CA | MET | A | 324 | 27.168 | 0.022 | 52.362 | 1.00 | 17.73 | A |
| ATOM | 2472 | CB | MET | A | 324 | 26.926 | −1.049 | 51.290 | 1.00 | 17.86 | A |
| ATOM | 2473 | CG | MET | A | 324 | 26.067 | −0.601 | 50.116 | 1.00 | 18.32 | A |
| ATOM | 2474 | SD | MET | A | 324 | 24.323 | −0.405 | 50.580 | 1.00 | 19.61 | A |
| ATOM | 2475 | CE | MET | A | 324 | 23.587 | 0.034 | 48.988 | 1.00 | 18.17 | A |

APPENDIX C-continued

18xCHS Mutant

| ATOM | # | TYPE | RES | | | X | Y | Z | OCC | B | |
|------|---|------|-----|---|---|---|---|---|-----|---|---|
| ATOM | 2476 | C | MET | A | 324 | 27.619 | −0.658 | 53.657 | 1.00 | 17.26 | A |
| ATOM | 2477 | O | MET | A | 324 | 27.054 | −1.685 | 54.044 | 1.00 | 17.39 | A |
| ATOM | 2478 | N | ASN | A | 325 | 28.620 | −0.099 | 54.332 | 1.00 | 17.04 | A |
| ATOM | 2479 | CA | ASN | A | 325 | 29.105 | −0.689 | 55.578 | 1.00 | 16.26 | A |
| ATOM | 2480 | CB | ASN | A | 325 | 30.138 | 0.227 | 56.249 | 1.00 | 16.89 | A |
| ATOM | 2481 | CG | ASN | A | 325 | 31.544 | 0.043 | 55.694 | 1.00 | 17.31 | A |
| ATOM | 2482 | OD1 | ASN | A | 325 | 31.792 | −0.825 | 54.856 | 1.00 | 17.48 | A |
| ATOM | 2483 | ND2 | ASN | A | 325 | 32.475 | 0.865 | 56.170 | 1.00 | 16.86 | A |
| ATOM | 2484 | C | ASN | A | 325 | 27.996 | −1.000 | 56.592 | 1.00 | 15.84 | A |
| ATOM | 2485 | O | ASN | A | 325 | 27.873 | −2.134 | 57.061 | 1.00 | 15.57 | A |
| ATOM | 2486 | N | ALA | A | 326 | 27.194 | 0.006 | 56.931 | 1.00 | 14.81 | A |
| ATOM | 2487 | CA | ALA | A | 326 | 26.127 | −0.162 | 57.918 | 1.00 | 14.14 | A |
| ATOM | 2488 | CB | ALA | A | 326 | 25.499 | 1.199 | 58.243 | 1.00 | 14.41 | A |
| ATOM | 2489 | C | ALA | A | 326 | 25.043 | −1.152 | 57.501 | 1.00 | 14.35 | A |
| ATOM | 2490 | O | ALA | A | 326 | 24.589 | −1.967 | 58.313 | 1.00 | 14.78 | A |
| ATOM | 2491 | N | THR | A | 327 | 24.635 | −1.079 | 56.241 | 1.00 | 13.41 | A |
| ATOM | 2492 | CA | THR | A | 327 | 23.605 | −1.962 | 55.713 | 1.00 | 13.87 | A |
| ATOM | 2493 | CB | THR | A | 327 | 23.242 | −1.569 | 54.259 | 1.00 | 13.38 | A |
| ATOM | 2494 | OG1 | THR | A | 327 | 22.655 | −0.256 | 54.253 | 1.00 | 13.83 | A |
| ATOM | 2495 | CG2 | THR | A | 327 | 22.253 | −2.570 | 53.657 | 1.00 | 13.68 | A |
| ATOM | 2496 | C | THR | A | 327 | 24.072 | −3.421 | 55.753 | 1.00 | 14.01 | A |
| ATOM | 2497 | O | THR | A | 327 | 23.371 | −4.288 | 56.279 | 1.00 | 13.75 | A |
| ATOM | 2498 | N | ARG | A | 328 | 25.259 | −3.682 | 55.211 | 1.00 | 14.33 | A |
| ATOM | 2499 | CA | ARG | A | 328 | 25.814 | −5.040 | 55.182 | 1.00 | 14.77 | A |
| ATOM | 2500 | CB | ARG | A | 328 | 27.082 | −5.080 | 54.316 | 1.00 | 15.22 | A |
| ATOM | 2501 | CG | ARG | A | 328 | 26.835 | −4.886 | 52.812 | 1.00 | 16.37 | A |
| ATOM | 2502 | CD | ARG | A | 328 | 28.148 | −4.913 | 52.021 | 1.00 | 18.14 | A |
| ATOM | 2503 | NE | ARG | A | 328 | 27.969 | −4.631 | 50.597 | 1.00 | 19.53 | A |
| ATOM | 2504 | CZ | ARG | A | 328 | 27.457 | −5.483 | 49.715 | 1.00 | 20.66 | A |
| ATOM | 2505 | NH1 | ARG | A | 328 | 27.064 | −6.689 | 50.102 | 1.00 | 22.08 | A |
| ATOM | 2506 | NH2 | ARG | A | 328 | 27.345 | −5.136 | 48.439 | 1.00 | 21.33 | A |
| ATOM | 2507 | C | ARG | A | 328 | 26.116 | −5.620 | 56.573 | 1.00 | 15.06 | A |
| ATOM | 2508 | O | ARG | A | 328 | 26.114 | −6.836 | 56.748 | 1.00 | 15.82 | A |
| ATOM | 2509 | N | GLU | A | 329 | 26.381 | −4.762 | 57.555 | 1.00 | 14.77 | A |
| ATOM | 2510 | CA | GLU | A | 329 | 26.651 | −5.229 | 58.918 | 1.00 | 14.81 | A |
| ATOM | 2511 | CB | GLU | A | 329 | 27.125 | −4.067 | 59.799 | 1.00 | 15.33 | A |
| ATOM | 2512 | CG | GLU | A | 329 | 27.244 | −4.379 | 61.293 | 1.00 | 17.33 | A |
| ATOM | 2513 | CD | GLU | A | 329 | 28.431 | −5.268 | 61.645 | 1.00 | 18.89 | A |
| ATOM | 2514 | OE1 | GLU | A | 329 | 29.282 | −5.523 | 60.764 | 1.00 | 18.54 | A |
| ATOM | 2515 | OE2 | GLU | A | 329 | 28.519 | −5.702 | 62.818 | 1.00 | 20.32 | A |
| ATOM | 2516 | C | GLU | A | 329 | 25.378 | −5.840 | 59.509 | 1.00 | 14.36 | A |
| ATOM | 2517 | O | GLU | A | 329 | 25.425 | −6.885 | 60.163 | 1.00 | 13.91 | A |
| ATOM | 2518 | N | VAL | A | 330 | 24.243 | −5.185 | 59.278 | 1.00 | 13.59 | A |
| ATOM | 2519 | CA | VAL | A | 330 | 22.965 | −5.676 | 59.785 | 1.00 | 14.02 | A |
| ATOM | 2520 | CB | VAL | A | 330 | 21.856 | −4.604 | 59.629 | 1.00 | 13.99 | A |
| ATOM | 2521 | CG1 | VAL | A | 330 | 20.484 | −5.196 | 59.968 | 1.00 | 13.58 | A |
| ATOM | 2522 | CG2 | VAL | A | 330 | 22.157 | −3.425 | 60.556 | 1.00 | 14.00 | A |
| ATOM | 2523 | C | VAL | A | 330 | 22.549 | −6.968 | 59.077 | 1.00 | 14.02 | A |
| ATOM | 2524 | O | VAL | A | 330 | 22.062 | −7.899 | 59.721 | 1.00 | 13.94 | A |
| ATOM | 2525 | N | LEU | A | 331 | 22.738 | −7.029 | 57.759 | 1.00 | 13.64 | A |
| ATOM | 2526 | CA | LEU | A | 331 | 22.399 | −8.237 | 57.005 | 1.00 | 13.71 | A |
| ATOM | 2527 | CB | LEU | A | 331 | 22.655 | −8.037 | 55.502 | 1.00 | 14.19 | A |
| ATOM | 2528 | CG | LEU | A | 331 | 22.547 | −9.303 | 54.637 | 1.00 | 13.98 | A |
| ATOM | 2529 | CD1 | LEU | A | 331 | 21.135 | −9.876 | 54.726 | 1.00 | 13.96 | A |
| ATOM | 2530 | CD2 | LEU | A | 331 | 22.894 | −8.988 | 53.189 | 1.00 | 14.69 | A |
| ATOM | 2531 | C | LEU | A | 331 | 23.262 | −9.397 | 57.501 | 1.00 | 14.26 | A |
| ATOM | 2532 | O | LEU | A | 331 | 22.792 | −10.527 | 57.647 | 1.00 | 13.37 | A |
| ATOM | 2533 | N | SER | A | 332 | 24.531 | −9.099 | 57.760 | 1.00 | 15.11 | A |
| ATOM | 2534 | CA | SER | A | 332 | 25.485 | −10.097 | 58.225 | 1.00 | 16.35 | A |
| ATOM | 2535 | CB | SER | A | 332 | 26.903 | −9.509 | 58.174 | 1.00 | 17.12 | A |
| ATOM | 2536 | OG | SER | A | 332 | 27.870 | −10.444 | 58.619 | 1.00 | 19.44 | A |
| ATOM | 2537 | C | SER | A | 332 | 25.180 | −10.602 | 59.638 | 1.00 | 16.20 | A |
| ATOM | 2538 | O | SER | A | 332 | 25.254 | −11.799 | 59.902 | 1.00 | 16.47 | A |
| ATOM | 2539 | N | GLU | A | 333 | 24.821 | −9.689 | 60.536 | 1.00 | 15.96 | A |
| ATOM | 2540 | CA | GLU | A | 333 | 24.537 | −10.040 | 61.929 | 1.00 | 15.99 | A |
| ATOM | 2541 | CB | GLU | A | 333 | 24.922 | −8.872 | 62.848 | 1.00 | 17.32 | A |
| ATOM | 2542 | CG | GLU | A | 333 | 26.411 | −8.541 | 62.897 | 1.00 | 20.64 | A |
| ATOM | 2543 | CD | GLU | A | 333 | 27.242 | −9.659 | 63.496 | 1.00 | 22.34 | A |
| ATOM | 2544 | OE1 | GLU | A | 333 | 26.931 | −10.096 | 64.625 | 1.00 | 23.49 | A |
| ATOM | 2545 | OE2 | GLU | A | 333 | 28.211 | −10.096 | 62.843 | 1.00 | 23.53 | A |
| ATOM | 2546 | C | GLU | A | 333 | 23.105 | −10.454 | 62.279 | 1.00 | 14.90 | A |
| ATOM | 2547 | O | GLU | A | 333 | 22.887 | −11.062 | 63.328 | 1.00 | 14.01 | A |
| ATOM | 2548 | N | TYR | A | 334 | 22.135 | −10.144 | 61.421 | 1.00 | 13.81 | A |
| ATOM | 2549 | CA | TYR | A | 334 | 20.735 | −10.455 | 61.740 | 1.00 | 13.26 | A |
| ATOM | 2550 | CB | TYR | A | 334 | 20.031 | −9.174 | 62.216 | 1.00 | 13.56 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 2551 | CG | TYR | A | 334 | 20.683 | −8.494 | 63.398 | 1.00 | 14.44 | A |
| ATOM | 2552 | CD1 | TYR | A | 334 | 20.558 | −9.018 | 64.686 | 1.00 | 15.41 | A |
| ATOM | 2553 | CE1 | TYR | A | 334 | 21.191 | −8.413 | 65.774 | 1.00 | 16.14 | A |
| ATOM | 2554 | CD2 | TYR | A | 334 | 21.455 | −7.342 | 63.225 | 1.00 | 14.72 | A |
| ATOM | 2555 | CE2 | TYR | A | 334 | 22.088 | −6.729 | 64.303 | 1.00 | 15.69 | A |
| ATOM | 2556 | CZ | TYR | A | 334 | 21.954 | −7.270 | 65.572 | 1.00 | 16.75 | A |
| ATOM | 2557 | OH | TYR | A | 334 | 22.584 | −6.668 | 66.639 | 1.00 | 17.76 | A |
| ATOM | 2558 | C | TYR | A | 334 | 19.878 | −11.071 | 60.631 | 1.00 | 12.57 | A |
| ATOM | 2559 | O | TYR | A | 334 | 18.802 | −11.600 | 60.907 | 1.00 | 12.41 | A |
| ATOM | 2560 | N | GLY | A | 335 | 20.333 | −10.993 | 59.387 | 1.00 | 12.22 | A |
| ATOM | 2561 | CA | GLY | A | 335 | 19.537 | −11.522 | 58.287 | 1.00 | 11.80 | A |
| ATOM | 2562 | C | GLY | A | 335 | 18.447 | −10.524 | 57.912 | 1.00 | 11.96 | A |
| ATOM | 2563 | O | GLY | A | 335 | 18.430 | −9.404 | 58.429 | 1.00 | 11.44 | A |
| ATOM | 2564 | N | ASN | A | 336 | 17.535 | −10.928 | 57.028 | 1.00 | 11.66 | A |
| ATOM | 2565 | CA | ASN | A | 336 | 16.433 | −10.071 | 56.577 | 1.00 | 11.70 | A |
| ATOM | 2566 | CB | ASN | A | 336 | 15.957 | −10.540 | 55.189 | 1.00 | 11.42 | A |
| ATOM | 2567 | CG | ASN | A | 336 | 14.806 | −9.710 | 54.638 | 1.00 | 12.51 | A |
| ATOM | 2568 | OD1 | ASN | A | 336 | 14.090 | −9.039 | 55.382 | 1.00 | 13.12 | A |
| ATOM | 2569 | ND2 | ASN | A | 336 | 14.610 | −9.770 | 53.318 | 1.00 | 12.55 | A |
| ATOM | 2570 | C | ASN | A | 336 | 15.272 | −10.144 | 57.573 | 1.00 | 11.85 | A |
| ATOM | 2571 | O | ASN | A | 336 | 14.529 | −11.132 | 57.589 | 1.00 | 11.61 | A |
| ATOM | 2572 | N | MET | A | 337 | 15.125 | −9.103 | 58.396 | 1.00 | 11.75 | A |
| ATOM | 2573 | CA | MET | A | 337 | 14.066 | −9.023 | 59.406 | 1.00 | 11.30 | A |
| ATOM | 2574 | CB | MET | A | 337 | 14.616 | −8.402 | 60.702 | 1.00 | 11.74 | A |
| ATOM | 2575 | CG | MET | A | 337 | 15.776 | −9.162 | 61.347 | 1.00 | 11.23 | A |
| ATOM | 2576 | SD | MET | A | 337 | 16.500 | −8.267 | 62.775 | 1.00 | 12.05 | A |
| ATOM | 2577 | CE | MET | A | 337 | 17.454 | −7.023 | 61.918 | 1.00 | 10.68 | A |
| ATOM | 2578 | C | MET | A | 337 | 12.872 | −8.185 | 58.912 | 1.00 | 11.73 | A |
| ATOM | 2579 | O | MET | A | 337 | 12.185 | −7.521 | 59.705 | 1.00 | 11.01 | A |
| ATOM | 2580 | N | SER | A | 338 | 12.636 | −8.220 | 57.606 | 1.00 | 10.58 | A |
| ATOM | 2581 | CA | SER | A | 338 | 11.540 | −7.480 | 56.987 | 1.00 | 11.13 | A |
| ATOM | 2582 | CB | SER | A | 338 | 10.194 | −8.129 | 57.344 | 1.00 | 11.47 | A |
| ATOM | 2583 | OG | SER | A | 338 | 9.133 | −7.611 | 56.541 | 1.00 | 11.75 | A |
| ATOM | 2584 | C | SER | A | 338 | 11.539 | −5.995 | 57.365 | 1.00 | 10.94 | A |
| ATOM | 2585 | O | SER | A | 338 | 12.580 | −5.341 | 57.318 | 1.00 | 10.10 | A |
| ATOM | 2586 | N | SER | A | 339 | 10.380 | −5.466 | 57.753 | 1.00 | 10.98 | A |
| ATOM | 2587 | CA | SER | A | 339 | 10.266 | −4.044 | 58.084 | 1.00 | 10.99 | A |
| ATOM | 2588 | CB | SER | A | 339 | 8.838 | −3.709 | 58.543 | 1.00 | 11.08 | A |
| ATOM | 2589 | OG | SER | A | 339 | 8.561 | −4.237 | 59.829 | 1.00 | 10.91 | A |
| ATOM | 2590 | C | SER | A | 339 | 11.259 | −3.494 | 59.107 | 1.00 | 10.72 | A |
| ATOM | 2591 | O | SER | A | 339 | 11.591 | −2.311 | 59.059 | 1.00 | 10.36 | A |
| ATOM | 2592 | N | ALA | A | 340 | 11.743 | −4.338 | 60.015 | 1.00 | 10.25 | A |
| ATOM | 2593 | CA | ALA | A | 340 | 12.678 | −3.877 | 61.048 | 1.00 | 10.47 | A |
| ATOM | 2594 | CB | ALA | A | 340 | 12.734 | −4.900 | 62.192 | 1.00 | 10.31 | A |
| ATOM | 2595 | C | ALA | A | 340 | 14.102 | −3.553 | 60.584 | 1.00 | 10.95 | A |
| ATOM | 2596 | O | ALA | A | 340 | 14.793 | −2.763 | 61.230 | 1.00 | 10.69 | A |
| ATOM | 2597 | N | CYS | A | 341 | 14.542 | −4.153 | 59.480 | 1.00 | 11.51 | A |
| ATOM | 2598 | CA | CYS | A | 341 | 15.907 | −3.939 | 58.978 | 1.00 | 12.12 | A |
| ATOM | 2599 | CB | CYS | A | 341 | 16.080 | −4.551 | 57.582 | 1.00 | 13.41 | A |
| ATOM | 2600 | SG | CYS | A | 341 | 16.004 | −6.345 | 57.497 | 1.00 | 15.80 | A |
| ATOM | 2601 | C | CYS | A | 341 | 16.407 | −2.501 | 58.911 | 1.00 | 11.76 | A |
| ATOM | 2602 | O | CYS | A | 341 | 17.434 | −2.167 | 59.511 | 1.00 | 11.11 | A |
| ATOM | 2603 | N | VAL | A | 342 | 15.704 | −1.653 | 58.165 | 1.00 | 11.06 | A |
| ATOM | 2604 | CA | VAL | A | 342 | 16.152 | −0.274 | 58.010 | 1.00 | 11.17 | A |
| ATOM | 2605 | CB | VAL | A | 342 | 15.254 | 0.506 | 57.021 | 1.00 | 10.53 | A |
| ATOM | 2606 | CG1 | VAL | A | 342 | 15.371 | −0.118 | 55.637 | 1.00 | 10.75 | A |
| ATOM | 2607 | CG2 | VAL | A | 342 | 13.812 | 0.501 | 57.493 | 1.00 | 10.96 | A |
| ATOM | 2608 | C | VAL | A | 342 | 16.266 | 0.487 | 59.321 | 1.00 | 10.94 | A |
| ATOM | 2609 | O | VAL | A | 342 | 17.048 | 1.436 | 59.423 | 1.00 | 11.24 | A |
| ATOM | 2610 | N | LEU | A | 343 | 15.501 | 0.073 | 60.328 | 1.00 | 10.28 | A |
| ATOM | 2611 | CA | LEU | A | 343 | 15.576 | 0.736 | 61.623 | 1.00 | 9.58 | A |
| ATOM | 2612 | CB | LEU | A | 343 | 14.298 | 0.479 | 62.435 | 1.00 | 9.47 | A |
| ATOM | 2613 | CG | LEU | A | 343 | 13.005 | 0.940 | 61.735 | 1.00 | 9.16 | A |
| ATOM | 2614 | CD1 | LEU | A | 343 | 11.828 | 0.841 | 62.708 | 1.00 | 9.75 | A |
| ATOM | 2615 | CD2 | LEU | A | 343 | 13.160 | 2.381 | 61.236 | 1.00 | 10.29 | A |
| ATOM | 2616 | C | LEU | A | 343 | 16.832 | 0.261 | 62.374 | 1.00 | 9.66 | A |
| ATOM | 2617 | O | LEU | A | 343 | 17.470 | 1.051 | 63.073 | 1.00 | 9.55 | A |
| ATOM | 2618 | N | PHE | A | 344 | 17.197 | −1.014 | 62.223 | 1.00 | 10.11 | A |
| ATOM | 2619 | CA | PHE | A | 344 | 18.417 | −1.525 | 62.858 | 1.00 | 10.35 | A |
| ATOM | 2620 | CB | PHE | A | 344 | 18.593 | −3.040 | 62.626 | 1.00 | 10.60 | A |
| ATOM | 2621 | CG | PHE | A | 344 | 17.946 | −3.924 | 63.674 | 1.00 | 11.60 | A |
| ATOM | 2622 | CD1 | PHE | A | 344 | 16.560 | −4.063 | 63.743 | 1.00 | 11.33 | A |
| ATOM | 2623 | CD2 | PHE | A | 344 | 18.737 | −4.673 | 64.551 | 1.00 | 12.06 | A |
| ATOM | 2624 | CE1 | PHE | A | 344 | 15.970 | −4.939 | 64.664 | 1.00 | 12.07 | A |
| ATOM | 2625 | CE2 | PHE | A | 344 | 18.162 | −5.551 | 65.477 | 1.00 | 12.12 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 2626 | CZ | PHE | A | 344 | 16.773 | −5.686 | 65.533 | 1.00 | 12.33 | A |
| ATOM | 2627 | C | PHE | A | 344 | 19.605 | −0.804 | 62.204 | 1.00 | 10.33 | A |
| ATOM | 2628 | O | PHE | A | 344 | 20.588 | −0.460 | 62.870 | 1.00 | 9.78 | A |
| ATOM | 2629 | N | ILE | A | 345 | 19.514 | −0.574 | 60.895 | 1.00 | 9.91 | A |
| ATOM | 2630 | CA | ILE | A | 345 | 20.598 | 0.092 | 60.168 | 1.00 | 10.19 | A |
| ATOM | 2631 | CB | ILE | A | 345 | 20.360 | 0.029 | 58.632 | 1.00 | 9.96 | A |
| ATOM | 2632 | CG2 | ILE | A | 345 | 21.463 | 0.791 | 57.893 | 1.00 | 9.91 | A |
| ATOM | 2633 | CG1 | ILE | A | 345 | 20.345 | −1.438 | 58.180 | 1.00 | 10.15 | A |
| ATOM | 2634 | CD1 | ILE | A | 345 | 19.967 | −1.653 | 56.722 | 1.00 | 9.55 | A |
| ATOM | 2635 | C | ILE | A | 345 | 20.798 | 1.539 | 60.624 | 1.00 | 10.60 | A |
| ATOM | 2636 | O | ILE | A | 345 | 21.938 | 2.006 | 60.728 | 1.00 | 11.29 | A |
| ATOM | 2637 | N | LEU | A | 346 | 19.706 | 2.254 | 60.889 | 1.00 | 10.89 | A |
| ATOM | 2638 | CA | LEU | A | 346 | 19.809 | 3.633 | 61.375 | 1.00 | 11.20 | A |
| ATOM | 2639 | CB | LEU | A | 346 | 18.414 | 4.251 | 61.580 | 1.00 | 10.69 | A |
| ATOM | 2640 | CG | LEU | A | 346 | 17.624 | 4.627 | 60.321 | 1.00 | 10.61 | A |
| ATOM | 2641 | CD1 | LEU | A | 346 | 16.187 | 4.996 | 60.695 | 1.00 | 11.25 | A |
| ATOM | 2642 | CD2 | LEU | A | 346 | 18.313 | 5.790 | 59.617 | 1.00 | 11.23 | A |
| ATOM | 2643 | C | LEU | A | 346 | 20.561 | 3.627 | 62.707 | 1.00 | 11.84 | A |
| ATOM | 2644 | O | LEU | A | 346 | 21.406 | 4.492 | 62.965 | 1.00 | 12.64 | A |
| ATOM | 2645 | N | ASP | A | 347 | 20.258 | 2.644 | 63.550 | 1.00 | 12.06 | A |
| ATOM | 2646 | CA | ASP | A | 347 | 20.908 | 2.537 | 64.857 | 1.00 | 13.39 | A |
| ATOM | 2647 | CB | ASP | A | 347 | 20.217 | 1.450 | 65.690 | 1.00 | 13.78 | A |
| ATOM | 2648 | CG | ASP | A | 347 | 20.591 | 1.508 | 67.163 | 1.00 | 15.67 | A |
| ATOM | 2649 | OD1 | ASP | A | 347 | 20.710 | 2.629 | 67.706 | 1.00 | 14.75 | A |
| ATOM | 2650 | OD2 | ASP | A | 347 | 20.746 | 0.432 | 67.783 | 1.00 | 15.69 | A |
| ATOM | 2651 | C | ASP | A | 347 | 22.408 | 2.245 | 64.710 | 1.00 | 13.67 | A |
| ATOM | 2652 | O | ASP | A | 347 | 23.239 | 2.873 | 65.367 | 1.00 | 13.64 | A |
| ATOM | 2653 | N | GLU | A | 348 | 22.751 | 1.301 | 63.838 | 1.00 | 14.56 | A |
| ATOM | 2654 | CA | GLU | A | 348 | 24.147 | 0.938 | 63.592 | 1.00 | 15.36 | A |
| ATOM | 2655 | CB | GLU | A | 348 | 24.215 | −0.210 | 62.579 | 1.00 | 16.27 | A |
| ATOM | 2656 | CG | GLU | A | 348 | 25.617 | −0.592 | 62.092 | 1.00 | 17.76 | A |
| ATOM | 2657 | CD | GLU | A | 348 | 26.541 | −1.082 | 63.200 | 1.00 | 18.78 | A |
| ATOM | 2658 | OE1 | GLU | A | 348 | 26.047 | −1.562 | 64.242 | 1.00 | 19.58 | A |
| ATOM | 2659 | OE2 | GLU | A | 348 | 27.773 | −1.002 | 63.019 | 1.00 | 19.89 | A |
| ATOM | 2660 | C | GLU | A | 348 | 24.946 | 2.134 | 63.071 | 1.00 | 15.06 | A |
| ATOM | 2661 | O | GLU | A | 348 | 26.049 | 2.405 | 63.541 | 1.00 | 14.81 | A |
| ATOM | 2662 | N | MET | A | 349 | 24.388 | 2.853 | 62.104 | 1.00 | 14.78 | A |
| ATOM | 2663 | CA | MET | A | 349 | 25.079 | 4.008 | 61.540 | 1.00 | 15.19 | A |
| ATOM | 2664 | CB | MET | A | 349 | 24.265 | 4.625 | 60.401 | 1.00 | 15.22 | A |
| ATOM | 2665 | CG | MET | A | 349 | 24.931 | 5.857 | 59.811 | 1.00 | 17.23 | A |
| ATOM | 2666 | SD | MET | A | 349 | 24.032 | 6.538 | 58.421 | 1.00 | 18.52 | A |
| ATOM | 2667 | CE | MET | A | 349 | 24.320 | 5.238 | 57.186 | 1.00 | 16.39 | A |
| ATOM | 2668 | C | MET | A | 349 | 25.390 | 5.100 | 62.563 | 1.00 | 14.73 | A |
| ATOM | 2669 | O | MET | A | 349 | 26.503 | 5.624 | 62.599 | 1.00 | 14.30 | A |
| ATOM | 2670 | N | ARG | A | 350 | 24.409 | 5.453 | 63.384 | 1.00 | 14.34 | A |
| ATOM | 2671 | CA | ARG | A | 350 | 24.615 | 6.498 | 64.379 | 1.00 | 15.08 | A |
| ATOM | 2672 | CB | ARG | A | 350 | 23.272 | 6.950 | 64.962 | 1.00 | 14.45 | A |
| ATOM | 2673 | CG | ARG | A | 350 | 22.518 | 5.897 | 65.756 | 1.00 | 14.44 | A |
| ATOM | 2674 | CD | ARG | A | 350 | 22.510 | 6.236 | 67.247 | 1.00 | 14.54 | A |
| ATOM | 2675 | NE | ARG | A | 350 | 21.567 | 5.396 | 67.984 | 1.00 | 14.41 | A |
| ATOM | 2676 | CZ | ARG | A | 350 | 21.013 | 5.735 | 69.144 | 1.00 | 14.88 | A |
| ATOM | 2677 | NH1 | ARG | A | 350 | 21.308 | 6.902 | 69.701 | 1.00 | 14.87 | A |
| ATOM | 2678 | NH2 | ARG | A | 350 | 20.159 | 4.912 | 69.745 | 1.00 | 14.52 | A |
| ATOM | 2679 | C | ARG | A | 350 | 25.571 | 6.066 | 65.492 | 1.00 | 15.83 | A |
| ATOM | 2680 | O | ARG | A | 350 | 26.360 | 6.873 | 65.987 | 1.00 | 15.01 | A |
| ATOM | 2681 | N | LYS | A | 351 | 25.514 | 4.795 | 65.880 | 1.00 | 16.14 | A |
| ATOM | 2682 | CA | LYS | A | 351 | 26.411 | 4.305 | 66.921 | 1.00 | 17.27 | A |
| ATOM | 2683 | CB | LYS | A | 351 | 25.988 | 2.909 | 67.382 | 1.00 | 18.64 | A |
| ATOM | 2684 | CG | LYS | A | 351 | 24.844 | 2.916 | 68.386 | 1.00 | 20.60 | A |
| ATOM | 2685 | CD | LYS | A | 351 | 24.438 | 1.494 | 68.767 | 1.00 | 22.37 | A |
| ATOM | 2686 | CE | LYS | A | 351 | 23.636 | 1.480 | 70.061 | 1.00 | 23.69 | A |
| ATOM | 2687 | NZ | LYS | A | 351 | 22.393 | 2.293 | 69.986 | 1.00 | 24.80 | A |
| ATOM | 2688 | C | LYS | A | 351 | 27.860 | 4.286 | 66.430 | 1.00 | 17.14 | A |
| ATOM | 2689 | O | LYS | A | 351 | 28.771 | 4.696 | 67.152 | 1.00 | 16.83 | A |
| ATOM | 2690 | N | LYS | A | 352 | 28.073 | 3.817 | 65.203 | 1.00 | 16.98 | A |
| ATOM | 2691 | CA | LYS | A | 352 | 29.419 | 3.767 | 64.627 | 1.00 | 17.64 | A |
| ATOM | 2692 | CB | LYS | A | 352 | 29.416 | 2.966 | 63.323 | 1.00 | 18.76 | A |
| ATOM | 2693 | CG | LYS | A | 352 | 29.490 | 1.470 | 63.526 | 1.00 | 21.91 | A |
| ATOM | 2694 | CD | LYS | A | 352 | 30.857 | 1.068 | 64.077 | 1.00 | 23.41 | A |
| ATOM | 2695 | CE | LYS | A | 352 | 30.896 | −0.405 | 64.432 | 1.00 | 24.84 | A |
| ATOM | 2696 | NZ | LYS | A | 352 | 29.886 | −0.731 | 65.483 | 1.00 | 26.79 | A |
| ATOM | 2697 | C | LYS | A | 352 | 29.995 | 5.156 | 64.363 | 1.00 | 17.19 | A |
| ATOM | 2698 | O | LYS | A | 352 | 31.204 | 5.369 | 64.500 | 1.00 | 16.04 | A |
| ATOM | 2699 | N | SER | A | 353 | 29.138 | 6.094 | 63.970 | 1.00 | 16.74 | A |
| ATOM | 2700 | CA | SER | A | 353 | 29.583 | 7.460 | 63.710 | 1.00 | 17.39 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 2701 | CB | SER | A | 353 | 28.435 | 8.297 | 63.138 | 1.00 | 17.32 | A |
| ATOM | 2702 | OG | SER | A | 353 | 28.067 | 7.843 | 61.848 | 1.00 | 16.97 | A |
| ATOM | 2703 | C | SER | A | 353 | 30.073 | 8.088 | 65.012 | 1.00 | 18.27 | A |
| ATOM | 2704 | O | SER | A | 353 | 31.043 | 8.850 | 65.025 | 1.00 | 18.81 | A |
| ATOM | 2705 | N | THR | A | 354 | 29.391 | 7.768 | 66.106 | 1.00 | 18.39 | A |
| ATOM | 2706 | CA | THR | A | 354 | 29.749 | 8.290 | 67.420 | 1.00 | 19.76 | A |
| ATOM | 2707 | CB | THR | A | 354 | 28.618 | 8.011 | 68.435 | 1.00 | 20.00 | A |
| ATOM | 2708 | OG1 | THR | A | 354 | 27.443 | 8.729 | 68.043 | 1.00 | 20.37 | A |
| ATOM | 2709 | CG2 | THR | A | 354 | 29.027 | 8.435 | 69.839 | 1.00 | 20.74 | A |
| ATOM | 2710 | C | THR | A | 354 | 31.036 | 7.618 | 67.899 | 1.00 | 20.00 | A |
| ATOM | 2711 | O | THR | A | 354 | 31.959 | 8.272 | 68.399 | 1.00 | 19.48 | A |
| ATOM | 2712 | N | GLN | A | 355 | 31.080 | 6.303 | 67.730 | 1.00 | 20.15 | A |
| ATOM | 2713 | CA | GLN | A | 355 | 32.222 | 5.493 | 68.128 | 1.00 | 21.65 | A |
| ATOM | 2714 | CB | GLN | A | 355 | 31.913 | 4.019 | 67.837 | 1.00 | 22.91 | A |
| ATOM | 2715 | CG | GLN | A | 355 | 33.095 | 3.066 | 67.958 | 1.00 | 25.78 | A |
| ATOM | 2716 | CD | GLN | A | 355 | 32.778 | 1.685 | 67.405 | 1.00 | 27.34 | A |
| ATOM | 2717 | OE1 | GLN | A | 355 | 31.862 | 1.009 | 67.874 | 1.00 | 29.12 | A |
| ATOM | 2718 | NE2 | GLN | A | 355 | 33.532 | 1.264 | 66.398 | 1.00 | 28.38 | A |
| ATOM | 2719 | C | GLN | A | 355 | 33.530 | 5.889 | 67.432 | 1.00 | 21.31 | A |
| ATOM | 2720 | O | GLN | A | 355 | 34.562 | 6.071 | 68.086 | 1.00 | 21.87 | A |
| ATOM | 2721 | N | ASN | A | 356 | 33.488 | 6.027 | 66.111 | 1.00 | 20.41 | A |
| ATOM | 2722 | CA | ASN | A | 356 | 34.692 | 6.352 | 65.356 | 1.00 | 20.53 | A |
| ATOM | 2723 | CB | ASN | A | 356 | 34.655 | 5.657 | 63.992 | 1.00 | 21.37 | A |
| ATOM | 2724 | CG | ASN | A | 356 | 34.710 | 4.143 | 64.116 | 1.00 | 22.05 | A |
| ATOM | 2725 | OD1 | ASN | A | 356 | 35.340 | 3.608 | 65.029 | 1.00 | 22.39 | A |
| ATOM | 2726 | ND2 | ASN | A | 356 | 34.060 | 3.447 | 63.193 | 1.00 | 23.15 | A |
| ATOM | 2727 | C | ASN | A | 356 | 35.027 | 7.829 | 65.182 | 1.00 | 19.88 | A |
| ATOM | 2728 | O | ASN | A | 356 | 35.927 | 8.179 | 64.413 | 1.00 | 19.58 | A |
| ATOM | 2729 | N | GLY | A | 357 | 34.301 | 8.687 | 65.894 | 1.00 | 19.15 | A |
| ATOM | 2730 | CA | GLY | A | 357 | 34.563 | 10.117 | 65.848 | 1.00 | 18.39 | A |
| ATOM | 2731 | C | GLY | A | 357 | 34.155 | 10.930 | 64.634 | 1.00 | 18.00 | A |
| ATOM | 2732 | O | GLY | A | 357 | 34.839 | 11.896 | 64.289 | 1.00 | 17.19 | A |
| ATOM | 2733 | N | LEU | A | 358 | 33.056 | 10.564 | 63.982 | 1.00 | 17.83 | A |
| ATOM | 2734 | CA | LEU | A | 358 | 32.599 | 11.325 | 62.819 | 1.00 | 18.37 | A |
| ATOM | 2735 | CB | LEU | A | 358 | 31.641 | 10.487 | 61.960 | 1.00 | 18.29 | A |
| ATOM | 2736 | CG | LEU | A | 358 | 32.261 | 9.431 | 61.033 | 1.00 | 18.70 | A |
| ATOM | 2737 | CD1 | LEU | A | 358 | 33.183 | 10.113 | 60.032 | 1.00 | 18.64 | A |
| ATOM | 2738 | CD2 | LEU | A | 358 | 33.028 | 8.392 | 61.841 | 1.00 | 18.14 | A |
| ATOM | 2739 | C | LEU | A | 358 | 31.905 | 12.589 | 63.329 | 1.00 | 18.28 | A |
| ATOM | 2740 | O | LEU | A | 358 | 31.430 | 12.621 | 64.465 | 1.00 | 19.60 | A |
| ATOM | 2741 | N | LYS | A | 359 | 31.847 | 13.625 | 62.497 | 1.00 | 18.13 | A |
| ATOM | 2742 | CA | LYS | A | 359 | 31.245 | 14.894 | 62.902 | 1.00 | 18.17 | A |
| ATOM | 2743 | CB | LYS | A | 359 | 31.862 | 16.033 | 62.085 | 1.00 | 19.78 | A |
| ATOM | 2744 | CG | LYS | A | 359 | 33.378 | 16.146 | 62.242 | 1.00 | 22.00 | A |
| ATOM | 2745 | CD | LYS | A | 359 | 33.773 | 16.502 | 63.672 | 1.00 | 24.21 | A |
| ATOM | 2746 | CE | LYS | A | 359 | 33.331 | 17.915 | 64.027 | 1.00 | 26.14 | A |
| ATOM | 2747 | NZ | LYS | A | 359 | 33.637 | 18.270 | 65.443 | 1.00 | 27.55 | A |
| ATOM | 2748 | C | LYS | A | 359 | 29.713 | 14.990 | 62.861 | 1.00 | 17.59 | A |
| ATOM | 2749 | O | LYS | A | 359 | 29.147 | 15.972 | 63.337 | 1.00 | 17.60 | A |
| ATOM | 2750 | N | THR | A | 360 | 29.046 | 13.992 | 62.286 | 1.00 | 16.40 | A |
| ATOM | 2751 | CA | THR | A | 360 | 27.577 | 13.975 | 62.247 | 1.00 | 15.45 | A |
| ATOM | 2752 | CB | THR | A | 360 | 26.992 | 14.499 | 60.911 | 1.00 | 15.82 | A |
| ATOM | 2753 | OG1 | THR | A | 360 | 27.231 | 13.539 | 59.877 | 1.00 | 15.65 | A |
| ATOM | 2754 | CG2 | THR | A | 360 | 27.613 | 15.840 | 60.524 | 1.00 | 16.52 | A |
| ATOM | 2755 | C | THR | A | 360 | 27.116 | 12.532 | 62.413 | 1.00 | 14.68 | A |
| ATOM | 2756 | O | THR | A | 360 | 27.897 | 11.598 | 62.215 | 1.00 | 14.27 | A |
| ATOM | 2757 | N | THR | A | 361 | 25.852 | 12.348 | 62.777 | 1.00 | 13.61 | A |
| ATOM | 2758 | CA | THR | A | 361 | 25.307 | 11.008 | 62.965 | 1.00 | 13.33 | A |
| ATOM | 2759 | CB | THR | A | 361 | 23.919 | 11.066 | 63.629 | 1.00 | 13.09 | A |
| ATOM | 2760 | OG1 | THR | A | 361 | 23.093 | 11.988 | 62.915 | 1.00 | 12.47 | A |
| ATOM | 2761 | CG2 | THR | A | 361 | 24.043 | 11.529 | 65.081 | 1.00 | 13.05 | A |
| ATOM | 2762 | C | THR | A | 361 | 25.194 | 10.256 | 61.645 | 1.00 | 13.18 | A |
| ATOM | 2763 | O | THR | A | 361 | 24.936 | 9.050 | 61.633 | 1.00 | 13.52 | A |
| ATOM | 2764 | N | GLY | A | 362 | 25.394 | 10.973 | 60.542 | 1.00 | 13.05 | A |
| ATOM | 2765 | CA | GLY | A | 362 | 25.325 | 10.368 | 59.222 | 1.00 | 13.54 | A |
| ATOM | 2766 | C | GLY | A | 362 | 26.693 | 10.220 | 58.572 | 1.00 | 13.80 | A |
| ATOM | 2767 | O | GLY | A | 362 | 26.921 | 10.676 | 57.447 | 1.00 | 13.72 | A |
| ATOM | 2768 | N | GLU | A | 363 | 27.606 | 9.578 | 59.292 | 1.00 | 14.30 | A |
| ATOM | 2769 | CA | GLU | A | 363 | 28.969 | 9.342 | 58.823 | 1.00 | 14.87 | A |
| ATOM | 2770 | CB | GLU | A | 363 | 28.951 | 8.326 | 57.672 | 1.00 | 15.38 | A |
| ATOM | 2771 | CG | GLU | A | 363 | 28.092 | 7.101 | 58.010 | 1.00 | 16.94 | A |
| ATOM | 2772 | CD | GLU | A | 363 | 28.216 | 5.954 | 57.023 | 1.00 | 17.95 | A |
| ATOM | 2773 | OE1 | GLU | A | 363 | 28.357 | 6.202 | 55.808 | 1.00 | 18.60 | A |
| ATOM | 2774 | OE2 | GLU | A | 363 | 28.144 | 4.789 | 57.472 | 1.00 | 19.19 | A |
| ATOM | 2775 | C | GLU | A | 363 | 29.682 | 10.634 | 58.414 | 1.00 | 15.17 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 2776 | O | GLU | A | 363 | 30.481 | 10.655 | 57.475 | 1.00 | 14.88 | A |
| ATOM | 2777 | N | GLY | A | 364 | 29.388 | 11.711 | 59.136 | 1.00 | 15.36 | A |
| ATOM | 2778 | CA | GLY | A | 364 | 30.023 | 12.986 | 58.851 | 1.00 | 16.19 | A |
| ATOM | 2779 | C | GLY | A | 364 | 29.429 | 13.764 | 57.693 | 1.00 | 16.44 | A |
| ATOM | 2780 | O | GLY | A | 364 | 29.856 | 14.884 | 57.418 | 1.00 | 16.69 | A |
| ATOM | 2781 | N | LEU | A | 365 | 28.445 | 13.184 | 57.012 | 1.00 | 16.46 | A |
| ATOM | 2782 | CA | LEU | A | 365 | 27.813 | 13.853 | 55.880 | 1.00 | 16.91 | A |
| ATOM | 2783 | CB | LEU | A | 365 | 27.494 | 12.831 | 54.786 | 1.00 | 16.94 | A |
| ATOM | 2784 | CG | LEU | A | 365 | 28.696 | 11.997 | 54.320 | 1.00 | 17.07 | A |
| ATOM | 2785 | CD1 | LEU | A | 365 | 28.228 | 10.876 | 53.405 | 1.00 | 17.97 | A |
| ATOM | 2786 | CD2 | LEU | A | 365 | 29.703 | 12.889 | 53.610 | 1.00 | 16.75 | A |
| ATOM | 2787 | C | LEU | A | 365 | 26.544 | 14.587 | 56.323 | 1.00 | 16.99 | A |
| ATOM | 2788 | O | LEU | A | 365 | 26.039 | 14.354 | 57.421 | 1.00 | 17.16 | A |
| ATOM | 2789 | N | GLU | A | 366 | 26.034 | 15.469 | 55.467 | 1.00 | 16.87 | A |
| ATOM | 2790 | CA | GLU | A | 366 | 24.838 | 16.252 | 55.787 | 1.00 | 17.25 | A |
| ATOM | 2791 | CB | GLU | A | 366 | 24.941 | 17.644 | 55.144 | 1.00 | 19.11 | A |
| ATOM | 2792 | CG | GLU | A | 366 | 23.629 | 18.432 | 55.109 | 1.00 | 21.19 | A |
| ATOM | 2793 | CD | GLU | A | 366 | 23.828 | 19.896 | 54.758 | 1.00 | 22.96 | A |
| ATOM | 2794 | OE1 | GLU | A | 366 | 24.687 | 20.198 | 53.905 | 1.00 | 23.65 | A |
| ATOM | 2795 | OE2 | GLU | A | 366 | 23.111 | 20.748 | 55.328 | 1.00 | 24.80 | A |
| ATOM | 2796 | C | GLU | A | 366 | 23.499 | 15.611 | 55.410 | 1.00 | 16.91 | A |
| ATOM | 2797 | O | GLU | A | 366 | 22.589 | 15.540 | 56.244 | 1.00 | 16.56 | A |
| ATOM | 2798 | N | TRP | A | 367 | 23.374 | 15.153 | 54.168 | 1.00 | 15.76 | A |
| ATOM | 2799 | CA | TRP | A | 367 | 22.127 | 14.535 | 53.703 | 1.00 | 15.43 | A |
| ATOM | 2800 | CB | TRP | A | 367 | 21.699 | 15.136 | 52.358 | 1.00 | 15.92 | A |
| ATOM | 2801 | CG | TRP | A | 367 | 21.584 | 16.640 | 52.362 | 1.00 | 17.29 | A |
| ATOM | 2802 | CD2 | TRP | A | 367 | 20.521 | 17.420 | 52.924 | 1.00 | 17.28 | A |
| ATOM | 2803 | CE2 | TRP | A | 367 | 20.843 | 18.781 | 52.714 | 1.00 | 17.73 | A |
| ATOM | 2804 | CE3 | TRP | A | 367 | 19.327 | 17.101 | 53.587 | 1.00 | 17.91 | A |
| ATOM | 2805 | CD1 | TRP | A | 367 | 22.483 | 17.535 | 51.848 | 1.00 | 17.11 | A |
| ATOM | 2806 | NE1 | TRP | A | 367 | 22.043 | 18.823 | 52.054 | 1.00 | 17.26 | A |
| ATOM | 2807 | CZ2 | TRP | A | 367 | 20.014 | 19.823 | 53.142 | 1.00 | 18.10 | A |
| ATOM | 2808 | CZ3 | TRP | A | 367 | 18.500 | 18.139 | 54.014 | 1.00 | 17.80 | A |
| ATOM | 2809 | CH2 | TRP | A | 367 | 18.849 | 19.483 | 53.789 | 1.00 | 18.48 | A |
| ATOM | 2810 | C | TRP | A | 367 | 22.243 | 13.021 | 53.551 | 1.00 | 14.85 | A |
| ATOM | 2811 | O | TRP | A | 367 | 23.335 | 12.493 | 53.340 | 1.00 | 14.03 | A |
| ATOM | 2812 | N | GLY | A | 368 | 21.105 | 12.333 | 53.643 | 1.00 | 13.90 | A |
| ATOM | 2813 | CA | GLY | A | 368 | 21.093 | 10.883 | 53.510 | 1.00 | 13.64 | A |
| ATOM | 2814 | C | GLY | A | 368 | 19.786 | 10.357 | 52.939 | 1.00 | 12.46 | A |
| ATOM | 2815 | O | GLY | A | 368 | 18.826 | 11.110 | 52.773 | 1.00 | 13.28 | A |
| ATOM | 2816 | N | VAL | A | 369 | 19.739 | 9.064 | 52.633 | 1.00 | 12.00 | A |
| ATOM | 2817 | CA | VAL | A | 369 | 18.530 | 8.470 | 52.077 | 1.00 | 11.30 | A |
| ATOM | 2818 | CB | VAL | A | 369 | 18.634 | 8.356 | 50.533 | 1.00 | 11.23 | A |
| ATOM | 2819 | CG1 | VAL | A | 369 | 19.762 | 7.405 | 50.155 | 1.00 | 10.95 | A |
| ATOM | 2820 | CG2 | VAL | A | 369 | 17.316 | 7.871 | 49.952 | 1.00 | 11.34 | A |
| ATOM | 2821 | C | VAL | A | 369 | 18.265 | 7.083 | 52.656 | 1.00 | 11.73 | A |
| ATOM | 2822 | O | VAL | A | 369 | 19.198 | 6.334 | 52.936 | 1.00 | 11.94 | A |
| ATOM | 2823 | N | LEU | A | 370 | 16.989 | 6.759 | 52.848 | 1.00 | 11.77 | A |
| ATOM | 2824 | CA | LEU | A | 370 | 16.580 | 5.456 | 53.371 | 1.00 | 11.76 | A |
| ATOM | 2825 | CB | LEU | A | 370 | 15.911 | 5.606 | 54.749 | 1.00 | 11.28 | A |
| ATOM | 2826 | CG | LEU | A | 370 | 15.397 | 4.333 | 55.445 | 1.00 | 11.66 | A |
| ATOM | 2827 | CD1 | LEU | A | 370 | 15.368 | 4.547 | 56.960 | 1.00 | 11.65 | A |
| ATOM | 2828 | CD2 | LEU | A | 370 | 14.015 | 3.962 | 54.918 | 1.00 | 12.29 | A |
| ATOM | 2829 | C | LEU | A | 370 | 15.595 | 4.857 | 52.376 | 1.00 | 11.86 | A |
| ATOM | 2830 | O | LEU | A | 370 | 14.646 | 5.527 | 51.971 | 1.00 | 11.90 | A |
| ATOM | 2831 | N | PHE | A | 371 | 15.828 | 3.604 | 51.984 | 1.00 | 11.79 | A |
| ATOM | 2832 | CA | PHE | A | 371 | 14.968 | 2.912 | 51.027 | 1.00 | 11.80 | A |
| ATOM | 2833 | CB | PHE | A | 371 | 15.755 | 2.528 | 49.761 | 1.00 | 12.26 | A |
| ATOM | 2834 | CG | PHE | A | 371 | 16.049 | 3.680 | 48.835 | 1.00 | 13.18 | A |
| ATOM | 2835 | CD1 | PHE | A | 371 | 15.017 | 4.364 | 48.199 | 1.00 | 13.53 | A |
| ATOM | 2836 | CD2 | PHE | A | 371 | 17.364 | 4.053 | 48.569 | 1.00 | 13.39 | A |
| ATOM | 2837 | CE1 | PHE | A | 371 | 15.291 | 5.401 | 47.309 | 1.00 | 14.13 | A |
| ATOM | 2838 | CE2 | PHE | A | 371 | 17.650 | 5.090 | 47.680 | 1.00 | 14.61 | A |
| ATOM | 2839 | CZ | PHE | A | 371 | 16.612 | 5.765 | 47.049 | 1.00 | 14.39 | A |
| ATOM | 2840 | C | PHE | A | 371 | 14.350 | 1.633 | 51.580 | 1.00 | 11.83 | A |
| ATOM | 2841 | O | PHE | A | 371 | 15.024 | 0.837 | 52.242 | 1.00 | 11.89 | A |
| ATOM | 2842 | N | GLY | A | 372 | 13.069 | 1.442 | 51.278 | 1.00 | 11.66 | A |
| ATOM | 2843 | CA | GLY | A | 372 | 12.357 | 0.238 | 51.677 | 1.00 | 11.23 | A |
| ATOM | 2844 | C | GLY | A | 372 | 11.875 | −0.413 | 50.386 | 1.00 | 12.03 | A |
| ATOM | 2845 | O | GLY | A | 372 | 11.381 | 0.290 | 49.504 | 1.00 | 11.11 | A |
| ATOM | 2846 | N | PHE | A | 373 | 12.034 | −1.732 | 50.254 | 1.00 | 12.31 | A |
| ATOM | 2847 | CA | PHE | A | 373 | 11.604 | −2.446 | 49.043 | 1.00 | 12.91 | A |
| ATOM | 2848 | CB | PHE | A | 373 | 12.815 | −3.026 | 48.281 | 1.00 | 13.68 | A |
| ATOM | 2849 | CG | PHE | A | 373 | 13.966 | −2.063 | 48.107 | 1.00 | 14.91 | A |
| ATOM | 2850 | CD1 | PHE | A | 373 | 13.784 | −0.832 | 47.485 | 1.00 | 15.93 | A |

APPENDIX C-continued

18xCHS Mutant

| ATOM | # | TYPE | RES | | | X | Y | Z | OCC | B | |
|---|---|---|---|---|---|---|---|---|---|---|---|
| ATOM | 2851 | CD2 | PHE | A | 373 | 15.245 | −2.406 | 48.547 | 1.00 | 15.06 | A |
| ATOM | 2852 | CE1 | PHE | A | 373 | 14.859 | 0.046 | 47.303 | 1.00 | 16.22 | A |
| ATOM | 2853 | CE2 | PHE | A | 373 | 16.327 | −1.538 | 48.372 | 1.00 | 15.66 | A |
| ATOM | 2854 | CZ | PHE | A | 373 | 16.133 | −0.309 | 47.749 | 1.00 | 15.82 | A |
| ATOM | 2855 | C | PHE | A | 373 | 10.698 | −3.609 | 49.450 | 1.00 | 12.82 | A |
| ATOM | 2856 | O | PHE | A | 373 | 10.962 | −4.269 | 50.455 | 1.00 | 11.69 | A |
| ATOM | 2857 | N | GLY | A | 374 | 9.650 | −3.879 | 48.672 | 1.00 | 13.46 | A |
| ATOM | 2858 | CA | GLY | A | 374 | 8.756 | −4.979 | 49.019 | 1.00 | 14.44 | A |
| ATOM | 2859 | C | GLY | A | 374 | 7.629 | −5.288 | 48.041 | 1.00 | 15.41 | A |
| ATOM | 2860 | O | GLY | A | 374 | 7.630 | −4.787 | 46.916 | 1.00 | 15.04 | A |
| ATOM | 2861 | N | PRO | A | 375 | 6.639 | −6.108 | 48.457 | 1.00 | 16.00 | A |
| ATOM | 2862 | CD | PRO | A | 375 | 6.560 | −6.647 | 49.828 | 1.00 | 16.19 | A |
| ATOM | 2863 | CA | PRO | A | 375 | 5.467 | −6.538 | 47.680 | 1.00 | 16.73 | A |
| ATOM | 2864 | CB | PRO | A | 375 | 4.529 | −7.081 | 48.751 | 1.00 | 16.44 | A |
| ATOM | 2865 | CG | PRO | A | 375 | 5.475 | −7.711 | 49.703 | 1.00 | 16.06 | A |
| ATOM | 2866 | C | PRO | A | 375 | 4.799 | −5.474 | 46.820 | 1.00 | 18.46 | A |
| ATOM | 2867 | O | PRO | A | 375 | 4.691 | −4.298 | 47.206 | 1.00 | 17.70 | A |
| ATOM | 2868 | N | GLY | A | 376 | 4.319 | −5.915 | 45.660 | 1.00 | 20.24 | A |
| ATOM | 2869 | CA | GLY | A | 376 | 3.682 | −5.010 | 44.731 | 1.00 | 21.94 | A |
| ATOM | 2870 | C | GLY | A | 376 | 4.800 | −4.070 | 44.412 | 1.00 | 23.04 | A |
| ATOM | 2871 | O | GLY | A | 376 | 4.606 | −2.851 | 44.335 | 1.00 | 24.98 | A |
| ATOM | 2872 | N | LEU | A | 377 | 5.977 | −4.666 | 44.214 | 1.00 | 22.83 | A |
| ATOM | 2873 | CA | LEU | A | 377 | 7.203 | −3.935 | 43.963 | 1.00 | 20.77 | A |
| ATOM | 2874 | CB | LEU | A | 377 | 7.742 | −4.194 | 42.562 | 1.00 | 22.54 | A |
| ATOM | 2875 | CG | LEU | A | 377 | 8.891 | −5.198 | 42.724 | 1.00 | 23.55 | A |
| ATOM | 2876 | CD1 | LEU | A | 377 | 9.542 | −5.485 | 41.399 | 1.00 | 24.83 | A |
| ATOM | 2877 | CD2 | LEU | A | 377 | 9.919 | −4.634 | 43.709 | 1.00 | 23.91 | A |
| ATOM | 2878 | C | LEU | A | 377 | 7.042 | −2.465 | 44.240 | 1.00 | 19.02 | A |
| ATOM | 2879 | O | LEU | A | 377 | 6.897 | −1.629 | 43.344 | 1.00 | 17.12 | A |
| ATOM | 2880 | N | THR | A | 378 | 7.057 | −2.194 | 45.537 | 1.00 | 16.80 | A |
| ATOM | 2881 | CA | THR | A | 378 | 6.910 | −0.873 | 46.096 | 1.00 | 14.86 | A |
| ATOM | 2882 | CB | THR | A | 378 | 5.954 | −0.918 | 47.319 | 1.00 | 14.08 | A |
| ATOM | 2883 | OG1 | THR | A | 378 | 4.660 | −1.385 | 46.905 | 1.00 | 15.17 | A |
| ATOM | 2884 | CG2 | THR | A | 378 | 5.825 | 0.455 | 47.954 | 1.00 | 13.38 | A |
| ATOM | 2885 | C | THR | A | 378 | 8.279 | −0.393 | 46.565 | 1.00 | 14.33 | A |
| ATOM | 2886 | O | THR | A | 378 | 9.075 | −1.172 | 47.104 | 1.00 | 13.55 | A |
| ATOM | 2887 | N | ILE | A | 379 | 8.553 | 0.885 | 46.339 | 1.00 | 13.27 | A |
| ATOM | 2888 | CA | ILE | A | 379 | 9.803 | 1.500 | 46.772 | 1.00 | 12.71 | A |
| ATOM | 2889 | CB | ILE | A | 379 | 10.649 | 2.010 | 45.570 | 1.00 | 13.23 | A |
| ATOM | 2890 | CG2 | ILE | A | 379 | 11.892 | 2.740 | 46.078 | 1.00 | 13.06 | A |
| ATOM | 2891 | CG1 | ILE | A | 379 | 11.066 | 0.837 | 44.678 | 1.00 | 14.08 | A |
| ATOM | 2892 | CD1 | ILE | A | 379 | 11.854 | 1.247 | 43.439 | 1.00 | 15.36 | A |
| ATOM | 2893 | C | ILE | A | 379 | 9.425 | 2.703 | 47.633 | 1.00 | 12.32 | A |
| ATOM | 2894 | O | ILE | A | 379 | 8.763 | 3.615 | 47.151 | 1.00 | 12.02 | A |
| ATOM | 2895 | N | GLU | A | 380 | 9.804 | 2.682 | 48.911 | 1.00 | 11.67 | A |
| ATOM | 2896 | CA | GLU | A | 380 | 9.532 | 3.803 | 49.808 | 1.00 | 11.50 | A |
| ATOM | 2897 | CB | GLU | A | 380 | 9.123 | 3.317 | 51.212 | 1.00 | 11.02 | A |
| ATOM | 2898 | CG | GLU | A | 380 | 7.764 | 2.601 | 51.299 | 1.00 | 11.78 | A |
| ATOM | 2899 | CD | GLU | A | 380 | 6.607 | 3.522 | 51.695 | 1.00 | 11.77 | A |
| ATOM | 2900 | OE1 | GLU | A | 380 | 6.819 | 4.747 | 51.805 | 1.00 | 11.99 | A |
| ATOM | 2901 | OE2 | GLU | A | 380 | 5.479 | 3.019 | 51.897 | 1.00 | 11.77 | A |
| ATOM | 2902 | C | GLU | A | 380 | 10.848 | 4.576 | 49.907 | 1.00 | 11.95 | A |
| ATOM | 2903 | O | GLU | A | 380 | 11.912 | 3.971 | 50.076 | 1.00 | 11.95 | A |
| ATOM | 2904 | N | THR | A | 381 | 10.773 | 5.900 | 49.783 | 1.00 | 12.03 | A |
| ATOM | 2905 | CA | THR | A | 381 | 11.951 | 6.763 | 49.867 | 1.00 | 12.38 | A |
| ATOM | 2906 | CB | THR | A | 381 | 12.186 | 7.570 | 48.552 | 1.00 | 13.41 | A |
| ATOM | 2907 | OG1 | THR | A | 381 | 12.202 | 6.690 | 47.422 | 1.00 | 14.31 | A |
| ATOM | 2908 | CG2 | THR | A | 381 | 13.522 | 8.311 | 48.613 | 1.00 | 13.86 | A |
| ATOM | 2909 | C | THR | A | 381 | 11.777 | 7.791 | 50.987 | 1.00 | 12.43 | A |
| ATOM | 2910 | O | THR | A | 381 | 10.747 | 8.466 | 51.062 | 1.00 | 12.02 | A |
| ATOM | 2911 | N | VAL | A | 382 | 12.778 | 7.900 | 51.860 | 1.00 | 12.62 | A |
| ATOM | 2912 | CA | VAL | A | 382 | 12.754 | 8.882 | 52.942 | 1.00 | 13.01 | A |
| ATOM | 2913 | CB | VAL | A | 382 | 12.626 | 8.229 | 54.346 | 1.00 | 12.57 | A |
| ATOM | 2914 | CG1 | VAL | A | 382 | 12.612 | 9.321 | 55.414 | 1.00 | 12.79 | A |
| ATOM | 2915 | CG2 | VAL | A | 382 | 11.362 | 7.380 | 54.433 | 1.00 | 12.77 | A |
| ATOM | 2916 | C | VAL | A | 382 | 14.062 | 9.678 | 52.933 | 1.00 | 13.29 | A |
| ATOM | 2917 | O | VAL | A | 382 | 15.140 | 9.109 | 53.128 | 1.00 | 13.54 | A |
| ATOM | 2918 | N | VAL | A | 383 | 13.977 | 10.984 | 52.692 | 1.00 | 13.17 | A |
| ATOM | 2919 | CA | VAL | A | 383 | 15.178 | 11.819 | 52.698 | 1.00 | 13.33 | A |
| ATOM | 2920 | CB | VAL | A | 383 | 15.024 | 13.063 | 51.793 | 1.00 | 13.72 | A |
| ATOM | 2921 | CG1 | VAL | A | 383 | 16.291 | 13.928 | 51.870 | 1.00 | 13.77 | A |
| ATOM | 2922 | CG2 | VAL | A | 383 | 14.782 | 12.628 | 50.356 | 1.00 | 14.43 | A |
| ATOM | 2923 | C | VAL | A | 383 | 15.438 | 12.264 | 54.136 | 1.00 | 12.88 | A |
| ATOM | 2924 | O | VAL | A | 383 | 14.522 | 12.687 | 54.845 | 1.00 | 12.31 | A |
| ATOM | 2925 | N | LEU | A | 384 | 16.694 | 12.168 | 54.559 | 1.00 | 13.47 | A |

APPENDIX C-continued

18xCHS Mutant

| ATOM | # | TYPE | RES | | | X | Y | Z | OCC | B | |
|------|---|------|-----|---|-----|--------|--------|--------|------|-------|---|
| ATOM | 2926 | CA | LEU | A | 384 | 17.083 | 12.520 | 55.922 | 1.00 | 13.63 | A |
| ATOM | 2927 | CB | LEU | A | 384 | 17.542 | 11.257 | 56.662 | 1.00 | 13.93 | A |
| ATOM | 2928 | CG | LEU | A | 384 | 16.574 | 10.078 | 56.767 | 1.00 | 12.86 | A |
| ATOM | 2929 | CD1 | LEU | A | 384 | 17.339 | 8.831 | 57.206 | 1.00 | 12.88 | A |
| ATOM | 2930 | CD2 | LEU | A | 384 | 15.465 | 10.406 | 57.752 | 1.00 | 12.99 | A |
| ATOM | 2931 | C | LEU | A | 384 | 18.214 | 13.543 | 55.988 | 1.00 | 14.36 | A |
| ATOM | 2932 | O | LEU | A | 384 | 18.951 | 13.734 | 55.022 | 1.00 | 14.08 | A |
| ATOM | 2933 | N | ARG | A | 385 | 18.330 | 14.199 | 57.140 | 1.00 | 14.44 | A |
| ATOM | 2934 | CA | ARG | A | 385 | 19.402 | 15.163 | 57.400 | 1.00 | 15.65 | A |
| ATOM | 2935 | CB | ARG | A | 385 | 18.858 | 16.594 | 57.540 | 1.00 | 16.91 | A |
| ATOM | 2936 | CG | ARG | A | 385 | 19.954 | 17.674 | 57.630 | 1.00 | 19.02 | A |
| ATOM | 2937 | CD | ARG | A | 385 | 19.381 | 19.100 | 57.574 | 1.00 | 20.86 | A |
| ATOM | 2938 | NE | ARG | A | 385 | 20.430 | 20.114 | 57.422 | 1.00 | 23.18 | A |
| ATOM | 2939 | CZ | ARG | A | 385 | 21.158 | 20.611 | 58.419 | 1.00 | 24.39 | A |
| ATOM | 2940 | NH1 | ARG | A | 385 | 20.960 | 20.202 | 59.663 | 1.00 | 25.40 | A |
| ATOM | 2941 | NH2 | ARG | A | 385 | 22.096 | 21.518 | 58.171 | 1.00 | 25.36 | A |
| ATOM | 2942 | C | ARG | A | 385 | 20.001 | 14.701 | 58.731 | 1.00 | 15.04 | A |
| ATOM | 2943 | O | ARG | A | 385 | 19.268 | 14.342 | 59.653 | 1.00 | 14.72 | A |
| ATOM | 2944 | N | SER | A | 386 | 21.326 | 14.683 | 58.823 | 1.00 | 14.39 | A |
| ATOM | 2945 | CA | SER | A | 386 | 21.992 | 14.242 | 60.043 | 1.00 | 14.75 | A |
| ATOM | 2946 | CB | SER | A | 386 | 23.422 | 13.803 | 59.732 | 1.00 | 14.25 | A |
| ATOM | 2947 | OG | SER | A | 386 | 24.170 | 14.898 | 59.235 | 1.00 | 14.91 | A |
| ATOM | 2948 | C | SER | A | 386 | 22.030 | 15.347 | 61.093 | 1.00 | 14.95 | A |
| ATOM | 2949 | O | SER | A | 386 | 21.565 | 16.465 | 60.855 | 1.00 | 14.63 | A |
| ATOM | 2950 | N | VAL | A | 387 | 22.592 | 15.014 | 62.252 | 1.00 | 15.31 | A |
| ATOM | 2951 | CA | VAL | A | 387 | 22.734 | 15.943 | 63.369 | 1.00 | 16.50 | A |
| ATOM | 2952 | CB | VAL | A | 387 | 21.947 | 15.452 | 64.606 | 1.00 | 16.07 | A |
| ATOM | 2953 | CG1 | VAL | A | 387 | 22.214 | 16.364 | 65.796 | 1.00 | 15.48 | A |
| ATOM | 2954 | CG2 | VAL | A | 387 | 20.457 | 15.408 | 64.287 | 1.00 | 15.50 | A |
| ATOM | 2955 | C | VAL | A | 387 | 24.218 | 16.025 | 63.735 | 1.00 | 18.05 | A |
| ATOM | 2956 | O | VAL | A | 387 | 24.912 | 15.006 | 63.750 | 1.00 | 17.63 | A |
| ATOM | 2957 | N | ALA | A | 388 | 24.693 | 17.233 | 64.030 | 1.00 | 19.63 | A |
| ATOM | 2958 | CA | ALA | A | 388 | 26.095 | 17.455 | 64.389 | 1.00 | 22.13 | A |
| ATOM | 2959 | CB | ALA | A | 388 | 26.325 | 18.931 | 64.711 | 1.00 | 22.23 | A |
| ATOM | 2960 | C | ALA | A | 388 | 26.548 | 16.588 | 65.560 | 1.00 | 23.82 | A |
| ATOM | 2961 | O | ALA | A | 388 | 25.890 | 16.540 | 66.601 | 1.00 | 24.03 | A |
| ATOM | 2962 | N | ILE | A | 389 | 27.689 | 15.926 | 65.366 | 1.00 | 25.95 | A |
| ATOM | 2963 | CA | ILE | A | 389 | 28.306 | 15.023 | 66.338 | 1.00 | 27.95 | A |
| ATOM | 2964 | CB | ILE | A | 389 | 28.605 | 15.734 | 67.679 | 1.00 | 28.69 | A |
| ATOM | 2965 | CG2 | ILE | A | 389 | 28.958 | 14.707 | 68.752 | 1.00 | 29.02 | A |
| ATOM | 2966 | CG1 | ILE | A | 389 | 29.788 | 16.693 | 67.512 | 1.00 | 28.93 | A |
| ATOM | 2967 | CD1 | ILE | A | 389 | 29.524 | 17.871 | 66.590 | 1.00 | 29.88 | A |
| ATOM | 2968 | C | ILE | A | 389 | 27.470 | 13.775 | 66.607 | 1.00 | 28.74 | A |
| ATOM | 2969 | OT1 | ILE | A | 389 | 27.939 | 12.668 | 66.256 | 1.00 | 28.79 | A |
| ATOM | 2970 | OT2 | ILE | A | 389 | 26.354 | 13.915 | 67.157 | 1.00 | 29.65 | A |

That which is claimed is:

1. A method of producing a mutant chalcone synthase with altered substrate specificity, said method comprising substituting one or more amino acids of wild type chalcone synthase of SEQ ID NO:1 with the amino acid residues at the corresponding positions in a model structure of a plant polyketide synthase, wherein said one or more amino acids to be substituted are selected from the group consisting of positions 96, 98, 99, 100, 131, 133, 134, 135, 137, 157, 158, 159, 160, 165, 255, 257, 258, 266, 268, 269, 270 and 273 of SEQ ID NO:1, thereby producing said mutant chalcone synthase having altered substrate specificity.

2. The method of claim 1, wherein said wild type chalcone synthase comprises at least fourteen active site α-carbons having the structural coordinates of Table 1 (SEQ ID NO:1).

3. The method of claim 1, wherein said one or more substitutions are selected from the group consisting of D96A, V98L, V99A, V100M, T131S, S133T, G134T, V135P, M137L, Y157V, M158G, M159V, Y160F, Q165H, D255G, H257K, L258V, H266Q, L268K, K269G, D270A and G273D.

4. The method of claim 1, wherein said one or more amino acids comprise substitutions at each of positions 98, 131, 133, 134, 135 and 137.

5. The method of claim 4, wherein the substitutions comprise V98L, T131S, S133T, G134T, V135P, and M137L.

6. The method of claim 4, wherein said one or more amino acids further comprise substitutions at each of positions 96, 99 and 100.

7. The method of claim 5, wherein the substitutions further comprise D96A, V99A and V100M.

8. The method of claim 4, wherein said one or more amino acids further comprise substitutions at each of positions 158 and 160.

9. The method of claim 5, wherein the substitutions further comprise M158G and Y160F.

10. The method of claim 6, wherein said one or more amino acids further comprise substitutions at each of positions 158, 160 and 269.

11. The method of claim 7, wherein the substitutions further comprise M158G, Y160F and K269G.

12. The method of claim 8, wherein said one or more amino acids further comprise substitutions at each of positions 156, 159 and 165.

13. The method of claim 9, wherein the substitutions further comprise Y157V, M159V and Q165H.

14. The method of claim 10, wherein said one or more amino acids further comprise substitutions at each of positions 156, 158, 164, 267, 270 and 273.

15. The method of claim 11, wherein the substitutions further comprise Y157V, M159V, Q165H, L268K, D270A and G273D.

16. The method of claim 14, wherein said one or more amino acids further comprise substitutions at each of positions 254, 256, 258 and 266.

17. The method of claim 15, wherein the substitutions further comprise D255G, H257K, L258V and H266Q.

18. The method of claim 1, wherein said plant polyketide synthase is a stilbene synthase.

19. The method of claim 1, wherein said mutant chalcone synthase is produced in vitro.

20. The method of claim 1, wherein said mutant chalcone synthase is produced in vivo.

21. The method of claim 20, wherein said mutant chalcone synthase is produced in a plant.

22. A method of producing a mutant chalcone synthase with altered substrate specificity, said method comprising:
expressing an enzymatically active mutant chalcone synthase generated by substituting one or more amino acids of wild type chalcone synthase of SEQ ID NO:1 with one or more amino acid residues at the corresponding positions of a plant polyketide synthase,
wherein said one or more amino acids to be substituted are selected from the group consisting of positions 96, 98, 99, 100, 131, 133, 134, 135, 137, 157, 158, 159, 160, 165, 255, 257, 258, 266, 268, 269, 270 and 273 of SEQ ID NO:1,
wherein said amino acid residues to be substituted are selected by comparing a crystal structure of wild type chalcone synthase of SEQ ID NO:1 with a model structure of the plant polyketide synthase.

23. A method of altering the substrate specificity of a chalcone synthase, said method comprising:
(a) substituting one or more amino acids in the active site of wild type chalcone synthase with one or more amino acid residues at the corresponding positions in a plant polyketide synthase, wherein said one or more amino acids to be substituted correspond to positions selected from the group consisting of positions 132, 133, 137, 161, 194, 197, 211, 216, 254, 256, 263, 265, 267 and 338 of SEQ ID NO:1, thereby producing a chalcone synthase with altered substrate specificity; and
(b) testing the substrate specificity of the altered chalcone synthase and identifying those chalcone synthases having altered substrate specificity.

24. The method of claim 23, wherein the wild type chalcone synthase comprises at least fourteen active site α-carbons having the structural coordinates of Table 1 (SEQ ID NO:1).

25. A method of altering the activity of a chalcone synthase, said method comprising:
(a) substituting one or more amino acids in the active site of wild type chalcone synthase with one or more amino acid residues at the corresponding positions in a plant polyketide synthase, wherein said one or more amino acids to be substituted correspond to positions selected from the group consisting of positions 96, 98, 99, 131, 133, 134, 135, 137, 157, 158, 159, 160, 165, 255, 257, 258, 266, 268, 269, 270 and 273 of SEQ ID NO:1, thereby producing a chalcone synthase with altered activity; and
(b) testing the activity of the altered chalcone synthase and identifying those chalcone synthases having altered activity.

26. The method of claim 25, wherein the wild type chalcone synthase comprises at least fourteen active site α-carbons having the structural coordinates of Table 1 (SEQ ID NO:1).

27. The method of claim 25, wherein said one or more substitutions are selected from the group consisting of D96A, V98L, V99A, T131S, S133T, G134T, V135P, M137L, Y157V, M158G, M159V, Y160F, Q165H, D255G, H257K, L258V, H266Q, L268K, K269G, D270A and G273D.

28. The method of claim 25, wherein said plant polyketide synthase is a stilbene synthase.

29. The method of claim 25, wherein the altered activity results in the formation of the product of the plant polyketide synthase instead of the product of the wild type chalcone synthase.

30. The method of claim 25, wherein the altered activity results in the formation of both the product of the plant polyketide synthase and the product of the wild type chalcone synthase.

31. The method of claim 28, wherein the altered activity results in the formation of resveratrol instead of chalcone.

32. The method of claim 28, wherein the altered activity results in the formation of both resveratrol and chalcone.

33. A method of altering the activity of a chalcone synthase, said method comprising:
(a) substituting an amino acid in the active site of wild type chalcone synthase with an amino acid residue at the corresponding position in a plant polyketide synthase, wherein said amino acid to be substituted corresponds to position 100 of SEQ ID NO:1, thereby producing a chalcone synthase with altered activity; and (b) testing the activity of the altered chalcone synthase and identifying those chalcone synthases having altered activity.

34. The method of claim 33, wherein the wild type chalcone synthase comprises at least fourteen active site α-carbons having the structural coordinates of Table 1 (SEQ ID NO:1).

35. The method of claim 33, wherein said substitution is V100M.

36. The method of claim 33, wherein said plant polyketide synthase is a stilbene synthase.

37. The method of claim 33, wherein the altered activity results in the formation of the product of the plant polyketide synthase instead of the product of the wild type chalcone synthase.

38. The method of claim 33, wherein the altered activity results in the formation of both the product of the plant polyketide synthase and the product of the wild type chalcone synthase.

39. The method of claim 33, wherein the altered activity results in the formation of resveratrol instead of chalcone.

40. The method of claim 33, wherein the altered activity results in the formation of both resveratrol and chalcone.

* * * * *